United States Patent
Hearn et al.

(10) Patent No.: US 12,428,379 B2
(45) Date of Patent: Sep. 30, 2025

(54) ACYLSULFONAMIDE KAT6A INHIBITORS

(71) Applicants: Olema Pharmaceuticals, Inc., San Francisco, CA (US); Aurigene Oncology Limited, Karnataka (IN)

(72) Inventors: Brian R. Hearn, Moraga, CA (US); David C. Myles, Berkeley, CA (US); Reena Chawla, San Francisco, CA (US); David Yeghikyan, Fremont, CA (US); Chandregowda Venkateshappa, Bangalore (IN); Susanta Samajdar, Bangalore (IN); Kalisankar Bera, Bangalore (IN); Suraj Tatyasaheb Gore, Maharashtra (IN); Raymond A. Ng, Pleasant Hill, CA (US)

(73) Assignees: Olema Pharmaceuticals, Inc., San Francisco, CA (US); Aurigene Oncology Limited, Karnataka (IN)

( * ) Notice: Subject to any disclaimer, the term of this patent is extended or adjusted under 35 U.S.C. 154(b) by 0 days.

(21) Appl. No.: 18/999,331

(22) Filed: Dec. 23, 2024

(65) Prior Publication Data

US 2025/0136553 A1   May 1, 2025

Related U.S. Application Data

(63) Continuation of application No. PCT/IB2024/052546, filed on Mar. 15, 2024.

(30) Foreign Application Priority Data

Mar. 16, 2023  (IN) .............. 202311018002

(51) Int. Cl.
| | |
|---|---|
| C07D 231/12 | (2006.01) |
| A61K 31/415 | (2006.01) |
| A61K 31/4155 | (2006.01) |
| A61K 31/426 | (2006.01) |
| A61K 31/4439 | (2006.01) |
| A61K 31/444 | (2006.01) |
| A61K 31/505 | (2006.01) |
| A61K 31/506 | (2006.01) |
| A61P 35/00 | (2006.01) |
| C07D 239/34 | (2006.01) |
| C07D 277/34 | (2006.01) |
| C07D 401/06 | (2006.01) |
| C07D 401/14 | (2006.01) |
| C07D 403/06 | (2006.01) |
| C07D 405/12 | (2006.01) |
| C07D 405/14 | (2006.01) |

(52) U.S. Cl.
CPC .......... *C07D 231/12* (2013.01); *A61K 31/415* (2013.01); *A61K 31/4155* (2013.01); *A61K 31/426* (2013.01); *A61K 31/4439* (2013.01); *A61K 31/444* (2013.01); *A61K 31/505* (2013.01); *A61K 31/506* (2013.01); *A61P 35/00* (2018.01); *C07D 239/34* (2013.01); *C07D 277/34* (2013.01); *C07D 401/06* (2013.01); *C07D 401/14* (2013.01); *C07D 403/06* (2013.01); *C07D 405/12* (2013.01); *C07D 405/14* (2013.01)

(58) Field of Classification Search
CPC ................ C07D 231/12; C07D 239/34; C07D 277/34; C07D 401/06; C07D 401/14; C07D 403/06; C07D 405/12; C07D 405/14; A61K 31/415; A61K 31/4155; A61K 31/426; A61K 31/4439; A61K 31/444; A61K 31/505; A61K 31/506; A61P 35/00
See application file for complete search history.

(56) References Cited

U.S. PATENT DOCUMENTS

| | | |
|---|---|---|
| 5,103,014 A | 4/1992 | Musser et al. |
| 5,149,357 A | 9/1992 | Dixson et al. |
| 5,290,755 A | 3/1994 | Vogelbacher et al. |
| 2016/0095858 A1 | 4/2016 | Miller et al. |
| 2020/0385348 A1 | 12/2020 | Garneau-Tsodikova et al. |
| 2024/0254139 A1 | 8/2024 | Venkateshappa et al. |

FOREIGN PATENT DOCUMENTS

| | | |
|---|---|---|
| DE | 4126936 A1 | 2/1993 |
| DE | 4126937 A1 | 2/1993 |
| EP | 0527378 A1 | 2/1993 |

(Continued)

OTHER PUBLICATIONS

U.S. Appl. No. 18/718,391, filed Jun. 10, 2024.
Avvakumov, N. and Cote, J., The MYST family of histone acetyltransferases and their intimate links to cancer, Oncogene, 26:5395-5407 (2007).
Laak, A. et al., Discovery and Characterization of BAY-184: A New Potent and Selective Acylsulfonamide-Benzofuran In Vivo-Active KAT6AB Inhibitor, Journal of Medical Chemistry, 1-22 (2024).

(Continued)

*Primary Examiner* — Sarah Pihonak
*Assistant Examiner* — Padmaja S Rao
(74) *Attorney, Agent, or Firm* — Choate, Hall & Stewart LLP; Brenda Herschbach Jarrell; Michael A. Shinall

(57) ABSTRACT

The present disclosure describes acylsulfonamide compounds of Formula (J), and pharmaceutically acceptable salts, compositions, methods, and uses thereof. Such compounds are believed to be therapeutically useful as KAT6A inhibitors particularly in the treatment and/or prevention of diseases and disorders mediated by KAT6A in a subject.

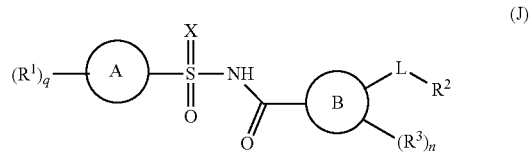

27 Claims, 3 Drawing Sheets

(56) References Cited

FOREIGN PATENT DOCUMENTS

| | | |
|---|---|---|
| JP | S58090555 A | 5/1983 |
| WO | WO-9222538 A1 | 12/1992 |
| WO | WO-9636613 A1 | 11/1996 |
| WO | WO-2016/057572 A1 | 4/2016 |
| WO | WO-2016/198507 A1 | 12/2016 |
| WO | WO-2019/108824 A1 | 6/2019 |
| WO | WO-2020/216701 A1 | 10/2020 |
| WO | WO-2020/254946 A1 | 12/2020 |
| WO | WO-2022/243983 A1 | 11/2022 |
| WO | WO-2023016484 A1 | 2/2023 |
| WO | WO-2023/088233 A1 | 5/2023 |
| WO | WO-2023/114710 A1 | 6/2023 |
| WO | WO-2024/189598 A2 | 9/2024 |
| WO | WO-2024/189598 A3 | 1/2025 |

OTHER PUBLICATIONS

Lv, D. et al., Histone Acetyltransferase KAT6A Upregulates PI3K/AKT Signaling through TRIM24 Binding, Cancer Research, 77(23):6190-6201 (2017).

Sheikh, Bn et al., Moz (MYST3, KAT6A) inhibits senescence via the INK4A-ARF pathway, Oncogene, 1-14 (2015).

International Search Report for PCT/IB24/52546, 4 pages (mailed Aug. 23, 2024).

Pubchem 441919164 deposited on Jul. 20, 2021 (Jul. 20, 2021) p. 1-5. pg. 2, structure.

Shi, et.al. Zarfirlukast Inhibits the Growth of Lung Adenocarcinoma via inhibiting TEMEM16A Channel Activity in J. Biol. Chem., 298(3):-13 (2022).

Written Opinion for PCT/IB24/52546, 5 pages (mailed Aug. 23, 2024).

ACYLSULFONAMIDE KAT6A INHIBITORS

CROSS-REFERENCES TO RELATED APPLICATIONS

This application is a Continuation of, and claims benefit of and priority to, PCT application number PCT/IB2024/052546, filed on Mar. 15, 2024, which claims the benefit of and priority to Indian application number 202311018002, filed on Mar. 16, 2023; each of which is hereby incorporated by reference in its entirety for all purposes.

FIELD OF THE INVENTION

The present disclosure relates to an acylsulfonamide compound of Formula (J) or a pharmaceutically acceptable salt thereof, which is believed to be useful as a KAT6A inhibitor for the treatment of a disease or disorder mediated by KAT6A. The present application also describes a method of preparation of the compound and a pharmaceutical composition comprising the compound.

BACKGROUND OF THE INVENTION

The MYST family of histone acetyltransferases (HATs) is named after its four founding members MOZ, Ybf2 (Sas3), Sas2, and Tip60. Presence of zinc fingers and chromodomains is characteristic feature of these HATs. MYST acetylates lysine residues on histones H2A, H3, and H4. Several MYST family proteins contain zinc fingers as well as the highly conserved motif A found among GNATs that facilitate acetyl-CoA binding. MYST HATs are involved in several key nuclear processes and play critical roles in gene-specific transcription regulation, DNA damage response, repair and replication. The anomalous activity of these HATs or their associated complexes can easily lead to severe cellular malfunction, resulting in cell death or uncontrolled growth and malignancy. Indeed, the MYST family HATs have been implicated in several forms of human cancer. (Avvakumov, N. et al. "The MYST family of histone acetyltransferases and their intimate links to cancer." Oncogene 26.37 (2007): 5395-5407.)

MOZ (monocytic leukemia zinc finger protein) is known as oncogene in human. MOZ plays a key role as transcriptional coactivator and epigenetic regulator in the process of proliferation and the differentiation of hematopoietic progenitor and stem cells. The insights into the deregulation of these processes indicate that MOZ fusion proteins are related to the formation of leukemic stem cells and interfere with the activities of key proteins such as transcription factors, which render MOZ as a promising target for acute myeloid leukaemia therapy. Targeting MOZ by small molecules will hold promise for acute myeloid leukaemia therapy. (Zhou C. et al. "MOZ/KAT6A: a promising target for acute myeloid leukaemia therapy." (2020): 759-761).

Cellular senescence plays a key role to restrict tumor growth. KAT6A has been shown to repress cellular senescence in mouse embryonic fibroblasts (MEFs) while not affecting apoptosis or DNA damage. MOZ is believed to directly bind to genes that inhibit senescence including Cdc6, E2f2, Ezh2 and Melk, and in its absence, H3K9ac and H3K27ac at the TSS of these loci is reduced. (Sheikh, B. N., et al. "MOZ (MYST3, KAT6A) inhibits senescence via the INK4A-ARF pathway." Oncogene 34.47 (2015): 5807-5820).

Histone acetyltransferase KAT6A-upregulated PI3K/AKT signalling through TRIM24 binding is believed critical for cell proliferation and tumor growth in gliomas. KAT6A has been shown to promote H3K23 acetylation and association with TRIM24, leading to increased PIK3CA expression and PI3K/Akt signalling activation, resulting in enhanced glioma tumorigenesis. Hence, KAT6A is believed to function as an oncogene in gliomas. (Lv, D., et al. "Histone acetyltransferase KAT6A upregulates PI3K/AKT signalling through TRIM24 binding." Cancer research 77.22 (2017): 6190-6201).

Many publications disclose small molecule compounds and their derivatives capable of targeting KAT target proteins. Because there are currently no FDA-approved targeted therapeutics for specific KAT6A or KAT6B target protein, there is a need for the development of compounds, compositions, and methods for treating KAT6A- or KAT6B-activated proliferative disorders and autoimmune diseases.

SUMMARY

In some embodiments, a compound of the present disclosure is represented by Formula (J):

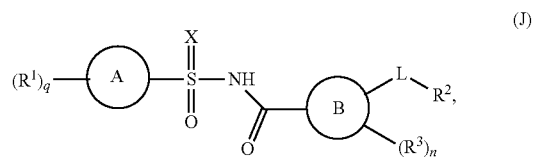

or a pharmaceutically acceptable salt thereof,
wherein
X is O or $NR^4$;
ring A is a phenyl or heteroaryl;
ring B is a phenyl or heteroaryl;
each $R^1$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{1a}$, —C(O)O$R^{1a}$, —OC(O)$R^{1a}$, —C(O)N($R^{1a}$)($R^{1b}$), —N($R^{1a}$)C(O)($R^{1b}$), —OC(O)N($R^{1a}$)($R^{1b}$), —N($R^{1a}$)C(O)(O$R^{1b}$), —S(O)$R^{1a}$, —S(O)$_2R^{1a}$, —S(O)$_2$N($R^{1a}$)($R^{1b}$), —S(O)(NH)$R^{1a}$, —S(O)(NH)N($R^{1a}$)($R^{1b}$), —N($R^{1a}$)($R^{1b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{1c}$, each alkoxy and alkynyl is substituted with 0, 1, 2, or 3 $R^{1d}$, and each cycloalkyl, heterocycloalkyl, aryl, and heteroaryl is substituted with 0, 1, 2, or 3 $R^{1e}$;
each $R^{1a}$ and $R^{1b}$ is independently hydrogen or $C_1$-$C_6$ alkyl;
each $R^{1c}$ is independently $C_1$-$C_6$ alkoxy, halogen, $C_1$-$C_6$ haloalkoxy, —N$R^{1c1}R^{1c2}$, OH, or —CN;
each $R^{1c1}$ and $R^{1c2}$ is independently hydrogen or $C_1$-$C_6$ alkyl;
each $R^{1d}$ is independently deuterium, $C_3$-$C_8$ cycloalkyl, heterocycloalkyl, $C_6$-$C_{10}$ aryl, or heteroaryl;
each $R^{1e}$ is independently $C_1$-$C_6$ alkyl, $C_1$-$C_6$ alkoxy, halogen, $C_1$-$C_6$ haloalkyl, $C_1$-$C_6$ haloalkoxy, OH, or —CN;
alternatively, two $R^1$ groups on adjacent carbons together with the atoms to which they are attached combine to form a $C_5$-$C_8$ cycloalkyl or a heterocycloalkyl substituted with 0, 1, 2, 3, 4, 5, or 6 halogen, $C_1$-$C_4$ alkyl, OH or —CN;

L is —$C_1$-$C_4$ alkylene-, —($C_1$-$C_4$ alkylene)-O—, or —O—;

$R^2$ is a heteroaryl, which is substituted with 0, 1, 2, 3, or 4 $R^{2a}$;

each $R^{2a}$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{2b}$, —C(O)O$R^{2b}$, —OC(O)$R^{2b}$, —C(O)N($R^{2b}$)($R^{2c}$), —N($R^{2b}$)C(O)($R^{2c}$), —S(O)$_2R^{2b}$, —S(O)$_2$N($R^{2b}$)($R^{2c}$), —N($R^{2b}$)($R^{2c}$), OH, —CN, or —NO$_2$;

each $R^{2b}$ and $R^{2c}$ is independently hydrogen or $C_1$-$C_6$ alkyl;

each $R^3$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —OC(O)N($R^{3a}$)($R^{3b}$), —N($R^{3a}$)C(O)(O$R^{3b}$), —S(O)$R^{3a}$, —S(O)$_2R^{3a}$, —S(O)$_2$N($R^{3a}$)($R^{3b}$), —S(O)(NH)$R^{3a}$, —S(O)(NH)N($R^{3a}$)($R^{3b}$), —N($R^{3a}$)($R^{3b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{3c}$, each alkoxy is substituted with 0, 1, 2, or 3 $R^{3d}$, and each cycloalkyl, heterocycloalkyl, aryl, and heteroaryl is substituted with 0, 1, 2, or 3 $R^{3e}$; or, two $R^3$ on the same carbon atom together represent an oxo group;

each $R^{3a}$ and $R^{3b}$ is independently hydrogen or $C_1$-$C_6$ alkyl;

each $R^{3c}$ is independently $C_1$-$C_6$ alkoxy, halogen, $C_1$-$C_6$ haloalkoxy, —N$R^{3c1}R^{3c2}$, OH, or —CN;

each $R^{3c1}$ and $R^{3c2}$ is independently hydrogen or $C_1$-$C_6$ alkyl;

each $R^{3d}$ is independently $C_3$-$C_8$ cycloalkyl, heterocycloalkyl, phenyl, or heteroaryl;

each $R^{3e}$ is independently $C_1$-$C_6$ alkyl, $C_1$-$C_6$ alkoxy, halogen, $C_1$-$C_6$ haloalkyl, or $C_1$-$C_6$ haloalkoxy;

$R^4$ is hydrogen or $C_1$-$C_6$ alkyl;

subscript n is 0, 1, 2, 3, or 4; and subscript q is 0, 1, 2, 3, or 4;

wherein each heterocycloalkyl is a 3- to 8-membered ring that includes 1 to 4 heteroatoms each independently N, O or S; and each heteroaryl is a 5- to 6-membered ring that includes 1 to 4 heteroatoms each independently N, O or S.

In some embodiments, a composition of the present invention is a pharmaceutical composition comprising a compound of the present invention, or a pharmaceutically acceptable salt thereof and a pharmaceutically acceptable carrier or excipient. In some embodiments, a compound of the present invention is a compound or a pharmaceutically acceptable salt thereof for use as a medicament. In some embodiments, a compound of the present invention is a compound for use in the treatment of a disease or disorder mediated by KAT6A. In some embodiments, a method of the present invention is a method of modulating KAT6A in a subject comprising administering to the subject in need thereof, a therapeutically effective amount of compound of the present invention or a pharmaceutically acceptable salt thereof.

In some embodiments, a method of the present invention is a method of treating a disease or disorder mediated by KAT6A in a subject comprising administering to the subject in need thereof a therapeutically effective amount of a compound of the present invention or a pharmaceutically acceptable salt thereof.

DETAILED DESCRIPTION OF CERTAIN EMBODIMENTS

I. General

Figure 1:
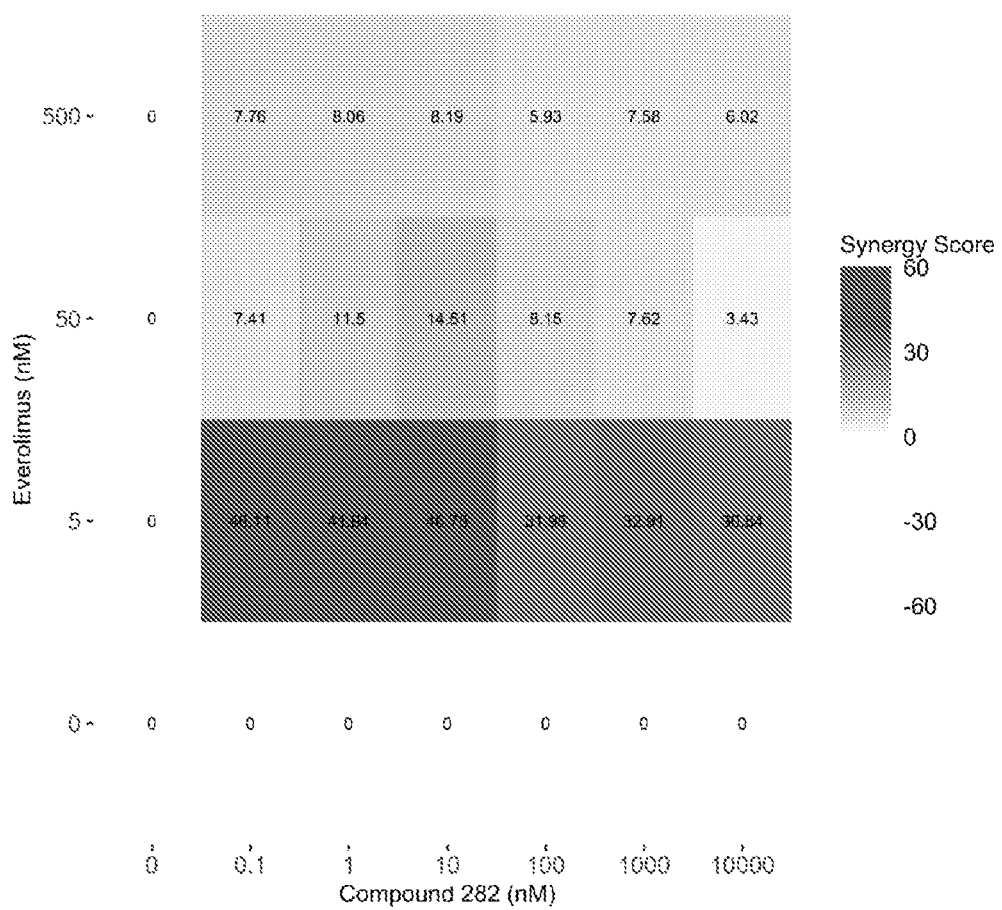
FIG. 1 provides synergy scores of Compound 282 in combination with everolimus at various concentrations.

The present disclosure provides, among other things, acylsulfonamide compounds represented by formula (J) and pharmaceutically acceptable salts thereof. Also described herein are pharmaceutical compositions comprising the compounds which are believed useful as KAT6A inhibitors for the treatment of diseases or disorders dependent on or mediated by KAT6A. The present disclosure also includes a preparation of compound of formula (J) or a pharmaceutically acceptable salt thereof.

II. Definitions

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

"Alkyl" refers to monovalent saturated aliphatic groups, including but not limited to $C_1$-$C_{10}$ straight-chain alkyl groups or $C_3$-$C_{10}$ branched-chain alkyl groups. In some embodiments, an alkyl group is a $C_1$-$C_6$ straight-chain alkyl group or $C_3$-$C_8$ branched-chain alkyl group. In some embodiments, the alkyl group refers to $C_1$-$C_4$ straight-chain alkyl groups or $C_3$-$C_6$ branched-chain alkyl groups. Examples of alkyl include, but are not limited to, methyl, ethyl, 1-propyl, 2-propyl, isopropyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The alkyl group may be optionally substituted.

An "alkylene" refers to a divalent saturated aliphatic group, including but not limited to $C_1$-$C_{10}$ straight-chain alkylene groups or $C_3$-$C_{10}$ branched-chain alkylene groups. In some embodiments, the alkylene refers to $C_1$-$C_6$ straight-chain alkylene groups or $C_3$-$C_8$ branched-chain alkylene groups. In some embodiments, the alkylene group refers to $C_1$-$C_4$ straight-chain alkylene groups or $C_3$-$C_6$ branched-chain alkylene groups. Examples of alkylene include, but are not limited to, methylene, ethylene, 1-propylene, 2-propylene, isopropylene, n-butylene, and sec-butylene. The "alkylene" group may further be optionally substituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to the group —O-alkyl, where alkyl groups are as defined above. In some embodiments, the alkoxy group refers to $C_1$-$C_6$ straight-chain alkoxy groups or $C_3$-$C_8$ branched-chain alkoxy groups. In some embodiments, the alkoxy group refers to $C_1$-$C_4$ straight-chain alkoxy groups or $C_3$-$C_6$ branched-chain alkoxy groups. Exemplary $C_1$-$C_{10}$ alkoxy group include but are not limited to methoxy, ethoxy, n-propoxy, n-butoxy or t-butoxy. An alkoxy group can be optionally substituted with one or more suitable groups, as described herein.

"Alkoxyalkyl" refers to an alkyl group substituted with one or more alkoxy groups, wherein the alkyl and alkoxy groups are as defined above. In some embodiments, alkoxyalkyl represents ($C_1$-$C_6$)alkyl($C_1$-$C_6$)alkoxy or ($C_1$-$C_4$)alkyl($C_1$-$C_4$)alkoxy. Exemplary alkoxyalkyl group include, but are not limited to methoxymethyl, ethoxymethyl and ethoxyethyl.

The term "halo" or "halogen" alone or in combination with other term(s) means fluorine, chlorine, bromine or iodine.

"Haloalkyl" refers to alkyl substituted with one or more halogen atoms, wherein the 'halogen' and 'alkyl' groups are as defined above. Examples of haloalkyl include but are not limited to fluoromethyl, difluoromethyl, chloromethyl, trifluoromethyl and 2,2,2-trifluoroethyl.

"Haloalkoxy" refers to an alkoxy group substituted with one or more halogen atoms (i.e., halo$C_{1-8}$alkoxy). Examples of haloalkoxy include but are not limited to fluoromethoxy, difluoromethoxy, trifluoromethoxy, 2,2,2-trifluoroethoxy, pentafluoroethoxy, pentachloroethoxy, chloromethoxy, dichloromethoxy, trichloromethoxy and 1-bromoethoxy.

"Amino" refers to an —NH$_2$ group.

"Hydroxy" or "hydroxyl" alone or in combination with other term(s) means —OH.

"Hydroxyalkyl" refers to an alkyl group substituted with one or more hydroxyls.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. Cycloalkyl groups also include multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g. tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Heteroatom" as used herein designates a sulfur, nitrogen or oxygen atom.

"Heterocycloalkyl" refers to a non-aromatic, saturated or partially saturated, bridged bicyclic, monocyclic or polycyclic ring system of 3- to 15-member, unless the ring size is specifically mentioned, having at least one heteroatom or hetero group selected from O, N, S, S(O), S(O)$_2$, NH or C(O) with the remaining ring atoms being independently selected from the group consisting of carbon, oxygen, nitrogen and sulfur. Heterocycloalkyl also refers to the bridged bicyclic ring system having at least one heteroatom or hetero group selected from O, N, S, S(O), S(O)$_2$, NH or C(O). Examples of heterocycloalkyl include, but not limited to, aziridinyl, oxiranyl, thiiranyl, azetidinyl, oxetanyl, imidazolidinyl, pyrrolidinyl, oxazolidinyl, thiazolidinyl, pyrazolidinyl, tetrahydrofuranyl, piperidinyl, dihydropyridinyl, piperazinyl, tetrahydropyranyl, morpholinyl, thiomorpholinyl, 1,4-dioxanyl, dioxidothiomorpholinyl, oxopiperazinyl, oxopiperidinyl, tetrahydrofuryl, tetrahydropyranyl, tetrahydrothiophenyl, dihydropyranyl, indolinyl, indolinylmethyl, isoindolinyl, oxoisoindolinyl, dioxoisoindolinyl, aza-bicyclooctanyl, diazabicyclooctanyl, azocinyl, chromanyl, isochromanyl and xanthenyl. Attachment of a heterocycloalkyl substituent can occur via either a carbon atom or a heteroatom. A heterocycloalkyl group can be optionally substituted with one or more suitable groups. In some embodiments, heterocycloalkyl refers to 4- to 6-membered ring (unless the ring size is specifically mentioned) selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl and thiomorpholinyl. Heterocycloalkyl groups are optionally substituted by one or more groups described herein.

"Aryl" is an optionally substituted monocyclic, bicyclic or polycyclic aromatic hydrocarbon ring system of about 6 to 14 carbon atoms. In some embodiments, aryl includes 6- to 10-membered aromatic hydrocarbon ring systems. Examples of a $C_6$-$C_{14}$ aryl groups include, but are not limited to phenyl, naphthyl, biphenyl, anthryl, tetrahydronaphthyl, fluorenyl, indanyl, biphenylenyl and acenaphthyl. Aryl group can be optionally substituted with one or more suitable groups, described herein.

"Heteroaryl" refers to a completely unsaturated and aromatic ring system containing a total of 5 to 14 ring atoms, unless the ring size is specifically mentioned. At least one of the ring atoms is a heteroatom (i.e., O, N or S), with the remaining ring atoms/groups being independently selected from C, N, O or S. A heteroaryl may be a single-ring (monocyclic) or multiple rings (bicyclic, tricyclic or polycyclic) fused together or linked covalently. In some embodiments, the heteroaryl is a 5- to 6-membered ring. The rings may contain from 1 to 4 heteroatoms selected from N, O and S, wherein the N atom is optionally quarternized. Any suitable ring position of the heteroaryl moiety may be covalently linked to the defined chemical structure. Examples of heteroaryls include but are not limited to furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl (pyridinyl), pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carbolinyl, indolizinyl, benzoisothiazolyl, benzoxazolyl, pyrrolopyridyl, purinyl, benzothiadiazolyl, benzooxadiazolyl, benzotriazolyl, benzotriadiazolyl, carbazolyl, dibenzothienyl, acridinyl and the like. A heteroaryl can be further substituted.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

"Pharmaceutically acceptable salt" refers to a product obtained by reaction of the compound of the present invention with a suitable acid or a base. In some cases, a medicament can be present in the form of a pharmaceutically acceptable salt. In some instances, a pharmaceutically acceptable salt can be a salt described in Berge et al, J. Pharm. Sci, 1977. In some instances, a pharmaceutically acceptable salts can include those salts derived from a mineral, organic acid or inorganic base. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids.

The pharmaceutically acceptable salts of the present invention can be prepared from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20$^{th}$ ed., Mack Publishing Company, Easton, Pa., (1985); and in "Handbook of Pharmaceutical Salts: Properties, Selection and Use" by Stahl and Wermuth (Wiley-VCH, Weinheim, Germany, 2002).

"Composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant or emulsifier that has been approved by the United States Food and Drug Administration as being acceptable for use in humans or domestic animals.

"Administer," "administering," and/or "administration" as used in this disclosure refer to either directly administering one or more disclosed compounds or a pharmaceutically acceptable salt of one or more disclosed compounds or a composition comprising one or more disclosed compounds to a subject or analog of the compound or a pharmaceutically acceptable salt of the compound or composition to the subject, which can form an equivalent amount of active compound within the subject's body.

"Carrier" encompasses carriers, excipients and diluents and means a material, composition or vehicle, such as a liquid or solid filler, diluent, excipient, solvent or encapsulating material, involved in carrying or transporting a pharmaceutical agent from one organ or portion of the body to another organ or portion of the body of a subject.

"Treat", "treating", and/or "treatment" refer to a method of alleviating or abrogating a disease and/or one or more symptoms associated with the disease.

"Prevent", "preventing", and/or "prevention" refer to a method of preventing the onset of a disease and/or its attendant symptoms or barring a subject from acquiring a disease. Prevent, preventing, and/or prevention also include delaying the onset of a disease and/or one or more symptoms associated with the disease and reducing a subject's risk of acquiring a disease.

"Subject" or "patient" refers to an animal, such as a mammal, for instance, a human. In some embodiments, the subject is a mammal, such as a mouse, a rat, a dog, a cat, another veterinary animal, such as a goat, a pig, a horse, a cow, or a donkey; or a primate, such as a non-human primate, e.g., a cynomolgous monkey, rhesus monkey, or chimpanzee, or a human. In some embodiments, the subject is a human.

"Therapeutically effective amount" refers to an amount of a compound of formula (J) or a pharmaceutically acceptable salt or a stereoisomer or a tautomer thereof; or a composition comprising the compound of formula (J) or a pharmaceutically acceptable salt or a stereoisomer or a tautomer thereof, effective in producing the desired therapeutic response in a particular patient suffering from a diseases or disorder, in particular their use in diseases or disorder associated with cancer. A therapeutically effective amount includes the amount of the compound of formula (J) or a pharmaceutically acceptable salt or a stereoisomer or a tautomer thereof, when administered, that induces a positive modification in the disease or disorder to be treated or is sufficient to prevent development of or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

III. Compounds

In some embodiments, a compound of the present disclosure is represented by Formula (J):

$$(R^1)_q-A-\overset{X}{\underset{O}{S}}(=O)-NH-C(=O)-B(L-R^2)(R^3)_n \tag{J}$$

or a pharmaceutically acceptable salt thereof,
wherein
X is O or $NR^4$;
ring A is a phenyl or heteroaryl;
ring B is a phenyl or heteroaryl;
each $R^1$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{1a}$, —C(O)O$R^{1a}$, —OC(O)$R^{1a}$, —C(O)N($R^{1a}$)($R^{1b}$), —N($R^{1a}$)C(O)($R^{1b}$), —OC(O)N($R^{1a}$)($R^{1b}$), —N($R^{1a}$)C(O)(O$R^{1b}$), —S(O)$R^{1a}$, —S(O)$_2R^{1a}$, —S(O)$_2$N($R^{1a}$)($R^{1b}$), —S(O)(NH)$R^{1a}$, —S(O)(NH)N($R^{1a}$)($R^{1b}$), —N($R^{1a}$)($R^{1b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{1c}$, each alkoxy and alkynyl is substituted with 0, 1, 2, or 3 $R^{1d}$, and each cycloalkyl, heterocycloalkyl, aryl, and heteroaryl is substituted with 0, 1, 2, or 3 $R^{1e}$;
each $R^{1a}$ and $R^{1b}$ is independently hydrogen or $C_1$-$C_6$ alkyl;
each $R^{1c}$ is independently $C_1$-$C_6$ alkoxy, halogen, $C_1$-$C_6$ haloalkoxy, —N$R^{1c1}R^{1c2}$, OH, or —CN;
each $R^{1c1}$ and $R^{1c2}$ is independently hydrogen or $C_1$-$C_6$ alkyl;
each $R^{1d}$ is independently deuterium, $C_3$-$C_8$ cycloalkyl, heterocycloalkyl, $C_6$-$C_{10}$ aryl, or heteroaryl;
each $R^{1e}$ is independently $C_1$-$C_6$ alkyl, $C_1$-$C_6$ alkoxy, halogen, $C_1$-$C_6$ haloalkyl, $C_1$-$C_6$ haloalkoxy, OH, or —CN;
alternatively, two $R^1$ groups on adjacent carbons together with the atoms to which they are attached combine to form a $C_5$-$C_8$ cycloalkyl or a heterocycloalkyl substituted with 0, 1, 2, 3, 4, 5, or 6 halogen, $C_1$-$C_4$ alkyl, OH or —CN;
L is —$C_1$-$C_4$ alkylene-, —($C_1$-$C_4$ alkylene)-O—, or —O—;
$R^2$ is a heteroaryl, which is substituted with 0, 1, 2, 3, or 4 $R^{2a}$;
each $R^{2a}$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{2b}$, —C(O)O$R^{2b}$, —OC(O)$R^{2b}$, —C(O)N($R^{2b}$)($R^{2c}$), —N($R^{2b}$)C(O)($R^{2c}$), —S(O)$_2R^{2b}$, —S(O)$_2$N($R^{2b}$)($R^{2c}$), —N($R^{2b}$)($R^{2c}$), OH, —CN, or —NO$_2$;
each $R^{2b}$ and $R^{2c}$ is independently hydrogen or $C_1$-$C_6$ alkyl;
each $R^3$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —OC(O)N($R^{3a}$)($R^{3b}$), —N($R^{3a}$)C(O)(O$R^{3b}$), —S(O)$R^{3a}$, —S(O)$_2R^{3a}$, —S(O)$_2$N($R^{3a}$)($R^{3b}$), —S(O)(NH)$R^{3a}$, —S(O)(NH)N($R^{3a}$)($R^{3b}$), —N($R^{3a}$)($R^{3b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{3c}$, each alkoxy is substituted with 0, 1, 2, or 3 $R^{3d}$, and each cycloalkyl, heterocycloalkyl, aryl, and heteroaryl is substituted with 0, 1, 2, or 3 $R^{3e}$; or,
two $R^3$ on the same carbon atom together represent an oxo group;
each $R^{3a}$ and $R^{3b}$ is independently hydrogen or $C_1$-$C_6$ alkyl;
each $R^{3c}$ is independently $C_1$-$C_6$ alkoxy, halogen, $C_1$-$C_6$ haloalkoxy, —N$R^{3c1}R^{3c2}$, OH, or —CN;
each $R^{3c1}$ and $R^{3c2}$ is independently hydrogen or $C_1$-$C_6$ alkyl;
each $R^{3d}$ is independently $C_3$-$C_8$ cycloalkyl, heterocycloalkyl, phenyl, or heteroaryl;
each $R^{3e}$ is independently $C_1$-$C_6$ alkyl, $C_1$-$C_6$ alkoxy, halogen, $C_1$-$C_6$ haloalkyl, or $C_1$-$C_6$ haloalkoxy;
$R^4$ is hydrogen or $C_1$-$C_6$ alkyl;
subscript n is 0, 1, 2, 3, or 4; and
subscript q is 0, 1, 2, 3, or 4;
wherein
each heterocycloalkyl is a 3- to 8-membered ring that includes 1 to 4 heteroatoms each independently N, O or S; and
each heteroaryl is a 5- to 6-membered ring that includes 1 to 4 heteroatoms each independently N, O or S.

In some embodiments, X is O. In some embodiments, X is NH.

In some embodiments, ring B is heteroaryl. In some embodiments, ring B is a pyrrolyl, furyl, thienyl, pyrazolyl, isoxazolyl, oxazolyl, isothiazolyl, thiazolyl, triazolyl, oxadiazolyl, thiadiazolyl, pyridyl, pyridazinyl, pyrimidyl, or pyrazinyl. In some embodiments, ring B is a pyridyl, pyridazinyl, pyrimidyl, or pyrazinyl. In some embodiments, ring B is pyridyl or pyrimidinyl. In some embodiments, ring B is phenyl.

In some embodiments, a compound of Formula (J), or pharmaceutically acceptable salt thereof, is a compound of Formula (I), Formula (II), Formula (III), or Formula (IV):

(I)

(II)

-continued

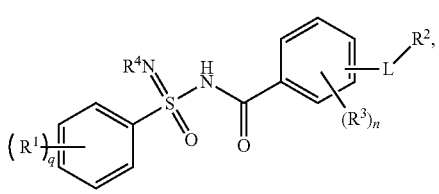
(III)

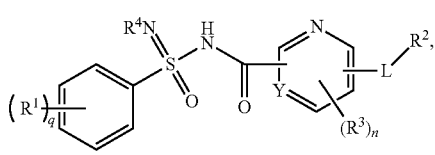
(IV)

or a pharmaceutically acceptable salt thereof, wherein $R^1$, q, $R^2$, L, $R^3$, $R^4$, and n are as described in classes and subclasses herein, both singly and in combination, and Y is N, CH, or $CR^3$.

In some embodiments, a compound of Formula (J), or pharmaceutically acceptable salt thereof, is a compound of Formula (I):

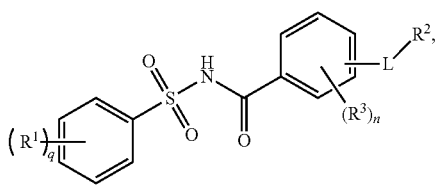
(I)

or a pharmaceutically acceptable salt thereof, wherein $R^1$, q, $R^2$, L, $R^3$, and n are as described in classes and subclasses herein, both singly and in combination.

In some embodiments, a compound of Formula (J), or pharmaceutically acceptable salt thereof, is a compound of Formula (II):

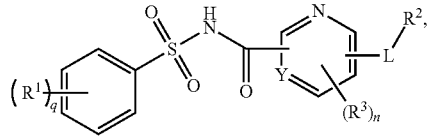
(II)

Or a pharmaceutically acceptable salt thereof, wherein $R^1$, q, $R^2$, L, $R^3$, and n are as described in classes and subclasses herein, both singly and in combination, and Y is N, CH, or $CR^3$.

In some embodiments, a compound of Formula (J), or pharmaceutically acceptable salt thereof, is a compound of Formula (III):

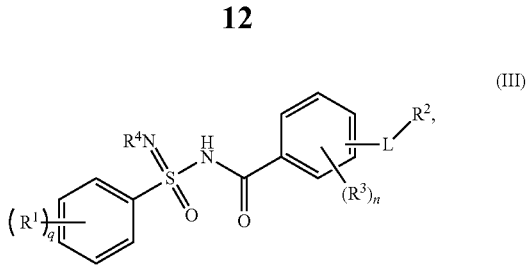
(III)

or a pharmaceutically acceptable salt thereof, wherein $R^1$, q, $R^2$, L, $R^3$, $R^4$, and n are as described in classes and subclasses herein, both singly and in combination.

In some embodiments, a compound of Formula (J), or pharmaceutically acceptable salt thereof, is a compound of Formula (IV):

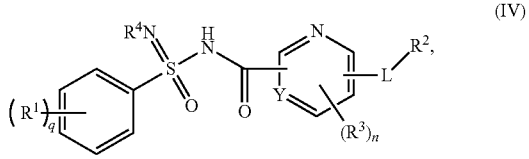
(IV)

Or a pharmaceutically acceptable salt thereof, wherein $R^1$, q, $R^2$, L, $R^3$, $R^4$, and n are as described in classes and subclasses herein, both singly and in combination, and Y is N, CH, or $CR^3$.

In some embodiments, a compound of Formula (J) or pharmaceutically acceptable salt thereof is represented by Formula (I):

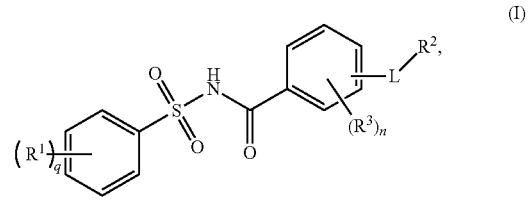
(I)

or a pharmaceutically acceptable salt thereof, wherein:
each $R^1$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{1a}$, —C(O)O$R^{1a}$, —OC(O)$R^{1a}$, —C(O)N($R^{1a}$)($R^{1b}$), —N($R^{1a}$)C(O)($R^{1b}$), —OC(O)N($R^{1a}$)($R^{1b}$), —N($R^{1a}$)C(O)(O$R^{1b}$), —S(O)$R^{1a}$, —S(O)$_2$$R^{1a}$, —S(O)$_2$N($R^{1a}$)($R^{1b}$), —S(O)(NH)$R^{1a}$, —S(O)(NH)N($R^{1a}$)($R^{1b}$), —N($R^{1a}$)($R^{1b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{1c}$, each alkoxy and alkynyl is substituted with 0, 1, 2, or 3 $R^{1d}$, and each cycloalkyl, heterocycloalkyl, aryl, and heteroaryl is substituted with 0, 1, 2 or 3 $R^{1e}$;
each $R^{1a}$ and $R^{1b}$ is independently hydrogen or $C_1$-$C_6$ alkyl;
each $R^{1c}$ is independently $C_1$-$C_6$ alkoxy, halogen, $C_1$-$C_6$ haloalkoxy, —N$R^{1c1}$$R^{1c2}$, OH, or —CN;

each $R^{1c1}$ and $R^{1c2}$ is independently hydrogen or $C_1$-$C_6$ alkyl;

each $R^{1d}$ is independently deuterium, $C_3$-$C_8$ cycloalkyl, heterocycloalkyl, $C_6$-$C_{10}$ aryl, or heteroaryl;

each $R^{1e}$ is independently $C_1$-$C_6$ alkyl, $C_1$-$C_6$ alkoxy, halogen, $C_1$-$C_6$ haloalkyl, $C_1$-$C_6$ haloalkoxy, OH, or —CN;

alternatively, two $R^1$ groups on adjacent carbons together with the atoms to which they are attached combine to form a $C_5$-$C_8$ cycloalkyl or a heterocycloalkyl substituted with 0, 1, 2, 3, 4, 5, or 6 halogen, $C_1$-$C_4$ alkyl, OH or —CN;

L is —$C_1$-$C_4$ alkylene-, —($C_1$-$C_4$ alkylene)-O—, or —O—;

$R^2$ is a heteroaryl, which is substituted with 0, 1, 2, 3, or 4 $R^{2a}$;

each $R^{2a}$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{2b}$, —C(O)O$R^{2b}$, —OC(O)$R^{2b}$, —C(O)N($R^{2b}$)($R^{2c}$), —N($R^{2b}$)C(O)($R^{2c}$), —S(O)$_2$$R^{2b}$, —S(O)$_2$N($R^{2b}$)($R^{2c}$), —N($R^{2b}$)($R^{2c}$), OH, —CN, or —NO$_2$;

each $R^{2b}$ and $R^{2c}$ is independently hydrogen or $C_1$-$C_6$ alkyl;

each $R^3$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —OC(O)N($R^{3a}$)($R^{3b}$), —N($R^{3a}$)C(O)(O$R^{3b}$), —S(O)$R^{3a}$, —S(O)$_2$$R^{3a}$, —S(O)$_2$N($R^{3a}$)($R^{3b}$), —S(O)(NH)$R^{3a}$, —S(O)(NH)N($R^{3a}$)($R^{3b}$), —N($R^{3a}$)($R^{3b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{3c}$, each alkoxy is substituted with 0, 1, 2, or 3 $R^{3d}$, and each cycloalkyl, heterocycloalkyl, aryl, and heteroaryl is substituted with 0, 1, 2, or 3 $R^{3e}$; or, two $R^3$ on the same carbon atom together represent an oxo group;

each $R^{3a}$ and $R^{3b}$ is independently hydrogen or $C_1$-$C_6$ alkyl;

each $R^{3c}$ is independently $C_1$-$C_6$ alkoxy, halogen, $C_1$-$C_6$ haloalkoxy, —N$R^{3c1}$$R^{3c2}$, OH, or —CN;

each $R^{3c1}$ and $R^{3c2}$ is independently hydrogen or $C_1$-$C_6$ alkyl;

each $R^{3d}$ is independently $C_3$-$C_8$ cycloalkyl, heterocycloalkyl, phenyl, or heteroaryl;

each $R^{3e}$ is independently $C_1$-$C_6$ alkyl, $C_1$-$C_6$ alkoxy, halogen, $C_1$-$C_6$ haloalkyl, or $C_1$-$C_6$ haloalkoxy;

subscript n is 0, 1, 2, 3, or 4; and subscript q is 0, 1, 2, 3, or 4;

wherein each heterocycloalkyl is a 3- to 8-membered ring that includes 1 to 4 heteroatoms each independently N, O or S; and each heteroaryl is a 5- to 6-membered ring that includes 1 to 4 heteroatoms each independently N, O or S.

In some embodiments, a compound of Formula (J), Formula (I), or pharmaceutically acceptable salt thereof is represented by Formula (Ia):

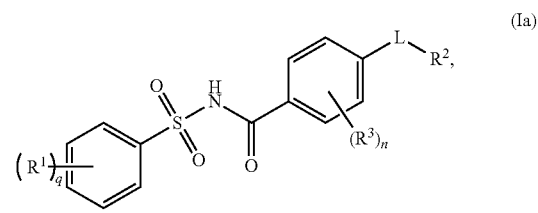

or a pharmaceutically acceptable salt thereof, wherein $R^1$, q, $R^2$, L, $R^3$, and n are as described in classes and subclasses herein, both singly and in combination.

In some embodiments, a compound of Formula (J), (I), and/or (Ia), or pharmaceutically acceptable salt thereof, is represented by Formula (Ib):

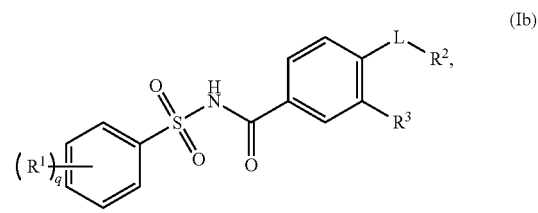

or a pharmaceutically acceptable salt thereof, wherein $R^1$, q, $R^2$, L, and $R^3$ are as described in classes and subclasses herein, both singly and in combination.

In some embodiments, a compound of Formula (J), (I), (Ia), and/or (Ib), or pharmaceutically acceptable salt thereof, is a compound, or pharmaceutically acceptable salt thereof, wherein the group

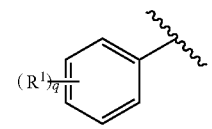

has the structure:

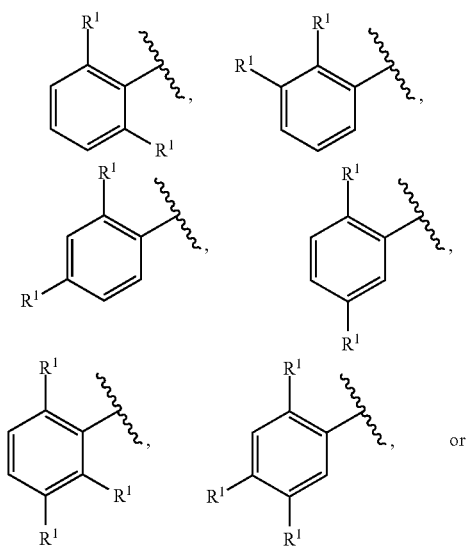

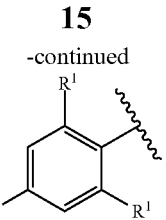

wherein $R^1$ is as described in classes and subclasses herein, wherein $R^1$ is as described in classes and subclasses herein.

In some embodiments, a compound of Formula (J), (I), (Ia), and/or (Ib), or pharmaceutically acceptable salt thereof, is a compound, or pharmaceutically acceptable salt thereof, wherein each $R^1$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, OH, —CN, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, or heteroaryl, wherein each alkyl is substituted with 0, 1, 2, or 3 $R^{1c}$, and each alkoxy and alkynyl is substituted with 0, 1, 2, or 3 $R^{1d}$; or alternatively, two $R^1$ on adjacent carbons together with the atoms to which they are attached combine to form a $C_5$-$C_8$ cycloalkyl or a heterocycloalkyl.

In some embodiments, a compound of Formula (J), (I), (Ia), and/or (Ib), or pharmaceutically acceptable salt thereof, is a compound, or pharmaceutically acceptable salt thereof, wherein each $R^1$ is independently $C_1$-$C_6$ alkyl, $C_1$-$C_6$ alkoxy, $C_1$-$C_6$ hydroxyalkyl, halogen, $C_1$-$C_6$ haloalkyl, $C_1$-$C_6$ haloalkoxy, OH, $C_3$-$C_8$ cycloalkyl, ($C_1$-$C_3$ alkyl)($C_3$-$C_8$ cycloalkyl), —O—($C_3$-$C_8$ cycloalkyl), $C_6$-$C_{10}$ aryl, or heteroaryl, wherein each alkyl is substituted with 0 or 1 $R^{1c}$, and each alkoxy and alkynyl is substituted with 0 or 1 $R^{1d}$; or alternatively, two $R^1$ on adjacent carbons together with the atoms to which they are attached combine to form a $C_5$-$C_8$ cycloalkyl or a heterocycloalkyl.

In some embodiments, a compound of Formula (J), (I), (Ia), and/or (Ib), or pharmaceutically acceptable salt thereof, is a compound, or pharmaceutically acceptable salt thereof, wherein each $R^{1a}$ and $R^{1b}$ is independently hydrogen or $C_1$-$C_4$ alkyl.

In some embodiments, a compound of Formula (J), (I), (Ia), and/or (Ib), or pharmaceutically acceptable salt thereof, is a compound wherein each $R^{1c}$ is halogen, —$NR^{11}R^{1c2}$, OH, or —CN.

In some embodiments, a compound of Formula (J), (I), (Ia), and/or (Ib), or pharmaceutically acceptable salt thereof, is a compound, or pharmaceutically acceptable salt thereof, wherein each $R^{1d}$ is independently heteroaryl.

In some embodiments, a compound of Formula (J), (I), (Ia), and/or (Ib), or pharmaceutically acceptable salt thereof, is a compound, or pharmaceutically acceptable salt thereof, wherein each $R^1$ is independently $C_1$-$C_4$ alkyl, $C_1$-$C_4$ alkoxy, halogen, $C_1$-$C_4$ haloalkyl, or —CN.

In some embodiments, a compound of Formula (J), (I), (Ia), and/or (Ib), or pharmaceutically acceptable salt thereof, is a compound, or pharmaceutically acceptable salt thereof, wherein each $R^1$ is independently $CH_3$, $CH_2CH_3$, —C($CH_3$)$_3$, $OCH_3$, —$OCH(CH_3)_2$, $OCH_2$-pyridyl, $C(CH_3)_2OH$, F, Cl, Br, $CF_3$, $OCHF_2$, $OCF_3$, $OCH_2CF_3$, OH, cyclopropyl, cyclopropyloxy, cyclobutyloxy, phenyl, pyrazolyl, or

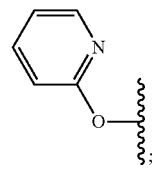 [SMILES: *Oc1ccccn1]

or alternatively, two $R^1$ on adjacent carbons together with the atoms to which they are attached combine to form a cyclopentyl, cyclohexyl, dihydrofuran, tetrahydrofuran, methyltetrahydrofuran, 1,3-dioxole, dihydro-1,3-oxazine, difluorodihydrofuran, or methyldihydrofuran. In some embodiments, two $R^1$ on adjacent carbon atoms combine to form:

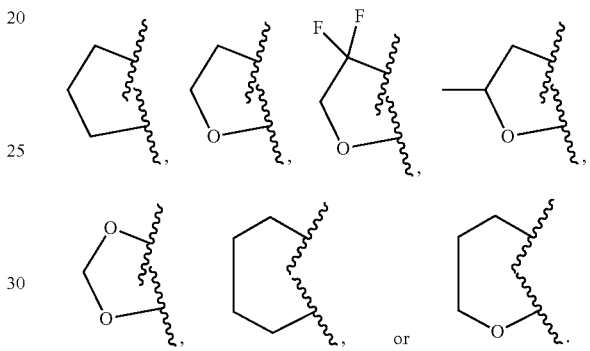

In some embodiments, a compound of Formula (J), (I), (Ia), and/or (Ib), or pharmaceutically acceptable salt thereof, is a compound, or pharmaceutically acceptable salt thereof, wherein L is —$CH_2$—, —O—, or —$CH_2O$—.

In some embodiments, a compound of Formula (J), (I), (Ia), and/or (Ib), or pharmaceutically acceptable salt thereof, is a compound, or pharmaceutically acceptable salt thereof, wherein L is —$CH_2$—.

In some embodiments, a compound of Formula (J), (I), (Ia), and/or (Ib), or pharmaceutically acceptable salt thereof, is a compound, or pharmaceutically acceptable salt thereof, wherein $R^2$ is pyrrolyl, furyl, thienyl, pyrazolyl, isoxazolyl, oxazolyl, isothiazolyl, thiazolyl, triazolyl, oxadiazolyl, thiadiazolyl, pyridyl, pyridazinyl, pyrimidyl, or pyrazinyl, which are each substituted by 0, 1, or 2 $R^{2a}$.

In some embodiments, a compound of Formula (J), (I), (Ia), and/or (Ib), or pharmaceutically acceptable salt thereof, is a compound, or pharmaceutically acceptable salt thereof, wherein each $R^{2a}$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, OH, or —CN.

In some embodiments, a compound of Formula (J), (I), (Ia), and/or (Ib), or pharmaceutically acceptable salt thereof, is a compound, or pharmaceutically acceptable salt thereof, wherein each $R^{2b}$ and $R^{2c}$ is independently hydrogen or $C_1$-$C_4$ alkyl.

In some embodiments, a compound of Formula (J), (I), (Ia), and/or (Ib), or pharmaceutically acceptable salt thereof, is a compound, or pharmaceutically acceptable salt thereof, wherein $R^2$ is

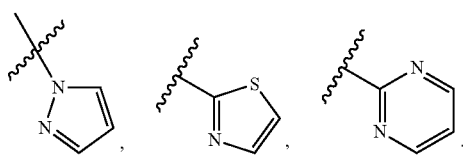

In some embodiments, a compound of Formula (J), (I), (Ia), and/or (Ib), or pharmaceutically acceptable salt thereof, is a compound, or pharmaceutically acceptable salt thereof, wherein $R^2$ is

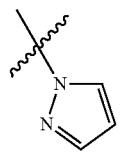

In some embodiments, a compound of Formula (J), (I), (Ia), and/or (Ib), or pharmaceutically acceptable salt thereof, is a compound, or pharmaceutically acceptable salt thereof, wherein each $R^3$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —S(O)$_2$$R^{3a}$, —S(O)$_2$N($R^{3a}$)($R^{3b}$), OH, —CN, $C_3$-$C_8$ cycloalkyl, or heterocycloalkyl.

In some embodiments, a compound of Formula (J), (I), (Ia), and/or (Ib), or pharmaceutically acceptable salt thereof, is a compound, or pharmaceutically acceptable salt thereof, wherein two $R^3$ on the same carbon atom together represent an oxo group.

In some embodiments, a compound of Formula (J), (I), (Ia), and/or (Ib), or pharmaceutically acceptable salt thereof, is a compound, or pharmaceutically acceptable salt thereof, wherein each $R^{3a}$ and $R^{3b}$ is independently hydrogen or $C_1$-$C_4$ alkyl.

In some embodiments, a compound of Formula (J), (I), (Ia), and/or (Ib), or pharmaceutically acceptable salt thereof, is a compound, or pharmaceutically acceptable salt thereof, wherein each $R^{3c}$ is halogen, —N$R^{3c1}R^{3c2}$, OH, or —CN.

In some embodiments, a compound of Formula (J), (I), (Ia), and/or (Ib), or pharmaceutically acceptable salt thereof, is a compound, or pharmaceutically acceptable salt thereof, wherein each $R^{3d}$ is independently heteroaryl.

In some embodiments, a compound of Formula (J), (I), (Ia), and/or (Ib), or pharmaceutically acceptable salt thereof, is a compound, or pharmaceutically acceptable salt thereof, wherein each $R^{3e}$ is independently $C_1$-$C_4$ alkyl, $C_1$-$C_4$ alkoxy, halogen, or $C_1$-$C_4$ haloalkyl.

In some embodiments, a compound of Formula (J), (I), (Ia), and/or (Ib), or pharmaceutically acceptable salt thereof, is a compound, or pharmaceutically acceptable salt thereof, wherein each $R^3$ is independently $C_1$-$C_6$ alkyl, $C_1$-$C_6$ alkoxy, halogen, $C_1$-$C_6$ haloalkyl, $C_1$-$C_6$ haloalkoxy, —CN, or $C_3$-$C_8$ cycloalkyl.

In some embodiments, a compound of Formula (J), (I), (Ia), and/or (Ib), or pharmaceutically acceptable salt thereof, is a compound, or pharmaceutically acceptable salt thereof, wherein each $R^3$ is independently $C_1$-$C_4$ alkyl, $C_1$-$C_4$ alkoxy, halogen, $C_1$-$C_4$ haloalkyl, $C_1$-$C_4$ haloalkoxy, —CN, or $C_3$-$C_6$ cycloalkyl.

In some embodiments, a compound of Formula (J), (I), (Ia), and/or (Ib), or pharmaceutically acceptable salt thereof, is a compound, or pharmaceutically acceptable salt thereof, wherein each $R^3$ is independently Me, OMe, OEt, CHF$_2$, CF$_3$, OCHF$_2$, OCF$_3$, F, Br, CN, or cyclopropyl.

In some embodiments, a compound of Formula (J), (I), (Ia), and/or (Ib), or pharmaceutically acceptable salt thereof, is a compound, or pharmaceutically acceptable salt thereof, wherein subscript q is 1, 2, or 3.

In some embodiments, a compound of Formula (J), (I), (Ia), and/or (Ib), or pharmaceutically acceptable salt thereof, is a compound, or pharmaceutically acceptable salt thereof, wherein subscript n is 1 or 2.

In some embodiments, a compound of Formula (J), (I), (Ia), and/or (Ib), or pharmaceutically acceptable salt thereof, is a compound having the structure of a compound shown in Table 1, or pharmaceutically acceptable salt thereof.

TABLE 1

Compounds

| No. | Structure | Name |
|---|---|---|
| 1 | 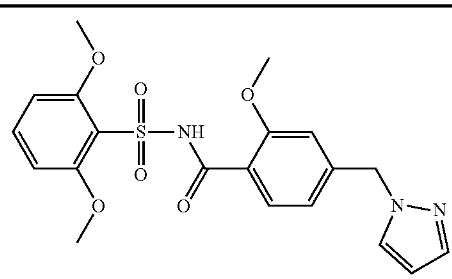 | 4-((1H-pyrazol-1-yl)methyl)-N-((2,6-dimethoxyphenyl)sulfonyl)-2-methoxybenzamide |
| 2 | 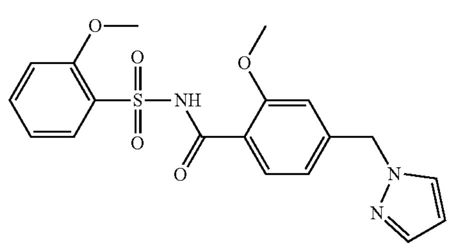 [SMILES: COc1cc(Cn2cccn2)ccc1C(=O)NS(=O)(=O)c1ccccc1OC] | 4-((1H-pyrazol-1-yl)methyl)-2-methoxy-N-((2-methoxyphenyl)sulfonyl)benzamide |

TABLE 1-continued

| No. | Structure | Name |
|---|---|---|
| 3 | 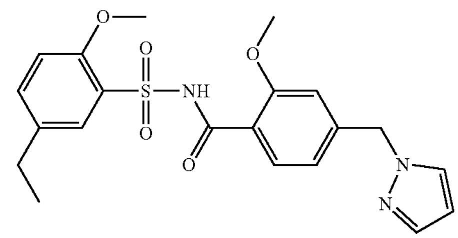 [SMILES: CCc1ccc(OC)c(S(=O)(=O)NC(=O)c2ccc(Cn3cccn3)cc2OC)c1] | 4-((1H-pyrazol-1-yl)methyl)-N-((5-ethyl-2-methoxyphenyl)sulfonyl)-2-methoxybenzamide |
| 4 | 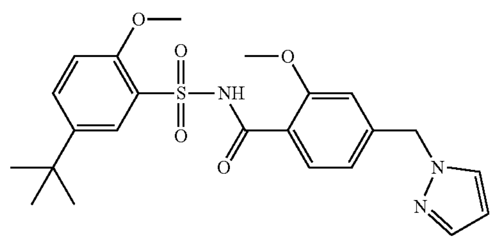 [SMILES: COc1cc(Cn2cccn2)ccc1C(=O)NS(=O)(=O)c1cc(C(C)(C)C)ccc1OC] | 4-(1H-pyrazol-1-yl)methyl)-N-(5-(tert-butyl)-2-methoxyphenyl)sulfonyl)-2-methoxybenzamide |
| 5 | 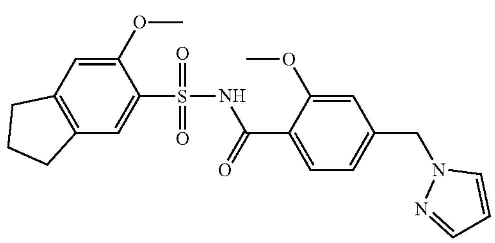 [SMILES: COc1cc(Cn2cccn2)ccc1C(=O)NS(=O)(=O)c1cc2c(cc1OC)CCC2] | 4-((1H-pyrazol-1-yl)methyl)-2-methoxy-N-((6-methoxy-2,3-dihydro-1H-inden-5-yl)sulfonyl)benzamide |
| 6 | 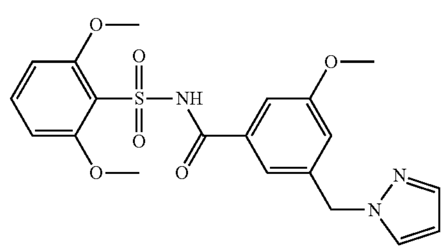 [SMILES: COc1cc(Cn2cccn2)cc(C(=O)NS(=O)(=O)c2c(OC)cccc2OC)c1] | 3-((1H-pyrazol-1-yl)methyl)-N-((2,6-dimethoxyphenyl)sulfonyl)-5-methoxybenzamide |
| 7 | 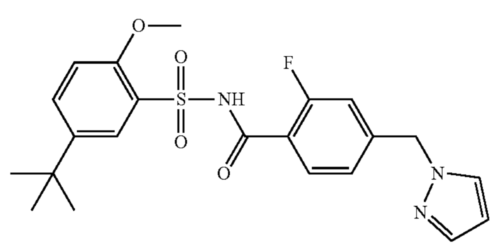 [SMILES: COc1ccc(C(C)(C)C)cc1S(=O)(=O)NC(=O)c1ccc(Cn2cccn2)cc1F] | 4-((1H-pyrazol-1-yl)methyl)-N-((5-(tert-butyl)-2-methoxyphenyl)sulfonyl)-2-fluorobenzamide |
| 8 | 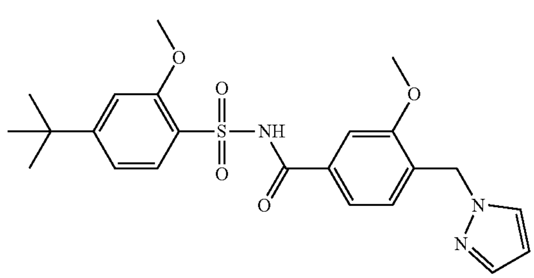 [SMILES: COc1cc(C(=O)NS(=O)(=O)c2ccc(C(C)(C)C)cc2OC)ccc1Cn1cccn1] | 4-((1H-pyrazol-1-yl)methyl)-N-((4-(tert-butyl)-2-methoxyphenyl)sulfonyl)-3-methoxybenzamide |

TABLE 1-continued

| No. | Structure | Name |
|---|---|---|
| 9 | 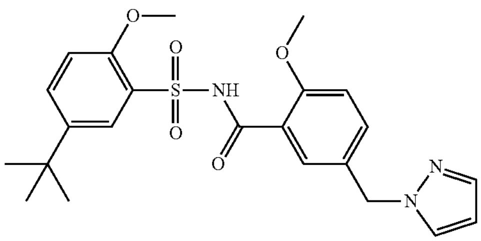 [SMILES: COc1ccc(Cn2cccn2)cc1C(=O)NS(=O)(=O)c1cc(C(C)(C)C)ccc1OC] | 5-((1H-pyrazol-1-yl)methyl)-N-((5-(tert-butyl)-2-methoxyphenyl)sulfonyl)-2-methoxybenzamide |
| 10 | 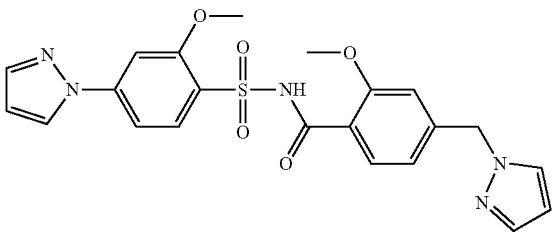 [SMILES: COc1cc(Cn2cccn2)ccc1C(=O)NS(=O)(=O)c1ccc(-n2cccn2)cc1OC] | 4-((1H-pyrazol-1-yl)methyl)-2-methoxy-N-((2-methoxy-4-(1H-pyrazol-1-yl)phenyl)sulfonyl)benzamide |
| 11 | 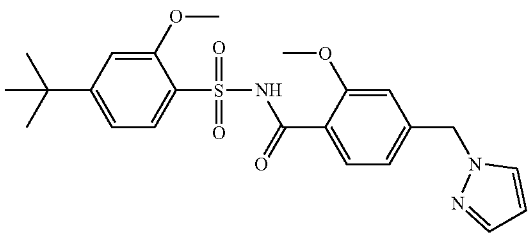 [SMILES: COc1cc(Cn2cccn2)ccc1C(=O)NS(=O)(=O)c1ccc(C(C)(C)C)cc1OC] | 4-((1H-pyrazol-1-yl)methyl)-N-((4-(tert-butyl)-2-methoxyphenyl)sulfonyl)-2-methoxybenzamide |
| 12 | 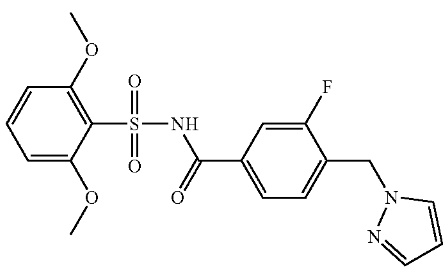 [SMILES: COc1cccc(OC)c1S(=O)(=O)NC(=O)c1ccc(Cn2cccn2)c(F)c1] | 4-((1H-pyrazol-1-yl)methyl)-N-((2,6-dimethoxyphenyl)sulfonyl)-3-fluorobenzamide |
| 13 | 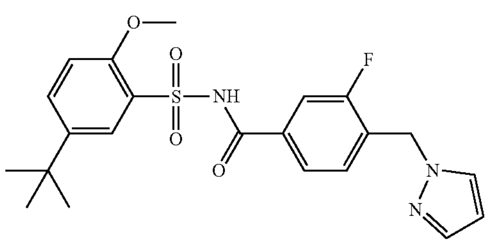 [SMILES: COc1ccc(C(C)(C)C)cc1S(=O)(=O)NC(=O)c1ccc(Cn2cccn2)c(F)c1] | 4-((1H-pyrazol-1-yl)methyl)-N-((5-(tert-butyl)-2-methoxyphenyl)sulfonyl)-3-fluorobenzamide |
| 14 | 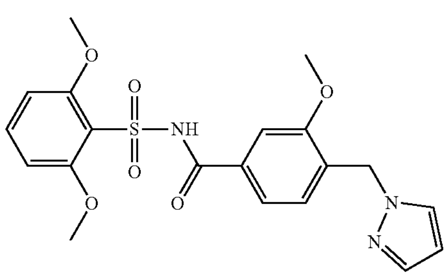 [SMILES: COc1cc(C(=O)NS(=O)(=O)c2c(OC)cccc2OC)ccc1Cn1cccn1] | 4-(1H-pyrazol-1-yl)methyl)-N-((2,6-dimethoxyphenyl)sulfonyl)-3-methoxybenzamide |

TABLE 1-continued

| No. | Structure | Name |
|---|---|---|
| 15 | 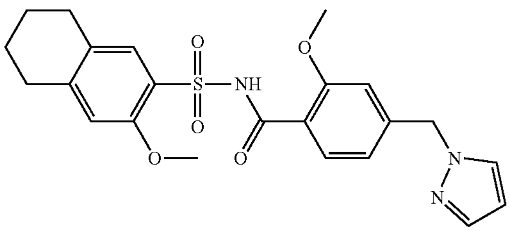 [SMILES: COc1cc(Cn2cccn2)ccc1C(=O)NS(=O)(=O)c1cc2c(cc1OC)CCCC2] | 4-((1H-pyrazol-1-yl)methyl)-2-methoxy-N-((3-methoxy-5,6,7,8-tetrahydronaphthalen-2-yl)sulfonyl)benzamide |
| 16 | 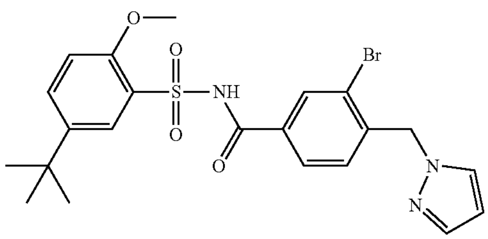 | 4-((1H-pyrazol-1-yl)methyl)-3-bromo-N-((5-(tert-butyl)-2-methoxyphenyl)sulfonyl)benzamide |
| 17 | 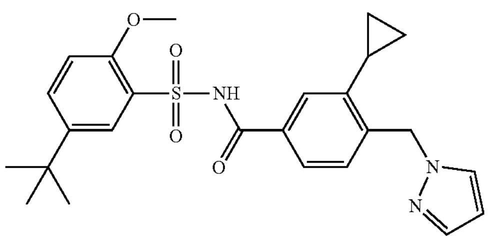 [SMILES: COc1ccc(C(C)(C)C)cc1S(=O)(=O)NC(=O)c1ccc(Cn2cccn2)c(C2CC2)c1] | 4-((1H-pyrazol-1-yl)methyl)-N-((5-(tert-butyl)-2-methoxyphenyl)sulfonyl)-3-cyclopropylbenzamide |
| 18 | 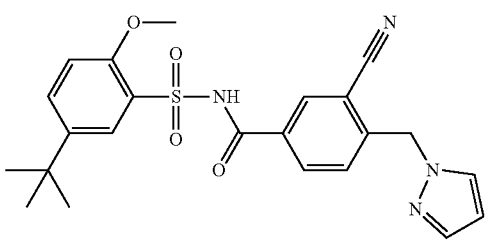 [SMILES: COc1ccc(C(C)(C)C)cc1S(=O)(=O)NC(=O)c1ccc(Cn2cccn2)c(C#N)c1] | 4-(1H-pyrazol-1-yl)methyl)-N-(5-(tert-butyl)-2-methoxyphenyl)sulfonyl)-3-cyanobenzamide |
| 19 | 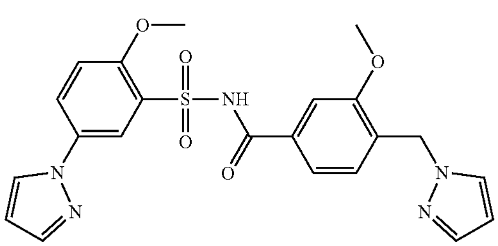 | 4-((1H-pyrazol-1-yl)methyl)-3-methoxy-N-((2-methoxy-5-(1H-pyrazol-1-yl)phenyl)sulfonyl)benzamide |
| 20 | 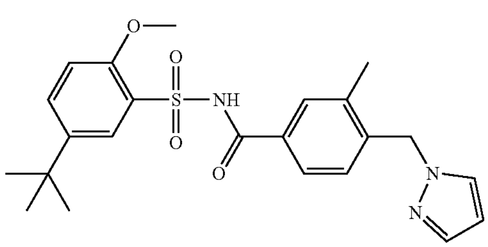 [SMILES: COc1ccc(C(C)(C)C)cc1S(=O)(=O)NC(=O)c1ccc(Cn2cccn2)c(C)c1] | 4-((1H-pyrazol-1-yl)methyl)-N-((5-(tert-butyl)-2-methoxyphenyl)sulfonyl)-3-methylbenzamide |

TABLE 1-continued

| No. | Structure | Name |
|---|---|---|
| 21 | 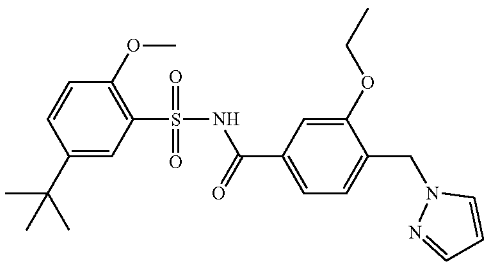 [SMILES: CCOc1cc(C(=O)NS(=O)(=O)c2cc(C(C)(C)C)ccc2OC)ccc1Cn1cccn1] | 4-((1H-pyrazol-1-yl)methyl)-N-((5-(tert-butyl)-2-methoxyphenyl)sulfonyl)-3-ethoxybenzamide |
| 22 | 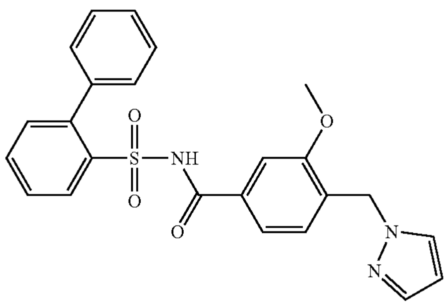 [SMILES: COc1cc(C(=O)NS(=O)(=O)c2ccccc2-c2ccccc2)ccc1Cn1cccn1] | 4-((1H-pyrazol-1-yl)methyl)-N-([1,1'-biphenyl]-2-ylsulfonyl)-3-methoxybenzamide |
| 23 | 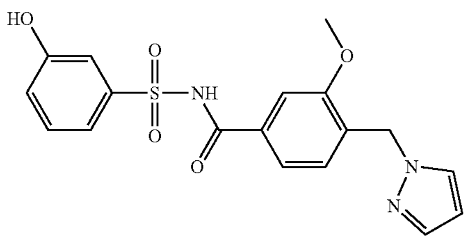 [SMILES: COc1cc(C(=O)NS(=O)(=O)c2cccc(O)c2)ccc1Cn1cccn1] | 4-((1H-pyrazol-1-yl)methyl)-N-((3-hydroxyphenyl)sulfonyl)-3-methoxybenzamide |
| 24 | 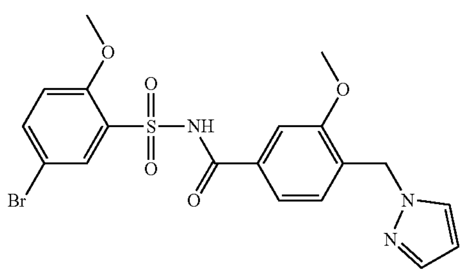 [SMILES: COc1cc(C(=O)NS(=O)(=O)c2cc(Br)ccc2OC)ccc1Cn1cccn1] | 4-((1H-pyrazol-1-yl)methyl)-N-((5-bromo-2-methoxyphenyl)sulfonyl)-3-methoxybenzamide |
| 25 | 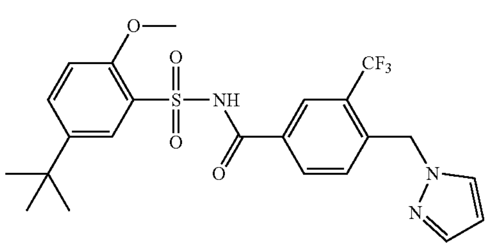 [SMILES: COc1ccc(C(C)(C)C)cc1S(=O)(=O)NC(=O)c1ccc(Cn2cccn2)c(C(F)(F)F)c1] | 4-((1H-pyrazol-1-yl)methyl)-N-((5-(tert-butyl)-2-methoxyphenyl)sulfonyl)-3-(trifluoromethyl)benzamide |

TABLE 1-continued

| No. | Structure | Name |
|---|---|---|
| 26 | 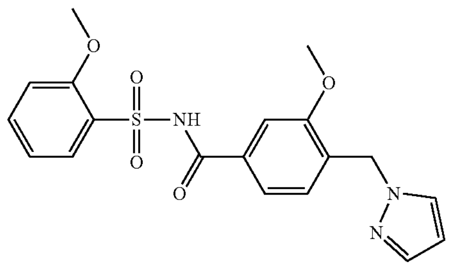 [SMILES: COc1cc(C(=O)NS(=O)(=O)c2ccccc2OC)ccc1Cn1cccn1] | 4-((1H-pyrazol-1-yl)methyl)-3-methoxy-N-((2-methoxyphenyl)sulfonyl)benzamide |
| 27 | 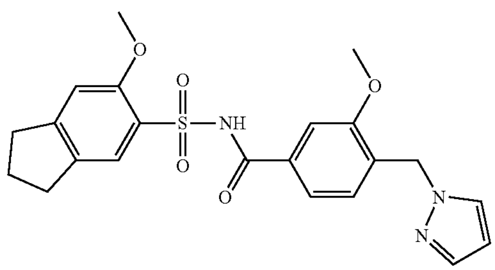 [SMILES: COc1cc(C(=O)NS(=O)(=O)c2cc3c(cc2OC)CCC3)ccc1Cn1cccn1] | 4-((1H-pyrazol-1-yl)methyl)-3-methoxy-N-((6-methoxy-2,3-dihydro-1H-inden-5-yl)sulfonyl)benzamide |
| 28 | 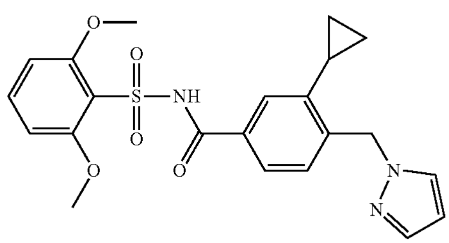 [SMILES: COc1cccc(OC)c1S(=O)(=O)NC(=O)c1ccc(Cn2cccn2)c(C2CC2)c1] | 4-((1H-pyrazol-1-yl)methyl)-3-cyclopropyl-N-((2,6-dimethoxyphenyl)sulfonyl)benzamide |
| 29 | 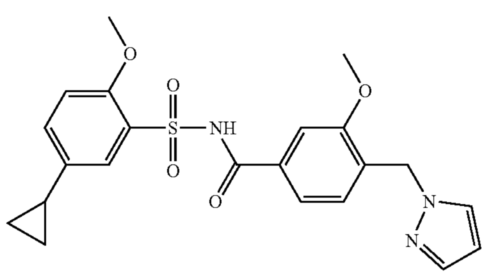 | 4-((1H-pyrazol-1-yl)methyl)-N-((5-cyclopropyl-2-methoxyphenyl)sulfonyl)-3-methoxybenzamide |
| 30 | 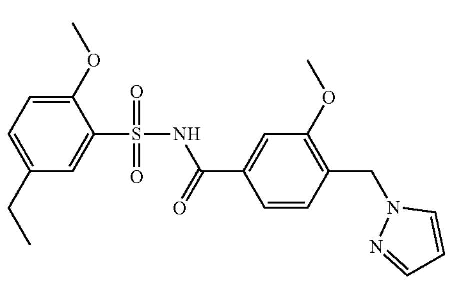 [SMILES: CCc1ccc(OC)c(S(=O)(=O)NC(=O)c2ccc(Cn3cccn3)c(OC)c2)c1] | 4-((1H-pyrazol-1-yl)methyl)-N-((5-ethyl-2-methoxyphenyl)sulfonyl)-3-methoxybenzamide |

TABLE 1-continued

| No. | Structure | Name |
|---|---|---|
| 31 | 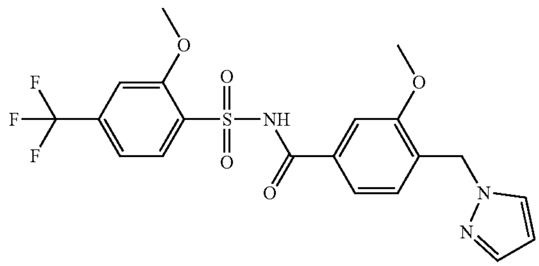 [SMILES: COc1cc(C(=O)NS(=O)(=O)c2ccc(C(F)(F)F)cc2OC)ccc1Cn1cccn1] | 4-((1H-pyrazol-1-yl)methyl)-3-methoxy-N-((2-methoxy-4-(trifluoromethyl)phenyl)sulfonyl)benzamide |
| 32 | 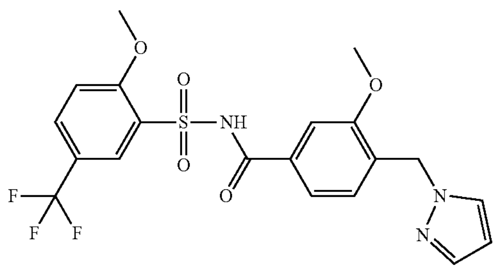 [SMILES: COc1cc(C(=O)NS(=O)(=O)c2cc(C(F)(F)F)ccc2OC)ccc1Cn1cccn1] | 4-((1H-pyrazol-1-yl)methyl)-3-methoxy-N-((2-methoxy-5-(trifluoromethyl)phenyl)sulfonyl)benzamide |
| 33 | 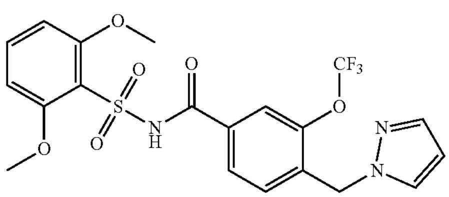 [SMILES: COc1cccc(OC)c1S(=O)(=O)NC(=O)c1ccc(Cn2cccn2)c(OC(F)(F)F)c1] | 4-((1H-pyrazol-1-yl)methyl)-N-((2,6-dimethoxyphenyl)sulfonyl)-3-(trifluoromethoxy)benzamide |
| 34 | 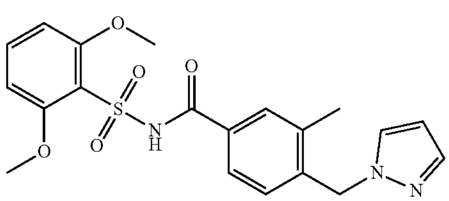 [SMILES: COc1cccc(OC)c1S(=O)(=O)NC(=O)c1ccc(Cn2cccn2)c(C)c1] | 4-((1H-pyrazol-1-yl)methyl)-N-((2,6-dimethoxyphenyl)sulfonyl)-3-methylbenzamide |
| 35 | 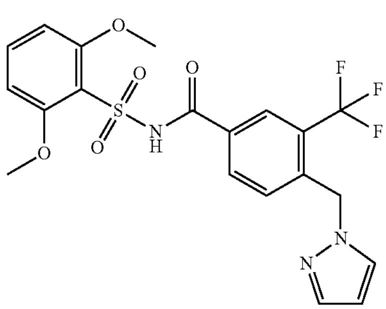 [SMILES: COc1cccc(OC)c1S(=O)(=O)NC(=O)c1ccc(Cn2cccn2)c(C(F)(F)F)c1] | 4-(1H-pyrazol-1-yl)methyl)-N-(2,6-dimethoxyphenyl)sulfonyl)-3-(trifluoromethyl)benzamide |
| 36 | 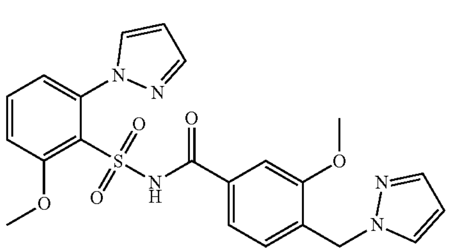 [SMILES: COc1cc(C(=O)NS(=O)(=O)c2c(OC)cccc2-n2cccn2)ccc1Cn1cccn1] | 4-((1H-pyrazol-1-yl)methyl)-3-methoxy-N-((2-methoxy-6-(1H-pyrazol-1-yl)phenyl)sulfonyl)benzamide |

TABLE 1-continued

| No. | Structure | Name |
|---|---|---|
| 37 | 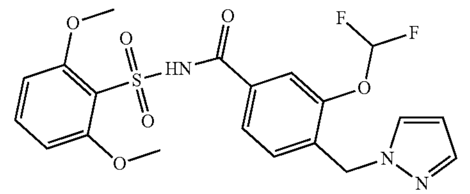 [SMILES: COc1cccc(OC)c1S(=O)(=O)NC(=O)c1ccc(Cn2cccn2)c(OC(F)F)c1] | 4-((1H-pyrazol-1-yl)methyl)-3-(difluoromethoxy)-N-((2,6-dimethoxyphenyl)sulfonyl)benzamide |
| 38 | 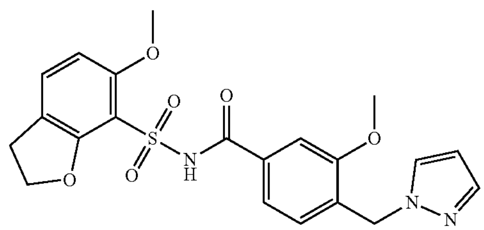 [SMILES: COc1cc(C(=O)NS(=O)(=O)c2c(OC)ccc3c2OCC3)ccc1Cn1cccn1] | 4-((1H-pyrazol-1-yl)methyl)-3-methoxy-N-((6-methoxy-2,3-dihydrobenzofuran-7-yl)sulfonyl)benzamide |
| 39 | 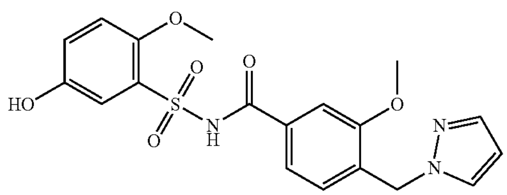 [SMILES: COc1cc(C(=O)NS(=O)(=O)c2cc(O)ccc2OC)ccc1Cn1cccn1] | 4-((1H-pyrazol-1-yl)methyl)-N-((5-hydroxy-2-methoxyphenyl)sulfonyl)-3-methoxybenzamide |
| 40 | 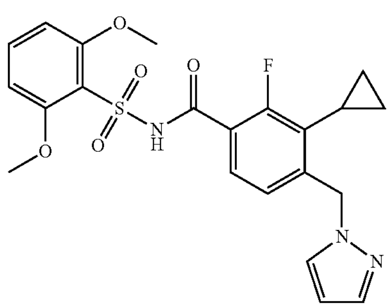 [SMILES: COc1cccc(OC)c1S(=O)(=O)NC(=O)c1ccc(Cn2cccn2)c(C2CC2)c1F] | 4-((1H-pyrazol-1-yl)methyl)-3-cyclopropyl-N-((2,6-dimethoxyphenyl)sulfonyl)-2-fluorobenzamide |
| 41 | 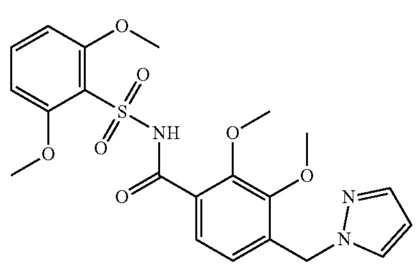 [SMILES: COc1cccc(OC)c1S(=O)(=O)NC(=O)c1ccc(Cn2cccn2)c(OC)c1OC] | 4-((1H-pyrazol-1-yl)methyl)-N-((2,6-dimethoxyphenyl)sulfonyl)-2,3-dimethoxybenzamide |
| 42 | 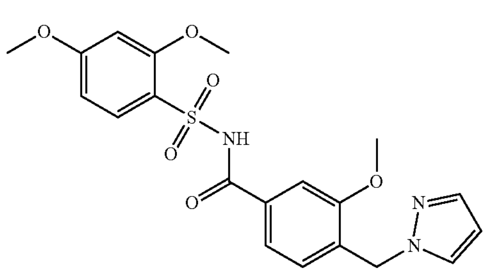 [SMILES: COc1ccc(S(=O)(=O)NC(=O)c2ccc(Cn3cccn3)c(OC)c2)c(OC)c1] | 4-((1H-pyrazol-1-yl)methyl)-N-((2,4-dimethoxyphenyl)sulfonyl)-3-methoxybenzamide |

TABLE 1-continued

| No. | Structure | Name |
|-----|-----------|------|
| 43 | 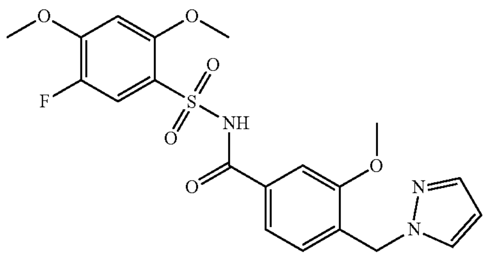 [SMILES: COc1cc(OC)c(S(=O)(=O)NC(=O)c2ccc(Cn3cccn3)c(OC)c2)cc1F] | 4-((1H-pyrazol-1-yl)methyl)-N-((5-fluoro-2,4-dimethoxyphenyl)sulfonyl)-3-methoxybenzamide |
| 44 | 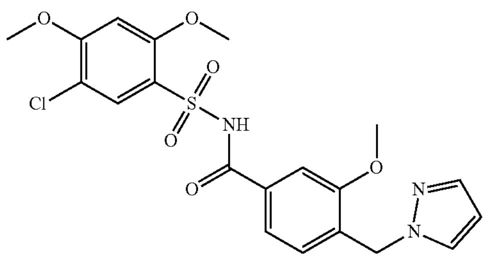 [SMILES: COc1cc(OC)c(S(=O)(=O)NC(=O)c2ccc(Cn3cccn3)c(OC)c2)cc1Cl] | 4-((1H-pyrazol-1-yl)methyl)-N-((5-chloro-2,4-dimethoxyphenyl)sulfonyl)-3-methoxybenzamide |
| 45 | 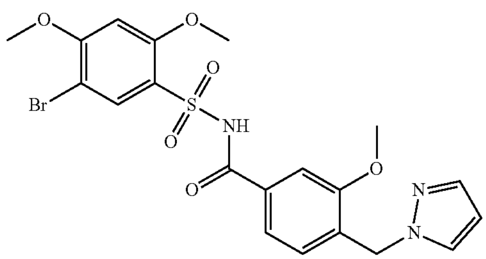 [SMILES: COc1cc(OC)c(S(=O)(=O)NC(=O)c2ccc(Cn3cccn3)c(OC)c2)cc1Br] | 4-((1H-pyrazol-1-yl)methyl)-N-((5-bromo-2,4-dimethoxyphenyl)sulfonyl)-3-methoxybenzamide |
| 46 | 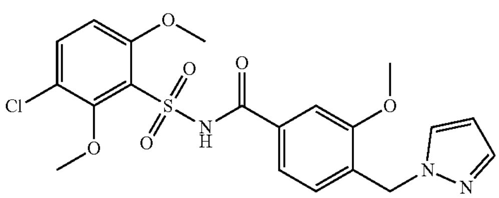 [SMILES: COc1cc(C(=O)NS(=O)(=O)c2c(OC)ccc(Cl)c2OC)ccc1Cn1cccn1] | 4-((1H-pyrazol-1-yl)methyl)-N-((3-chloro-2,6-dimethoxyphenyl)sulfonyl)-3-methoxybenzamide |
| 47 | 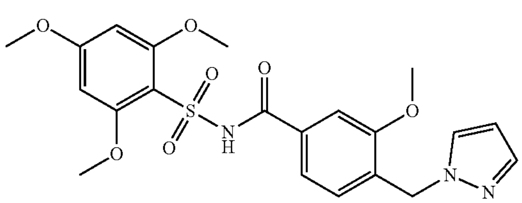 [SMILES: COc1cc(OC)c(S(=O)(=O)NC(=O)c2ccc(Cn3cccn3)c(OC)c2)c(OC)c1] | 4-((1H-pyrazol-1-yl)methyl)-3-methoxy-N-((2,4,6-trimethoxyphenyl)sulfonyl)benzamide |
| 48 | 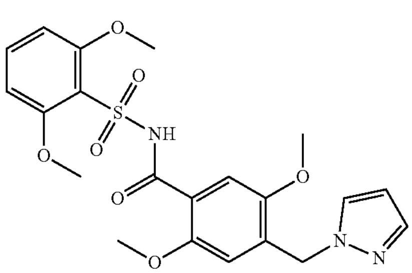 [SMILES: COc1cc(C(=O)NS(=O)(=O)c2c(OC)cccc2OC)c(OC)cc1Cn1cccn1] | 4-((1H-pyrazol-1-yl)methyl)-N-((2,6-dimethoxyphenyl)sulfonyl)-2,5-dimethoxybenzamide |

TABLE 1-continued

| No. | Structure | Name |
|---|---|---|
| 49 | 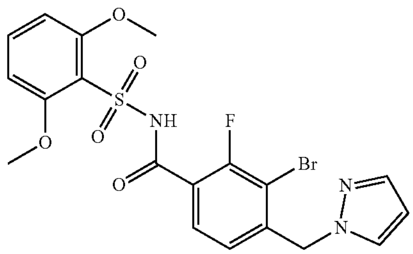 [SMILES: COc1cccc(OC)c1S(=O)(=O)NC(=O)c1ccc(Cn2cccn2)c(Br)c1F] | 4-((1H-pyrazol-1-yl)methyl)-3-bromo-N-((2,6-dimethoxyphenyl)sulfonyl)-2-fluorobenzamide |
| 50 | 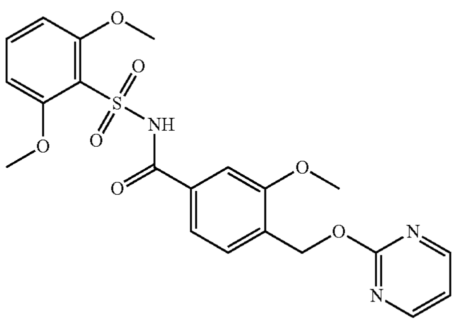 [SMILES: COc1cc(C(=O)NS(=O)(=O)c2c(OC)cccc2OC)ccc1COc1ncccn1] | N-((2,6-dimethoxyphenyl)sulfonyl)-3-methoxy-4-((pyrimidin-2-yloxy)methyl)benzamide |
| 51 | 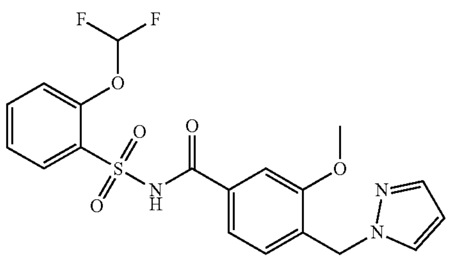 [SMILES: COc1cc(C(=O)NS(=O)(=O)c2ccccc2OC(F)F)ccc1Cn1cccn1] | 4-((1H-pyrazol-1-yl)methyl)-N-((2-(difluoromethoxy)phenyl)sulfonyl)-3-methoxybenzamide |
| 52 | 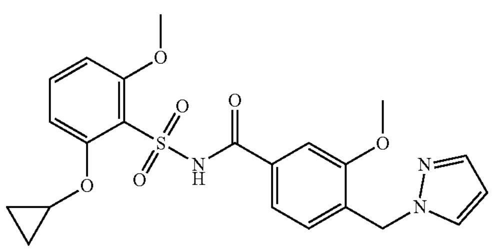 [SMILES: COc1cc(C(=O)NS(=O)(=O)c2c(OC)cccc2OC2CC2)ccc1Cn1cccn1] | 4-((1H-pyrazol-1-yl)methyl)-N-((2-cyclopropoxy-6-methoxyphenyl)sulfonyl)-3-methoxybenzamide |
| 53 | 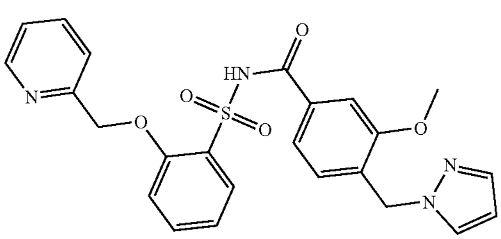 [SMILES: COc1cc(C(=O)NS(=O)(=O)c2ccccc2OCc2ccccn2)ccc1Cn1cccn1] | 4-((1H-pyrazol-1-yl)methyl)-3-methoxy-N-((2-(pyridin-2-ylmethoxy)phenyl)sulfonyl)benzamide |
| 54 | 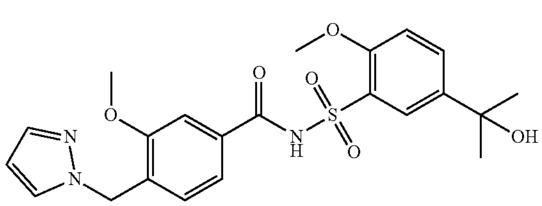 [SMILES: COc1cc(C(=O)NS(=O)(=O)c2cc(C(C)(C)O)ccc2OC)ccc1Cn1cccn1] | 4-((1H-pyrazol-1-yl)methyl)-N-((5-(2-hydroxypropan-2-yl)-2-methoxyphenyl)sulfonyl)-3-methoxybenzamide |

TABLE 1-continued

Compounds

| No. | Structure | Name |
|---|---|---|
| 55 | 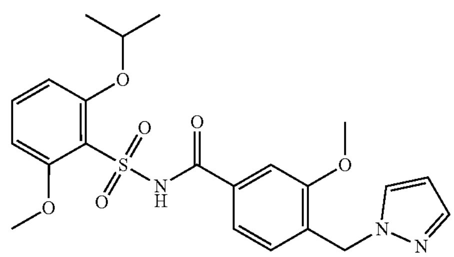 [SMILES: COc1cc(C(=O)NS(=O)(=O)c2c(OC)cccc2OC(C)C)ccc1Cn1cccn1] | 4-((1H-pyrazol-1-yl)methyl)-N-((2-isopropoxy-6-methoxyphenyl)sulfonyl)-3-methoxybenzamide |
| 56 | 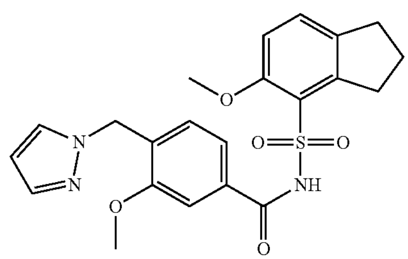 | 4-((1H-pyrazol-1-yl)methyl)-3-methoxy-N-((5-methoxy-2,3-dihydro-1H-inden-4-yl)sulfonyl)benzamide |
| 57 | 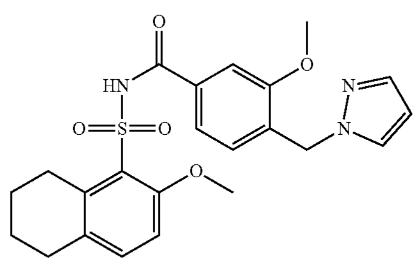 [SMILES: COc1cc(C(=O)NS(=O)(=O)c2c(OC)ccc3c2CCCC3)ccc1Cn1cccn1] | 4-((1H-pyrazol-1-yl)methyl)-3-methoxy-N-((2-methoxy-5,6,7,8-tetrahydronaphthalen-1-yl)sulfonyl)benzamide |
| 58 | 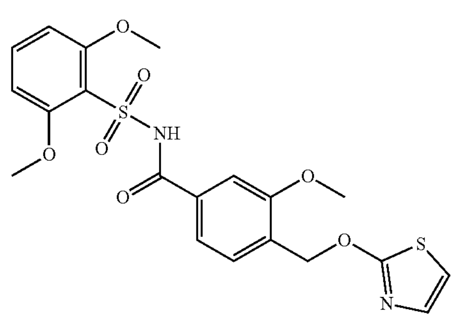 [SMILES: COc1cc(C(=O)NS(=O)(=O)c2c(OC)cccc2OC)ccc1COc1nccs1] | N-((2,6-dimethoxyphenyl)sulfonyl)-3-methoxy-4-((thiazol-2-yloxy)methyl)benzamide |
| 59 | 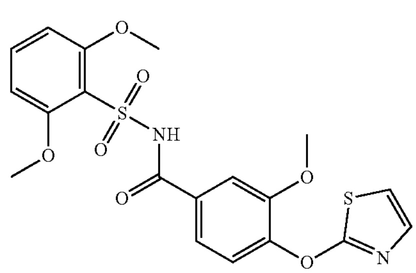 [SMILES: COc1cc(C(=O)NS(=O)(=O)c2c(OC)cccc2OC)ccc1Oc1nccs1] | N-((2,6-dimethoxyphenyl)sulfonyl)-3-methoxy-4-(thiazol-2-yloxy)benzamide |

TABLE 1-continued

| No. | Name |
|---|---|
| 60 | 4-((1H-pyrazol-1-yl)methyl)-N-((2,6-dimethoxy-3-methylphenyl)sulfonyl)-3-methoxybenzamide |
| 61 | 4-((1H-pyrazol-1-yl)methyl)-N-((3-cyclopropyl-2,6-dimethoxyphenyl)sulfonyl)-3-methoxybenzamide |
| 62 | 4-((1H-pyrazol-1-yl)methyl)-N-((2-cyclopropoxyphenyl)sulfonyl)-3-methoxybenzamide |
| 63 | 4-((1H-pyrazol-1-yl)methyl)-N-((5-chloro-2,3-dihydrobenzofuran-7-yl)sulfonyl)-3-methoxybenzamide |
| 64 | 4-((1H-pyrazol-1-yl)methyl)-N-((2,3-dihydrobenzofuran-5-yl)sulfonyl)-3-methoxybenzamide |
| 65 | 4-((1H-pyrazol-1-yl)methyl)-N-((3-chloro-4-methoxyphenyl)sulfonyl)-3-methoxybenzamide |
| 66 | 4-((1H-pyrazol-1-yl)methyl)-N-((3-ethyl-2,6-dimethoxyphenyl)sulfonyl)-3-methoxybenzamide |

TABLE 1-continued

| No. | Structure | Name |
|---|---|---|
| 67 | 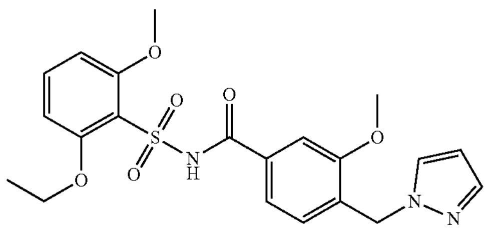 [SMILES: CCOc1cccc(OC)c1S(=O)(=O)NC(=O)c1ccc(Cn2cccn2)c(OC)c1] | 4-((1H-pyrazol-1-yl)methyl)-N-((2-ethoxy-6-methoxyphenyl)sulfonyl)-3-methoxybenzamide |
| 68 | 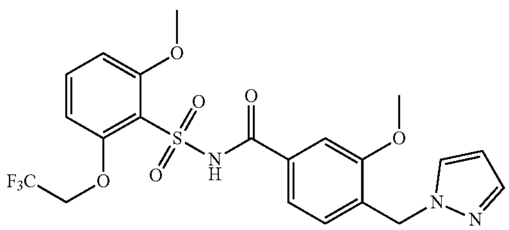 [SMILES: COc1cc(C(=O)NS(=O)(=O)c2c(OC)cccc2OCC(F)(F)F)ccc1Cn1cccn1] | 4-((1H-pyrazol-1-yl)methyl)-3-methoxy-N-((2-methoxy-6-(2,2,2-trifluoroethoxy)phenyl)sulfonyl)benzamide |
| 69 | 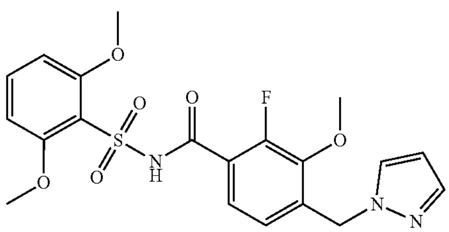 [SMILES: COc1cccc(OC)c1S(=O)(=O)NC(=O)c1ccc(Cn2cccn2)c(OC)c1F] | 4-((1H-pyrazol-1-yl)methyl)-N-((2,6-dimethoxyphenyl)sulfonyl)-2-fluoro-3-methoxybenzamide |
| 70 | 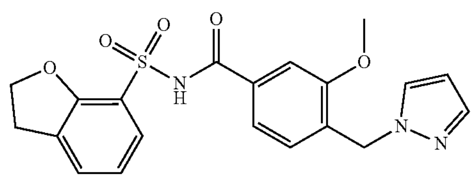 [SMILES: COc1cc(C(=O)NS(=O)(=O)c2cccc3c2OCC3)ccc1Cn1cccn1] | 4-((1H-pyrazol-1-yl)methyl)-N-((2,3-dihydrobenzofuran-7-yl)sulfonyl)-3-methoxybenzamide |
| 309 | 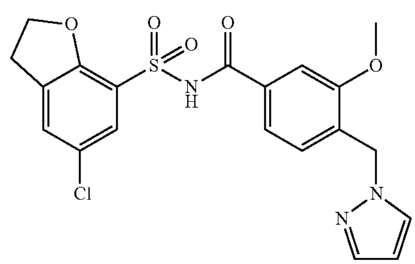 [SMILES: COc1cc(C(=O)NS(=O)(=O)c2cc(Cl)cc3c2OCC3)ccc1Cn1cccn1] | 4-((1H-pyrazol-1-yl)methyl)-N-((5-chloro-2,3-dihydrobenzofuran-7-yl)sulfonyl)-3-methoxybenzamide |
| 310 | 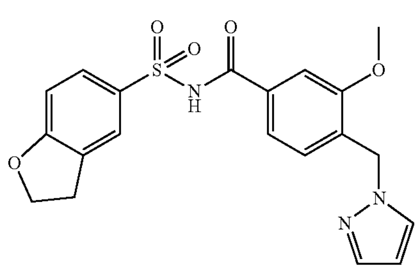 [SMILES: COc1cc(C(=O)NS(=O)(=O)c2ccc3c(c2)CCO3)ccc1Cn1cccn1] | 4-((1H-pyrazol-1-yl)methyl)-N-((2,3-dihydrobenzofuran-5-yl)sulfonyl)-3-methoxybenzamide |

TABLE 1-continued

Compounds

| No. | Structure | Name |
|---|---|---|
| 311 | 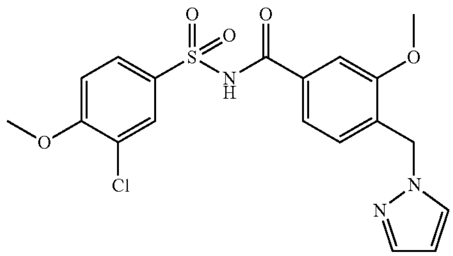 [SMILES: COc1ccc(S(=O)(=O)NC(=O)c2ccc(Cn3cccn3)c(OC)c2)cc1Cl] | 4-((1H-pyrazol-1-yl)methyl)-N-((3-chloro-4-methoxyphenyl)sulfonyl)-3-methoxybenzamide |
| 312 | 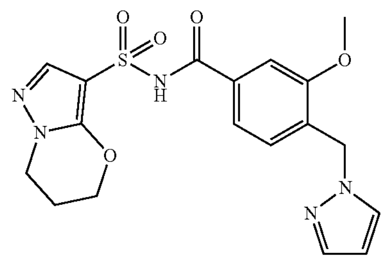 [SMILES: COc1cc(C(=O)NS(=O)(=O)c2cnn3c2OCCC3)ccc1Cn1cccn1] | 4-((1H-pyrazol-1-yl)methyl)-N-((6,7-dihydro-5H-pyrazolo[5,1-b][1,3]oxazin-3-yl)sulfonyl)-3-methoxybenzamide |
| 314 | 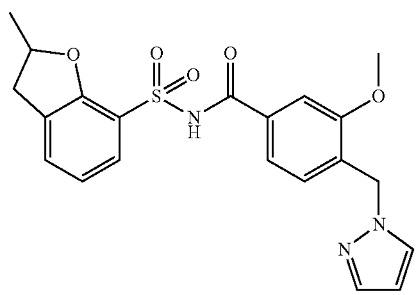 [SMILES: COc1cc(C(=O)NS(=O)(=O)c2cccc3c2OC(C)C3)ccc1Cn1cccn1] | 4-((1H-pyrazol-1-yl)methyl)-3-methoxy-N-((2-methyl-2,3-dihydrobenzofuran-7-yl)sulfonyl)benzamide |
| 315 | 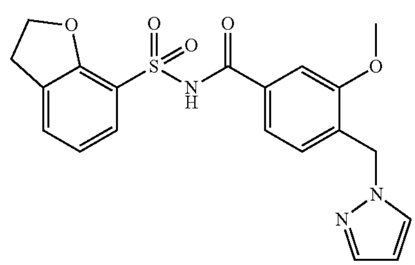 [SMILES: COc1cc(C(=O)NS(=O)(=O)c2cccc3c2OCC3)ccc1Cn1cccn1] | 4-((1H-pyrazol-1-yl)methyl)-N-((2,3-dihydrobenzofuran-7-yl)sulfonyl)-3-methoxybenzamide |

In some embodiments, a compound of Formula (J), (I), (Ia), and/or (Ib), or pharmaceutically acceptable salt thereof, is a compound wherein the compound has the structure:

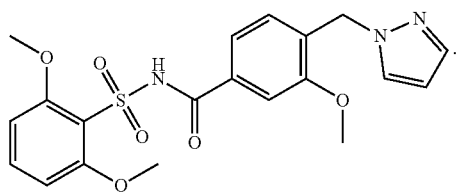 [SMILES: COc1cc(C(=O)NS(=O)(=O)c2c(OC)cccc2OC)ccc1Cn1cccn1]

In some embodiments, a compound of Formula (J), (I), (Ia), and/or (Ib), is a compound wherein the compound has the structure:

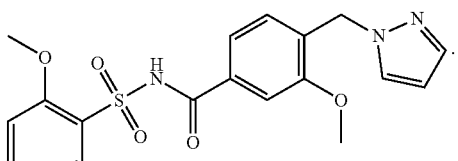

In some embodiments, a compound of Formula (J), (I), (Ia), and/or (Ib), or pharmaceutically acceptable salt thereof, is a compound wherein the compound has the structure:

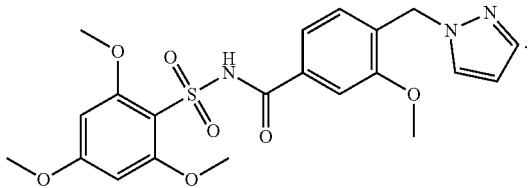 [SMILES: COc1cc(OC)c(S(=O)(=O)NC(=O)c2ccc(Cn3cccn3)c(OC)c2)c(OC)c1]

In some embodiments, a compound of Formula (J), (I), (Ia), and/or (Ib), is a compound wherein the compound has the structure:

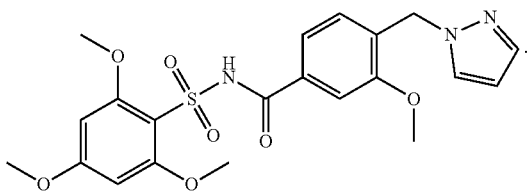 [SMILES: COc1cc(OC)c(S(=O)(=O)NC(=O)c2ccc(Cn3cccn3)c(OC)c2)c(OC)c1]

In some embodiments, a compound of Formula (J) is represented by Formula (II):

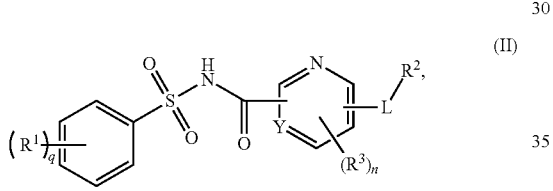

or a pharmaceutically acceptable salt thereof, wherein
each $R^1$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{1a}$, —C(O)O$R^{1a}$, —OC(O)$R^{1a}$, —C(O)N($R^{1a}$)($R^{1b}$), —N($R^{1a}$)C(O)($R^{1b}$), —OC(O)N($R^{1a}$)($R^{1b}$), —N($R^{1a}$)C(O)(O$R^{1b}$), —S(O)$R^{1a}$, —S(O)$_2$$R^{1a}$, —S(O)$_2$N($R^{1a}$)($R^{1b}$), —S(O)(NH)$R^{1a}$, —S(O)(NH)N($R^{1a}$)($R^{1b}$), —N($R^{1a}$)($R^{1b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{1c}$, each alkoxy and alkynyl is substituted with 0, 1, 2, or 3 $R^{1d}$, and each cycloalkyl, heterocycloalkyl, aryl, and heteroaryl is substituted with 0, 1, 2, or 3 $R^{1e}$;
each $R^{1a}$ and $R^{1b}$ is independently hydrogen or $C_1$-$C_6$ alkyl;
each $R^{1c}$ is independently $C_1$-$C_6$ alkoxy, halogen, $C_1$-$C_6$ haloalkoxy, —N$R^{1c1}$$R^{1c2}$, OH, or —CN;
each $R^{11}$ and $R^{1c2}$ is independently hydrogen or $C_1$-$C_6$ alkyl;
each $R^{1d}$ is independently deuterium, $C_3$-$C_8$ cycloalkyl, heterocycloalkyl, $C_6$-$C_{10}$ aryl, or heteroaryl;
each $R^{1e}$ is independently $C_1$-$C_6$ alkyl, $C_1$-$C_6$ alkoxy, halogen, $C_1$-$C_6$ haloalkyl, $C_1$-$C_6$ haloalkoxy, OH, or —CN;

alternatively, two $R^1$ groups on adjacent carbons together with the atoms to which they are attached combine to form a $C_5$-$C_8$ cycloalkyl or a heterocycloalkyl substituted with 0, 1, 2, 3, 4, 5, or 6 halogen, $C_1$-$C_4$ alkyl, OH or —CN;
L is —$C_1$-$C_4$ alkylene-, —($C_1$-$C_4$ alkylene)-O—, or —O—;
$R^2$ is a heteroaryl, which is substituted with 0, 1, 2, 3, or 4 $R^{2a}$;
each $R^{2a}$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{2b}$, —C(O)O$R^{2b}$, —OC(O)$R^{2b}$, —C(O)N($R^{2b}$)($R^{2c}$), —N($R^{2b}$)C(O)($R^{2c}$), —S(O)$_2$$R^{2b}$, —S(O)$_2$N($R^{2b}$)($R^{2c}$), —N($R^{2b}$)($R^{2c}$), OH, —CN, or —NO$_2$;
each $R^{2b}$ and $R^{2c}$ is independently hydrogen or $C_1$-$C_6$ alkyl;
Y is CH, CR$^3$, or N;
each $R^3$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —OC(O)N($R^{3a}$)($R^{3b}$), —N($R^{3a}$)C(O)(O$R^{3b}$), —S(O)$R^{3a}$, —S(O)$_2$$R^{3a}$, —S(O)$_2$N($R^{3a}$)($R^{3b}$), —S(O)(NH)$R^{3a}$, —S(O)(NH)N($R^{3a}$)($R^{3b}$), —N($R^{3a}$)($R^{3b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{3c}$, each alkoxy is substituted with 0, 1, 2, or 3 $R^{3d}$, and each cycloalkyl, heterocycloalkyl, aryl, and heteroaryl is substituted with 0, 1, 2, or 3 $R^{3e}$; or,
two $R^3$ on the same carbon atom together represent an oxo group;
each $R^{3a}$ and $R^{3b}$ is independently hydrogen or $C_1$-$C_6$ alkyl;
each $R^{3c}$ is independently $C_1$-$C_6$ alkoxy, halogen, $C_1$-$C_6$ haloalkoxy, —N$R^{3c1}$$R^{3c2}$, OH, or —CN;
each $R^{3c1}$ and $R^{3c2}$ is independently hydrogen or $C_1$-$C_6$ alkyl;
each $R^{3d}$ is independently $C_3$-$C_8$ cycloalkyl, heterocycloalkyl, phenyl, or heteroaryl;
each $R^{3e}$ is independently $C_1$-$C_6$ alkyl, $C_1$-$C_6$ alkoxy, halogen, $C_1$-$C_6$ haloalkyl, or $C_1$-$C_6$ haloalkoxy;
subscript n is 0, 1, 2, 3, or 4; and
subscript q is 0, 1, 2, 3, or 4;
wherein
each heterocycloalkyl is a 3- to 8-membered ring that includes 1 to 4 heteroatoms each independently N, O or S; and
each heteroaryl is a 5- to 6-membered ring that includes 1 to 4 heteroatoms each independently N, O or S.

In some embodiments of Formula (II), Y is N. In some embodiments, Y is CR$^3$. In some embodiments, Y is CH.

In some embodiments, a compound of Formula (J), Formula (II), or pharmaceutically acceptable salt thereof, is represented by Formula (IIa):

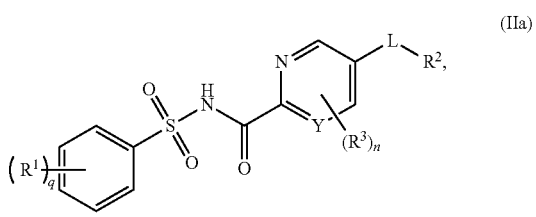

(IIa)

or a pharmaceutically acceptable salt thereof, wherein $R^1$, q, $R^2$, L, $R^3$, and n are as described in classes and subclasses herein, both singly and in combination, and Y is N, CH, or $CR^3$.

In some embodiments, a compound of Formula (J), (II), and/or (IIa), or pharmaceutically acceptable salt thereof, is represented by Formula (IIb):

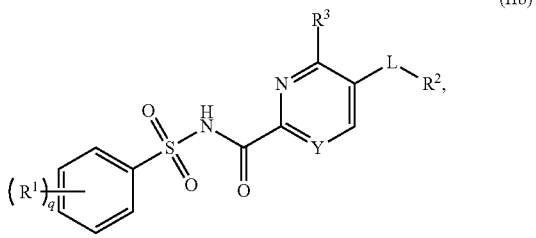

(IIb)

or a pharmaceutically acceptable salt thereof, wherein $R^1$, q, $R^2$, L, and $R^3$ are as described in classes and subclasses herein, both singly and in combination, and Y is N, CH, or $CR^3$.

In some embodiments, a compound of Formula (J), (II), (IIa), and/or (IIb), or pharmaceutically acceptable salt thereof, is a compound, or pharmaceutically acceptable salt thereof, wherein Y is N. In some embodiments, Y is $CR^3$. In some embodiments, Y is CH.

In some embodiments, a compound of Formula (J), (II), (IIa), and/or (IIb), or pharmaceutically acceptable salt thereof, is represented by Formula (IIc):

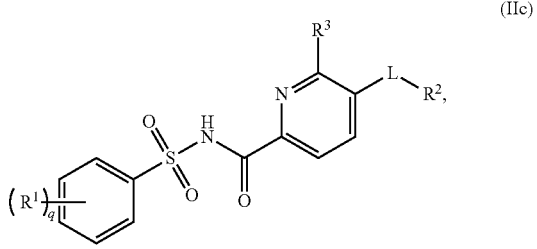

(IIc)

or a pharmaceutically acceptable salt thereof, wherein $R^1$, q, $R^2$, L, and $R^3$ are as described in classes and subclasses herein, both singly and in combination.

In some embodiments, a compound of Formula (J), (II), (IIa), (IIb), and/or (IIc), or a pharmaceutically acceptable salt thereof, is a compound, or pharmaceutically acceptable salt thereof, wherein the group

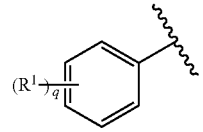

has the structure:

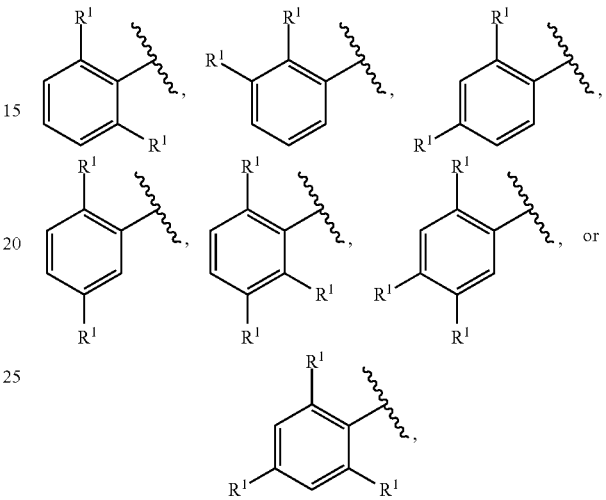

or a pharmaceutically acceptable salt thereof, wherein $R^1$ is as described in classes and subclasses herein.

In some embodiments, a compound of Formula (J), (II), (IIa), (IIb), and/or (IIc), or a pharmaceutically acceptable salt thereof, is a compound, or pharmaceutically acceptable salt thereof, wherein each $R^1$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, OH, —CN, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, or heteroaryl, wherein each alkyl is substituted with 0, 1, 2, or 3 $R^{1c}$, and each alkoxy and alkynyl is substituted with 0, 1, 2, or 3 $R^{1d}$; or alternatively, two $R^1$ on adjacent carbons together with the atoms to which they are attached combine to form a $C_5$-$C_8$ cycloalkyl or a heterocycloalkyl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^1$ is independently $C_1$-$C_6$ alkyl, $C_1$-$C_6$ alkoxy, $C_1$-$C_6$ hydroxyalkyl, halogen, $C_1$-$C_6$ haloalkyl, $C_1$-$C_6$ haloalkoxy, OH, $C_3$-$C_8$ cycloalkyl, ($C_1$-$C_3$ alkyl) ($C_3$-$C_8$ cycloalkyl), —O—($C_3$-$C_8$ cycloalkyl), $C_6$-$C_{10}$ aryl, or heteroaryl, wherein each alkyl is substituted with 0 or 1 $R^{1c}$, and each alkoxy and alkynyl is substituted with 0 or 1 $R^{1d}$; or alternatively, two $R^1$ on adjacent carbons together with the atoms to which they are attached combine to form a $C_5$-$C_8$ cycloalkyl or a heterocycloalkyl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{1a}$ and $R^{1b}$ is independently hydrogen or $C_1$-$C_3$ alkyl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{1c}$ is halogen, $-NR^{11}R^{1c2}$, OH, or $-CN$.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{1d}$ is independently heteroaryl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^1$ is independently $C_1$-$C_4$ alkyl, $C_1$-$C_4$ alkoxy, halogen, $C_1$-$C_4$ haloalkyl, or $-CN$.

In some embodiments, a compound of Formula (J), (II), (IIa), (IIb), and/or (IIc), or a pharmaceutically acceptable salt thereof, is a compound, or pharmaceutically acceptable salt thereof, wherein each $R^1$ is independently $-CH_3$, $-CH_2CH_3$, $-C(CH_3)_3$, $-OCH_3$, $-OCD_3$, $-C(CH_3)_2OCH_3$, $-C(CH_3)_2CH_2OH$, $-OCH(CH_3)_2$, $-C(CH_3)_2OH$, $-C(CH_3)(CH_2CH_3)OH$, F, Cl, Br, $CF_3$, $OCHF_2$, $OCF_3$, $OCH_2CF_3$, cyclopropyl, cyclopropyloxy, cyclobutyloxy,

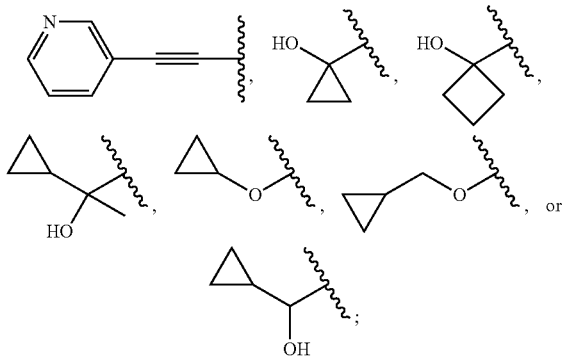

or
two $R^1$ on adjacent carbons together with the atoms to which they are attached combine to form a cyclopentyl, cyclohexyl, dihydrofuran, tetrahydrofuran, methyltetrahydrofuran, 1,3-dioxole, dihydro-1,3-oxazine, or methyldihydrofuran. In some embodiments, two R on adjacent carbon atoms combine to form:

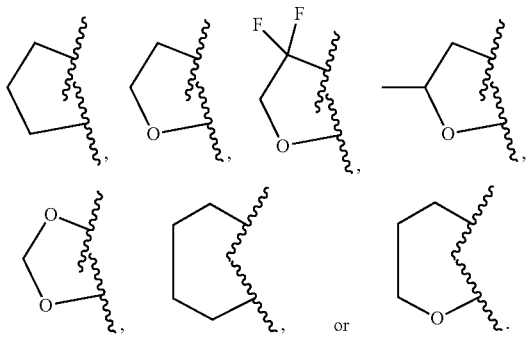

In some embodiments, a compound of Formula (J), (II), (IIa), (IIb), and/or (IIc), or a pharmaceutically acceptable salt thereof, is a compound, or pharmaceutically acceptable salt thereof, wherein L is $-CH_2-$, $-CH_2O-$, or $-O-$.

In some embodiments, a compound of Formula (J), (II), (IIa), (IIb), and/or (IIc), or a pharmaceutically acceptable salt thereof, is a compound, or pharmaceutically acceptable salt thereof, wherein L is $-CH_2-$.

In some embodiments, a compound of Formula (J), (II), (IIa), (IIb), and/or (IIc), or a pharmaceutically acceptable salt thereof, is a compound, or pharmaceutically acceptable salt thereof, wherein $R^2$ is pyrrolyl, furyl, thienyl, pyrazolyl, isoxazolyl, oxazolyl, isothiazolyl, thiazolyl, triazolyl, oxadiazolyl, thiadiazolyl, pyridyl, pyridazinyl, pyrimidyl, or pyrazinyl, which are each substituted by 0, 1, or 2 $R^{2a}$.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{2a}$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, OH, or $-CN$.

In some embodiments, a compound of Formula (J), (II), (IIa), (IIb), and/or (IIc), or a pharmaceutically acceptable salt thereof, is a compound wherein each $R^{2b}$ and $R^{2c}$ is independently hydrogen or $C_1$-$C_4$ alkyl, or a pharmaceutically acceptable salt thereof.

In some embodiments, a compound of Formula (J), (II), (IIa), (IIb), and/or (IIc), or pharmaceutically acceptable salt thereof, is a compound, or pharmaceutically acceptable salt thereof, wherein $R^2$ is

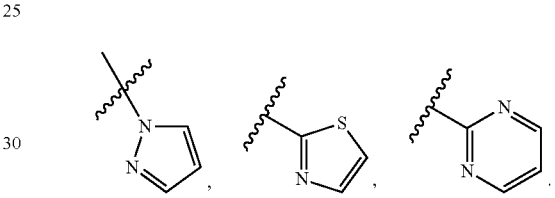

In some embodiments, a compound of Formula (J), (II), (IIa), (IIb), and/or (IIc), or a pharmaceutically acceptable salt thereof, is a compound, or pharmaceutically acceptable salt thereof, wherein $R^2$ is

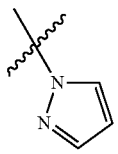

In some embodiments, a compound of Formula (J), (II), (IIa), (IIb), and/or (IIc), or a pharmaceutically acceptable salt thereof, is a compound, or pharmaceutically acceptable salt thereof, wherein each $R^3$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, $-C(O)R^{3a}$, $-C(O)OR^{3a}$, $-OC(O)R^{3a}$, $-C(O)N(R^{3a})(R^{3b})$, $-N(R^{3a})C(O)(R^{3b})$, $-S(O)_2R^{3a}$, $-S(O)_2N(R^{3a})(R^{3b})$, OH, $-CN$, $C_3$-$C_8$ cycloalkyl, or heterocycloalkyl.

In some embodiments, a compound of Formula (J), (II), (IIa), (IIb), and/or (IIc), or pharmaceutically acceptable salt thereof, is a compound, or pharmaceutically acceptable salt thereof, wherein two $R^3$ on the same carbon atom together represent an oxo group.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{3a}$ and $R^{3b}$ is independently hydrogen or $C_1$-$C_4$ alkyl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{3c}$ is halogen, —$NR^{3c1}R^{3c2}$, OH, or —CN.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{3d}$ is independently heteroaryl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^{3e}$ is independently $C_1$-$C_4$ alkyl, $C_1$-$C_4$ alkoxy, halogen, or $C_1$-$C_4$ haloalkyl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^3$ is independently $C_1$-$C_6$ alkyl, $C_1$-$C_6$ alkoxy, $C_1$-$C_6$ haloalkyl, $C_1$-$C_6$ haloalkoxy, —CN, or $C_3$-$C_8$ cycloalkyl.

In some embodiments, a compound of Formula (J), (II), (IIa), (IIb), and/or (IIc), or a pharmaceutically acceptable salt thereof, is a compound, or pharmaceutically acceptable salt thereof, wherein each $R^3$ is independently $C_1$-$C_4$ alkyl, $C_1$-$C_4$ alkoxy, $C_1$-$C_4$ haloalkyl, $C_1$-$C_4$ haloalkoxy, —CN, or $C_3$-$C_6$ cycloalkyl.

In some embodiments, a compound of Formula (J), (II), (IIa), (IIb), and/or (IIc), or a pharmaceutically acceptable salt thereof, wherein each $R^3$ is independently Me, Ome, $CHF_2$, $CF_3$, $OCHF_2$, $OCF_3$, or cyclopropyl.

In some embodiments, a compound of Formula (J), (II), (IIa), (IIb), and/or (IIc), or a pharmaceutically acceptable salt thereof, is a compound wherein subscript q is 1, 2, or 3, or a pharmaceutically acceptable salt thereof.

In some embodiments, a compound of Formula (J), (II), (IIa), (IIb), and/or (IIc), or a pharmaceutically acceptable salt thereof, is a compound, or pharmaceutically acceptable salt thereof, wherein subscript n is 0 or 1.

In some embodiments, a compound of Formula (J), (II), (IIa), (IIb), and/or (IIc), or a pharmaceutically acceptable salt thereof, is a compound wherein the compound has the structure of a compound shown in Table 2, or a pharmaceutically acceptable salt thereof.

TABLE 2

Compounds

| No. | Structure | Name |
|---|---|---|
| 201 | 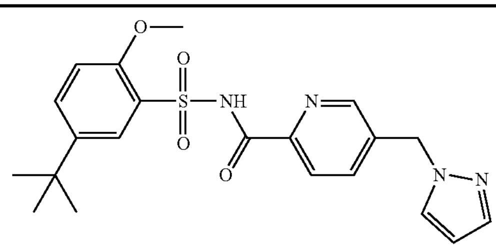 | 5-((1H-pyrazol-1-yl)methyl)-N-((5-(tert-butyl)-2-methoxyphenyl)sulfonyl)picolinamide |
| 202 | 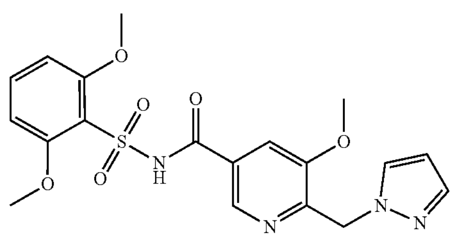 [SMILES: COc1cc(C(=O)NS(=O)(=O)c2c(OC)cccc2OC)cnc1Cn1cccn1] | 6-((1H-pyrazol-1-yl)methyl)-N-((2,6-dimethoxyphenyl)sulfonyl)-5-methoxynicotinamide |
| 203 | 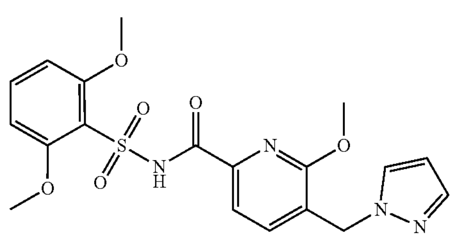 [SMILES: COc1cccc(OC)c1S(=O)(=O)NC(=O)c1ccc(Cn2cccn2)c(OC)n1] | 5-((1H-pyrazol-1-yl)methyl)-N-((2,6-dimethoxyphenyl)sulfonyl)-6-methoxypicolinamide |
| 204 | 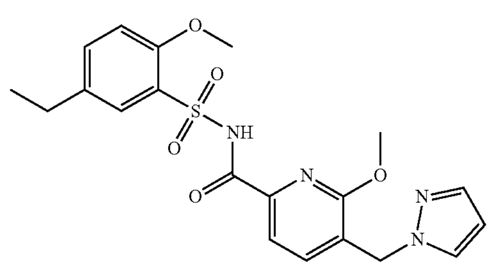 [SMILES: CCc1ccc(OC)c(S(=O)(=O)NC(=O)c2ccc(Cn3cccn3)c(OC)n2)c1] | 5-((1H-pyrazol-1-yl)methyl)-N-((5-ethyl-2-methoxyphenyl)sulfonyl)-6-methoxypicolinamide |

TABLE 2-continued

| No. | Structure | Name |
|---|---|---|
| 205 | 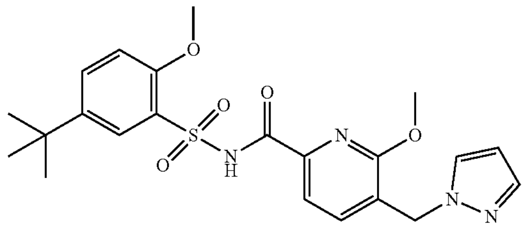 [SMILES: COc1ccc(C(C)(C)C)cc1S(=O)(=O)NC(=O)c1ccc(Cn2cccn2)c(OC)n1] | 5-((1H-pyrazol-1-yl)methyl)-N-((5-(tert-butyl)-2-methoxyphenyl)sulfonyl)-6-methoxypicolinamide |
| 206 | 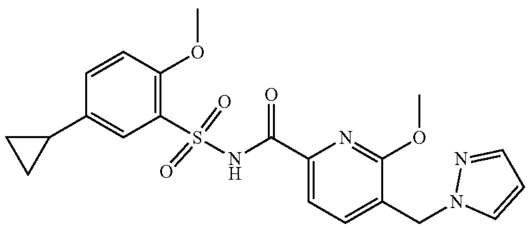 [SMILES: COc1ccc(C2CC2)cc1S(=O)(=O)NC(=O)c1ccc(Cn2cccn2)c(OC)n1] | 5-((1H-pyrazol-1-yl)methyl)-N-((5-cyclopropyl-2-methoxyphenyl)sulfonyl)-6-methoxypicolinamide |
| 207 | 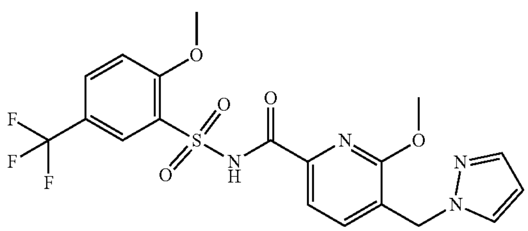 [SMILES: COc1ccc(C(F)(F)F)cc1S(=O)(=O)NC(=O)c1ccc(Cn2cccn2)c(OC)n1] | 5-((1H-pyrazol-1-yl)methyl)-6-methoxy-N-((2-methoxy-5-(trifluoromethyl)phenyl)sulfonyl)picolinamide |
| 208 | 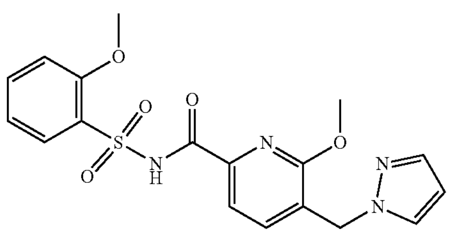 [SMILES: COc1ccccc1S(=O)(=O)NC(=O)c1ccc(Cn2cccn2)c(OC)n1] | 5-((1H-pyrazol-1-yl)methyl)-6-methoxy-N-((2-methoxyphenyl)sulfonyl)picolinamide |
| 209 | 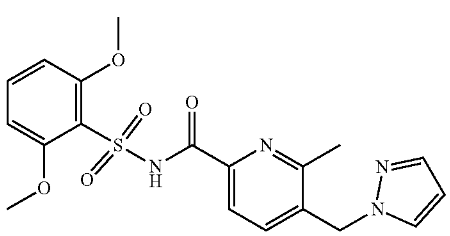 [SMILES: COc1cccc(OC)c1S(=O)(=O)NC(=O)c1ccc(Cn2cccn2)c(C)n1] | 5-((1H-pyrazol-1-yl)methyl)-N-((2,6-dimethoxyphenyl)sulfonyl)-6-methylpicolinamide |
| 210 | 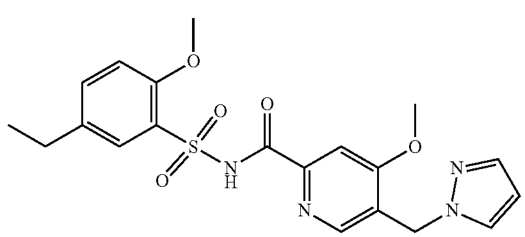 [SMILES: CCc1ccc(OC)c(S(=O)(=O)NC(=O)c2cc(OC)c(Cn3cccn3)cn2)c1] | 5-((1H-pyrazol-1-yl)methyl)-N-((5-ethyl-2-methoxyphenyl)sulfonyl)-4-methoxypicolinamide |

TABLE 2-continued

| No. | Structure | Name |
|---|---|---|
| 211 | 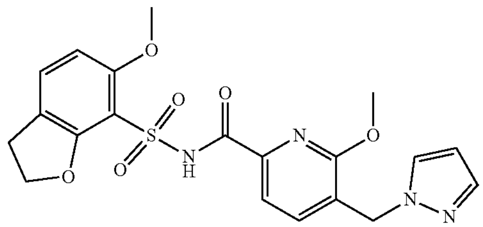 [SMILES: COc1ccc2c(c1S(=O)(=O)NC(=O)c1ccc(Cn3cccn3)c(OC)n1)OCC2] | 5-((1H-pyrazol-1-yl)methyl)-6-methoxy-N-((6-methoxy-2,3-dihydrobenzofuran-7-yl)sulfonyl)picolinamide |
| 212 | 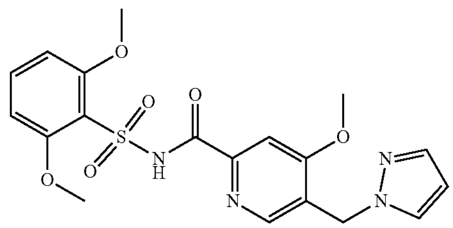 [SMILES: COc1cc(C(=O)NS(=O)(=O)c2c(OC)cccc2OC)ncc1Cn1cccn1] | 5-((1H-pyrazol-1-yl)methyl)-N-((2,6-dimethoxyphenyl)sulfonyl)-4-methoxypicolinamide |
| 213 | 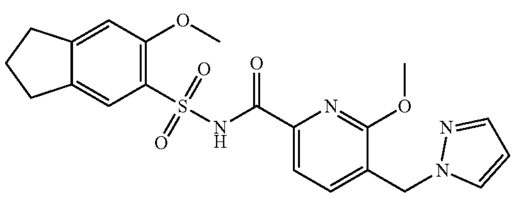 [SMILES: COc1cc2c(cc1S(=O)(=O)NC(=O)c1ccc(Cn3cccn3)c(OC)n1)CCC2] | 5-((1H-pyrazol-1-yl)methyl)-6-methoxy-N-((6-methoxy-2,3-dihydro-1H-inden-5-yl)sulfonyl)picolinamide |
| 214 | 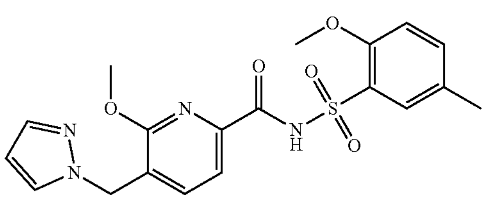 [SMILES: COc1ccc(C)cc1S(=O)(=O)NC(=O)c1ccc(Cn2cccn2)c(OC)n1] | 5-((1H-pyrazol-1-yl)methyl)-6-methoxy-N-((2-methoxy-5-methylphenyl)sulfonyl)picolinamide |
| 215 | 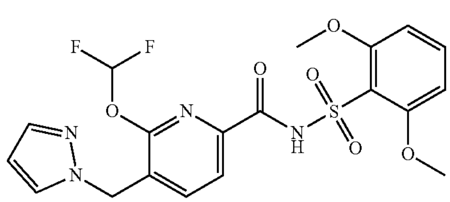 [SMILES: COc1cccc(OC)c1S(=O)(=O)NC(=O)c1ccc(Cn2cccn2)c(OC(F)F)n1] | 5-((1H-pyrazol-1-yl)methyl)-6-(difluoromethoxy)-N-((2,6-dimethoxyphenyl)sulfonyl)picolinamide |
| 216 | 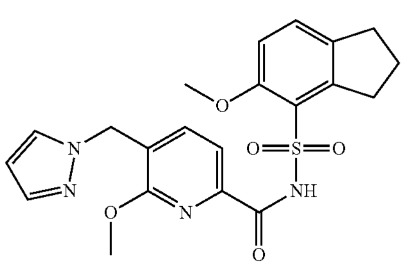 [SMILES: COc1ccc2c(c1S(=O)(=O)NC(=O)c1ccc(Cn3cccn3)c(OC)n1)CCC2] | 5-((1H-pyrazol-1-yl)methyl)-6-methoxy-N-((5-methoxy-2,3-dihydro-1H-inden-4-yl)sulfonyl)picolinamide |

TABLE 2-continued

| No. | Structure | Name |
|---|---|---|
| 217 | 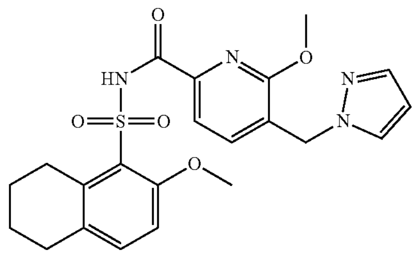 [SMILES: COc1ccc2c(c1S(=O)(=O)NC(=O)c1ccc(Cn3cccn3)c(OC)n1)CCCC2] | 5-((1H-pyrazol-1-yl)methyl)-6-methoxy-N-((2-methoxy-5,6,7,8-tetrahydronaphthalen-1-yl)sulfonyl)picolinamide |
| 218 | 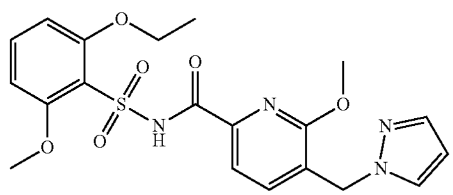 [SMILES: CCOc1cccc(OC)c1S(=O)(=O)NC(=O)c1ccc(Cn2cccn2)c(OC)n1] | 5-((1H-pyrazol-1-yl)methyl)-N-((2-ethoxy-6-methoxyphenyl)sulfonyl)-6-methoxypicolinamide |
| 219 | 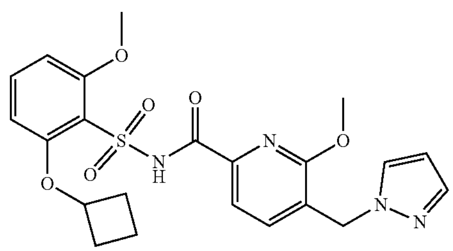 [SMILES: COc1cccc(OC2CCC2)c1S(=O)(=O)NC(=O)c1ccc(Cn2cccn2)c(OC)n1] | 5-((1H-pyrazol-1-yl)methyl)-N-((2-cyclobutoxy-6-methoxyphenyl)sulfonyl)-6-methoxypicolinamide |
| 220 | 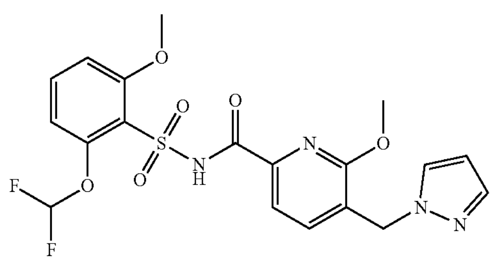 [SMILES: COc1cccc(OC(F)F)c1S(=O)(=O)NC(=O)c1ccc(Cn2cccn2)c(OC)n1] | 5-((1H-pyrazol-1-yl)methyl)-N-((2-(difluoromethoxy)-6-methoxyphenyl)sulfonyl)-6-methoxypicolinamide |
| 221 | 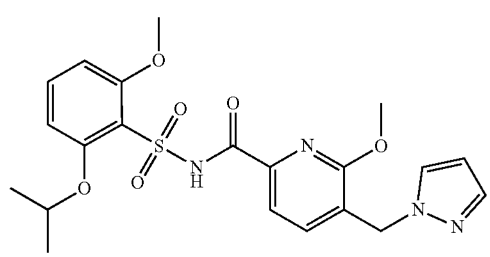 [SMILES: COc1cccc(OC(C)C)c1S(=O)(=O)NC(=O)c1ccc(Cn2cccn2)c(OC)n1] | 5-((1H-pyrazol-1-yl)methyl)-N-((2-isopropoxy-6-methoxyphenyl)sulfonyl)-6-methoxypicolinamide |
| 222 | 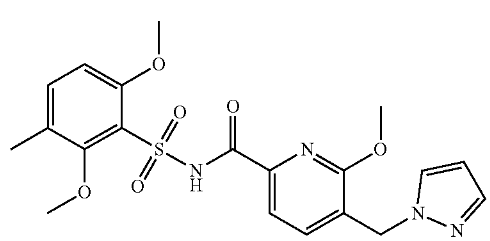 [SMILES: COc1ccc(C)c(OC)c1S(=O)(=O)NC(=O)c1ccc(Cn2cccn2)c(OC)n1] | 5-((1H-pyrazol-1-yl)methyl)-N-((2,6-dimethoxy-3-methylphenyl)sulfonyl)-6-methoxypicolinamide |

TABLE 2-continued

| No. | Structure | Name |
|---|---|---|
| 223 | 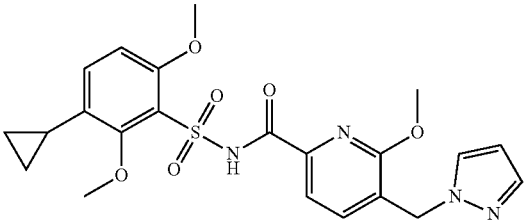 [SMILES: COc1ccc(C2CC2)c(OC)c1S(=O)(=O)NC(=O)c1ccc(Cn2cccn2)c(OC)n1] | 5-((1H-pyrazol-1-yl)methyl)-N-((3-cyclopropyl-2,6-dimethoxyphenyl)sulfonyl)-6-methoxypicolinamide |
| 224 | 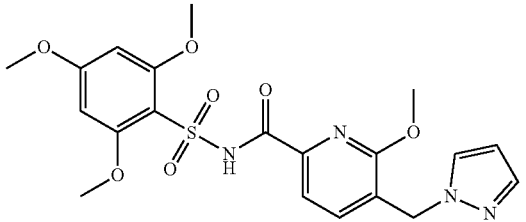 [SMILES: COc1cc(OC)c(S(=O)(=O)NC(=O)c2ccc(Cn3cccn3)c(OC)n2)c(OC)c1] | 5-((1H-pyrazol-1-yl)methyl)-6-methoxy-N-((2,4,6-trimethoxyphenyl)sulfonyl)picolinamide |
| 225 | 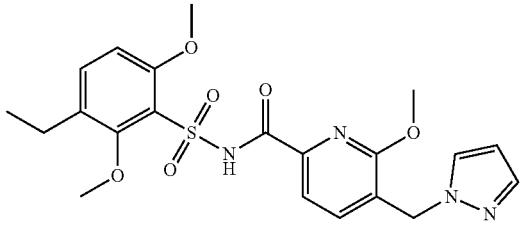 [SMILES: CCc1ccc(OC)c(S(=O)(=O)NC(=O)c2ccc(Cn3cccn3)c(OC)n2)c1OC] | 5-((1H-pyrazol-1-yl)methyl)-N-((3-ethyl-2,6-dimethoxyphenyl)sulfonyl)-6-methoxypicolinamide |
| 226 | 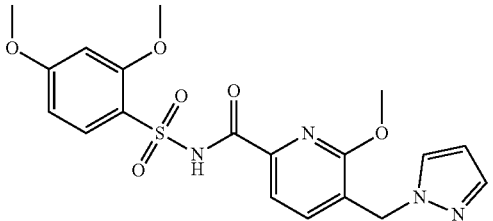 [SMILES: COc1ccc(S(=O)(=O)NC(=O)c2ccc(Cn3cccn3)c(OC)n2)c(OC)c1] | 5-((1H-pyrazol-1-yl)methyl)-N-((2,4-dimethoxyphenyl)sulfonyl)-6-methoxypicolinamide |
| 227 | 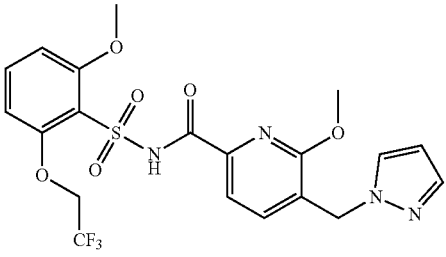 [SMILES: COc1cccc(OCC(F)(F)F)c1S(=O)(=O)NC(=O)c1ccc(Cn2cccn2)c(OC)n1] | 5-((1H-pyrazol-1-yl)methyl)-6-methoxy-N-((2-methoxy-6-(2,2,2-trifluoroethoxy)phenyl)sulfonyl)picolinamide |
| 228 | 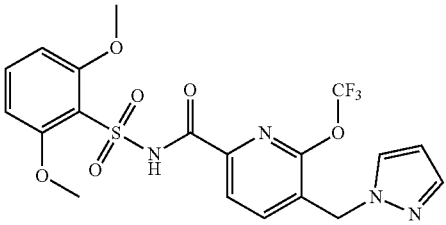 [SMILES: COc1cccc(OC)c1S(=O)(=O)NC(=O)c1ccc(Cn2cccn2)c(OC(F)(F)F)n1] | 5-((1H-pyrazol-1-yl)methyl)-N-((2,6-dimethoxyphenyl)sulfonyl)-6-(trifluoromethoxy)picolinamide |

TABLE 2-continued

| No. | Structure | Name |
|---|---|---|
| 229 | 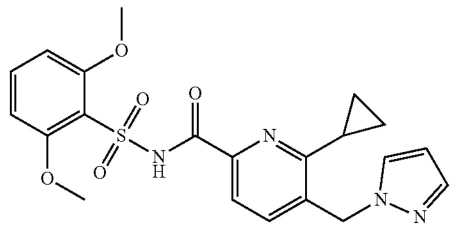 [SMILES: COc1cccc(OC)c1S(=O)(=O)NC(=O)c1ccc(Cn2cccn2)c(C2CC2)n1] | 5-((1H-pyrazol-1-yl)methyl)-6-cyclopropyl-N-((2,6-dimethoxyphenyl)sulfonyl)picolinamide |
| 230 | 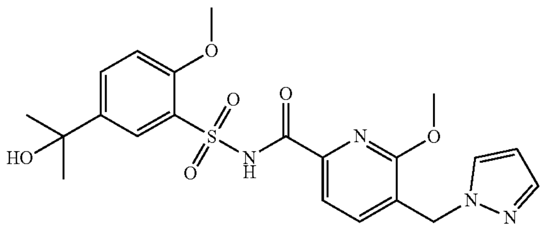 [SMILES: COc1ccc(C(C)(C)O)cc1S(=O)(=O)NC(=O)c1ccc(Cn2cccn2)c(OC)n1] | 5-((1H-pyrazol-1-yl)methyl)-N-((5-(2-hydroxypropan-2-yl)-2-methoxyphenyl)sulfonyl)-6-methoxypicolinamide |
| 231 | 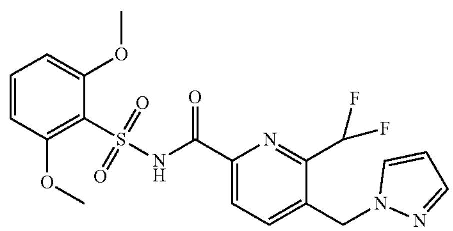 [SMILES: COc1cccc(OC)c1S(=O)(=O)NC(=O)c1ccc(Cn2cccn2)c(C(F)F)n1] | 5-((1H-pyrazol-1-yl)methyl)-6-(difluoromethyl)-N-((2,6-dimethoxyphenyl)sulfonyl)picolinamide |
| 233 | 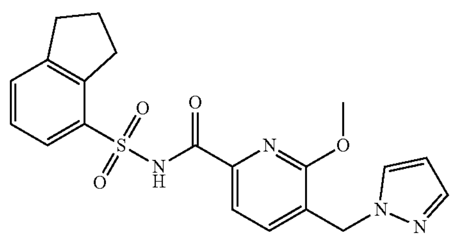 [SMILES: COc1nc(C(=O)NS(=O)(=O)c2cccc3c2CCC3)ccc1Cn1cccn1] | 5-((1H-pyrazol-1-yl)methyl)-N-((2,3-dihydro-1H-inden-4-yl)sulfonyl)-6-methoxypicolinamide |
| 234 | 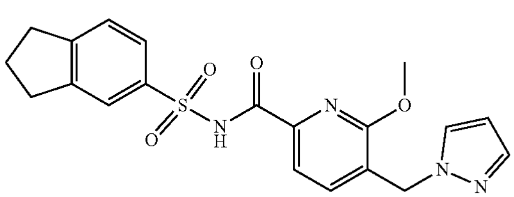 [SMILES: COc1nc(C(=O)NS(=O)(=O)c2ccc3c(c2)CCC3)ccc1Cn1cccn1] | 5-((1H-pyrazol-1-yl)methyl)-N-((2,3-dihydro-1H-inden-5-yl)sulfonyl)-6-methoxypicolinamide |
| 235 | 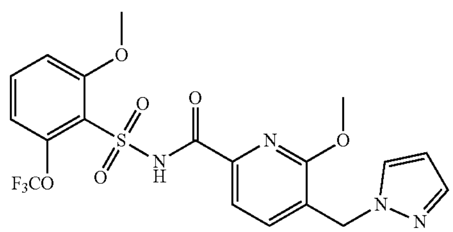 [SMILES: COc1cccc(OC(F)(F)F)c1S(=O)(=O)NC(=O)c1ccc(Cn2cccn2)c(OC)n1] | 5-((1H-pyrazol-1-yl)methyl)-6-methoxy-N-((2-methoxy-6-(trifluoromethoxy)phenyl)sulfonyl)picolinamide |

TABLE 2-continued

| No. | Structure | Name |
|---|---|---|
| 236 | 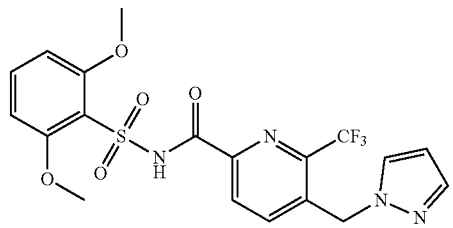 [SMILES: COc1cccc(OC)c1S(=O)(=O)NC(=O)c1ccc(Cn2cccn2)c(C(F)(F)F)n1] | 5-((1H-pyrazol-1-yl)methyl)-N-((2,6-dimethoxyphenyl)sulfonyl)-6-(trifluoromethyl)picolinamide |
| 237 | 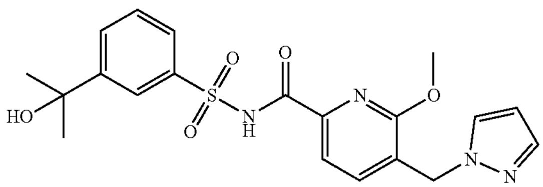 [SMILES: COc1nc(C(=O)NS(=O)(=O)c2cccc(C(C)(C)O)c2)ccc1Cn1cccn1] | 5-((1H-pyrazol-1-yl)methyl)-N-((3-(2-hydroxypropan-2-yl)phenyl)sulfonyl)-6-methoxypicolinamide |
| 238 | 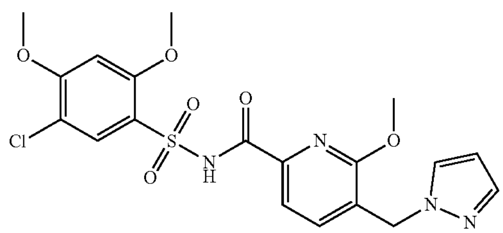 [SMILES: COc1cc(OC)c(S(=O)(=O)NC(=O)c2ccc(Cn3cccn3)c(OC)n2)cc1Cl] | 5-((1H-pyrazol-1-yl)methyl)-N-((5-chloro-2,4-dimethoxyphenyl)sulfonyl)-6-methoxypicolinamide |
| 239 | 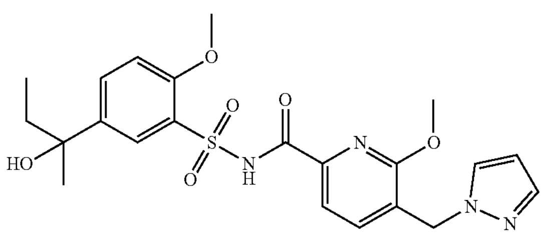 [SMILES: CCC(C)(O)c1ccc(OC)c(S(=O)(=O)NC(=O)c2ccc(Cn3cccn3)c(OC)n2)c1] | 5-((1H-pyrazol-1-yl)methyl)-N-((5-(2-hydroxybutan-2-yl)-2-methoxyphenyl)sulfonyl)-6-methoxypicolinamide |
| 240 | 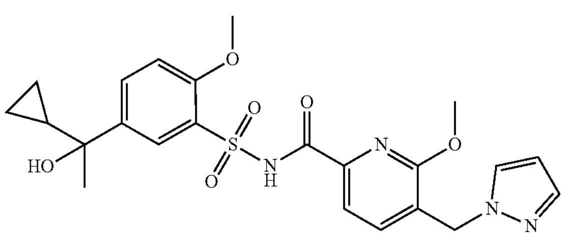 [SMILES: COc1ccc(C(C)(O)C2CC2)cc1S(=O)(=O)NC(=O)c1ccc(Cn2cccn2)c(OC)n1] | 5-((1H-pyrazol-1-yl)methyl)-N-((5-(1-cyclopropyl-1-hydroxyethyl)-2-methoxyphenyl)sulfonyl)-6-methoxypicolinamide |
| 241 | 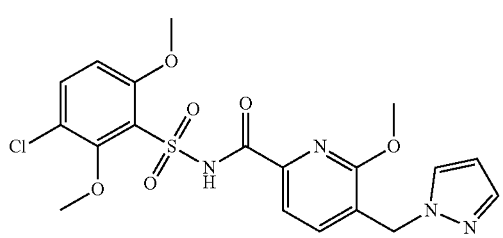 [SMILES: COc1ccc(Cl)c(OC)c1S(=O)(=O)NC(=O)c1ccc(Cn2cccn2)c(OC)n1] | 5-((1H-pyrazol-1-yl)methyl)-N-((3-chloro-2,6-dimethoxyphenyl)sulfonyl)-6-methoxypicolinamide |

TABLE 2-continued

| No. | Structure | Name |
|---|---|---|
| 246 | 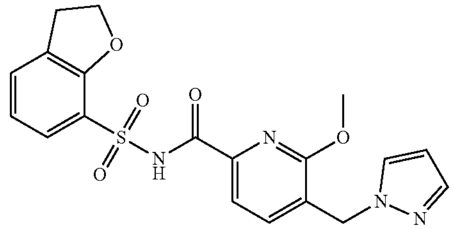 [SMILES: COc1nc(C(=O)NS(=O)(=O)c2cccc3c2OCC3)ccc1Cn1cccn1] | 5-((1H-pyrazol-1-yl)methyl)-N-((2,3-dihydrobenzofuran-7-yl)sulfonyl)-6-methoxypicolinamide |
| 249 | 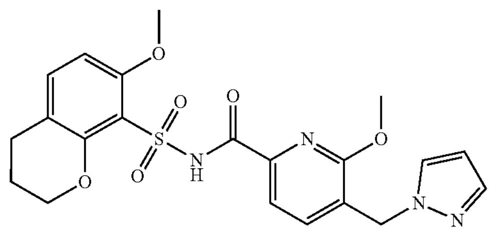 [SMILES: COc1ccc2c(c1S(=O)(=O)NC(=O)c1ccc(Cn3cccn3)c(OC)n1)OCCC2] | 5-((1H-pyrazol-1-yl)methyl)-6-methoxy-N-((7-methoxychroman-8-yl)sulfonyl)picolinamide |
| 251 | 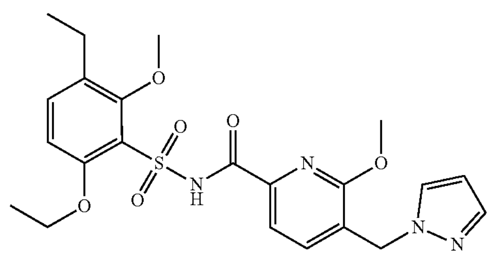 [SMILES: CCOc1ccc(CC)c(OC)c1S(=O)(=O)NC(=O)c1ccc(Cn2cccn2)c(OC)n1] | 5-((1H-pyrazol-1-yl)methyl)-N-((6-ethoxy-3-ethyl-2-methoxyphenyl)sulfonyl)-6-methoxypicolinamide |
| 252 | 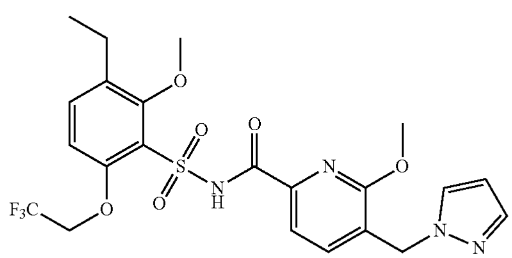 [SMILES: CCc1ccc(OCC(F)(F)F)c(S(=O)(=O)NC(=O)c2ccc(Cn3cccn3)c(OC)n2)c1OC] | 5-((1H-pyrazol-1-yl)methyl)-N-((3-ethyl-2-methoxy-6-(2,2,2-trifluoroethoxy)phenyl)sulfonyl)-6-methoxypicolinamide |
| 253 | 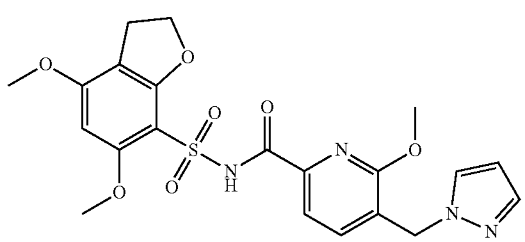 [SMILES: COc1cc(OC)c(S(=O)(=O)NC(=O)c2ccc(Cn3cccn3)c(OC)n2)c2c1CCO2] | 5-((1H-pyrazol-1-yl)methyl)-N-((4,6-dimethoxy-2,3-dihydrobenzofuran-7-yl)sulfonyl)-6-methoxypicolinamide |
| 254 | 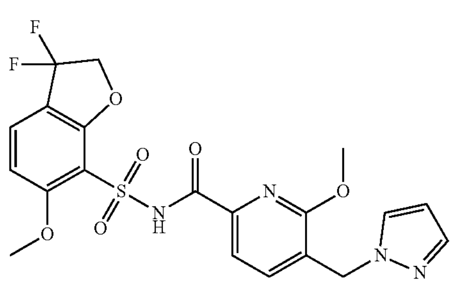 [SMILES: COc1ccc2c(c1S(=O)(=O)NC(=O)c1ccc(Cn3cccn3)c(OC)n1)OCC2(F)F] | 5-((1H-pyrazol-1-yl)methyl)-N-((3,3-difluoro-6-methoxy-2,3-dihydrobenzofuran-7-yl)sulfonyl)-6-methoxypicolinamide |

TABLE 2-continued

| No. | Structure | Name |
|---|---|---|
| 255 | 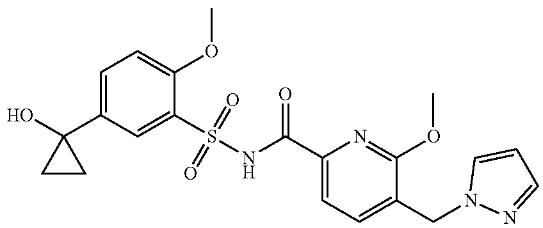 [SMILES: COc1ccc(C2(O)CC2)cc1S(=O)(=O)NC(=O)c1ccc(Cn2cccn2)c(OC)n1] | 5-((1H-pyrazol-1-yl)methyl)-N-((5-(1-hydroxycyclopropyl)-2-methoxyphenyl)sulfonyl)-6-methoxypicolinamide |
| 256 | 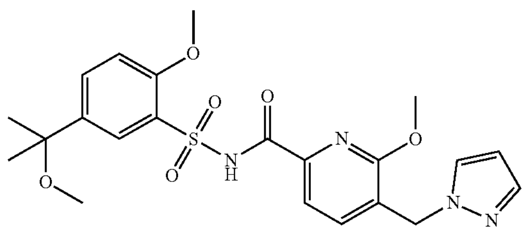 [SMILES: COc1ccc(C(C)(C)OC)cc1S(=O)(=O)NC(=O)c1ccc(Cn2cccn2)c(OC)n1] | 5-((1H-pyrazol-1-yl)methyl)-6-methoxy-N-((2-methoxy-5-(2-methoxypropan-2-yl)phenyl)sulfonyl)picolinamide |
| 258 | 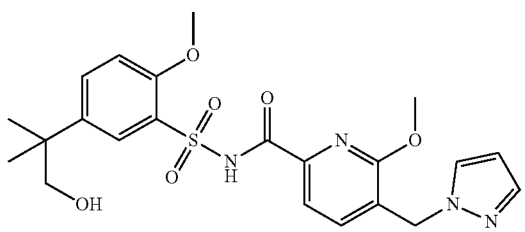 [SMILES: COc1ccc(C(C)(C)CO)cc1S(=O)(=O)NC(=O)c1ccc(Cn2cccn2)c(OC)n1] | 5-((1H-pyrazol-1-yl)methyl)-N-((5-(1-hydroxy-2-methylpropan-2-yl)-2-methoxyphenyl)sulfonyl)-6-methoxypicolinamide |
| 259 | 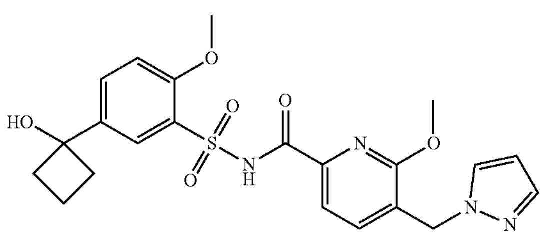 [SMILES: COc1ccc(C2(O)CCC2)cc1S(=O)(=O)NC(=O)c1ccc(Cn2cccn2)c(OC)n1] | 5-((1H-pyrazol-1-yl)methyl)-N-((5-(1-hydroxycyclobutyl)-2-methoxyphenyl)sulfonyl)-6-methoxypicolinamide |
| 264 | 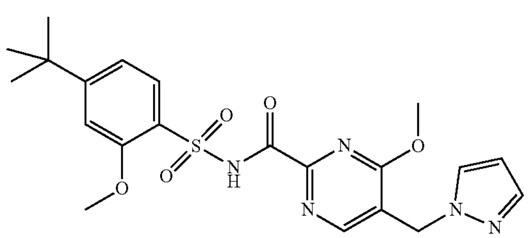 [SMILES: COc1cc(C(C)(C)C)ccc1S(=O)(=O)NC(=O)c1ncc(Cn2cccn2)c(OC)n1] | 5-((1H-pyrazol-1-yl)methyl)-N-((4-(tert-butyl)-2-methoxyphenyl)sulfonyl)-4-methoxypyrimidine-2-carboxamide |
| 265 | 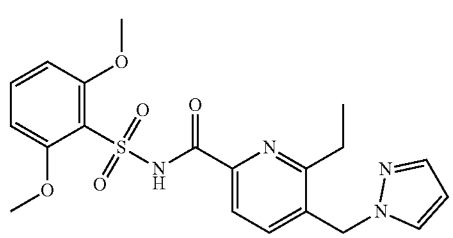 [SMILES: CCc1nc(C(=O)NS(=O)(=O)c2c(OC)cccc2OC)ccc1Cn1cccn1] | 5-(1H-pyrazol-1-yl)methyl)-N-(2,6-dimethoxyphenyl)sulfonyl)-6-ethylpicolinamide |

TABLE 2-continued

| No. | Structure | Name |
|---|---|---|
| 266 | 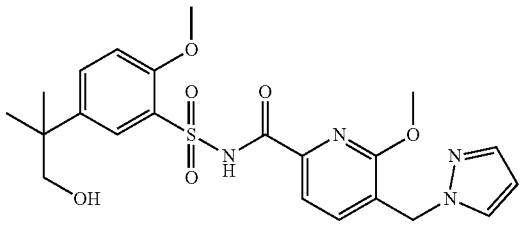 [SMILES: COc1ccc(C(C)(C)CO)cc1S(=O)(=O)NC(=O)c1ccc(Cn2cccn2)c(OC)n1] | 5-((1H-pyrazol-1-yl)methyl)-N-((5-(1-hydroxy-2-methylpropan-2-yl)-2-methoxyphenyl)sulfonyl)-6-methoxypicolinamide |
| 267 | 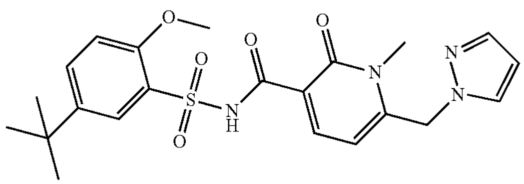 [SMILES: COc1ccc(C(C)(C)C)cc1S(=O)(=O)NC(=O)c1ccc(Cn2cccn2)n(C)c1=O] | 6-((1H-pyrazol-1-yl)methyl)-N-(5-(tert-butyl)-2-methoxyphenyl)sulfonyl)-1-methyl-2-oxo-1,2-dihydropyridine-3-carboxamide |
| 268 | 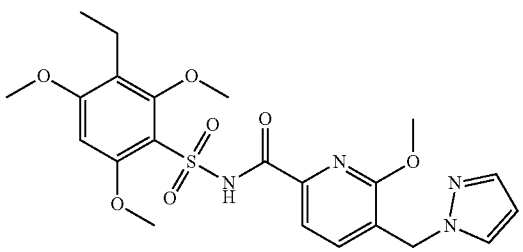 [SMILES: CCc1c(OC)cc(OC)c(S(=O)(=O)NC(=O)c2ccc(Cn3cccn3)c(OC)n2)c1OC] | 5-((1H-pyrazol-1-yl)methyl)-N-((3-ethyl-2,4,6-trimethoxyphenyl)sulfonyl)-6-methoxypicolinamide |
| 269 | 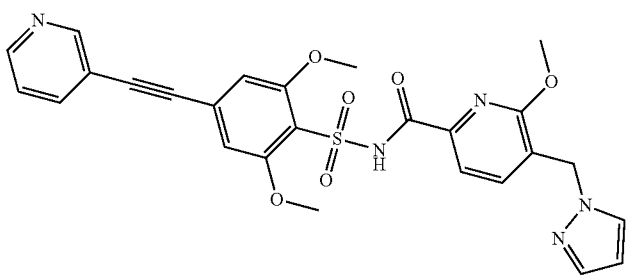 [SMILES: COc1cc(C#Cc2cccnc2)cc(OC)c1S(=O)(=O)NC(=O)c1ccc(Cn2cccn2)c(OC)n1] | 5-((1H-pyrazol-1-yl)methyl)-N-((2,6-dimethoxy-4-(pyridin-3-ylethynyl)phenyl)sulfonyl)-6-methoxypicolinamide |
| 270 | 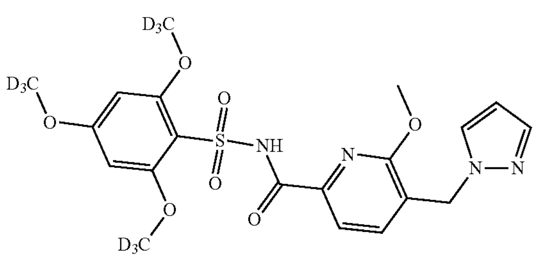 [SMILES: [2H]C([2H])([2H])Oc1cc(OC([2H])([2H])[2H])c(S(=O)(=O)NC(=O)c2ccc(Cn3cccn3)c(OC)n2)c(OC([2H])([2H])[2H])c1] | 5-((1H-pyrazol-1-yl)methyl)-6-methoxy-N-((2,4,6-tris(methoxy-d3)phenyl)sulfonyl)picolinamide |
| 271 | 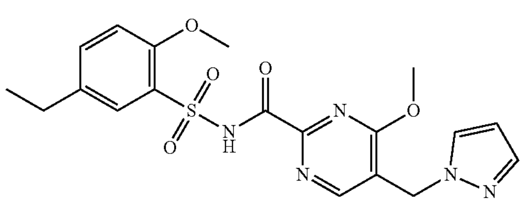 [SMILES: CCc1ccc(OC)c(S(=O)(=O)NC(=O)c2ncc(Cn3cccn3)c(OC)n2)c1] | 5-((1H-pyrazol-1-yl)methyl)-N-((5-ethyl-2-methoxyphenyl)sulfonyl)-4-methoxypyrimidine-2-carboxamide |

TABLE 2-continued

| No. | Structure | Name |
|---|---|---|
| 272 | 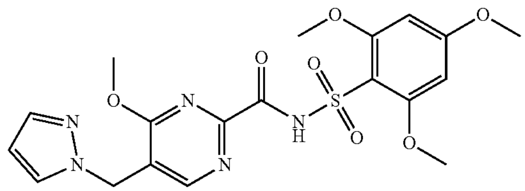 [SMILES: COc1cc(OC)c(S(=O)(=O)NC(=O)c2ncc(Cn3cccn3)c(OC)n2)c(OC)c1] | 5-((1H-pyrazol-1-yl)methyl)-4-methoxy-N-((2,4,6-trimethoxyphenyl)sulfonyl)pyrimidine-2-carboxamide |
| 273 | 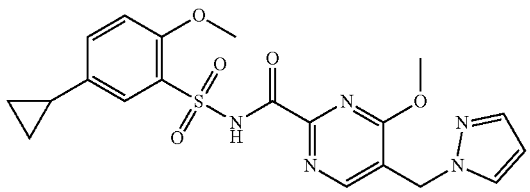 [SMILES: COc1ccc(C2CC2)cc1S(=O)(=O)NC(=O)c1ncc(Cn2cccn2)c(OC)n1] | 5-((1H-pyrazol-1-yl)methyl)-N-((5-cyclopropyl-2-methoxyphenyl)sulfonyl)-4-methoxypyrimidine-2-carboxamide |
| 274 | 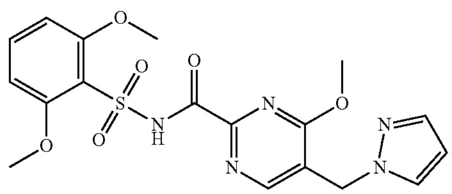 [SMILES: COc1cccc(OC)c1S(=O)(=O)NC(=O)c1ncc(Cn2cccn2)c(OC)n1] | 5-((1H-pyrazol-1-yl)methyl)-N-((2,6-dimethoxyphenyl)sulfonyl)-4-methoxypyrimidine-2-carboxamide |
| 275 | 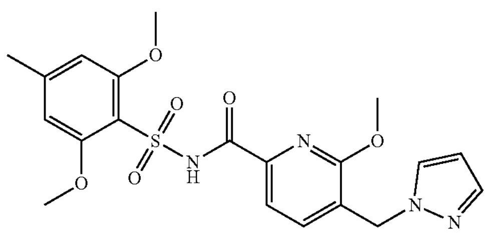 [SMILES: COc1cc(C)cc(OC)c1S(=O)(=O)NC(=O)c1ccc(Cn2cccn2)c(OC)n1] | 5-((1H-pyrazol-1-yl)methyl)-N-((2,6-dimethoxy-4-methylphenyl)sulfonyl)-6-methoxypicolinamide |
| 276 | 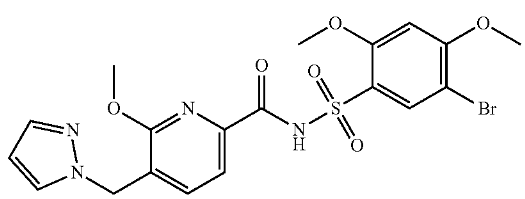 [SMILES: COc1cc(OC)c(S(=O)(=O)NC(=O)c2ccc(Cn3cccn3)c(OC)n2)cc1Br] | 5-((1H-pyrazol-1-yl)methyl)-N-((5-bromo-2,4-dimethoxyphenyl)sulfonyl)-6-methoxypicolinamide |
| 277 | 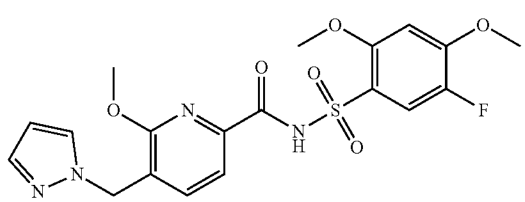 [SMILES: COc1cc(OC)c(S(=O)(=O)NC(=O)c2ccc(Cn3cccn3)c(OC)n2)cc1F] | 5-((1H-pyrazol-1-yl)methyl)-N-((5-fluoro-2,4-dimethoxyphenyl)sulfonyl)-6-methoxypicolinamide |
| 278 | 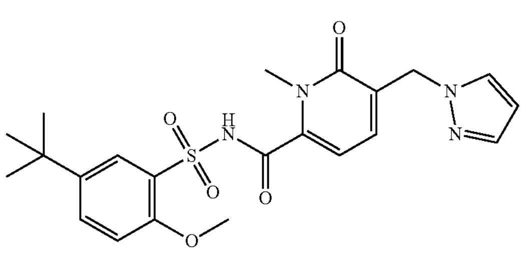 [SMILES: COc1ccc(C(C)(C)C)cc1S(=O)(=O)NC(=O)c1ccc(Cn2cccn2)c(=O)n1C] | 5-((1H-pyrazol-1-yl)methyl)-N-((5-(tert-butyl)-2-methoxyphenyl)sulfonyl)-1-methyl-6-oxo-1,6-dihydropyridine-2-carboxamide |

TABLE 2-continued

| No. | Structure | Name |
|---|---|---|
| 279 | 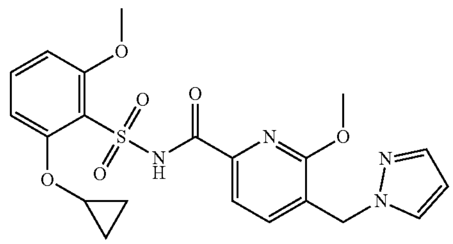 [SMILES: COc1cccc(OC2CC2)c1S(=O)(=O)NC(=O)c1ccc(Cn2cccn2)c(OC)n1] | 5-((1H-pyrazol-1-yl)methyl)-N-((2-cyclopropoxy-6-methoxyphenyl)sulfonyl)-6-methoxypicolinamide |
| 280 | 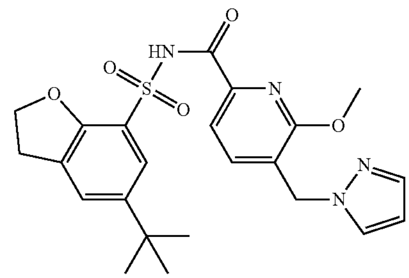 [SMILES: COc1nc(C(=O)NS(=O)(=O)c2cc(C(C)(C)C)cc3c2OCC3)ccc1Cn1cccn1] | 5-((1H-pyrazol-1-yl)methyl)-N-((5-(tert-butyl)-2,3-dihydrobenzofuran-7-yl)sulfonyl)-6-methoxypicolinamide |
| 281 | 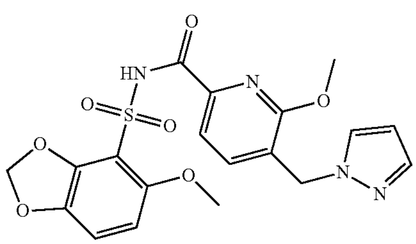 [SMILES: COc1ccc2c(c1S(=O)(=O)NC(=O)c1ccc(Cn3cccn3)c(OC)n1)OCO2] | 5-((1H-pyrazol-1-yl)methyl)-6-methoxy-N-((5-methoxybenzo[d][1,3]dioxol-4-yl)sulfonyl)picolinamide |
| 282 | 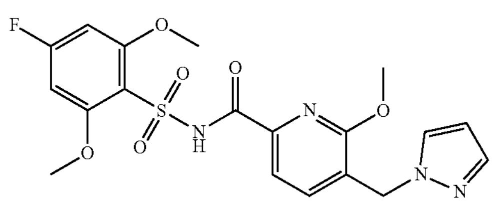 [SMILES: COc1cc(F)cc(OC)c1S(=O)(=O)NC(=O)c1ccc(Cn2cccn2)c(OC)n1] | 5-((1H-pyrazol-1-yl)methyl)-N-((4-fluoro-2,6-dimethoxyphenyl)sulfonyl)-6-methoxypicolinamide |
| 283 | 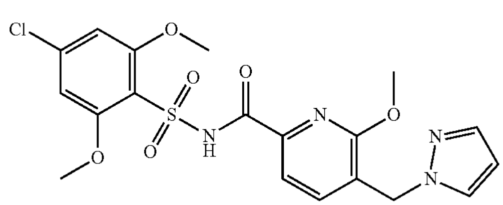 [SMILES: COc1cc(Cl)cc(OC)c1S(=O)(=O)NC(=O)c1ccc(Cn2cccn2)c(OC)n1] | 5-((1H-pyrazol-1-yl)methyl)-N-((4-chloro-2,6-dimethoxyphenyl)sulfonyl)-6-methoxypicolinamide |
| 284 | 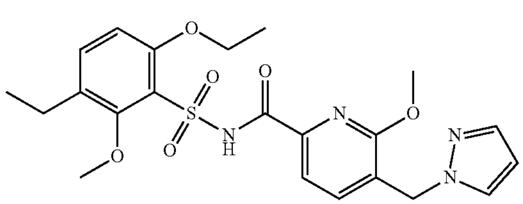 [SMILES: CCOc1ccc(CC)c(OC)c1S(=O)(=O)NC(=O)c1ccc(Cn2cccn2)c(OC)n1] | 5-((1H-pyrazol-1-yl)methyl)-N-((6-ethoxy-3-ethyl-2-methoxyphenyl)sulfonyl)-6-methoxypicolinamide |
| 285 | 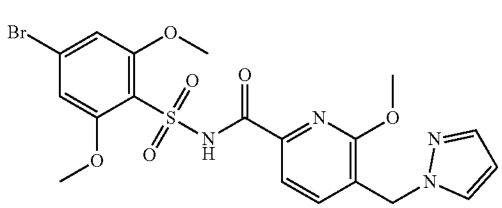 [SMILES: COc1cc(Br)cc(OC)c1S(=O)(=O)NC(=O)c1ccc(Cn2cccn2)c(OC)n1] | 5-((1H-pyrazol-1-yl)methyl)-N-((4-bromo-2,6-dimethoxyphenyl)sulfonyl)-6-methoxypicolinamide |

TABLE 2-continued

Compounds

| No. | Structure | Name |
|---|---|---|
| 286 | 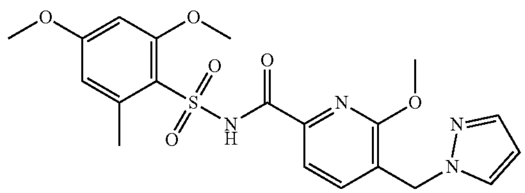 [SMILES: COc1cc(C)c(S(=O)(=O)NC(=O)c2ccc(Cn3cccn3)c(OC)n2)c(OC)c1] | 5-((1H-pyrazol-1-yl)methyl)-N-((2,4-dimethoxy-6-methylphenyl)sulfonyl)-6-methoxypicolinamide |
| 287 | 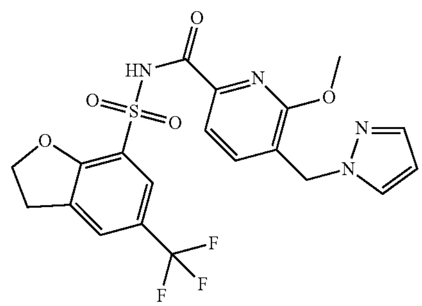 [SMILES: COc1nc(C(=O)NS(=O)(=O)c2cc(C(F)(F)F)cc3c2OCC3)ccc1Cn1cccn1] | 5-((1H-pyrazol-1-yl)methyl)-6-methoxy-N-((5-(trifluoromethyl)-2,3-dihydrobenzofuran-7-yl)sulfonyl)picolinamide |
| 288 | 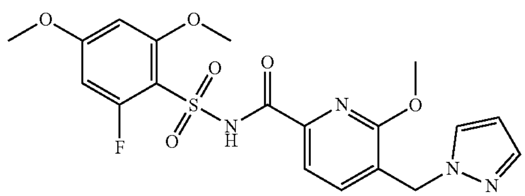 [SMILES: COc1cc(F)c(S(=O)(=O)NC(=O)c2ccc(Cn3cccn3)c(OC)n2)c(OC)c1] | 5-((1H-pyrazol-1-yl)methyl)-N-((2-fluoro-4,6-dimethoxyphenyl)sulfonyl)-6-methoxypicolinamide |
| 289 | 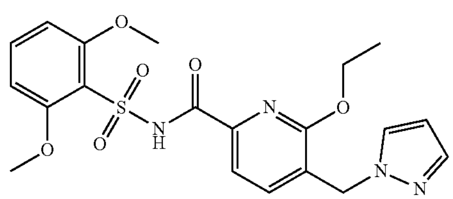 [SMILES: CCOc1nc(C(=O)NS(=O)(=O)c2c(OC)cccc2OC)ccc1Cn1cccn1] | 5-((1H-pyrazol-1-yl)methyl)-N-((2,6-dimethoxyphenyl)sulfonyl)-6-ethoxypicolinamide |

In some embodiments, a compound of Formula (J), (II), (IIa), (IIb), and/or (IIc), or a pharmaceutically acceptable salt thereof, is a compound wherein the compound has the structure:

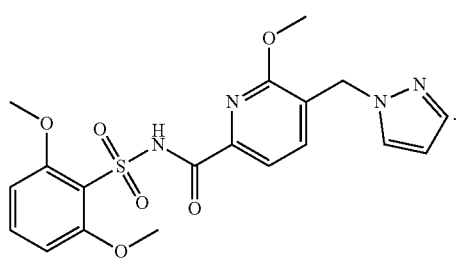 [SMILES: COc1cccc(OC)c1S(=O)(=O)NC(=O)c1ccc(Cn2cccn2)c(OC)n1]

In some embodiments, a compound of Formula (J), (II), (IIa), (IIb), and/or (IIc), is a compound wherein the compound has the structure:

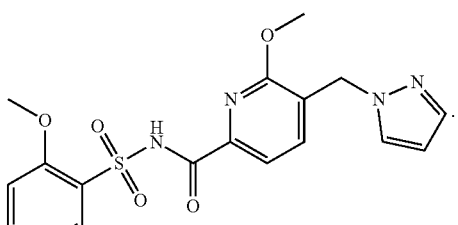

In some embodiments, a compound of Formula (J), (II), (IIa), (IIb), and/or (IIc), or a pharmaceutically acceptable salt thereof, is a compound wherein the compound has the structure:

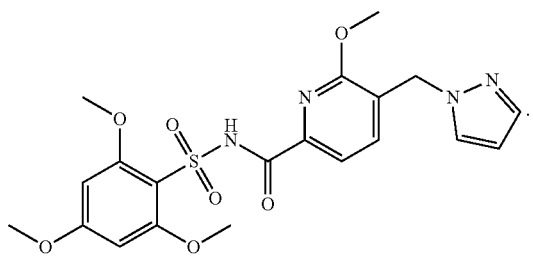 [SMILES: COc1cc(OC)c(S(=O)(=O)NC(=O)c2ccc(Cn3cccn3)c(OC)n2)c(OC)c1]

In some embodiments of a compound of Formula (J), (II), (IIa), (IIb), and/or (IIc), is a compound wherein the compound has the structure:

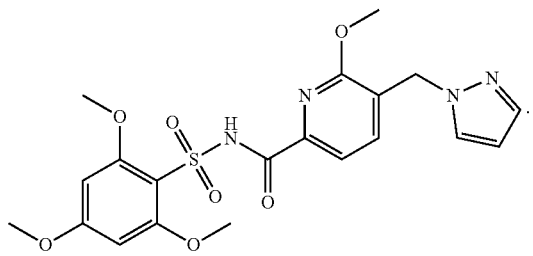 [SMILES: COc1cc(OC)c(S(=O)(=O)NC(=O)c2ccc(Cn3cccn3)c(OC)n2)c(OC)c1]

In some embodiments, a compound of Formula (J), (II), (IIa), (IIb), and/or (IIc), or a pharmaceutically acceptable salt thereof, is a compound wherein the compound has the structure:

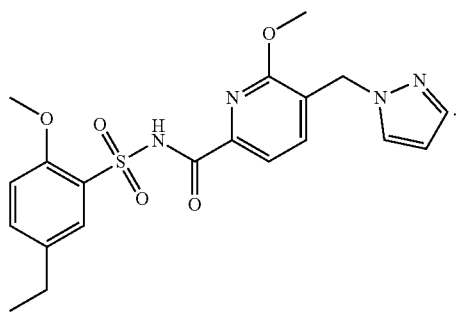 [SMILES: CCc1ccc(OC)c(S(=O)(=O)NC(=O)c2ccc(Cn3cccn3)c(OC)n2)c1]

In some embodiments of a compound of Formula (J), (II), (IIa), (IIb), and/or (IIc), is a compound wherein the compound has the structure:

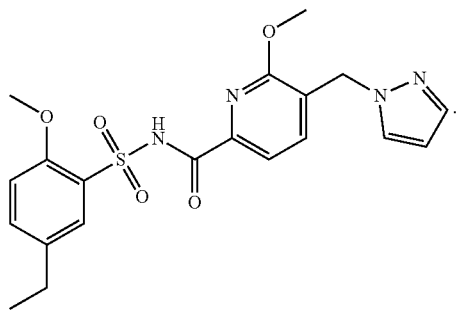 [SMILES: CCc1ccc(OC)c(S(=O)(=O)NC(=O)c2ccc(Cn3cccn3)c(OC)n2)c1]

In some embodiments, a compound of Formula (J) or pharmaceutically acceptable salt thereof is represented by Formula (III):

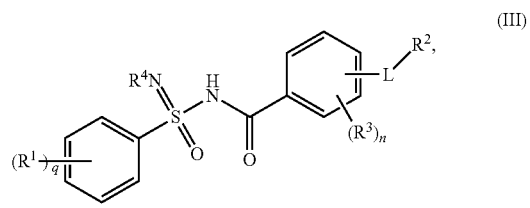

(III)

or a pharmaceutically acceptable salt thereof, wherein
each $R^1$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{1a}$, —C(O)O$R^{1a}$, —OC(O)$R^{1a}$, —C(O)N($R^{1a}$)($R^{1b}$), —N($R^{1a}$)C(O)($R^{1b}$), —OC(O)N($R^{1a}$)($R^{1b}$), —N($R^{1a}$)C(O)(O$R^{1b}$), —S(O)$R^{1a}$, —S(O)$_2$$R^{1a}$, —S(O)$_2$N($R^{1a}$)($R^{1b}$), —S(O)(NH)$R^{1a}$, —S(O)(NH)N($R^{1a}$)($R^{1b}$), —N($R^{1a}$)($R^{1b}$), OH, —CN, —NO$_2$, $C_3$-$C_8$ cycloalkyl, ($C_1$-$C_3$ alkyl)($C_3$-$C_8$ cycloalkyl), heterocycloalkyl, —O—($C_3$-$C_8$ cycloalkyl), ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{1c}$, each alkoxy and alkynyl is substituted with 0, 1, 2, or 3 $R^{1d}$, and each cycloalkyl, heterocycloalkyl, aryl, and heteroaryl is substituted with 0, 1, 2, or 3 $R^{1e}$;

each $R^{1a}$ and $R^{1b}$ is independently hydrogen or $C_1$-$C_6$ alkyl;

each $R^{1c}$ is independently $C_1$-$C_6$ alkoxy, halogen, $C_1$-$C_6$ haloalkoxy, —N$R^{1c1}$$R^{1c2}$, OH, or —CN;

each $R^{11}$ and $R^{1c2}$ is independently hydrogen or $C_1$-$C_6$ alkyl;

each $R^{1d}$ is independently deuterium, $C_3$-$C_8$ cycloalkyl, heterocycloalkyl, $C_6$-$C_{10}$ aryl, or heteroaryl;

each $R^{1e}$ is independently $C_1$-$C_6$ alkyl, $C_1$-$C_6$ alkoxy, halogen, $C_1$-$C_6$ haloalkyl, $C_1$-$C_6$ haloalkoxy, OH, or —CN;

alternatively, two $R^1$ groups on adjacent carbons together with the atoms to which they are attached combine to form a $C_5$-$C_8$cycloalkyl or a heterocycloalkyl substituted with 0, 1, 2, 3, 4, 5, or 6 halogen, $C_1$-$C_4$ alkyl, OH or —CN;

L is —$C_1$-$C_4$ alkylene-, —($C_1$-$C_4$ alkylene)-O—, or —O—;

$R^2$ is a heteroaryl, which is substituted with 0, 1, 2, 3, or 4 $R^{2a}$;

each $R^{2a}$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{2b}$, —C(O)O$R^{2b}$, —OC(O)$R^{2b}$, —C(O)N($R^{2b}$)($R^{2c}$), —N($R^{2b}$)C(O)($R^{2c}$), —S(O)$_2$$R^{2b}$, —S(O)$_2$N($R^{2b}$)($R^{2c}$), —N($R^{2b}$)($R^{2c}$), OH, —CN, or —NO$_2$;

each $R^{2b}$ and $R^{2c}$ is independently hydrogen or $C_1$-$C_6$ alkyl;

each $R^3$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —OC(O)N $(R^{3a})(R^{3b})$, —N($R^{3a}$)C(O)(O$R^{3b}$), —S(O)$R^{3a}$, —S(O)$_2R^{3a}$, —S(O)$_2$N($R^{3a}$)($R^{3b}$), —S(O)(NH)$R^{3a}$, —S(O)(NH)N($R^{3a}$)($R^{3b}$), —N($R^{3a}$)($R^{3b}$), OH, —CN, —NO$_2$, C$_3$-C$_8$ cycloalkyl, (C$_1$-C$_3$ alkyl)(C$_3$-C$_8$ cycloalkyl), —O—(C$_3$-C$_8$ cycloalkyl), heterocycloalkyl, (C$_1$-C$_3$ alkyl)(heterocycloalkyl), —O-(heterocycloalkyl), C$_6$-C$_{10}$ aryl, (C$_1$-C$_3$ alkyl)(C$_6$-C$_{10}$ aryl), —O—(C$_6$-C$_{10}$ aryl), heteroaryl, (C$_1$-C$_3$ alkyl)(heteroaryl), or —O-(heteroaryl), wherein each alkyl is substituted with 0, 1, 2, 3, 4, 5, or 6 $R^{3c}$, each alkoxy is substituted with 0, 1, 2, or 3 $R^{3d}$, and each cycloalkyl, heterocycloalkyl, aryl, and heteroaryl is substituted with 0, 1, 2, or 3 $R^{3e}$; or, two $R^3$ on the same carbon atom together represent an oxo group;

each $R^{3a}$ and $R^{3b}$ is independently hydrogen or C$_1$-C$_6$ alkyl;

each $R^{3c}$ is independently C$_1$-C$_6$ alkoxy, halogen, C$_1$-C$_6$ haloalkoxy, —NR$^{3c1}$R$^{3c2}$, OH, or —CN;

each $R^{3c1}$ and $R^{3c2}$ is independently hydrogen or C$_1$-C$_6$ alkyl;

each $R^{3d}$ is independently C$_3$-C$_8$ cycloalkyl, heterocycloalkyl, phenyl, or heteroaryl;

each $R^{3e}$ is independently C$_1$-C$_6$ alkyl, C$_1$-C$_6$ alkoxy, halogen, C$_1$-C$_6$ haloalkyl, or C$_1$-C$_6$ haloalkoxy;

$R^4$ is hydrogen or C$_1$-C$_6$ alkyl;

subscript n is 0, 1, 2, 3, or 4; and subscript q is 0, 1, 2, 3, or 4;

wherein each heterocycloalkyl is a 3- to 8-membered ring that includes 1 to 4 heteroatoms each independently N, O or S; and each heteroaryl is a 5- to 6-membered ring that includes 1 to 4 heteroatoms each independently N, O or S.

In some embodiments, a compound of Formula (J) or Formula (III) is represented by Formula (IIIa):

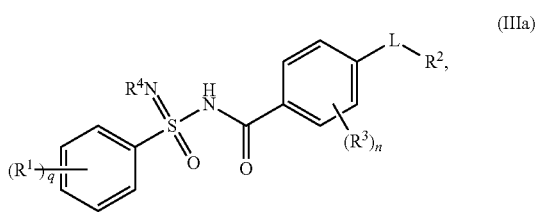

(IIIa)

or a pharmaceutically acceptable salt thereof, wherein $R^1$, q, $R^2$, L, $R^3$, n, and $R^4$ are as described in classes and subclasses herein, both singly and in combination.

In some embodiments, a compound of Formula (J), (III), and/or (IIIa), or pharmaceutically acceptable salt thereof, is represented by Formula (IIIb):

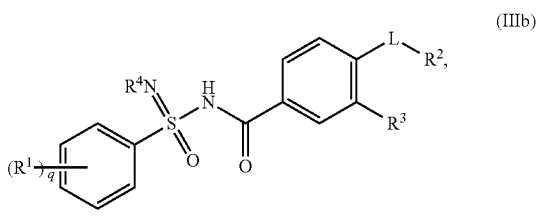

(IIIb)

or a pharmaceutically acceptable salt thereof, wherein $R^1$, q, $R^2$, L, $R^3$, and $R^4$ are as described in classes and subclasses herein, both singly and in combination.

In some embodiments of a compound of Formula (J), (III), (IIIa), and/or (IIIb), or pharmaceutically acceptable salt thereof, the group

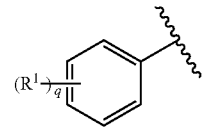

has the structure:

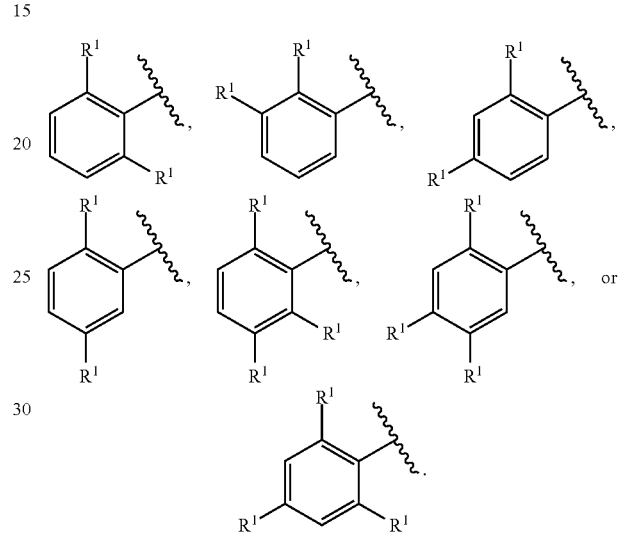

In some embodiments of a compound of Formula (J), (III), (IIIa), and/or (IIIb), or pharmaceutically acceptable salt thereof, each $R^1$ is independently C$_1$-C$_6$ alkyl, C$_1$-C$_6$ alkoxy, C$_1$-C$_6$ hydroxyalkyl, C$_2$-C$_6$ alkoxyalkyl, halogen, C$_1$-C$_6$ haloalkyl, C$_1$-C$_6$ haloalkoxy, OH, —CN, C$_3$-C$_8$ cycloalkyl, (C$_1$-C$_3$ alkyl)(C$_3$-C$_8$ cycloalkyl), —O—(C$_3$-C$_8$ cycloalkyl), heterocycloalkyl, (C$_1$-C$_3$ alkyl)(heterocycloalkyl), —O-(heterocycloalkyl), C$_6$-C$_{10}$ aryl, or heteroaryl, wherein each alkyl is substituted with 0, 1, 2, or 3 $R^{1c}$, and each alkoxy and alkynyl is substituted with 0, 1, 2, or 3 $R^{1d}$; or alternatively, two $R^1$ on adjacent carbons together with the atoms to which they are attached combine to form a C$_5$-C$_8$cycloalkyl or a heterocycloalkyl.

In some embodiments of a compound of Formula (J), (III), (IIIa), and/or (IIIb), or pharmaceutically acceptable salt thereof, each $R^1$ is independently C$_1$-C$_6$ alkyl, C$_1$-C$_6$ alkoxy, C$_1$-C$_6$ hydroxyalkyl, halogen, C$_1$-C$_6$ haloalkyl, C$_1$-C$_6$ haloalkoxy, OH, C$_3$-C$_8$ cycloalkyl, (C$_1$-C$_3$ alkyl)(C$_3$-C$_8$ cycloalkyl), —O—(C$_3$-C$_8$ cycloalkyl), C$_6$-C$_{10}$ aryl, or heteroaryl, wherein each alkyl is substituted with 0 or 1 $R^{1c}$, and each alkoxy and alkynyl is substituted with 0 or 1 Rid; or alternatively, two $R^1$ on adjacent carbons together with the atoms to which they are attached combine to form a C$_5$-C$_8$cycloalkyl or a heterocycloalkyl.

In some embodiments of a compound of Formula (J), (III), (IIIa), and/or (IIIb), or pharmaceutically acceptable salt thereof, each $R^{1a}$ and $R^{1b}$ is independently hydrogen or C$_1$-C$_4$ alkyl.

In some embodiments of a compound of Formula (J), (III), (IIIa), and/or (IIIb), or pharmaceutically acceptable salt thereof, each $R^{1c}$ is halogen, —NR$^{1'1}$R$^{1c2}$, OH, or —CN.

In some embodiments of a compound of Formula (J), (III), (IIIa), and/or (IIIb), or pharmaceutically acceptable salt thereof, each $R^{1d}$ is independently heteroaryl.

In some embodiments of a compound of Formula (J), (III), (IIIa), and/or (IIIb), or pharmaceutically acceptable salt thereof, each $R^{1c}$ is independently $C_1$-$C_4$ alkyl, $C_1$-$C_4$ alkoxy, halogen, $C_1$-$C_4$ haloalkyl, or —CN.

In some embodiments of a compound of Formula (J), (III), (IIIa), and/or (IIIb), or pharmaceutically acceptable salt thereof, each $R^1$ is independently —$CH_3$, —$CH_2CH_3$, —$C(CH_3)_3$, —$OCH_3$, —$OCH(CH_3)_2$, —$OCH_2$-pyridyl, —$C(CH_3)_2OH$, F, Cl, Br, —$CF_3$, —$OCHF_2$, —$OCF_3$, —$OCH_2CF_3$, —$C(CH_3)_2CH_2OH$, —OH, cyclopropyl, cyclopropyloxy, cyclobutyloxy, phenyl, or pyrazolyl; or alternatively, two $R^1$ on adjacent carbons together with the atoms to which they are attached combine to form a cyclopentyl, cyclohexyl, dihydrofuran, tetrahydrofuran, methyltetrahydrofuran, 1,3-dioxole, dihydro-1,3-oxazine, or methyldihydrofuran. In some embodiments, two $R^1$ on adjacent carbon atoms combine to form:

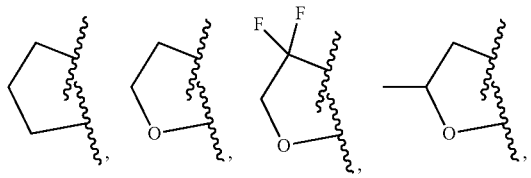

In some embodiments of a compound of Formula (J), (III), (IIIa), and/or (IIIb), or pharmaceutically acceptable salt thereof, L is —$CH_2$—, —$CH_2O$—, or —O—.

In some embodiments of a compound of Formula (J), (III), (IIIa), and/or (IIIb), or pharmaceutically acceptable salt thereof, L is —$CH_2$—.

In some embodiments of a compound of Formula (J), (III), (IIIa), and/or (IIIb), or pharmaceutically acceptable salt thereof, $R^2$ is pyrrolyl, furyl, thienyl, pyrazolyl, isoxazolyl, oxazolyl, isothiazolyl, thiazolyl, triazolyl, oxadiazolyl, thiadiazolyl, pyridyl, pyridazinyl, pyrimidyl, or pyrazinyl, which are each substituted by 0, 1, or 2 $R^{2a}$.

In some embodiments of a compound of Formula (J), (III), (IIIa), and/or (IIIb), or pharmaceutically acceptable salt thereof, each $R^{2a}$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, OH, or —CN.

In some embodiments of a compound of Formula (J), (III), (IIIa), and/or (IIIb), or pharmaceutically acceptable salt thereof, each $R^{2b}$ and $R^{2c}$ is independently hydrogen or $C_1$-$C_4$ alkyl.

In some embodiments of a compound of Formula (J), (III), (IIIa), and/or (IIIb), or pharmaceutically acceptable salt thereof, $R^2$ is

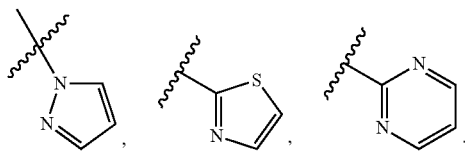

In some embodiments of a compound of Formula (J), (III), (IIIa), and/or (IIIb), or pharmaceutically acceptable salt thereof, $R^2$ is

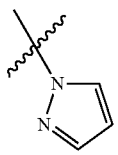

In some embodiments of a compound of Formula (J), (III), (IIIa), and/or (IIIb), or pharmaceutically acceptable salt thereof, each $R^3$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —$C(O)R^{3a}$, —$C(O)OR^{3a}$, —$OC(O)R^{3a}$, —$C(O)N(R^{3a})(R^{3b})$, —$N(R^{3a})C(O)(R^{3b})$, —$S(O)_2R^{3a}$, —$S(O)_2N(R^{3a})(R^{3b})$, OH, —CN, $C_3$-$C_8$ cycloalkyl, or heterocycloalkyl.

In some embodiments, a compound of Formula (J), (III), (IIIa), and/or (IIIb), or pharmaceutically acceptable salt thereof, is a compound, or pharmaceutically acceptable salt thereof, wherein two $R^3$ on the same carbon atom together represent an oxo group.

In some embodiments of a compound of Formula (J), (III), (IIIa), and/or (IIIb), or pharmaceutically acceptable salt thereof, each $R^{3a}$ and $R^{3b}$ is independently hydrogen or $C_1$-$C_4$ alkyl.

In some embodiments of a compound of Formula (J), (III), (IIIa), and/or (IIIb), or pharmaceutically acceptable salt thereof, each $R^{3c}$ is halogen, —$NR^{3c1}R^{3c2}$, OH, or —CN.

In some embodiments of a compound of Formula (J), (III), (IIIa), and/or (IIIb), or pharmaceutically acceptable salt thereof, each $R^{3d}$ is independently heteroaryl.

In some embodiments of a compound of Formula (J), (III), (IIIa), and/or (IIIb), or pharmaceutically acceptable salt thereof, each $R^{3e}$ is independently $C_1$-$C_4$ alkyl, $C_1$-$C_4$ alkoxy, halogen, or $C_1$-$C_4$ haloalkyl.

In some embodiments of a compound of Formula (J), (III), (IIIa), and/or (IIIb), or pharmaceutically acceptable salt thereof, each $R^3$ is independently $C_1$-$C_6$ alkyl, $C_1$-$C_6$ alkoxy, halogen, $C_1$-$C_6$ haloalkyl, $C_1$-$C_6$ haloalkoxy, —CN, or $C_3$-$C_8$ cycloalkyl.

In some embodiments of a compound of Formula (J), (III), (IIIa), and/or (IIIb), or pharmaceutically acceptable salt thereof, each $R^3$ is independently $C_1$-$C_4$ alkyl, $C_1$-$C_4$ alkoxy, halogen, $C_1$-$C_4$ haloalkyl, $C_1$-$C_4$ haloalkoxy, —CN, or $C_3$-$C_6$ cycloalkyl.

In some embodiments of a compound of Formula (J), (III), (IIIa), and/or (IIIb), or pharmaceutically acceptable salt thereof, each $R^3$ is independently Me, OMe, OEt, $CHF_2$, $CF_3$, $OCHF_2$, $OCF_3$, F, Br, CN, or cyclopropyl.

In some embodiments of a compound of Formula (J), (III), (IIIa), and/or (IIIb), or pharmaceutically acceptable salt thereof, $R^4$ is hydrogen or $C_1$-$C_4$ alkyl. In some embodiments, $R^4$ is Me, Et, or iPr. In some embodiments, $R^4$ is hydrogen.

In some embodiments of a compound of Formula (J), (III), (IIIa), and/or (IIIb), or pharmaceutically acceptable salt thereof, subscript q is 1, 2, or 3.

In some embodiments of a compound of Formula (J), (III), (IIIa), and/or (IIIb), or pharmaceutically acceptable salt thereof, subscript n is 1 or 2.

In some embodiments, a compound of Formula (J), (III), (IIIa), and/or (IIIb), or a pharmaceutically acceptable salt thereof, is a compound wherein the compound has the structure of a compound shown in Table 3, or a pharmaceutically acceptable salt thereof.

TABLE 3

| No. | Structure | Name |
| --- | --- | --- |
| 71 | 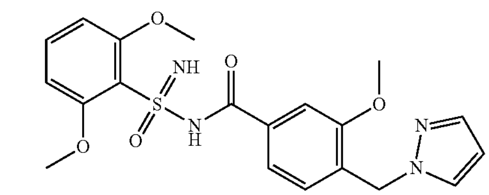 | 4-((1H-pyrazol-1-yl)methyl)-N-(2,6-dimethoxyphenylsulfonimidoyl)-3-methoxybenzamide |
| 72 | 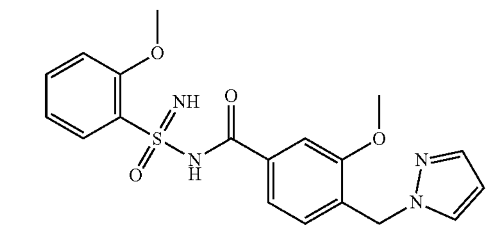 [SMILES: COc1cc(C(=O)NS(=N)(=O)c2ccccc2OC)ccc1Cn1cccn1] | 4-((1H-pyrazol-1-yl)methyl)-3-methoxy-N-(2-methoxyphenylsulfonimidoyl)benzamide |
| 73 | 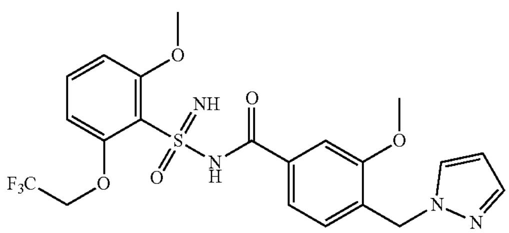 [SMILES: COc1cc(C(=O)NS(=N)(=O)c2c(OC)cccc2OCC(F)(F)F)ccc1Cn1cccn1] | 4-((1H-pyrazol-1-yl)methyl)-3-methoxy-N-(2-methoxy-6-(2,2,2-trifluoroethoxy)phenylsulfonimidoyl)benzamide |
| 74 | 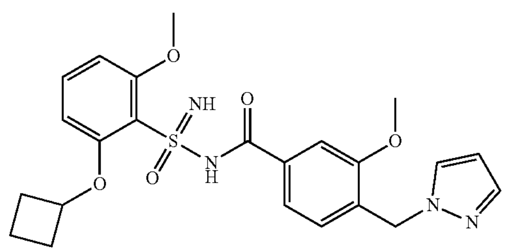 [SMILES: COc1cc(C(=O)NS(=N)(=O)c2c(OC)cccc2OC2CCC2)ccc1Cn1cccn1] | 4-((1H-pyrazol-1-yl)methyl)-N-(2-cyclobutoxy-6-methoxyphenylsulfonimidoyl)-3-methoxybenzamide |
| 75 | 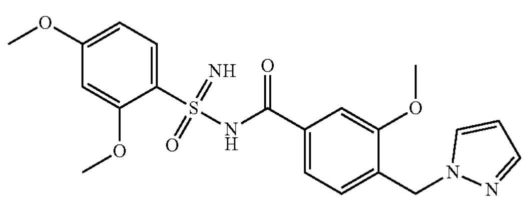 [SMILES: COc1ccc(S(=N)(=O)NC(=O)c2ccc(Cn3cccn3)c(OC)c2)c(OC)c1] | 4-((1H-pyrazol-1-yl)methyl)-N-(2,4-dimethoxyphenylsulfonimidoyl)-3-methoxybenzamide |
| 291a | 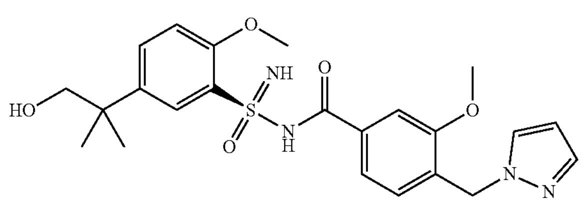 [SMILES: COc1cc(C(=O)N[S@@](=N)(=O)c2cc(C(C)(C)CO)ccc2OC)ccc1Cn1cccn1] | (R)-4-((1H-pyrazol-1-yl)methyl)-N-(5-(1-hydroxy-2-methylpropan-2-yl)-2-methoxyphenylsulfonimidoyl)-3-methoxybenzamide |

TABLE 3-continued

| No. | Structure | Name |
|---|---|---|
| 291b | 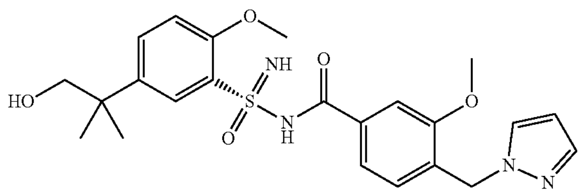 [SMILES: COc1cc(C(=O)N[S@](=N)(=O)c2cc(C(C)(C)CO)ccc2OC)ccc1Cn1cccn1] | (S)-4-((1H-pyrazol-1-yl)methyl)-N-(5-(1-hydroxy-2-methylpropan-2-yl)-2-methoxyphenylsulfonimidoyl)-3-methoxybenzamide |
| 292 | 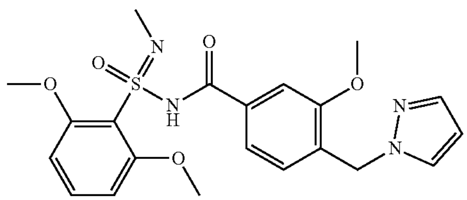 [SMILES: CN=S(=O)(NC(=O)c1ccc(Cn2cccn2)c(OC)c1)c1c(OC)cccc1OC] | 4-((1H-pyrazol-1-yl)methyl)-N-((2,6-dimethoxyphenyl)(methylamino)(oxo)-16-sulfaneylidene)-3-methoxybenzamide |
| 295a | 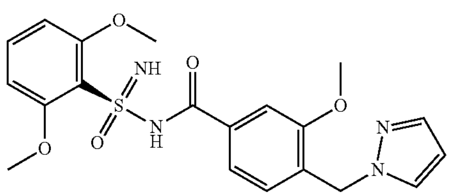 [SMILES: COc1cc(C(=O)N[S@@](=N)(=O)c2c(OC)cccc2OC)ccc1Cn1cccn1] | (R)-4-((1H-pyrazol-1-yl)methyl)-N-(2,6-dimethoxyphenylsulfonimidoyl)-3-methoxybenzamide |
| 295b | 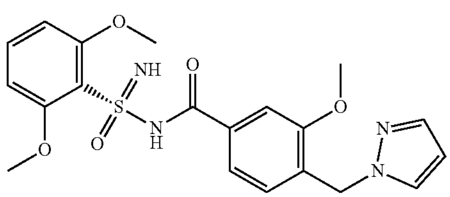 | (S)-4-((1H-pyrazol-1-yl)methyl)-N-(2,6-dimethoxyphenylsulfonimidoyl)-3-methoxybenzamide |
| 299 | 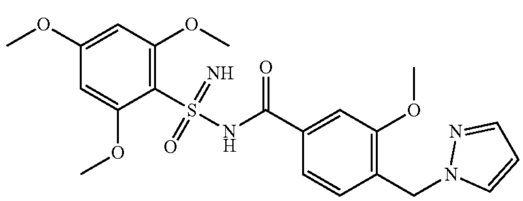 | 4-((1H-pyrazol-1-yl)methyl)-3-methoxy-N-(2,4,6-trimethoxyphenylsulfonimidoyl)benzamide |
| 299a | 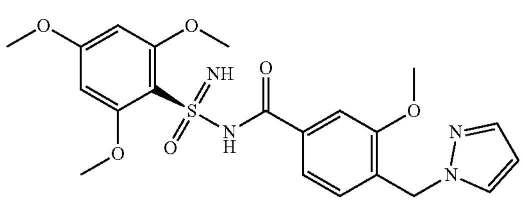 | (R)-4-((1H-pyrazol-1-yl)methyl)-3-methoxy-N-(2,4,6-trimethoxyphenylsulfonimidoyl)benzamide |
| 299b | 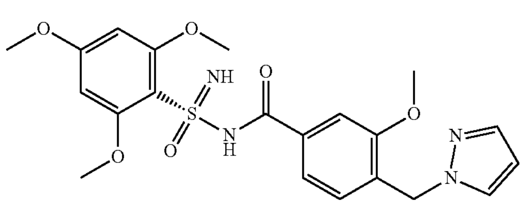 | (S)-4-((1H-pyrazol-1-yl)methyl)-3-methoxy-N-(2,4,6-trimethoxyphenylsulfonimidoyl)benzamide |

TABLE 3-continued

Compounds

| No. | Structure | Name |
|---|---|---|
| 300a | 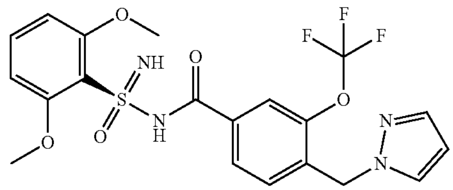 [SMILES: COc1cccc(OC)c1[S@](=N)(=O)NC(=O)c1ccc(Cn2cccn2)c(OC(F)(F)F)c1] | (R)-4-((1H-pyrazol-1-yl)methyl)-N-(2,6-dimethoxyphenylsulfonimidoyl)-3-(trifluoromethoxy)benzamide |
| 300b | 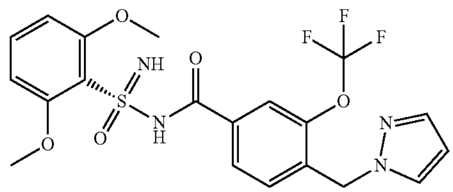 [SMILES: COc1cccc(OC)c1[S@@](=N)(=O)NC(=O)c1ccc(Cn2cccn2)c(OC(F)(F)F)c1] | (S)-4-((1H-pyrazol-1-yl)methyl)-N-(2,6-dimethoxyphenylsulfonimidoyl)-3-(trifluoromethoxy)benzamide |
| 302a | 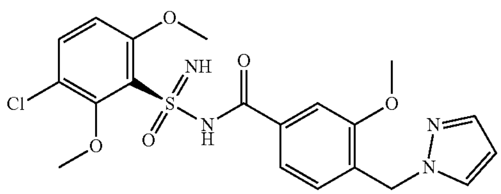 [SMILES: COc1cc(C(=O)N[S@@](=N)(=O)c2c(OC)ccc(Cl)c2OC)ccc1Cn1cccn1] | (R)-4-((1H-pyrazol-1-yl)methyl)-N-(3-chloro-2,6-dimethoxyphenylsulfonimidoyl)-3-methoxybenzamide |
| 302b | 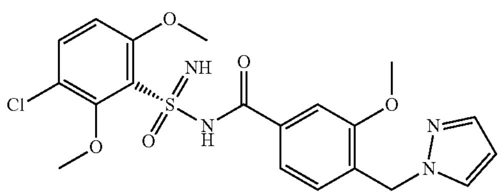 [SMILES: COc1cc(C(=O)N[S@](=N)(=O)c2c(OC)ccc(Cl)c2OC)ccc1Cn1cccn1] | (S)-4-((1H-pyrazol-1-yl)methyl)-N-(3-chloro-2,6-dimethoxyphenylsulfonimidoyl)-3-methoxybenzamide |
| 304a | 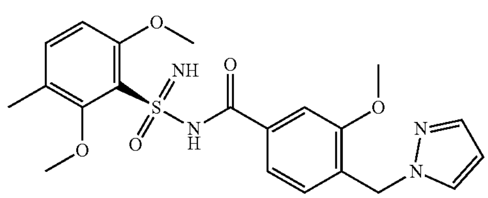 | (R)-4-((1H-pyrazol-1-yl)methyl)-N-(2,6-dimethoxy-3-methylphenylsulfonimidoyl)-3-methoxybenzamide |
| 304b | 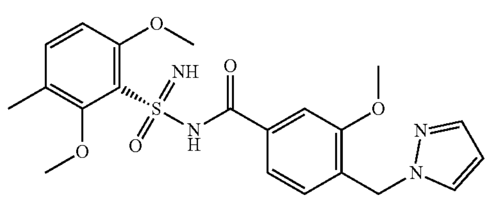 [SMILES: COc1cc(C(=O)N[S@](=N)(=O)c2c(OC)ccc(C)c2OC)ccc1Cn1cccn1] | (S)-4-((1H-pyrazol-1-yl)methyl)-N-(2,6-dimethoxy-3-methylphenylsulfonimidoyl)-3-methoxybenzamide |

In some embodiments, a compound of Formula (J) is represented by Formula (IV):

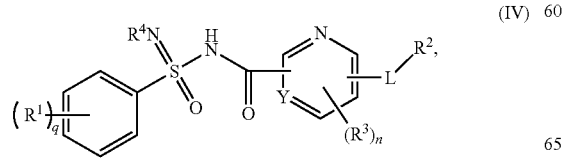

(IV)

or a pharmaceutically acceptable salt thereof, wherein each $R^1$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{1a}$, —C(O)O$R^{1a}$, —OC(O)$R^{1a}$, —C(O)N($R^{1a}$)($R^{1b}$), —N($R^{1a}$)C(O)($R^{1b}$), —OC(O)N($R^{1a}$)($R^{1b}$), —N($R^{1a}$)C(O)(O$R^{1b}$), —S(O)$R^{1a}$, —S(O)$_2$$R^{1a}$, —S(O)$_2$N($R^{1a}$)($R^{1b}$), —S(O)(NH)$R^{1a}$, —S(O)(NH)N($R^{1a}$)($R^{1b}$), —N($R^{1a}$)($R^{1b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-

(heteroaryl), wherein each alkyl is substituted with 0, 1, 2, 3, 4, 5, or 6 $R^{1c}$, each alkoxy and alkynyl is substituted with 0, 1, 2, or 3 $R^{1d}$, and each cycloalkyl, heterocycloalkyl, aryl, and heteroaryl is substituted with 0, 1, 2, or 3 $R^{1e}$;

each $R^{1a}$ and $R^{1b}$ is independently hydrogen or $C_1$-$C_6$ alkyl;

each $R^{1c}$ is independently $C_1$-$C_6$ alkoxy, halogen, $C_1$-$C_6$ haloalkoxy, —$NR^{1c1}R^{1c2}$, OH, or —CN;

each $R^{1c1}$ and $R^{1c2}$ is independently hydrogen or $C_1$-$C_6$ alkyl;

each $R^{1d}$ is independently deuterium, $C_3$-$C_8$ cycloalkyl, heterocycloalkyl, $C_6$-$C_{10}$ aryl, or heteroaryl;

each $R^{1e}$ is independently $C_1$-$C_6$ alkyl, $C_1$-$C_6$ alkoxy, halogen, $C_1$-$C_6$ haloalkyl, $C_1$-$C_6$ haloalkoxy, OH, or —CN;

alternatively, two $R^1$ groups on adjacent carbons together with the atoms to which they are attached combine to form a $C_5$-$C_8$ cycloalkyl or a heterocycloalkyl substituted with 0, 1, 2, 3, 4, 5, or 6 halogen, $C_1$-$C_4$ alkyl, OH or —CN;

L is —$C_1$-$C_4$ alkylene-, —($C_1$-$C_4$ alkylene)-O—, or —O—;

$R^2$ is a heteroaryl, which is substituted with 0, 1, 2, 3, or 4 $R^{2a}$;

each $R^{2a}$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{2b}$, —C(O)O$R^{2b}$, —OC(O)$R^{2b}$, —C(O)N($R^{2b}$)($R^{2c}$), —N($R^{2b}$)C(O)($R^{2c}$), —S(O)$_2$$R^{2b}$, —S(O)$_2$N($R^{2b}$)($R^{2c}$), —N($R^{2b}$)($R^{2c}$), OH, —CN, or —NO$_2$;

each $R^{2b}$ and $R^{2c}$ is independently hydrogen or $C_1$-$C_6$ alkyl;

Y is CH, $CR^3$, or N;

each $R^3$ is independently $C_1$-$C_6$ alkyl, $C_2$-$C_6$ alkenyl, $C_2$-$C_6$ alkynyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —OC(O)N($R^{3a}$)($R^{3b}$), —N($R^{3a}$)C(O)(O$R^{3b}$), —S(O)$R^{3a}$, —S(O)$_2$$R^{3a}$, —S(O)$_2$N($R^{3a}$)($R^{3b}$), —S(O)(NH)$R^{3a}$, —S(O)(NH)N($R^{3a}$)($R^{3b}$), —N($R^{3a}$)($R^{3b}$), OH, —CN, —NO$_2$, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, ($C_1$-$C_3$ alkyl)($C_6$-$C_{10}$ aryl), —O—($C_6$-$C_{10}$ aryl), heteroaryl, ($C_1$-$C_3$ alkyl)(heteroaryl), or —O-(heteroaryl), wherein each alkyl is substituted with 0, 1, 2, 3, 4, 5, or 6 $R^{3c}$, each alkoxy is substituted with 0, 1, 2, or 3 $R^{3d}$, and each cycloalkyl, heterocycloalkyl, aryl, and heteroaryl is substituted with 0, 1, 2, or 3 $R^{3e}$; or, two $R^3$ on the same carbon atom together represent an oxo group;

each $R^{3a}$ and $R^{3b}$ is independently hydrogen or $C_1$-$C_6$ alkyl;

each $R^{3c}$ is independently $C_1$-$C_6$ alkoxy, halogen, $C_1$-$C_6$ haloalkoxy, —$NR^{3c1}R^{3c2}$, OH, or —CN;

each $R^{3c1}$ and $R^{3c2}$ is independently hydrogen or $C_1$-$C_6$ alkyl;

each $R^{3d}$ is independently $C_3$-$C_8$ cycloalkyl, heterocycloalkyl, phenyl, or heteroaryl;

each $R^{3e}$ is independently $C_1$-$C_6$ alkyl, $C_1$-$C_6$ alkoxy, halogen, $C_1$-$C_6$ haloalkyl, or $C_1$-$C_6$ haloalkoxy;

$R^4$ is hydrogen or $C_1$-$C_6$ alkyl;

subscript n is 0, 1, 2, 3, or 4; and subscript q is 0, 1, 2, 3, or 4;

wherein each heterocycloalkyl is a 3- to 8-membered ring that includes 1 to 4 heteroatoms each independently N, O or S; and each heteroaryl is a 5- to 6-membered ring that includes 1 to 4 heteroatoms each independently N, O or S.

In some embodiments, a compound of Formula (J), Formula (IV), or a pharmaceutically acceptable salt thereof is represented by Formula (IVa):

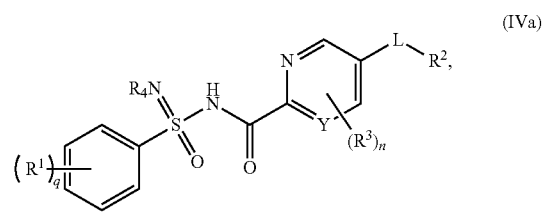

(IVa)

or a pharmaceutically acceptable salt thereof, wherein $R^1$, q, $R^2$, L, $R^3$, n, and $R^4$ are as described in classes and subclasses herein, both singly and in combination, and Y is N, CH, or $CR^3$.

In some embodiments, a compound of Formula (J), (IV), and/or (IVa), or a pharmaceutically acceptable salt thereof is represented by Formula (IVb):

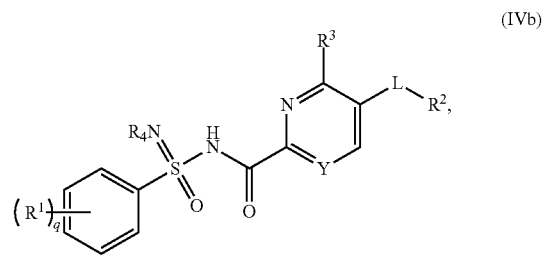

(IVb)

or a pharmaceutically acceptable salt thereof, wherein $R^1$, q, $R^2$, L, $R^3$, and $R^4$ are as described in classes and subclasses herein, both singly and in combination, and Y is N, CH, or $CR^3$.

In some embodiments, a compound of Formula (J), (IV), (IVa), and/or (IVb), or pharmaceutically acceptable salt thereof, is a compound, or pharmaceutically acceptable salt thereof, wherein Y is N. In some embodiments, Y is $CR^3$. In some embodiments, Y is CH.

In some embodiments, a compound of (J), (IV), (IVa), and/or (IVb) is represented by Formula (IVc):

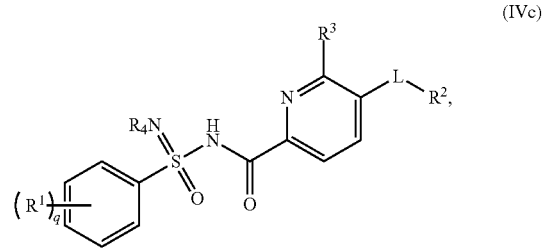

(IVc)

or a pharmaceutically acceptable salt thereof, wherein $R^1$, q, $R^2$, L, $R^3$, and $R^4$ are as described in classes and subclasses herein, both singly and in combination.

In some embodiments of a compound of Formula (J), (IV), (IVa), (IVb), and/or (IVc), or a pharmaceutically acceptable salt thereof,
the group

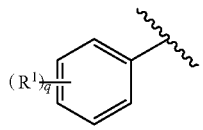

has the structure:

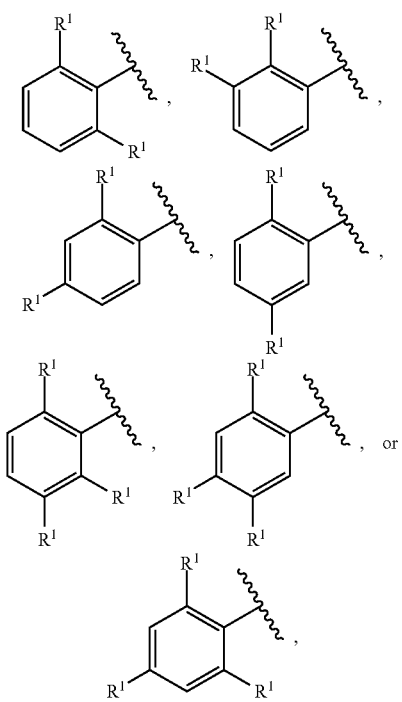

wherein $R^1$ is as described in classes and subclasses herein.

In some embodiments of a compound of Formula (J), (IV), (IVa), (IVb), and/or (IVc), or a pharmaceutically acceptable salt thereof, each $R^1$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, OH, —CN, $C_3$-$C_8$ cycloalkyl, ($C_1$-$C_3$ alkyl)($C_3$-$C_8$ cycloalkyl), —O—($C_3$-$C_8$ cycloalkyl), heterocycloalkyl, ($C_1$-$C_3$ alkyl)(heterocycloalkyl), —O-(heterocycloalkyl), $C_6$-$C_{10}$ aryl, or heteroaryl, wherein each alkyl is substituted with 0, 1, 2, or 3 $R^{1c}$, and each alkoxy and alkynyl is substituted with 0, 1, 2, or 3 $R^{1d}$; or alternatively, two $R^1$ on adjacent carbons together with the atoms to which they are attached combine to form a $C_5$-$C_8$ cycloalkyl or a heterocycloalkyl.

In some embodiments of a compound of Formula (J), (IV), (IVa), (IVb), and/or (IVc), or a pharmaceutically acceptable salt thereof, each $R^1$ is independently $C_1$-$C_6$ alkyl, $C_1$-$C_6$ alkoxy, $C_1$-$C_6$ hydroxyalkyl, halogen, $C_1$-$C_6$ haloalkyl, $C_1$-$C_6$ haloalkoxy, OH, $C_3$-$C_8$ cycloalkyl, ($C_1$-$C_3$ alkyl)($C_3$-$C_8$ cycloalkyl), —O—($C_3$-$C_8$ cycloalkyl), $C_6$-$C_{10}$ aryl, or heteroaryl, wherein each alkyl is substituted with 0 or 1 $R^{1c}$, and each alkoxy and alkynyl is substituted with 0 or 1 $R^{1d}$; or alternatively, two $R^1$ on adjacent carbons together with the atoms to which they are attached combine to form a $C_5$-$C_8$ cycloalkyl or a heterocycloalkyl.

In some embodiments of a compound of Formula (J), (IV), (IVa), (IVb), and/or (IVc), or a pharmaceutically acceptable salt thereof, each $R^{1a}$ and $R^{1b}$ is independently hydrogen or $C_1$-$C_3$ alkyl.

In some embodiments of a compound of Formula (J), (IV), (IVa), (IVb), and/or (IVc), or a pharmaceutically acceptable salt thereof, each $R^{1c}$ is halogen, —$NR^{1c1}R^{1c2}$, OH, or —CN.

In some embodiments of a compound of Formula (J), (IV), (IVa), (IVb), and/or (IVc), or a pharmaceutically acceptable salt thereof, each $R^{1d}$ is independently heteroaryl.

In some embodiments of a compound of Formula (J), (IV), (IVa), (IVb), and/or (IVc), or a pharmaceutically acceptable salt thereof, each $R^{1e}$ is independently $C_1$-$C_4$ alkyl, $C_1$-$C_4$ alkoxy, halogen, $C_1$-$C_4$ haloalkyl, or —CN.

In some embodiments of a compound of Formula (J), (IV), (IVa), (IVb), and/or (IVc), or a pharmaceutically acceptable salt thereof, each $R^1$ is independently —$CH_3$, —$CH_2CH_3$, —$C(CH_3)_3$, —$OCH_3$, —$OCH(CH_3)_2$, —$C(CH_3)_2OH$, —$C(CH_3)_2CH_2$ OH, —$C(CH_3)(CH_2CH_3)$ OH, F, Cl, Br, —$CF_3$, —$OCHF_2$, —$OCF_3$, —$OCH_2CF_3$, cyclopropyl, cyclopropyloxy, cyclobutyloxy,

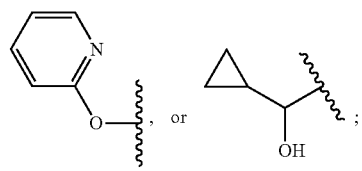 [SMILES: *Oc1ccccn1 ; *C(O)C1CC1]

or
two $R^1$ on adjacent carbons together with the atoms to which they are attached combine to form a cyclopentyl, cyclohexyl, dihydrofuran, tetrahydrofuran, methyltetrahydrofuran, 1,3-dioxole, dihydro-1,3-oxazine, or methyldihydrofuran. In some embodiments, two $R^1$ on adjacent carbon atoms combine to form:

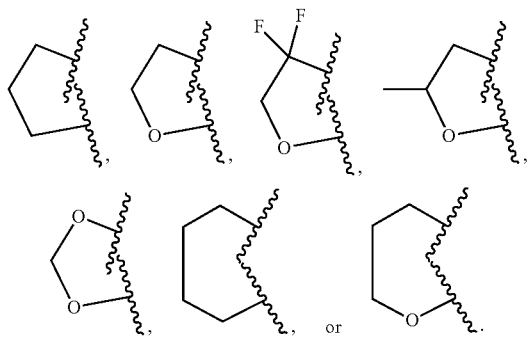

In some embodiments of a compound of Formula (J), (IV), (IVa), (IVb), and/or (IVc), or a pharmaceutically acceptable salt thereof, L is —$CH_2$—, —$CH_2O$—, or —O—.

In some embodiments of a compound of Formula (J), (IV), (IVa), (IVb), and/or (IVc), or a pharmaceutically acceptable salt thereof, L is —$CH_2$—.

In some embodiments of a compound of Formula (J), (IV), (IVa), (IVb), and/or (IVc), or a pharmaceutically acceptable salt thereof, $R^2$ is pyrrolyl, furyl, thienyl, pyrazolyl, isoxazolyl, oxazolyl, isothiazolyl, thiazolyl, triazolyl, oxadiazolyl, thiadiazolyl, pyridyl, pyridazinyl, pyrimidyl, or pyrazinyl, which are each substituted by 0, 1, or 2 $R^{2a}$.

In some embodiments of a compound of Formula (J), (IV), (IVa), (IVb), and/or (IVc), or a pharmaceutically acceptable salt thereof, each $R^{2a}$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, OH, or —CN.

In some embodiments of a compound of Formula (J), (IV), (IVa), (IVb), and/or (IVc), or a pharmaceutically acceptable salt thereof, each $R^{2b}$ and $R^{2c}$ is independently hydrogen or $C_1$-$C_4$ alkyl.

In some embodiments of a compound of Formula (J), (IV), (IVa), (IVb), and/or (IVc), or pharmaceutically acceptable salt thereof, $R^2$ is

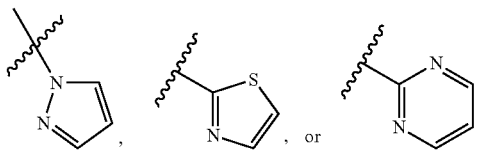

, or

In some embodiments of a compound of Formula (J), (IV), (IVa), (IVb), and/or (IVc), or a pharmaceutically acceptable salt thereof, $R^2$ is

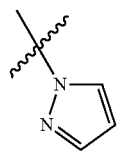

.

In some embodiments of a compound of Formula (J), (IV), (IVa), (IVb), and/or (IVc), or a pharmaceutically acceptable salt thereof, each $R^3$ is independently $C_1$-$C_6$ alkyl, $C_1$-$C_6$ alkoxy, $C_1$-$C_6$ hydroxyalkyl, $C_2$-$C_6$ alkoxyalkyl, halogen, $C_1$-$C_6$ haloalkyl, $C_1$-$C_6$ haloalkoxy, —C(O)$R^{3a}$, —C(O)O$R^{3a}$, —OC(O)$R^{3a}$, —C(O)N($R^{3a}$)($R^{3b}$), —N($R^{3a}$)C(O)($R^{3b}$), —S(O)$_2$$R^{3a}$, —S(O)$_2$N($R^{3a}$)($R^{3b}$), OH, —CN, $C_3$-$C_8$ cycloalkyl, or heterocycloalkyl.

In some embodiments, a compound of Formula (J), (IV), (IVa), (IVb), and/or (IVc), or pharmaceutically acceptable salt thereof, is a compound, or pharmaceutically acceptable salt thereof, wherein two $R^3$ on the same carbon atom together represent an oxo group.

In some embodiments of a compound of Formula (J), (IV), (IVa), (IVb), and/or (IVc), or a pharmaceutically acceptable salt thereof, each $R^{3a}$ and $R^{3b}$ is independently hydrogen or $C_1$-$C_4$ alkyl.

In some embodiments of a compound of Formula (J), (IV), (IVa), (IVb), and/or (IVc), or a pharmaceutically acceptable salt thereof, each $R^{3c}$ is halogen, —N$R^{3c1}$$R^{3c2}$, OH, or —CN.

In some embodiments of a compound of Formula (J), (IV), (IVa), (IVb), and/or (IVc), or a pharmaceutically acceptable salt thereof, each $R^{3d}$ is independently heteroaryl.

In some embodiments of a compound of Formula (J), (IV), (IVa), (IVb), and/or (IVc), or a pharmaceutically acceptable salt thereof, each $R^{3e}$ is independently $C_1$-$C_4$ alkyl, $C_1$-$C_4$ alkoxy, halogen, or $C_1$-$C_4$ haloalkyl.

In some embodiments of a compound of Formula (J), (IV), (IVa), (IVb), and/or (IVc), or a pharmaceutically acceptable salt thereof, each $R^3$ is independently $C_1$-$C_6$ alkyl, $C_1$-$C_6$ alkoxy, $C_1$-$C_6$ haloalkyl, $C_1$-$C_6$ haloalkoxy, —CN, or $C_3$-$C_8$ cycloalkyl.

In some embodiments of a compound of Formula (J), (IV), (IVa), (IVb), and/or (IVc), or a pharmaceutically acceptable salt thereof, each $R^3$ is independently $C_1$-$C_4$ alkyl, $C_1$-$C_4$ alkoxy, $C_1$-$C_4$ haloalkyl, $C_1$-$C_4$ haloalkoxy, —CN, or $C_3$-$C_6$ cycloalkyl.

In some embodiments of a compound of Formula (J), (IV), (IVa), (IVb), and/or (IVc), or a pharmaceutically acceptable salt thereof, each $R^3$ is independently Me, Ome, $CHF_2$, $CF_3$, $OCHF_2$, $OCF_3$, or cyclopropyl.

In some embodiments of a compound of Formula (J), (IV), (IVa), (IVb), and/or (IVc), pharmaceutically acceptable salt thereof, $R^4$ is hydrogen or $C_1$-$C_4$ alkyl. In some embodiments, $R^4$ is Me, Et, or iPr. In some embodiments, $R^4$ is hydrogen.

In some embodiments of a compound of Formula (J), (IV), (IVa), (IVb), and/or (IVc), or a pharmaceutically acceptable salt thereof, subscript q is 1, 2, or 3.

In some embodiments of a compound of Formula (J), (IV), (IVa), (IVb), and/or (IVc), or a pharmaceutically acceptable salt thereof, subscript n is 0 or 1.

In some embodiments, a compound of Formula (J), (IV), (IVa), (IVb), and/or (IVc), or a pharmaceutically acceptable salt thereof, is a compound wherein the compound has the structure of a compound shown in Table 4, or a pharmaceutically acceptable salt thereof.

TABLE 4

Compounds

| No. | Structure | Name |
| --- | --- | --- |
| 232 | 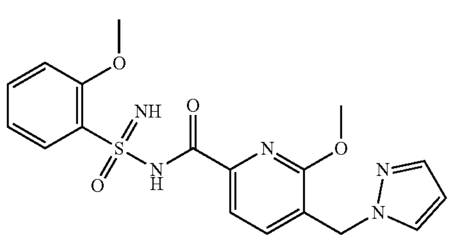 [SMILES: COc1ccccc1S(=N)(=O)NC(=O)c1ccc(Cn2cccn2)c(OC)n1] | 5-((1H-pyrazol-1-yl)methyl)-6-methoxy-N-(2-methoxyphenylsulfonimidoyl)picolinamide |

TABLE 4-continued

Compounds

| No. | Structure | Name |
|---|---|---|
| 243 | 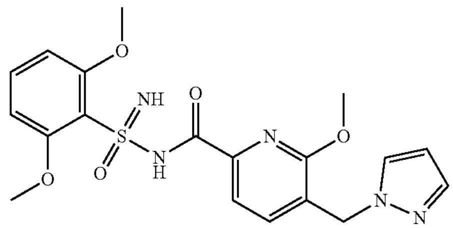 [SMILES: COc1cccc(OC)c1S(=N)(=O)NC(=O)c1ccc(Cn2cccn2)c(OC)n1] | 5-((1H-pyrazol-1-yl)methyl)-N-(2,6-dimethoxyphenylsulfonimidoyl)-6-methoxypicolinamide |
| 260 | 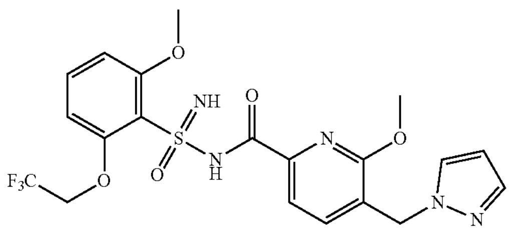 [SMILES: COc1cccc(OCC(F)(F)F)c1S(=N)(=O)NC(=O)c1ccc(Cn2cccn2)c(OC)n1] | 5-((1H-pyrazol-1-yl)methyl)-6-methoxy-N-(2-methoxy-6-(2,2,2-trifluoroethoxy)phenylsulfonimidoyl)picolinamide |
| 261 | 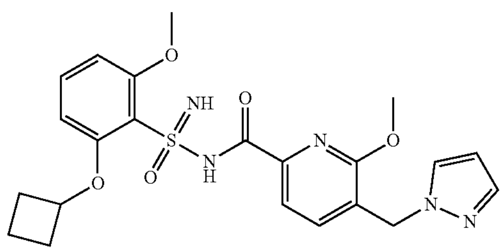 [SMILES: COc1cccc(OC2CCC2)c1S(=N)(=O)NC(=O)c1ccc(Cn2cccn2)c(OC)n1] | 5-((1H-pyrazol-1-yl)methyl)-N-(2-cyclobutoxy-6-methoxyphenylsulfonimidoyl)-6-methoxypicolinamide |
| 262 | 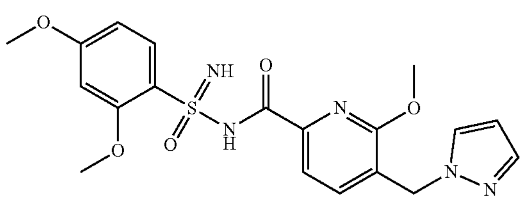 [SMILES: COc1ccc(S(=N)(=O)NC(=O)c2ccc(Cn3cccn3)c(OC)n2)c(OC)c1] | 5-((1H-pyrazol-1-yl)methyl)-N-(2,4-dimethoxyphenylsulfonimidoyl)-6-methoxypicolinamide |
| 263 | 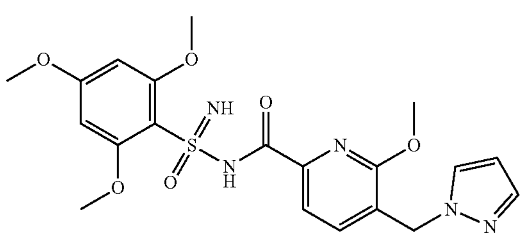 [SMILES: COc1cc(OC)c(S(=N)(=O)NC(=O)c2ccc(Cn3cccn3)c(OC)n2)c(OC)c1] | 5-((1H-pyrazol-1-yl)methyl)-6-methoxy-N-(2,4,6-trimethoxyphenylsulfonimidoyl)picolinamide |
| 290a | 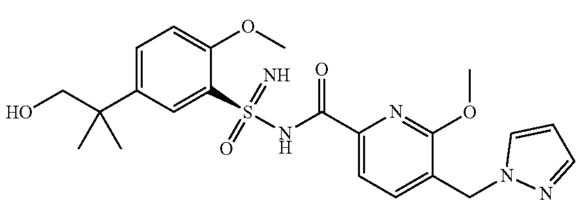 [SMILES: COc1ccc(C(C)(C)CO)cc1[S@](=N)(=O)NC(=O)c1ccc(Cn2cccn2)c(OC)n1] | (R)-5-((1H-pyrazol-1-yl)methyl)-N-(5-(1-hydroxy-2-methylpropan-2-yl)-2-methoxyphenylsulfonimidoyl)-6-methoxypicolinamide |
| 290b | 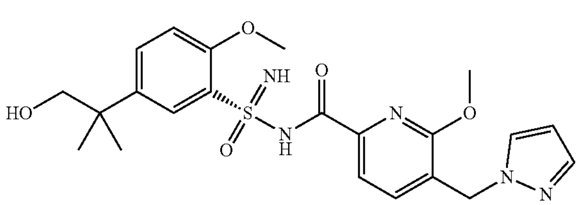 [SMILES: COc1ccc(C(C)(C)CO)cc1[S@@](=N)(=O)NC(=O)c1ccc(Cn2cccn2)c(OC)n1] | (S)-5-((1H-pyrazol-1-yl)methyl)-N-(5-(1-hydroxy-2-methylpropan-2-yl)-2-methoxyphenylsulfonimidoyl)-6-methoxypicolinamide |

TABLE 4-continued

| No. | Structure | Name |
|---|---|---|
| 293a | 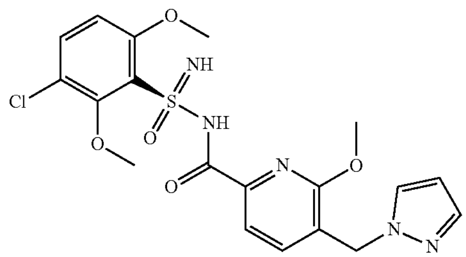 [SMILES: COc1ccc(Cl)c(OC)c1[S@](=N)(=O)NC(=O)c1ccc(Cn2cccn2)c(OC)n1] | (R)-5-((1H-pyrazol-1-yl)methyl)-N-(3-chloro-2,6-dimethoxyphenylsulfonimidoyl)-6-methoxypicolinamide |
| 293b | 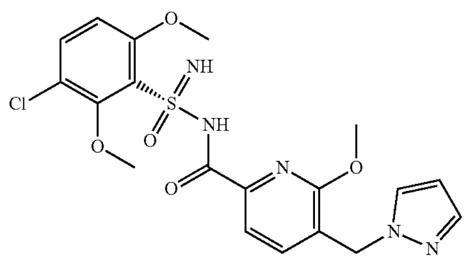 [SMILES: COc1ccc(Cl)c(OC)c1[S@@](=N)(=O)NC(=O)c1ccc(Cn2cccn2)c(OC)n1] | (S)-5-((1H-pyrazol-1-yl)methyl)-N-(3-chloro-2,6-dimethoxyphenylsulfonimidoyl)-6-methoxypicolinamide |
| 294 | 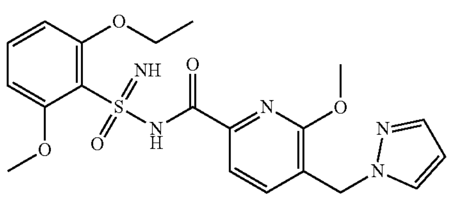 [SMILES: CCOc1cccc(OC)c1S(=N)(=O)NC(=O)c1ccc(Cn2cccn2)c(OC)n1] | 5-((1H-pyrazol-1-yl)methyl)-N-(2-ethoxy-6-methoxyphenylsulfonimidoyl)-6-methoxypicolinamide |
| 294a | 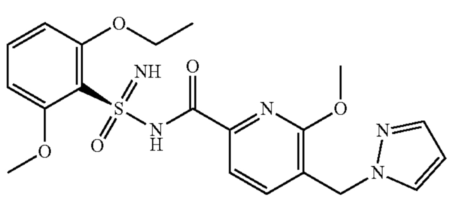 [SMILES: CCOc1cccc(OC)c1[S@](=N)(=O)NC(=O)c1ccc(Cn2cccn2)c(OC)n1] | (R)-5-((1H-pyrazol-1-yl)methyl)-N-(2-ethoxy-6-methoxyphenylsulfonimidoyl)-6-methoxypicolinamide |
| 294b | 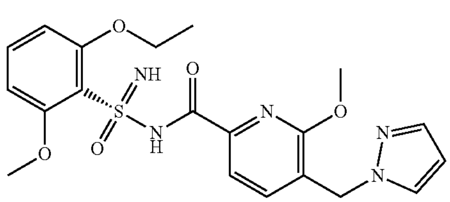 | (S)-5-((1H-pyrazol-1-yl)methyl)-N-(2-ethoxy-6-methoxyphenylsulfonimidoyl)-6-methoxypicolinamide |
| 296a | 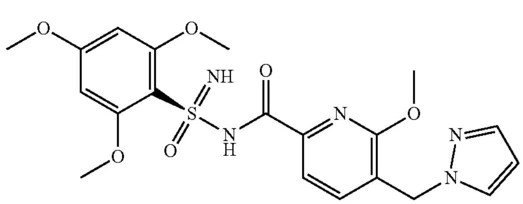 [SMILES: COc1cc(OC)c([S@](=N)(=O)NC(=O)c2ccc(Cn3cccn3)c(OC)n2)c(OC)c1] | (R)-5-((1H-pyrazol-1-yl)methyl)-6-methoxy-N-(2,4,6-trimethoxyphenylsulfonimidoyl)picolinamide |
| 296b | 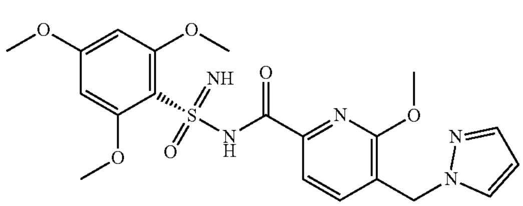 [SMILES: COc1cc(OC)c([S@@](=N)(=O)NC(=O)c2ccc(Cn3cccn3)c(OC)n2)c(OC)c1] | (S)-5-((1H-pyrazol-1-yl)methyl)-6-methoxy-N-(2,4,6-trimethoxyphenylsulfonimidoyl)picolinamide |

TABLE 4-continued

| No. | Structure | Name |
|---|---|---|
| 297 | 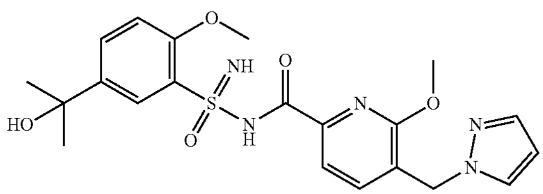 [SMILES: COc1ccc(C(C)(C)O)cc1S(=N)(=O)NC(=O)c1ccc(Cn2cccn2)c(OC)n1] | 5-((1H-pyrazol-1-yl)methyl)-N-(5-(2-hydroxypropan-2-yl)-2-methoxyphenylsulfonimidoyl)-6-methoxypicolinamide |
| 298a | 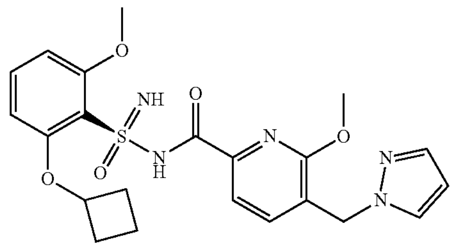 [SMILES: COc1cccc(OC2CCC2)c1[S@](=N)(=O)NC(=O)c1ccc(Cn2cccn2)c(OC)n1] | (R)-5-((1H-pyrazol-1-yl)methyl)-N-(2-cyclobutoxy-6-methoxyphenylsulfonimidoyl)-6-methoxypicolinamide |
| 298b | 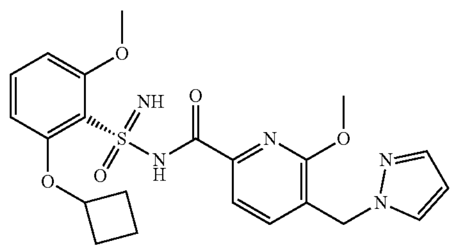 [SMILES: COc1cccc(OC2CCC2)c1[S@@](=N)(=O)NC(=O)c1ccc(Cn2cccn2)c(OC)n1] | (S)-5-((1H-pyrazol-1-yl)methyl)-N-(2-cyclobutoxy-6-methoxyphenylsulfonimidoyl)-6-methoxypicolinamide |
| 301a | 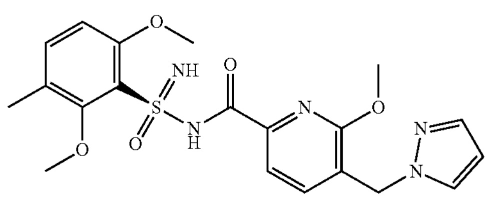 [SMILES: COc1ccc(C)c(OC)c1[S@](=N)(=O)NC(=O)c1ccc(Cn2cccn2)c(OC)n1] | (R)-5-((1H-pyrazol-1-yl)methyl)-N-(2,6-dimethoxy-3-methylphenylsulfonimidoyl)-6-methoxypicolinamide |
| 301b | 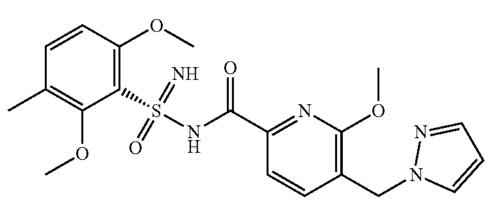 [SMILES: COc1ccc(C)c(OC)c1[S@@](=N)(=O)NC(=O)c1ccc(Cn2cccn2)c(OC)n1] | (S)-5-((1H-pyrazol-1-yl)methyl)-N-(2,6-dimethoxy-3-methylphenylsulfonimidoyl)-6-methoxypicolinamide |
| 303a | 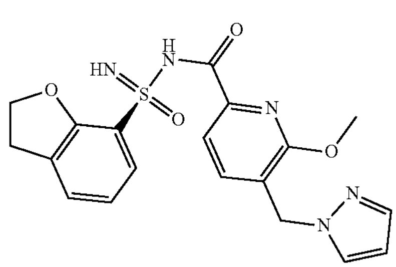 [SMILES: COc1nc(C(=O)N[S@@](=N)(=O)c2cccc3c2OCC3)ccc1Cn1cccn1] | (R)-5-((1H-pyrazol-1-yl)methyl)-N-(2,3-dihydrobenzofuran-7-sulfonimidoyl)-6-methoxypicolinamide |

TABLE 4-continued

| No. | Structure | Name |
|---|---|---|
| 303b | 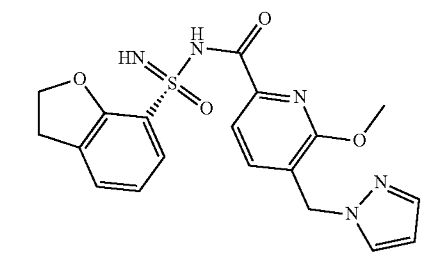 [SMILES: COc1nc(C(=O)N[S@](=N)(=O)c2cccc3c2OCC3)ccc1Cn1cccn1] | (S)-5-((1H-pyrazol-1-yl)methyl)-N-(2,3-dihydrobenzofuran-7-sulfonimidoyl)-6-methoxypicolinamide |
| 305a | 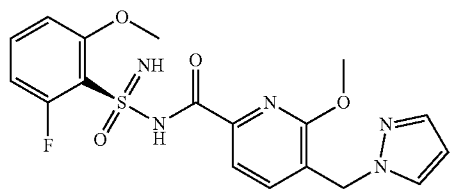 [SMILES: COc1cccc(F)c1[S@](=N)(=O)NC(=O)c1ccc(Cn2cccn2)c(OC)n1] | (R)-5-((1H-pyrazol-1-yl)methyl)-N-(2-fluoro-6-methoxyphenylsulfonimidoyl)-6-methoxypicolinamide |
| 305b | 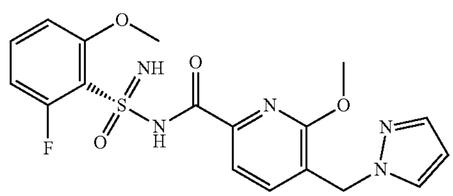 [SMILES: COc1cccc(F)c1[S@@](=N)(=O)NC(=O)c1ccc(Cn2cccn2)c(OC)n1] | (S)-5-((1H-pyrazol-1-yl)methyl)-N-(2-fluoro-6-methoxyphenylsulfonimidoyl)-6-methoxypicolinamide |
| 306a | 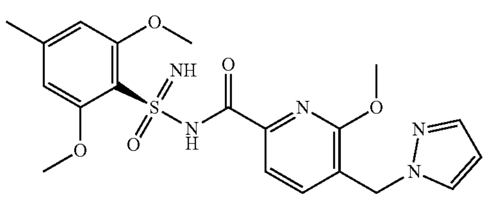 [SMILES: COc1cc(C)cc(OC)c1[S@](=N)(=O)NC(=O)c1ccc(Cn2cccn2)c(OC)n1] | (R)-5-((1H-pyrazol-1-yl)methyl)-N-(2,6-dimethoxy-4-methylphenylsulfonimidoyl)-6-methoxypicolinamide |
| 306b | 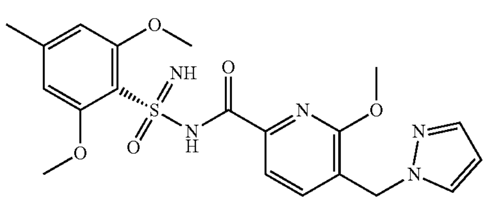 [SMILES: COc1cc(C)cc(OC)c1[S@@](=N)(=O)NC(=O)c1ccc(Cn2cccn2)c(OC)n1] | (S)-5-((1H-pyrazol-1-yl)methyl)-N-(2,6-dimethoxy-4-methylphenylsulfonimidoyl)-6-methoxypicolinamide |
| 307a | 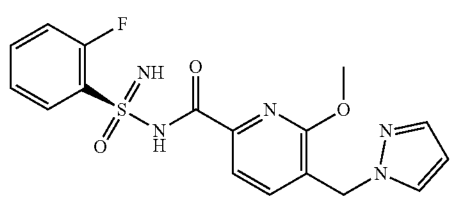 [SMILES: COc1nc(C(=O)N[S@@](=N)(=O)c2ccccc2F)ccc1Cn1cccn1] | (R)-5-((1H-pyrazol-1-yl)methyl)-N-(2-fluorophenylsulfonimidoyl)-6-methoxypicolinamide |
| 307b | 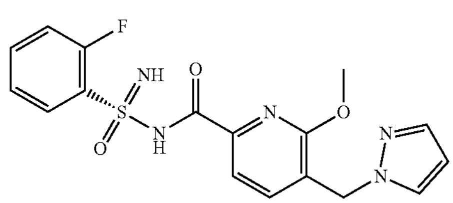 [SMILES: COc1nc(C(=O)N[S@](=N)(=O)c2ccccc2F)ccc1Cn1cccn1] | (S)-5-((1H-pyrazol-1-yl)methyl)-N-(2-fluorophenylsulfonimidoyl)-6-methoxypicolinamide |

TABLE 4-continued

Compounds

| No. | Structure | Name |
|---|---|---|
| 308a | 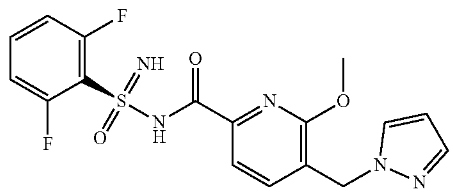 [SMILES: COc1nc(C(=O)N[S@@](=N)(=O)c2c(F)cccc2F)ccc1Cn1cccn1] | (R)-5-((1H-pyrazol-1-yl)methyl)-N-(2,6-difluorophenylsulfonimidoyl)-6-methoxypicolinamide |
| 308b | 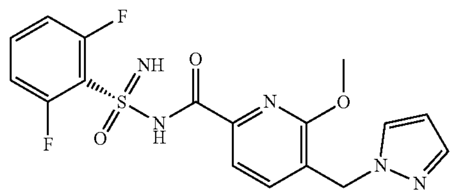 [SMILES: COc1nc(C(=O)N[S@](=N)(=O)c2c(F)cccc2F)ccc1Cn1cccn1] | (S)-5-((1H-pyrazol-1-yl)methyl)-N-(2,6-difluorophenylsulfonimidoyl)-6-methoxypicolinamide |

In some embodiments, a compound of Formula (J), (IV), (IVa), (IVb), and/or (IVc), or pharmaceutically acceptable salt thereof, is selected from the group consisting of:
4-((1H-pyrazol-1-yl)methyl)-N-((2,6-dimethoxyphenyl)sulfonyl)-3-methoxybenzamide (14)e
4-((1H-pyrazol-1-yl)methyl)-3-methoxy-N-((2,4,6-trimethoxyphenyl)sulfonyl)benzamide
4-((1H-pyrazol-1-yl)methyl)-N-((2-ethoxy-6-methoxyphenyl)sulfonyl)-3-methoxybenzamide (67),
5-((1H-pyrazol-1-yl)methyl)-N-((2,6-dimethoxyphenyl)sulfonyl)-6-methoxypicolinamide (203),
5-((1H-pyrazol-1-yl)methyl)-N-((5-ethyl-2-methoxyphenyl)sulfonyl)-6-methoxypicolinamide (204),
5-((1H-pyrazol-1-yl)methyl)-6-methoxy-N-((2,4,6-trimethoxyphenyl)sulfonyl)picolinamide (224),
5-((1H-pyrazol-1-yl)methyl)-6-cyclopropyl-N-((2,6-dimethoxyphenyl)sulfonyl)picolinamide (229),
5-((1H-pyrazol-1-yl)methyl)-N-((3-chloro-2,6-dimethoxyphenyl)sulfonyl)-6-methoxypicolinamide (241),
5-((1H-pyrazol-1-yl)methyl)-N-((4-bromo-2,6-dimethoxyphenyl)sulfonyl)-6-methoxypicolinamide (285),
4-((1H-pyrazol-1-yl)methyl)-3-methoxy-N-((2-methyl-2,3-dihydrobenzofuran-7-yl)sulfonyl)benzamide (314),
and pharmaceutically acceptable salts thereof.

In some embodiments, a compound of Formula (J), (IV), (IVa), (IVb), and/or (IVc), or pharmaceutically acceptable salt thereof, is 4-((1H-pyrazol-1-yl)methyl)-N-((2,6-dimethoxyphenyl)sulfonyl)-3-methoxybenzamide, or a pharmaceutically acceptable salt thereof. In some embodiments, a compound of Formula (J), (IV), (IVa), (IVb), and/or (IVc), or pharmaceutically acceptable salt thereof, is 4-((1H-pyrazol-1-yl)methyl)-3-methoxy-N-((2,4,6-trimethoxyphenyl)sulfonyl)benzamide, or a pharmaceutically acceptable salt thereof. In some embodiments, a compound of Formula (J), (IV), (IVa), (IVb), and/or (IVc), or pharmaceutically acceptable salt thereof, is 4-((1H-pyrazol-1-yl)methyl)-N-((2-ethoxy-6-methoxyphenyl)sulfonyl)-3-methoxybenzamide, or a pharmaceutically acceptable salt thereof. In some embodiments, a compound of Formula (J), (IV), (IVa), (IVb), and/or (IVc), or pharmaceutically acceptable salt thereof, is 5-((1H-pyrazol-1-yl)methyl)-N-((2,6-dimethoxyphenyl)sulfonyl)-6-methoxypicolinamide, or a pharmaceutically acceptable salt thereof. In some embodiments, a compound of Formula (J), (IV), (IVa), (IVb), and/or (IVc), or pharmaceutically acceptable salt thereof, is 5-((1H-pyrazol-1-yl)methyl)-N-((5-ethyl-2-methoxyphenyl)sulfonyl)-6-methoxypicolinamide, or a pharmaceutically acceptable salt thereof. In some embodiments, a compound of Formula (J), (IV), (IVa), (IVb), and/or (IVc), or pharmaceutically acceptable salt thereof, is 5-((1H-pyrazol-1-yl)methyl)-6-methoxy-N-((2,4,6-trimethoxyphenyl)sulfonyl)picolinamide, or a pharmaceutically acceptable salt thereof. In some embodiments, a compound of Formula (J), (IV), (IVa), (IVb), and/or (IVc), or pharmaceutically acceptable salt thereof, is 5-((1H-pyrazol-1-yl)methyl)-6-cyclopropyl-N-((2,6-dimethoxyphenyl)sulfonyl)picolinamide, or a pharmaceutically acceptable salt thereof. In some embodiments, a compound of Formula (J), (IV), (IVa), (IVb), and/or (IVc), or pharmaceutically acceptable salt thereof, is 5-((1H-pyrazol-1-yl)methyl)-N-((3-chloro-2,6-dimethoxyphenyl)sulfonyl)-6-methoxypicolinamide, or a pharmaceutically acceptable salt thereof. In some embodiments, a compound of Formula (J), (IV), (IVa), (IVb), and/or (IVc), or pharmaceutically acceptable salt thereof, is 5-((1H-pyrazol-1-yl)methyl)-N-((4-bromo-2,6-dimethoxyphenyl)sulfonyl)-6-methoxypicolinamide, or a pharmaceutically acceptable salt thereof. In some embodiments, a compound of Formula (J), (IV), (IVa), (IVb), and/or (IVc), or pharmaceutically acceptable salt thereof, is 4-((1H-pyrazol-1-yl)methyl)-3-methoxy-N-((2-methyl-2,3-dihydrobenzofuran-7-yl)sulfonyl)benzamide, or a pharmaceutically acceptable salt thereof.

IV. Compositions

In some embodiments, the pharmaceutical composition of the present invention comprises a compound of the present invention, such as a compound of Formula (J), (I), (Ia), (Ib), (II), (IIa), (IIb), (IIc), (III), (IIIa), (IIIb), (IV), (IVa), (IVb), and/or (IVc), or pharmaceutically acceptable salt thereof, and a pharmaceutically acceptable carrier.

The compounds of the present invention may be used as single drug or as a pharmaceutical composition in which the compound is mixed with various pharmacologically acceptable excipients.

The compounds of the invention are typically administered in the form of a pharmaceutical composition. Such compositions can be prepared using procedures well known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents and solvents.

The pharmaceutical composition can be administered by oral, parenteral or inhalation routes. Examples of the parenteral administration include administration by injection, percutaneous, transmucosal, transnasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavoring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide a desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions and sterile injectable liquids, such as suspensions or solutions.

Topical dosage forms of the compounds include ointments, pastes, creams, lotions, powders, solutions, eye or ear drops, impregnated dressings and may contain appropriate conventional additives such as preservatives, solvents to assist drug penetration.

The pharmaceutical compositions of the present patent application may be prepared by conventional techniques known in literature.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms and suitable pharmaceutical excipients can also be well used and adjusted by those skilled in the art. All changes and modifications are envisioned within the scope of the present patent application.

In some embodiments, a pharmaceutical composition of the present invention is a pharmaceutical composition comprising a compound of Formula (J) or a pharmaceutically acceptable salt thereof as described herein and at least one pharmaceutically acceptable excipient (such as a pharmaceutically acceptable carrier or diluent). In some embodiments, the pharmaceutical composition comprises a therapeutically effective amount of at least one compound described herein. The composition described herein the present invention may be associated with a pharmaceutically acceptable excipient (such as a carrier or a diluent) or be diluted by a carrier or enclosed within a carrier which can be in the form of a capsule, sachet, paper or other container.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (for example, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions can also include adjuvants such as wetting agents, emulsifying and suspending agents, sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration can be suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, including but not limited to tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to the compounds of this application, excipients such as lactose, talc, silicic acid, aluminum hydroxide, calcium silicates and polyamide powder or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Administration of the disclosed compounds and pharmaceutical compositions can be accomplished via any mode of administration for therapeutic agents. These modes include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions or the like, sometimes in unit dosages and consistent with conventional pharmaceutical practices. Likewise, they can also be administered in intravenous (both bolus and infusion), intraperitoneal, subcutaneous or intramuscular form and all using forms well known to those skilled in the pharmaceutical arts.

Illustrative pharmaceutical compositions are tablets and gelatin capsules comprising one or more compounds of the present disclosure and a pharmaceutically acceptable carrier, such as, but not limited to, a) a diluent, e.g., purified water, triglyceride oils, such as hydrogenated or partially hydrogenated vegetable oil or mixtures thereof, corn oil, olive oil, sunflower oil, safflower oil, fish oils, such as EPA or DHA or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, one or more disclosed compound is dissolved in or mixed with a pharmaceutically acceptable solvent such as, for example, water, saline, aqueous dextrose, glycerol, ethanol and the like, to thereby form an injectable isotonic solution or suspension. Proteins such as albumin, chylomicron particles or serum proteins can be used to solubilize the disclosed compounds.

One or more disclosed compounds or compositions can be delivered by parental administration. The parental injectable administration is generally used for subcutaneous, intramuscular or intravenous injections and infusions. Injectables can be prepared in conventional forms, either as liquid solutions or suspensions or solid forms suitable for dissolving in liquid prior to injection.

In some embodiments, a pharmaceutical composition of the present invention comprises a compound of Formula (J), (I), (Ia), (Tb), (II), (IIa), (IIb), (IIc), (III), (IIIa), (IIb), (IV), (IVa), (IVb), and/or (IVc), or a pharmaceutically acceptable salt thereof and at least one pharmaceutically acceptable excipient (such as a pharmaceutically acceptable carrier or diluent).

In some embodiments, a pharmaceutical composition of the present invention comprising a compound of Formula (J), (I), (Ta), (Ib), (II), (IIa), (IIb), (IIc), (III), (IIIa), (IIIb), (IV), (IVa), (IVb), and/or (IVc), or a pharmaceutically acceptable salt thereof is for use as a medicament.

In some embodiments, a pharmaceutical composition of the present invention comprising a compound of Formula (J), (I), (Ta), (Ib), (II), (IIa), (IIb), (IIc), (III), (IIIa), (IIIb), (IV), (IVa), (IVb), and/or (IVc), or a pharmaceutically acceptable salt thereof is for treating a disease or disorder that is dependent on or mediated by KAT6A.

V. Administration

The compound of the present disclosure may be administered to an individual in accordance with an effective dosing regimen for a desired period of time or duration, such as at least about one week, at least about two weeks, at least about three weeks, one month, at least about 2 months, at least about 3 months, at least about 6 months, or at least about 12 months or longer. In one variation, the compound is administered on a daily or intermittent schedule for the required duration, up to the individual's life.

The dosage or dosing frequency of the compound of the present disclosure may be adjusted over the course of the treatment, based on the judgment of the administering physician.

The compound may be administered to an individual, such as a human in an effective amount.

The compound of the present invention can be administered by any useful route and means, such as by oral or parenteral (e.g., intravenous) administration. Therapeutically effective amounts of the compound of the present invention are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day.

Therapeutically effective amounts of the compound of the present invention, are from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of the present invention are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present invention are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month.

VI. Methods and/or Uses

In some embodiments, a method of the present invention is a method of treating a disease or a disorder comprising administering a therapeutically effective amount of a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof to a subject, e.g., a human, in need thereof.

In some embodiments, a use of the present invention is a use of a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof for the manufacture of a medicament for treating a disease or condition, e.g., cancer.

In some embodiments, a compound for use of the present invention is a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, for use in the treatment of diseases or disorders mediated by KAT6A.

In some embodiments, a method of the present invention is a method of inhibiting KAT6A in a subject comprising administering to the subject in need thereof, a therapeutically effective amount of a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof.

In some embodiments, a method of the present invention is a method for treating a disease or disorder mediated by KAT6A, in a subject comprising administering to the subject in need thereof a therapeutically effective amount of a compound of Formula ((J), (I), (Ia), (Ib), (II), (IIa), (IIb), (IIc), (III), (IIIa), (IIIb), (IV), (IVa), (IVb), and/or (IVc), or a pharmaceutically acceptable salt thereof.

In some embodiments, a compound for use of the present invention is a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, for use as a medicament.

In some embodiments, a method of the present invention is a method of modulating KAT6A in a subject in need thereof, comprising administering to the subject a therapeutically effective amount of compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof.

In some embodiments, a use of the present invention is a use of a pharmaceutical composition comprising a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, in the manufacture of a medicament for treating a disease or disorder mediated by KAT6A. In some embodiments, the use of a pharmaceutical composition comprises a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, in the manufacture of a medicament for treating cancer that is mediated by KAT6A.

In some embodiments, a use of the present invention is a use of compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, in the manufacture of a medicament for treating or preventing a disease or disorder mediated by KAT6A.

In some embodiments, the disease or disorder is dependent upon or mediated by KAT6A is cancer.

In some embodiments, the cancer is selected from brain gliomas, glioblastomas, astrocytomas, multiforme, Bannayan-Zonana syndrome, Cowden disease, Lhermitte-Duclos disease, breast cancer, colon cancer, head and neck cancer, kidney, liver, lung cancer, bone cancer, colorectal cancer, germ cell cancer, melanoma, ovarian cancer, pancreatic cancer, adenocarcinoma, ductal adenocarcinoma, adenosquamous carcinoma, acinar cell carcinoma, glucagonoma, insulinoma, prostate, sarcoma and thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, uterine cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, gastrointestinal stromal tumor (GIST), neuroendocrine cancers, testicular cancer, and virus-related cancer.

In some embodiments, a use of the present invention is a use of compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, in the manufacture of a medicament for treating cancer selected from brain gliomas, glioblastomas, astrocytomas, multiforme, Bannayan-Zonana syndrome, Cowden disease, Lhermitte-Duclos disease, breast cancer, colon cancer, head and neck cancer, kidney, liver, lung cancer, bone cancer, colorectal cancer, germ cell cancer, melanoma, ovarian cancer, pancreatic cancer, adenocarcinoma, ductal adenocarcinoma, adenosquamous carcinoma, acinar cell carcinoma, glucagonoma, insulinoma, prostate, sarcoma and thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, uterine cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, gastrointestinal stromal tumor (GIST), neuroendocrine cancers, testicular cancer, and virus-related cancer.

In some embodiments, a compound for use of the present invention is a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, for use in treating of a disease or disorder mediated by KAT6A.

In some embodiments, a compound for use of the present invention is a compound of Formula (J), (I), (Ia), (Ib), (II), (IIa), (IIb), (IIc), (III), (IIIa), (IIIb), (IV), (IVa), (IVb), and/or (IVc), or a pharmaceutically acceptable salt thereof, for use in treating or preventing cancer selected from brain gliomas, glioblastomas, astrocytomas, multiforme, Bannayan-Zonana syndrome, Cowden disease, Lhermitte-Duclos disease, breast cancer, colon cancer, head and neck cancer, kidney, liver, lung cancer, bone cancer, colorectal cancer, germ cell cancer, melanoma, ovarian cancer, pancreatic cancer, adenocarcinoma, ductal adenocarcinoma, adenosquamous carcinoma, acinar cell carcinoma, glucagonoma, insulinoma, prostate, sarcoma and thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, uterine cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, gastrointestinal stromal tumor (GIST), neuroendocrine cancers, testicular cancer, and virus-related cancer.

In some embodiments, the present disclosure provides compounds for use in combination with other compounds or biologic entities for treatment of disease or disorder. Suitable combinations and doses of compounds for combination therapy used in treating the diseases or disorders described herein can be determined by those skilled in the relevant art. Combination therapies for compounds of the present disclosure can be used for treatment of disease or disorder. In some embodiments, the disease or disorder is cancer.

In some embodiments, the present disclosure provides compounds for use in a method of treating a disease or disorder in a subject that comprises administering to the subject the compound in combination or alternation with an estrogen receptor antagonist or a estrogen receptor partial antagonist. As described herein, an estrogen receptor "partial" antagonist refers to an estrogen receptor antagonist that exhibits antagonist activity in estrogen receptor antagonist assays, but also exhibits detectable estrogen receptor agonist activity in estrogen receptor agonist assays.

In some embodiments, the present disclosure provides compounds for use in a method of treating a disease or disorder in a subject that comprises administering to the subject the compound in combination or alternation with a Selective Estrogen Receptor Modulator (SERM). In some embodiments, the SERM is tamoxifen, endoxifene, raloxifene, toremifene, lasofoxifene, ospemifene, elacestrant or bazedoxifene.

In some embodiments, the present disclosure provides compounds for use in a method of treating a disease or disorder in a subject that comprises administering to the subject the compound in combination or alternation with a Selective Estrogen Receptor Degrader. In some embodiments, the SERD is fulvestrant, camizestrant, palazestrant, imlunestrant, elacestrant, or giredestrant.

In some embodiments, the present disclosure provides compounds for use in a method of treating a disease or disorder in a subject that comprises administering to the subject the compound in combination or alternation with a Complete Estrogen Receptor Antagonist (CERAN). In some embodiments, the CERAN is fulvestrant or palazestrant. In some embodiments, the CERAN is fulvestrant. In some embodiments, the CERAN is palazestrant.

In some embodiments, the present disclosure provides compounds for use in a method of treating a disease or disorder in a subject that comprises administering to the subject the compound in combination or alternation with an additional anti-cancer agent. In some embodiments, an additional anti-cancer agent is selected from a HER2 inhibitor, an mTOR inhibitor, a CDK4/6 inhibitor, a CDK2-selective inhibitor, a CDK4-selective inhibitor, a PI3 kinase inhibitor, a PIK3CA inhibitor, an aromatase inhibitor, an antibody to or inhibitor of PD-1, PD-L1 or CTLA-4, an antibody to or inhibitor of EGFR, PGFR, or IGFR, a USP1 inhibitor or an AKT inhibitor.

In some embodiments, an additional anti-cancer agent is a CDK2 inhibitor. In some embodiments, a CDK2 inhibitor is PF-07104091 (tagtociclib).

In some embodiments, an additional anti-cancer agent is a HER2 inhibitor. In some embodiments, a HER2 inhibitor is selected from tucatinib, trastuzumab, pertuzumab, ado-trastuzumab, trastuzumab emtansine, ado-trastuzumab emtansine, trastuzumab deruxtecan pertuzumab, lapatinib, and neratinib.

In some embodiments, an additional anti-cancer agent is an mTOR inhibitor. In some embodiments, an mTOR inhibitor is selected from everolimus, sirolimus, temsirolimus, and LY3023414.

In some embodiments, an additional anti-cancer agent is a CDK4/6 inhibitor. In some embodiments, a CDK4/6 inhibitor is selected from palbociclib, abemaciclib, ribociclib, lerociclib, trilaciclib, and SHR6390.

In some embodiments, an additional anti-cancer agent is a CDK4-selective inhibitor. In some embodiments, a CDK-4 selective inhibitor is PF-07220060 (atirmociclib).

In some embodiments, an additional anti-cancer agent is a PI3 kinase inhibitor. In some embodiments, a PI3 kinase inhibitor is selected from perifosine, CAL101, BEZ235, XL147, XL765, GDC-0941, and IPI-145.

In some embodiments, a PI3 kinase inhibitor is a PIK3CA inhibitor. In some embodiments, a PIK3CA inhibitor is selected from alpelisib, taselisib, LY3023414, Inavolisib, STX-478, RLY-2608, LOXO-783, OKI-219, and TOS-358.

In some embodiments, an additional anti-cancer agent is an aromatase inhibitor. In some embodiments, an aromatase inhibitor is selected from aminoglutethimide, testolactone, anastrozole, letrozole, exemestane, vorozole, formestane, fadrozole, 4-hydroxyandrostenedione, 1,4,6-androstatrien-3,17-dione, and 4-androstene-3,6,17-trione.

In some embodiments, an additional anti-cancer agent is an antibody to or inhibitor of PD-1, PD-L1 or CTLA-4.

In some embodiments, an additional anti-cancer agent is an antibody to or inhibitor of EGFR, PGFR, or IGFR. In some embodiments, an anti-cancer agent is erlotinib or gefitinib.

In some embodiments, an additional anti-cancer agent is a USP1 inhibitor.

In some embodiments, an additional anti cancer agent is an AKT inhibitor. In some embodiments, an additional anti cancer agent is capivasertib.

VII. Examples

While specific embodiments of the subject invention have been discussed, the specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The following abbreviations refer respectively to the definitions below:

DMSO—dimethylsulfoxide;
THF—tetrahydrofuran;
DCM—dichloromethane;
LiHMDS—lithium bis(trimethylsilyl)amide;
Pd(Amphos)Cl$_2$—bis(di-tert-butyl(4-dimethylaminophenyl)phosphine)dichloropalladium(II);
NH$_4$Cl—ammonium chloride;
Na$_2$SO$_4$—sodium sulfate;
BPO—benzoyl peroxide;
br—broad;
° C.—degree Celsius;
DMSO-d$_6$—deuterated dimethylsulfoxide;
DMF—N, N-dimethylformamide;
Et—ethyl;
g—gram;
h—hours;
H—proton;
iPr—isopropyl;
LC-MS—liquid chromatography-mass spectroscopy;
Me—methyl;
MHz—megahertz (frequency);
MS—mass spectroscopy;
Ms—methanesulfonyl;
M—molar;
mmol—millimole;
mL—millilitre;
min—minutes;
mol—moles;
M$^{+/-}$—molecular ion; m/z—mass to charge ratio;
NBS—N-bromosuccinimide;
NMR—nuclear magnetic resonance;
ppm—parts per million;
rt or RT—room temperature;
RM—reaction mixture;
br—broad;
s—singlet;
d—doublet;
t—triplet;
q—quartet;
m—multiplet;
dd—doublet of doublets;
TLC—thin layer chromatography;
%—percentage; and
δ—delta.

a) Sulfonamide Intermediates

Intermediate 15:
2-Methoxy-4-(1H-pyrazol-1-yl)benzenesulfonamide

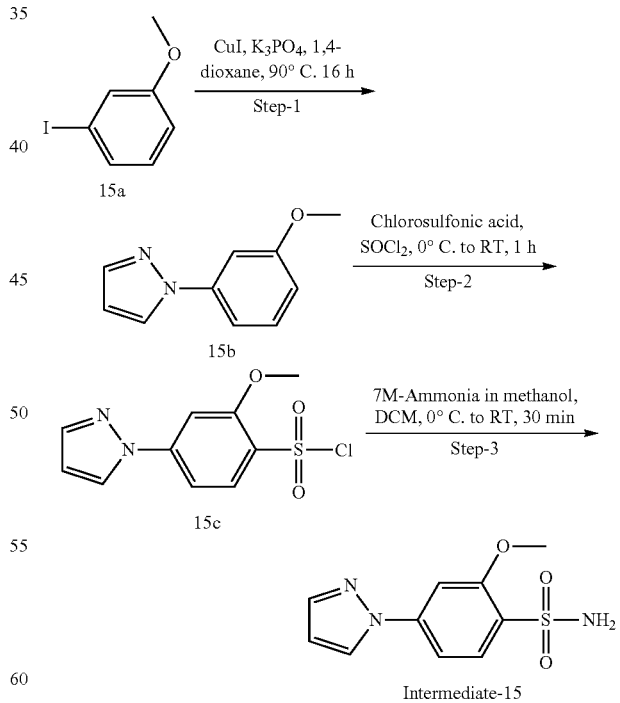

Step 1: 1-(3-Methoxyphenyl)-1H-pyrazole

To a degassed solution of 1-iodo-3-methoxybenzene (10 g, 42.7 mmol) in 1,4-dioxane (100 mL) were added 1H-pyrazole (3.49 g, 51.2 mmol), CuI (0.81 g, 4.2 mmol) and K$_3$PO$_4$ (18.1 g, 85.4 mmol) at RT. Then the reaction mixture was heated to 90° C. for 16 h. The reaction mixture was cooled to RT and was added water and extracted with ethyl acetate. The organic layer was dried over Na$_2$SO$_4$, filtered, and concentrated to get crude compound. The crude compound was purified by combi flash chromatography using 20% ethyl acetate in hexane to afford the title compound (6.5 g, 87.3%). LC-MS: 175.1 [M+H]$^+$.

Step 2:
2-Methoxy-4-(1H-pyrazol-1-yl)benzenesulfonyl chloride

To a solution of 1-(3-methoxyphenyl)-1H-pyrazole (2 g, 11.4 mmol) in chlorosulfonic acid (13.3 g, 114.8 mmol) was added thionyl chloride (1.6 g, 13.7 mmol) dropwise at 0° C. Reaction mixture was brought to RT and stirred for 1 h. The reaction mixture was diluted with ice water and extracted with DCM. The organic layer was washed with saturated NaHCO$_3$, dried over Na$_2$SO$_4$, and concentrated to get the title compound (1.2 g). LC-MS: 273.0 [M+H]$^+$.

Step 3:
2-Methoxy-4-(1H-pyrazol-1-yl)benzenesulfonamide

To a solution of 2-methoxy-4-(1H-pyrazol-1-yl)benzenesulfonyl chloride (1.2 g, 4.4 mmol) in DCM (10 mL) was added 7M methanolic ammonia dropwise at 0° C. The reaction mixture was warmed to RT and stirred for 30 min. The reaction mixture was diluted with water and extracted with DCM. The organic layer was washed with saturated Aq. NaHCO$_3$, dried over Na$_2$SO$_4$, and concentrated to afford the title compound (0.3 g). LC-MS: 254.0 [M+H]$^+$.

Intermediate 16

The following Intermediate 16 listed below was prepared by following similar procedure to that described above for Intermediate 15 using appropriate reagents with suitable modifications known to the one skilled in the art.

| Intermediate | Structure | Spectral data |
|---|---|---|
| 16 | 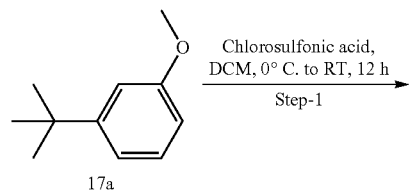 | LC-MS: 254.0 [M + H]$^+$. |

Intermediate 17:
4-(Tert-butyl)-2-methoxybenzenesulfonamide

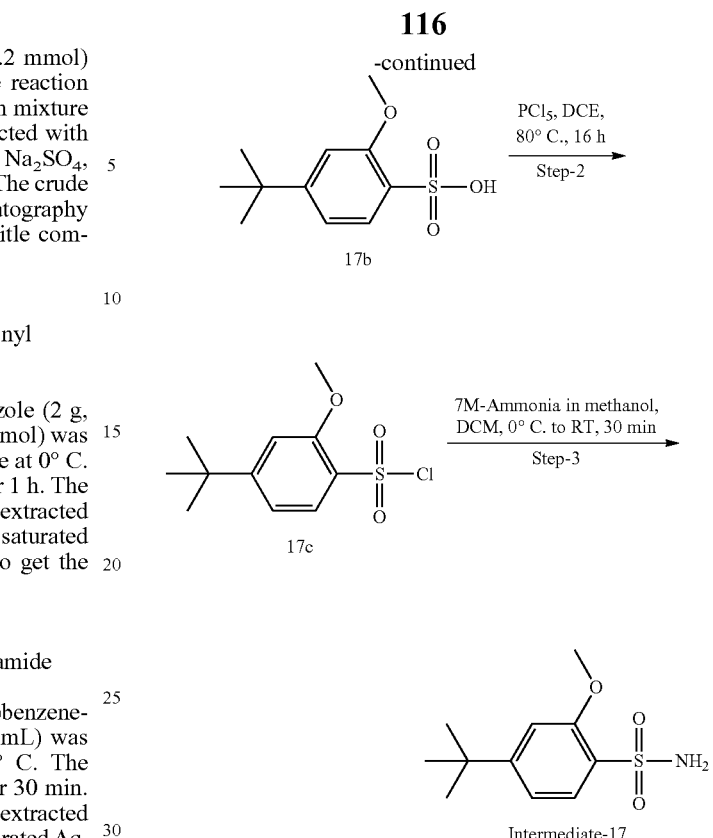

Step 1: 4-(Tert-butyl)-2-methoxybenzenesulfonic acid

To solution of 1-(tert-butyl)-3-methoxybenzene (6 g, 36.5 mmol) in anhydrous DCM (90 mL) was added chlorosulfonic acid (5.1 g, 43.8 mmol) dropwise at 0° C. for 15 min. Then reaction mixture was gradually warmed to room temperature and stirred for overnight. The reaction mixture was quenched with ice water and extracted with DCM. The organic layer was washed with saturated Aq. NaHCO$_3$, dried over Na$_2$SO$_4$, and concentrated to afford the title compound (5 g). LC-MS: 243.0 [M–H]$^-$.

Step 2: 4-(Tert-butyl)-2-methoxybenzenesulfonyl chloride

To a solution of 4-(tert-butyl)-2-methoxybenzenesulfonic acid (5 g, 20.4 mmol) in 1,2-DCE (75 mL) was added PCl$_5$ (8.5 g, 40.9 mmol) in portions at 0° C. After completion of addition, the reaction mixture was heated to 80° C. for 16 h. The reaction mixture was then cooled to RT and concentrated to yield the crude compound. The crude compound was purified by combi flash chromatography using 50% EtOAc in hexane to afford thetitle compound (6.3 g, 74.3%).

Step 3:
4-(Tert-butyl)-2-methoxybenzenesulfonamide

The title compound was prepared using similar procedure to that described in Step 3 of Intermediate 15 using appropriate reagents with suitable modifications. LC-MS: 244.1 [M+H]$^+$.

Intermediate 18: 3-Methoxy-5,6,7,8-tetrahydronaphthalene-2-sulfonamide

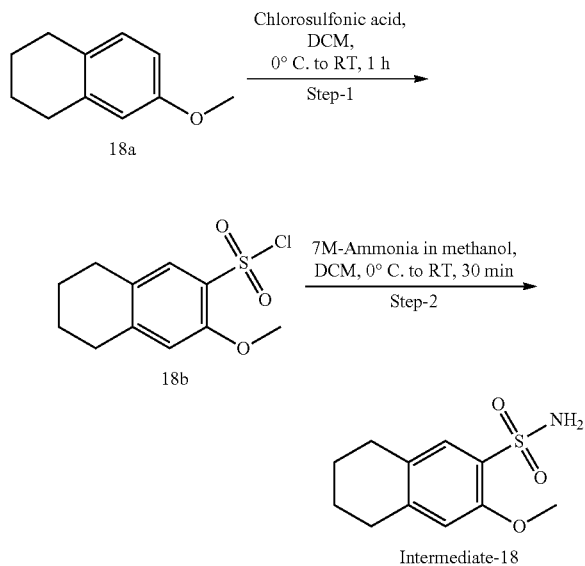

Step 1: 3-Methoxy-5,6,7,8-tetrahydronaphthalene-2-sulfonyl chloride

To a stirred solution of 6-methoxy-1,2,3,4-tetrahydronaphthalene (0.5 g, 3.08 mmol) in DCM (15 mL) was added chlorosulfonic acid (1.07 g, 9.2 mmol) dropwise at 0° C. The reaction mixture was gradually warmed to RT and stirred for 1 h at RT. The reaction mixture was then poured into ice cold water and extracted with DCM. The organic layer was washed with aqueous $NaHCO_3$, dried over $Na_2SO_4$ and concentrated to afford the title compound (0.52 g, 65%).

Step 2: 3-Methoxy-5,6,7,8-tetrahydronaphthalene-2-sulfonamide

The title compound was prepared using similar procedure to that described in Step 3 of Intermediate 15 using appropriate reagents with suitable modifications. LC-MS: 241.9 $[M+H]^+$.

Intermediates 19 to 26f

The following intermediates in Table 5 were prepared by following similar procedure to that described above for Intermediate 18 using appropriate reagents with suitable modifications known to the one skilled in the art. In some instances, procedures began with commercially available sulfonyl chloride building blocks.

TABLE 5

| Intermediate | Structure | Spectral data |
|---|---|---|
| 19 | 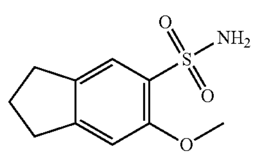 | LC-MS: 228.0 $[M + H]^+$. |
| 20 | 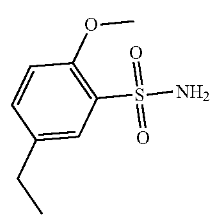 | $^1$H NMR, DMSO-$d_6$, 400 MHz): δ 7.56 (d, 1H), 7.41 (dd, 1H), 7.12 (d, 1H), 7.0 (s, 2H), 3.87 (s, 3H), 2.61 (q, 2H), 1.19 (t, 3H). |
| 21 | 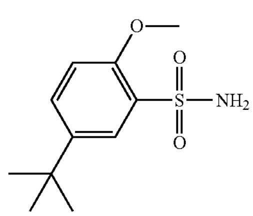 [SMILES: COc1ccc(C(C)(C)C)cc1S(N)(=O)=O] | LC-MS: 244.1 $[M + H]^+$. |

TABLE 5-continued

| Intermediates | | |
|---|---|---|
| Intermediate | Structure | Spectral data |
| 22 | (2,6-dimethoxybenzenesulfonamide) | LC-MS: 218.0 [M + H]⁺. |
| 23 | (biphenyl-2-sulfonamide) | LC-MS: 232.0 [M − H]⁻. |
| 24 | (3-hydroxybenzenesulfonamide) | LC-MS: 174.0 [M + H]⁺. |
| 25 | (5-bromo-2-methoxybenzenesulfonamide) | LC-MS: 267.8 [M + H]⁺. |
| 26a | (2,4-dimethoxybenzenesulfonamide) | LC-MS: 218 [M + H]⁺. |
| 26b | (5-fluoro-2,4-dimethoxybenzenesulfonamide) | LC-MS: 236 [M + H]⁺. |
| 26c | (5-chloro-2,4-dimethoxybenzenesulfonamide) | LC-MS: 252 [M + H]⁺. |

TABLE 5-continued
Intermediates
| Intermediate | Structure | Spectral data |
| --- | --- | --- |
| 26d | 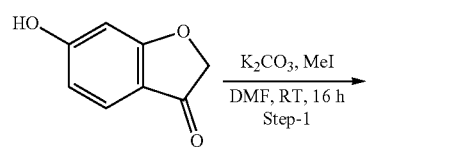 | LC-MS: 297 [M + H]$^+$. |
| 26e | 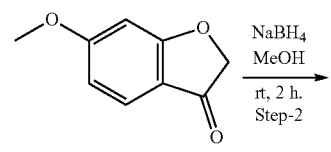 | LC-MS: 252 [M + H]$^+$. |
| 26f | 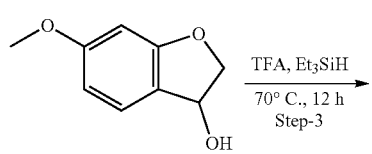 | LC-MS: 224 [M + H]$^+$. |
Intermediate 50:
6-Methoxy-2,3-dihydrobenzofuran-7-sulfonamide
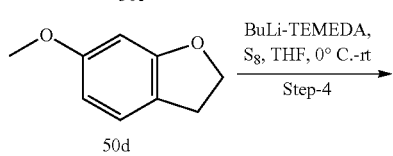
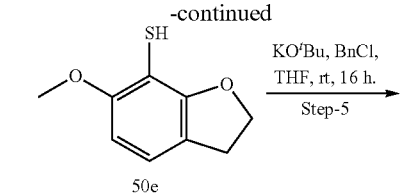
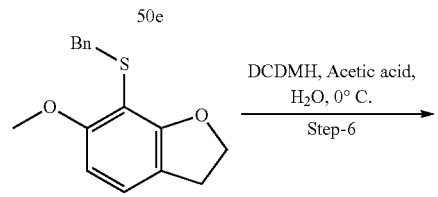

Step 1: 6-Methoxybenzofuran-3 (2H)-one

To a solution of 6-hydroxybenzofuran-3 (2H)-one (7.2 g 48.62 mmol) in DMF (80 mL) were added $K_2CO_3$ (13.44 g, 97.25 mmol) and MeI (11.45 g, 80.71 mmol) at 0° C. The reaction mixture was slowly warmed to RT and stirred for 16 h. The reaction mixture was diluted with water, extracted with EtOAc. The organic layer was washed with brine, dried over $Na_2SO_4$, filtered, and concentrated to get the crude compound which was used in next step without further purification (6.10 g, 88.60%). $^1$H NMR (DMSO-$d_6$, 400 MHz): δ 7.53 (d, 1H), 6.83 (d, 1H), 6.71 (dd, 1H), 4.77 (s, 2H), 3.87 (s, 3H).

Step 2: 6-Methoxy-2,3-dihydrobenzofuran-3-ol

To a solution of 6-methoxybenzofuran-3 (2H)-one (7.0 g, 42.64 mmol) in MeOH (80 mL) was added $NaBH_4$ (3.22 g, 85.27 mmol) at 0° C. The reaction mixture slowly warmed to RT and stirred for 2 h. The reaction mixture was quenched with ice-water and extracted with ethyl acetate. The organic layer was washed with brine, dried over $Na_2SO_4$, filtered, and concentrated to obtain the title compound (6.20 g, 84.80%). $^1$H NMR (DMSO-$d_6$, 400 MHz): δ 7.23 (d, 1H), 6.46 (dd, 1H), 6.41 (s, 1H), 5.43 (d, 1H), 5.21-5.16 (m, 1H), 4.52-4.48 (m, 1H), 4.25-4.21 (m, 1H), 3.72 (s, 3H).

Step 3: 6-Methoxy-2,3-dihydrobenzofuran

To a solution of 6-methoxy-2,3-dihydrobenzofuran-3-ol (6.0 g, 48.62 mmol) in TFA (8.22 g, 72.21 mmol) was added triethylsilane (4.1 g, 36.10 mmol) at 0° C. and then heated at 70° C. for 12 h. The reaction mixture was poured in aqueous sodium bicarbonate solution and extracted with ethyl acetate. The organic layer was washed with water, brine, dried over solid sodium sulphate, filtered, and concentrated to afford crude. The crude was purified by silica-gel flash column chromatography using 10% of ethyl acetate in hexane as eluent to obtain pure compound (1.40 g, 25.8%). $^1$H NMR, DMSO-$d_6$, 400 MHz): δ 7.11 (d, 1H), 6.39 (d, 1H), 6.37 (s, 1H), 4.55 (t, 2H), 3.72 (s, 3H), 3.08 (t, 2H).

Step 4: 6-Methoxy-2,3-dihydrobenzofuran-7-thiol

To a solution of 6-methoxy-2,3-dihydrobenzofuran (1.40 g, 9.32 mmol) in THF (14 mL) was slowly added n-BuLi (5.59 mL, 13.99 mmol) dropwise and followed by TMEDA (0.10 g, 0.93 mmol) at 0° C. The reaction mixture was slowly warmed to RT and stirred at same temperature for 20 min. Sulphur powder (0.28 g, 8.39 mmol) in toluene (4 mL) solution was added to the reaction mixture at 0° C. The reaction mixture was stirred at RT for 12 h. The reaction was quenched with 1N HCl solution and extracted with ethyl acetate. The combined organic layer was dried over solid sodium sulphate, filtered, and concentrated to afford crude. The crude was purified by silica-gel flash column chromatography using 15% of ethyl acetate in hexane as eluent to obtain the title compound (1.0 g, 58.86%). LC-MS: 181.0 [M−H]⁻.

Step 5: 7-(Benzylthio)-6-methoxy-2,3-dihydrobenzofuran

To a solution of 6-methoxy-2,3-dihydrobenzofuran-7-thiol (1.0 g, 5.48 mmol) in THF (10 mL) was added potassium tertiary butoxide (0.739 g, 6.58 mmol) and followed by benzyl chloride (0.69 g, 5.48 mmol) at 0° C. The reaction mixture was slowly warmed to RT and stirred for 16 h. The reaction mixture was quenched with water and extracted with ethyl acetate. The organic layer was washed with brine, dried over sodium sulphate, filtered, and concentrated to afford the crude. The crude was purified by silica-gel flash column chromatography using 5-15% of ethyl acetate in hexane as eluent to obtain the title compound (0.45 g, 30.11%). LC-MS: 273.0 [M+H]⁺.

Step 6: 6-Methoxy-2,3-dihydrobenzofuran-7-sulfonyl chloride

To a solution of 7-(benzylthio)-6-methoxy-2,3-dihydrobenzofuran (0.25 g, 0.98 mmol) in acetonitrile (3 mL), acetic acid (2 mL) and water (1 mL), was added DCDMH (0.21 g, 1.10 mmol) at 0° C. and stirred for 15 min. The reaction mixture was quenched with water and extracted with ethyl acetate. The combined organic layer was washed with sodium bicarbonate solution, brine, dried over anhydrous sodium sulphate, and concentrated to afford the crude material. The crude compound was purified by silica-gel flash column chromatography using 15-20% ethyl acetate in hexane as eluent to obtain the title compound (0.17 g, 74.5%). $^1$H NMR (DMSO-$d_6$, 400 MHz): δ 7.09 (d, 1H), 6.39 (d, 1H), 4.47 (t, 2H), 3.69 (s, 3H), 3.06 (t, 2H).

Step 7: 6-Methoxy-2,3-dihydrobenzofuran-7-sulfonamide

The title compound was prepared using similar procedure to that described in Step 3 of Intermediate 15 using appropriate reagents with suitable modifications $^1$H NMR (DMSO-$d_6$, 400 MHz): δ 7.31 (d, 1H), 6.96 (s, 2H), 6.56 (d, 1H), 4.59 (t, 2H), 3.81 (s, 3H), 3.11 (t, 2H).

Intermediate 51: 2-Methoxy-6-(1H-pyrazol-1-yl)benzenesulfonamide

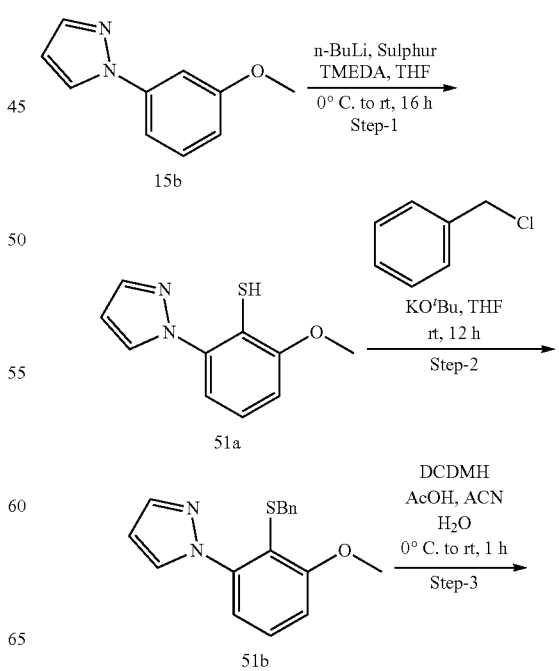

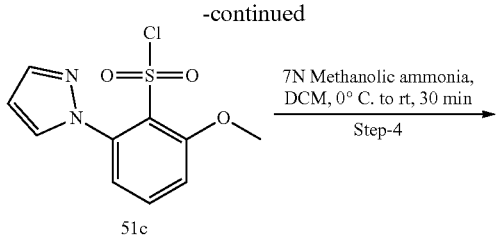

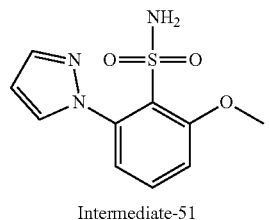

Intermediate-51

Step 1: 2-Methoxy-6-(1H-pyrazol-1-yl)benzenethiol

The title compound was prepared using similar procedure to that described in Step 4 of Intermediate 50 using appropriate reagents with suitable modifications. $^1$H NMR (CDCl$_3$, 400 MHz): δ 7.62 (d, 1H), 7.32 (t, 1H), 6.97-6.90 (m, 3H), 6.50 (d, 1H), 3.86 (s, 1H), 3.82 (s, 3H)

Step 2: 1-(2-(Benzylthio)-3-methoxyphenyl)-1H-pyrazole

The title compound was prepared using similar procedure to that described in Step 5 of Intermediate 50 using appropriate reagents with suitable modifications. LC-MS: 297.1.1 [M+H]$^+$.

Step 3: 2-Methoxy-6-(1H-pyrazol-1-yl)benzenesulfonyl chloride

The title compound was prepared using similar procedure to that described in Step 6 of Intermediate 50 using appropriate reagents with suitable modifications: LC-MS: 273.0 [M+H]$^+$.

Step 4: 2-Methoxy-6-(1H-pyrazol-1-yl)benzenesulfonamide

The title compound was prepared using similar procedure to that described in Step 3 of Intermediate 15 using appropriate reagents with suitable modifications: LC-MS: 254.0 [M+H]$^+$.

Intermediate 52: 2-(Pyridin-2-ylmethoxy)benzenesulfonamide

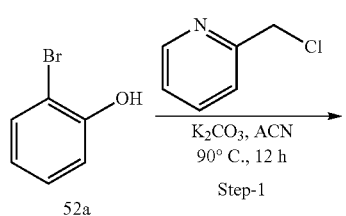

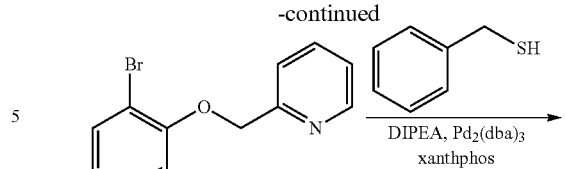

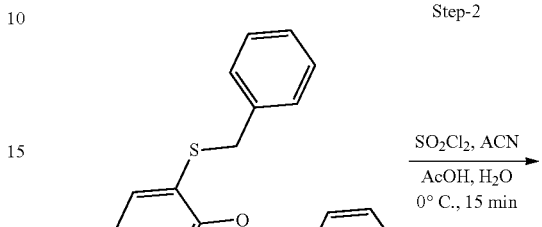

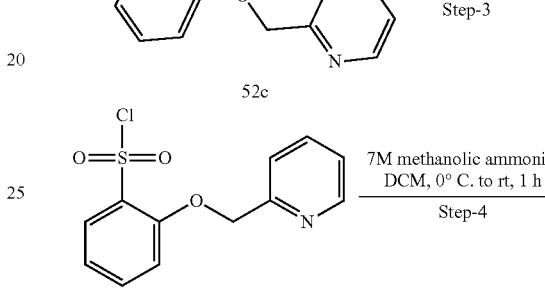

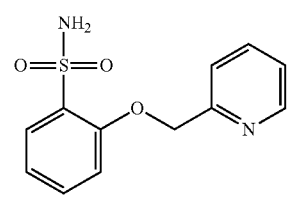

Intermediate-52

Step 1: 2-((2-Bromophenoxy methyl) pyridine

To a solution of 2-bromophenol (2 g, 11.56 mmol) and K$_2$CO$_3$ (3.19 g 23.12 mmol) in acetonitrile (ACN, 20 mL) was added 2-(chloromethyl) pyridine (1.17 g, 13.87 mmol) and stirred at 90° C. for 12 h. The reaction mixture was cooled to RT, diluted with EtOAc, washed with 2 N NaOH solution (10 mL), and brine. The organic layer was dried over sodium sulphate, filtered, and concentrated to afford the crude. The crude was purified by silica-gel flash column chromatography using 10-15% of ethyl acetate in hexane as eluent to obtain the title compound (2.8 g, 91.7%). LC-MS: 264.8 [M+H]+

Step 2: 2-((2-(Benzylthio)phenoxy)methyl)pyridine

To a degassed solution of 2-((2-bromophenoxy methyl pyridine) (2.8 g, 10.60 mmol) and benzyl mercaptan (1.31 g, 10.60 mmol), N,N-diisopropylethylamine (2.74 g, 21.20 mmol) and XantPhos (1.22 g, 2.22 mmol) in 1,4-Dioxane (30 mL) was added Pd$_2$(dba)$_3$ (1.94 gm 2.12 mmol) and stirred at to 80° C. for 2 h. The reaction mixture was passed through the celite and washed with ethyl acetate. The filtrate was concentrated to get crude product which was purified by silica-gel flash column chromatography using 0-10% ethyl acetate in hexane as eluent to afford the title compound (2.5 g, 76.7%). LC-MS: 306.1 [M−H]$^-$

Step 3: 2-(Pyridin-2-ylmethoxy)benzenesulfonyl chloride

To a solution of 2-((2-(benzylthio)phenoxy)methyl)pyridine (1.5 g, 4.87 mmol) in acetonitrile (12 mL), acetic acid (6 mL) and water (3 mL) was added sulfuryl chloride (1.31 g, 9.75 mmol) at a 0° C. and stirred at same temperature for 15 min. The reaction mixture was quenched with water and extracted with ethyl acetate. The organic layer was washed with aqueous sodium bicarbonate solution, brine, dried over sodium sulphate, filtered, and concentrated to afford the crude compound. The crude compound was purified by silica-gel flash column chromatography using 3-5% ethyl acetate in hexane as eluent to afford the title compound (0.35 g, 25.3%). LC-MS: 281.9 [M–H]–

Step 4: 2-(Pyridin-2-ylmethoxy)benzenesulfonamide

The title compound was prepared using similar procedure to that described in Step 3 of Intermediate 15 using appropriate reagents with suitable modifications. LC-MS: 263.0 [M–H]⁻.

Intermediate 53: 5-Methoxy-1-methyl-1H-indazole-4-sulfonamide

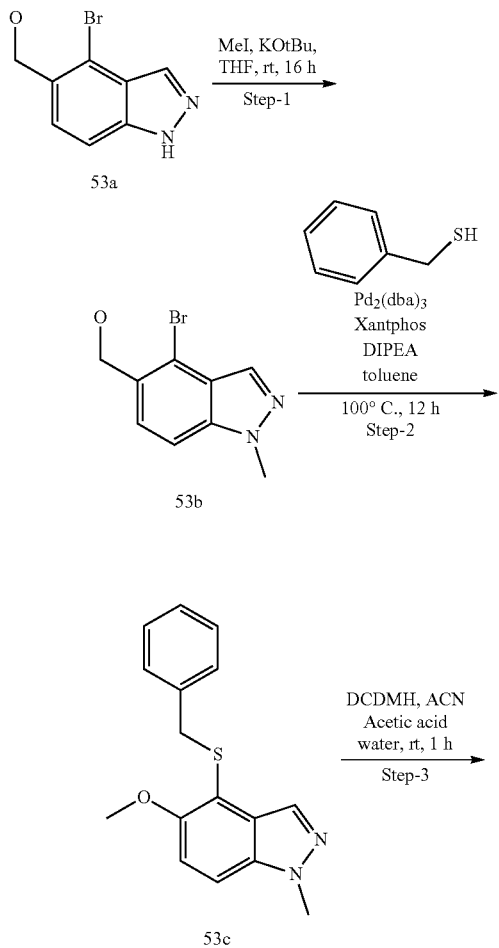

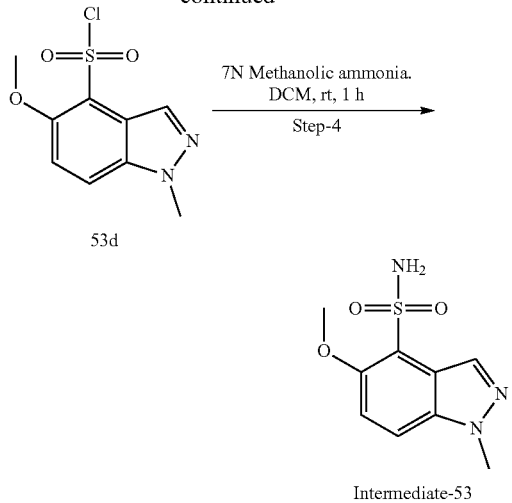

Step 1: 4-Bromo-5-methoxy-1-methyl-1H-indazole

To a solution of 4-bromo-5-methoxy-1H-indazole (0.8 g 3.52 mmol) in THF (40 mL) were added KO$^t$Bu (0.59 g, 5.28 mmol) and followed by MeI (5 g, 35.2 mmol) at 0° C. The reaction mixture was slowly warmed to RT and stirred for 16 h. The reaction mixture was quenched with water and extracted with ethyl acetate. The organic layer was dried over $Na_2SO_4$, filtered, and concentrated to afford the crude compound. The crude compound was purified by silica-gel flash column chromatography using 40-50% ethyl acetate in hexane as eluent to obtain the title compound (0.8 g, 94.1%). LC-MS: 240.7 [M+H]⁺.

Step 2: 4-(Benzylthio)-5-methoxy-1-methyl-1H-indazole

To a degassed solution of 4-bromo-5-methoxy-1-methyl-1H-indazole (0.86 g, 3.57 mmol) and benzyl mercaptan (0.443 g, 3.57 mmol) in toluene (15 mL) was added $Pd_2(dba)_3$ (0.326 gm 0.35 mmol), N,N-Diisopropylethylamine (0.922 g, 7.13 mmol) and XantPhos (0.413 g, 0.71 mmol) to the reaction mixture at RT. The reaction mixture was heated at 100° C. for 12 h. After completion of the reaction the mixture was passed through the celite and washed with ethyl acetate and concentrated under reduced pressure to afford crude compound. The crude compound was purified by silica gel flash column chromatography using 30-40% EtOAc in hexane as eluent to afford the title compound (0.65 g, 64.05%); LC-MS: 285.1 [M+H]⁺.

Step 3: 5-Methoxy-1-methyl-1H-indazole-4-sulfonyl chloride

The title compound was prepared using similar procedure to that described in Step 6 of Intermediate 50 using appropriate reagents with suitable modifications. LC-MS: 261.0 [M+H]⁺.

Step 4: 5-Methoxy-1-methyl-1H-indazole-4-sulfonamide

The title compound was prepared using similar procedure to that described in Step 3 of Intermediate 15 using appropriate reagents with suitable modifications. LC-MS: 242.1 [M+H]⁺.

Intermediate 54: 5-(2-Hydroxypropan-2-yl)-2-methoxybenzenesulfonamide

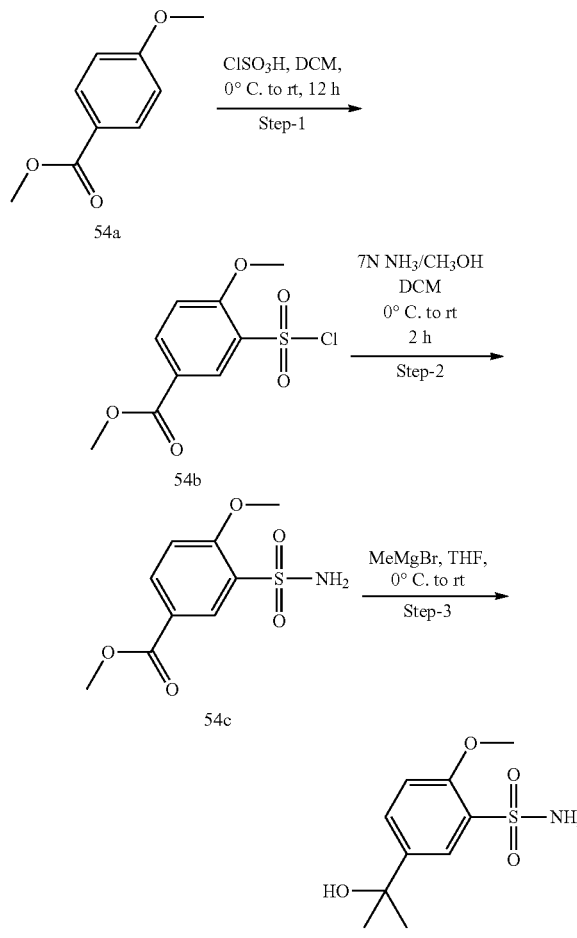

Step 1: Methyl 3-(chlorosulfonyl)-4-methoxybenzoate

The title compound was prepared using similar procedure to that described in Step 1 of Intermediate 18 using appropriate reagents with suitable modifications. LC-MS: 264.1 [M+H]+.

Step 2: Methyl 4-methoxy-3-sulfamoylbenzoate

The title compound was prepared using similar procedure to that described in Step 3 of Intermediate 15 using appropriate reagents with suitable modifications. LC-MS: 246.1 [M+H]+.

Step 3: 5-(2-Hydroxypropan-2-yl)-2-methoxybenzenesulfonamide

To a solution of methyl 4-methoxy-3-sulfamoylbenzoate (0.1 g, 0.408 mmol) in THF (2 mL) was added MeMgBr (1.2 mL, 1.22 mmol, 1 M in THF) at 0° C. and then stirred at rt for 2 h. The reaction was quenched with ice-water and extracted with ethyl acetate. The organic layer was dried over sodium sulphate, filtered, and concentrated to afford the crude material. The crude compound was purified by silica-gel flash column chromatography using 80% EtOAc in hexane to afford the title compound (0.075 g, 75%). LC-MS: 246.0 [M+H]+.

Intermediate 55: 2-Isopropoxy-6-methoxybenzenesulfonamide

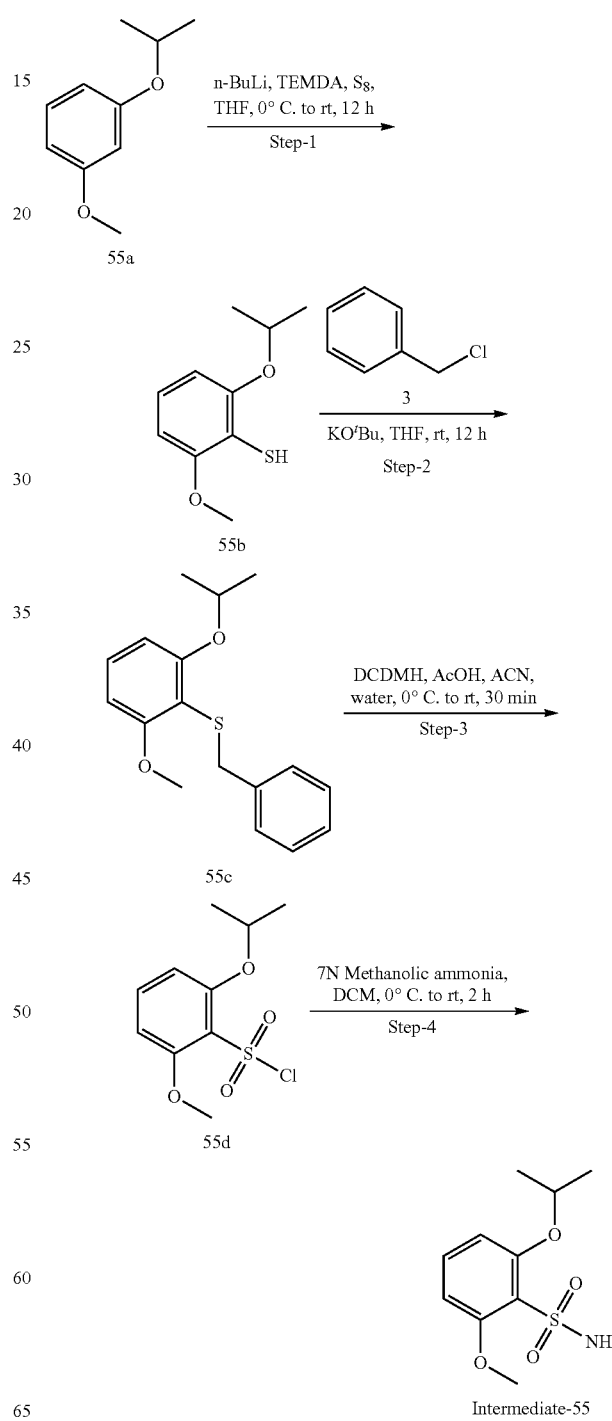

Step 1: 2-Isopropoxy-6-methoxybenzenethiol

The title compound was prepared using similar procedure to that described in Step 4 of Intermediate 50 using appropriate reagents with suitable modifications. $^1$H NMR (CDCl$_3$, 400 MHz): δ 7.20 (t, 1H), 6.50 (d, 1H), 6.48 (d, 1H), 4.40-4.37 (m, 1H), 3.90 (s, 3H), 1.21 (d, 6H).

Step 2: Benzyl(2-isopropoxy-6-methoxyphenyl)sulfane

The title compound was prepared using similar procedure to that described in Step 5 of Intermediate 50 using appropriate reagents with suitable modifications $^1$H NMR (CDCl$_3$, 400 MHz): δ 7.28-7.16 (m, 6H), 6.55 (d, 1H), 6.50 (d, 1H), 4.54-4.51 (m, 1H), 4.03 (s, 2H), 3.84 (s, 3H), 1.36 (d, 6H).

Step 3: 2-Isopropoxy-6-methoxybenzenesulfonyl chloride

The title compound was prepared using similar procedure to that described in Step 6 of Intermediate 50 using appropriate reagents with suitable modifications. LC-MS: 264.9 [M+H]$^+$.

Step 4: 2-Isopropoxy-6-methoxybenzenesulfonamide

The title compound was prepared using similar procedure to that described in Step 3 of Intermediate 15 using appropriate reagents with suitable modifications. $^1$H NMR (DMSO-d$_6$, 400 MHz): δ 7.38 (t, 1H), 7.15 (d, 1H), 6.82 (s, 2H), 6.68 (d, 1H), 4.61-4.58 (m, 1H), 3.82 (s, 3H), 1.28 (d, 6H).

Intermediate 56: 5-Methoxy-2,3-dihydro-1H-indene-4-sulfonamide

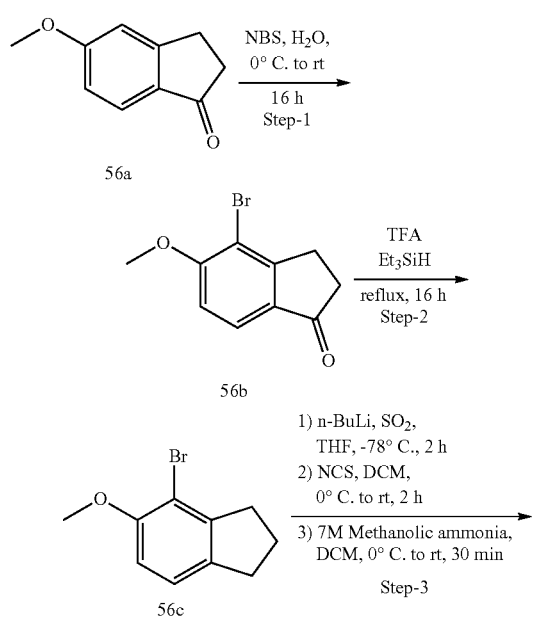

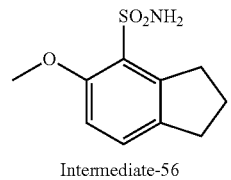

Intermediate-56

Step 1: 4-Bromo-5-methoxy-2,3-dihydro-1H-inden-1-one

To a solution of 5-methoxy-2,3-dihydro-1H-inden-1-one (10 g, 61.65 mmol) in water (120 mL) was added NBS (10.97 g, 61.65 mmol) at 0° C. The reaction mixture was warmed to RT and stirred for 16 h. The reaction was quenched with ice water and extracted with ethyl acetate. The organic layer was dried over sodium sulphate, filtered, and concentrated to afford the crude material. Crude compound was purified by silica-gel flash column chromatography using 5% ethyl acetate in hexane as eluent to afford the title compound (12 g, 80.7%). LC-MS: 240.7 [M+H]$^+$.

Step 2: 4-Bromo-5-methoxy-2,3-dihydro-1H-indene

To a solution of 4-bromo-5-methoxy-2,3-dihydro-1H-inden-1-one (10 g, 41.47 mmol) in TFA (60 mL) was added triethylsilane (2.39 g, 20.74 mmol) at 0° C. The reaction mixture was slowly warmed to RT and then stirred for 16 h under reflux. The reaction was diluted with ice water, quenched with aqueous NaHCO$_3$, and extracted with ethyl acetate. The organic layer was dried over sodium sulphate, filtered, and concentrated to afford the crude material. Crude compound was purified by silica-gel flash column chromatography using hexane as eluent to afford the title compound (6 g, 63.7%). LC-MS: 227.9 [M+H]$^+$.

Step 3: 5-Methoxy-2,3-dihydro-1H-indene-4-sulfonamide

To a solution of 4-bromo-5-methoxy-2,3-dihydro-1H-indene (0.2 g, 0.88 mmol) in THF (7 mL) was added n-BuLi (1.65 mL, 2.64 mmol) at −78° C. and stirred at the same temperature for 1 h. Then SO$_2$ gas was bubbled into the reaction mixture for 30 min at −78° C. The reaction mixture was slowly warmed to RT and stirred for 1 h. The reaction mixture was concentrated to obtain the solid. The solid was dissolved in DCM and NCS (0.35 g, 2.64 mmol) was added to it at 0° C. The reaction mixture was warmed to RT and stirred for 2 h. The reaction was quenched with ice water and extracted with DCM. The organic layer was dried over sodium sulphate, filtered, and concentrated to afford the crude material. The crude compound was dissolved in DCM and 7N methanolic ammonia (5 mL) was added to it at RT. The reaction mixture was stirred for 30 min at RT. The reaction mixture was diluted with water and extracted with DCM. The organic layer was dried over sodium sulphate, filtered, and concentrated to afford the crude compound. Crude compound was purified by silica-gel flash column chromatography using 50% ethyl acetate in hexane as eluent to afford the title compound (6 g, 63.7%). LC-MS: 228.1 [M+H]$^+$.

Intermediate 57: 2-Methoxy-5,6,7,8-tetrahydronaphthalene-1-sulfonamide

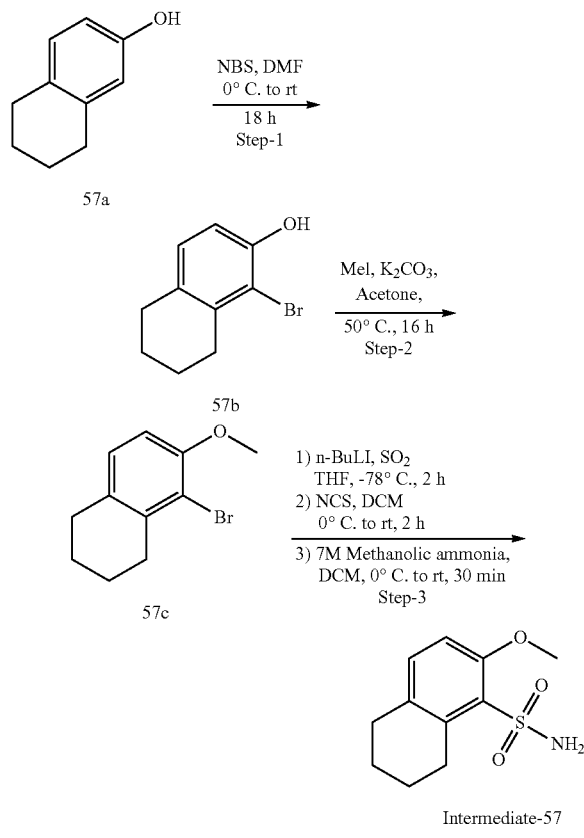

Step 1: 1-Bromo-5,6,7,8-tetrahydronaphthalen-2-ol

To a solution of 5,6,7,8-tetrahydronaphthalen-2-ol (5 g, 33.73 mmol) in DMF (60 mL) was added NBS (6 g, 33.73 mmol) at 0° C. The reaction mixture was slowly warmed to RT and stirred for 18 h. The reaction was quenched with ice water and extracted with ethyl acetate. The organic layer was dried over sodium sulphate, filtered, and concentrated to afford the crude material. Crude compound was purified by silica-gel flash column chromatography using 5% EtOAc in hexane as eluent to afford the title compound (6 g, 78.32%). $^1$H NMR (CDCl$_3$, 400 MHz): δ 6.95 (d, 1H), 6.85 (d, 1H), 5.54 (s, 1H), 2.75-2.68 (m, 4H), 1.88-1.83 (m, 2H), 1.79-1.73 (m, 2H).

Step 2: 5-Bromo-6-methoxy-1,2,3,4-tetrahydronaphthalene

To a solution of 1-bromo-5,6,7,8-tetrahydronaphthalen-2-ol (6 g, 26.42 mmol) and K$_2$CO$_3$ (7.9 g, 57.24 mmol) in acetone (60 mL) was added MeI (12.2 g, 85.86 mmol) and stirred at RT for 16 h. The reaction was quenched with ice water and extracted with ethyl acetate. The organic layer was dried over sodium sulphate, filtered, and concentrated to afford the crude material. Crude compound was purified by silica-gel flash column chromatography using 5% ethyl acetate in hexane to afford the title compound (4.5 g, 70.64%). $^1$H NMR (CDCl$_3$, 400 MHz): δ 7.00 (d, 1H), 6.73 (d, 1H), 3.88 (s, 3H), 2.80-2.71 (m, 4H), 1.86-1.79 (m, 2H), 1.78-1.72 (m, 2H).

Step 3: 2-Methoxy-5,6,7,8-tetrahydronaphthalene-1-sulfonamide

The title compound was prepared using similar procedure to that described in Step 3 of Intermediate 56 using appropriate reagents with suitable modifications. LC-MS: 242.1 [M+H]$^+$.

Intermediate 58: 2-Ethoxy-6-methoxybenzenesulfonamide

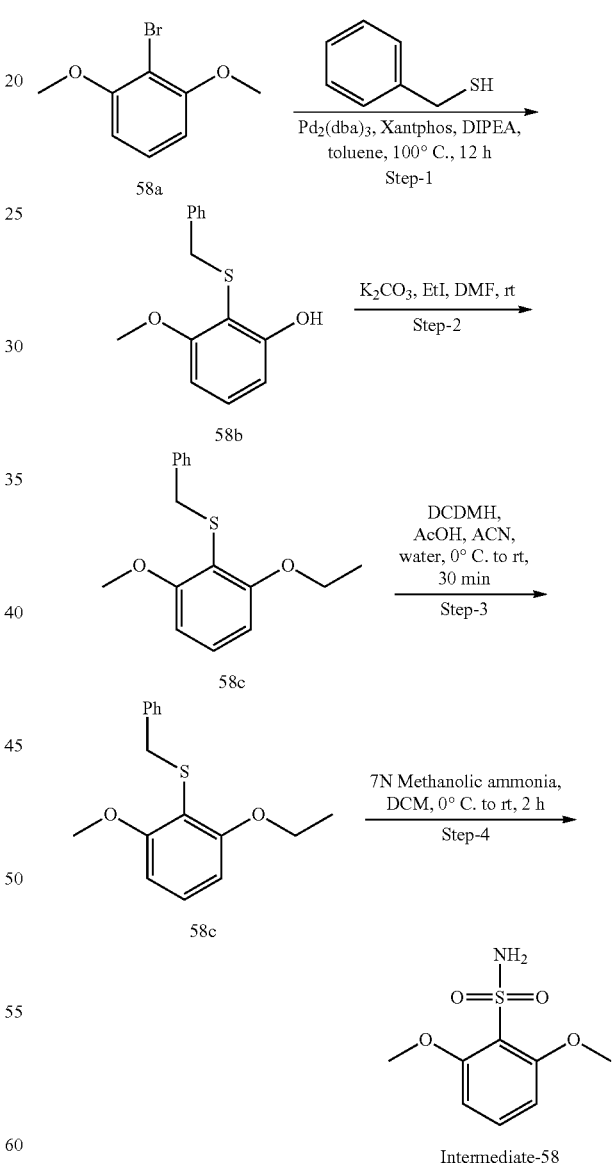

Step 1: 2-(Benzylthio)-3-methoxyphenol

To a degassed solution of 2-bromo-3-methoxyphenol (2 g, 9.84 mmol) and phenylmethenethiol (1.22 g, 9.84 mmol), N,N-Diisopropylethylamine (3.42 mL, 19.7 mmol) and Xantphos (1.14 g, 0.1.97 mmol) in toluene (30 mL) was added Pd$_2$(dba)$_3$ (0.901 gm 0.98 mmol) and stirred at 100° C. for 16 h. The reaction mixture was cooled to RT, passed through the celite pad, washed with ethyl acetate, and concentrated under reduced pressure to afford crude compound. The crude compound was purified by silica-gel flash column chromatography using 30-40% EtOAc in hexane as eluent to afford the title compound (0.4 g, 16.5%); LC-MS: 245.0 [M+H]$^+$.

Step 2: Benzyl(2-ethoxy-6-methoxyphenyl)sulfane

This compound was prepared using similar procedure to that described in Step 1 of Intermediate 50 using appropriate reagents with suitable modifications. LC-MS: 275.1 [M+H]$^+$.

Step 3: 2-Ethoxy-6-methoxybenzenesulfonyl chloride

The title compound was prepared using similar procedure to that described in Step 6 of Intermediate 50 using appropriate reagents with suitable modifications. $^1$H NMR (DMSO-d$_6$, 400 MHz): δ 7.25 (t, 1H), 6.64 (d, 1H), 6.63 (d, 1H), 4.00 (q, 2H), 3.72 (s, 3H), 1.28 (t, 3H).

Step 4: 2-Ethoxy-6-methoxybenzenesulfonamide

The title compound was prepared using similar procedure to that described in Step 3 of Intermediate 15 using appropriate reagents with suitable modifications. LC-MS: 232.0 [M+H]$^+$.

Intermediate 59:
2-Cyclobutoxy-6-methoxybenzenesulfonamide

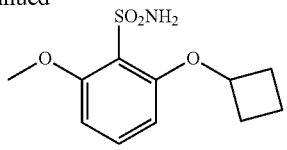

Intermediate-59

Step 1: Benzyl(2-cyclobutoxy-6-methoxyphenyl)sulfane

The title compound was prepared using similar procedure to that described in Step 2 of Intermediate 53 using appropriate reagents with suitable modifications. LC-MS: 301.1 [M–H]–

Step 2: 2-Cyclobutoxy-6-methoxybenzenesulfonyl chloride

The title compound was prepared using similar procedure to that described in Step 6 of Intermediate 50 using appropriate reagents with suitable modifications. $^1$H NMR (DMSO-d$_6$, 400 MHz): δ 7.50 (t, 1H), 6.62 (d, 1H), 6.49 (d, 1H), 4.81-4.73 (m, 1H), 3.99 (s, 3H), 2.25-2.21 (m, 2H), 1.92-1.87 (m, 2H), 1.51-1.46 (m, 2H).

Step 3:
2-Cyclobutoxy-6-methoxybenzenesulfonamide

The title compound was prepared using similar procedure to that described in Step 3 of Intermediate 15 using appropriate reagents with suitable modifications. LC-MS: 256.0 [M–H]$^-$.

Intermediate 63:
2-(Difluoromethoxy)-6-methoxybenzenesulfonamide

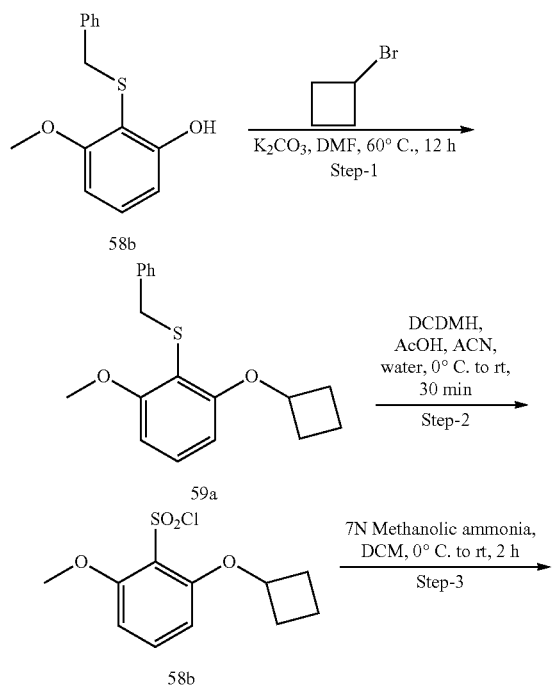

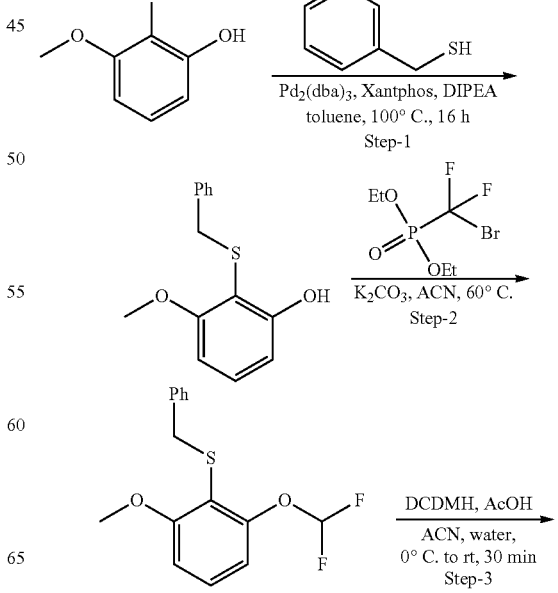

-continued

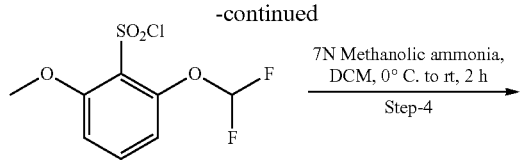

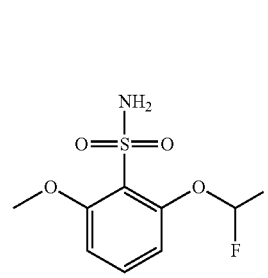

Intermediate-63

Step 1: 2-(Benzylthio)-3-methoxyphenol

This compound was prepared using similar procedure to that described in Step 2 of Intermediate 52 using appropriate reagents with suitable modifications. LC-MS: 245.1 [M–H]⁻.

Step 2: Benzyl(2-(difluoromethoxy)-6-methoxyphenyl)sulfane

To a solution of 2-(benzylthio)-3-methoxyphenol (0.3 g, 1.217 mmol) and diethyl (bromodifluoromethyl)phosphonate (0.650 g, 2.43 mmol) in acetonitrile (20 mL) was added potassium hydroxide (0.342 g, 6.09 mmol) at 0° C. Then the reaction mixture was slowly warmed to RT and stirred for 16 h. The reaction mixture was quenched with water and extracted with ethyl acetate. The combined organic layer was washed with aqueous sodium bicarbonate, brine, dried over anhydrous sodium sulphate, filtered, and concentrated to afford the crude material. The crude material was purified by silica-gel flash column chromatography using 0-20% ethyl acetate in hexane as eluent to obtain the title compound (0.2 g, 55.41%). $^1$H NMR (DMSO-d$_6$, 400 MHz): δ 7.48-7.15 (m, 6H), 7.00 (dd, 1H), 6.79 (t, 1H), 6.76 (dd, 1H), 4.03 (s, 2H), 3.85 (s, 3H).

Step 3: 2-(Difluoromethoxy)-6-methoxybenzenesulfonyl chloride

The title compound was prepared using similar procedure to that described in Step 6 of Intermediate 50 using appropriate reagents with suitable modifications LC-MS: 270.8 [M–H]⁻.

Step 4: 2-(Difluoromethoxy)-6-methoxybenzenesulfonamide

The title compound was prepared using similar procedure to that described in Step 3 of Intermediate 15 using appropriate reagents with suitable modifications LC-MS: 252.0 [M–H]⁻.

Intermediate 64: 3-Ethyl-2,6-dimethoxybenzenesulfonamide

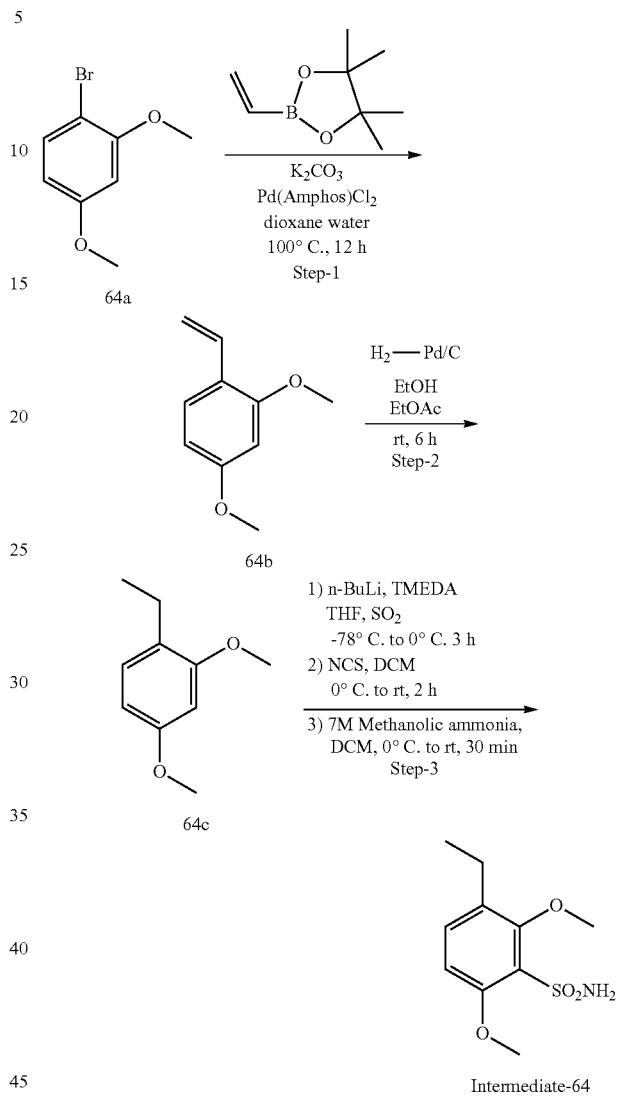

Step 1: 2,4-Dimethoxy-1-vinylbenzene

To a degassed solution of 1-bromo-2,4-dimethoxybenzene (3.0 g, 13.82 mmol), 4,4,5,5-tetramethyl-2-vinyl-1,3,2-dioxaborolane (4.25 g, 27.64 mmol), and K$_2$CO$_3$ (5.73 g, 41.46 mmol) in 1,4-dioxane (50 mL), water (10 mL) was added Pd(Amphos)Cl$_2$ (0.97 g, 1.38 mmol) and stirred at 100° C. for 12 h. The reaction mixture was cooled to RT, diluted with water, and extracted with 10% methanol in DCM. The organic layer was dried over Na$_2$SO$_4$, filtered, and concentrated to afford crude compound. The crude compound was purified by silica-gel flash column chromatography using 10-15% ethyl acetate in hexane to afford the title compound (2.0 g, 88.14%). $^1$H NMR (DMSO-D6, 400 MHz): δ 7.42 (d, 1H), 6.85 (dd, 1H), 6.55-6.50 (m, 2H), 5.63 (dd, 1H), 5.09 (d, 1H), 3.80 (s, 3H), 3.77 (s, 3H).

Step 2: 1-Ethyl-2,4-dimethoxybenzene

A mixture of 1-ethyl-2,4-dimethoxybenzene (1.9 g, 11.57 mmol) and Pd—C (1.84 g, 17.35 mmol) in ethanol (25 mL)

and ethyl acetate (25 mL) was stirred under positive pressure of hydrogen using bladder for 6 h. The reaction mixture was filtered through celite pad and washed with 5% methanol in DCM. The filtrate was concentrated to afford the crude compound, which was taken to the next step without purification (1.85 g). $^1$H NMR (DMSO-D6, 400 MHz): δ 7.01 (d, 1H), 6.51 (s, 1H), 6.43 (dd, 1H), 3.75 (s, 3H), 3.73 (s, 3H), 2.49 (q, 2H), 1.18 (t, 3H).

Step 3: 3-Ethyl-2,6-dimethoxybenzenesulfonamide

To a solution of 1-ethyl-2,4-dimethoxybenzene (1.8 g, 10.82 mmol) in THF (20 mL) was added TMEDA (2.13 g, 18.4 mmol), n-BuLi (0.73 mL, 18.4 mmol) at 0° C. and stirred at the same temperature for 1 h. Then SO$_2$ gas was bubbled into the reaction mixture for 30 min at −78° C. The reaction mixture was slowly warmed to 0° C. and stirred for 1 h. The reaction mixture was concentrated to obtain the solid. The solid was dissolved in DCM and NCS (2.26 g, 16.93 mmol) was added to the reaction mixture at 0° C. The reaction mixture was warmed to RT and stirred for 2 h. The reaction was quenched with ice water and extracted with DCM. The organic layer was dried over sodium sulphate, filtered, and concentrated to afford the crude material. The crude compound was dissolved in DCM (10 mL) and 7N methanolic ammonia (10 mL) was added to the reaction mixture and stirred for 30 min at RT. The reaction mixture was diluted with water and extracted with DCM. The organic layer was dried over sodium sulphate, filtered, and concentrated to afford the crude compound. Crude compound was purified by silica-gel flash column chromatography using 50% ethyl acetate in hexane as eluent to afford the title compound (0.6 g). LC-MS: 244.0 [M−H]$^-$.

Intermediate 65:
2,6-Dimethoxy-3-methylbenzenesulfonamide

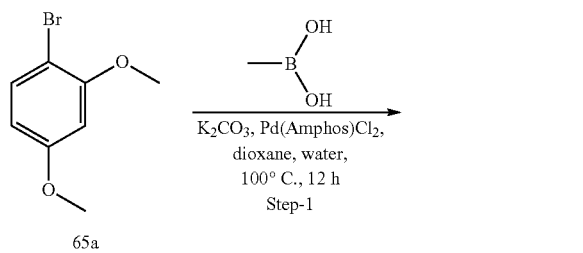

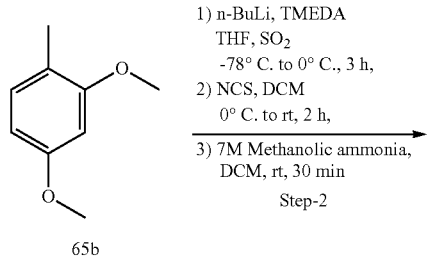

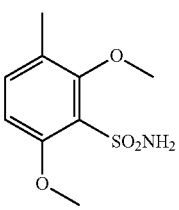

Intermediate-65

Step 1: 2,4-Dimethoxy-1-methylbenzene

The title compound was prepared using similar procedure to that described in Step 1 of Intermediate 64 using appropriate reagents with suitable modifications. $^1$H NMR, CDCl$_3$, 400 MHz): δ 7.40 (d, 1H), 6.46 (d, 1H), 6.42 (dd, 1H), 3.83 (s, 3H), 3.82 (s, 3H), 2.17 (S, 3H).

Step 2:
2,6-Dimethoxy-3-methylbenzenesulfonamide

The title compound was prepared using similar procedure to that described in Step 3 of Intermediate 64 using appropriate reagents with suitable modifications. LC-MS: 230.0 [M−H]$^-$.

Intermediate 66:
3-Cyclopropyl-2,6-dimethoxybenzenesulfonamide

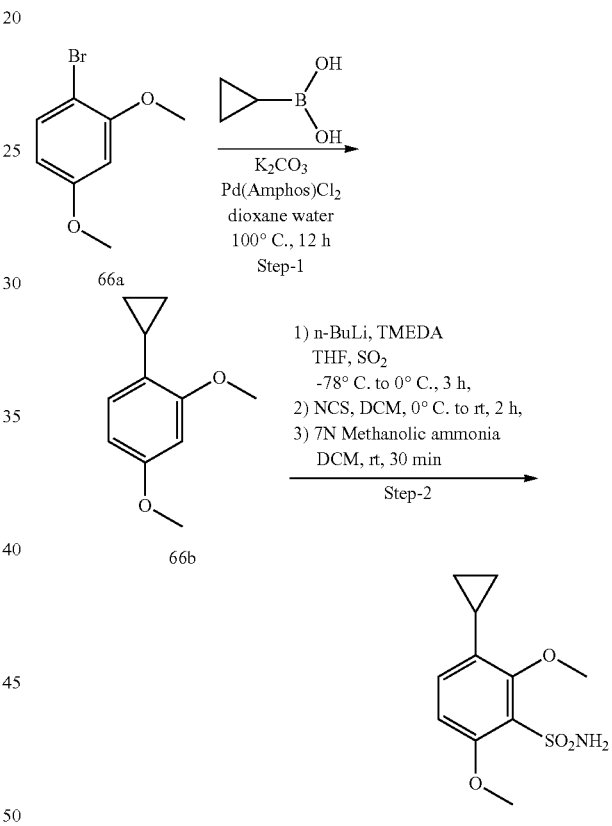

Step 1: 1-Cyclopropyl-2,4-dimethoxybenzene

The title compound was prepared using similar procedure to that described in Step 1 of Intermediate 64 using appropriate reagents with suitable modifications. LC-MS: 179.1 [M+H]$^+$.

Step 2:
3-Cyclopropyl-2,6-dimethoxybenzenesulfonamide

The title compound was prepared using similar procedure to that described in Step 3 of Intermediate 64 using appropriate reagents with suitable modifications. LC-MS: 256.1 [M−H]$^-$.

Intermediate 67: 5-Cyclopropyl-2-methoxybenzenesulfonamide

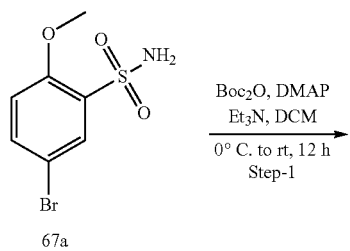

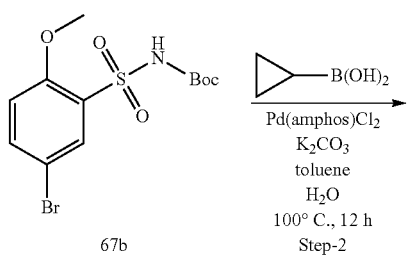

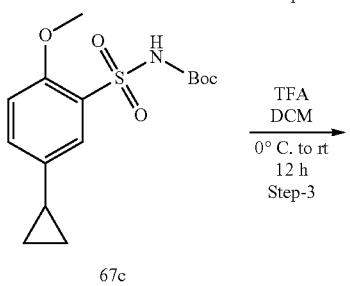

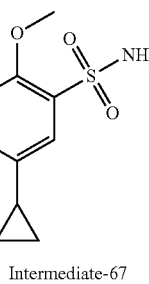

Intermediate-67

Step 1: Tert-butyl ((5-bromo-2-methoxyphenyl)sulfonyl)carbamate

To a solution of 5-bromo-2-methoxybenzenesulfonamide (10 g, 37.57 mmol) in DCM (100 mL) was added DIPEA (15.36 mL, 112.73 mmol), DMAP (0.46 g, 3.75 mmol) and followed by (Boc)₂O (12.3 g, 56.36 mmol) at 0° C. The reaction mixture was slowly warmed to RT and stirred at rt for 12 h. The reaction was quenched with ice water and extracted with DCM. The organic layer was dried over sodium sulphate, filtered, and concentrated to afford the crude material. Crude material was purified by silica-gel flash column chromatography using 30-50% ethyl acetate in hexane as eluent to afford the title compound (6.5 g, 47.23%). LC-MS: 363.9 [M–H]⁻.

Step 2: Tert-butyl ((5-cyclopropyl-2-methoxyphenyl)sulfonyl)carbamate

The title compound was prepared using similar procedure to that described in Step 6 of Intermediate 35 using appropriate reagents with suitable modifications. LC-MS: 326.0 [M–H]⁻.

Step 3: 5-Cyclopropyl-2-methoxybenzenesulfonamide

To a solution of tert-butyl ((5-cyclopropyl-2-methoxyphenyl)sulfonyl)carbamate (0.8 g, 2.44 mmol) in DCM (10 mL) was added TFA (1.12 mL, 14.65 mmol) to the reaction mixture at 0° C. The reaction mixture stirred at rt for 2 h. The reaction mass was quenched with saturated NaHCO₃ solution and extracted with DCM. The organic layer was washed with water, brine, dried over Na₂SO₄, filtered, and concentrated to get the crude compound. Crude compound was purified by silica-gel flash column chromatography using 40-50% ethyl acetate in hexane as eluent to obtain the title compound (0.25 g, 45%). LC-MS: 226.0 [M–H]⁻.

Intermediate 68: 2-Methoxy-6-(2,2,2-trifluoroethoxy)benzenesulfonamide

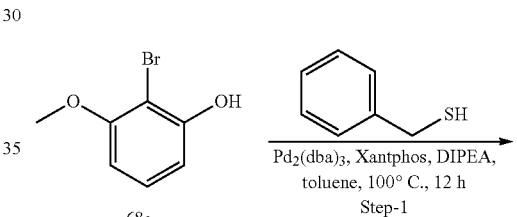

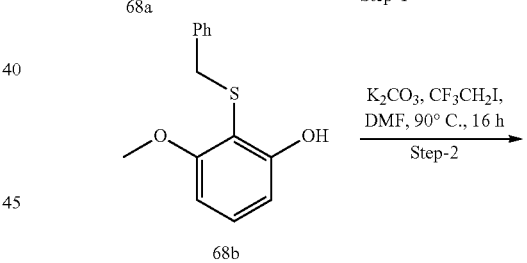

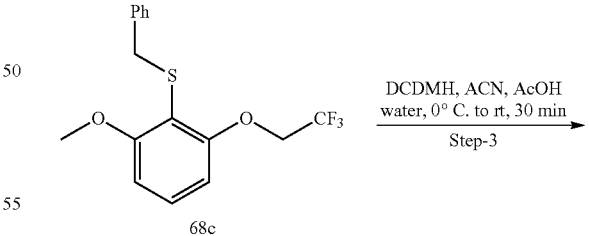

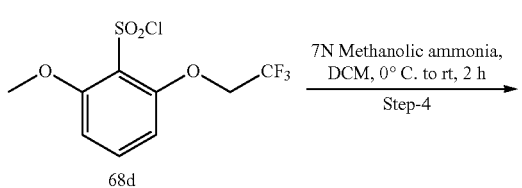

-continued

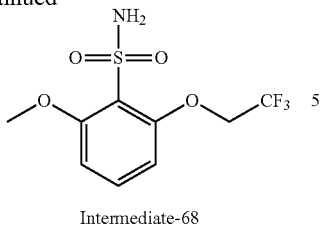

Intermediate-68

Step 1: 2-(Benzylthio)-3-methoxyphenol

The title compound was prepared using similar procedure to that described in Step 2 of Intermediate 53 using appropriate reagents with suitable modifications. LC-MS: 245.1 [M−H]⁻.

Step 2: Benzyl(2-methoxy-6-(2,2,2-trifluoroethoxy) phenyl)sulfane

The title compound was prepared using similar procedure to that described in Step 1 of Intermediate 52 using appropriate reagents with suitable modifications. LC-MS: 327.1 [M−H]⁻.

Step 3: 2-Methoxy-6-(2,2,2-trifluoroethoxy)benzenesulfonyl chloride

The title compound was prepared using similar procedure to that described in Step 6 of Intermediate 50 using appropriate reagents with suitable modifications. $^1$H NMR (DMSO-D6, 400 MHz): δ 7.23 (t, 1H), 6.79 (d, 1H), 6.63 (d, 1H), 4.55 (q, 2H), 3.72 (s, 3H).

Step 4: 2-Methoxy-6-(2,2,2-trifluoroethoxy)benzenesulfonamide

The title compound was prepared using similar procedure to that described in Step 3 of Intermediate 15 using appropriate reagents with suitable modifications. LC-MS: 284.0 [M−H]⁻.

Intermediate 69: 2-(Cyclopropylmethoxy)-6-methoxybenzenesulfonamide

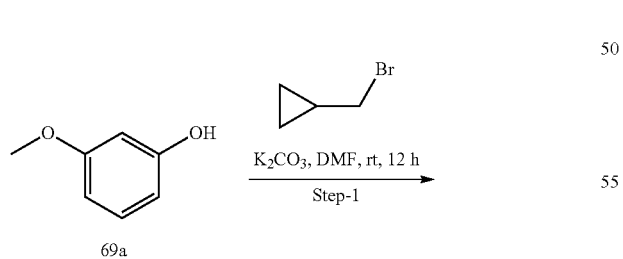

69a

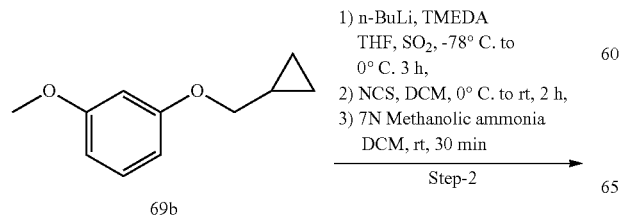

69b

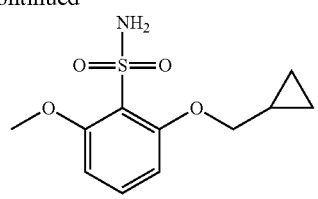

Intermediate-69

Step 1: 1-(Cyclopropylmethoxy)-3-methoxybenzene

The title compound was prepared using similar procedure to that described in Step 1 of Intermediate 50 using appropriate reagents with suitable modifications. LC-MS: 179.1 [M+H]⁺.

Step 2: 2-(Cyclopropylmethoxy)-6-methoxybenzenesulfonamide

The title compound was prepared using similar procedure to that described in Step 3 of Intermediate 64 using appropriate reagents with suitable modifications. LC-MS: 256.0 [M−H]⁻.

Intermediate 73: 2-Methoxy-6-(trifluoromethyl)benzenesulfonamide

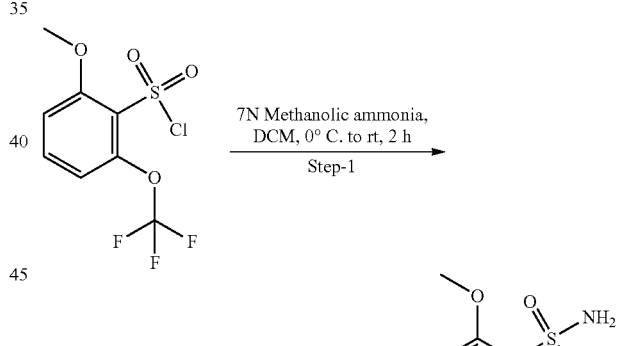

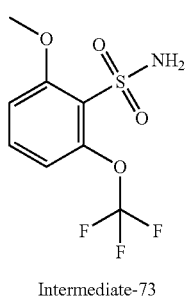

Intermediate-73

Step 1: 2-Methoxy-6-(trifluoromethyl)benzenesulfonamide

The title compound was prepared using similar procedure to that described in Step 3 of Intermediate 15 using appropriate reagents with suitable modifications. $^1$H NMR (DMSO-D6, 400 MHz): δ 7.64 (dd, 1H), 7.38 (s, 2H), 7.28 (d, 1H), 7.03 (d, 1H), 3.95 (s, 3H).

Intermediate 74: 5-(1-Cyclopropyl-1-hydroxyethyl)-2-methoxybenzenesulfonamide

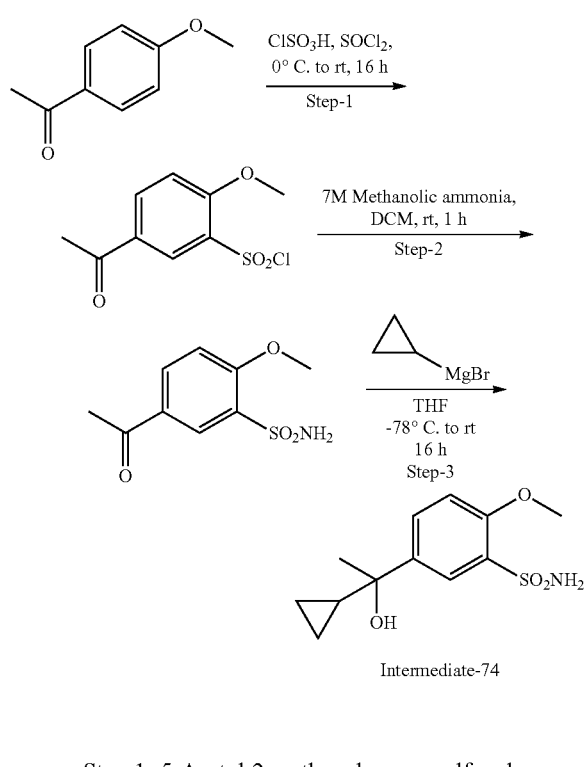

Intermediate-74

Step 1: 5-Acetyl-2-methoxybenzenesulfonyl chloride

To a stirred solution of chlorosulfonic acid (13.96 g, 119.85 mmol) and SOCl$_2$ (4.75 g, 39.95 mmol) was added 1-(4-methoxyphenyl)ethan-1-one (3.0 g, 19.97 mmol) dropwise at 0° C. The reaction mixture was gradually warmed to RT and stirred for 16 h at RT. The reaction mixture was then poured into ice-cold water to get a precipitate. The precipitate was filtered and dried under vacuum to afford the title compound (4.0 g, 81.6%). LC-MS: 249.0 [M+H]$^+$.

Step 2: 5-Acetyl-2-methoxybenzenesulfonamide

The title compound was prepared using similar procedure to that described in Step 3 of Intermediate 15 using appropriate reagents with suitable modifications. LC-MS: 230.0 [M+H]$^+$.

Step 3: 5-(1-Cyclopropyl-1-hydroxyethyl)-2-methoxybenzenesulfonamide

To a solution of 5-acetyl-2-methoxybenzenesulfonamide (0.3 g, 1.30 mmol) in THF (3 mL) was added cyclopropyl magnesium bromide (2.61 mL, 7.84 mmol, 3 M in THF) at −78° C. and then stirred at rt for 16 h. The reaction was quenched with saturated ammonium chloride solution and extracted with ethyl acetate. The organic layer was dried over sodium sulphate, filtered, and concentrated to afford the crude material. The crude material was purified by silica-gel flash column chromatography using 5% methanol in DCM as eluent to afford the title compound (0.30 g, 45%). LC-MS: 270.0 [M−H]$^-$.

Intermediate 75: 5-(2-hydroxybutan-2-yl)-2-methoxybenzenesulfonamide

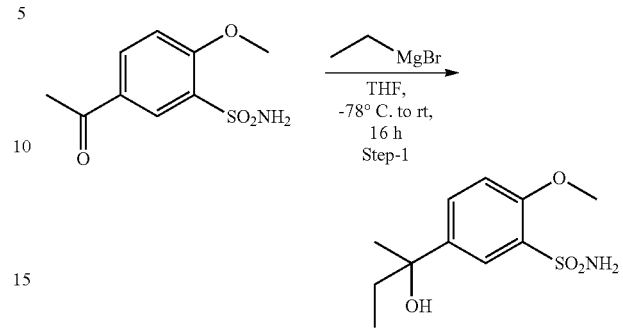

Intermediate-74

The title compound was prepared using similar procedure to that described in Step 3 of Intermediate-74 using appropriate reagents with suitable modifications. LC-MS: 258.1 [M−H]$^-$.

Intermediate 78: 3-Chloro-2,6-dimethoxybenzenesulfonamide

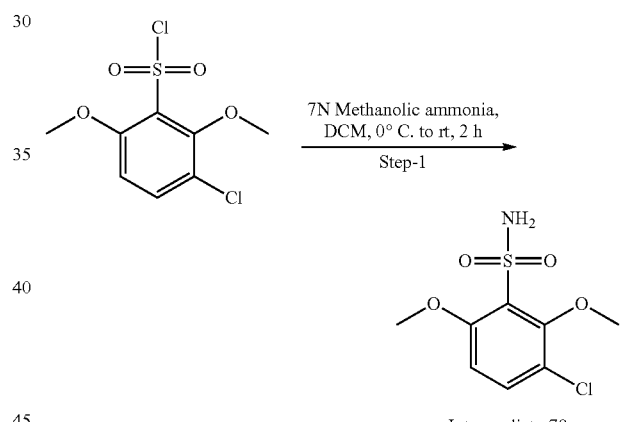

Intermediate-78

Step 1: 3-Chloro-2,6-dimethoxybenzenesulfonamide

The title compound was prepared using similar procedure to that described in Step-3 of Intermediate-15 using appropriate reagents with suitable modifications. LC-MS: 250.0 [M−H]$^-$.

Intermediate 79: 4,6-Dimethoxy-2,3-dihydrobenzofuran-7-sulfonamide

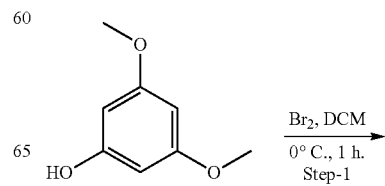

-continued

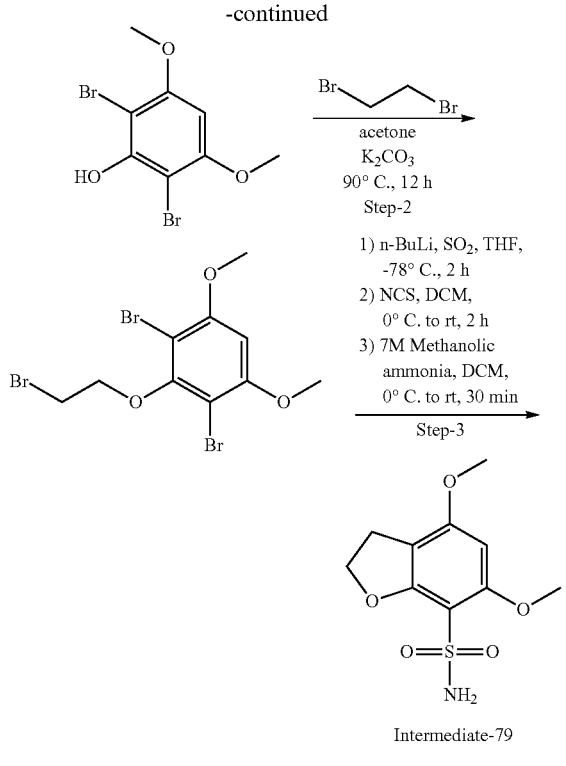

Intermediate-79

Step 1: 2,6-Dibromo-3,5-dimethoxyphenol

To a solution of 3,5-dimethoxyphenol (1.0 g, 6.48 mmol) in DCM (30 mL) was added bromine (2.07 g, 12.97 mmol) at 0° C. and stirred for 1 h. The reaction mixture was then warmed to RT and quenched with aqueous sodium thiosulphate solution and extracted with DCM. The organic layer was washed with water, dried over Na$_2$SO$_4$, filtered, and concentrated to get the crude compound. The crude was purified by silica-gel flash column chromatography using 0-20% ethyl acetate in hexane as eluent to afford the title compound (2.2 g, 90.5%). LC-MS: 312.9 [M+H]$^+$.

Step 2: 2,4-Dibromo-3-(2-bromoethoxy)-1,5-dimethoxybenzene

To a stirred solution of 2,6-dibromo-3,5-dimethoxyphenol (1.0 g, 3.20 mmol), and 1,2-dibromoethane (2.40 g, 12.82 mmol) in acetone was added K$_2$CO$_3$ (1.32 g, 9.61 mmol) and stirred at 80° C. for 12 h. The reaction mixture was concentrated, then diluted with water and extracted with EtOAc. The organic layer was washed with brine, dried over Na$_2$SO$_4$, filtered, and concentrated to afford crude compound. The crude compound was purified by silica-gel flash column chromatography using 20% ethyl acetate in hexane as eluent to afford the title compound (1.1 g, 81.9%). $^1$H NMR (DMSO-D6, 400 MHz): δ 6.72 (s, 1H), 4.24 (t, 2H), 3.91 (s, 6H), 3.84 (t, 2H).

Step 3: 4,6-Dimethoxy-2,3-dihydrobenzofuran-7-sulfonamide

To a solution of 2,4-dibromo-3-(2-bromoethoxy)-1,5-dimethoxybenzene (0.2 g, 0.47 mmol) in THF (7 mL) was added n-BuLi (1.48 mL, 2.38 mmol) at −78° C. and stirred at the same temperature for 1 h. Then SO$_2$ gas was bubbled into the reaction mixture for 30 min at −78° C. The reaction mixture was slowly warmed to RT and stirred for 1 h. Then reaction mixture was concentrated to obtain the solid. The solid was dissolved in DCM and NCS (0.19 g, 1.43 mmol) was added to the reaction mixture at 0° C. The reaction mixture was warmed to RT and stirred for 2 h. The reaction was quenched with ice water and extracted with DCM. The organic layer was dried over sodium sulphate, filtered, and concentrated to afford the crude material. The crude was dissolved in DCM and 7N methanolic ammonia (8 mL) was added to the reaction mixture at RT. The reaction mixture was stirred for 30 min at RT. The reaction mixture was diluted with water and extracted with DCM. The organic layer was dried over sodium sulphate, filtered, and concentrated to afford the crude compound. Crude compound was washed with 50% diethyl ether in n-pentane to obtain the title compound. (0.07 g, 32.6%). LC-MS: 258.0 [M−H]−

Intermediate 88: 6-Ethoxy-3-ethyl-2-methoxybenzenesulfonamide

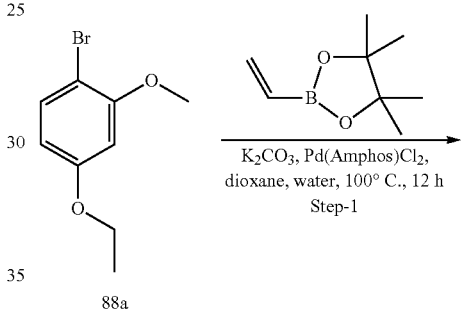

88a

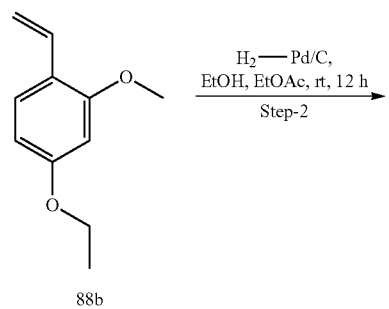

88b

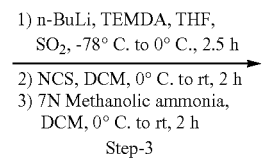

88c

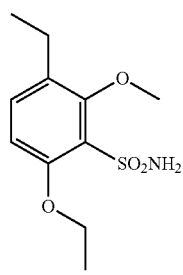

Intermediate-88

Step 1: 4-Ethoxy-2-methoxy-1-vinylbenzene

To a degassed solution of 1-bromo-4-ethoxy-2-methoxybenzene (1.8 g, 7.79 mmol), 4,4,5,5-tetramethyl-2-vinyl-1,3,2-dioxaborolane (2.4 g, 15.58 mmol), and $K_2CO_3$ (3.23 g, 23.36 mmol) in 1,4-dioxane (20 mL), water (4 mL) was added Pd(Amphos)$Cl_2$ (0.55 g, 0.77 mmol) and stirred at 100° C. for 12 h. The reaction mixture was cooled to RT, diluted with water, and extracted with ethyl acetate. The organic layer was dried over $Na_2SO_4$, filtered, and concentrated to get crude. The crude compound was purified by silica-gel flash column chromatography using 5-7% ethyl acetate in hexane to afford the title compound (1.1 g, 79.24%). $^1$H NMR (DMSO-D6, 400 MHz): δ 7.08 (d, 1H), 6.95-6.88 (m, 2H), 6.68-6.61 (m, 1H), 5.72 (dd, 1H), 5.13 (dd, 1H), 4.00 (q, 2H), 3.79 (s, 3H), 1.32 (t, 3H).

Step 2: 4-Ethoxy-1-ethyl-2-methoxybenzene

A mixture of 4-ethoxy-2-methoxy-1-vinylbenzene (2.0 g, 11.22 mmol) and Pd—C (1.79 g, 16.83 mmol) in ethanol (25 mL) and ethyl acetate (25 mL) was stirred under positive pressure of hydrogen using bladder for 12 h. The reaction mixture was filtered through celite pad and washed with 5% methanol in DCM. The filtrate was concentrated to afford the crude compound, which was taken for the next step without purification (2.0 g). LC-MS: 181.1.0 [M+H]$^+$.

Step 3: 6-Ethoxy-3-ethyl-2-methoxybenzenesulfonamide

To a solution of 4-ethoxy-1-ethyl-2-methoxybenzene (0.3 g, 1.66 mmol) in THF (4 mL) was added TMEDA (0.58 g, 4.99 mmol), n-BuLi (3.1 mL, 4.99 mmol) at 0° C. and stirred at the same temperature for 1 h. Then $SO_2$ gas was bubbled into the reaction mixture for 30 min at −78° C. The reaction mixture was slowly warmed to 0° C. and stirred for 1 h. The reaction mixture was concentrated to obtain the solid. The solid was dissolved in DCM (10 mL) and NCS (0.4 g, 2.99 mmol) was added to the reaction mixture at 0° C. The reaction mixture was warmed to RT and stirred for 2 h. The reaction was quenched with ice water and extracted with DCM. The organic layer was dried over sodium sulphate, filtered, and concentrated to afford the crude material. The crude compound was dissolved in DCM (2 mL) and 7N methanolic ammonia (10 mL) was added to the reaction mixture and stirred for 30 min at RT. The reaction mixture was diluted with water and extracted with DCM. The organic layer was dried over sodium sulphate, filtered, and concentrated to afford the crude. Crude compound was recrystallized using 50% EtOAc in pentane to afford the title compound (0.11 g, 59.16%). LC-MS: 260.1 [M+H]$^+$.

Intermediate 89: 5-(Trifluoromethyl)-2,3-dihydrobenzofuran-7-sulfonamide

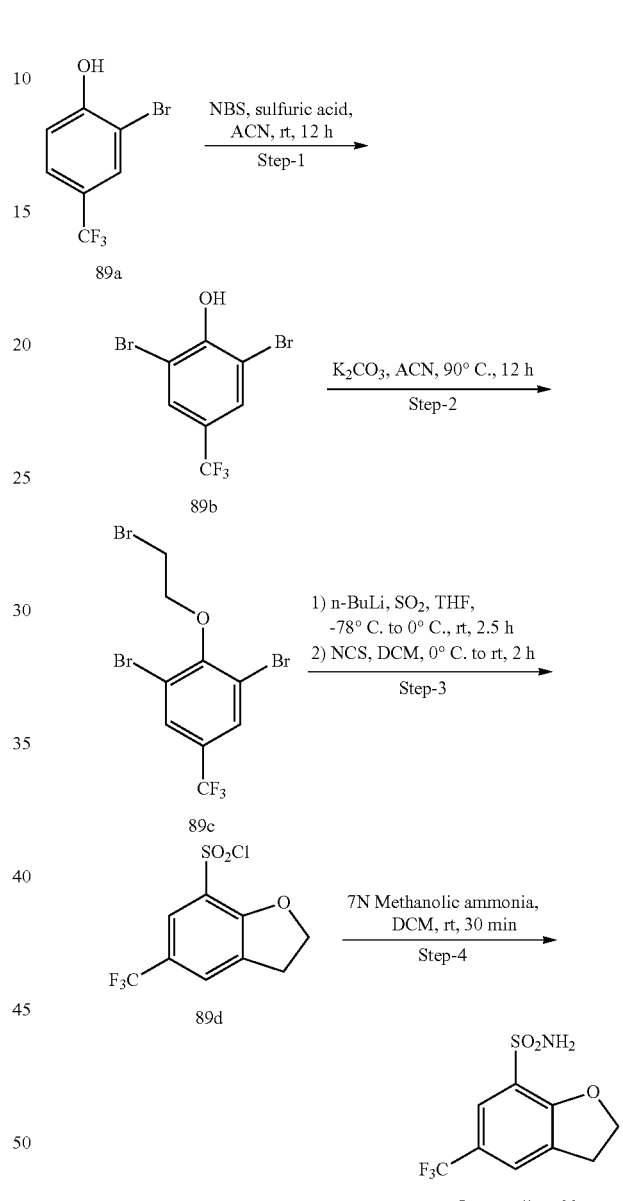

Intermediate-89

Step 1: 2,6-Dibromo-4-(trifluoromethyl)phenol

Sulfuric acid (0.22 mL, 4.15 mmol) was added dropwise to a solution of 2-bromo-4-(trifluoromethyl)phenol (1.0 g, 4.15 mmol) in ACN (10 mL) and stirred at RT for 10 min followed by addition of N-bromosuccinimide (0.775 g, 4.35 mmol). The reaction mixture was stirred for 12 h at RT. The reaction mixture was quenched with water and extracted with DCM. The organic layer was dried over $Na_2SO_4$, filtered, and concentrated to get crude compound. The crude compound was purified by silica-gel flash column chromatography using 0-10% ethyl acetate in hexane as eluent to obtain the title compound. (1.2 g, 60.3%). LC-MS: 318.8 [M+H]⁺.

Step 2: 1,3-Dibromo-2-(2-bromoethoxy)-5-(trifluoromethyl)benzene

To a solution of 2,6-dibromo-4-(trifluoromethyl)phenol (0.8 g, 2.50 mmol) and $K_2CO_3$ (1.04 g, 7.50 mmol) ACN (20 mL) was added 1,2-dibromoethane (1.88 g, 10.00 mmol) and stirred at 90° C. for 12 h. The reaction mixture was quenched with water and extracted with ethyl acetate. The organic layer was dried over sodium sulphate, filtered, and concentrated to afford the crude compound. The crude compound was purified by silica-gel flash column chromatography using 1-3% ethyl acetate in hexane as eluent to afford the title compound (0.7 g, 65.6%). ¹H NMR (DMSO-d6, 400 MHz): δ 8.14 (s, 2H), 4.38 (t, 2H), 3.88 (t, 2H).

Step 3: 5-(Trifluoromethyl)-2,3-dihydrobenzofuran-7-sulfonyl chloride

To a solution of 1,3-dibromo-2-(2-bromoethoxy)-5-(trifluoromethyl)benzene (0.5 g, 1.17 mmol) in THF (10 mL) was added n-BuLi (4.39 mL, 7.02 mmol) at −78° C. and stirred at the same temperature for 1 h. Then $SO_2$ gas was bubbled into the reaction mixture for 30 min at −78° C. The reaction mixture was slowly warmed to RT and stirred for 1 h. The reaction mixture was concentrated to obtain the solid. The solid was dissolved in DCM and NCS (0.47 g, 3.51 mmol) was added to it at 0° C. The reaction mixture was warmed to RT and stirred for 2 h. The reaction was quenched with ice water and extracted with DCM. The organic layer was dried over sodium sulphate, filtered, and concentrated to afford the crude title compound (0.5 g). ¹H NMR (DMSO-d6, 400 MHz): δ 7.65 (s, 1H), 7.54 (s, 1H), 4.62 (m, 2H), 3.69 (t, 2H).

Step 4: 5-(Trifluoromethyl)-2,3-dihydrobenzofuran-7-sulfonamide

To a solution of 5-(trifluoromethyl)-2,3-dihydrobenzofuran-7-sulfonyl chloride (0.5 g, 1.74 mmol) in DCM (7 mL) was added 7M methanolic ammonia dropwise (7 mL) at 0° C. The reaction mixture was warmed to RT and stirred for 30 min. The reaction mixture was diluted with water and extracted with DCM. The organic layer was washed with saturated Aq. $NaHCO_3$, dried over $Na_2SO_4$, and concentrated to afford the title compound (0.3 g). LC-MS: 265.9 [M−H]⁻.

Intermediate 90:
5-(tert-Butyl)-2,3-dihydrobenzofuran-7-sulfonamide

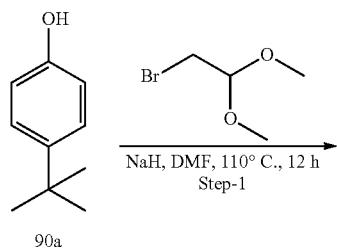

90a

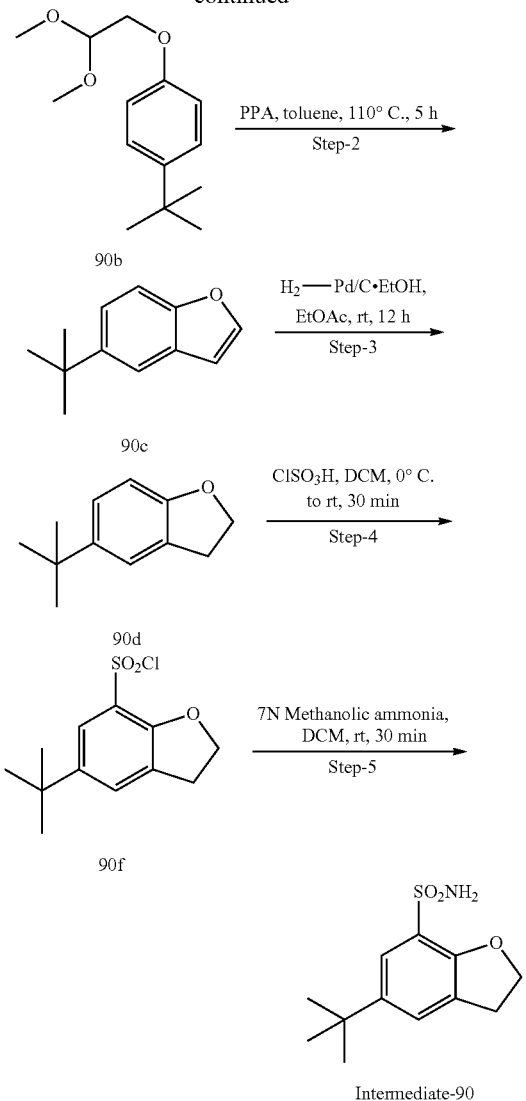

Step 1:
1-(tert-Butyl)-4-(2,2-dimethoxyethoxy)benzene

To a stirred solution of 4-(tert-butyl)phenol (2.0 g, 13.31 mmol) in DMF (75 mL) was added NaH (1.02 g, 26.62 mmol) at 0° C. and stirred for 30 min, followed by addition of 2-bromo-1,1-dimethoxyethane (2.7 g, 15.98 mmol) at 0° C. The reaction mixture was warmed to RT and stirred at 110° C. for 12 h. The reaction mixture was added into ice water and extracted with EtOAc. The organic layer was washed with brine solution, dried over $Na_2SO_4$, and concentrated to afford the crude title compound (3.5 g). ¹H NMR (CDCl3, 400 MHz): δ 7.30 (d, 2H), 6.88 (d, 2H), 4.72 (t, 1H), 4.01 (d, 2H), 3.45 (s, 6H), 1.30 (s, 9H).

Step 2: 5-(tert-Butyl)benzofuran

To a solution of 1-(tert-butyl)-4-(2,2-dimethoxyethoxy)benzene (2.0 g, 8.39 mmol) in toluene (25 mL) was added polyphosphoric acid (2.18 g, 10.07 mmol) and stirred at 110° C. for 5 h. The reaction mixture was quenched with water and extracted with ethyl acetate. The organic layer was dried over Na$_2$SO$_4$, filtered, and concentrated to afford crude title compound (1.5 g). $^1$H NMR (CDCl3, 400 MHz): δ 7.63-7.61 (m, 2H), 7.46 (d, 1H), 7.39 (d, 1H), 6.77 (d, 1H), 1.41 (s, 9H).

Step 3: 5-(tert-Butyl)-2,3-dihydrobenzofuran

The title compound was prepared using a similar procedure to that described in Step 2 of Intermediate 88 using appropriate reagents with suitable modifications (0.36 g). LC-MS: 177.2 [M+H]$^+$.

Step 4: 5-(tert-Butyl)-2,3-dihydrobenzofuran-7-sulfonyl chloride

To a stirred solution of 5-(tert-butyl)-2,3-dihydrobenzofuran (0.2 g, 1.14 mmol) in DCM (40 mL) was added chlorosulfonic acid (0.66 g, 5.67 mmol) dropwise at 0° C. The reaction mixture was gradually warmed to RT and stirred for 30 min at RT. The reaction mixture was then poured into ice-cold water quenched with NaHCO$_3$ solution extracted with DCM. The organic layer was dried over Na$_2$SO$_4$, filtered, and concentrated to obtain crude title compound (0.15 g). $^1$H NMR (DMSO-d6, 400 MHz): δ 7.36 (d, 1H), 7.20 (d, 1H), 4.46 (t, 2H), 3.11 (t, 2H), 1.23 (s, 9H).

Step 5: 5-(tert-Butyl)-2,3-dihydrobenzofuran-7-sulfonamide

The title compound was prepared using a similar procedure to that described in Step 4 of Intermediate 89 using appropriate reagents with suitable modifications. LC-MS: 256.1 [M+H]$^+$.

The following compounds listed in Table 6 were prepared by following a similar procedure as described above in Step 4 & Step 5 of Intermediate 90 using appropriate reagents with suitable modifications known to the one skilled in the art.

TABLE 6

Intermediates

| Intermediate | Structure | Spectral data |
| --- | --- | --- |
| 91 | 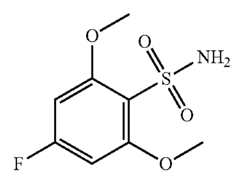 | $^1$H NMR (DMSO-d6, 400 MHz): δ 7.00 (brs, 2H), 6.69 (d, 2H), 3.83 (s, 6H). |
| 92 | 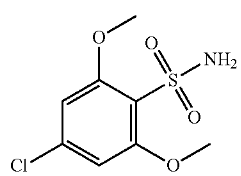 | $^1$H NMR (DMSO-d6, 400 MHz): δ 7.06 (brs, 2H), 6.88 (s, 2H), 3.95 (s, 6H). |
| 93 | 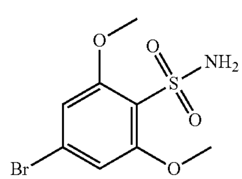 | $^1$H NMR (DMSO-d6, 400 MHz): δ 7.06 (brs, 2H), 7.00 (s, 2H), 3.85 (s, 6H). |
| 94 | 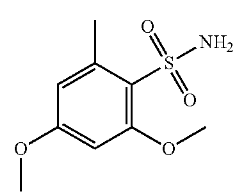 | $^1$H NMR (DMSO-d6, 400 MHz): δ 6.86 (brs, 2H), 6.57 (d, 1H), 6.45 (d, 1H), 3.87 (s, 3H), 3,81 (s, 3H), 2.51 (s, 3H). |
| 95 | 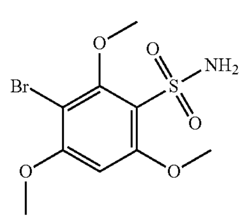 [SMILES: COc1cc(OC)c(S(N)(=O)=O)c(OC)c1Br] | LC-MS: 325.9 [M + H]$^+$. |

TABLE 6-continued

Intermediates

| Intermediate | Structure | Spectral data |
|---|---|---|
| 96 | 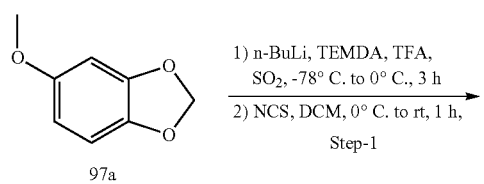 | $^1$H NMR (DMSO-d6, 400 MHz): δ 7.12 (s, 2H), 7.04 (brs, 2H), 3.83 (s, 6H). |

Intermediate 97: 5-Methoxybenzo[d][1,3]dioxole-4-sulfonamide

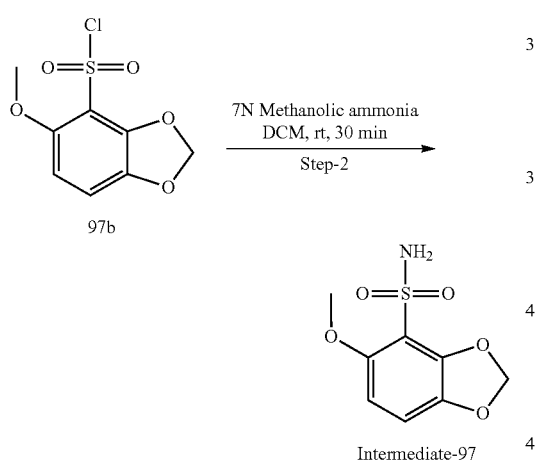

Step 1: 5-Methoxybenzo[id][1,3]dioxole-4-sulfonyl chloride

To a solution of 5-methoxybenzo[d][1,3]dioxole (0.2 g, 1.31 mmol) in THF (4 mL) was added TMEDA (0.305 g, 2.62 mmol), n-BuLi (2.46 mL, 3.94 mmol) at 0° C. and stirred at the same temperature for 1 h. Then SO$_2$ gas was bubbled into the reaction mixture for 30 min at −78° C. The reaction mixture was slowly warmed to 0° C. and stirred for 2 h. The reaction mixture was concentrated to obtain a solid. The solid was dissolved in DCM (5 mL) and NCS (0.526 g, 3.94 mmol) was added to the reaction mixture at 0° C. The reaction mixture was warmed to RT and stirred for 1 h. The reaction was quenched with ice water and extracted with DCM. The organic layer was dried over sodium sulphate, filtered, and concentrated to afford the crude material (0.3 g). $^1$H NMR (DMSO-d6, 400 MHz): δ 6.75 (d, 1H), 6.33 (d, 1H), 5.90 (s, 2H), 3.65 (s, 3H).

Step 2: 5-Methoxybenzo[d][1,3]dioxole-4-sulfonamide

The title compound was prepared using a similar procedure to that described in Step 4 of Intermediate 89 using appropriate reagents with suitable modifications. LC-MS: 232.0 [M+H]$^+$.

Intermediate 98: 2,6-Dimethoxy-4-methylbenzenesulfonamide

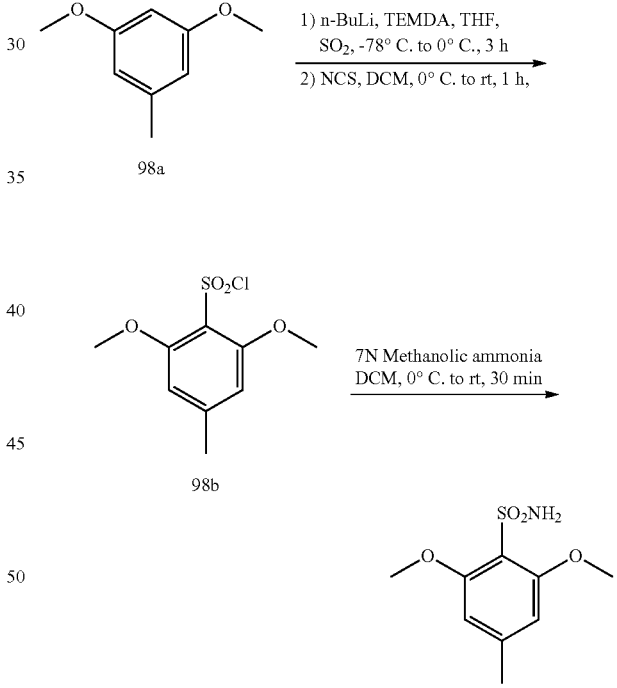

Step 1: 2,6-Dimethoxy-4-methylbenzenesulfonyl chloride

The title compound was prepared using a similar procedure to that described in Step 1 of Intermediate 97 using appropriate reagents with suitable modifications (1 g). $^1$H NMR (DMSO-D6, 400 MHz): δ 6.49 (s, 2H), 3.72 (s, 6H), 2.57 (s, 3H).

Step 2: 2,6-Dimethoxy-4-methylbenzenesulfonamide

The title compound was prepared using a similar procedure to that described in Step 4 of Intermediate 89 using appropriate reagents with suitable modifications. LC-MS: 232.0 [M+H]⁺.

Intermediate 107: 2-Cyclopropoxy-6-methoxybenzenesulfonamide

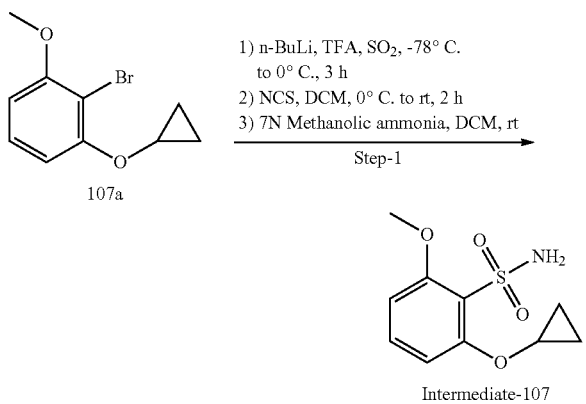

Step 1: 2-Cyclopropoxy-6-methoxybenzenesulfonamide

The title compound was prepared using a similar procedure to that described in Step 6 of Intermediate 102 g in Example 16 using appropriate reagents with suitable modifications. LC-MS: 244.0 [M+H]⁺.

Intermediate 108: 3-Chloro-2,6-dimethoxybenzenesulfinamide

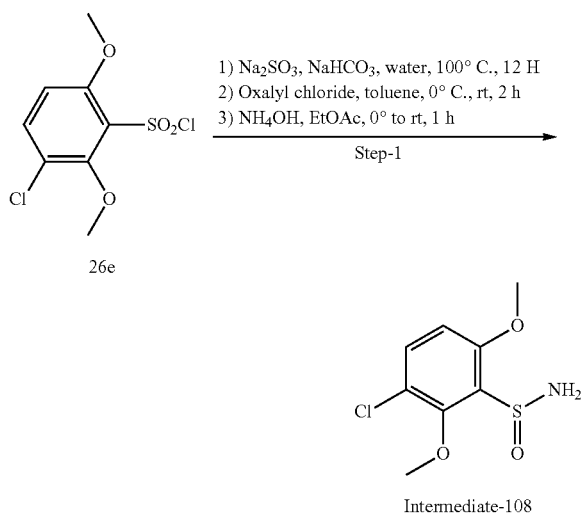

Step 1: 3-Chloro-2,6-dimethoxybenzenesulfinamide

To a solution of 3-chloro-2,6-dimethoxybenzenesulfonyl chloride (3.8 g, 14.06 mmol) in water (50 mL) was added NaHCO$_3$ (2.35 g, 28.03 mmol) and Na$_2$SO$_3$ (7.06 g, 28.03 mmol) at rt and then stirred at 100° C. for 12 h. Reaction mixture was concentrated, then diluted with EtOH (80 mL) and stirred for 10 min. The inorganic salt was filtered and filtrate was concentrated to get the crude compound. The crude was dissolved in toluene (50 mL), and oxalyl chloride (1.42 mL, 16.82 mmol) was added to it at 0° C. The reaction mixture was warmed to rt and stirred for 1 h. The reaction mixture was concentrated to obtain the crude compound. The crude was dissolved in EtOAc (30 mL), and aqueous NH$_4$OH (30 mL) was added to it at 0° C. The reaction mixture was warmed to rt and stirred for 1 h. The reaction mixture was diluted with water and extracted with ethyl acetate. The organic layer was dried over sodium sulphate, filtered, and concentrated to afford the crude compound. The crude compound was washed with 50% diethyl ether in pentane to obtain the title compound (0.5 g, 34.5%). LC-MS: 236.0 [M+H]⁺.

Intermediates 109 to 117

The following intermediates in Table 7 were prepared by following similar procedure to that described above for Intermediate 108 using appropriate reagents with suitable modifications known to the one skilled in the art. In some instances, procedures began with commercially available sulfonyl chloride building blocks.

TABLE 7

| Intermediates | | |
|---|---|---|
| Intermediate | Structure | Spectral data |
| 109 | | LC-MS: 216.1 [M + H]⁺. |
| 110 | | LC-MS: 232.1 [M + H]⁺. |
| 111 | | LC-MS: 184.0 [M + H]⁺. |
| 112 | | LC-MS: 190.0 [M + H]⁺. |

TABLE 7-continued

Intermediates

| Intermediate | Structure | Spectral data |
|---|---|---|
| 113 | 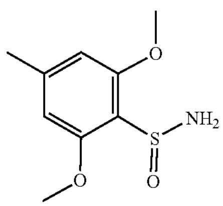 | LC-MS: 216.1 [M + H]+. |
| 114 | 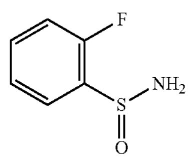 | LC-MS: 160.0 [M + H]+. |
| 115 | 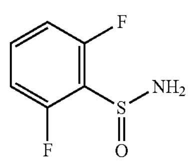 [SMILES: NS(=O)c1c(F)cccc1F] | LC-MS: 178.0 [M + H]+. |
| 116 | 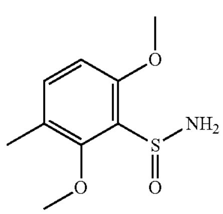 | LC-MS: 216.1 [M + H]+. |
| 117 | 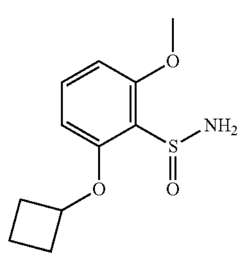 [SMILES: COc1cccc(OC2CCC2)c1S(N)=O] | LC-MS: 242.1 [M + H]+. |

Intermediate 118: 5-(2-Hydroxypropan-2-yl)-2-methoxybenzenesulfinamide

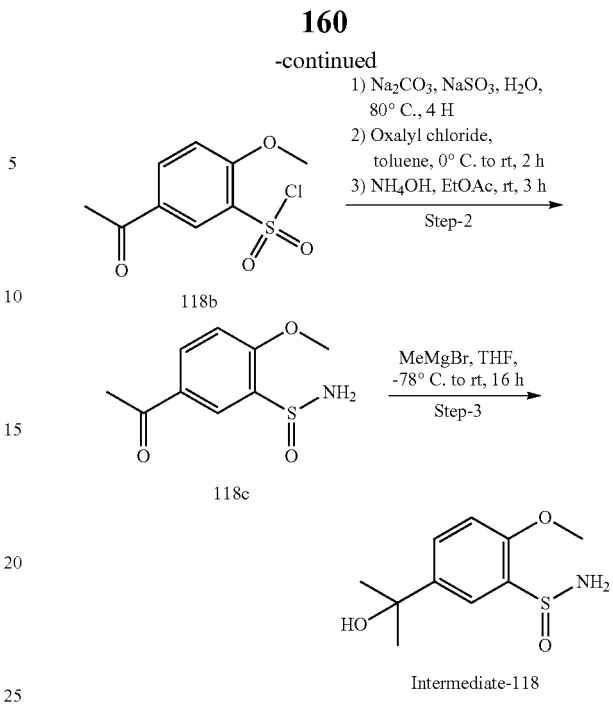

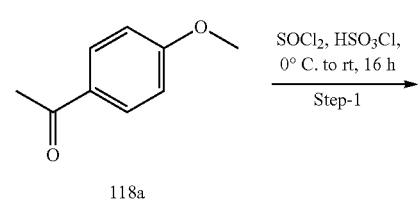

Step 1: 5-Acetyl-2-methoxybenzenesulfonyl chloride

A mixture of chlorosulfonic acid (3.32 ml, 49.93 mmol) and thionyl chloride (5.0 mL) was stirred in an ice bath for 30 min. Subsequently 1-(4-methoxyphenyl)ethan-1-one (5.0 g, 33.29 mmol) was added portion wise to the reaction mixture and stirred at room temperature for 16 h. the reaction mixture was slowly quenched with ice-water to get the precipitate. The precipitate was filtered and washed with water to afford the title compound (10.0 g). LC-MS: 249.0 [M+H]+.

Step 2: 5-Acetyl-2-methoxybenzenesulfinamide

The title compound was prepared using a similar procedure to that described in Step 1 of Intermediate 108 using appropriate reagents with suitable modifications (0.50 g); LC-MS: 214.0 [M+H]+.

Step 3: 5-(2-Hydroxypropan-2-yl)-2-methoxybenzenesulfinamide

To a solution of 5-acetyl-2-methoxybenzenesulfinamide (0.30 g, 1.30 mmol) in THF (12 mL) was added MeMgBr (3.49 mL, 10.47 mmol, 3 M in diethyl ether) at −78° C. and stirred at same temperature for 30 min. Then reaction mixture was warmed to RT and stirred for 16 h. The reaction mixture was cooled, quenched with saturated ammonium chloride solution, and extracted with ethyl acetate. The organic layer was dried over anhydrous sodium sulphate, filtered, and concentrated to afford crude compound. The crude compound was purified by silica-gel flash column chromatography using 5% methanol in DCM as eluent to afford title compound (0.250 g, 83.35%). LC-MS: 230.0[M+H]+.

b) Benzoic Acid Intermediates

Intermediate 1:
4-((1H-pyrazol-1-yl)methyl)-2-methoxybenzoic acid

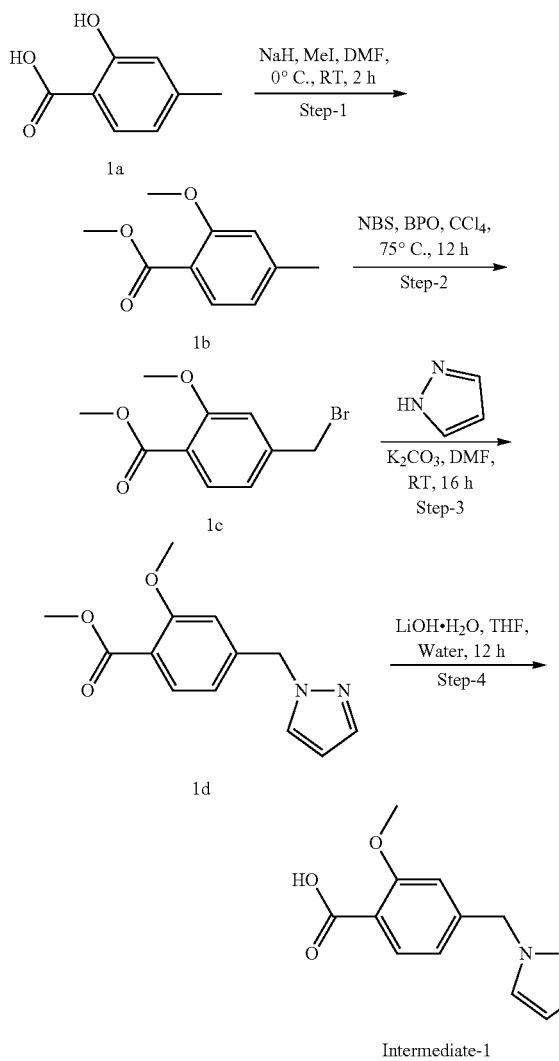

Intermediate-1

Step 1: Methyl 2-methoxy-4-methylbenzoate

A stirred solution of 2-hydroxy-4-methylbenzoic acid (5 g, 32.8 mmol) in DMF (50 mL) was cooled to 0° C. and added NaH (1.97 g, 82.1 mmol) followed by methyl iodide (5.6 g, 49.2 mmol) at 0° C. The reaction mixture was warmed to RT and stirred at RT for 2 h. The reaction mixture was added into ice water and extracted with EtOAc. The organic layer was washed with brine solution, dried over $Na_2SO_4$, and concentrated to afford the crude compound. The crude compound was purified by combi flash chromatography using 0-10% ethyl acetate in hexane to afford the title compound (3 g, 50.6%). LC-MS: 181.1 [M+H]+.

Step 2: Methyl 4-(bromomethyl)-2-methoxybenzoate

To a solution of methyl 2-methoxy-4-methylbenzoate (2.6 g, 14.4 mmol) in $CCl_4$ (30 mL) were added N-bromosuccinimide (NBS, 2.5 g, 14.4 mmol) and benzoyl peroxide (BPO, 0.035 g, 0.14 mmol) and heated to reflux for overnight. Reaction mixture was then cooled to RT and diluted with DCM and washed with water. The organic layer was dried over $Na_2SO_4$ and concentrated to get the crude compound. The crude compound was purified by combi flash chromatography using 0-20% ethyl acetate in hexane to afford the title compound (2.5 g, 66.8%). LC-MS: 261.0 [M+H]+.

Step 3: Methyl 4-((1H-pyrazol-1-yl)methyl)-2-methoxybenzoate

To a stirred solution of methyl 4-(bromomethyl)-2-methoxybenzoate (2.5 g, 9.6 mmol), 1H-pyrazole (0.98 g, 14.4 mmol) in DMF was added $K_2CO_3$ (4 g, 28.4 mmol) and stirred at RT for 16 h. Reaction mixture was diluted with water and extracted with EtOAc. The organic layer was washed with water, brine, dried over $Na_2SO_4$ and concentrated to get crude compound. The crude compound was purified by combi flash chromatography using 40% ethyl acetate in hexane to afford the title compound (2 g, 84.1%). LC-MS: 247.1 [M+H]+.

Step 4: 4-((1H-pyrazol-1-yl)methyl)-2-methoxybenzoic acid

To a stirred solution of methyl 4-((1H-pyrazol-1-yl) methyl)-2-methoxybenzoate (0.8 g, 3.2 mmol) in THF (6 mL) and water (2 mL) was added LiOH·$H_2O$ (0.38 g, 16.2 mmol) and stirred for 12 h at room temperature. Reaction mixture was diluted with ice-cold water, pH was adjusted to 5 using Aq. citric acid, and extracted with 20% methanol in DCM. The organic layer was dried over $Na_2SO_4$ and concentrated to afford the title compound (0.6 g). LC-MS: 233.1 [M+H]+.

Intermediates 2 to 7, 9 and 10

The following intermediates from Intermediate 2 to Intermediate 10 listed in Table 8 were prepared by following similar procedures described above for Intermediate 1 using appropriate reagents with suitable modifications known to the one skilled in the art.

TABLE 8

| Intermediate | Structure | Spectral data |
| --- | --- | --- |
| 2 | 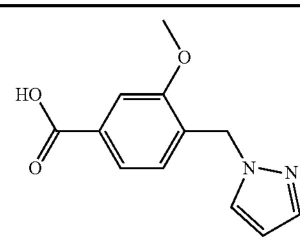 | LC-MS: 233.0 [M + H]+. |
| 3 | 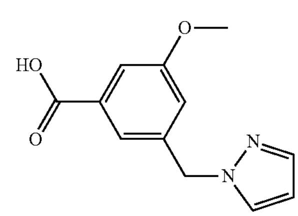 [SMILES: COc1cc(Cn2cccn2)cc(C(=O)O)c1] | LC-MS: 233.2 [M + H]+. |

TABLE 8-continued

Intermediates.

| Intermediate | Structure | Spectral data |
|---|---|---|
| 4 | 4-((1H-pyrazol-1-yl)methyl)-2-fluorobenzoic acid | LC-MS: 221.05 [M + H]+. |
| 5 | 2-methoxy-5-((1H-pyrazol-1-yl)methyl)benzoic acid | LC-MS: 233.2 [M + H]+. |
| 6 | 4-((1H-pyrazol-1-yl)methyl)-3-fluorobenzoic acid | LC-MS: 221.0 [M + H]+. |
| 7 | 3-bromo-4-((1H-pyrazol-1-yl)methyl)benzoic acid | LC-MS: 282.9 [M + H]+. |
| 9 | 2-methoxy-4-(pyrrolidin-1-ylmethyl)benzoic acid | LC-MS: 236.1 [M + H]+. |
| 10 | 3-ethoxy-4-((1H-pyrazol-1-yl)methyl)benzoic acid | LC-MS: 247.1 [M + H]+. |

Intermediate 2a: 3-methoxy-4-(pyrazol-1-ylmethyl)benzamide

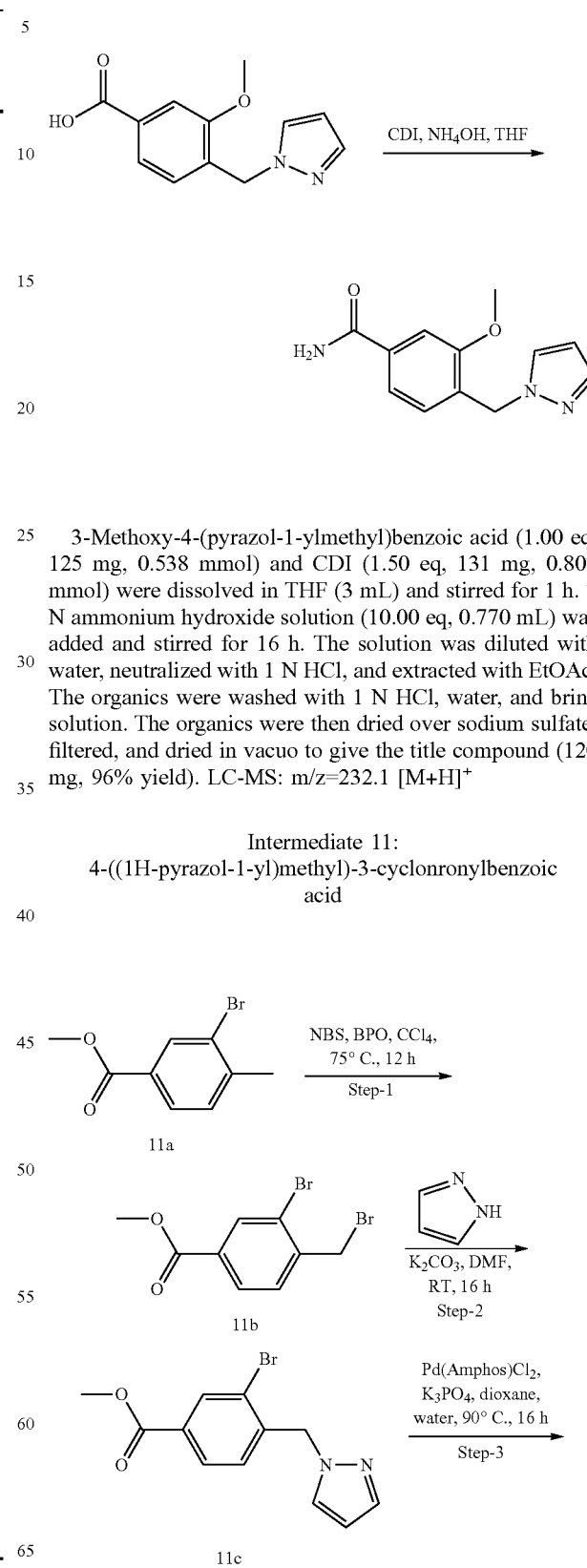

3-Methoxy-4-(pyrazol-1-ylmethyl)benzoic acid (1.00 eq, 125 mg, 0.538 mmol) and CDI (1.50 eq, 131 mg, 0.807 mmol) were dissolved in THF (3 mL) and stirred for 1 h. 7 N ammonium hydroxide solution (10.00 eq, 0.770 mL) was added and stirred for 16 h. The solution was diluted with water, neutralized with 1 N HCl, and extracted with EtOAc. The organics were washed with 1 N HCl, water, and brine solution. The organics were then dried over sodium sulfate, filtered, and dried in vacuo to give the title compound (120 mg, 96% yield). LC-MS: m/z=232.1 [M+H]+

Intermediate 11: 4-((1H-pyrazol-1-yl)methyl)-3-cyclopronylbenzoic acid

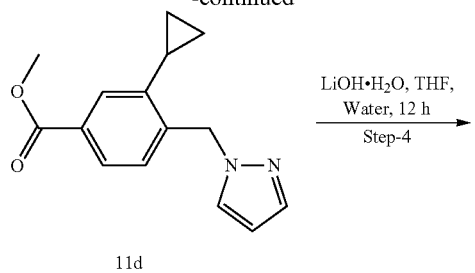

11d

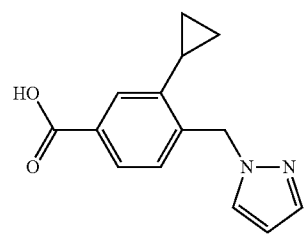

Intermediate-11

Step 1: Methyl 3-bromo-4-(bromomethyl)benzoate

The title compound was prepared using similar procedure to that described in Step 2 of Intermediate 1 using appropriate reagents with suitable modifications.

Step 2: Methyl 4-((1H-pyrazol-1-yl)methyl)-3-bromobenzoate

The title compound was prepared using similar procedure to that described in Step 3 of Intermediate 1 using appropriate reagents with suitable modifications. LC-MS: 295.0 $[M+H]^+$.

Step 3: Methyl 4-((1H-pyrazol-1-yl)methyl)-3-cyclopropylbenzoate

To a degassed solution of methyl 4-((1H-pyrazol-1-yl)methyl)-3-bromobenzoate (0.4 g, 1.35 mmol), cyclopropyl boronic acid (0.466 g, 5.41 mmol) in 1,4-dioxane (12 mL) and water (3 mL) were added Pd(Amphos)Cl$_2$ (0.096 g, 0.13 mmol) and K$_3$PO$_4$ (0.86 g, 4 mmol). The reaction mixture was heated to 90° C. for 16 h. The reaction mass was cooled to RT, diluted with water, and extracted with 10% methanol in DCM. The organic layer was dried over Na$_2$SO$_4$, filtered and concentrated to get crude. The crude compound was purified by combi flash chromatography using 20-25% ethyl acetate in hexane to afford the title compound. LC-MS: 257.1 $[M+H]^+$.

Step 4: 4-((1H-pyrazol-1-yl)methyl)-3-cyclopropylbenzoic acid

The title compound was prepared using similar procedure to that described in Step 4 of Intermediate 1 using appropriate reagents with suitable modifications. LC-MS: 243.1 $[M+H]^+$.

Intermediate 12

The following Intermediate 12 shown below was prepared by following similar procedure to that described above for Intermediate 11 using appropriate reagents with suitable modifications known to the one skilled in the art.

| Intermediate | Structure | Spectral data |
|---|---|---|
| 12 | 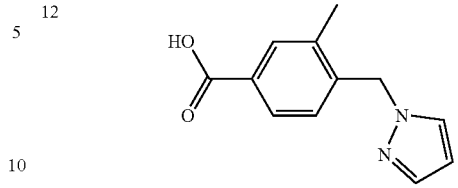 | LC-MS: 217.1 $[M + H]^+$. |

Intermediate 13: 4-((1H-pyrazol-1-yl)methyl)-3-cyanobenzoic acid

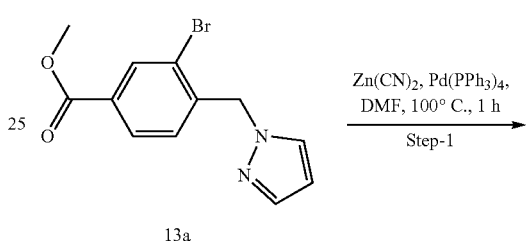

13a

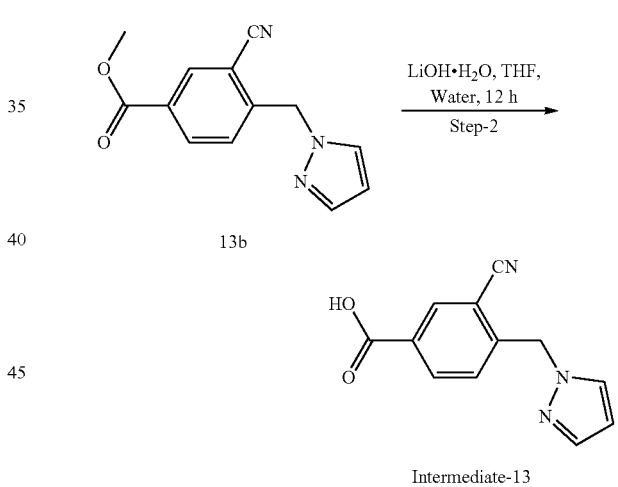

Intermediate-13

Step 1: Methyl 4-((1H-pyrazol-1-yl)methyl)-3-cyanobenzoate

To a degassed solution of methyl 4-((1H-pyrazol-1-yl)methyl)-3-bromobenzoate (0.3 g, 1.01 mmol), Zn(CN)$_2$ (0.14 g, 1.21 mmol) in DMF (4 mL) was added Pd(PPh$_3$)$_4$ and stirred at 100° C. for 1 h. The reaction mixture was cooled to room temperature, diluted with water and extracted with ethyl acetate. The organic layer was washed with water, dried over Na$_2$SO$_4$ and concentrated to get crude compound. The crude compound was purified by combi flash chromatography using 0-25% ethyl acetate in hexane to afford the title compound (0.18 g). LC-MS: 242.1 $[M+H]^+$.

Step 2: 4-((1H-pyrazol-1-yl)methyl)-3-cyanobenzoic acid

The title compound was prepared using similar procedure to that described in Step 4 of Intermediate 1 using appropriate reagents with suitable modifications. LC-MS: 228.0 [M+H]⁺.

Intermediate 14: 4-((1H-pyrazol-1-yl)methyl)-3-(trifluoromethyl)benzoic acid

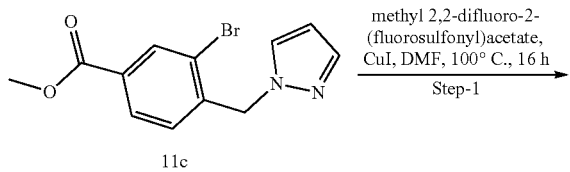

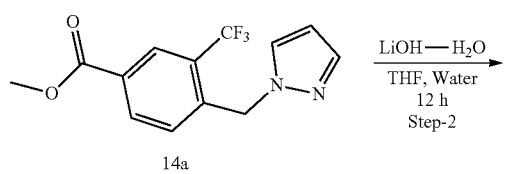

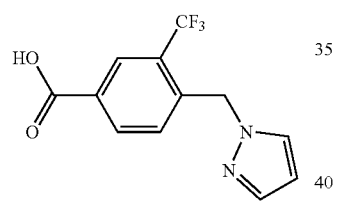

Intermediate-14

Step 1: Methyl 4-((1H-pyrazol-1-yl)methyl)-3-(trifluoromethyl)benzoate

To a stirred solution of methyl 4-((1H-pyrazol-1-yl)methyl)-3-bromobenzoate (0.15 g, 0.5 mmol) in DMF (2 mL) was added methyl 2,2-difluoro-2-(fluorosulfonyl)acetate (0.48 g, 2.54 mmol) followed by CuI (0.19 g, 1 mmol) at RT. The mixture was heated at 100° C. for 16 h. The reaction mass was cooled to RT, quenched with ice cold water, and washed with brine solution. The organic layer was dried over Na₂SO₄, filtered, and concentrated to afford crude compound (0.15 g) which was used in next step without purification. LC-MS: 285.1 [M+H]⁺.

Step 2: 4-((1H-pyrazol-1-yl)methyl)-3-(trifluoromethyl)benzoic acid

The title compound was prepared using similar procedure to that described in Step 4 of Intermediate 1 using appropriate reagents with suitable modifications. LC-MS: 271.1 [M+H]⁺.

Intermediate 31: Perfluorophenyl 4-((1H-pyrazol-1-yl)methyl)-3-trifluoromethoxy)benzoate

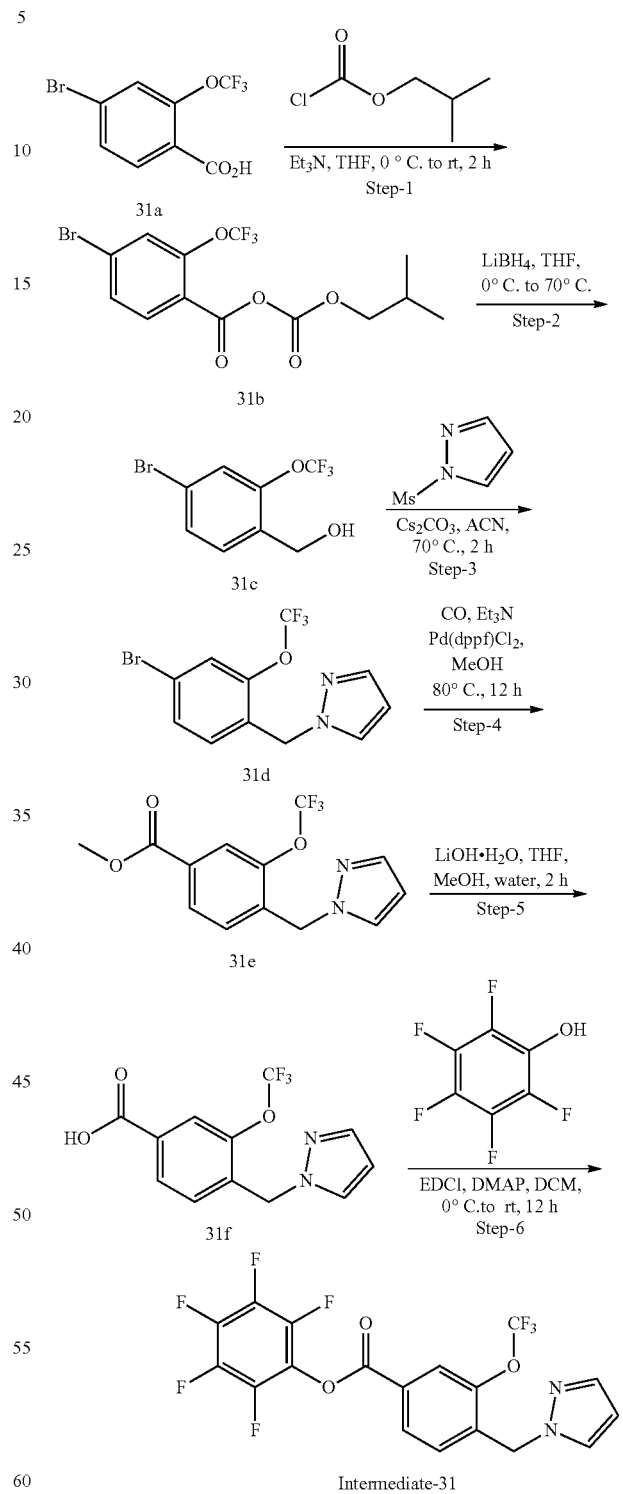

Step 1: 4-Bromo-2-(trifluoromethoxy)benzoic (isobutyl carbonic) anhydride

To a solution of 4-bromo-2-(trifluoromethoxy)benzoic acid (3.0 g, 10.52 mmol), in THF (45 mL) was added Et₃N (1.6 g, 15.78 mmol) followed by isobutyl chloroformate (1.8 g, 13.16 mmol) at 0° C. The reaction was warmed to room temperature and stirred for 2 h. The reaction mixture was quenched with ice water and extracted with ethyl acetate. The organic layer was dried over $Na_2SO_4$, filtered, and concentrated to obtain the title compound (3.8 g, 95%). $^1$H NMR (DMSO-$d_6$, 400 MHz): δ 7.94 (d, 1H), 7.61 (d, 1H), 7.60 (s, 1H), 4.15 (d, 2H), 2.11-2.06 (m, 1H), 1.01 (d, 6H).

Step 2:
(4-Bromo-2-(trifluoromethoxy)phenyl)methanol

To a stirred solution of methyl 4-bromo-2-(trifluoromethoxy)benzoic (isobutyl carbonic) anhydride (3.8 g, 9.90 mmol) in THF (45 mL) was added $LiBH_4$ (1.76 g, 11.8 mmol) at 0° C. and stirred at 70° C. for 2 h. The reaction mixture was quenched with ice water and extracted with ethyl acetate. The organic layer was dried over $Na_2SO_4$, filtered, and concentrated to obtain the title compound (2.8 g, 90%). $^1$H NMR (DMSO-$d_6$, 400 MHz): δ 7.48 (d, 1H), 7.47 (s, 1H), 7.42 (d, 1H), 4.75 (s, 2H).

Step 3:
1-(4-Bromo-2-(trifluoromethoxy)benzyl)-1H-pyrazole

To a solution of (4-bromo-2-(trifluoromethoxy)phenyl) methanol (1.5 g, 5.53 mmol), and 1-(methylsulfonyl)-1H-pyrazole (0.97 g, 6.64 mmol) in acetonitrile (15 mL) was added $Cs_2CO_3$ (2.16 g, 6.64 mmol) and stirred at 70° C. for 2 h. The reaction mixture was quenched with ice water and extracted with ethyl acetate. The organic layer was dried over $Na_2SO_4$, filtered, and concentrated to afford the crude compound, which was further purified by silica-gel flash column chromatography using 30% ethyl acetate in hexane as eluent to obtain the title compound (1.5 g, 84.4%). LC-MS: 322.9 [M+H]$^+$.

Step 4: Methyl 4-((1H-pyrazol-1-yl)methyl)-3-(trifluoromethoxy)benzoate

To a degassed solution of 1-(4-bromo-2-(trifluoromethoxy)benzyl)-1H-pyrazole (1.5 g, 4.67 mmol), triethylamine (1.41 g, 14.01 mmol) in methanol (60 mL) was added Pd(dppf)Cl$_2$-DCM (0.38 g, 0.46 mmol). The reaction mixture was heated to 80° C. in autoclave with 80 PSI pressure of carbon monoxide for 16 h. The reaction mixture was cooled to RT, filtered through a pad of celite and concentrated to afford the title compound (1.0 g, 71.3%). LC-MS: 301.0 [M+H]$^+$.

Step 5: 4-((1H-pyrazol-1-yl)methyl)-3-(trifluoromethoxy)benzoic acid

To a stirred solution of methyl 4-((1H-pyrazol-1-yl) methyl)-3-(trifluoromethoxy)benzoate (0.5 g, 1.66 mmol) in THF (5 mL), Methanol (3 mL) and water (2 mL) was added lithium hydroxide hydrate (0.15 g, 6.66 mmol) and stirred for 12 h at room temperature. Reaction mixture was diluted with ice-cold water, pH was adjusted to 5 using iN HCl, and extracted with 20% methanol in DCM. The organic layer was dried over $Na_2SO_4$ and concentrated to afford the title compound (0.4 g, 83.9%). LC-MS: 287.0 [M+H]$^+$.

Step 6: Perfluorophenyl 4-((1H-pyrazol-1-yl) methyl)-3-(trifluoromethoxy)benzoate To a solution of 4-((1H-pyrazol-1-yl)methyl)-3-(trifluoromethoxy)benzoic acid (0.2 g, 0.69 mmol), 2,3,4,5,6-pentafluorophenol (0.15 g, 0.84 mmol) and DMAP (0.017 g, 0.14 mmol) in DCM (20 mL) was added EDC·HCl (0.201 g, 1.04 mmol) at 0° C. and the solution was then stirred at RT for 12 h. The reaction mixture was quenched with ice water and extracted with DCM. The organic layer was dried over $Na_2SO_4$, filtered, and concentrated to afford the crude compound which was further purified by silica-gel flash column chromatography using 10-15% ethyl acetate in hexane as eluent to obtain the title compound (0.27 g, 85.4%). LC-MS: 453.0 [M+H]$^+$. $^1$H NMR (DMSO-$d_6$, 400 MHz): δ 8.19 (d, 1H), 8.06 (s, 1H), 7.91 (d, 1H), 7.54 (d, 1H), 7.28 (d, 1H), 6.35 (t, 1H), 5.59 (s, 2H).

Intermediate 35: Perfluorophenyl 4-((1H-pyrazol-1-yl)methyl)-3-cyclopropyl-2-fluorobenzoate

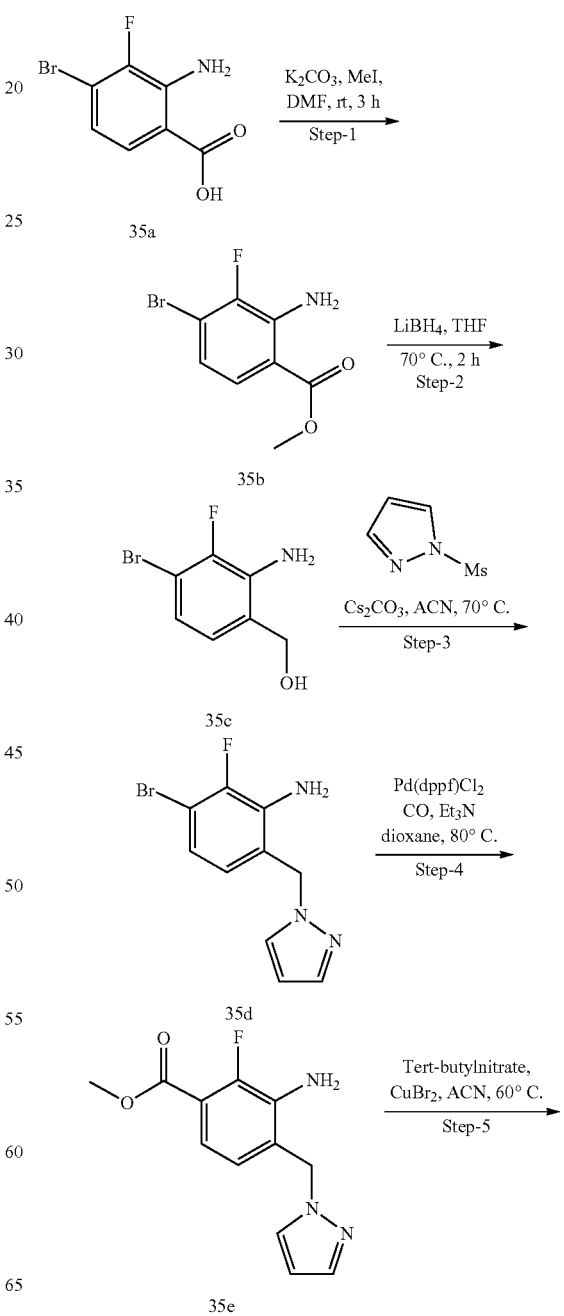

-continued

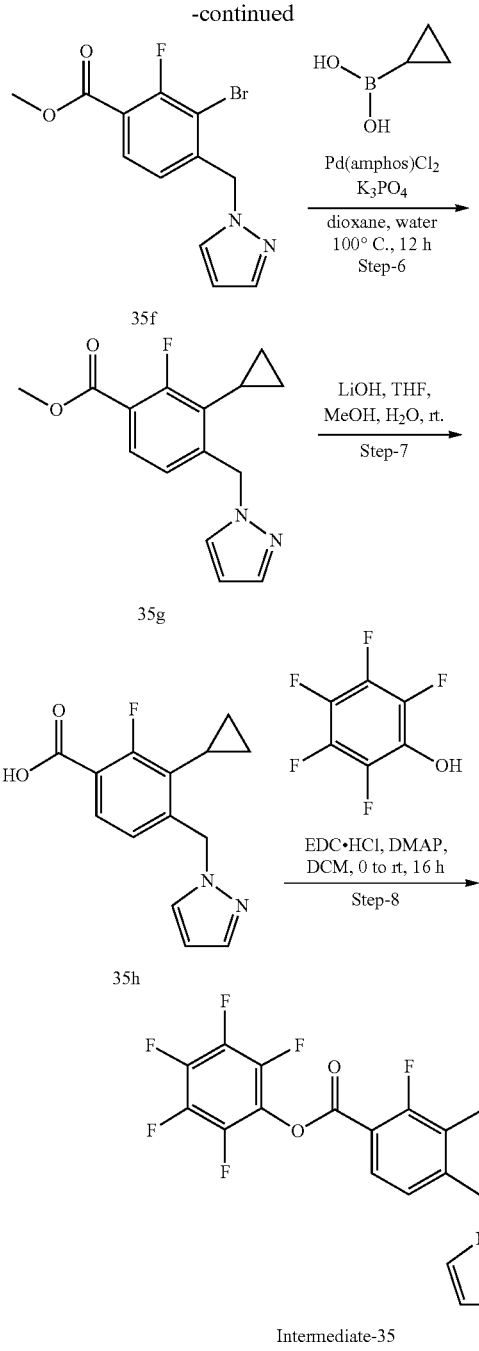

Step 1: Methyl 2-amino-4-bromo-3-fluorobenzoate

To a solution of 2-amino-4-bromo-3-fluorobenzoic acid (5.0 g, 21.36 mmol) in DMF was added dipotassium carbonate (4.42 g, 32.04 mmol), followed by iodomethane (3.63 g, 25.63 mmol) and stirred at RT for 3 h. The reaction mixture was diluted with water and extracted with EtOAc. The organic layer was washed with water, brine, dried over $Na_2SO_4$ and concentrated to get the crude compound. The crude compound was purified by silica gel flash column chromatography using 40% ethyl acetate in hexane as eluent to afford the title compound (4.8 g). LC-MS: 248.9 $[M+H]^+$.

Step 2: (2-Amino-4-bromo-3-fluorophenyl)methanol

The title compound was prepared using similar procedure to that described in Step 2 of Intermediate 31 using appropriate reagents with suitable modifications. LC-MS: 221.0 $[M+H]^+$.

Step 3: 6-((1H-pyrazol-1-yl)methyl)-3-bromo-2-fluoroaniline

The title compound was prepared using similar procedure to that described in Step 3 of Intermediate 31 using appropriate reagents with suitable modifications. LC-MS: 272.0 $[M+H]^+$.

Step 4: Methyl 4-((1H-pyrazol-1-yl) methyl)-3-amino-2-fluorobenzoate

The title compound was prepared using similar procedure to that described in Step 4 of Intermediate 31 using appropriate reagents with suitable modifications. LC-MS: 250.0 $[M+H]^+$.

Step 5: Methyl 4-((1H-pyrazol-1-yl) methyl)-3-bromo-2-fluorobenzoate

To a solution of methyl 4-((1H-pyrazol-1-yl)methyl)-3-amino-2-fluorobenzoate (0.9 g, 3.61 mmol), and copper(I) bromide (0.80 g, 3.61 mmol) in acetonitrile (10 mL) was added tert-butyl nitrile (0.41 g, 3.97 mmol) and stirred at 60° C. for 10 min. The reaction mixture was cooled to RT, diluted with water, and extracted with ethyl acetate. The organic layer was washed with water, brine, dried over $Na_2SO_4$, filtered, and concentrated under reduced pressure to afford the title compound (0.6 g, 53.07%). LC-MS: 314.0 $[M+H]^+$.

Step 6: Methyl 4-((1H-pyrazol-1-yl)methyl)-3-cyclopropyl-2-fluorobenzoate

To a degassed solution of methyl 4-((1H-pyrazol-1-yl) methyl)-3-bromo-2-fluorobenzoate (0.3 g, 0.95 mmol), cyclopropyl boronic acid (0.32 g, 3.83 mmol), and K3PO4 (0.610 g, 2.87 mmol) in 1,4-dioxane (2.7 mL) and water (0.3 mL) was added Pd(Amphos)Cl$_2$ (0.068 g, 0.090 mmol) and stirred at 100° C. for 12 h. The reaction mixture was cooled to RT, filtered through celite, and washed with 10% methanol in DCM. The filtrate was washed with water, aqueous $NaHCO_3$, dried over anhydrous $Na_2SO_4$, filtered, and concentrated and purified by silica gel flash column chromatography using 20% ethyl acetate in hexane as eluent to afford the title compound (0.150 g, 57%). LC-MS: 275.1 $[M+H]^+$.

Step 7: 4-((1H-pyrazol-1-yl) methyl)-3-cyclopropyl-2-fluorobenzoic acid

The title compound was prepared using similar procedure to that described in Step 4 of Intermediate 1 using appropriate reagents with suitable modifications. LC-MS: 261.0 $[M+H]^+$.

Step 8: Perfluorophenyl 4-((1H-pyrazol-1-yl) methyl)-3-cyclopropyl-2-fluorobenzoate The title compound was prepared using similar procedure to that described in Step 6 of Intermediate 31 using appropriate reagents with suitable modifications. LC-MS: 427.0 $[M+H]^+$.

Intermediate 36: Perfluorophenyl 4-((1H-pyrazol-1-yl)methyl)-2,3-dimethoxybenzoate

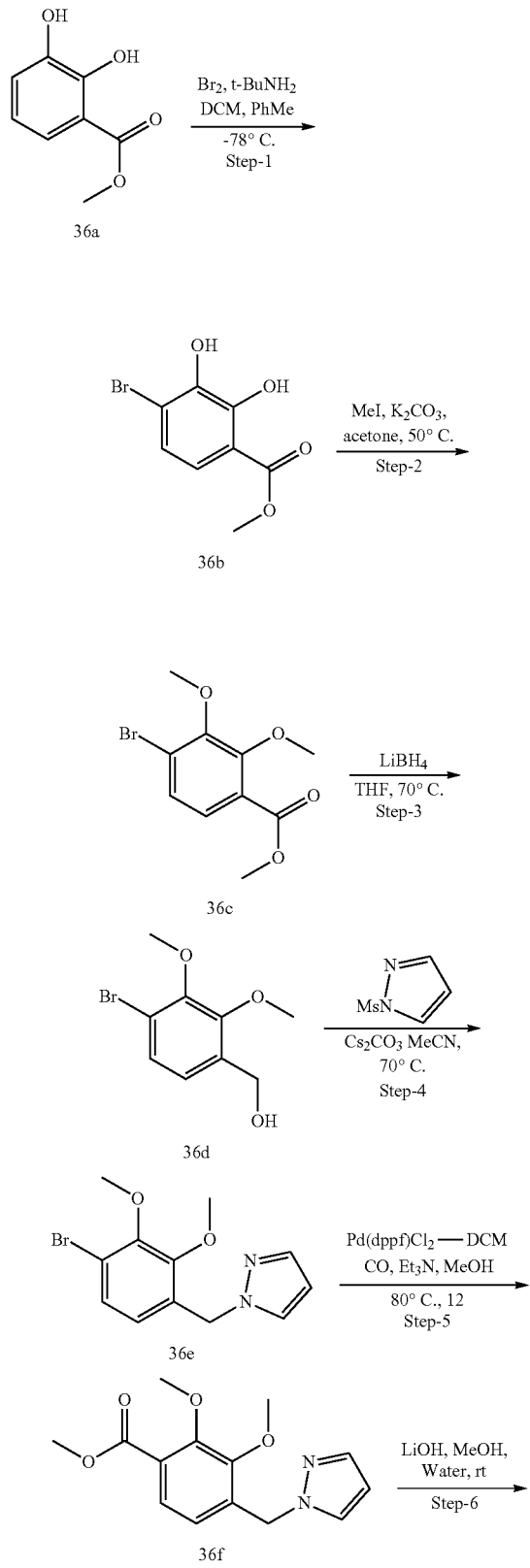

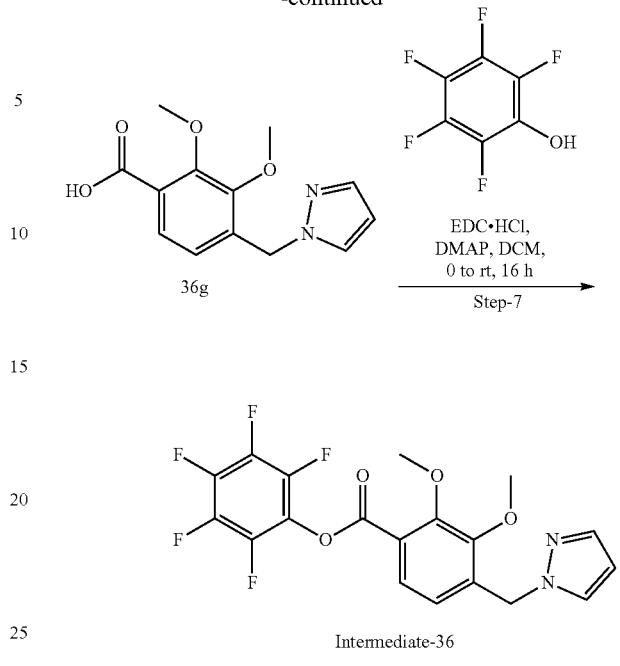

Step 1: Methyl 4-bromo-2,3-dihydroxybenzoate

Methyl 2,3-dihydroxybenzoate (3.0 g, 17.84 mmol) in DCM was added dropwise to a premix solution of 2-methylpropan-2-amine (2.61 g, 35.68 mmol) and bromine (2.85 g, 35.68 mmol) in toluene and DCM at −78° C. and stirred at same temperature for 30 min. The reaction mixture was slowly warmed to RT and stirred for 16 h. The reaction mixture was dilute with EtOAc, wash with 1M HCl. The organic layer was washed with brine, dried over $Na_2SO_4$, filtered, and concentrated under vacuum to afford crude material. The crude material was purified by silica gel flash column chromatography 10% using ethyl acetate in hexane as eluent to afford the title compound (1.80 g, 40.8%). LC-MS: 246.9 [M−H]⁻.

Step 2: Methyl 4-bromo-2,3-dimethoxybenzoate

To a solution of methyl 4-bromo-2,3-dihydroxybenzoate (1.8 g, 7.28 mmol) and $K_2CO_3$ (3.0 g, 21.85 mmol) in acetone was added methyl iodide (10.34 g, 72.86 mmol) and stirred at 50° C. for 5 h. The mixture was cooled to RT, diluted with water, and extracted with ethyl acetate. The organic layer was washed with water, brine, dried over $Na_2SO_4$, filtered, and concentrated under reduced pressure to get crude compound which was purified by silica-gel flash column chromatography using 20% ethyl acetate in hexane as eluent to afford title compound (1.75 g, 87.3%). LC-MS: 275.0 [M+H]⁺.

Step 3: (4-Bromo-2,3-dimethoxyphenyl)methanol

The title compound was prepared using similar procedure to that described in Step 2 of Intermediate 31 using appropriate reagents with suitable modifications. ¹H NMR, DMSO-$d_6$, 400 MHz): δ 7.35 (d, 1H), 7.11 (d, 1H), 5.18 (t, 1H), 4.49 (d, 2H), 3.79 (s, 3H), 3.78 (s, 3H).

Step 4: Methyl 1-(4-bromo-2,3-dimethoxybenzyl)-1H-pyrazole

The title compound was prepared using similar procedure to that described in Step 3 of Intermediate 31 using appropriate reagents with suitable modifications. LC-MS: 299.0 [M+H]$^+$.

Step 5: Methyl 4-((1H-pyrazol-1-yl)methyl)-2,3-dimethoxybenzoate

The title compound was prepared using similar procedure to that described in Step 4 of Intermediate 31 using appropriate reagents with suitable modifications. LC-MS: 277.0 [M+H]$^+$.

Step 6: 4-((1H-pyrazol-1-yl)methyl)-2,3-dimethoxybenzoic acid

The title compound was prepared using similar procedure to that described in Step 4 of Intermediate 1 using appropriate reagents with suitable modifications. LC-MS: 263.1 [M+H]$^+$.

Step 7: Perfluorophenyl 4-((1H-pyrazol-1-yl)methyl)-2,3-dimethoxybenzoate

The title compound was prepared using similar procedure to that described in Step 6 of Intermediate 31 using appropriate reagents with suitable modifications. LC-MS: 429.0 [M+H]$^+$.

Intermediate 37: Perfluorophenyl 4-((1H-pyrazol-1-yl)methyl)-2,5-dimethoxybenzoate

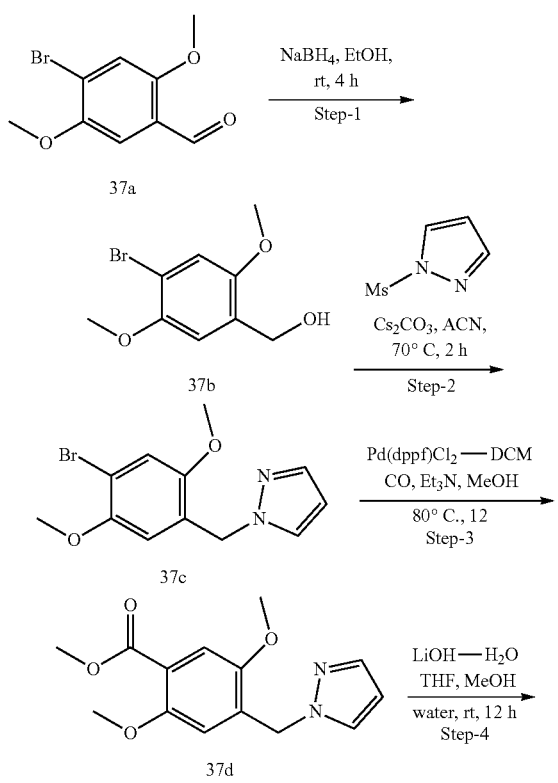

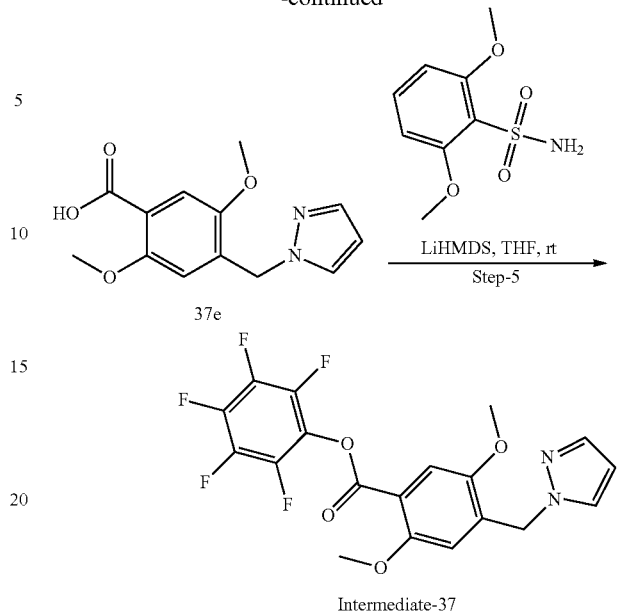

Intermediate-37

Step 1: (4-Bromo-2,5-dimethoxyphenyl)methanol

To a solution of 4-bromo-2,5-dimethoxybenzaldehyde (1.0 g, 4.08 mmol) in EtOH (10 mL) was added NaBH$_4$ (0.67 g, 16.32 mmol) 0° C. The mixture was warmed to RT and stirred for 4 h. The reaction mass was quenched with water at RT, extracted with ethyl acetate, washed with water, brine solution, dried over Na$_2$SO$_4$, filtered, and concentrated under reduced pressure to afford the title compound (1.0 g). $^1$H NMR, DMSO-d$_6$, 400 MHz): δ 1H NMR, DMSO-d$_6$, 400 MHz): δ 7.15 (s, 1H), 7.14 (s, 1H), 5.16 (t, 1H), 4.45 (d, 2H), 3.80 (s, 3H), 3.74 (s, 3H).

Step 2: 1-(4-Bromo-2,5-dimethoxybenzyl)-1H-pyrazole

The title compound was prepared using similar procedure to that described in Step 3 of Intermediate 31 using appropriate reagents with suitable modifications. LC-MS: 299.0 [M+H]$^+$.

Step 3: Methyl 4-((1H-pyrazol-1-yl)methyl)-2,5-dimethoxybenzoate

The title compound was prepared using similar procedure to that described in Step 4 of Intermediate 31 using appropriate reagents with suitable modifications. LC-MS: 277.1 [M+H]$^+$.

Step 4: 4-((1H-pyrazol-1-yl)methyl)-2,5-dimethoxybenzoic acid

The title compound was prepared using similar procedure to that described in Step 4 of Intermediate 1 using appropriate reagents with suitable modifications. LC-MS: 263.1 [M+H]$^+$.

Step 5: Perfluorophenyl 4-((1H-pyrazol-1-yl)methyl)-2,5-dimethoxybenzoate

The title compound was prepared using similar procedure to that described in Step 6 of Intermediate 31 using appropriate reagents with suitable modifications. LC-MS: 429.1 [M+H]+.

Intermediate 39: 4-((1H-pyrazol-1-yl)methyl)-3-bromo-2-fluorobenzoic acid

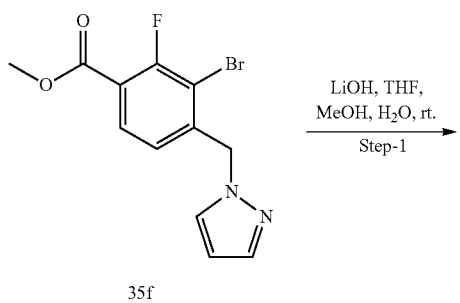

Step 1: 4-((1H-pyrazol-1-yl)methyl)-3-cyclopropyl-2-fluorobenzoic acid

The title compound was prepared using similar procedure to that described in Step 4 of Intermediate 1 using appropriate reagents with suitable modifications. LC-MS: 301.0 [M+H]+.

Intermediate 60: Perfluorophenyl 4-((1H-pyrazol-1-yl)methyl)-3-methoxybenzoate

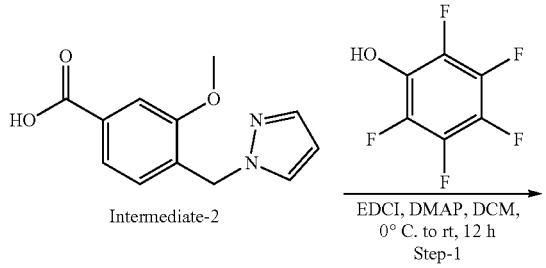

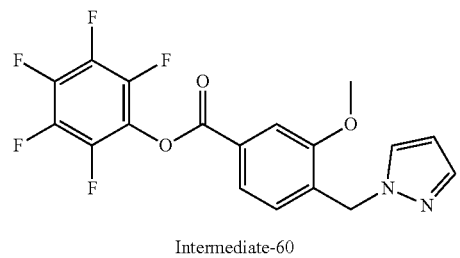

Step 1: Perfluorophenyl 4-((1H-pyrazol-1-yl)methyl)-3-methoxybenzoate

The title compound was prepared using similar procedure to that described in Step 6 of Intermediate 31 using appropriate reagents with suitable modifications. LC-MS: 399.1 [M+H]+.

Intermediate 62: Perfluorophenyl 4-((1H-pyrazol-1-yl)methyl)-3-(difluoromethoxy)benzoate

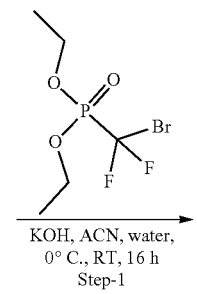

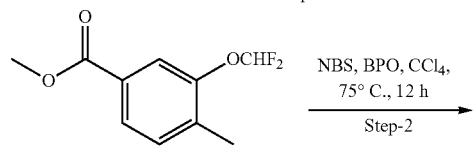

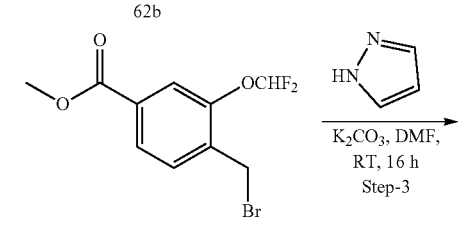

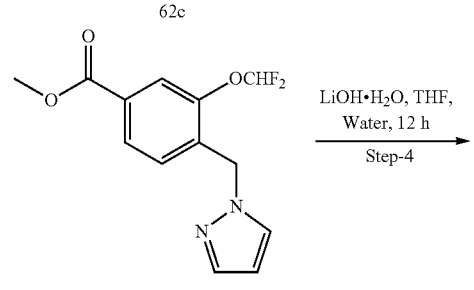

-continued

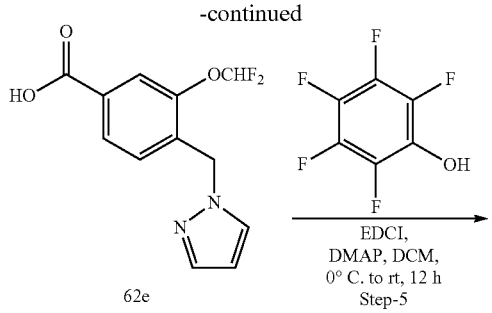

62e

EDCI, DMAP, DCM, 0° C. to rt, 12 h
Step-5

Intermediate-62

Step 1: Methyl 3-(difluoromethoxy)-4-methylbenzoate

To a solution of methyl 3-hydroxy-4-methylbenzoate (2 g, 12.03 mmol) in ACN (80 mL) was added 5N KOH solution (10 mL, 60.17 mmol) and followed by diethyl (bromodifluoromethyl)phosphonate (6.42 g, 24.07 mmol) at 0° C. The reaction mixture was slowly warmed to RT and stirred for 16 h. The reaction was quenched with ice water and extracted with ethyl acetate. The organic layer was dried over sodium sulphate, filtered, and concentrated to afford the crude material. Crude compound was purified by silica-gel flash column chromatography using 10-20% ethyl acetate in hexane as eluent to afford the title compound (0.85 g, 32.7%). $^1$H NMR (DMSO-$d_6$, 400 MHz): δ 7.76 (dd, 1H), 7.67 (s, 1H), 7.49 (d, 1H), 7.31 (t, 1H), 3.86 (s, 3H), 2.31 (s, 3H).

Step 2: Methyl 4-(bromomethyl)-3-(difluoromethoxy)benzoate

The title compound was prepared using similar procedure to that described in Step 2 of Intermediate 1 using appropriate reagents with suitable modifications. $^1$H NMR (DMSO-$d_6$, 400 MHz): δ 7.83 (dd, 1H), 7.74-7.22 (m, 2H), 7.44 (t, 1H), 4.71 (s, 2H), 3.90 (s, 3H).

Step 3: Methyl 4-((1H-pyrazol-1-yl)methyl)-3-(difluoromethoxy)benzoate

The title compound was prepared using similar procedure to that described in Step 3 of Intermediate 1 using appropriate reagents with suitable modifications LC-MS: 283.0 [M+H]$^+$.

Step 4: 4-((1H-pyrazol-1-yl)methyl)-3-(difluoromethoxy)benzoic acid

The title compound was prepared using similar procedure to that described in Step 4 of Intermediate 1 using appropriate reagents with suitable modifications LC-MS: 269.1 [M+H]$^+$.

Step 5: Perfluorophenyl 4-((1H-pyrazol-1-yl)methyl)-3-(difluoromethoxy)benzoate The title compound was prepared using similar procedure to that described in Step 6 of Intermediate 31 using appropriate reagents with suitable modifications LC-MS: 445.0 [M+H]$^+$.

Intermediate 70: 3-methoxy-4-(pyrimidin-2-yloxymethyl)benzoic acid

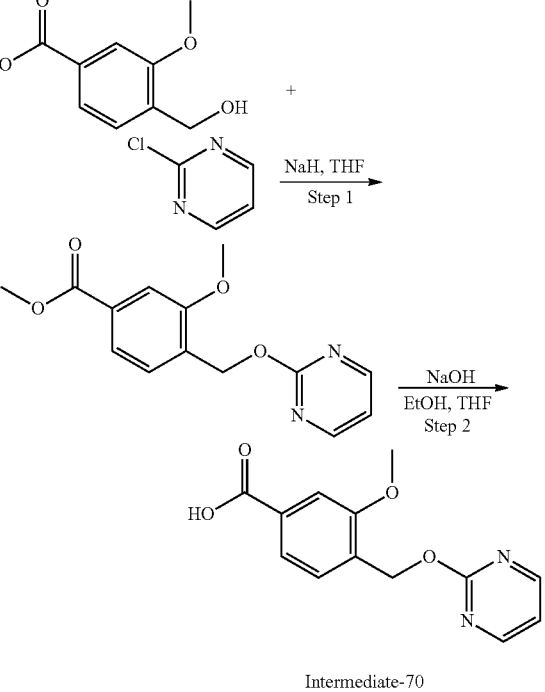

Intermediate-70

Step 1: methyl 3-methoxy-4-(pyrimidin-2-yloxymethyl)benzoate

To a mixture of methyl 4-(hydroxymethyl)-3-methoxybenzoate (1.50 eq, 154 mg, 0.786 mmol) and tetrahydrofuran (12.0 mL) was added sodium hydride (1.50 eq, 19 mg, 0.786 mmol) portion wise. After 10 min, 2-chloropyrimidine (1.00 eq, 60 mg, 0.524 mmol) was added, and the mixture was stirred at room temperature over the weekend. The mixture was concentrated under reduced pressure. The residue was partitioned between ethyl acetate and water. The separated organic phase was washed with brine, dried over sodium sulfate, filtered, and concentrated under reduced pressure to afford the title compound (153 mg, 0.556 mmol, 106.13%). LC-MS: 275 [M+H]$^+$.

Step 2: 3-methoxy-4-(pyrimidin-2-yloxymethyl)benzoic acid

A mixture of methyl 3-methoxy-4-(pyrimidin-2-yloxymethyl)benzoate (150 mg, 0.5469 mmol) and 3 N NaOH solution (1.4 mL, 4.3751 mmol) were stirred in 1 mL of EtOH and 1 mL of THF at ambient temperature overnight. The reaction was diluted with EtOAc, acidified with 1 N HCl (to pH 5) and extracted with EtOAc. The organics were washed with brine solution, dried over sodium sulfate, filtered, and concentrated in vacuo to afford the title compound (110 mg, 0.423 mmol, 77%). LC-MS: 261 [M+H]$^+$.

Intermediates 71 and 72

The following intermediates listed in Table 9 were prepared by following similar procedures described above for Intermediate 70 using appropriate reagents with suitable modifications known to the one skilled in the art.

TABLE 9

Intermediates

| Intermediate | Structure | LC-MS data |
|---|---|---|
| 71 | (structure) | LC-MS: 266 [M + H]$^+$. |
| 72 | (structure) | LC-MS: 252 [M + H]$^+$. | c) Pyridine- & Pyrimidine-Carboxy Intermediates

Intermediate 8: 5-((1H-pyrazol-1-yl)methyl)picolinic acid

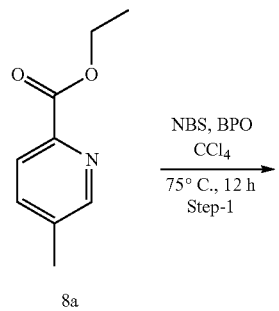

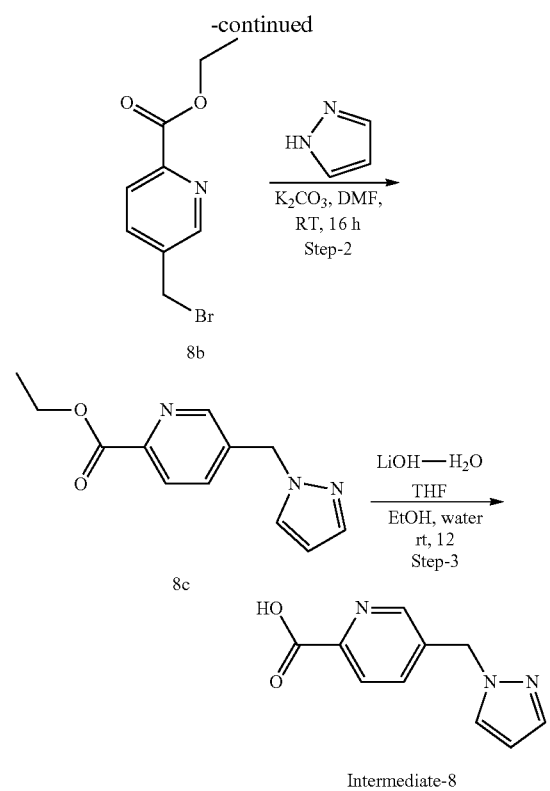

Step 1: Ethyl 5-(bromomethyl)picolinate

To a solution of ethyl 5-methylpicolinate (2.0 g, 12.10 mmol) in CCl$_4$ (15 mL) were added NBS (2.15 g, 12.10 mmol) and benzoyl peroxide (0.293 g, 1.21 mmol) and stirred at 75° C. for 12 h. Reaction mixture was then cooled to RT and diluted with DCM and washed with water. The organic layer was dried over Na$_2$SO$_4$ and concentrated to afford the crude compound. The crude compound was purified by silica gel flash column chromatography using 15-20% ethyl acetate in hexane to afford the title compound (1.8 g, 60.9%). LC-MS: 244.0 [M+H]$^+$.

Step 2: Ethyl 5-((1H-pyrazol-1-yl)methyl)picolinate

To a stirred solution of ethyl 5-(bromomethyl)picolinate (1.8 g, 7.37 mmol), 1H-pyrazole (0.653 g, 9.58 mmol) in DMF (15 mL) was added K$_2$CO$_3$ (3.05 g, 22.11 mmol) and stirred at RT for 16 h. Reaction mixture was diluted with water and extracted with EtOAc. The organic layer was washed with water, brine, dried over Na$_2$SO$_4$ and concentrated to afford crude compound. The crude compound was purified by silica gel flash column chromatography using 30% ethyl acetate in hexane to afford the title compound (0.8 g, 46.9%). LC-MS: 232.1 [M+H]$^+$.

Step 3: 5-((1H-pyrazol-1-yl)methyl)picolinic acid

To a stirred solution of ethyl 5-((1H-pyrazol-1-yl)methyl)picolinate (0.2 g, 3.2 mmol) in THF (4 mL), EtOH (3 mL) and water (2 mL) was added LiOH·H$_2$O (0.104 g, 4.32 mmol) and stirred for 12 h at room temperature. Reaction mixture was evaporated and diluted with ice-cold water, and pH was adjusted to 5 using aqueous citric acid solution to obtain solid. The solid was filtered, washed with ice cold water and dried under vacuum to afford the title compound (0.16 g, 91%). LC-MS: 204.1 [M+H]⁺.

Intermediate 29: 6-((1H-pyrazol-1-yl)methyl)-N-((2,6-dimethoxyphenyl)sulfonyl)-5-methoxynicotinamide

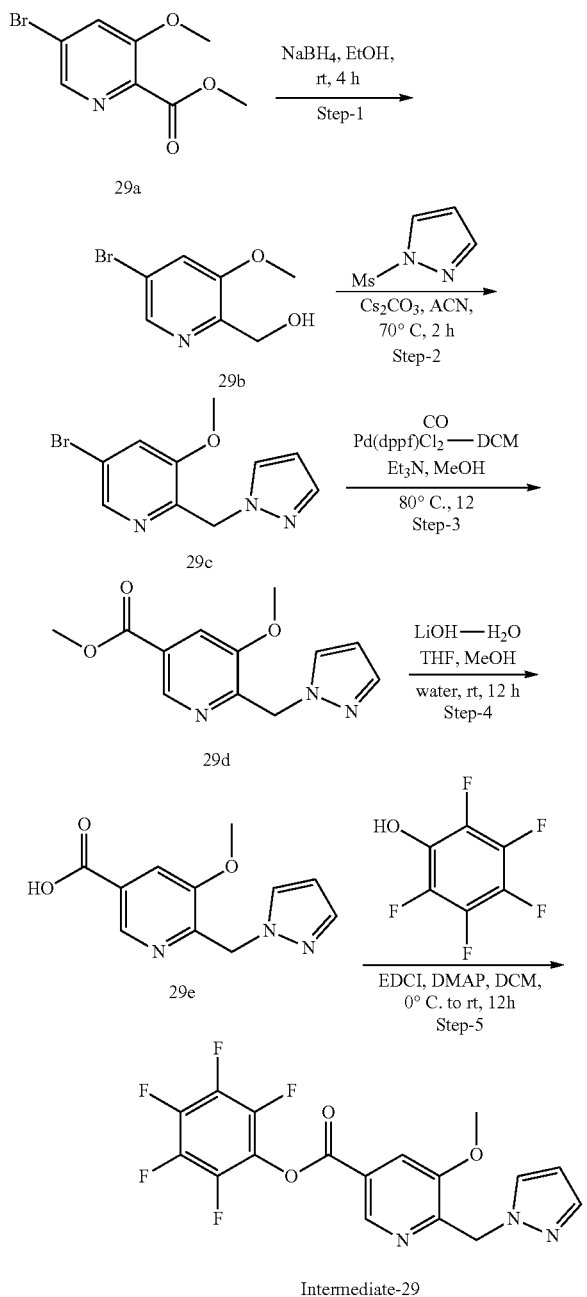

Intermediate-29

Step 1: 5-Bromo-3-methoxypyridin-2-yl)methanol

To a stirred solution of methyl 5-bromo-3-methoxypicolinate (3 g, 12.19 mmol), in EtOH (30 mL) was added NaBH₄ (1.38 g, 36.57 mmol) at 0° C. and stirred at RT for 4 h. The reaction mixture was quenched with ice water and extracted with ethyl acetate. The organic layer was dried over Na₂SO₄, filtered, and concentrated to afford the crude compound, which was further purified by silica-gel flash column chromatography using 20% ethyl acetate in hexane as eluent to obtain the title compound (1.4 g, 53%). LC-MS: 220.0 [M+H]⁺.

Step 2: 2-((1H-pyrazol-1-yl)methyl)-5-bromo-3-methoxypyridine

To a solution of (5-bromo-3-methoxypyridin-2-yl)methanol (1.5 g, 6.87 mmol), and 1-(methylsulfonyl)-1H-pyrazole (1.20. 8.25 mmol) in acetonitrile (15 mL) was added Cs₂CO₃ (2.69 g, 8.25 mmol) and stirred at 70° C. for 1 h. The reaction mixture was quenched with ice water and extracted with ethyl acetate. The organic layer was dried over Na₂SO₄, filtered, and concentrated to afford the crude compound, which was further purified by silica-gel flash column chromatography using 30% ethyl acetate in hexane as eluent to obtain the title compound (1.5 g, 81%). LC-MS: 270.0 [M+H]⁺.

Step 3: Methyl 6-((1H-pyrazol-1-yl)methyl)-5-methoxynicotinate

To a degassed solution of 2-((1H-pyrazol-1-yl)methyl)-5-bromo-3-methoxypyridine (1.5 g, 5.59 mmol) in methanol (60 mL) was added Et₃N (2.32 mL, 16.78 mmol), Pd(dppf)Cl₂·DCM (0.32 g, 0.39 mmol). The reaction mixture was heated to 80° C. in autoclave with 80 PSI pressure of carbon monoxide for 16 h. The reaction mixture was cooled to RT, filtered through a pad of celite and concentrated to get crude compound. The crude compound was purified by silica-gel flash column chromatograph using 40% ethyl acetate in hexane as eluent to afford the title compound (1.1 g, 79.5%). LC-MS: 248.1 [M+H]⁺.

Step 4: 6-((1H-pyrazol-1-yl)methyl)-5-methoxynicotinic acid

To a stirred solution of methyl 6-((1H-pyrazol-1-yl)methyl)-5-methoxynicotinate (0.8 g, 3.23 mmol) in THF (8 mL), MeOH (4 mL) and water (4 mL) was added LiOH·H₂O (0.387 g, 16.18 mmol) and stirred for 12 h at room temperature. Reaction mixture was evaporated and diluted with ice-cold water, pH was adjusted to 5 using 1N HCl to obtain the solid. The solid was filtered, washed with ice cold water, and dried under vacuum to afford the title compound (0.45 g, 60%). LC-MS: 234.1 [M+H]⁺.

Step 5: Perfluorophenyl 6-((1H-pyrazol-1-yl)methyl)-5-methoxynicotinate

To a solution of 6-((1H-pyrazol-1-yl)methyl)-5-methoxynicotinic acid (0.2 g, 0.85 mmol), 2,3,4,5,6-pentafluorophenol (0.19 g, 1.03 mmol) and DMAP (0.021 g, 0.17 mmol) in DCM (4 mL) was added EDC·HCl (0.247 g, 1.28 mmol) at 0° C. and then stirred at RT for 12 h. The reaction mixture was quenched with ice water and extracted with DCM. The organic layer was dried over Na₂SO₄, filtered, and concentrated to afford the crude compound which was further purified by silica-gel flash column chromatography using 10-15% ethyl acetate in hexane as eluent to obtain the title compound (0.12 g, 35%). LC-MS: 400.0 [M+H]⁺.

Intermediate 30: Perfluorophenyl 5-((1H-pyrazol-1-yl)methyl)-6-methoxypicolinate

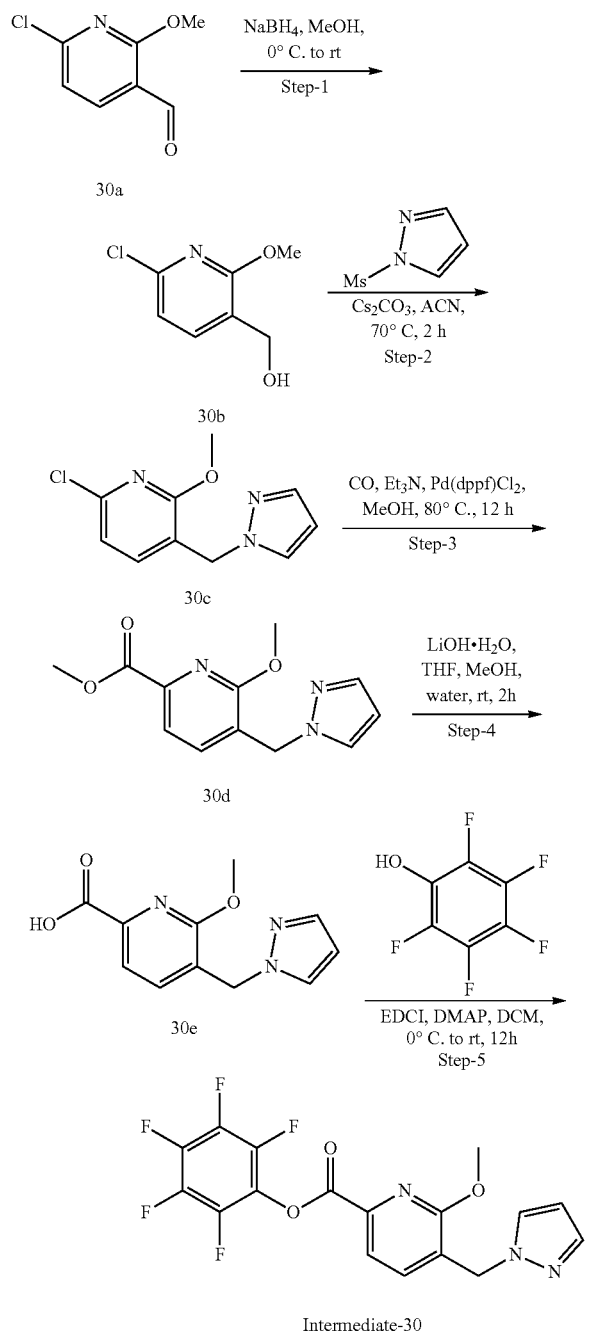

Step 1: (6-Chloro-2-methoxypyridin-3-yl)methanol

To a solution of 6-chloro-2-methoxynicotinaldehyde (2.0 g, 11.65 mmol), in MeOH (60 mL) was added NaBH₄ (1.76 g, 11.65 mmol) at 0° C. and stirred at RT for 2 h. The reaction mixture was quenched with ice water and extracted with ethyl acetate. The organic layer was dried over anhydrous Na₂SO₄, filtered, and concentrated to obtain the title compound (2 g, 99%). LC-MS: 174.1 [M+H]⁺.

Step 2: 3-((1H-pyrazol-1-yl)methyl)-6-chloro-2-methoxypyridine

The title compound was prepared using similar procedure to that described in Step 2 of Intermediate 29 using appropriate reagents with suitable modifications (2 g, 80%). LC-MS: 224 [M+H]⁺.

Step 3: Methyl 5-((1H-pyrazol-1-yl)methyl)-6-methoxypicolinate

The title compound was prepared using similar procedure to that described in Step 3 of Intermediate 29 using appropriate reagents with suitable modifications. LC-MS: 248.1 [M+H]⁺.

Step 4: 5-((1H-pyrazol-1-yl)methyl)-6-methoxypicolinic acid

The title compound was prepared using similar procedure to that described in Step 4 of Intermediate 29 using appropriate reagents with suitable modifications. LC-MS: 234.1 [M+H]⁺.

Step 5: Perfluorophenyl 5-((1H-pyrazol-1-yl)methyl)-6-methoxypicolinate

The title compound was prepared using similar procedure to that described in Step 5 of Intermediate 29 using appropriate reagents with suitable modifications. LC-MS: 400.0 [M+H]⁺.

Intermediate 40: Perfluoronhenyl 5-((1H-pyrazol-1-yl)methyl)-6-methylpicolinate

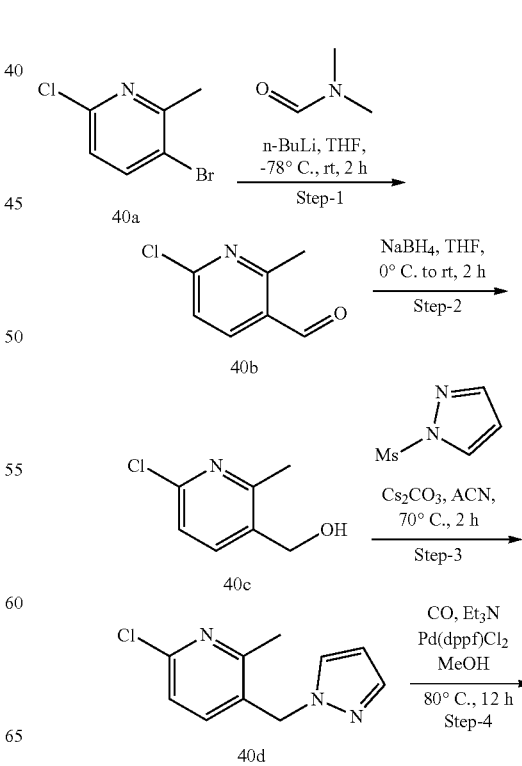

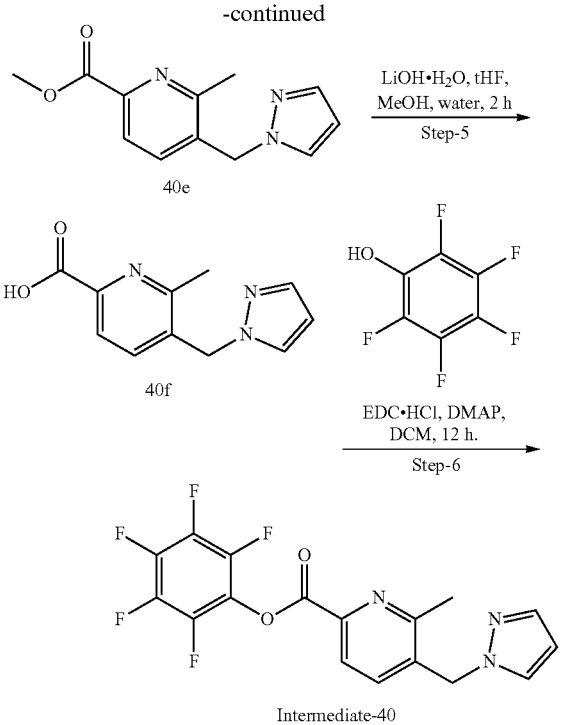

Step 4: Methyl 5-((1H-pyrazol-1-yl)methyl)-6-methylpicolinate

The title compound was prepared using similar procedure to that described in Step 3 of Intermediate 29 using appropriate reagents with suitable modifications. LC-MS: 232.2 [M+H]+.

Step 5: 5-((1H-pyrazol-1-yl)methyl)-6-methylpicolinic acid

The title compound was prepared using similar procedure to that described in Step 4 of Intermediate 29 using appropriate reagents with suitable modifications. LC-MS: 218.1 [M+H]+.

Step 6: Perfluorophenyl 5-((1H-pyrazol-1-yl)methyl)-6-methylpicolinate

The title compound was prepared using similar procedure to that described in Step 5 of Intermediate 29 using appropriate reagents with suitable modifications. LC-MS: 384.2 [M+H]+.

Intermediate 41: 5-((1H-pyrazol-1-yl)methyl)-4-methoxypicolinic acid

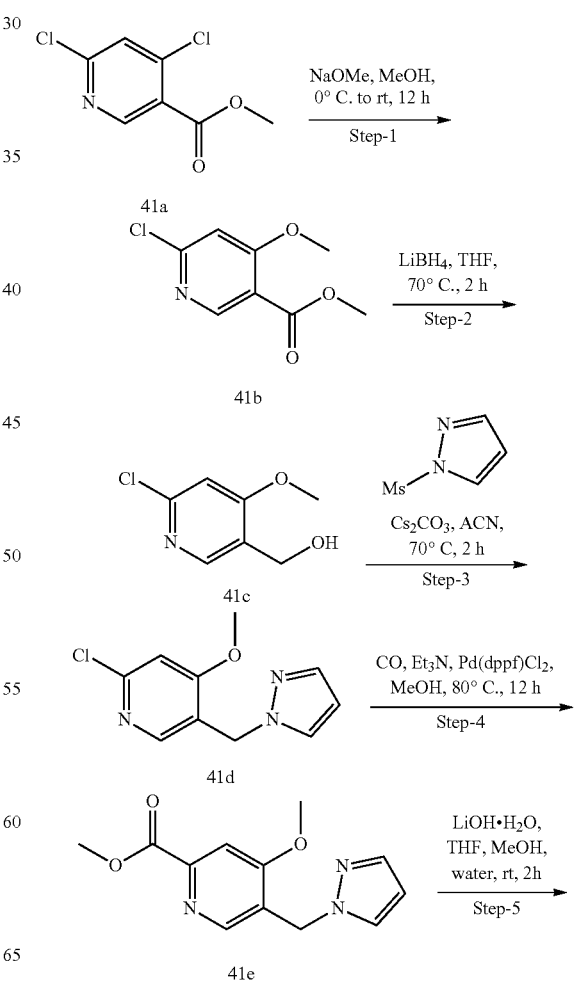

Step 1: 6-Chloro-2-methylnicotinaldehyde

To a solution of 3-bromo-6-chloro-2-methylpyridine (2.0 g, 9.68 mmol) in THF was added n-BuLi (7.26 mL, 11.62 mmol, 1.6 M in THF) at −78° C. and stirred at same temperature for 30 min. Then to the reaction mixture was added DMF (1.41 g, 19.37 mmol) drop wise at −78° C. and slowly warmed to RT and stirred for 2 h. The reaction mixture was cooled to −78° C., quenched with brine, and extracted with diethyl ether. The organic layer was dried over anhydrous sodium sulphate, filtered, and concentrated to afford crude compound. The crude compound which was purified by silica-gel flash column chromatography using 20% ethyl acetate in hexane as eluent to afford the title compound (0.61 g, 40%). LC-MS: 154.2 [M−H]−.

Step 2: (6-Chloro-2-methylpyridin-3-yl)methanol

To a stirred solution of 6-chloro-2-methylnicotinaldehyde (0.6 g, 3.85 mmol), in THF (20 mL) was added NaBH4 (0.438 g, 37.83 mmol) at 0° C. and stirred at RT for 1 h. The reaction mixture was quenched with ice water and extracted with ethyl acetate. The organic layer was dried over Na2SO4, filtered, and concentrated to afford the title compound (0.51 g, 85%). LC-MS: 158.1 [M+H]+.

Step 3: 3-((1H-pyrazol-1-yl)methyl)-6-chloro-2-methylpyridine

The title compound was prepared using similar procedure to that described in Step 2 of Intermediate 29 using appropriate reagents with suitable modifications. LC-MS: 208.0 [M+H]+.

-continued

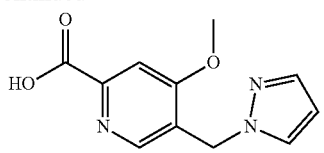

Intermediate-41

Step 1: Methyl 6-chloro-4-methoxynicotinate

To a solution of methyl 4,6-dichloronicotinate (5.0 g, 24.26 mmol) in methanol (50 mL) was added NaOMe (5.4 g, 100.13 mmol) at 0° C. and slowly warmed reaction mixture to RT and stirred for 12 h. The reaction mixture was poured into water and extracted with ethyl acetate. The organic layer was washed with brine, dried over sodium sulphate, filtered, and concentrated to afford the title compound which was taken to the next step without further purification (2.0 g, 41%): LC-MS: 202.0 [M+H]$^+$.

Step 2: (6-Chloro-4-methoxypyridin-3-yl)methanol

To a stirred solution of methyl 6-chloro-4-methoxynicotinate (2.5 g, 12.4 mmol) in THF (40 mL) was added LiBH$_4$ (12.4 mL, 24.8 mmol) at 0° C. and stirred at 70° C. for 2 h. The reaction mixture was quenched with ice water and extracted with ethyl acetate. The organic layer was dried over Na$_2$SO$_4$, filtered, and concentrated to obtain the title compound (2.12 g, 99%). LC-MS: 173.4 [M+H]$^+$.

Step 3: 5-((1H-pyrazol-1-yl)methyl)-2-chloro-4-methoxypyridine

The title compound was prepared using similar procedure to that described in Step 2 of Intermediate 29 using appropriate reagents with suitable modifications. LC-MS: 223.7 [M+H]$^+$.

Step 4: Methyl 5-((1H-pyrazol-1-yl)methyl)-4-methoxypicolinate

The title compound was prepared using similar procedure to that described in Step 3 of Intermediate 29 using appropriate reagents with suitable modifications. LC-MS: 248.9 [M+H]$^+$.

Step 5: 5-((1H-pyrazol-1-yl)methyl)-4-methoxypicolinic acid

The title compound was prepared using similar procedure to that described in Step 4 of Intermediate 29 using appropriate reagents with suitable modifications. LC-MS: 234.1 [M+H]$^+$.

Intermediate 45: 5-((1H-pyrazol-1-yl)methyl)-6-(difluoromethoxy)picolinic acid

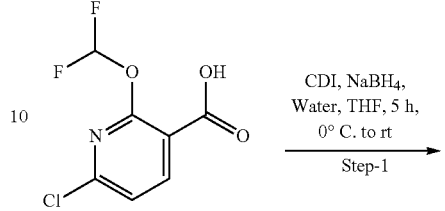

45a

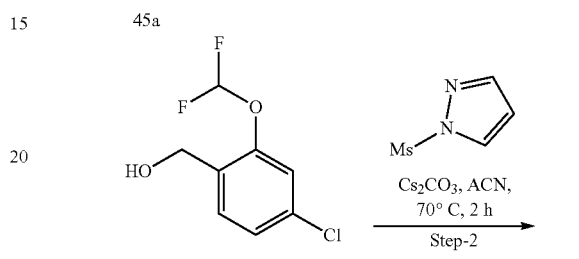

45b

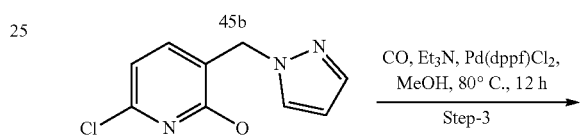

45c

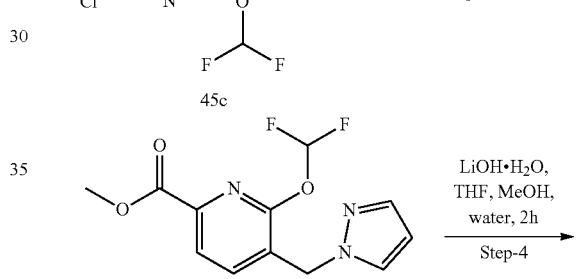

45d

Intermediate-45

Step 1: (6-Chloro-2-(difluoromethoxy)pyridin-3-yl)methanol

To a solution of 6-chloro-2-(difluoromethoxy)nicotinic acid (0.5 g, 2.23 mmol) in THF was added 1,1'-carbonyldiimidazole (0.72 g, 4.47 mmol) was added at 0° C. Then reaction mixture was slowly warmed to RT and for 5 h. Then sodium borohydride (0.42 g, 11.18 mmol) was added to the reaction mixture at 0° C. Then reaction mixture was slowly warmed to RT and for 1 h. The reaction mixture was quenched with water and extracted with ethyl acetate. The organic layer was washed with water brine, dried over sodium sulfate, filtered, and concentrated to get the crude material. The crude material was purified by silica-gel flash column chromatography using 10% ethyl acetate in hexane as eluent to afford the title compound (0.45 g, 96%). LC-MS: 207.6 [M−H]−.

Step 2: 3-((1H-pyrazol-1-yl)methyl)-6-chloro-2-(difluoromethoxy)pyridine

The title compound was prepared using similar procedure to that described in Step 2 of Intermediate 29 using appropriate reagents with suitable modifications. LC-MS: 259.8 [M+H]+.

Step 3: Methyl 5-((1H-pyrazol-1-yl)methyl)-6-(difluoromethoxy)picolinate

The title compound was prepared using similar procedure to that described in Step 3 of Intermediate 29 using appropriate reagents with suitable modifications. LC-MS: 283.0 [M+H]+.

Step 4: 5-((1H-pyrazol-1-yl)methyl)-6-(difluoromethoxy)picolinic acid

The title compound was prepared using similar procedure to that described in Step 4 of Intermediate 29 using appropriate reagents with suitable modifications. LC-MS: 268.0 [M−H]−.

Intermediate 76: 5-((1H-pyrazol-1-yl)methyl)-6-(trifluoromethoxy)picolinic acid

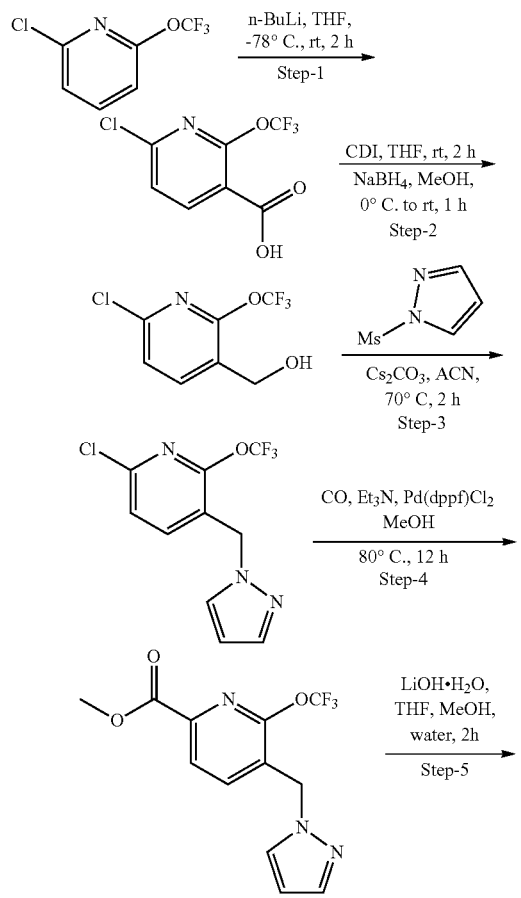

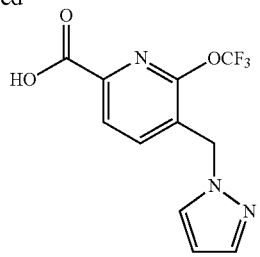

Intermediate-76

Step 1: 6-Chloro-2-(trifluoromethoxy)nicotinic acid

To a solution of 2-chloro-6-(trifluoromethoxy)pyridine (1.0 g, 5.06 mmol) in anhydrous THF (30 mL) was added LDA (freshly prepared from n-BuLi (2.0 mL, 5.0 mmol, 2.5 M in hexane) and diisopropylamine (0.65 g, 5.06 mmol) in THF (10 mL)) at −78° C. The reaction mixture was stirred at −78° C. for 2 h. Using cannula, the reaction mixture transferred in crushed dry ice RB flask at 0° C. and stirred at rt for 30 min. The reaction mixture was quenched with ice water and adjusted pH-3 using 2N HCl to get the precipitate. The precipitate was filtered and dried under vacuum to afford the title compound (0.5 g, 40.9%) LC-MS: 240.0 [M−H]−.

Step 2: (6-Chloro-2-(trifluoromethoxy)pyridin-3-yl)methanol

To a solution of 6-chloro-2-(trifluoromethoxy)nicotinic acid (0.40 g, 1.655 mmol) in THF (10 ml) was added CDI (0.806 g, 4.96 mmol) at 0° C. and stirred the reaction mixture at rt for 2 h. NaBH4 (0.43 g, 11.59 mmol) in water (2 ml) solution was added to the reaction mixture at 0° C. and the entire reaction mixture was stirred at rt for 1 h. The reaction mixture was acidified with HCl and extracted with ethyl acetate. The organic layer was dried over sodium sulphate, filtered, and concentrated to afford the crude material. The crude compound was purified by silica-gel flash column chromatography using 5% methanol in DCM as eluent to afford the title compound (0.2 g, 53.07%). $^1$H NMR (DMSO-D6, 400 MHz): δ 8.12 (d, 1H), 7.58 (d, 1H), 5.58 (s, 1H), 4.52 (s, 2H).

Step 3: 3-((1H-pyrazol-1-yl)methyl)-6-chloro-2-(trifluoromethoxy)pyridine

The title compound was prepared using similar procedure to that described in Step 2 of Intermediate 29 using appropriate reagents with suitable modifications. LC-MS: 278.0 [M+H]+

Step 4: Methyl 5-((1H-pyrazol-1-yl)methyl)-6-(trifluoromethoxy)picolinate

The title compound was prepared using similar procedure to that described in Step 3 of Intermediate 28 using appropriate reagents with suitable modifications. LC-MS: 302.1 [M+H]+.

Step 5: 5-((1H-pyrazol-1-yl)methyl)-6-(trifluoromethoxy)picolinic acid

The title compound was prepared using similar procedure to that described in Step 4 of Intermediate 1 using appropriate reagents with suitable modifications. LC-MS: 288.0 [M+H]⁺

Intermediate 77: Perfluorophenyl 5-((1H-pyrazol-1-yl)methyl)-6-(difluoromethyl)picolinate

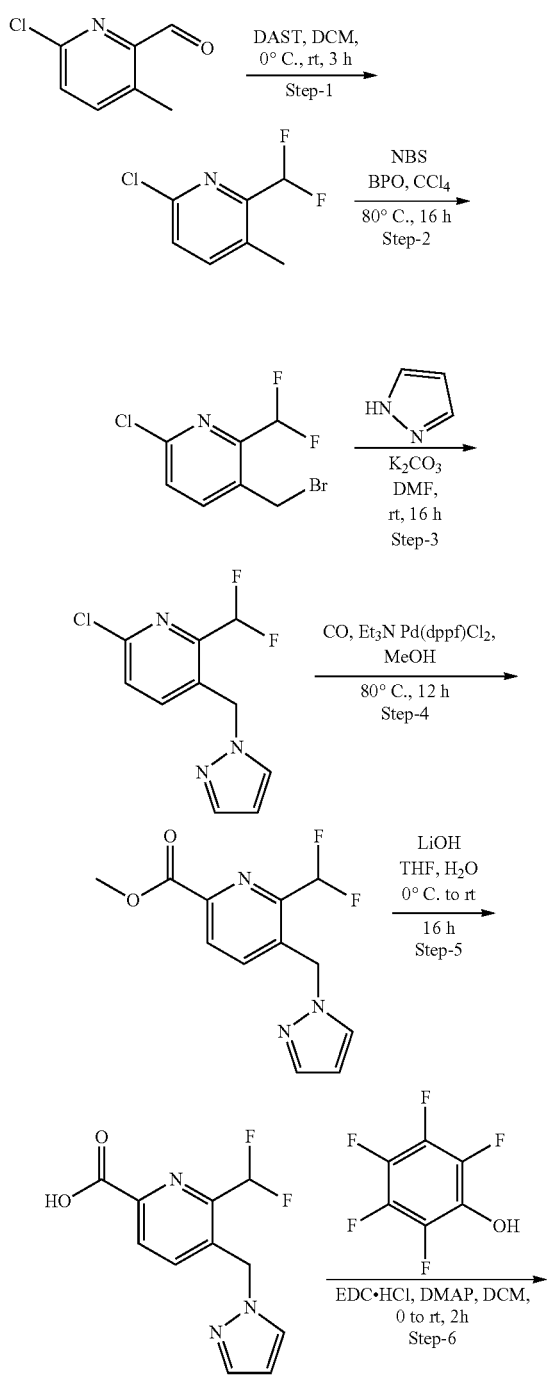

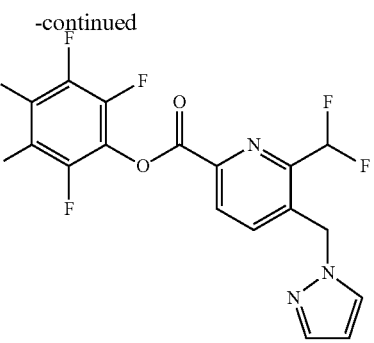

Intermediate-77

Step 1: 6-Chloro-2-(difluoromethyl)-3-methylpyridine

To a solution of 6-chloro-3-methylpicolinaldehyde (0.9 g, 5.78 mmol) in DCM (20 ml) was added DAST (2.79 g, 17.35 mmol) over 10 minutes at 0° C. Then the reaction mixture was warmed to RT and stirred for 3 h. The reaction mixture was quenched with aqueous sodium bicarbonate solution and extracted with ethyl acetate. The organic layer was dried over sodium sulphate, filtered, and concentrated to afford the crude material. The crude material was purified by silica-gel flash column chromatography using 5% methanol in DCM as eluent to afford the title compound (0.91 g, 88.58%). LC-MS: 178.0 [M+H]⁺

Step 2: 3-(Bromomethyl)-6-chloro-2-(difluoromethyl)pyridine

The title compound was prepared using similar procedure to that described in Step 2 of Intermediate 1 using appropriate reagents with suitable modifications. ¹H NMR (DMSO-D6, 400 MHz): δ 7.92 (d, 1H), 7.48 (d, 1H), 6.70 (t, 1H), 4.69 (s, 2H).

Step 3: 3-((1H-pyrazol-1-yl)methyl)-6-chloro-2-(difluoromethyl)pyridine

The title compound was prepared using similar procedure to that described in Step 3 of Intermediate 1 using appropriate reagents with suitable modifications. LC-MS: 244.1 [M+H]⁺.

Step 4: Methyl 5-((1H-pyrazol-1-yl)methyl)-6-(difluoromethyl)picolinate

The title compound was prepared using similar procedure to that described in Step 3 of Intermediate 28 using appropriate reagents with suitable modifications. LC-MS: 268.1 [M+H]⁺.

Step 5: 5-((1H-pyrazol-1-yl)methyl)-6-(difluoromethyl)picolinic acid

The title compound was prepared using similar procedure to that described in Step 4 of Intermediate 1 using appropriate reagents with suitable modifications. LC-MS: 254.1 [M+H]⁺.

Step 6: Perfluorophenyl 5-((1H-pyrazol-1-yl) methyl)-6-(difluoromethyl)picolinate The title compound was prepared using similar procedure to that described in Step 5 of Intermediate 29 using appropriate reagents with suitable modifications. LC-MS: 420.1 [M+H]+.

Intermediate 80: Perfluorophenyl 5-((1H-pyrazol-1-yl) methyl)-6-(trifluoromethyl)picolinate

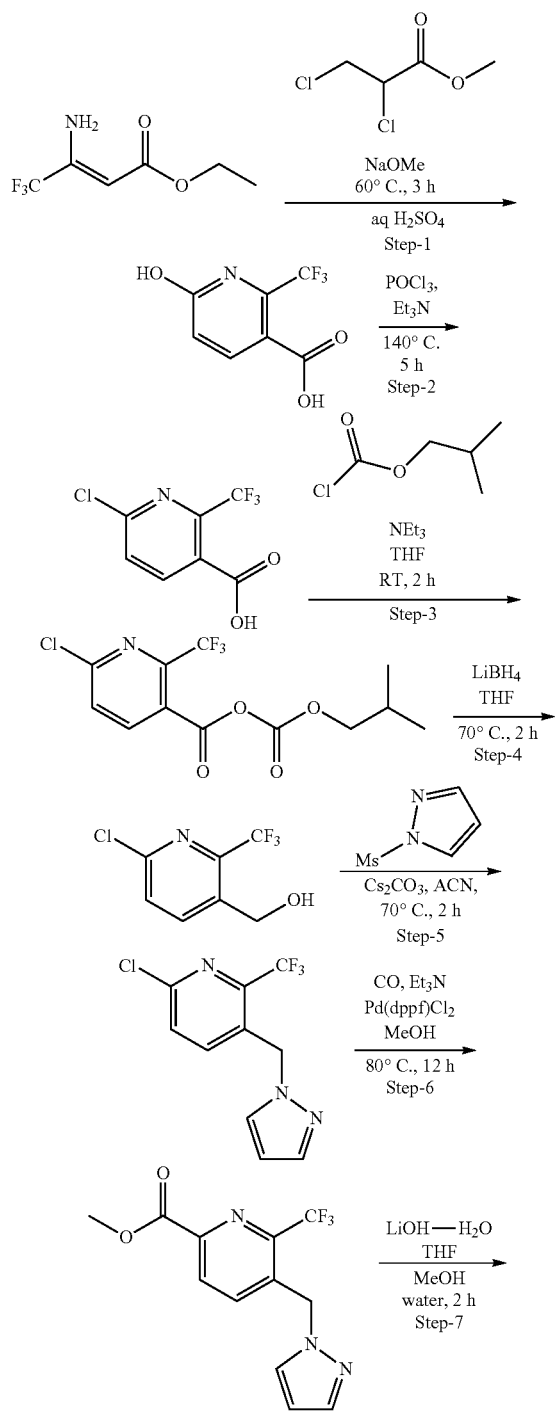

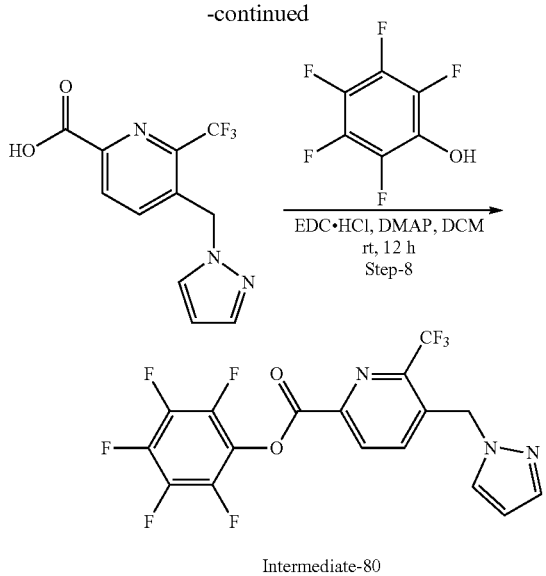

Intermediate-80

Step 1: 6-Hydroxy-2-(trifluoromethyl)nicotinic acid

To a stirred solution of ethyl (Z)-3-amino-4,4,4-trifluorobut-2-enoate (5.0 g 27.30 mmol) in 25% sodium methoxide in methanol (29.5 mL) was added methyl 2,3-dichloropropanoate (4.71 g, 30.03 mmol)) drop wise at 0° C. and stirred for 30 min at 0° C. Then the reaction mixture was heated to 60° C. Subsequently 20% aqueous sodium hydroxide (73.5 mL) was added slowly to the reaction mixture over 2 h at 60° C. The reaction mixture cooled to 0° C. and adjusted pH-3 using con. HCl to get the precipitate. The precipitate was filtered and washed with water to obtain the title compound (4.3 g, 90.6%). LC-MS: 208.0 [M+H]+.

Step 2: 6-Chloro-2-(trifluoromethyl)nicotinic acid

To a stirred solution of 6-hydroxy-2-(trifluoromethyl) nicotinic acid (2.5 g, 12.05 mmol) and Et$_3$N (2.4 g 24.14 mmol) in xylene (2.5 mL) was added POCl$_3$ (2.5 mL 27.03 mmol) at 0° C. and then stirred at 140° C. for 5 h. The reaction mixture was cooled to RT, adjusted to pH-3 using aqueous sulfuric acid solution. The aqueous layer was extracted with xylene. The combined organic layer was dried over anhydrous sodium sulphate and concentrated to afford crude compound (2.2 g). LC-MS: 226.0 [M+H]+

Step 3: 6-Chloro-2-(trifluoromethyl)nicotinic (isobutyl carbonic) anhydride

To a stirred solution of 6-chloro-2-(trifluoromethyl) nicotinic acid (2.2 g, 9.75 mmol) and isobutyl carbonochloridate (1.66 g, 12.19 mmol) in THF (25 mL) was added Et$_3$N (1.48 g 14.63 mmol) at 0° C. and then stirred at RT for 2 h. The reaction was quenched with ice water and extracted with ethyl acetate. The organic layer was dried over sodium sulphate, filtered, and concentrated to afford the crude material. The crude was purified by silica-gel flash column chromatography using 5% ethyl acetate in hexane as eluent to afford the title compound (1.51 g, 47.5%). $^1$H NMR, CDCl$_3$, 400 MHz): δ 7.21 (d, 1H), 7.69 (d, 1H), 4.18 (d, 2H), 2.14-2.06 (m, 1H), 0.96 (d, 6H).

Step 4: (6-Chloro-2-(trifluoromethyl)pyridine-3-yl) methanol

The title compound was prepared using similar procedure to that described in Step 2 of Intermediate 31 using appropriate reagents with suitable modifications. LC-MS: 212.0 [M+H]+

Step 5: 3-((1H-pyrazol-1-yl)methyl)-6-chloro-2-(trifluoromethyl)pyridine

The title compound was prepared using similar procedure to that described in Step 2 of Intermediate 29 using appropriate reagents with suitable modifications. LC-MS: 262.0 [M+H]+.

Step 6: Methyl 5-((1H-pyrazol-1-yl)methyl)-6-(trifluoromethyl)picolinate

The title compound was prepared using similar procedure to that described in Step 3 of Intermediate 28 using appropriate reagents with suitable modifications. LC-MS: 286.1 [M+H]+.

Step 7: 5-((1H-pyrazol-1-yl) methyl)-6-(trifluoromethyl)picolinic acid

The title compound was prepared using similar procedure to that described in Step 4 of Intermediate 1 using appropriate reagents with suitable modifications. LC-MS: 272.0 [M+H]+.

Step 8: Perfluorophenyl 5-((1H-pyrazol-1-yl)methyl)-6-(trifluoromethyl)picolinate The title compound was prepared using similar procedure to that described in Step 5 of Intermediate 29 using appropriate reagents with suitable modifications. LC-MS: 438.0 [M+H]+.

Intermediate 81: Perfluorophenyl 5-((1H-pyrazol-1-yl)methyl)-6-cyclopropylpicolinate

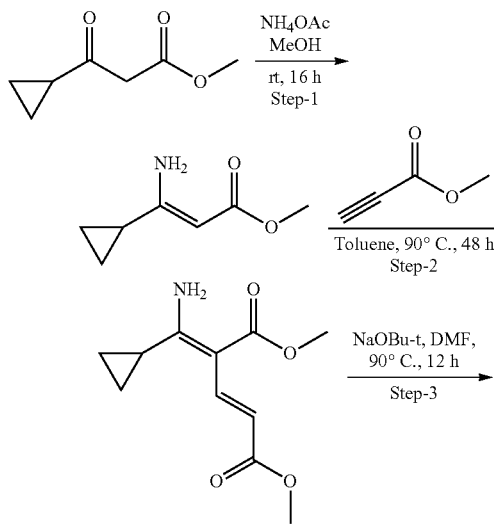

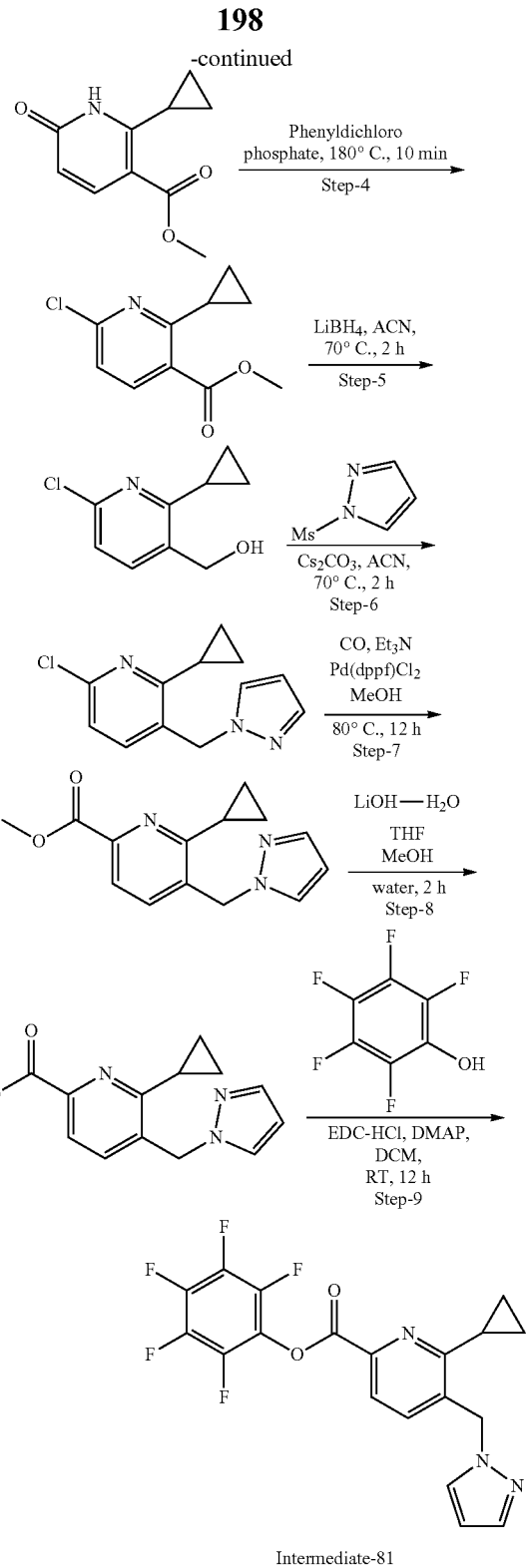

Intermediate-81

Step 1: Ethyl (Z)-3-amino-3-cyclopropylacrylate

To a stirred solution of ethyl 3-cyclopropyl-3-oxopropanoate (5.0 g, 35.17 mmol) in MeOH (100 mL) was added ammonium acetate (13.55 g 175.87 mmol) and stirred at RT for 16 h. The reaction mixture was concentrated, then diluted with DCM (50 mL) and stirred for 30 min to obtain solid.

The solid was filtered and washed with DCM. The combined filtrate was concentrated to afford crude compound (6.55 g). LC-MS: 142.2 [M+H]+.

Step 2: 5-Ethyl 1-methyl (2E,4Z)-4-(amino(cyclopropyl)methylene)pent-2-enedioate To a stirred solution of ethyl (Z)-3-amino-3-cyclopropylacrylate (6.5 g, 46.04 mmol) in toluene (75 mL) was added methyl propiolate (5.42 g, 55.25 mmol) and stirred at 90° C. for 48 h. The reaction mixture was cooled to RT and concentrated to get the crude compound which was used in next step without any further purification (5.11 g, 46.38%). LC-MS: 238.1 [M−H]−.

Step 3: Methyl 2-cyclopropyl-6-oxo-1,6-dihydropyridine-3-carboxylate

A stirred solution of 5-ethyl 1-methyl (2E,4Z)-4-(amino(cyclopropyl)methylene)pent-2-enedioate (5.1 g, 21.31 mmol) in DMF (50 mL) was added NaOtBu (0.30 g, 3.19 mmol) at 0° C. and then stirred at 90° C. for 12 h. The reaction mixture was cooled to RT and quenched with ice-water and extracted with EtOAc. The organic layer was washed with brine, dried over $Na_2SO_4$, filtered, and concentrated to get the crude compound. The crude compound was purified by silica-gel flash column chromatography using 60-70% ethyl acetate in hexane as eluent to afford the title compound (1.2 g, 29.14%). LC-MS: 194.1 [M+H]+.

Step 4: Methyl 6-chloro-2-cyclopropylnicotinate

A stirred solution of methyl 2-cyclopropyl-6-oxo-1,6-dihydropyridine-3-carboxylate (1.1 g, 5.69 mmol) in phenyldichloro phosphate (10 mL) and stirred at 180° C. for 10 min The reaction mixture was added into ice water and extracted with EtOAc. The organic layer was washed with aqueous sodium bicarbonate solution, dried over $Na_2SO_4$, filtered, and concentrated to get the crude compound. The crude compound was purified by silica-gel flash column chromatography using 05-10% ethyl acetate in hexane as eluent to afford the title compound (1.2 g, 29.1%). LC-MS: 212.0 [M+H]+.

Step 5: (6-Chloro-2-cyclopropylpyridin-3-yl)methanol

The title compound was prepared using similar procedure to that described in Step 2 of Intermediate 31 using appropriate reagents with suitable modifications. LC-MS: 184.1 [M+H]+.

Step 6: 3-((1H-pyrazol-1-yl)methyl)-6-chloro-2-cyclopropylpyridine

The title compound was prepared using similar procedure to that described in Step 2 of Intermediate 29 using appropriate reagents with suitable modifications. LC-MS: 234.1 [M+H]+.

Step 7: Methyl 5-((1H-pyrazol-1-yl)methyl)-6-cyclopropylpicolinate

The title compound was prepared using similar procedure to that described in Step 3 of Intermediate 28 using appropriate reagents with suitable modifications. LC-MS: 258.1 [M+H]+.

Step 8: 5-((1H-pyrazol-1-yl)methyl)-6-cyclopropylpicolinic acid

The title compound was prepared using similar procedure to that described in Step 4 of Intermediate 1 using appropriate reagents with suitable modifications. LC-MS: 244.1 [M+H]+.

Step 9: Perfluorophenyl 5-((1H-pyrazol-1-yl)methyl)-6-cyclopropylpicolinate

The title compound was prepared using similar procedure to that described in Step 5 of Intermediate 29 using appropriate reagents with suitable modifications. LC-MS: 410.1 [M+H]+.

Intermediate 99: 5-((1H-pyrazol-1-yl)methyl)-1-methyl-6-oxo-1,6-dihydropyridine-2-carboxylic acid

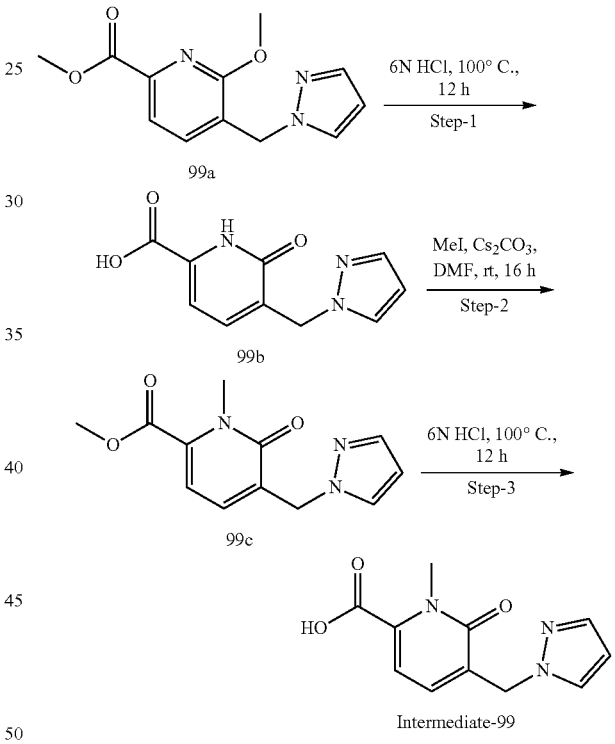

Step 1: 5-((1H-Pyrazol-1-yl)methyl)-6-oxo-1,6-dihydropyridine-2-carboxylic acid Methyl 5-((1H-pyrazol-1-yl)methyl)-6-methoxypicolinate (0.5 g, 2.02 mmol) was dissolved in 6 N HCl in water (12 mL) and refluxed at 100° C. for 12 h. The reaction mixture was concentrated and washed with diethyl ether to get the crude title compound (0.5 g). LC-MS: 220.1 [M+H]+.

Step 2: Methyl 5-((1H-pyrazol-1-yl)methyl)-1-methyl-6-oxo-1,6-dihydropyridine-2-carboxylate To a solution of 5-((1H-pyrazol-1-yl)methyl)-6-oxo-1,6-dihydropyridine-2-carboxylic acid (0.3 g, 1.37 mmol) in DMF (10 mL) was added $Cs_2CO_3$ (0.892 g, 2.73 mmol) and followed by MeI (0.389 g, 2.73 mmol) at 0° C. The reaction mixture was slowly warmed to RT and stirred for 16 h. The reaction mixture was quenched with water and extracted with ethyl acetate. The organic layer was dried over Na$_2$SO$_4$, filtered, and concentrated to get crude. The crude compound was purified by silica-gel flash column chromatography using 0-5% methanol in dichloromethane as eluent to obtain the title compound. (0.26 g, 76.9%). LC-MS: 248.1 [M+H]$^+$.

Step 3: 5-((1H-pyrazol-1-yl)methyl)-1-methyl-6-oxo-1,6-dihydropyridine-2-carboxylic acid Methyl 5-((1H-pyrazol-1-yl)methyl)-1-methyl-6-oxo-1,6-dihydropyridine-2-carboxylate (0.26 g, 1.05 mmol) was dissolved in 6N HCl in water (12 mL) and refluxed at 100° C. for 12 h. The reaction mixture was concentrated and washed with diethyl ether to get the crude title compound (0.24 g). LC-MS: 234.1 [M+H]$^+$.

Intermediate 100: Perfluoronhenyl 5-((1H-pyrazol-1-yl)methyl)-6-ethoxynicolinate

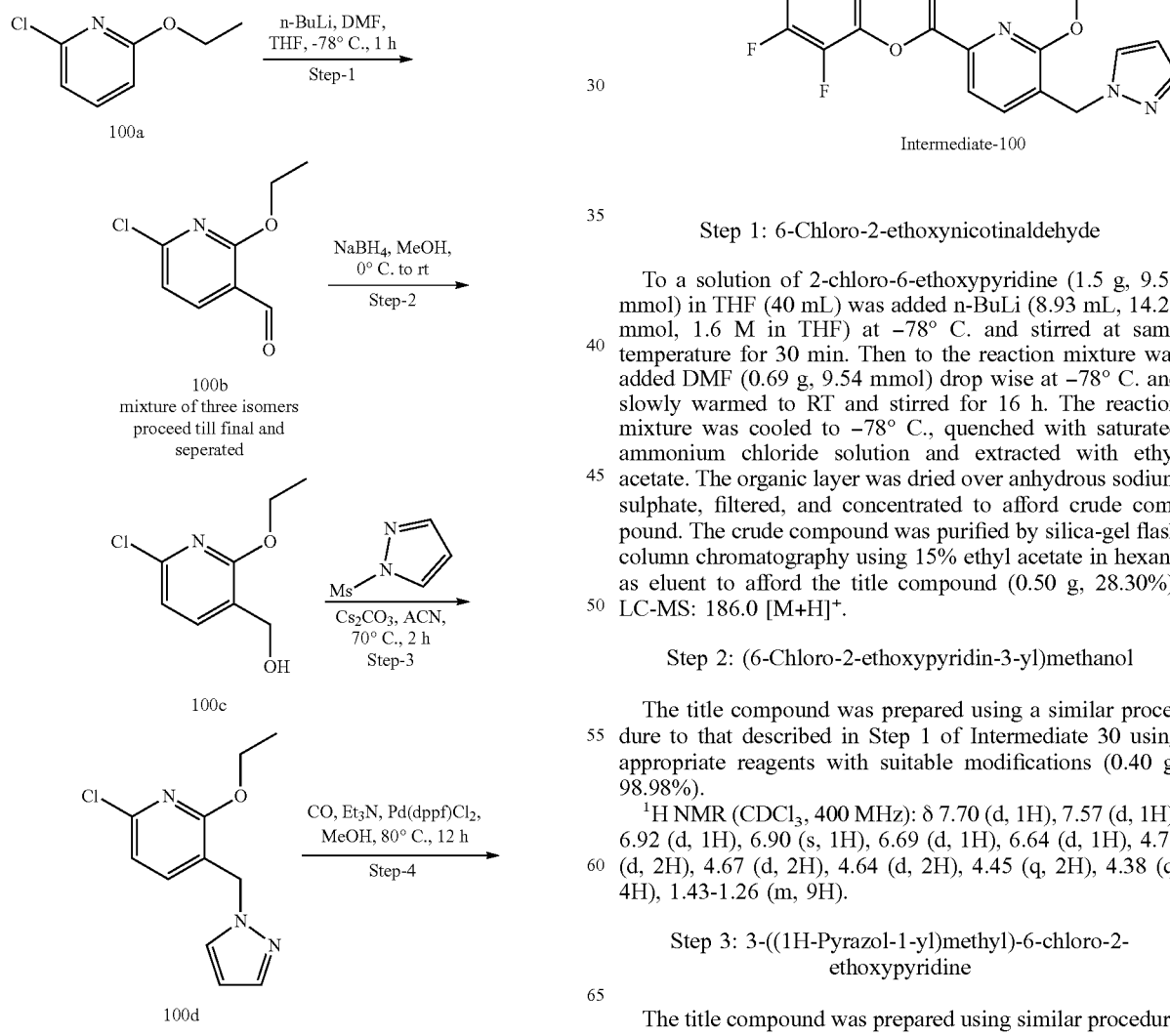

Step 1: 6-Chloro-2-ethoxynicotinaldehyde

To a solution of 2-chloro-6-ethoxypyridine (1.5 g, 9.51 mmol) in THF (40 mL) was added n-BuLi (8.93 mL, 14.29 mmol, 1.6 M in THF) at −78° C. and stirred at same temperature for 30 min. Then to the reaction mixture was added DMF (0.69 g, 9.54 mmol) drop wise at −78° C. and slowly warmed to RT and stirred for 16 h. The reaction mixture was cooled to −78° C., quenched with saturated ammonium chloride solution and extracted with ethyl acetate. The organic layer was dried over anhydrous sodium sulphate, filtered, and concentrated to afford crude compound. The crude compound was purified by silica-gel flash column chromatography using 15% ethyl acetate in hexane as eluent to afford the title compound (0.50 g, 28.30%). LC-MS: 186.0 [M+H]$^+$.

Step 2: (6-Chloro-2-ethoxypyridin-3-yl)methanol

The title compound was prepared using a similar procedure to that described in Step 1 of Intermediate 30 using appropriate reagents with suitable modifications (0.40 g, 98.98%).

$^1$H NMR (CDCl$_3$, 400 MHz): δ 7.70 (d, 1H), 7.57 (d, 1H), 6.92 (d, 1H), 6.90 (s, 1H), 6.69 (d, 1H), 6.64 (d, 1H), 4.71 (d, 2H), 4.67 (d, 2H), 4.64 (d, 2H), 4.45 (q, 2H), 4.38 (q, 4H), 1.43-1.26 (m, 9H).

Step 3: 3-((1H-Pyrazol-1-yl)methyl)-6-chloro-2-ethoxypyridine

The title compound was prepared using similar procedure to that described in Step 2 of Intermediate 29 using appropriate reagents with suitable modifications (0.48 g, 95.71%). $^1$H NMR (DMSO-D$_6$, 400 MHz): δ 7.88 (d, 1H), 7.79 (d, 1H), 7.78 (d, 1H), 7.53 (dd, 1H), −7.48-7.46 (m, 2H), 7.42 (d, 1H), 7.27 (d, 1H), 7.04 (d, 1H), 6.82 (d, 1H), 6.79 (s, 1H), 6.42 (d, 1H), 6.33 (d, 1H), 6.28-6.27 (m, 2H), 5.38 (s, 2H), 5.35 (s, 2H), 5.26 (s, 2H), 4.30 (q, 2H), 4.26 (q, 4H), 1.33-1.28 (m, 9H).

Step 4: Methyl 5-((1H-pyrazol-1-yl)methyl)-6-ethoxypicolinate

The title compound was prepared using similar procedure to that described in Step 3 of Intermediate 29 using appropriate reagents with suitable modifications (0.40 g, 80.87%). $^1$H NMR (CDCl$_3$, 400 MHz): δ 7.61 (d, 1H), 7.58-7.57 (m, 3H), 7.5d-7.52 (m, 3H), 7.48 (d, 1H), 7.24-7.21 (m, 2H), 6.84-6.82 (m, 1H), 6.57 (dd, 1H), 6.37 (dd, 1H), 6.33 (dd, 1H), 6.31 (dd, 1H), 5.66 (s, 2H), 5.36 (s, 2H), 5.35 (s, 2H), 4.55 (q, 2H), 4.46-4.38 (m, 4H), 3.99 (s, 3H), 3.96 (s, 6H), 1.46-1.26 (m, 9H).

Step 5: 5-((1H-Pyrazol-1-yl)methyl)-6-ethoxypicolinic acid

The title compound was prepared using similar procedure to that described in Step 4 of Intermediate 29 using appropriate reagents with suitable modifications (0.25 g): LC-MS: 248.1 [M+H]$^+$.

Step 6: Perfluorophenyl 5-((1H-pyrazol-1-yl)methyl)-6-ethoxypicolinate

The title compound was prepared using a similar procedure to that described in Step 5 of Intermediate 29 using appropriate reagents with suitable modifications (0.22 g, 54.82%). LC-MS: 414.1 [M+H]$^+$.

d) Sulfinyl Intermediates

Intermediate 82: 5-((1H-pyrazol-1-yl)methyl)-N-((2,6-dimethoxyphenyl)sulfinyl)-6-methoxypicolinamide

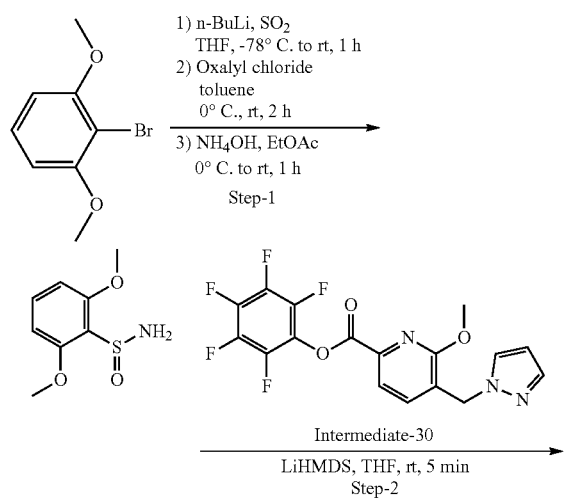

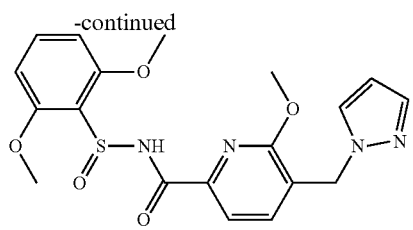

Step 1: 2,6-Dimethoxybenzenesulfinamide

To a solution of 2-bromo-1,3-dimethoxybenzene (2 g, 9.21 mmol) in THF (15 mL) was added n-BuLi (17.3 mL, 27.64 mmol, 1.6M in hexane) at −78° C. and stirred at the same temperature for 1 h. Then SO$_2$ gas was bubbled into the reaction mixture for 30 min at −78° C. The entire reaction mixture was stirred at 0° C. for 1 h. The reaction mixture was concentrated to obtain the solid. The solid was dissolved in toluene and oxalyl chloride (0.93 mL, 10.8 mmol) was added to the reaction mixture at 0° C. The reaction mixture was warmed to RT and stirred for 2 h. The reaction was quenched with ice-water and extracted with DCM. The organic layer was dried over sodium sulphate, filtered, and concentrated to afford the crude compound. The crude compound was again dissolved in DCM (10 mL) and 7N methanolic ammonia (30 mL) was added to the reaction mixture and stirred for 30 min at RT. The reaction mixture was diluted with water and extracted with DCM. The organic layer was dried over sodium sulphate, filtered, and concentrated to afford the crude compound. The crude compound was purified by silica-gel flash column chromatography using 60% ethyl acetate in hexane as eluent to afford the title compound (0.5 g, 34.5%). LC-MS: 202.1 [M+H]$^+$.

Step 2: 5-((1H-pyrazol-1-yl)methyl)-N-((2,6-dimethoxyphenyl)sulfinyl)-6-methoxypicolinamide To a solution of perfluorophenyl 5-((1H-pyrazol-1-yl)methyl)-6-methoxypicolinate (0.15 g, 0.37 mmol), and 2,6-dimethoxybenzenesulfinamide (0.091 g, 0.45 mmol) in THF (5 mL) was added LiHMDS (1.12 mL, 1.13 mmol, 1.0 M in THF) and stirred at RT for 10 min. The reaction mixture was quenched with saturated NH$_4$Cl solution and extracted with 10% MeOH in DCM. The organic layer was dried over Na$_2$SO$_4$, filtered, and concentrated to afford the crude compound. Crude compound was purified by silica-gel flash column chromatography using 2-5% MeOH in DCM as eluent to afford the title compound (0.12 g, 76.6%). LC-MS: 415.0 [M−H]$^−$.

Intermediates 83 to 87

The following intermediates listed in Table 10 were prepared by following similar procedures described above for Intermediate 82 using appropriate reagents with suitable modifications known to the one skilled in the art.

TABLE 10

| Intermediate | Structure | LC-MS |
|---|---|---|
| 83 | 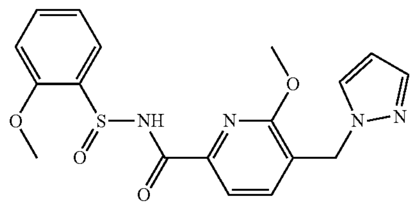 [SMILES: COc1ccccc1S(=O)NC(=O)c1ccc(Cn2cccn2)c(OC)n1] | LC-MS: 385 [M − H]⁻. |
| 84 | 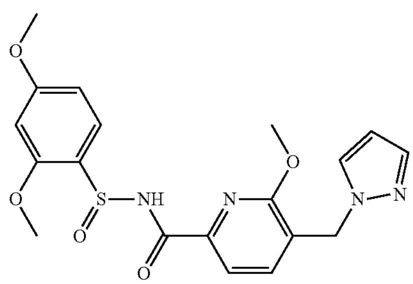 [SMILES: COc1ccc(S(=O)NC(=O)c2ccc(Cn3cccn3)c(OC)n2)c(OC)c1] | LC-MS: 415.0 [M − H]⁻. |
| 85 | 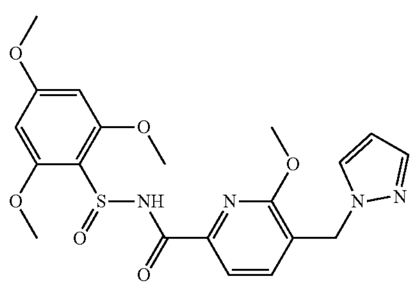 [SMILES: COc1cc(OC)c(S(=O)NC(=O)c2ccc(Cn3cccn3)c(OC)n2)c(OC)c1] | LC-MS: 445.0 [M − H]⁻. |
| 86 | 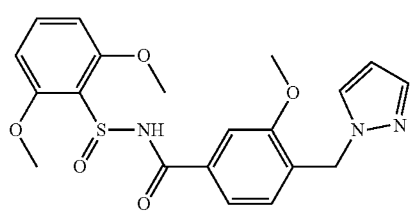 [SMILES: COc1cc(C(=O)NS(=O)c2c(OC)cccc2OC)ccc1Cn1cccn1] | LC-MS: 416.1 [M + H]⁺. |
| 87 | 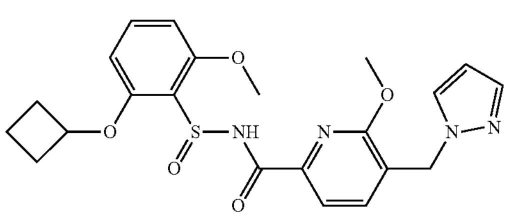 [SMILES: COc1cccc(OC2CCC2)c1S(=O)NC(=O)c1ccc(Cn2cccn2)c(OC)n1] | LC-MS: 455.1 [M − H]⁻. |

Intermediate 119: 5-((1H-Pyrazol-1-yl)methyl)-N-((3-chloro-2,6-dimethoxyphenyl)sulfinyl)-6-methoxypicolinamide

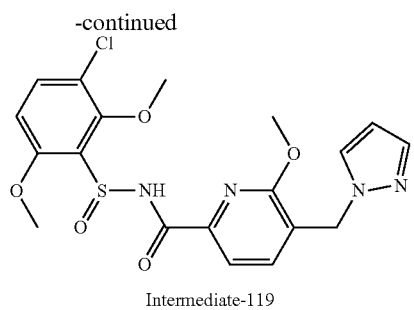

Intermediate-119

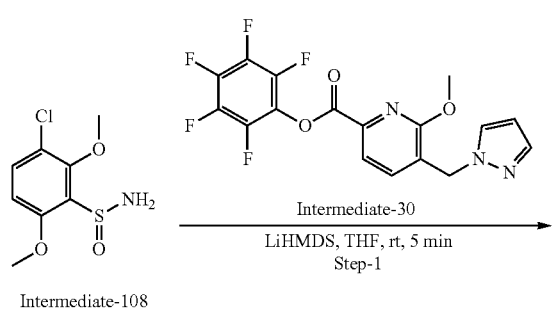

Step 1: 5-((1H-pyrazol-1-yl)methyl)-N-((2,6-dimethoxyphenyl)sulfinyl)-6-methoxypicolinamide The title compound was prepared using a similar procedure to that described in Step 2 of Intermediate 82 using appropriate reagents with suitable modifications. (0.2 g, 17.71%). LC-MS: 449.0 [M–H]⁻.

Intermediates 120 to 131

The following intermediates listed in Table 11 were prepared by following similar procedures described above for Intermediate 119 and Step 2 of Intermediate 82 using appropriate reagents with suitable modifications known to the one skilled in the art.

TABLE 11

| Intermediate | Structure | Spectral data |
|---|---|---|
| 120 | 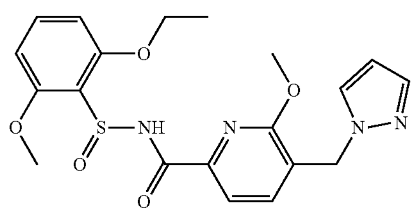 [SMILES: CCOc1cccc(OC)c1S(=O)NC(=O)c1ccc(Cn2cccn2)c(OC)n1] | LC-MS: 429.05 [M − H]⁻. |
| 121 | 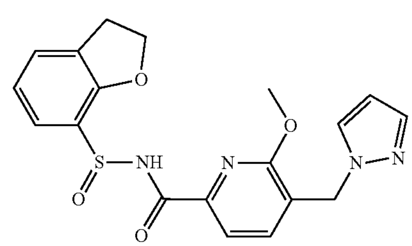 [SMILES: COc1nc(C(=O)NS(=O)c2cccc3c2OCC3)ccc1Cn1cccn1] | LC-MS: 397.1 [M − H]⁻. |
| 122 | 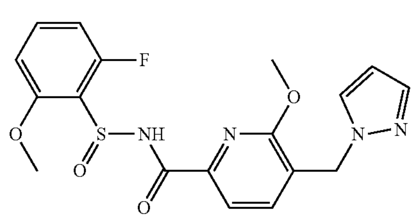 [SMILES: COc1cccc(F)c1S(=O)NC(=O)c1ccc(Cn2cccn2)c(OC)n1] | LC-MS: 403.0 [M − H]⁻. |

TABLE 11-continued

| Intermediate | Structure | Spectral data |
| --- | --- | --- |
| 123 | 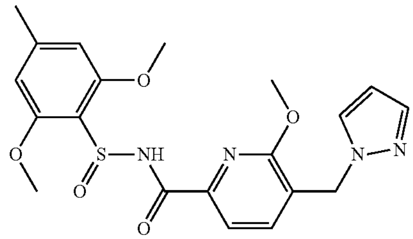 [SMILES: COc1cc(C)cc(OC)c1S(=O)NC(=O)c1ccc(Cn2cccn2)c(OC)n1] | LC-MS: 429.3 [M − H]⁻. |
| 124 | 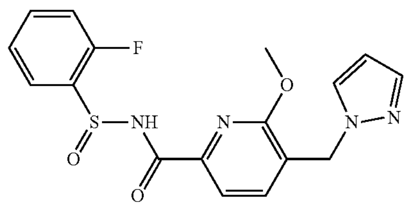 [SMILES: COc1nc(C(=O)NS(=O)c2ccccc2F)ccc1Cn1cccn1] | LC-MS: 375.1 [M + H]⁺. |
| 125 | 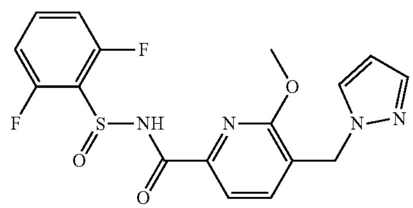 [SMILES: COc1nc(C(=O)NS(=O)c2c(F)cccc2F)ccc1Cn1cccn1] | LC-MS: 393.0 [M + H]⁺. |
| 126 | 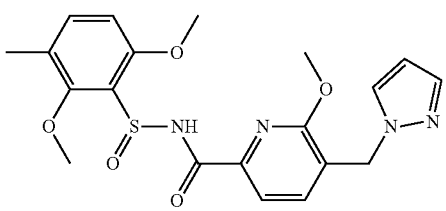 | LC-MS: 429.0 [M − H]⁻. |
| 127 | 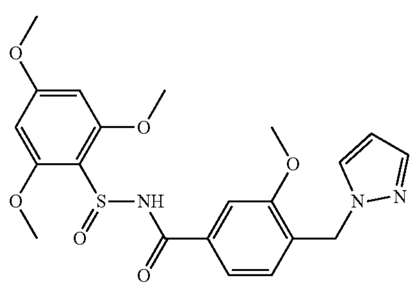 [SMILES: COc1cc(OC)c(S(=O)NC(=O)c2ccc(Cn3cccn3)c(OC)c2)c(OC)c1] | LC-MS: 444.1 [M − H]⁻. |
| 128 | 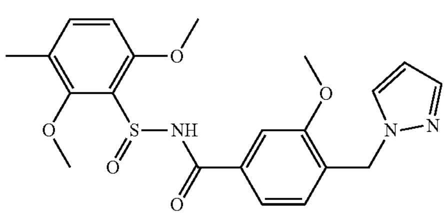 [SMILES: COc1cc(C(=O)NS(=O)c2c(OC)ccc(C)c2OC)ccc1Cn1cccn1] | LC-MS: 430.1 [M + H]⁺. |
| 129 | 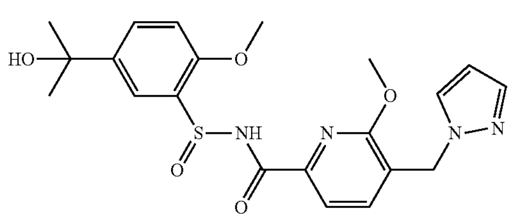 [SMILES: COc1ccc(C(C)(C)O)cc1S(=O)NC(=O)c1ccc(Cn2cccn2)c(OC)n1] | LC-MS: 443.2 [M − H]⁻. |

TABLE 11-continued

| Intermediate | Structure | Spectral data |
|---|---|---|
| 130 | 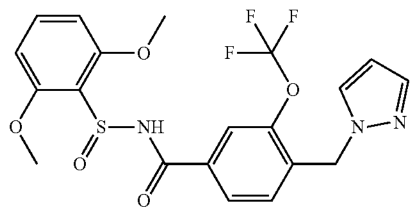 [SMILES: COc1cccc(OC)c1S(=O)NC(=O)c1ccc(Cn2cccn2)c(OC(F)(F)F)c1] | LC-MS: 468.4 [M − H]−. |
| 131 | 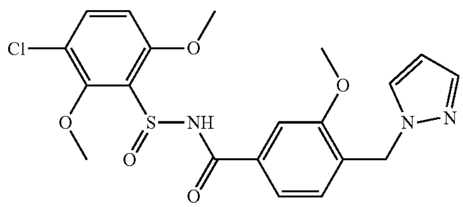 [SMILES: COc1cc(C(=O)NS(=O)c2c(OC)ccc(Cl)c2OC)ccc1Cn1cccn1] | LC-MS: 450.1 [M + H]+. |

General Synthetic Schemes:

Certain compounds of the present invention can be made by following the process as given in General scheme-I.

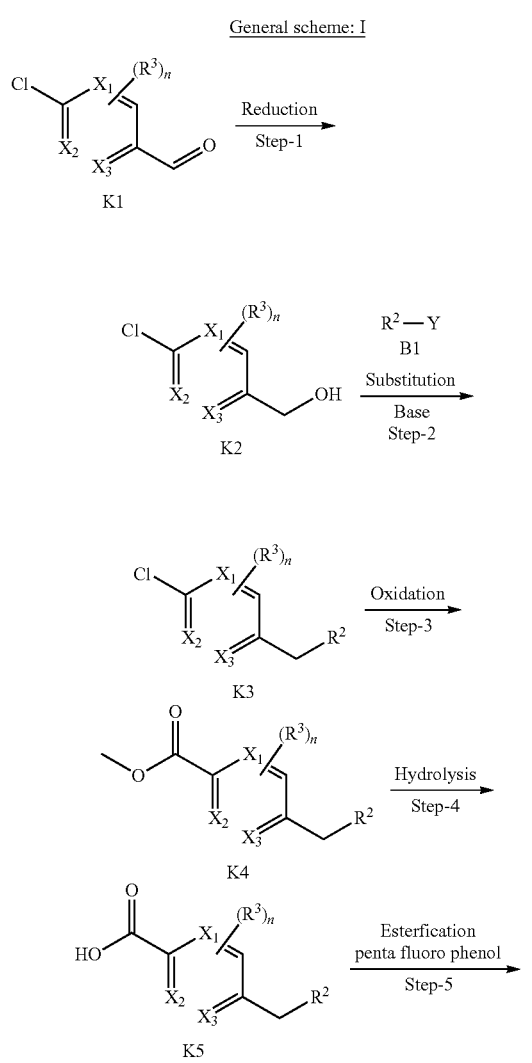

Formula I'

$R^3$, $R^1$, $R^2$, 'n' and 'q' as same as define in compound of formula J;
$X_1$, $X_2$ and $X_3$ are CH or N.

The general scheme-I for the synthesis of compound represented by formula (I') is depicted in above scheme. The compound of formula ($K_1$) is undergoing reduction reaction in suitable solvent and suitable reducing reagent to yield compound of formula ($K_2$) which upon further react compound of formula ($B_1$) in presence of suitable substituent reagent and solvent can provide compound of formula ($K_3$). The compound of formula ($K_3$) undergoes oxidation reaction followed by substitution reaction to result in compound of formula ($K_4$) which further hydrolysis with suitable base and solvent to yield compound of formula ($K_5$). The compound of formula ($K_5$) reacts with pentafluoro phenol with suitable solvent to result ester compound of ($K_6$). The compound of formula ($K_6$) can react with formula ($B_2$) in suitable reagent and solvent to result in the compound of formula (I').

General scheme: II

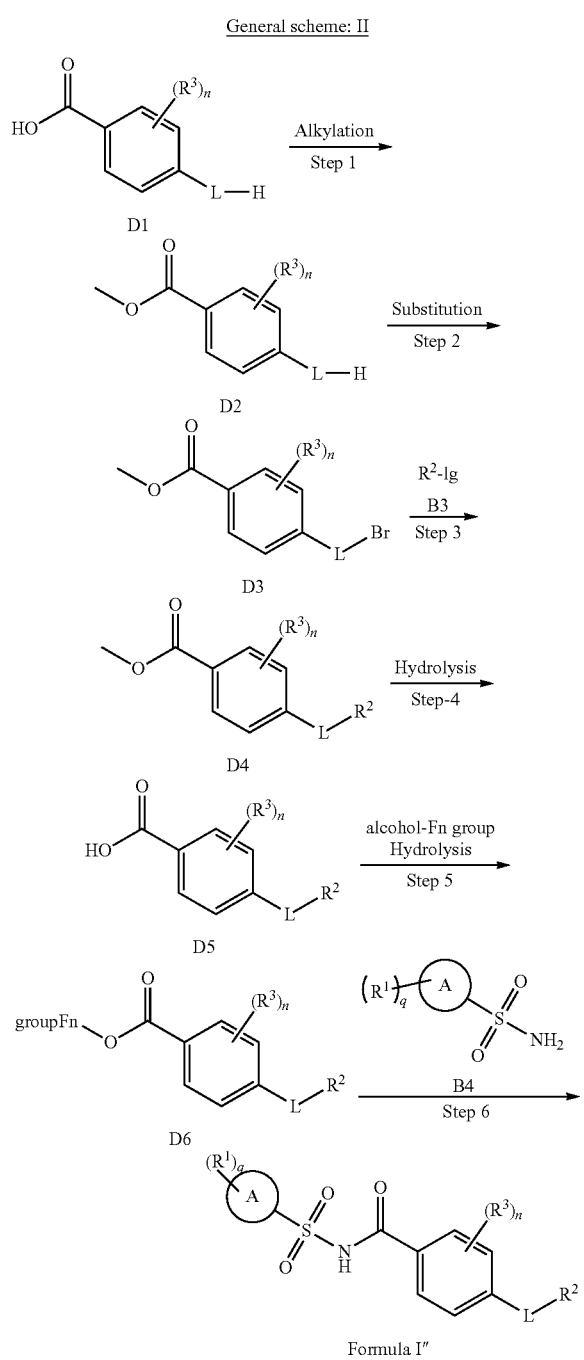

$R^1$, $R^2$, $R^3$, L, ring A, 'n' and 'q' are same as define in formula J;
lg = leaving group
Fn = Functional group The general scheme-II for the synthesis of compound represented by formula (I") is depicted in above scheme. The compound of formula ($D_1$) is reacted with alkylation reagent in suitable solvent and to yield compound of formula ($D_2$) which upon further undergoes substitution reaction in presence of suitable substituent reagent and solvent can provide compound of formula ($D_3$). The compound of formula ($D_3$) reacts with formula ($B_3$) to result in compound of formula ($D_4$) which further hydrolysis with suitable base and solvent to yield compound of formula ($D_5$). The compound of formula ($D_5$) reacts with alcohol in suitable solvent to result in ester compound of ($D_6$). The compound of formula ($D_6$) can react with formula ($B_4$) in suitable reagent and solvent to result in the compound of formula (I").

e) Compound Examples

Example 1. Compound 1: 4-((1H-pyrazol-1-yl)methyl)-N-((2,6-dimethoxyphenyl)sulfonyl)-2-methoxybenzamide

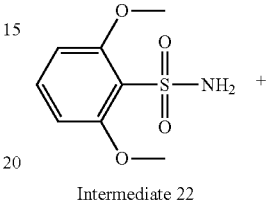

Intermediate 22

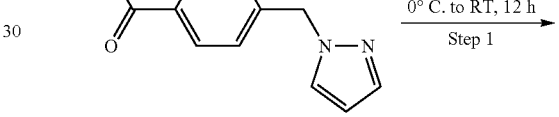

Intermediate 1

Compound 1

To a solution of 4-((1H-pyrazol-1-yl)methyl)-2-methoxybenzoic acid (0.2 g, 0.86 mmol) in THF (10 mL) was added CDI (0.16 g, 1.03 mmol) and stirred at RT for 1 h. The reaction mixture was cooled to 0° C., were added 2,6-dimethoxybenzenesulfonamide (0.2 g, 0.94 mmol), DBU (0.18 g, 1.2 mmol) and stirred for 15 minutes at same temperature, then gradually warmed to RT and stirred for overnight. The reaction mixture was concentrated to get crude compound. The crude compound was purified by preparative HPLC to afford the title compound (0.015 g, 4%).

Preparative HPLC method: Mobile phase A-0.05% TFA in water; B-Acetonitrile; column used-Luna Omega PS, C-18 (250×21.2 mm), 5p. Gradient programme: 0% B at 10 minutes, 20% B at 2 minutes, 40% B at 10 minutes. LC-MS: 432.2 [M+H]$^+$; $^1$H NMR (DMSO-$d_6$, 400 MHz): δ 11.27 (s, 1H), 7.87 (d, 1H), 7.55-7.45 (m, 3H), 7.07, (s, 1H), 6.80 (s, 1H), 6.78 (s, 1H), 6.75 (d, 1H), 6.30 (t, 1H), 5.39 (s, 2H), 3.88 (s, 3H), 3.79 (s, 6H).

Example 2. Compound 26: N-(2-methoxyphenyl)sulfonyl-3-methoxy-4-(pyrazol-1-ylmethyl)benzamide

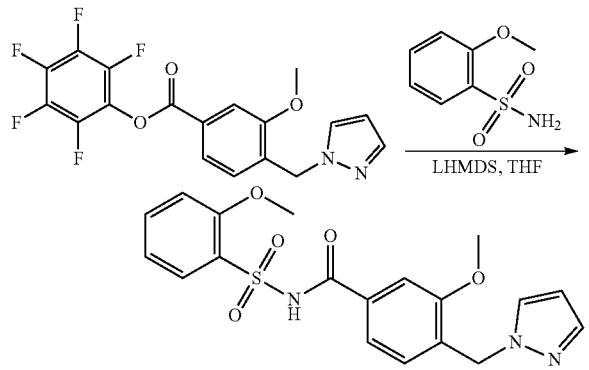

To a solution of perfluorophenyl 4-((1H-pyrazol-1-yl)methyl)-3-methoxybenzoate (0.100 g, 0.251 mmol), 2-methoxybenzenesulfonamide (0.056 g, 0.301 mmol) in THF (3 mL) was added LiHMDS (1.0 M in THF solution) (1.0 mL, 1.0 mmol) and the entire reaction mixture stirred at RT for 10 min. The reaction mixture was quenched ice then diluted with saturated NH4Cl solution and extracted with ethyl acetate. The organic layer was dried over Na$_2$SO$_4$ and concentrated to afford the crude compound, which was further purified by prep TLC eluted at 80% ethyl acetate in hexane (0.03 g, 30%): LC-MS: 402.3 [M+H]$^+$; $^1$H NMR (DMSO-d$_6$, 400 MHz): δ 12.50 (s, 1H), 7.91 (dd, 1H), 7.78 (d, 1H), 7.63 (dd, 1H), 7.55 (d, 1H), 7.47 (dd, 1H), 7.41 (dd, 1H), 7.21 (d, 1H), 7.16 (t, 1H), 6.78 (d, 1H), 6.31 (t, 1H), 5.33 (s, 2H), 3.91 (d, 3H), 3.85 (d, 3H).

Example 3. Compound 45: N-(5-bromo-2,4-dimethoxy-phenyl)sulfonyl-3-methoxy-4-(pyrazol-1-ylmethyl)benzamide

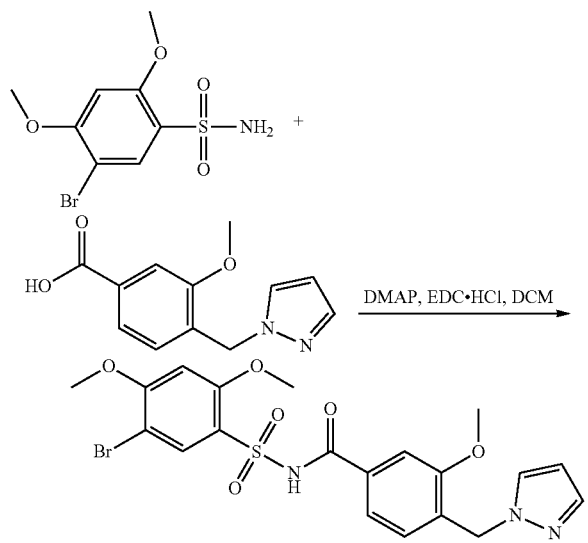

A vial equipped with a stir bar was charged with 5-bromo-2,4-dimethoxybenzenesulfonamide (1.00 eq, 40 mg, 0.135 mmol) and 3-methoxy-4-(pyrazol-1-ylmethyl)benzoic acid (1.24 eq, 39 mg, 0.167 mmol) in DCM (1.4 mL) and 4-dimethylaminopyridine (4.00 eq, 66 mg, 0.540 mmol) and 1-(3-dimethylaminopropyl)-3-ethylcarbodimide hydrochloride (1.50 eq, 39 mg, 0.203 mmol) was added to the reaction vial and left to stir at room temperature under nitrogen for 1.5 h. Reaction mixture diluted with DCM (5 mL), quenched with water (15 mL), and extracted with DCM (10 mL×3). The combined organic layers were dried over sodium sulfate, filtered, and concentrated. Crude product was purified via HPLC (Column: Luna 5 uM, C18, LC column 100×30 mm. Flow rate: 42 mL/min. Gradient: 13-70%; isocratic at 70%; Acetonitrile-water. Run time: 14 min. Modifier: 0.1% formic acid) to yield the title compound (48 mg, 0.092 mmol, 68%): LC-MS: 512 [M+H]$^+$; $^1$H NMR (400 MHz, DMSO-d6) δ 12.54 (s, 1H), 7.94 (s, 1H), 7.78 (dd, J=2.3, 0.6 Hz, 1H), 7.54 (d, J=1.6 Hz, 1H), 7.47 (dd, J=1.9, 0.7 Hz, 1H), 7.41 (dd, J=7.9, 1.6 Hz, 1H), 6.86 (s, 1H), 6.78 (d, J=7.9 Hz, 1H), 6.28 (t, J=2.1 Hz, 1H), 5.33 (s, 2H), 3.97 (s, 3H), 3.91 (d, J=6.1 Hz, 6H).

Example 4. Compound 70: N-(2,3-dihydrobenzofuan-7-yl)sulfonyl-3-methoxy-4-(pyrazol-1-ylmethyl)benzamide

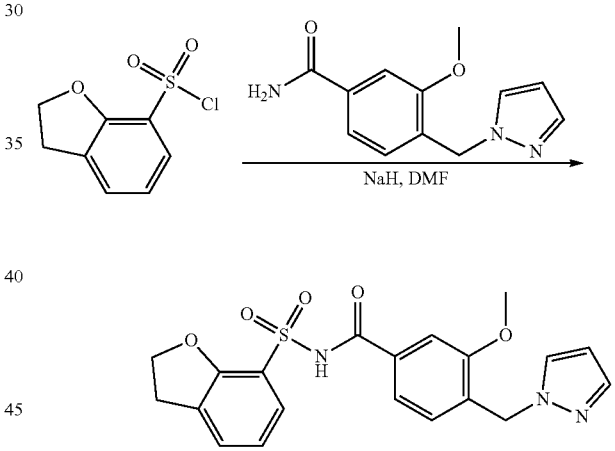

3-Methoxy-4-(pyrazol-1-ylmethyl)benzamide (1.00 eq, 40 mg, 0.173 mmol) was dissolved in DMF (1.5 mL) and cooled to 0° C. Sodium hydride 60% in mineral oil (1.30 eq, 5.4 mg, 0.225 mmol) was added and stirred for 30 min. 2,3-Dihydro-1-benzofuran-7-sulfonyl chloride (1.10 eq, 42 mg, 0.190 mmol) was added and stirred for 2 h allowing to warm to room temperature. The reaction mixture was directly purified by HPLC on a Kinetex 5 um C18 100 Å column (size: 100×30.0 mm; gradient: 5-55% 0.1% formic acid in ACN in 0.1% formic acid in water) then lyophilized to give the title compound (3.4 mg, 5% yield): LC-MS: m/z=414.1 [M+H]$^+$. 1H NMR (400 MHz, DMSO) δ 7.75 (s, 1H), 7.54 (d, J=1.5 Hz, 2H), 7.46 (d, J=1.8 Hz, 1H), 7.42 (dd, J=7.8, 1.5 Hz, 1H), 6.77 (d, J=7.8 Hz, 1H), 6.53 (d, J=3.2 Hz, 1H), 6.27 (t, J=2.1 Hz, 1H), 5.31 (s, 2H), 4.56 (s, 2H), 3.87 (s, 3H), 3.18 (s, 2H).

Example 5. Compound 14: 4-((1H-pyrazol-1-yl)methyl)-N-((2,6-dimethoxyphenyl)sulfonyl)-3-methoxybenzamide

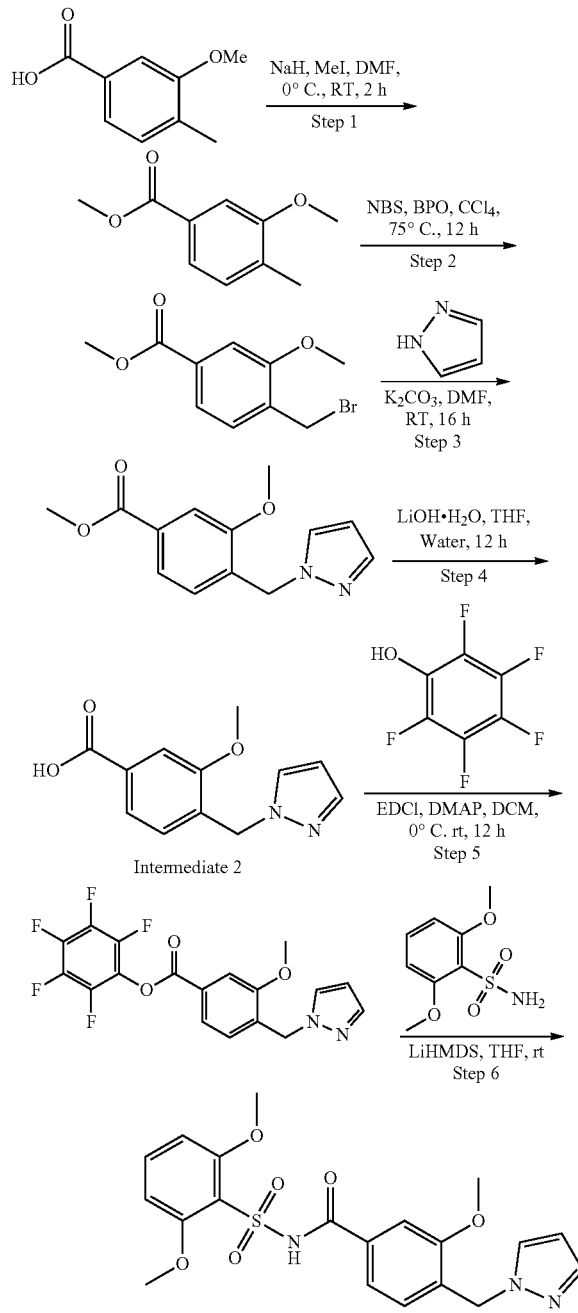

Step 1: Methyl 3-methoxy-4-methylbenzoate

To a stirred solution of 3-hydroxy-4-methylbenzoic acid (20 g, 32.8 mmol) in DMF (250 mL) was cooled to 0° C. and added NaH (7.9 g, 328.62 mmol) followed by methyl iodide (24.6 mL, 394.3 mmol) at 0° C. The reaction mixture was warmed to RT and stirred for 1 h. The reaction mixture was poured into ice water to obtain a precipitate, which was filtered and washed with water and dried under vacuum to obtain the title compound (20 g, 97.4%). LC-MS: 181.3 [M+H]$^+$.

Step 2: Methyl 4-(bromomethyl)-3-methoxybenzoate

To a solution of methyl 3-methoxy-4-methylbenzoate (23 g, 127.63 mmol) in CCl$_4$ (300 mL) were added NBS (31.8 g, 178.69 mmol) and benzoyl peroxide (BPO, 4.63 g, 19.14 mmol) and stirred at 75° C. for overnight. Reaction mixture was then cooled to RT and diluted with DCM and washed with water. The organic layer was dried over Na$_2$SO$_4$, filtered, and concentrated to afford the crude compound (33 g) which was used in the next step without further purification. LC-MS: 260.9 [M+H]$^+$.

Step 3: Methyl 4-((1H-pyrazol-1-yl)methyl)-3-methoxybenzoate

To a stirred solution of methyl 4-(bromomethyl)-3-methoxybenzoate (33 g, 127.36 mmol), and 1H-pyrazole (13 g, 191.04 mmol) in DMF (300 mL) was added K$_2$CO$_3$ (44 g, 318.41 mmol) and stirred at RT for 16 h. The reaction mixture was diluted with water and extracted with EtOAc. The organic layer was washed with water, brine, dried over Na$_2$SO$_4$, filtered, and concentrated to afford crude compound. The crude compound was purified by silica-gel flash column chromatography using 10-40% ethyl acetate in hexane as eluent to afford the title compound (11 g, 35%). LC-MS: 247.2 [M+H]$^+$.

Step 4: 4-((1H-pyrazol-1-yl)methyl)-3-methoxybenzoic acid

To a stirred solution of methyl 4-((1H-pyrazol-1-yl)methyl)-3-methoxybenzoate (10 g, 40.6 mmol) in THF (150 mL), MeOH (40 mL) and water (60 mL) was added LiOH·H$_2$O (4.87 g, 203.03 mmol) and stirred for 12 h at RT. The reaction mixture was diluted with ice-cold water, adjusted pH to 3 using 1N HCl solution to obtain a precipitate. The precipitate was filtered, washed with water, and dried under vacuum to afford the title compound (9 g, 95%). LC-MS: 233.2 [M+H]$^+$.

Step 5: Perfluorophenyl 4-((1H-pyrazol-1-yl)methyl)-3-methoxybenzoate

To a solution of 4-((1H-pyrazol-1-yl)methyl)-2-methoxybenzoic acid (1.2 g, 5.17 mmol), and 2,3,4,5,6-pentafluorophenol (1.14 g, 6.20 mmol) in DCM (25 mL) was added DMAP (0.127 g, 1.03 mmol) followed by EDC·HCl (1.49 g, 7.75 mmol) and stirred at RT for 12 h. The reaction mixture was quenched with ice water and extracted with DCM. The organic layer was dried over Na$_2$SO$_4$, filtered, and concentrated to afford the crude compound which was purified by silica-gel flash column chromatography using 10-15% ethyl acetate in hexanes as eluent to obtain the title compound (1.8 g, 87%). LC-MS: 399.1 [M+H]$^+$.

Step 6: 4-((1H-pyrazol-1-yl)methyl)-N-((2,6-dimethoxyphenyl)sulfonyl)-3-methoxybenzamide To a solution of perfluorophenyl 4-((1H-pyrazol-1-yl)methyl)-3-methoxybenzoate (1 g, 2.551 mmol), and 2,6- dimethoxybenzenesulfonamide (Intermediate 22, 0.545 g, 2.511 mmol) in THF (30 mL) was added LiHMDS (7.51 mL, 7.53 mmol, 1.0 M in THF) and stirred at RT for 10 min. The reaction mixture was quenched with saturated NH$_4$Cl solution and extracted with ethyl acetate. The organic layer was dried over Na$_2$SO$_4$, filtered, and concentrated to afford the crude compound. The crude compound was purified by silica-gel flash column chromatography using 60-80% EtOAc in hexane as eluent to get the title compound which was again triturated in ethyl acetate to obtain the title compound (0.3 g, 28%). LC-MS: 432.2 [M+H]$^+$; $^1$H NMR (DMSO-D6, 400 MHz): δ 12.20 (s, 1H), 7.80 (s, 1H), 7.58 (s, 1H), 7.48 (d, 1H), 7.45 (dd, 2H), 6.85-6.75 (m, 3H), 6.28 (t, 1H), 5.34 (s, 2H), 3.92 (s, 3H), 3.78 (s, 6H).

Example 6. Compounds 2 to 65

The following compounds listed in Table 12 were prepared by following similar procedures as described above using appropriate reagents with suitable modifications known to the one skilled in the art. Intermediates and Example procedure for coupling are shown in the table below. Intermediates are commercially available if syntheses are not indicated.

TABLE 12

Compound Synthesis and Characterization

| Comp. No. | Structure | Intermediates/ Coupling example | LC-MS and $^1$H NMR (400 MHz, DMSO-d$_6$) unless otherwise shown |
|---|---|---|---|
| 2 | 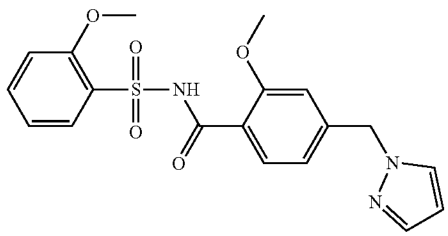 [SMILES: COc1cc(Cn2cccn2)ccc1C(=O)NS(=O)(=O)c1ccccc1OC] | Intermediate 1 & / Example 1 | LC-MS: 402.1 [M + H]$^+$; $^1$H NMR: δ 11.60 (s, 1H), 7.85-7.82 (m, 2H), 7.66-7.61 (m, 1H), 7.45 (d, 1H), 7.34 (d, 1H), 7.21 (d, 1H), 7.10 (t, 1H), 7.01 (s, 1H), 6.70 (d, 1H), 6.26 (t, 1H), 5.34 (s, 2H), 3.86 (s, 3H), 3.81 (s, 3H). |
| 3 | 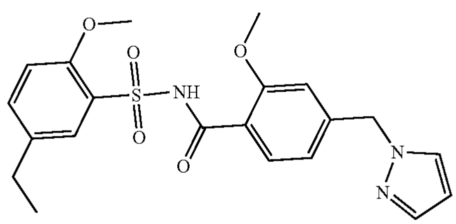 [SMILES: CCc1ccc(OC)c(S(=O)(=O)NC(=O)c2ccc(Cn3cccn3)cc2OC)c1] | Intermediate 1 & Intermediate 20/ Example 1 | LC-MS: 430.2 [M + H]$^+$; $^1$H NMR: δ 11.55 (1H), 7.83 (d, 1H), 7.65 (d, 1H), 7.48 (dd, 1H), 7.45 (d, 1H), 7.35 (d, 1H), 7.13 (d, 1H), 7.01 (s, 1H), 6.70 (d, 1H), 6.26 (t, 1H), 5.34 (s, 2H), 3.81 (s, 6H), 2.60 (q, 2H), 1.14 (t, 3H). |
| 4 | 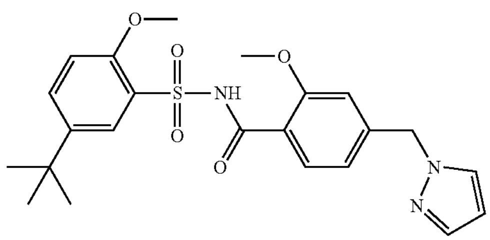 [SMILES: COc1cc(Cn2cccn2)ccc1C(=O)NS(=O)(=O)c1cc(C(C)(C)C)ccc1OC] | Intermediate 1 & Intermediate 21/ Example 1 | LC-MS: 458.3 [M + H]$^+$; $^1$H NMR (CD$_3$OD): δ 11.56 (s, 1H), 7.83 (d, 1H), 7.78 (d, 1H), 7.67 (dd, 1H), 7.45 (d, 1H), 7.36 (d, 1H), 7.14 (d, 1H), 7.01 (s, 1H), 6.70 (d, 1H), 6.26 (t, 1H), 5.34 (s, 2H), 3.83 (s, 3H), 3.81 (s, 3H), 1.26 (s, 9H). |
| 5 | 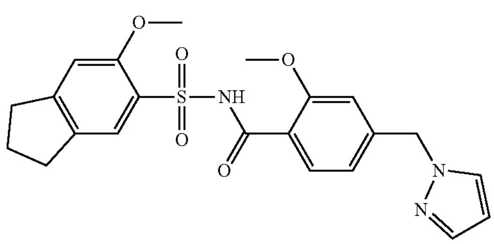 [SMILES: COc1cc(Cn2cccn2)ccc1C(=O)NS(=O)(=O)c1cc2c(cc1OC)CCC2] | Intermediate-1 & Intermediate-19/ Example 1 | LC-MS: 442.1 [M + H]$^+$; $^1$H NMR: δ 11.67 (s, 1H), 7.85 (dd, 1H), 7.68 (s, 1H), 7.48 (dd, 1H), 7.38 (d, 1H), 7.09 (s, 1H), 7.01 (s, 1H), 6.73 (dd, 1H), 6.29 (t, 1H), 5.36 (s, 2H), 3.82 (s, 6H), 2.91 (t, 2H), 2.86 (t, 2H), 2.09-2.01 (m, 2H). |
| 6 | 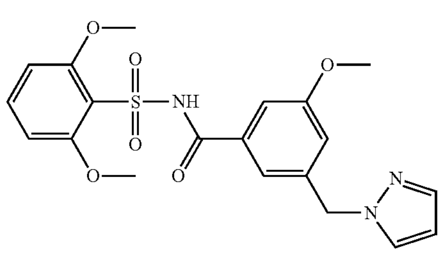 [SMILES: COc1cc(Cn2cccn2)cc(C(=O)NS(=O)(=O)c2c(OC)cccc2OC)c1] | Intermediate-3 & Intermediate 22/ Example 1 | LC-MS: 432.2 [M + H]$^+$; $^1$H NMR: δ 12.21 (s, 1H), 7.84 (dd, 1H), 7.52 (t, 1H), 7.47 (dd, 1H), 7.44 (dd, 1H), 7.31 (s, 1H), 6.99 (s, 1H), 6.79 (d, 2H), 6.28 (t, 1H), 5.34 (s, 2H), 3.81 (s, 3H), δ 3.77 (s, 6H). |

TABLE 12-continued

Compound Synthesis and Characterization

| Comp. No. | Structure | Intermediates/ Coupling example | LC-MS and $^1$H NMR (400 MHz, DMSO-d$_6$) unless otherwise shown |
|---|---|---|---|
| 7 | 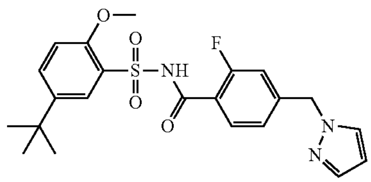 [SMILES: COc1ccc(C(C)(C)C)cc1S(=O)(=O)NC(=O)c1ccc(Cn2cccn2)cc1F] | Intermediate-4 & Intermediate 21/ Example 1 | LC-MS: 446.1 [M + H]$^+$; $^1$H NMR: δ 9.08 (dd, 1H), 8.42 (dd, 1H), 7.98 d, 1H), 7.61 (d, 1H), 7.51 (dd, 1H), 7.36 (d, 1H), 7.31-7.28 (m, 3H), 6.30 (t, 1H), 5.82 (s, 2H), 4.15 (s, 3H), 1.29 (s, 9H). |
| 8 | 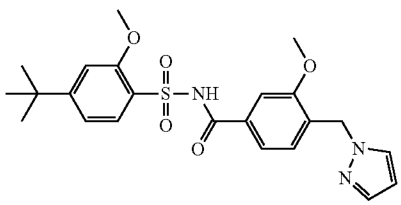 [SMILES: COc1cc(C(=O)NS(=O)(=O)c2ccc(C(C)(C)C)cc2OC)ccc1Cn1cccn1] | Intermediate 2 & Intermediate-17/ Example 1 | LC-MS: 458.2 [M + H]$^+$; $^1$H NMR: δ 12.46 (s, 1H), 7.86 (d, 1H), 7.79 (d, 1H), 7.69 (dd, 1H), 7.54 (d, 1H), 7.47 (d, 1H), 7.41 (dd, 1H), 7.14 (d, 1H), 6.77 (d, 1H), 6.28 (t, 1H), 5.33 (s, 2H), 3.90 (s, 3H), 3.83 (s, 3H), 1.30 (s, 9H). |
| 9 | 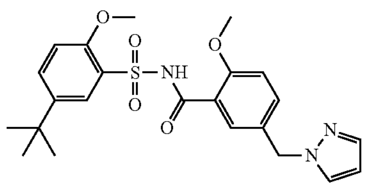 [SMILES: COc1ccc(Cn2cccn2)cc1C(=O)NS(=O)(=O)c1cc(C(C)(C)C)ccc1OC] | Intermediate-5 & Intermediate 21/ Example 1 | LC-MS: 458.0 [M + H]$^+$; $^1$H NMR: δ 11.66 (s,1H), 7.83 (d, 1H), 7.79 (d, 1H), 7.71 (dd, 1H), 7.44-7.41 (m, 2H), 7.35 (d, 1H), 7.19 (d, 1H), 7.14 (d, 1H), 6.24 (t, 1H), 5.27(s, 2H), 3.86 (d, 6H), 1.30 (s, 9H). |
| 10 | 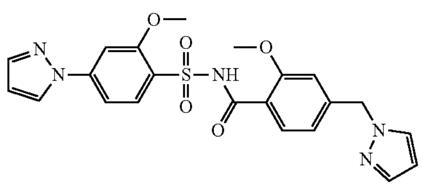 [SMILES: COc1cc(Cn2cccn2)ccc1C(=O)NS(=O)(=O)c1ccc(-n2cccn2)cc1OC] | Intermediate-1 & Intermediate-15/ Example 1 | LC-MS: 468.1 [M + H]$^+$; $^1$H NMR: δ 11.75 (s, 1H), 8.71 (d, 1H), 7.97 (d, 1H), 7.87-7.84 (m, 2H), 7.68-7.60 (m, 2H), 7.49 (s, 1H), 7.38 (d, 1H), 7.05 (s, 1H), 6.75 (d, 1H), 6.64 (s, 1H), 6.29 (s, 1H), 5.38 (s, 2H), 3.99 (s, 3H), 3.85 (s, 3H). |
| 11 | 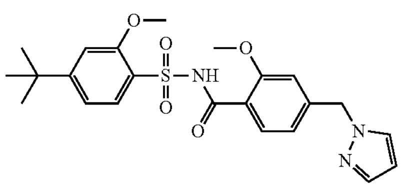 [SMILES: COc1cc(Cn2cccn2)ccc1C(=O)NS(=O)(=O)c1ccc(C(C)(C)C)cc1OC] | Intermediate-1 & Intermediate-17/ Example 1 | LC-MS: 458.1 [M + H]$^+$; $^1$H NMR: δ 11.52 (s, 1H), 7.86 (dd, 1H), 7.79 (d, 1H), 7.49 (d, 1H), 7.41 (d, 1H), 7.18-7.14 (m, 2H), 7.06 (s, 1H), 6.75 (dd, 1H), 6.30 (t, 1H), 5.38 (s, 2H), 3.92 (s, 3H), 3.86 (s, 3H), 1.32 (s, 9H). |
| 12 | 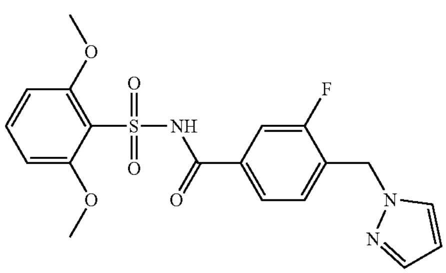 [SMILES: COc1cccc(OC)c1S(=O)(=O)NC(=O)c1ccc(Cn2cccn2)c(F)c1] | Intermediate-6 & Intermediate 22/ Example 1 | LC-MS: 420.0 [M + H]$^+$; $^1$H NMR: δ 12.30 (s, 1H), 7.87 (d, 1H), 7.76 (d, 1H), 7.71 (d, 1H), 7.54-7.49 (m, 2H), 7.14 (t, 1H), 6.78 (d, 2H), 6.30 (t, 1H), 5.46 (s, 2H), 3.77 (s, 6H). |
| 13 | 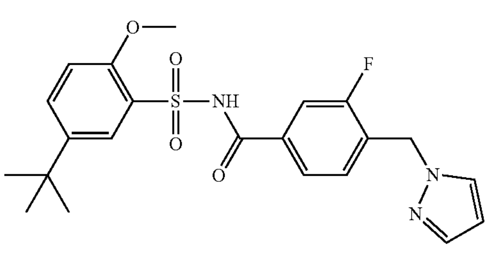 | Intermediate-6 & Intermediate 21/ Example 1 | LC-MS: 446.0 [M + H]$^+$; $^1$H NMR: δ 12.58 (s, 1H), 7.86-7.84 (m, 2H), 7.75-7.66 (m, 3H), 7.48 (d, 1H), 7.16-7.12 (m, 2H), 6.29 (t, 1H), 5.45 (s, 2H), 3.82 (s, 3H), 1.30 (s, 9H). |

TABLE 12-continued

Compound Synthesis and Characterization

| Comp. No. | Structure | Intermediates/ Coupling example | LC-MS and $^1$H NMR (400 MHz, DMSO-$d_6$) unless otherwise shown |
|---|---|---|---|
| 15 | 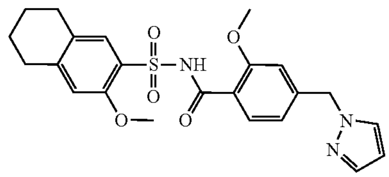 | Intermediate-1 & Intermediate-18/ Example 1 | LC-MS: 456.2 [M + H]$^+$; $^1$H NMR: δ 7.82 (d, 1H), 7.48-7.45 (m, 2H), 7.30 (d, 1H) 6.87 (s, 1H), 6.74 (s, 1H), 6.68 (d, 1H), 6.27 (t, 1H), 5.31 (s, 2H), 3.76 (s, 3H), 3.74 (s, 3H), 2.78-2.71 (m, 2H), 2.70-2.63 (m, 2H), 1.74-1.71(m, 4H). |
| 16 | 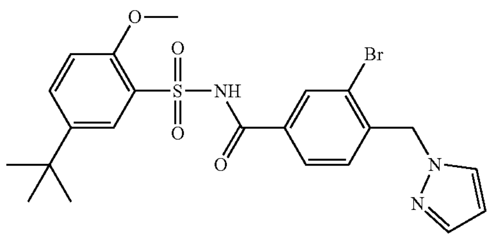 | Intermediate-7 & Intermediate 21/ Example 1 | LC-MS: 506.0 [M + H]$^+$; $^1$H NMR: δ 12.65 (s, 1H), 8.15 (d, 1H), 7.87 (d, 1H), 7.84 (d, 1H), 7.78 (dd, 1H), 7.54-7.52 (m, 2H), 7.08 (s, 1H), 6.79 (d, 1H), 6.33 (t, 1H), 5.45 (s, 2H), 3,76 (s, 3H), 1.29 (s, 9H). |
| 17 | 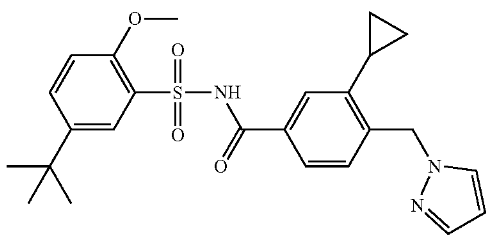 [SMILES: COc1ccc(C(C)(C)C)cc1S(=O)(=O)NC(=O)c1ccc(Cn2cccn2)c(C2CC2)c1] | Intermediate-11 & Intermediate 21/ Example 1 | LC-MS: 466.1 [M − H]$^-$; $^1$H NMR: δ 12.45 (s, 1H), 7.85 (d, 1H), 7.83 (d, 1H), 7.68 (brs, 1H), 7.60 (dd, 1H), 7.56 (d, 1H), 7.51 (d, 1H), 7.15 (brd, 1H), 6.80 (d, 1H), 6.31 (t, 1H), 5.58 (s, 2H), 3.81 (s, 3H), 2.10-2.04 (m, 1H), 1.30 (s, 9H), 0.99-0.94 (m, 2H), 0.79-0.70 (brm, 2H). |
| 18 | 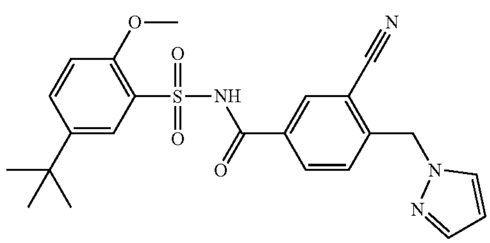 [SMILES: COc1ccc(C(C)(C)C)cc1S(=O)(=O)NC(=O)c1ccc(Cn2cccn2)c(C#N)c1] | Intermediate-13 & Intermediate 21/ Example 1 | LC-MS: 453.1 [M + H]$^+$; $^1$H NMR: δ12.7 (s, 1H), 8.33 (d, 1H), 8.05 (dd, 1H), 7.88 (d, 1H), 7.82 (d, 1H), 7.67 (dd, 1H), 7.48 (d, 1H), 7.17 (d, 1H), 7.12 (d, 1H), 6.30 (t, 1H), 5.58 (t, 2H), 3.79 (s, 3H), 1.27 (s, 9H). |
| 19 | 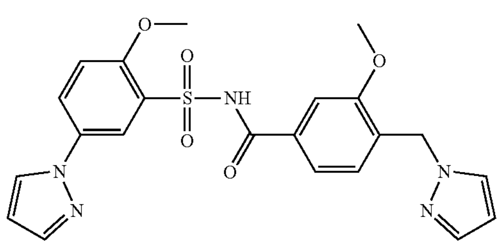 | Intermediate 2 & Intermediate-16/ Example 1 | LC-MS: 468.1 [M + H]$^+$; $^1$H NMR: δ 12.69 (s, 1H), 8.50 (brs, 1H), 8.32 (s, 1H), 8.03 (brs, 1H), 7.77-7.75 (m, 2H), 7.55 (s, 1H), 7.47 (dd, 1H), 7.42 (dd, 1H), 7.30 (brs, 1H), 6.78 (d, 1H), 6.56 (t, 1H), 6.28 (t, 1H), 5.32 (s, 2H), 3.89 (s, 3H), 3.86 (s, 3H). |
| 20 | 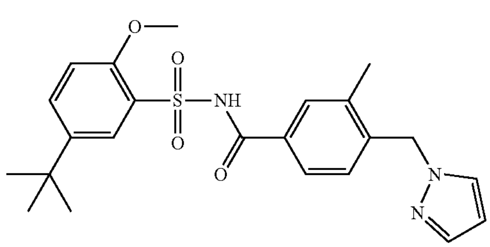 [SMILES: COc1ccc(C(C)(C)C)cc1S(=O)(=O)NC(=O)c1ccc(Cn2cccn2)c(C)c1] | Intermediate-12 & Intermediate 21/ Example 1 | LC-MS: 442.1[M + H]$^+$; $^1$H NMR: δ 12.37 (s, 1H), 7.86 (d, 1H), 7.79 (d, 1H), 7.73 (s, 1H), 7.67-7.64 (m, 2H), 7.50 (dd, 1H), 7.11 (d, 1H), 6.83 (d, 1H), 6.31 (t, 1H), 5.40 (s, 2H), 3.81 (s, 3H), 2.33 (s, 3H), 1.30 (s, 9H). |

TABLE 12-continued

Compound Synthesis and Characterization

| Comp. No. | Structure | Intermediates/ Coupling example | LC-MS and $^1$H NMR (400 MHz, DMSO-$d_6$) unless otherwise shown |
|---|---|---|---|
| 21 | 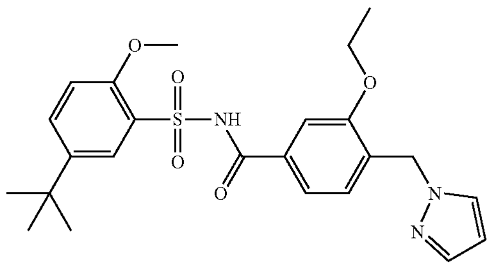 [SMILES: CCOc1cc(C(=O)NS(=O)(=O)c2cc(C(C)(C)C)ccc2OC)ccc1Cn1cccn1] | Intermediate-10 & Intermediate 21/ Example 1 | LC-MS: 472.05 [M + H]$^+$; $^1$H NMR: δ 12.44 (s, 1H), 7.86 (d, 1H), 7.78 (d, 1H), 7.68 (d, 1H), 7.54 (d, 1H), 7.47 (dd, 1H), 7.41 (dd, 1H), 7.14 (d, 1H), 6.84 (d, 1H), 6.29 (t, 1H), 5.33 (s, 2H), 4.16 (q, 2H), 3.82 (s, 3H), 1.38 (t, 3H), 1.31 (s, 9H). |
| 22 | 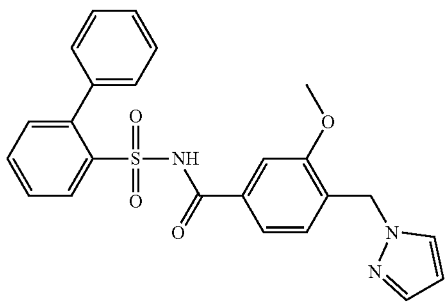 [SMILES: COc1cc(C(=O)NS(=O)(=O)c2ccccc2-c2ccccc2)ccc1Cn1cccn1] | Intermediate 2 & Intermediate 23/ Example 1 | LC-MS: 448.2 [M + H]$^+$; $^1$H NMR: δ 12.07 (s, 1H), 8.17 (dd, 1H), 7.78 (d, 1H), 7.77-7.61 (m, 2H), 7.48 (dd, 1H), 7.41-7.18 (m, 8H), 6.72 (d, 1H), 6.30 (t, 1H), 5.35 (s, 2H), 3.85 (s, 3H). |
| 23 | 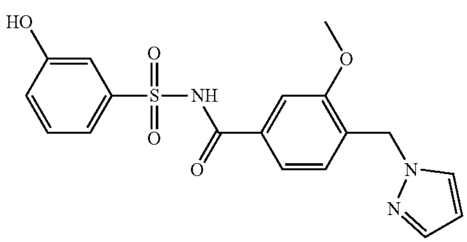 [SMILES: COc1cc(C(=O)NS(=O)(=O)c2cccc(O)c2)ccc1Cn1cccn1] | Intermediate 2 & Intermediate 24/ Example 1 | LC-MS: 388.0 [M + H]$^+$; $^1$H NMR: δ 12.50 (s, 1H), 10.21 (s, 1H), 7.77 (d, 1H), 7.45 (dd, 2H), 7.42-7.37 (m, 4H), 7.07-7.05 (m, 1H), 6.78 (d, 1H), 6.28 (t, 1H), 5.32 (s, 2H), 3.89 (s, 3H). |
| 24 | 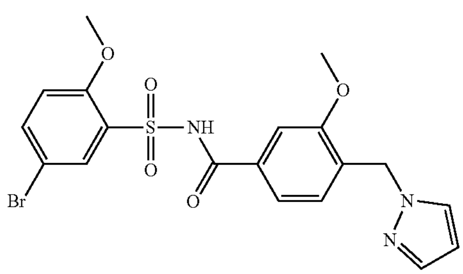 [SMILES: COc1cc(C(=O)NS(=O)(=O)c2cc(Br)ccc2OC)ccc1Cn1cccn1] | Intermediate 2 & Intermediate 25/ Example 1 | LC-MS: 480.0 [M + H]$^+$; $^1$H NMR: δ 12.75 (s, 1H), 8.14 (s, 1H), 7.93 (d, 1H), 7.77-7.76 (m, 1H), 7.53 (s, 1H), 7.47 (d, 1H), 7.43-7.42 (dd, 1H), 7.22-7.12 (m, 1H), 6.76 (d, 1H), 6.28 (t, 1H), 5.32 (s, 2H), 3.88 (s, 3H), 3.80 (s, 3H). |
| 25 | 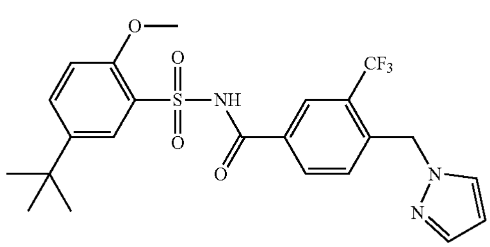 | Intermediate-14 & Intermediate 21/ Example 1 | LC-MS: 496.1[M + H]$^+$; $^1$H NMR: δ 12.79 (bs, 1H), 8.28 (s, 1H), 8.075 (d, 1H), 8.04 (s, 1H), 7.91 (d, 1H), 7.87 (d, 1H), 7.56 (dd, 1H), 7.17 (d, 1H), 6.87 (d, 1H), 6.37 (s, 1H), 5.61 (s, 2H), 3.83 (s, 3H), 1.30 (s, 9H). |

TABLE 12-continued

Compound Synthesis and Characterization

| Comp. No. | Structure | Intermediates/ Coupling example | LC-MS and ¹H NMR (400 MHz, DMSO-$d_6$) unless otherwise shown |
|---|---|---|---|
| 27 | 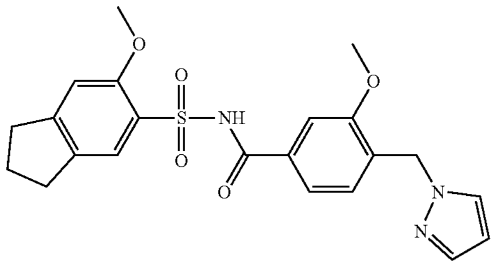 [SMILES: COc1cc(C(=O)NS(=O)(=O)c2cc3c(cc2OC)CCC3)ccc1Cn1cccn1] | Intermediate 2 & Intermediate-19/ Example 1 | LC-MS: 442.1 [M + H]⁺; ¹H NMR: δ 8.14 (s, 1H), 7.76 (d, 1H), 7.71 (s, 1H), 7.54 (d, 1H), 7.47 (dd, 1H), 7.38 (dd, 1H), 7.08(s, 1H), 6.76 (d, 1H), 6.28 (t, 1H), 5.32 (s, 2H), 3.90 (s, 3H), 3.80 (s, 3H), 2.92-2.84 (m, 4H), 2.09-2.01 (m, 2H) |
| 28 | 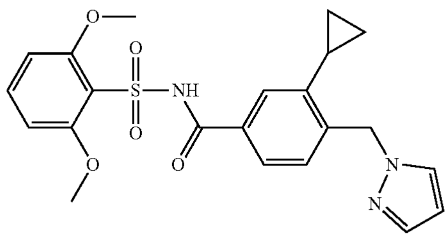 [SMILES: COc1cccc(OC)c1S(=O)(=O)NC(=O)c1ccc(Cn2cccn2)c(C2CC2)c1] | Intermediate-11 & Intermediate 22/ Example 1 | LC-MS: 442.1 [M + H]⁺; ¹H NMR: δ 12.18 (brs, 1H), 7.86 (dd, 1H), 7.64 (dd, 1H), 7.56 (d, 1H), 7.55-7.50 (m, 2H), 6.80-6.77 (m, 3H), 6.32 (d, 1H), 5.60 (s, 2H), 3.78 (s, 6H), 2.14-2.08 (m, 1H), 1.0-0.94 (m, 2H), 0.83-0.78 (m, 2H). |
| 29 | 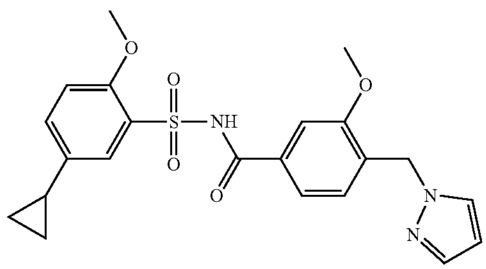 | Intermediate 2 & Intermediate 67/ Example 2 | LC-MS: 442.1 [M + H]⁺; ¹H NMR: δ 12.47 (s, 1H), 7.77 (d, 1H), 7.60 (s, 1H), 7.54 (d, 1H), 7.47 (d, 1H), 7.41 (dd, 1H), 7.25 (brs, 1H), 7.05 (brs, 1H), 6.77 (d, 1H), 6.28 (t, 1H), 5.32 (s, 2H), 3.89 (s, 3H), 3.77 (s, 3H), 2.10-1.92 (m, 1H), 0.98-0.93 (m, 2H), 0.64-0.60 (m, 2H). |
| 30 | 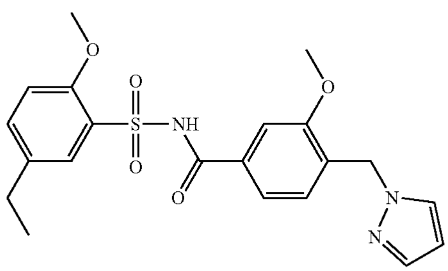 [SMILES: CCc1ccc(OC)c(S(=O)(=O)NC(=O)c2ccc(Cn3cccn3)c(OC)c2)c1] | Intermediate 2 & Intermediate 20/ Example 2 | LC-MS: 430.2 [M + H]⁺; ¹H NMR: δ 12.45 (s, 1H), 7.78 (d, 1H), 7.71 (s, 1H), 7.55-7.40 (m, 4H), 7.11 (brs, 1H), 6.77 (d, 1H), 6.29 (t, 1H), 5.33 (s, 2H), 3.90 (s, 3H), 3.80 (s, 3H), 2.64 (q, 2H), 1.19 (t, 3H). |
| 31 | 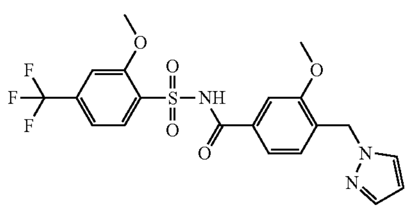 [SMILES: COc1cc(C(=O)NS(=O)(=O)c2ccc(C(F)(F)F)cc2OC)ccc1Cn1cccn1] | Intermediate 2 & [structure]/ Example 2 | LC-MS: 470.1 [M + H]⁺; ¹H NMR: δ 12.78 (brs, 1H), 8.12 (d, 1H), 7.78 (d, 1H), 7.56-7.51 (m, 3H), 7.48 (d, 1H), 7.42 (dd, 1H), 6.79 (d, 1H), 6.29 (t, 1H), 5.33 (s, 2H), 3.96 (s, 3H), 3.91 (s, 3H). |
| 32 | 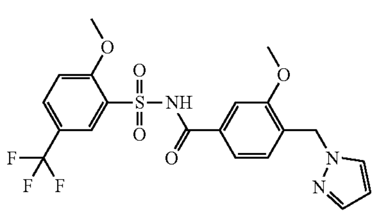 [SMILES: COc1cc(C(=O)NS(=O)(=O)c2cc(C(F)(F)F)ccc2OC)ccc1Cn1cccn1] | Intermediate 2 & [structure]/ Example 2 | LC-MS: 470.1 [M + H]⁺; ¹H NMR: δ 12.78 (s, 1H), 8.13 (d, 1H), 7.97 (brs, 1H), 7.76 (d, 1H), 7.53 (d, 1H), 7.47 (dd, 1H), 7.43 (d, 1H), 7.42 (d, 1H), 6.77 (d, 1H), 6.28 (t, 1H), 5.32 (s, 2H), 3.91 (s, 3H), 3.90 (s, 3H). |

TABLE 12-continued

Compound Synthesis and Characterization

| Comp. No. | Structure | Intermediates/ Coupling example | LC-MS and ¹H NMR (400 MHz, DMSO-$d_6$) unless otherwise shown |
|---|---|---|---|
| 33 | 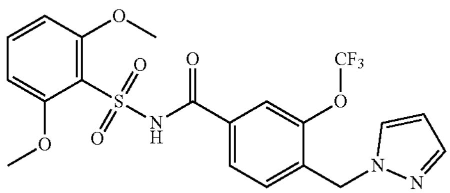 [SMILES: COc1cccc(OC)c1S(=O)(=O)NC(=O)c1ccc(Cn2cccn2)c(OC(F)(F)F)c1] | Intermediate 22 & Intermediate-31/ Example 2 | LC-MS: 486.1 [M + H]⁺. ¹H NMR: δ 12.62 (s, 1H), 7.85-7.81 (m, 3H), 7.50 (dd, 1H), 7.35-7.22 (m, 1H), 7.03 (d, 1H), 6.65 (d, 2H), 6.31 (dd, 1H), 5.44 (s, 2H), 3.66 (s, 6H). |
| 34 | 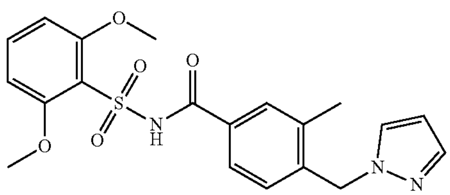 [SMILES: COc1cccc(OC)c1S(=O)(=O)NC(=O)c1ccc(Cn2cccn2)c(C)c1] | Intermediate 22 & Intermediate 12/ Example 1 | LCMS: 416.1 [M + H]⁺; ¹H NMR (CDCl₃): δ 7.68 (s, 1H), 7.61-7.59 (m, 2H), 7.46 (dd, 1H), 7.38 (d, 1H), 6.93 (d, 1H), 6.66 (d, 2H), 6.34 (dd, 1H), 5.37 (s, 2H), 3.93 (s, 6H), 2.33 (s, 3H). |
| 35 | 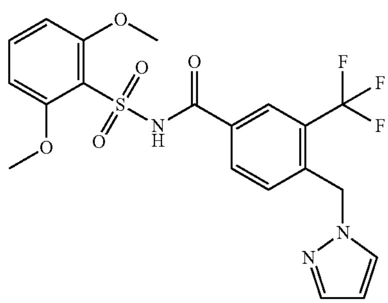 [SMILES: COc1cccc(OC)c1S(=O)(=O)NC(=O)c1ccc(Cn2cccn2)c(C(F)(F)F)c1] | Intermediate 22 & Intermediate 14/ Example 1 | LCMS: 470.0 [M + H]⁺; ¹H NMR (CDCl₃): δ 8.18 (s, 1H), 7.91 (d, 1H), 7.62 (d, 1H), 7.47 (d, 1H), 7.42 (dd, 1H), 6.87 (d, 1H), 6.63 (d, 2H), 6.38 (dd, 1H), 5.57 (s, 2H), 3.90 (s, 6H). |
| 36 | 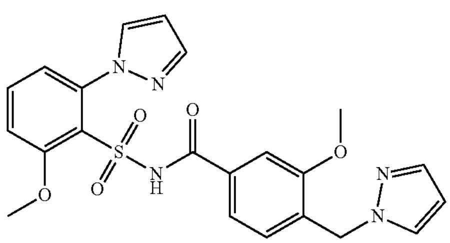 [SMILES: COc1cc(C(=O)NS(=O)(=O)c2c(OC)cccc2-n2cccn2)ccc1Cn1cccn1] | Intermediate 51 & Intermediate 2/ Example 1 | LC-MS: 468.2 [M + H]⁺; ¹H NMR: δ 7.87 (d, 1H), 7.79 (d, 1H), 7.49 (d, 1H), 7.38 (t, 1H), 7.28 (d, 1H), 7.25-7.22 (m, 2H), 7.08 (dd, 1H), 7.06 (dd, 1H), 7.02 (dd, 1H), 6.76 (d, 1H), 6.30 (dd, 1H), 5.33 (s, 2H), 3.86 (s, 3H), 3.62 (s, 3H). |
| 37 | 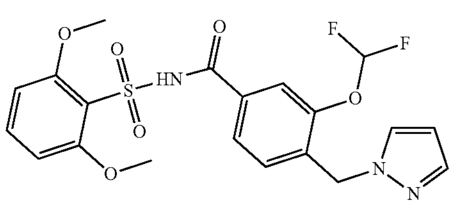 [SMILES: COc1cccc(OC)c1S(=O)(=O)NC(=O)c1ccc(Cn2cccn2)c(OC(F)F)c1] | Intermediate 22 & Intermediate 62/ Example 2 | LC-MS: 468.0 [M + H]⁺; ¹H NMR: δ 12.33 (brs, 1H), 7.83 (d, 1H), 7.73-7.12 (m, 2H), 7.52-7.48 (m, 1H), 7.33 (t, 1H), 6.97 (d, 1H), 6.82-6.73 (m, 2H), 6.32 (dd, 1H), 5.42 (s, 2H), 3.75 (s, 6H). |
| 38 | 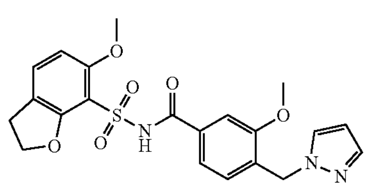 [SMILES: COc1cc(C(=O)NS(=O)(=O)c2c(OC)ccc3c2OCC3)ccc1Cn1cccn1] | Intermediate 50 & Intermediate 60/ Example 2 | LCMS: 444.1 [M + H]⁺; ¹H NMR: δ 12.28 (s, 1H), 7.79 (brs, 1H), 7.55 (s, 1H), 7.48 (d, 1H), 7.42 (dd, 1H), 7.40-7.34 (m, 1H), 6.78 (d, 1H), 6.56-6.54 (m, 1H), 6.29 (dd, 1H), 5.33 (s, 2H), 4.62 (t, 2H), 3.92 (s, 3H), 3.75 (s, 3H), 3.12 (t, 2H). |
| 39 | 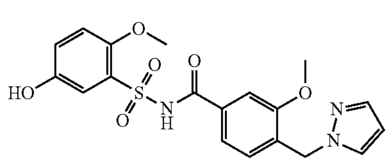 [SMILES: COc1cc(C(=O)NS(=O)(=O)c2cc(O)ccc2OC)ccc1Cn1cccn1] | & Intermediate 60/ Example 2 | LC-MS: 418.2 [M + H]⁺; ¹H NMR: δ 12.46 (brs, 1H), 9.60 (brs, 1H), 7.78 (d, 1H), 7.55 (d, 1H), 7.47 (d, 1H), 7.41 (dd, 1H), 7.33 (d, 1H), 7.04 (brs, 2H), 6.78 (d, 1H), 6.29 (dd, 1H), 5.33 (s, 2H), 3.91 (s, 3H), 3.75 (s, 3H). |

TABLE 12-continued

Compound Synthesis and Characterization

| Comp. No. | Structure | Intermediates/ Coupling example | LC-MS and ¹H NMR (400 MHz, DMSO-d₆) unless otherwise shown |
|---|---|---|---|
| 40 | 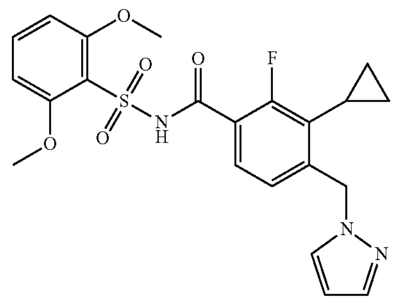 [SMILES: COc1cccc(OC)c1S(=O)(=O)NC(=O)c1ccc(Cn2cccn2)c(C2CC2)c1F] | Intermediate 22 & Intermediate 35/ Example 2 | LC-MS: 460.1 [M + H]⁺; ¹H NMR: δ 12.28 (s, 1H), 7.87 (d, 1H), 7.56-7.52 (m, 2H), 7.28 (dd, 1H), 6.81 (d, 2H), 6.52 (d, 1H), 6.33 (dd, 1H), 5.60 (s, 2H), 3.80 (s, 6H), 1.76-1.78 (m, 1H), 1.07-1.02 (m, 2H), 0.78-0.75 (m, 2H). |
| 41 | 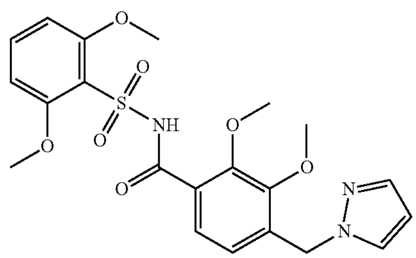 [SMILES: COc1cccc(OC)c1S(=O)(=O)NC(=O)c1ccc(Cn2cccn2)c(OC)c1OC] | Intermediate 22 & Intermediate 36/ Example 2 | LC-MS: 462.1 [M + H]⁺; ¹H NMR: δ 11.91 (s, 1H), 7.83 (dd, 1H), 7.54 (dd, 1H), 7.48 (dd, 1H), 7.10 (d, 1H), 6.81 (d, 2H), 6.70 (d, 1H), 6.30 (dd, 1H), 5.37 (s, 2H), 3.82 (s, 6H), 3.79 (s, 3H), 3.77 (s, 3H). |
| 42 | 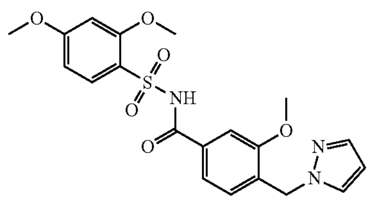 [SMILES: COc1ccc(S(=O)(=O)NC(=O)c2ccc(Cn3cccn3)c(OC)c2)c(OC)c1] | Intermediate 2 & Intermediate 26a/ Example 3 | LC-MS: 432.2 [M + H]⁺; ¹H NMR δ 12.35 (s, 1H), 7.85-7.81 (m, 1H), 7.78 (dd, J = 2.3, 0.7 Hz, 1H), 7.54 (d, J = 1.6 Hz, 1H), 7.47 (dd, J = 1.8, 0.7 Hz, 1H), 7.39 (dd, J = 7.8, 1.7 Hz, 1H), 6.78 (d, J = 7.9 Hz, 1H), 6.74-6.67 (m, 2H), 6.28 (t, J = 2.1 Hz, 1H), 5.33 (s, 2H), 3.91 (s, 3H), 3.85 (d, J = 2.2 Hz, 6H). |
| 43 | 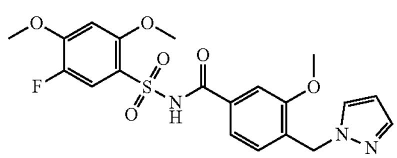 [SMILES: COc1cc(OC)c(S(=O)(=O)NC(=O)c2ccc(Cn3cccn3)c(OC)c2)cc1F] | Intermediate 2 & Intermediate 26b/ Example 1 | LC-MS: 450.2 [M + H]⁺; ¹H NMR δ 12.52 (s, 1H), 7.81-7.76 (m, 1H), 7.64 (d, J = 10.9 Hz, 1H), 7.55-7.51 (m, 1H), 7.47 (dd, J = 1.9, 0.7 Hz, 1H), 7.41 (dd, J = 7.9, 1.6 Hz, 1H), 6.93 (d, J = 6.8 Hz, 1H), 6.78 (d, J = 7.9 Hz, 1H), 6.29 (q, J = 2.0 Hz, 1H), 5.33 (s, 2H), 3.96 (s, 3H), 3.90 (d, J = 7.6 Hz, 6H). |
| 44 | 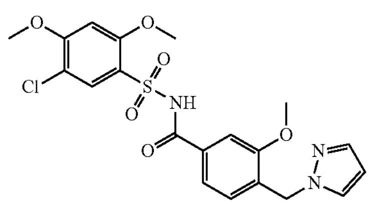 [SMILES: COc1cc(OC)c(S(=O)(=O)NC(=O)c2ccc(Cn3cccn3)c(OC)c2)cc1Cl] | Intermediate 2 & Intermediate 26c/ Example 1 | LC-MS: 466.2 [M + H]⁺. ¹H NMR δ 12.55 (s, 1H), 7.82-7.74 (m, 1H), 7.53 (d, J = 1.6 Hz, 1H), 7.41 (dd, J = 7.8, 1.6 Hz, 1H), 6.85 (s, 1H), 6.77 (d, J = 7.9 Hz, 1H), 6.52 (s, 1H), 6.27 (t, J = 2.0 Hz, 1H), 5.31 (s, 1H), 3.96 (s, 2H), 3.88 (d, J = 3.4 Hz, 3H), 3.32 (s, 6H). |
| 46 | 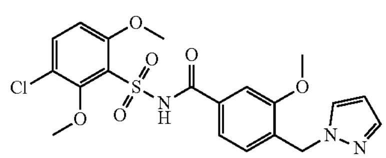 [SMILES: COc1cc(C(=O)NS(=O)(=O)c2c(OC)ccc(Cl)c2OC)ccc1Cn1cccn1] | Intermediate 2 & Intermediate 26e/ Example 3 | LC-MS: 466.3 [M + H]⁺; ¹H NMR δ 12.52 (s, 1H), 7.80 (d, J = 2.3 Hz, 1H), 7.74 (d, J = 9.0 Hz, 1H), 7.57 (d, J = 1.6 Hz, 1H), 7.50-7.42 (m, 1H), 7.03 (d, J = 9.2 Hz, 1H), 6.77 (d, J = 7.9 Hz, 1H), 6.29 (t, J = 2.1 Hz, 1H), 5.34 (s, 2H), 3.92 (d, J = 2.8 Hz, 6H), 3.79 (s, 3H). |
| 47 | 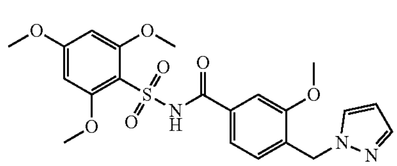 [SMILES: COc1cc(OC)c(S(=O)(=O)NC(=O)c2ccc(Cn3cccn3)c(OC)c2)c(OC)c1] | Intermediate 2 & Intermediate 26f/ Example 3 | LC-MS: 462.1 [M + H]⁺; ¹H NMR δ 12.07 (s, 1H), 7.79 (dd, J = 2.3, 0.7 Hz, 1H), 7.56 (d, J = 1.6 Hz, 1H), 7.47 (dd, J = 1.9, 0.7 Hz, 1H), 7.42 (dd, J = 7.9, 1.6 Hz, 1H), 6.76 (d, J = 7.9 Hz, 1H), 6.28 (q, J = 1.5 Hz, 3H), 5.33 (s, 2H), 3.91 (s, 3H), 3.83 (s, 3H), 3.77 (s, 6H). |

TABLE 12-continued

Compound Synthesis and Characterization

| Comp. No. | Structure | Intermediates/ Coupling example | LC-MS and $^1$H NMR (400 MHz, DMSO-$d_6$) unless otherwise shown |
|---|---|---|---|
| 48 | 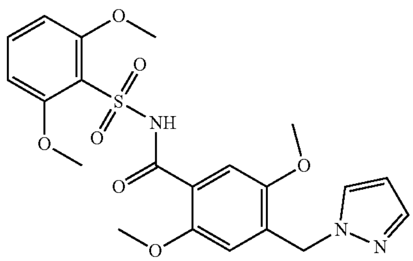 [SMILES: COc1cc(C(=O)NS(=O)(=O)c2c(OC)cccc2OC)c(OC)cc1Cn1cccn1] | Intermediate 22 & Intermediate 37/ Example 2 | LC-MS: 462.1 [M + H]$^+$; $^1$H NMR: δ 11.24 (s, 1H), 7.79 (d, 1H), 7.53 (dd, 1H), 7.49 (dd, 1H), 7.18 (s, 1H), 6.81 (d, 2H), 6.72 (s, 1H), 6.29 (dd, 1H), 5.33 (s, 2H), 3.81 (s, 6H), 3.80 (s, 3H), 3.78 (s, 3H). |
| 49 | 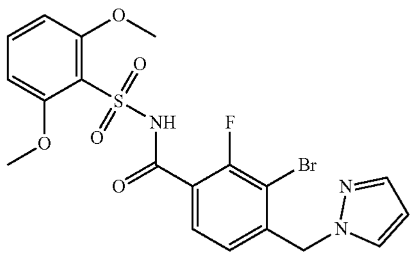 [SMILES: COc1cccc(OC)c1S(=O)(=O)NC(=O)c1ccc(Cn2cccn2)c(Br)c1F] | Intermediate 22 & Intermediate 39/ Example 1 | LC-MS: 498.1 [M + H]$^+$; $^1$H NMR: δ 12.45 (s, 1H), 7.90 (dd, 1H), 7.57-7.52 (m, 2H), 7.48 (dd, 1H), 6.81 (d, 2H), 6.62 (d, 1H), 6.35 (dd, 1H), 5.51 (s, 2H), 3.80 (s, 6H). |
| 50 | 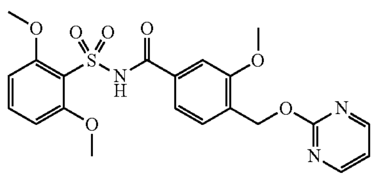 [SMILES: COc1cc(C(=O)NS(=O)(=O)c2c(OC)cccc2OC)ccc1COc1ncccn1] | Intermediate 70 & Intermediate 22/ Example 3 | LC-MS: 460.0 [M + H]$^+$. $^1$H NMR δ 12.23 (s, 1H), 8.63 (d, J = 4.8 Hz, 2H), 7.62-7.37 (m, 4H), 7.17 (t, J = 4.8 Hz, 1H), 6.79 (d, J = 8.5 Hz, 2H), 5.41 (s, 2H), 3.91 (s, 3H), 3.79 (s, 6H). |
| 52 | 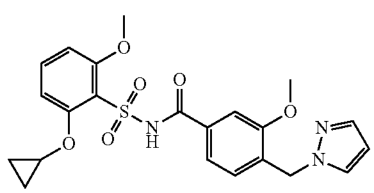 [SMILES: COc1cc(C(=O)NS(=O)(=O)c2c(OC)cccc2OC2CC2)ccc1Cn1cccn1] | & Intermediate 60/ Example 2 | LC-MS: 458.2 [M + H]$^+$; $^1$H NMR: δ 12.14 (brs, 1H), 7.80 (s, 1H), 7.61-7.49 (m, 3H), 7.44 (d, 1H), 7.06 (d, 1H), 6.81 (d, 1H), 6.76 (d, 1H), 6.30 (s, 1H), 5.35 (s, 2H), 3.92 (s, 4H), 3.79 (s, 3H), 0.72-0.65 (m, 2H), 0.58-0.52 (m, 2H). |
| 53 | 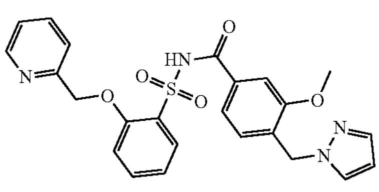 [SMILES: COc1cc(C(=O)NS(=O)(=O)c2ccccc2OCc2ccccn2)ccc1Cn1cccn1] | Intermediate 52 & Intermediate 60/ Example 2 | LC-MS: 479.1 [M + H]$^+$; $^1$H NMR: δ 8.45 (d, 1H), 7.93 (d, 1H), 7.75 (brs, 1H), 7.58-7.38 (m, 5H), 7.28-7.05 (m, 4H), 6.77 (d, 1H), 6.27 (dd, 1H), 5.34 (brs, 4H), 3.79 (s, 3H). |
| 54 | 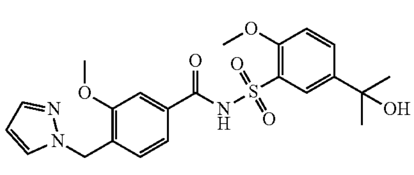 [SMILES: COc1cc(C(=O)NS(=O)(=O)c2cc(C(C)(C)O)ccc2OC)ccc1Cn1cccn1] | Intermediate 54 & Intermediate 60/ Example 2 | LC-MS: 458.1 [M − H]$^−$; $^1$H NMR: δ 12.46 (brs, 1H), 8.02 (brs, 1H), 7.79 (s, 1H), 7.73-7.64 (m, 1H), 7.55 (s, 1H), 7.47 (d, 1H), 7.42 (dd, 1H), 7.18-7.10 (m, 1H), 6.76 (d, 1H) 6.29 (dd, 1H), 5.33 (s, 2H), 5.23 (brs, 1H), 3.90 (s, 3H), 3.82 (s, 3H), 1.44 (s, 6H). |

TABLE 12-continued

Compound Synthesis and Characterization

| Comp. No. | Structure | Intermediates/ Coupling example | LC-MS and ¹H NMR (400 MHz, DMSO-$d_6$) unless otherwise shown |
|---|---|---|---|
| 55 | 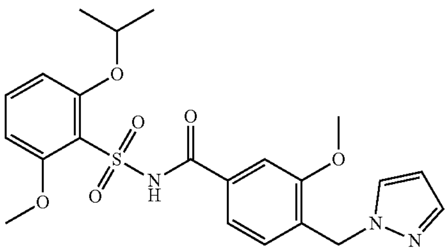 [SMILES: COc1cc(C(=O)NS(=O)(=O)c2c(OC)cccc2OC(C)C)ccc1Cn1cccn1] | Intermediate 55 & Intermediate 60/ Example 2 | LC-MS: 460.2 [M + H]⁺; ¹H NMR: δ 12.07 (brs, 1H), 7.80 (s, 1H), 7.63 (s, 1H), 7.49-7.46 (m, 3H), 6.80-6.73 (m, 3H), 6.30 (s, 1H), 5.35 (s, 2H), 4.76-4.64 (m, 1H), 3.92 (s, 3H), 3.78 (s, 3H), 1.18 (d, 6H). |
| 56 | 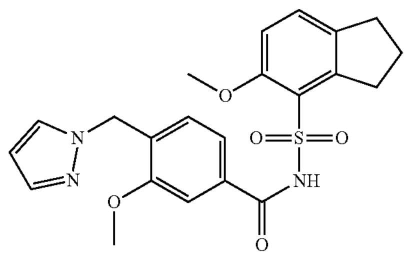 [SMILES: COc1cc(C(=O)NS(=O)(=O)c2c(OC)ccc3c2CCC3)ccc1Cn1cccn1] | Intermediate 56 & Intermediate 60/ Example 2 | LC-MS: 442.2 [M + H]⁺; ¹H NMR: δ 12.38 (s, 1H), 7.79 (d, 1H), 7.56 (d, 1H), 7.48-7.42 (m, 3H), 6.98 (d, 1H), 6.77 (d, 1H), 6.29 (dd, 1H), 5.33 (s, 2H), 3.91 (s, 3H) 3.79 (s, 3H), 3.31 (t, 2H), 2.85 (t, 2H), 2.08-1.98 (m, 2H). |
| 57 | 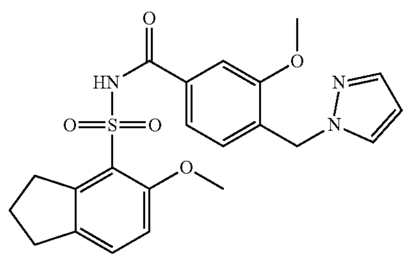 | Intermediate 57 & Intermediate 60/ Example 2 | LC-MS: 456.2 [M + H]⁺; ¹H NMR: δ 12.33 (s, 1H), 7.80 (d, 1H), 7.57 (d, 1H), 7.49 (d, 1H), 7.46 (dd, 1H), 7.31 (d, 1H), 7.0 (d, 1H), 6.77 (d, 1H), 6.29 (dd, 1H), 5.34 (s, 2H) 3.92 (s, 3H), 3.77 (s, 3H), 3.23 (t, 2H), 2.74 (t, 2H), 1.72-1.65 (m, 4H). |
| 58 | 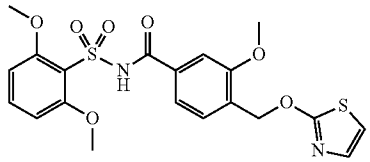 [SMILES: COc1cc(C(=O)NS(=O)(=O)c2c(OC)cccc2OC)ccc1COc1nccs1] | Intermediate 71 & Intermediate 22/ Example 3 | LC-MS: 465.0 [M + H]⁺. 1H NMR δ 12.25 (s, 1H), 7.60 (d, J = 1.4 Hz, 1H), 7.56-7.46 (m, 3H), 7.18 (d, J = 3.8 Hz, 1H), 7.07 (d, J = 3.8 Hz, 1H), 6.79 (d, J = 8.5 Hz, 2H), 5.45 (s, 2H), 3.91 (s, 3H), 3.78 (s, 6H). |
| 59 | 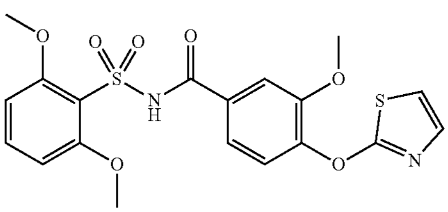 [SMILES: COc1cc(C(=O)NS(=O)(=O)c2c(OC)cccc2OC)ccc1Oc1nccs1] | Intermediate 72 & Intermediate 22/ Example 3 | MS: 451.0[M + H]⁺. ¹H NMR δ 12.28 (s, 1H), 7.76 (d, J = 2.0 Hz, 1H), 7.60-7.46 (m, 2H), 7.43 (d, J = 8.4 Hz, 1H), 7.21 (q, J = 3.7 Hz, 2H), 6.79 (d, J = 8.5 Hz, 2H), 3.85 (s, 3H), 3.80 (s, 6H). |
| 63 | 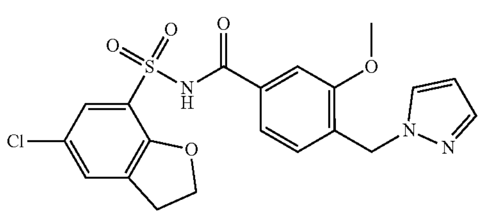 [SMILES: COc1cc(C(=O)NS(=O)(=O)c2cc(Cl)cc3c2OCC3)ccc1Cn1cccn1] | Intermediate 2 & Example 1 | LC-MS: 448.0 [M + H]⁺; ¹H NMR δ 7.75 (d, J = 2.3 Hz, 1H), 7.54-7.50 (m, 2H), 7.47-7.41 (m, 2H), 6.77 (d, J = 7.8 Hz, 1H), 6.53 (d, J = 3.0 Hz, 1H), 6.27 (t, J = 2.1 Hz, 1H), 5.31 (s, 2H), 4.60 (s, 2H), 3.87 (s, 3H), 3.19 (t, J = 8.9 Hz, 2H). |

TABLE 12-continued

Compound Synthesis and Characterization

| Comp. No. | Structure | Intermediates/ Coupling example | LC-MS and ¹H NMR (400 MHz, DMSO-d$_6$) unless otherwise shown |
|---|---|---|---|
| 64 | 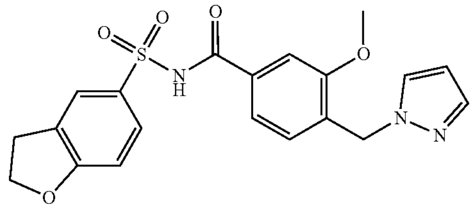 [SMILES: COc1cc(C(=O)NS(=O)(=O)c2ccc3c(c2)CCO3)ccc1Cn1cccn1] | Intermediate 2 & Example 1 | LC-MS: 414.1 [M + H]⁺; ¹H NMR δ 7.83 (d, J = 1.9 Hz, 1H), 7.77 (dt, J = 5.6, 2.4 Hz, 2H), 7.49 (dd, J = 12.7, 1.7 Hz, 2H), 7.41 (dd, J = 7.9, 1.7 Hz, 1H), 6.96 (d, J = 8.5 Hz, 1H), 6.79 (d, J = 7.9 Hz, 1H), 6.28 (t, J = 2.1 Hz, 1H), 5.33 (s, 2H), 4.66 (t, J = 8.8 Hz, 2H), 3.90 (s, 3H), 3.27 (t, J = 8.8 Hz, 2H). |
| 65 | 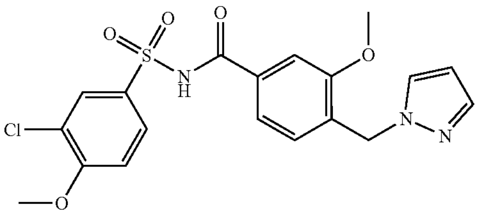 [SMILES: COc1ccc(S(=O)(=O)NC(=O)c2ccc(Cn3cccn3)c(OC)c2)cc1Cl] | Intermediate 2 & Example 1 | LC-MS: 436.0 [M + H]⁺; ¹H NMR δ 7.94 (d, J = 2.2 Hz, 1H), 7.90 (dd, J = 8.7, 2.3 Hz, 1H), 7.76 (dd, J = 2.2, 0.7 Hz, 1H), 7.50 (d, J = 1.6 Hz, 1H), 7.47 (dd, J = 1.9, 0.6 Hz, 1H), 7.41 (dd, J = 7.9, 1.6 Hz, 1H), 7.33 (d, J = 8.8 Hz, 1H), 6.78 (d, J = 7.9 Hz, 1H), 6.28 (t, J = 2.1 Hz, 1H), 5.32 (s, 2H), 3.95 (s, 3H), 3.88 (s, 3H). |

Example 7. Compound 201: 5-((1H-pyrazol-1-yl)methyl)-N-((5-(tert-butyl)-2-methoxyphenyl)sulfonyl)picolinamide

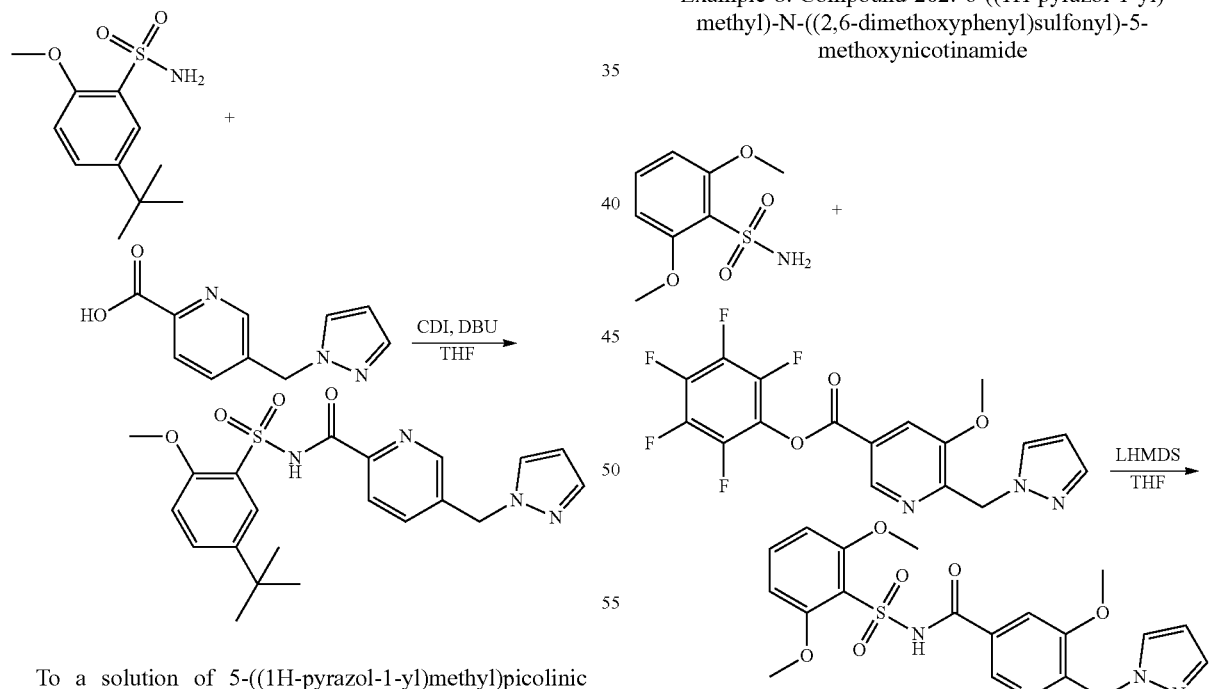

To a solution of 5-((1H-pyrazol-1-yl)methyl)picolinic acid (0.25 g, 1.229 mmol) in THF (5 mL) was added CDI (0.4 g, 2.46 mmol) and stirred at RT for 1 h. The reaction mixture was cooled to 0° C., were added 5-(tert-butyl)-2-methoxybenzenesulfonamide (Intermediate 17, 0.45 g, 1.84 mmol), DBU (0.75 g, 4.92 mmol) and stirred for 15 minutes at same temperature, then gradually warmed to RT and stirred for 12 h. The reaction mixture was concentrated to afford crude compound. The crude compound was purified by preparative HPLC to afford the title compound (0.03 g, 4%). LC-MS: 429.1 [M+H]⁺; ¹H NMR (DMSO-d$_6$, 400 MHz): δ11.71 (s, 1H), 8.57 (s, 1H), 7.95-7.91 (m, 2H), 7.87 (d, 1H), 7.74 (dd, 1H), 7.68 (d, 1H), 7.51 (dd, 1H), 7.12 (d, 1H), 6.31 (t, 1H), 5.51 (s, 2H), 3.78 (s, 3H), 1.29 (s, 9H).

Example 8. Compound 202: 6-((1H-pyrazol-1-yl)methyl)-N-((2,6-dimethoxyphenyl)sulfonyl)-5-methoxynicotinamide To a solution of perfluorophenyl 6-((1H-pyrazol-1-yl)methyl)-5-methoxynicotinate (0.12 g, 0.301 mmol), 2,6-dimethoxybenzenesulfonamide (Intermediate 22, 0.078 g, 0.361 mmol) in THF (4 mL) was added LiHMDS (1.0 M in THF solution) (1 mL, 1.2 mmol) and the entire reaction mixture was stirred at RT for 30 min. The reaction mixture was quenched with ice water followed by saturated NH$_4$Cl solution and extracted with ethyl acetate. The organic layer was dried over Na₂SO₄ and concentrated to afford the crude compound, which was further purified by preparative TLC and eluted at 80% ethyl acetate in hexane (0.01 g, 8%): LC-MS: 433.1 [M+H]⁺; ¹H NMR (DMSO-d₆, 400 MHz): δ 12.60 (s, 1H), 8.52 (s, 1H), 7.82 (br s, 1H), 7.72 (s, 1H), 7.38 (d, 1H), 7.33 (br s, 1H), 6.70 (br m, 2H), 6.23 (t, 1H), 5.42 (s, 2H), 3.89 (s, 3H), 3.70 (s, 6H).

Example 9. Compound 203: 5-((1H-pyrazol-1-yl)methyl)-N-((2,6-dimethoxyphenyl)sulfonyl)-6-methoxypicolinamide

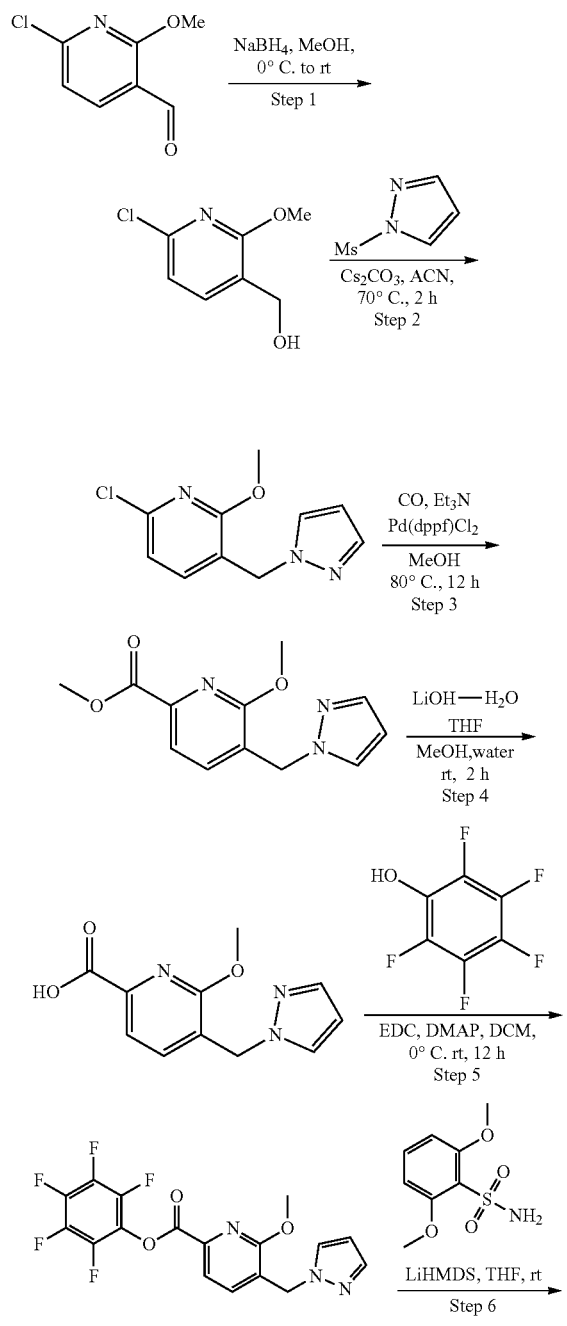

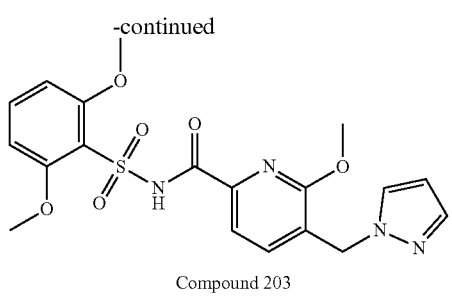

Compound 203

Step 1: (6-Chloro-2-methoxypyridin-3-yl)methanol

To a solution of 6-chloro-2-methoxynicotinaldehyde (10 g, 87.42 mmol), in MeOH (200 mL) was added NaBH₄ (13.3 g, 349.7 mmol) at 0° C. and stirred at RT for 2 h. The reaction mixture was quenched with ice water and extracted with ethyl acetate. The organic layer was dried over anhydrous Na₂SO₄, filtered, and concentrated to obtain the title compound (9.5 g, 94%). LC-MS: 174.0 [M+H]⁺.

Step 2: 3-((1H-pyrazol-1-yl)methyl)-6-chloro-2-methoxypyridine

To a solution of 6-chloro-2-methoxypyridin-3-yl)methanol (16 g, 92.16 mmol), and 1-(methylsulfonyl)-1H-pyrazole (16.16, 110.6 mmol) in acetonitrile (150 mL) was added Cs₂CO₃ (60 g, 325.82 mmol) and stirred at 70° C. for 2 h. The reaction mixture was quenched with ice water and extracted with ethyl acetate. The organic layer was dried over Na₂SO₄, filtered, and concentrated to afford the crude compound, which was further purified by silica-gel flash column chromatography using 20-30% ethyl acetate in hexane as eluent to obtain the title compound (20 g, 95.8%). LC-MS: 224.1 [M+H]⁺.

Step 3: Methyl 5-((1H-pyrazol-1-yl)methyl)-6-methoxypicolinate

To a degassed solution of 3-((1H-pyrazol-1-yl)methyl)-6-chloro-2-methoxypyridine (20 g, 89.42 mmol), and Et₃N (37.8 mL, 268.26 mmol) in methanol (400 mL) was added Pd(dppf)Cl₂-DCM (7.32 g, 8.94 mmol). The reaction mixture was heated to 80° C. in autoclave with 80 PSI pressure of carbon monoxide for 16 h. The reaction mixture was cooled to RT, filtered through a pad of celite and concentrated to get the crude compound. The crude compound was further purified by silica-gel flash column chromatography using 30-50% ethyl acetate in hexane as eluent to obtain the title compound (16 g, 72.37%). LC-MS: 248.0 [M+H]⁺.

Step 4: 5-((1H-pyrazol-1-yl)methyl)-6-methoxypicolinic acid

To a stirred solution of methyl 5-((1H-pyrazol-1-yl)methyl)-6-methoxypicolinate (5 g, 20.22 mmol) in THF (40 mL), Methanol (20 mL) and water (20 mL) was added LiOH·H₂O (3.4 g, 41.96 mmol) and stirred for 12 h at room temperature. Reaction mixture was diluted with ice-cold water, adjusted pH to 4 using aqueous citric acid solution to obtain a precipitate. The precipitate was filtered, washed with water, and dried under vacuum to obtain the title compound (4.5 g, 95.5%): LC-MS: 234.1[M+H]⁺.

Step 5: Perfluorophenyl 5-((1H-pyrazol-1-yl)methyl)-6-methoxypicolinate

To a solution of 5-((1H-pyrazol-1-yl)methyl)-6-methoxypicolinic acid (1.0 g, 4.28 mmol), 2,3,4,5,6-pentafluorophenol (0.947 g, 5.144 mmol) in DCM (20 mL) was added DMAP (0.106 g, 0.85 mmol) and followed by EDC-HCl (1.65 g, 8.57 mmol) at 0° C. and stirred at RT for 12 h. The reaction mixture was quenched with ice water and extracted with DCM. The organic layer was dried over $Na_2SO_4$, filtered, and concentrated to afford the crude compound. The crude compound was purified by silica-gel flash column chromatography using 15-30% ethyl acetate in hexane as eluent to obtain the title compound (1.5 g, 87.6%). LC-MS: 400.0 $[M+H]^+$.

Step 6: 5-((1H-pyrazol-1-yl)methyl)-N-((2,6-dimethoxyphenyl)sulfonyl)-6-methoxypicolinamide To a solution of perfluorophenyl 5-((1H-pyrazol-1-yl)methyl)-6-methoxypicolinate (0.6 g, 1.50 mmol), and 2,6-dimethoxybenzenesulfonamide (Intermediate 22, 0.327 g, 1.50 mmol) in THF (20 mL) was added LiHMDS (1.5 mL, 1.50 mmol, 1.0 M in THF) and stirred at RT for 10 min. The reaction mixture was quenched with ice water followed by saturated $NH_4Cl$ solution and extracted with 10% MeOH in DCM. The organic layer was dried over $Na_2SO_4$, filtered, and concentrated to afford the crude compound. The crude compound was further purified by silica gel flash column chromatography using 2-5% MeOH in DCM as eluent to obtain the crude compound. The crude compound was again triturated in ethyl acetate to obtain the pure title compound (0.2 g, 30.8%): LC-MS: 433.2 $[M+H]^+$; $^1$H NMR (DMSO-$d_6$, 400 MHz): δ 11.56 (s, 1H), 7.85 (dd, 1H), 7.55-7.48 (m, 3H), 7.20 (d, 1H), 6.78 (d, 2H), 6.32 (dd, 1H), 5.36 (s, 2H), 4.11 (s, 3H), 3.77 (s, 6H).

Example 10. Compound 224: 5-((1H-pyrazol-1-yl)methyl)-6-methoxy-N-((2,4,6-trimethoxyphenyl)sulfonyl)picolinamide

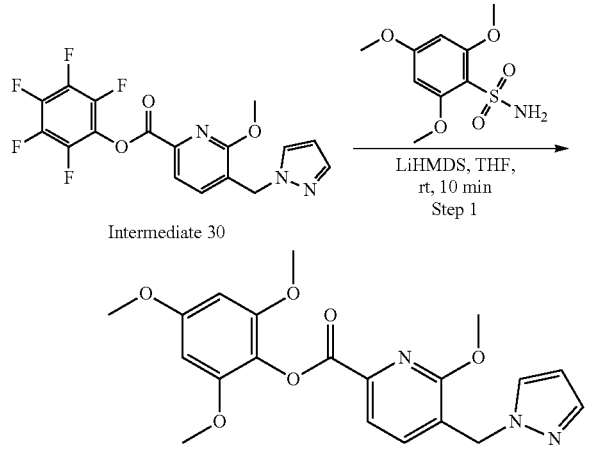

Compound 224

Step 1: 5-((1H-pyrazol-1-yl)methyl)-6-methoxy-N-((2,4,6-trimethoxyphenyl)sulfonyl)picolinamide To a solution of perfluorophenyl 5-((1H-pyrazol-1-yl)methyl)-6-methoxypicolinate (1.25 g, 3.15 mmol) and 2,4,6-trimethoxybenzenesulfonamide (commercial, 0.6 g, 2.43 mmol) in THF (40 mL) was added LiHMDS (2.5 mL, 2.43 mmol, 1.0 M in THF) and stirred at RT for 10 min. The reaction mixture was quenched with ice water followed by saturated $NH_4Cl$ solution and extracted with 10% MeOH in DCM. The organic layer was dried over $Na_2SO_4$, filtered, and concentrated to afford the crude compound. The crude compound was further purified by silica gel flash column chromatography using 2-5% MeOH in DCM as eluent and triturated in ethyl acetate to obtain the title compound (0.38 g, 34%): LC-MS: 461.1 $[M-H]^-$; $^1$H NMR (DMSO-$d_6$, 400 MHz): δ 11.51 (s, 1H), 7.83 (dd, 1H), 7.54-7.50 (m, 2H), 7.19 (d, 1H), 6.31 (dd, 1H), 6.27 (s, 2H), 5.35 (s, 2H), 4.07 (s, 3H), 3.82 (s, 3H), 3.76 (s, 6H).

Example 11. Compound 264: 5-((1H-pyrazol-1-yl)methyl)-N-((5-(tert-butyl)-2-methoxyphenyl)sulfonyl)-4-methoxypyrimidine-2-carboxamide

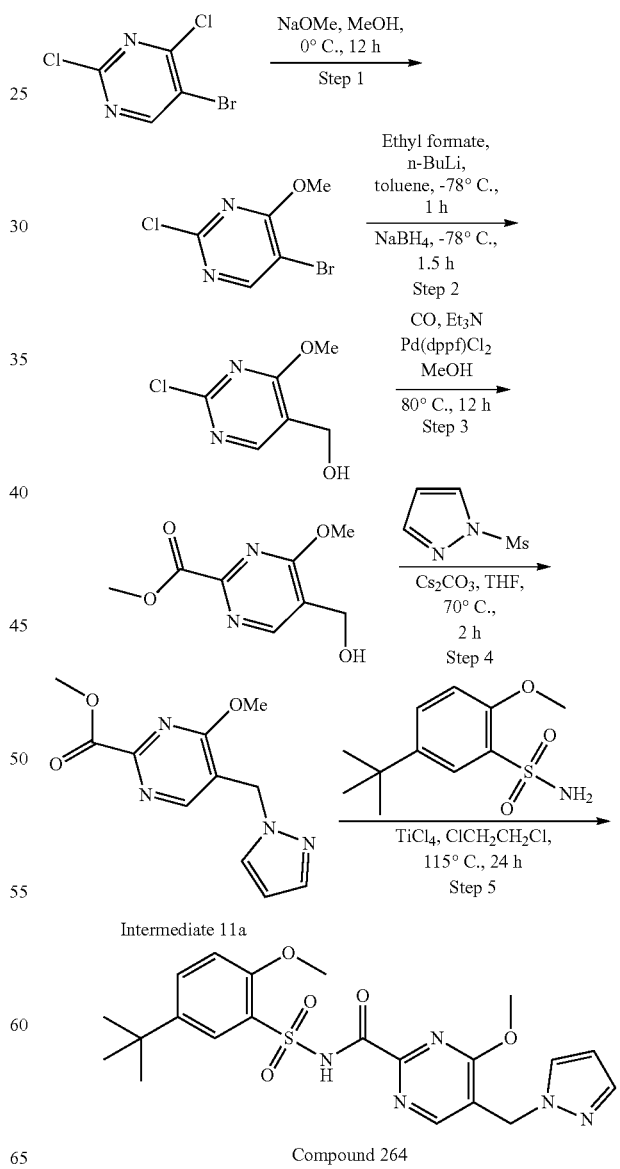

Compound 264

Step 1: 5-Bromo-2-chloro-4-methoxypyrimidine

To a solution of 5-bromo-2,4-dichloropyrimidine (10 g, 43.88 mmol) in MeOH (100 mL) was added NaOMe (7.7 mL, 43.88 mmol, 25% in MeOH) at 0° C. and stirred at same temperature for 2 h. The reaction was quenched with ice-water and evaporated the MeOH completely to obtain a precipitate. The precipitate was filtered and washed with water to obtain title compound (10 g). LC-MS: 224.9 [M+H]$^+$.

Step 2: (2-Chloro-4-methoxypyrimidin-5-yl)methanol

To a solution of 5-bromo-2-chloro-4-methoxypyrimidine (10 g, 44.75 mmol) in toluene (150 mL) was added n-BuLi (29.3 mL, 46.99 mmol, 1.6 M in hexane) at −78° C. and stirred at the same temperature for 30 min. Ethyl formate (3.98 g, 53.7 mmol) was added to the reaction mixture at −78° C. and stirred for 30 min. The reaction mixture was diluted with MeOH (20 mL) and NaBH$_4$ (2.03 g, 37.84 mmol) was added to it at −78° C. and stirred at same temperature for 15 min. The reaction was quenched with ice water and extracted with ethyl acetate. The organic layer was dried over sodium sulphate, filtered, and concentrated to afford the crude material. Crude compound was purified by silica-gel flash column chromatography using 40% ethyl acetate in hexane as eluent to afford the title compound (4 g, 51.2%). LC-MS: 175.1 [M+H]$^+$.

Step 3: Methyl 5-(hydroxymethyl)-4-methoxypyrimidine-2-carboxylate

The title compound was prepared using similar procedure to that described in Step 3 of Intermediate 28 using appropriate reagents with suitable modifications. LC-MS: 199.1 [M+H]$^+$.

Step 4: Methyl 5-((1H-pyrazol-1-yl)methyl)-4-methoxypyrimidine-2-carboxylate The title compound was prepared using similar procedure to that described in Step 2 of Intermediate 29 using appropriate reagents with suitable modifications. LC-MS: 249.1 [M+H]$^+$.

Step 5: 5-((1H-pyrazol-1-yl)methyl)-N-((5-(tert-butyl)-2-methoxyphenyl)sulfonyl)-4-methoxypyrimidine-2-carboxamide To a solution of methyl 5-((1H-pyrazol-1-yl)methyl)-4-methoxypyrimidine-2-carboxylate (0.2 g, 0.806 mmol), and 5-(tert-butyl)-2-methoxybenzenesulfonamide (Intermediate 17, 0.098 g, 0.403 mmol) in DCE (5 mL) was added titanium(IV) chloride (0.07 mL, 0.6 mmol) at 50° C. and then stirred at 115° C. for 16 h. The reaction was cooled to RT and extracted with 10% MeOH in DCM. The organic layer was dried over sodium sulphate, filtered, and concentrated to afford the crude compound. Crude compound was purified by preparative HPLC to obtain the title compound: LC-MS: 460.1 [M+H]$^+$; $^1$H NMR (CD$_3$OD, 400 MHz): δ 8.19 (s, 1H), 8.08 (d, 1H), 7.80 (d, 1H), 7.73 (dd, 10H), 7.57 (d, 1H), 7.13 (d, 1H), 6.38 (dd, 1H), 5.41 (s, 2H), 4.14 (s, 3H), 3.89 (s, 3H), 1.38 (s, 9H).

Example 12. Compounds 204 to 231, 235, 236, 239 to 241, 245 and 253

The following compounds listed in Table 13 were prepared by following a similar procedure as described above using appropriate reagents with suitable modifications known to the one skilled in the art. Intermediates and Example procedure for coupling are shown in the table below. Intermediates are commercially available if syntheses are not indicated.

TABLE 13

Compound Synthesis and Characterization

| Comp. No. | Structure | Intermediates/ Coupling example | LC-MS and $^1$H NMR (400 MHz, DMSO-d$_6$) unless otherwise shown |
|---|---|---|---|
| 204 | 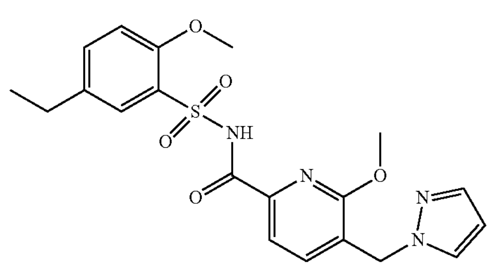 [SMILES: CCc1ccc(OC)c(S(=O)(=O)NC(=O)c2ccc(Cn3cccn3)c(OC)n2)c1] | Intermediate 20 & Intermediate 30/ Example 8 | LCMS: 431.1[M + H]$^+$; $^1$H NMR δ 11.69 (s, 1H), 7.84 (d, 1H), 7.73 (d, 1H), 7.52-7.60 (m, 3H), 7.20 (dd, 1H), 7.16 (d, 1H), 6.31 (dd, 1H), 5.36 (s, 2H), 4.13 (s, 3H), 3.82 (s, 3H), 2.68-2.61 (m, 2H), 1.19 (t, 3H). |
| 205 | 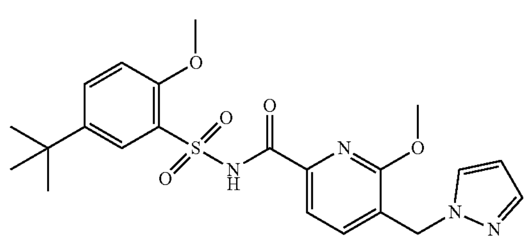 [SMILES: COc1ccc(C(C)(C)C)cc1S(=O)(=O)NC(=O)c1ccc(Cn2cccn2)c(OC)n1] | Intermediate 21 & Intermediate 30 Example 8 | LC-MS: 459.2 [M + H]$^+$; $^1$H NMR δ 11.74 (brs, 1H), 7.87 (d, 1H), 7.85 (d, 1H), 7.71 (dd, 1H), 7.51 (d, 1H), 7.21-7.15 (m, 2H), 7.17 (d, 1H), 6.31 (dd, 1H), 5.36 (s, 2H), 4.13 (s, 3H), 3.83 (s, 3H), 1.30 (s, 9H). |

TABLE 13-continued

Compound Synthesis and Characterization

| Comp. No. | Structure | Intermediates/ Coupling example | LC-MS and $^1$H NMR (400 MHz, DMSO-$d_6$) unless otherwise shown |
|---|---|---|---|
| 206 | 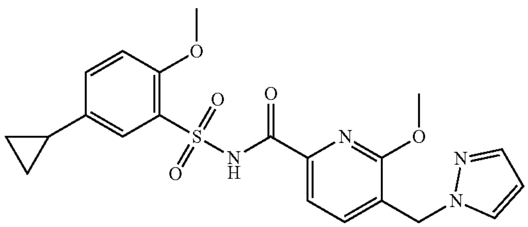 [SMILES: COc1ccc(C2CC2)cc1S(=O)(=O)NC(=O)c1ccc(Cn2cccn2)c(OC)n1] | Intermediate 67 & Intermediate 30/ Example 8 | LC-MS: 443.4 [M + H]$^+$; $^1$H NMR δ 11.76 (s, 1H), 7.84 (dd, 1H), 7.63 (d, 1H), 7.51-7.49 (m, 2H), 7.34 (dd, 1H), 7.20 (d, 1H), 7.12 (d, 1H), 6.31 (dd, 1H), 5.36 (s, 2H), 4.13 (s, 3H), 3.80 (s, 3H), 2.06-1.97 (m, 1H), 0.99-0.95 (m, 2H), 0.68-0.62 (m, 2H). |
| 207 | 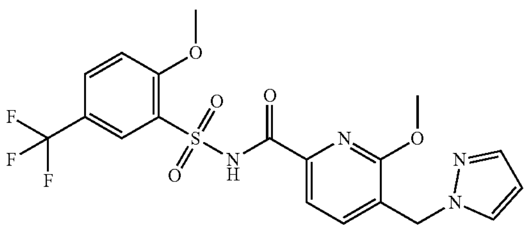 [SMILES: COc1ccc(C(F)(F)F)cc1S(=O)(=O)NC(=O)c1ccc(Cn2cccn2)c(OC)n1] | & Intermediate 30/ Example 8 | LC-MS: 471.1 [M + H]$^+$; $^1$H NMR δ 12.30 (s, 1H), 8.14 (d, 1H), 8.09 (dd, 1H), 7.84 (dd, 1H), 7.51-7.45 (m, 3H), 7.19 (d, 1H), 6.31 (dd, 1H), 5.36 (s, 2H), 4.14 (s, 3H), 3.96 (s, 3H). |
| 208 | 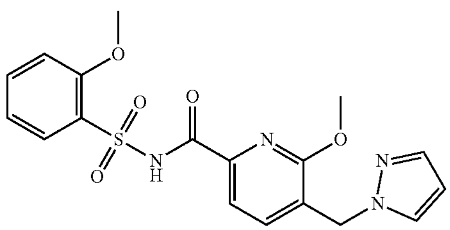 [SMILES: COc1ccccc1S(=O)(=O)NC(=O)c1ccc(Cn2cccn2)c(OC)n1] | & Intermediate 30/ Example 8 | LC-MS: 403.1 [M + H]$^+$; $^1$H NMR δ 11.75 (s, 1H), 7.92 (dd, 1H), 7.84 (d, 1H), 7.71-7.66 (m, 1H), 7.51-7.49 (m, 2H), 7.25-7.14 (m, 3H), 6.31 (dd, 1H), 5.36 (s, 2H), 4.14 (s, 3H), 3.86 (s, 3H). |
| 209 | 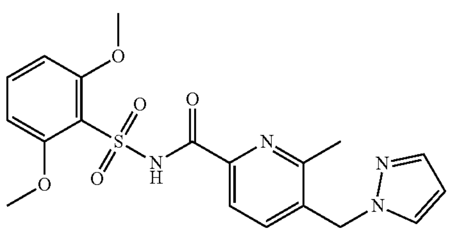 [SMILES: COc1cccc(OC)c1S(=O)(=O)NC(=O)c1ccc(Cn2cccn2)c(C)n1] | Intermediate 22 & Intermediate 40/ Example 8 | LC-MS: 417.1 [M + H]$^+$; $^1$H NMR (DMSO-$d_6$, 400 MHz): δ 11.23 (brs, 1H), 7.87 (dd, 1H), 7.80 (d, 1H), 7.56-7.51 (m, 2H), 7.29 (d, 1H), 6.80 (d, 2H), 6.34 (dd, 1H), 5.53 (s, 2H), 3.78 (s, 6H), 2.64 (s, 3H). |
| 210 | 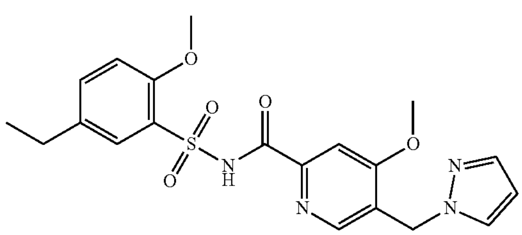 [SMILES: CCc1ccc(OC)c(S(=O)(=O)NC(=O)c2cc(OC)c(Cn3cccn3)cn2)c1] | Intermediate 20 & Intermediate 41/ Example 7 | LC-MS: 431.3 [M + H]$^+$; $^1$H NMR δ 8.07-(brs, 1H), 7.81 (d, 1H), 7.71 (s, 1H), 7.59 (s, 1H), 7.47 (d, 1H), 7.45-7.38 (brm, 1H), 7.11-7.03 (brm, 1H), 6.28 (dd, 1H), 5.36 (s, 2H), 3.94 (s, 3H), 3.75 (s, 3H), 2.62 (q, 2H), 1.18 (t, 3H). |
| 211 | 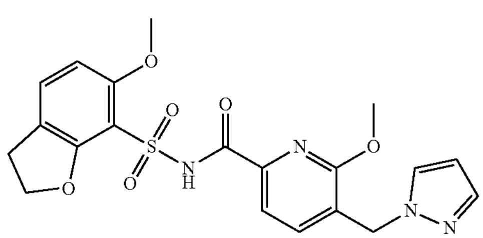 [SMILES: COc1ccc2c(c1S(=O)(=O)NC(=O)c1ccc(Cn3cccn3)c(OC)n1)OCC2] | Intermediate 50 & Intermediate 30/ Example 8 | LCMS: 445.2 [M + H]$^+$; $^1$H NMR δ 11.58 (brs, 1H), 7.83 (d, 1H), 7.54-7.50 (m, 2H), 7.31 (d, 1H), 7.19 (d, 1H), 6.52 (d, 1H), 6.31 (dd, 1H), 5.34 (s, 2H), 4.59 (t, 2H), 4.05 (s, 3H), 3.71 (s, 3H), 3.11 (t, 2H). |

TABLE 13-continued

Compound Synthesis and Characterization

| Comp. No. | Structure | Intermediates/ Coupling example | LC-MS and ¹H NMR (400 MHz, DMSO-d$_6$) unless otherwise shown |
|---|---|---|---|
| 212 | 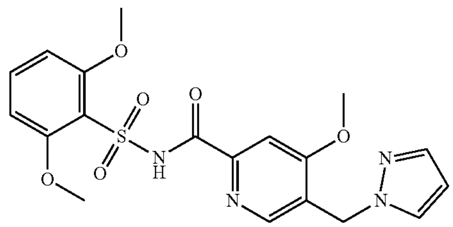 [SMILES: COc1cc(C(=O)NS(=O)(=O)c2c(OC)cccc2OC)ncc1Cn1cccn1] | Intermediate 22 & Intermediate 41/ Example 7 | LCMS: 433.1 [M + H]$^+$; ¹H NMR δ 8.42 (s, 1H), 7.79 (d, 1H), 7.65 (s, 1H), 7.46 (d, 1H), 7.26 (dd, 1H), 6.70 (d, 1H), 6.63 (d, 1H), 6.27 (dd, 1H), 5.33 (s, 2H), 3.94 (s, 3H), 3.67 (s, 6H). |
| 213 | 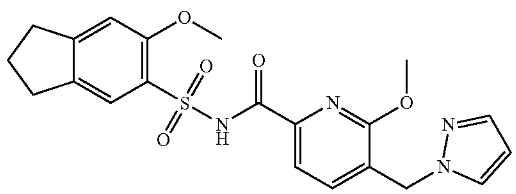 [SMILES: COc1cc2c(cc1S(=O)(=O)NC(=O)c1ccc(Cn3cccn3)c(OC)n1)CCC2] | Intermediate 19 & Intermediate 30/ Example 8 | LC-MS: 443.1 [M + H]$^+$; ¹H NMR δ 11.56 (s, 1H), 7.84 (d, 1H), 7.74 (s, 1H), 7.51-7.49 (m, 2H), 7.21 (d, 1H), 7.12 (s, 1H), 6.31 (dd, 1H), 5.36 (s, 2H), 4.13 (s, 3H), 3.81 (s, 3H), 2.93-2.86 (m, 4H), 2.11-2.00 (m, 2H). |
| 214 | 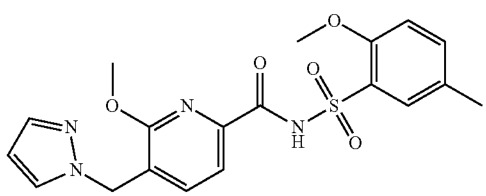 [SMILES: COc1ccc(C)cc1S(=O)(=O)NC(=O)c1ccc(Cn2cccn2)c(OC)n1] | & Intermediate 30/ Example 8 | LC-MS: 417.1 [M + H]$^+$; ¹H NMR δ 7.84 (d, 1H), 7.72 (d, 1H), 7.51-7.47 (m, 3H), 7.21 (d, 1H), 7.13 (d, 1H), 6.31 (dd, 1H), 5.36 (s, 2H), 4.13 (s, 3H), 3.82 (s, 3H), 2.34 (s, 3H). |
| 216 | 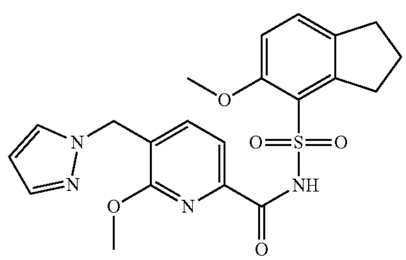 | Intermediate 56 & Intermediate 30/ Example 8 | LC-MS: 443.1 [M + H]$^+$; ¹H NMR δ 11.58 (s, 1H), 7.84 (d, 1H), 7.53-7.46 (m, 3H), 7.20 (d, 1H), 7.00 (d, 1H), 6.31 (dd, 1H), 5.36 (s, 2H), 4.13 (s, 3H), 3.79 (s, 3H) 3.32 (t, 2H), 2.85 (t, 2H), 2.08-2.02 (m, 2H). |
| 217 | 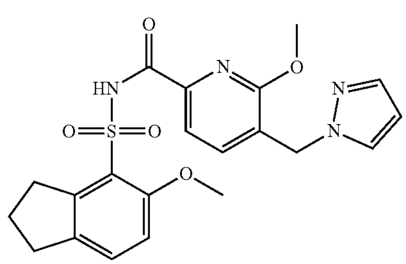 | Intermediate 57 & Intermediate 30/ Example 8 | LC-MS: 457.2 [M + H]$^+$; ¹H NMR δ 11.49 (s, 1H), 7.84 (d, 1H), 7.55-7.50 (m, 2H), 7.33 (d, 1H), 7.20 (d, 1H), 7.02 (d, 1H), 6.32 (dd, 1H), 5.36 (s, 2H), 4.13 (s, 3H) 3.78 (s, 3H), 3.23 (t, 2H), 2.74 (t, 2H), 1.73-1.67 (m, 4H). |
| 218 | 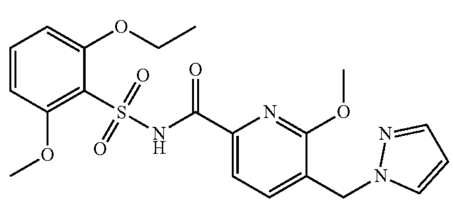 [SMILES: CCOc1cccc(OC)c1S(=O)(=O)NC(=O)c1ccc(Cn2cccn2)c(OC)n1] | Intermediate 58 & Intermediate 30/ Example 8 | LCMS: 447.2 [M + H]$^+$; ¹H NMR δ 11.25 (s, 1H), 7.85 (dd, 1H), 7.57 (d, 1H), 7.53-7.48 (m, 2H), 7.22 (d, 1H), 6.80-6.77 (m, 2H), 6.32 (dd, 1H), 5.38 (s, 2H), 4.12 (s, 3H), 4.10 (q, 2H), 3.79 (s, 3H), 1.21 (t, 3H). |

TABLE 13-continued

Compound Synthesis and Characterization

| Comp. No. | Structure | Intermediates/ Coupling example | LC-MS and $^1$H NMR (400 MHz, DMSO-$d_6$) unless otherwise shown |
|---|---|---|---|
| 219 | 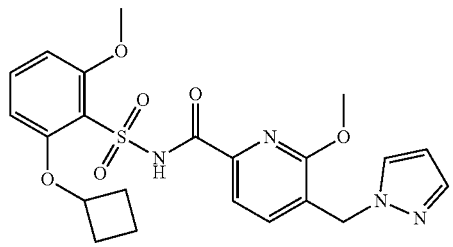 [SMILES: COc1cccc(OC2CCC2)c1S(=O)(=O)NC(=O)c1ccc(Cn2cccn2)c(OC)n1] | Intermediate 59 & Intermediate 30/ Example 8 | LC-MS: 473.2 [M + H]$^+$; $^1$H NMR δ 11.51 (brs, 1H), 7.83 (d, 1H), 7.58 (d, 1H), 7.51 (dd, 1H), 7.42 (dd, 1H), 7.22 (d, 1H), 6.75 (d, 1H), 6.54 (d, 1H), 6.31 (dd, 1H), 5.36 (s, 2H), 4.74-4.65 (m, 1H), 4.10 (s, 3H), 3.78 (s, 3H), 2.27-2.18 (m, 2H), 1.96-1.84 (m, 2H), 1.54-1.44 (m, 2H). |
| 220 | 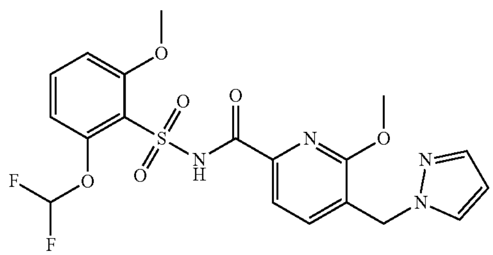 [SMILES: COc1cccc(OC(F)F)c1S(=O)(=O)NC(=O)c1ccc(Cn2cccn2)c(OC)n1] | Intermediate 63 & Intermediate 30/ Example 8 | LC-MS: 469.1 [M + H]$^+$; $^1$H NMR δ 11.96 (s, 1H), 7.85 (dd, 1H), 7.68 (t, 1H), 7.55 (d, 1H), 7.51 (dd, 1H), 7.26 (t, 1H) 7.21-7.16 (m, 2H), 6.96 (d, 1H), 6.32 (dd, 1H), 5.37 (s, 2H), 4.14 (s, 3H), 3.85 (s, 3H). |
| 222 | 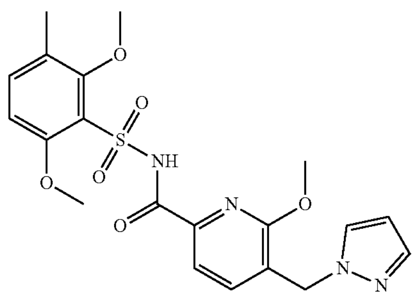 [SMILES: COc1ccc(C)c(OC)c1S(=O)(=O)NC(=O)c1ccc(Cn2cccn2)c(OC)n1] | Intermediate 65 & Intermediate 30/ Example 8 | LCMS: 447.1 [M + H]$^+$; $^1$H NMR δ 11.48 (s, 1H), 7.85 (dd, 1H), 7.55 (d, 1H), 7.51 (dd, 1H), 7.46 (d, 1H), 7.21 (d, 1H), 6.91 (d, 1H), 6.32 (dd, 1H), 5.37 (s, 2H), 4.14 (s, 3H), 3.85 (s, 3H), 3.75 (s, 3H), 2.21 (s, 3H). |
| 223 | 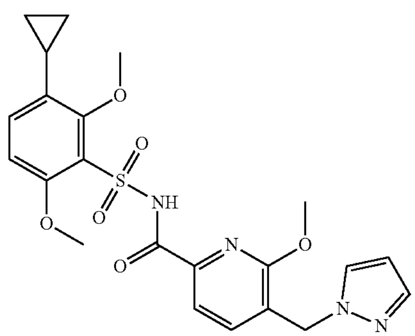 [SMILES: COc1ccc(C2CC2)c(OC)c1S(=O)(=O)NC(=O)c1ccc(Cn2cccn2)c(OC)n1] | Intermediate 66 & Intermediate 30/ Example 8 | LCMS: 473.1 [M + H]$^+$; $^1$H NMR δ 11.62 (brs, 1H), 7.85 (dd, 1H), 7.56 (d, 1H), 7.51 (dd, 1H), 7.20 (d, 1H), 7.09 (d, 1H), 6.86 (d, 1H), 6.32 (dd, 1H), 5.36 (s, 2H), 4.11 (s, 3H), 3.93 (s, 3H), 3.72 (s, 3H), 2.09-2.02 (m, 1H), 0.97-0.92 (m, 2H), 0.68-0.65 (m, 2H). |
| 225 | 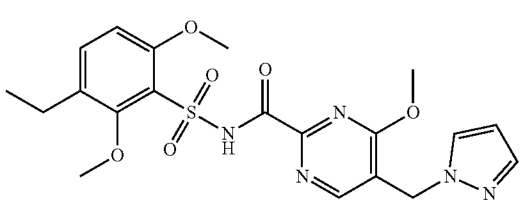 [SMILES: CCc1ccc(OC)c(S(=O)(=O)NC(=O)c2ncc(Cn3cccn3)c(OC)n2)c1OC] | Intermediate 64 & Intermediate 30/ Example 8 | LC-MS: 461.1 [M − H]$^−$; $^1$H NMR δ 11.47 (s, 1H), 7.85 (dd, 1H), 7.56 (d, 1H), 7.52-7.48 (m, 2H), 7.21 (d, 1H), 6.95 (d, 1H), 6.32 (dd, 1H), 5.38 (s, 2H), 4.14 (s, 3H), 3.86 (s, 3H), 3.76 (s, 3H), 2.59 (q, 2H), 1.16 (t, 3H). |

TABLE 13-continued

Compound Synthesis and Characterization

| Comp. No. | Structure | Intermediates/ Coupling example | LC-MS and ¹H NMR (400 MHz, DMSO-d$_6$) unless otherwise shown |
|---|---|---|---|
| 227 | 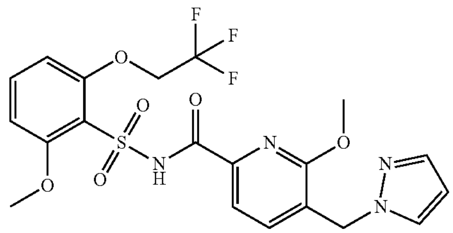 [SMILES: COc1cccc(OCC(F)(F)F)c1S(=O)(=O)NC(=O)c1ccc(Cn2cccn2)c(OC)n1] | Intermediate 68 & Intermediate 30/ Example 8 | LC-MS: 501.1 [M + H]⁺; ¹H NMR δ 11.34 (s, H), 7.85 (dd, 1H), 7.60 (t, 1H), 7.56 (d, 1H), 7.51 (dd, 1H), 7.21 (d, 1H), 6.94-6.90 (m, 2H), 6.32 (dd, 1H), 5.37 (s, 2H), 4.84 (q, 2H), 4.12 (s, 3H), 3.79 (s, 3H). |
| 228 | 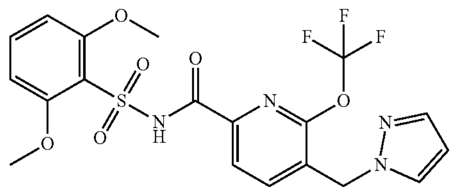 [SMILES: COc1cccc(OC)c1S(=O)(=O)NC(=O)c1ccc(Cn2cccn2)c(OC(F)(F)F)n1] | Intermediate 22 & Intermediate 76/ Example 7 | LC-MS: 487.1 [M + H]⁺; ¹H NMR δ 10.01 (s, 1H), 8.00 (d, 1H), 7.62 (dd, 1H), 7.54 (dd, 1H), 7.48-7.43 (m, 2H), 6.64 (d, 2H), 6.39 (dd, 1H), 5.45 (s, 2H), 3.93 (s, 6H). |
| 229 | 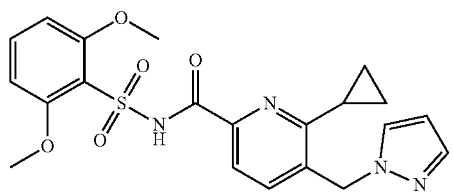 [SMILES: COc1cccc(OC)c1S(=O)(=O)NC(=O)c1ccc(Cn2cccn2)c(C2CC2)n1] | Intermediate 22 & Intermediate 28/ Example 8 | LC-MS: 443.1[M + H]⁺; ¹H NMR δ 8.27 (s, 1H), 7.82 (d, 1H), 7.63 (d, 1H), 7.50 (d, 1H), 7.31 (t, 1H), 7.21 (d, 1H), 6.67 (d, 2H), 6.31 (dd, 1H), 5.57 (s, 2H), 3.69 (s, 6H), 2.34-2.27 (m, 1H), 1.08-1.01 (m, 2H), 0.92-0.85 (m, 2H). |
| 230 | 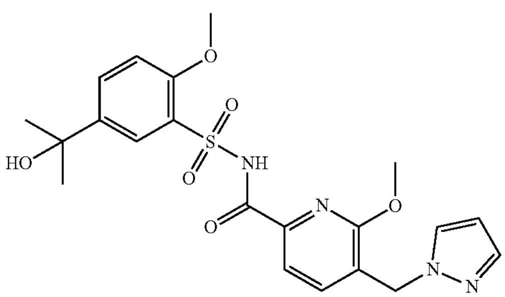 [SMILES: COc1ccc(C(C)(C)O)cc1S(=O)(=O)NC(=O)c1ccc(Cn2cccn2)c(OC)n1] | Intermediate 54 & Intermediate 30/ Example 8 | LC-MS: 459.0 [M − H]⁻; ¹H NMR δ 11.92 (s, 1H), 8.01 (d, 1H), 7.83 (d, 1H), 7.62 (brd, 1H), 7.52-7.49 (m, 2H), 7.18 (d, 1H), 7.08 (brd, 1H), 6.30 (dd, 1H), 5.34 (s, 2H), 5.16 (s, 1H), 4.06 (s, 3H), 3.78 (s, 3H), 1.43 (s, 6H). |
| 231 | 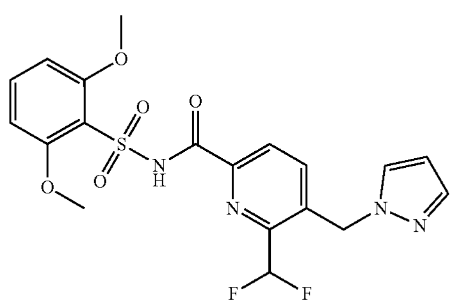 [SMILES: COc1cccc(OC)c1S(=O)(=O)NC(=O)c1ccc(Cn2cccn2)c(C(F)F)n1] | Intermediate 22 & Intermediate 77/ Example 8 | LC-MS: 453.2 [M + H]⁺; ¹H NMR δ 11.56 (s, 1H), 8.09 (d, 1H), 7.93 (dd, 1H), 7.57-7.56 (m, 2H), 7.46 (d, 1H), 7.36 (t, 1H), 6.80 (d, 2H), 6.36 (dd, 1H), 5.72 (s, 2H), 3.78 (s, 6H). |
| 235 | 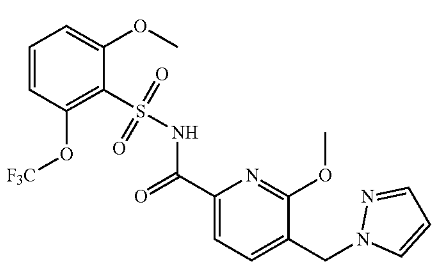 [SMILES: COc1cccc(OC(F)(F)F)c1S(=O)(=O)NC(=O)c1ccc(Cn2cccn2)c(OC)n1] | Intermediate 73 & Intermediate 30/ Example 8 | LC-MS: 487.0 [M + H]⁺; ¹H NMR δ 12.50 (s, 1H), 7.81 (d, 1H), 7.52-7.49 (m, 3H), 7.15-7.13 (m, 2H), 6.98 (brd, 1H), 6.30 (dd, 1H), 5.31 (s, 2H), 3.99 (s, 3H), 3.77 (s, 3H). |

TABLE 13-continued

Compound Synthesis and Characterization

| Comp. No. | Structure | Intermediates/ Coupling example | LC-MS and $^1$H NMR (400 MHz, DMSO-$d_6$) unless otherwise shown |
|---|---|---|---|
| 236 | 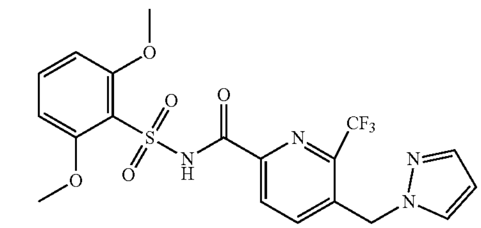 [SMILES: COc1cccc(OC)c1S(=O)(=O)NC(=O)c1ccc(Cn2cccn2)c(C(F)(F)F)n1] | Intermediate 22 & Intermediate 80/ Example 8 | LC-MS: 471.1 [M + H]$^+$; $^1$H NMR δ 11.71 (s, 1H), 8.17 (d, 1H), 7.94 (d, 1H), 7.58-7.52 (m, 2H), 7.42 (d, 1H), 6.80 (d, 2H), 6.38 (dd, 1H), 5.71 (s, 2H), 3.79 (s, 6H). |
| 239 | 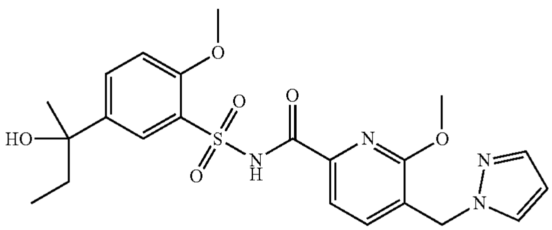 [SMILES: CCC(C)(O)c1ccc(OC)c(S(=O)(=O)NC(=O)c2ccc(Cn3cccn3)c(OC)n2)c1] | Intermediate 75 & Intermediate 30/ Example 8 | LC-MS: 473.1 [M − H]$^-$; $^1$H NMR δ 11.63 (s, 1H), 7.99 (d, 1H), 7.84 (d, 1H), 7.65 (dd, 1H), 7.52-7.50 (m, 2H), 7.21 (d, 1H), 7.16 (d, 1H), 6.31 (dd, 1H), 5.36 (s, 2H), 5.04 (s, 1H), 4.13 (s, 3H), 3.84 (s, 3H), 1.69 (q, 2H), 1.42 (s, 3H), 0.70 (t, 3H). |
| 240 | 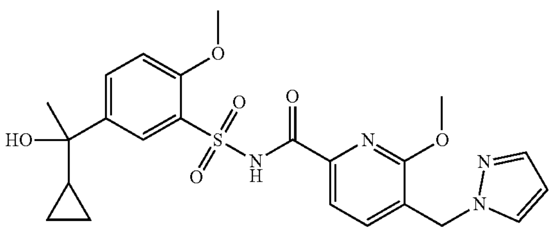 [SMILES: COc1ccc(C(C)(O)C2CC2)cc1S(=O)(=O)NC(=O)c1ccc(Cn2cccn2)c(OC)n1] | Intermediate 74 & Intermediate 30/ Example 8 | LC-MS: 485.1 [M − H]$^-$; $^1$H NMR δ 12.06 (s, 1H), 7.99 (d, 1H), 7.81 (d, 1H), 7.58 (d, 1H), 7.51-7.48 (m, 2H), 7.15 (d, 1H), 7.02 (d, 1H), 6.30 (dd, 1H), 5.32 (s, 2H), 4.77 (s, 1H), 4.00 (s, 3H), 3.75 (s, 3H), 1.41 (s, 3H), 1.24-1.11 (m, 1H), 0.45-0.40 (m, 1H), 0.40-0.31(m, 2H), 0.26-0.18 (m, 1H). |
| 241 | 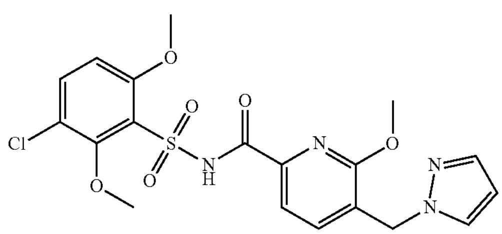 [SMILES: COc1ccc(Cl)c(OC)c1S(=O)(=O)NC(=O)c1ccc(Cn2cccn2)c(OC)n1] | Intermediate 78 & Intermediate 30/ Example 8 | LC-MS: 467.1 [M + H]$^+$; $^1$H NMR δ 11.86 (s, 1H), 7.85 (d, 1H), 7.76 (d, 1H), 7.55 (d, 1H), 7.51 (d, 1H), 7.20 (d, 1H), 7.05 (d, 1H), 6.32 (dd, 1H), 5.37 (s, 2H), 4.14 (s, 3H), 3.94 (s, 3H), 3.80 (s, 3H). |
| 245 | 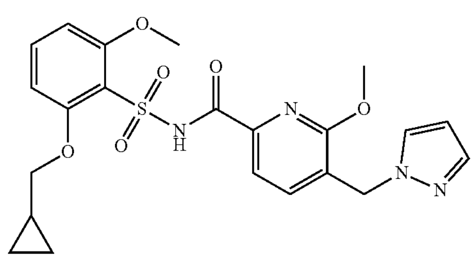 [SMILES: COc1cccc(OCC2CC2)c1S(=O)(=O)NC(=O)c1ccc(Cn2cccn2)c(OC)n1] | Intermediate 69 & Intermediate 30/ Example 8 | LC-MS: 473.2[M + H]$^+$; $^1$H NMR δ 11.19 (s, 1H), 7.84 (d, 1H), 7.57 (d, 1H), 7.51-7.47 (m, 2H), 7.23 (d, 1H), 6.78(d, 2H), 6.31 (dd, 1H), 5.37 (s, 2H), 4.11 (s, 3H), 3.91 (d, 2H), 3.78 (s, 3H), 1.99-1.11 (m, 1H), 0.39-0.36 (m, 2H), 0.27-0.24 (m, 2H). |
| 253 | 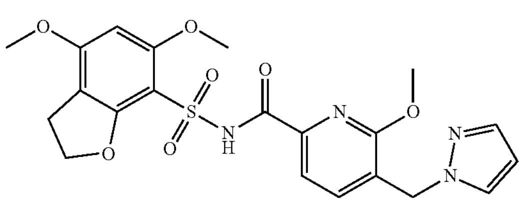 [SMILES: COc1cc(OC)c(S(=O)(=O)NC(=O)c2ccc(Cn3cccn3)c(OC)n2)c2c1CCO2] | Intermediate 79 & Intermediate 30/ Example 8 | LC-MS: 475.1 [M + H]$^+$; $^1$H NMR δ 7.85 (d, 1H), 7.54 (d, 1H), 7.51 (d, 1H), 7.22 (d, 1H), 6.32 (dd, 1H), 6.25 (s, 1H), 5.37 (s, 2H), 4.62 (t, 2H), 4.12 (s, 3H), 3.86 (s, 3H), 3.80 (s, 3H), 3.01 (t, 2H). |

Example 13. Compound 243: 5-((1H-pyrazol-1-yl)methyl)-N-(2,6-dimethoxyphenylsulfonimidoyl)-6-methoxypicolinamide

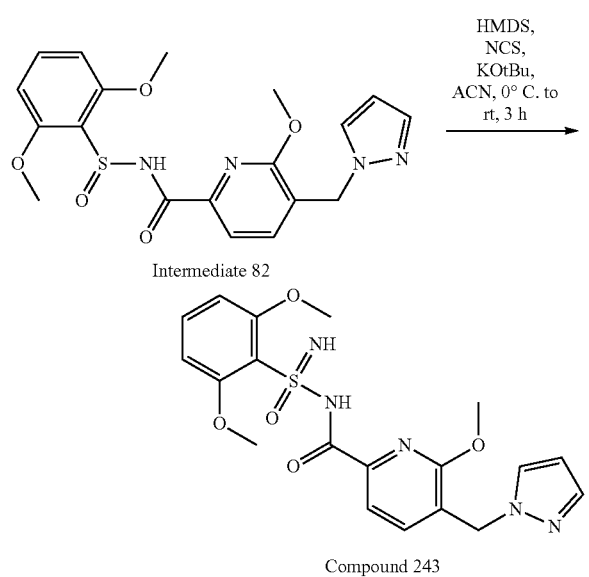

Intermediate 82

Compound 243

To a solution of 5-((1H-pyrazol-1-yl)methyl)-N-((2,6-dimethoxyphenyl)sulfinyl)-6-methoxypicolinamide (0.1 g, 0.24 mmol) in ACN (5 mL) was added KO$^t$Bu (0.05 g, 0.48) followed by HMDS (0.116 g, 0.72 mmol), and NCS (0.096 g, 0.72 mmol) at 0° C. and stirred for 15 min. Then additional HMDS (0.116 g, 0.72 mmol), and NCS (0.096 g, 0.72 mmol) was added to the reaction mixture 0° C. and then stirred at rt for 2 h. The reaction mixture was diluted with water and extracted with 10% MeOH in DCM. The organic layer was dried over sodium sulphate, filtered, and concentrated to afford the crude compound. Crude compound was purified by preparative HPLC to obtain the title compound (0.03 g). LC-MS: 432.2 [M+H]$^+$; $^1$H NMR (DMSO-d$_6$, 400 MHz): δ 7.82 (d, 1H), 7.63 (d, 1H), 7.50-7.48 (m, 2H), 7.46-7.43 (m, 2H), 7.18 (d, 1H), 6.78 (d, 2H), 6.31 (dd, 1H), 3.93 (s, 3H), 3.77 (s, 6H).

Compound 243 was separated by chiral HPLC into its respective isomers, with arbitrary assignment of stereochemistry.

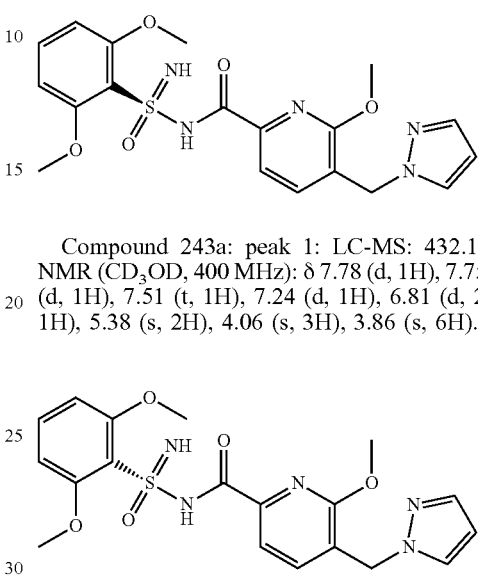

Compound 243a: peak 1: LC-MS: 432.1 [M+H]$^+$; $^1$H NMR (CD$_3$OD, 400 MHz): δ 7.78 (d, 1H), 7.75 (d, 1H), 7.56 (d, 1H), 7.51 (t, 1H), 7.24 (d, 1H), 6.81 (d, 2H), 6.37 (dd, 1H), 5.38 (s, 2H), 4.06 (s, 3H), 3.86 (s, 6H).

Compound 243b: peak 2: LC-MS: 432.1 [M+H]$^+$; $^1$H NMR (CD$_3$OD, 400 MHz): δ 7.78 (d, 1H), 7.75 (d, 1H), 7.56 (d, 1H), 7.51 (t, 1H), 7.24 (d, 1H), 6.81 (d, 2H), 6.37 (dd, 1H), 5.38 (s, 2H), 4.06 (s, 3H), 3.86 (s, 6H).

Example 14. Compounds 71, 232, and 261 to 263

The following compounds listed in Table 14 were prepared by following a similar procedure as described above for Compound 243 using appropriate reagents with suitable modifications known to the one skilled in the art.

TABLE 14

Compound Synthesis and Characterization

| Comp. No | Structure | Intermediates | LC-MS and $^1$H NMR (400 MHz, DMSO-d$_6$ unless otherwise shown |
|---|---|---|---|
| 71 | 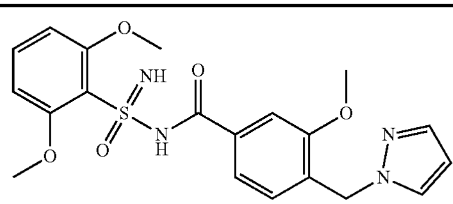 | Intermediate 82 | LC-MS: 431.1 [M + H]$^+$; $^1$H NMR δ 7.77 (d, 1H), 7.55-7.45 (m, 4H), 7.40 (brs, 1H), 6.81-6.75 (m, 3H), 6.28 (dd, 1H), 5.33 (s, 2H), 3.87 (s, 3H), 3.75 (s, 6H). |
| 232 | 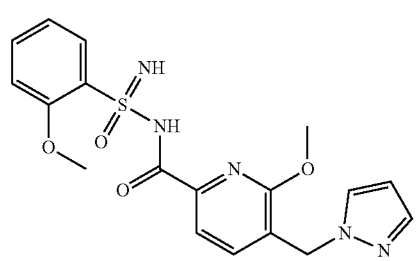 [SMILES: COc1ccccc1S(=N)(=O)NC(=O)c1ccc(Cn2cccn2)c(OC)n1] | Intermediate 83 | LC-MS: 402.1 [M + H]$^+$; $^1$H NMR δ 7.90 (dd, 1H), 7.81 (d, 1H), 7.64-7.55 (m, 4H), 7.49 (d, 1H), 7.21 (d, 1H), 7.19 (d, 1H), 7.15-7.10 (m, 1H), 6.30 (dd, 1H), 5.32 (s, 2H), 3.92 (s, 3H), 3.83 (s, 3H). |

TABLE 14-continued

Compound Synthesis and Characterization

| Comp. No | Structure | Intermediates | LC-MS and ¹H NMR (400 MHz, DMSO-$d_6$) unless otherwise shown |
|---|---|---|---|
| 261 | 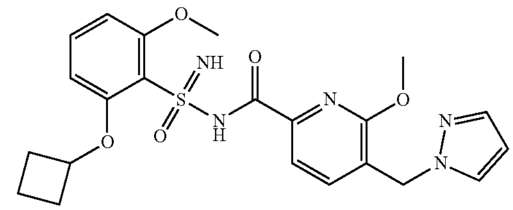 [SMILES: COc1cccc(OC2CCC2)c1S(=N)(=O)NC(=O)c1ccc(Cn2cccn2)c(OC)n1] | Intermediate 86 | LC-MS: 472.2 [M + H]⁺; ¹H NMR δ 8.48 (brs, 1H), 7.80 (d, 1H), 7.66 (d, 1H), 7.49 (d, 1H), 7.41 (t, 1H), 7.19 (d, 1H), 6.76 (d, 1H), 6.54 (d, 1H), 6.29 (dd, 1H), 5.32 (s, 2H), 4.72-4.64 (m, 1H), 3.93 (s, 3H), 3.79 (s, 3H), 2.29-2.16 (m, 2H), 1.98-1.84 (m, 2H), 1.55-1.45 (m, 2H). |
| 262 | 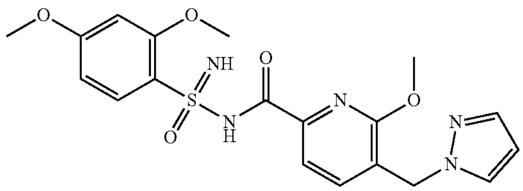 [SMILES: COc1ccc(S(=N)(=O)NC(=O)c2ccc(Cn3cccn3)c(OC)n2)c(OC)c1] | Intermediate 84 | LC-MS: 432.1 [M + H]⁺; ¹H NMR δ 8.34 (s, 1H), 7.81-7.78 (m, 2H), 7.60 (d, 1H), 7.49 (d, 1H), 7.19 (d, 1H), 6.69-6.66 (m, 2H), 6.30 (dd, 1H), 5.31 (s, 2H), 3.92 (s, 3H), 3.84 (s, 3H), 3.82 (s, 3H). |
| 263 | 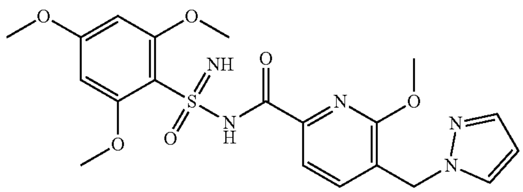 | Intermediate 85 | LC-MS: 462.1 [M + H]⁺; ¹H NMR δ 8.27 (s, 1H), 7.82 (d, 1H), 7.61 (d, 1H), 7.50 (d, 1H), 7.18 (d, 1H), 6.31-6.29 (m, 3H), 5.32 (s, 2H), 3.93 (s, 3H), 3.83 (s, 3H), 3.76 (s, 6H). |

Example 15: (Compound 265) 5-((1H-Pyrazol-1-yl)methyl)-N-((2,6-dimethoxyphenyl)sulfonyl)-6-ethylpicolinamide

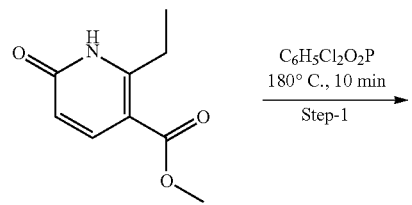

Intermediate 101a

C₆H₅Cl₂O₂P
180° C., 10 min
Step-1

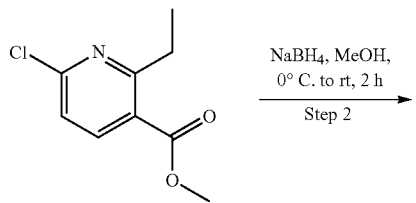

Intermediate 101b

NaBH₄, MeOH,
0° C. to rt, 2 h
Step 2

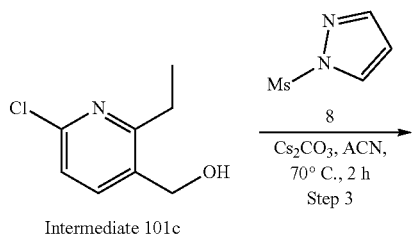

Intermediate 101c

8
Cs₂CO₃, ACN,
70° C., 2 h
Step 3

-continued

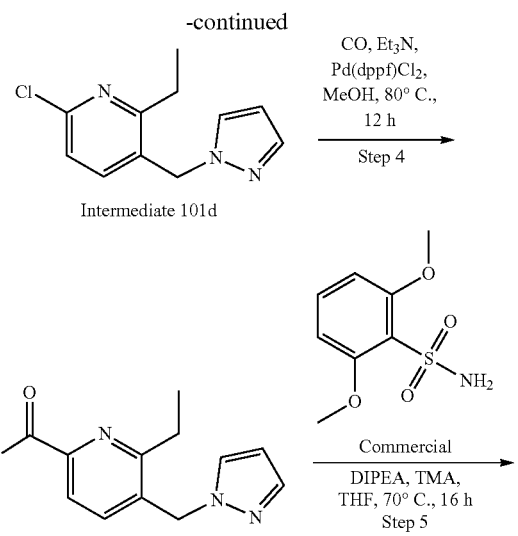

Intermediate 101d

CO, Et₃N,
Pd(dppf)Cl₂,
MeOH, 80° C.,
12 h
Step 4

Intermediate 101

Commercial
DIPEA, TMA,
THF, 70° C., 16 h
Step 5

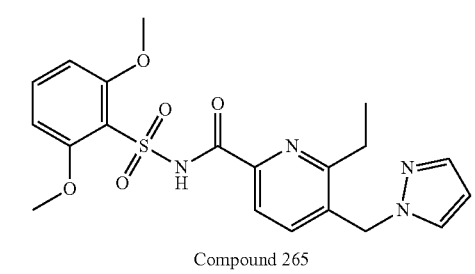

Compound 265

Step 1: Methyl 6-chloro-2-ethylnicotinate

To a solution of methyl 2-ethyl-6-oxo-1,6-dihydropyridine-3-carboxylate (1.0 g, 5.51 mmol) in dichloro-hydroxy-(phenoxy)phosphonium (11.64 g, 55.18 mmol) and stirred at 180° C. for 10 min. Reaction mixture was quenched with ice water and extracted with ethyl acetate. The organic layer was dried over $Na_2SO_4$, filtered, and concentrated to afford the crude compound, which was further purified by silica-gel flash column chromatography using 20-30% ethyl acetate in hexane as eluent to obtain the title compound as white solid (0.8 g, 72.61%). LC-MS: 200.1 [M+H]$^+$.

Step 2: (6-Chloro-2-ethylpyridin-3-yl)methanol

The title compound was prepared using a similar procedure to that described in Step 1 of Intermediate 30 using appropriate reagents with suitable modifications (0.7 g). LC-MS: 172.1 [M+H]$^+$.

Step 3: 3-((1H-pyrazol-1-yl)methyl)-6-chloro-2-ethylpyridine

The title compound was prepared using similar procedure to that described in Step 2 of Intermediate 29 using appropriate reagents with suitable modifications (0.9 g, 99.55%). LC-MS: 222.1 [M+H]$^+$.

Step 4: Methyl 5-((1H-pyrazol-1-yl)methyl)-6-ethylpicolinate

The title compound was prepared using similar procedure to that described in Step 3 of Intermediate 29 using appropriate reagents with suitable modifications. (0.65 g, 83.91%). LC-MS: 246.2 [M+H]$^+$.

Step 5: 5-((1H-Pyrazol-1-yl)methyl)-N-((2,6-dimethoxyphenyl)sulfonyl)-6-ethylpicolinamide To a stirred solution of methyl 5-((1H-pyrazol-1-yl)methyl)-6-ethylpicolinate (0.20 g, 0.815 mmol), 2,6-dimethoxybenzenesulfonamide (0.17 g, 0.0.815 mmol) in THF (40 mL) was added DIPEA (0.35 mL, 2.03 mmol) and TMA (0.14 g, 2.03 mmol) at 0° C. and stirred at 70° C. for 12 h. The reaction mixture was quenched with ice water and extracted with 10% methanol and DCM. The organic layer was dried over $Na_2SO_4$, filtered, and concentrated to obtain the title crude compound. Crude compound was purified by preparative HPLC to obtain the title compound (0.13 g, 37.05%). LC-MS: 431.1 [M+H]$^+$; $^1$H NMR (DMSO-D6, 400 MHz): δ 11.15 (brs, 1H), 7.87 (d, 1H), 7.80 (d, 1H), 7.55-7.51 (m, 2H), 7.34 (d, 1H), 6.80 (d, 2H), 6.34 (dd, 1H), 5.55 (s, 2H), 3.77 (s, 6H), 2.96 (q, 2H), 1.27 (t, 3H).

Example 16: (Compound-266) 5-((1H-Pyrazol-1-yl)methyl)-N-((5-(1-hydroxy-2-methylpropan-2-yl)-2-methoxyphenyl)sulfonyl)-6-methoxypicolinamide

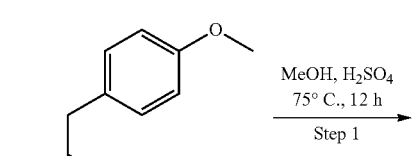

Intermediate 102a

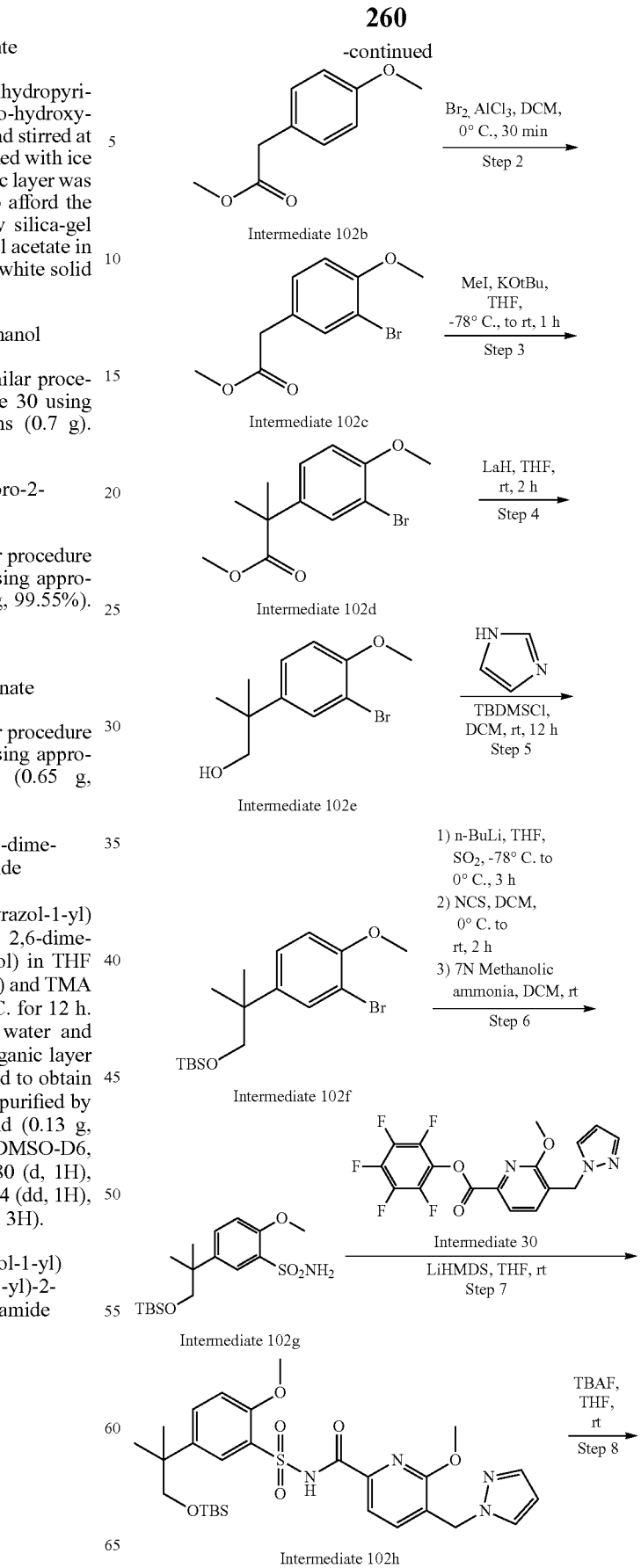

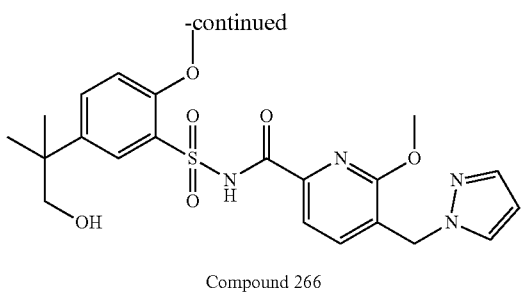

Compound 266

Step 1: Methyl 2-(4-methoxyphenyl)acetate

To a solution of 2-(4-methoxyphenyl)acetic acid (5.0 g, 30.08 mmol) in methanol (70 mL) was added sulfuric acid (2.95 g, 30.08 mmol) and stirred at 70° C. for 12 h. Reaction mixture was evaporated, quenched with ice water and extracted with ethyl acetate. The organic layer was washed with saturated sodium bicarbonate solution, brine, dried over $Na_2SO_4$, filtered, and concentrated to afford the crude compound, which was taken for the next step without purification (5.0 g). $^1$H NMR (CDCl3, 400 MHz): δ 7.23 (d, 2H), 6.90 (d, 2H), 3.82 (s, 3H), 3.71 (s, 3H), 3.62 (s, 2H).

Step 2: Methyl 2-(3-bromo-4-methoxyphenyl)acetate

To a stirred solution of $AlCl_3$ (1.11 g, 8.23 mmol), methyl 2-(4-methoxyphenyl) acetate (3.0 mL, 16.64 mmol) in DCM was add bromine (1.46 g, 18.31 mmol) dropwise at 0° C. The reaction mixture was warmed to rt and stirred for 1 h. Reaction mixture was quenched with ice water and extracted with DCM. The organic layer was washed with sodium thiosulphate, dried over $Na_2SO_4$, filtered, and concentrated to afford the crude compound, which was used in next step without purification. (3.0 g). $^1$H NMR (DMSO-$D_6$, 400 MHz): δ 7.49 (d, 2H), 7.24 (dd, 1H), 7.06 (d, 1H), 3.83 (s, 3H), 3.64 (s, 3H).

Step 3: Methyl 2-(3-bromo-4-methoxyphenyl)-2-methylpropanoate

To a solution of methyl 2-(3-bromo-4-methoxyphenyl) acetate (3.0 g, 11.57 mmol) and methyl iodide (4.93 g, 34.73 mmol) in THF (30 mL) was added KOt-Bu (3.89 g, 34.73 mmol) at −78° C. stirred at same temperature for 60 min. Then the reaction mixture was warmed to rt and stirred for 12 h. The reaction mixture was quenched with ice water and extracted with EtOAc. The organic layer was washed with brine solution, dried over $Na_2SO_4$, and concentrated to get the crude compound. The crude compound purified by silica-gel flash chromatography using 0-30% ethyl acetate in hexane as eluent to afford the pure title compound (3.2 g, 96.24%). LC-MS: 289.0 [M+2+H]$^+$.

Step 4: 2-(3-Bromo-4-methoxyphenyl)-2-methylpropan-1-ol

To a solution of methyl 2-(3-bromo-4-methoxyphenyl)-2-methylpropanoate (2.5 g, 8.70 mmol) in THF (15 mL) was added LAH (0.26 g, 0.80 mmol) at 0° C. and stirred at same temperature for 1 h. The reaction mixture was quenched with saturated sodium sulphate and extracted with ethyl acetate. The organic layer was washed with brine, dried over $Na_2SO_4$, filtered, and concentrated to afford the crude compound, which was used in next step without purification (2.3 g). $^1$H NMR (DMSO-d6, 400 MHz): δ 7.50 (s, 1H), 7.31 (d, 1H), 7.02 (d, 1H), 4.68 (t, 1H), 3.81 (s, 3H), 3.38 (d, 2H), 1.18 (s, 6H).

Step 5: (2-(3-Bromo-4-methoxyphenyl)-2-methylpropoxy)(tert-butyl)dimethylsilane To a solution of 2-(3-bromo-4-methoxyphenyl)-2-methylpropan-1-ol (1.0 g, 3.85 mmol) in DCM (25 mL) was added imidazole (0.52 g, 7.71 mmol) followed by TBDMSCl (0.68 g, 4.63 mmol) at 0° C. The reaction mixture was warmed to RT and stirred for 12 h. The reaction mixture was added into ice water and extracted with DCM. The organic layer was washed with brine, dried over $Na_2SO_4$, and concentrated to get the crude compound. The crude compound was purified by silica-gel flash chromatography using 0-10% ethyl acetate in hexane as eluent to afford the pure title compound (1 g, 69.40%). $^1$H NMR (DMSO-d6, 400 MHz): δ 7.52 (s, 1H), 7.33 (d, 1H), 7.02 (d, 1H), 3.81 (s, 3H), 3.48 (s, 2H), 1.21 (s, 6H), 0.82 (s, 9H), 0.014 (s, 6H).

Step 6: 5-(1-((tert-Butyldimethylsilyl)oxy)-2-methylpropan-2-yl)-2-methoxybenzenesulfonamide To a solution of (2-(3-bromo-4-methoxyphenyl)-2-methylpropoxy)(tert-butyl)dimethylsilane (1.0 g, 2.67 mmol) in THF (20 mL) was added n-BuLi (5.0 mL, 8.03 mmol, 1.6M in hexane) at −78° C. and stirred at the same temperature for 1 h. Then $SO_2$ gas was bubbled into the reaction mixture for 30 min at −78° C. The entire reaction mixture was stirred at 0° C. for 1 h. The reaction mixture was concentrated to obtain the solid. The solid was dissolved in DCM and NCS (1.07 g, 8.03 mmol) was added to the reaction mixture at 0° C. The reaction mixture was warmed to RT and stirred for 2 h. The reaction was quenched with ice-water and extracted with DCM. The organic layer was dried over sodium sulphate, filtered, and concentrated to afford the crude compound. The crude compound was again dissolved in DCM (5 mL) and 7N methanolic ammonia (10 mL) was added to the reaction mixture and stirred for 30 min at RT. The reaction mixture was diluted with water and extracted with DCM. The organic layer was dried over sodium sulphate, filtered, and concentrated to afford the crude which was taken for the next step without purification. (0.3 g). LC-MS: 374.2 [M+H]$^+$.

Step 7: 5-((1H-Pyrazol-1-yl)methyl)-N-((5-(1-((tert-butyldimethylsilyl)oxy)-2-methylpropan-2-yl)-2-methoxyphenyl)sulfonyl)-6-methoxypicolinamide To a solution of perfluorophenyl 5-((1H-pyrazol-1-yl) methyl)-6-methoxypicolinate (0.40 g, 1.002 mmol), and 5-(1-((tert-butyldimethylsilyl)oxy)-2-methylpropan-2-yl)-2-methoxybenzenesulfonamide (0.29 g, 0.80 mmol) in THF (10 mL) was added LiHMDS (2.0 mL, 2.0 mmol, 1.0 M in THF) and stirred at RT for 10 min. The reaction mixture was quenched with saturated $NH_4Cl$ solution and extracted with 10% MeOH in DCM. The organic layer was dried over $Na_2SO_4$, filtered, and concentrated to afford the crude compound. Crude compound was purified by silica-gel flash column chromatography using 2-5% MeOH in DCM as eluent to afford the title compound (0.3 g, 50.85%). LC-MS: 589.2 [M+H]$^+$.

Step 8: 5-((1H-pyrazol-1-yl)methyl)-N-((5-(1-hydroxy-2-methylpropan-2-yl)-2-methoxyphenyl)sulfonyl)-6-methoxypicolinamide To a solution of 5-((1H-pyrazol-1-yl)methyl)-N-((5-(1-((tert-butyldimethylsilyl)oxy)-2-methylpropan-2-yl)-2-methoxyphenyl)sulfonyl)-6-methoxypicolinamide (0.30 g, 0.51 mmol) in THF 15 mL) was added TBAF (0.28 g, 1.73 mmol) at 0° C. The reaction mixture was warmed to RT and stirred at RT for 12 h. The reaction mixture concentrated to get the crude compound. Crude compound was purified by preparative HPLC to obtain the title compound (0.140 g, 57.85%). LC-MS: 475.1 [M+H]$^+$; $^1$H NMR (DMSO-D6, 400 MHz): δ 11.65 (s, 1H), 7.87 (d, 1H), 7.84 (d, 1H), 7.67 (dd, 1H), 7.53-7.50 (m, 2H), 7.21 (d, 1H), 7.16 (d, 1H), 6.31 (dd, 1H), 5.36 (s, 2H), 4.13 (s, 3H), 3.83 (s, 3H), 3.41 (s, 2H), 1.24 (s, 6H).

Example 17: (Compound 267) 6-((1H-Pyrazol-1-yl)methyl)-N-((5-(tert-butyl)-2-methoxyphenyl)sulfonyl)-1-methyl-2-oxo-1,2-dihydropyridine-3-carboxamide

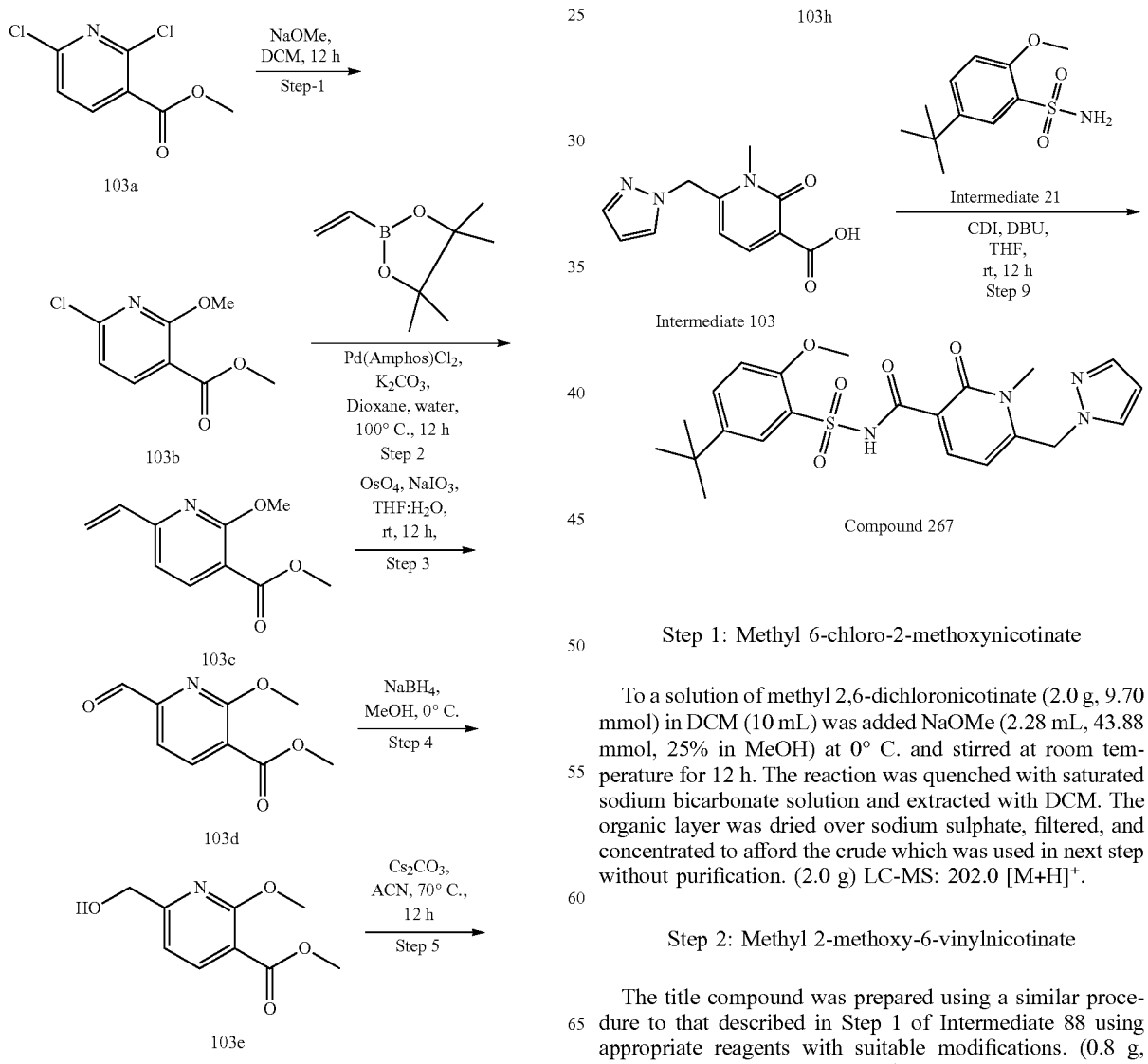

Step 1: Methyl 6-chloro-2-methoxynicotinate

To a solution of methyl 2,6-dichloronicotinate (2.0 g, 9.70 mmol) in DCM (10 mL) was added NaOMe (2.28 mL, 43.88 mmol, 25% in MeOH) at 0° C. and stirred at room temperature for 12 h. The reaction was quenched with saturated sodium bicarbonate solution and extracted with DCM. The organic layer was dried over sodium sulphate, filtered, and concentrated to afford the crude which was used in next step without purification. (2.0 g) LC-MS: 202.0 [M+H]$^+$.

Step 2: Methyl 2-methoxy-6-vinylnicotinate

The title compound was prepared using a similar procedure to that described in Step 1 of Intermediate 88 using appropriate reagents with suitable modifications. (0.8 g, 41.74%) LC-MS: 194.1 [M+H]$^+$.

Step 3: Methyl 6-formyl-2-methoxynicotinate

To a solution of methyl 2-methoxy-6-vinylnicotinate (0.5 g, 2.58 mmol) in water-THF (5 mL and 5 mL) was Added 4% aqueous solution of osmium tetroxide (0.007 g, 0.020 mmol), followed by sodium periodate (1.10 g, 5.17 mmol) at 0° C. The reaction mixture was warmed to RT and stirred at RT for 12 h. The reaction was quenched ice water and extracted with ethyl acetate. The organic layer was washed with brine, dried over $Na_2SO_4$, and concentrated to obtain the crude compound. The crude compound was purified by silica-gel flash column chromatography using 20-60% ethyl acetate in hexane as eluent to afford the title compound (0.3 g, 59.39%). LC-MS: 196.1 [M+H]⁺.

Step 4: Methyl 6-(hydroxymethyl)-2-methoxynicotinate

The title compound was prepared using a similar procedure to that described in Step 1 of Intermediate 30 using appropriate reagents with suitable modifications (0.25 g). LC-MS: 198.1 [M+H]⁺.

Step 5: Methyl 6-((1H-pyrazol-1-yl)methyl)-2-methoxynicotinate

The title compound was prepared using a similar procedure to that described in Step 2 of Intermediate 29 using appropriate reagents with suitable modifications (0.23 g, 73.36%). LC-MS: 248.1 [M+H]⁺.

Step 6: 6-((1H-Pyrazol-1-yl)methyl)-2-oxo-1,2-dihydropyridine-3-carboxylic acid The title compound was prepared using a similar procedure to that described in Step 1 of Intermediate 99 using appropriate reagents with suitable modifications (0.2 g). LC-MS: 220.1 [M+H]⁺.

Step 7: 6-((1H-Pyrazol-1-yl)methyl)-2-oxo-1,2-dihydropyridine-3-carboxylic acid The title compound was prepared using a similar procedure to that described in Step 2 of Intermediate 99 using appropriate reagents with suitable modifications (0.2 g). LC-MS: 248.1 [M+H]⁺.

Step 8: 6-((1H-pyrazol-1-yl)methyl)-1-methyl-2-oxo-1,2-dihydropyridine-3-carboxylic acid The title compound was prepared using a similar procedure to that described in Step 3 of Intermediate 99 using appropriate reagents with suitable modifications (0.07 g). LC-MS: 234.1 [M+H]⁺.

Step 9: 6-((1H-pyrazol-1-yl)methyl)-N-((5-(tert-butyl)-2-methoxyphenyl)sulfonyl)-1-methyl-2-oxo-1,2-dihydropyridine-3-carboxamide To a solution of 6-((1H-pyrazol-1-yl)methyl)-1-methyl-2-oxo-1,2-dihydropyridine-3-carboxylic acid (0.07 g, 0.3 mmol), in THF (5 mL) was added CDI (0.15 g, 0.900 mmol) and stirred at RT for 1 h. The reaction mixture was cooled to 0° C., and to it was added 5-(tert-butyl)-2-methoxybenzenesulfonamide (0.08 g, 0.36 mmol), DBU (0.14 g, 0.900 mmol) and stirred for 15 min at the same temperature. Then reaction mixture was warmed to RT and stirred for overnight. The reaction mixture was quenched with ice water and extracted with 10% methanol and DCM. The organic layer was dried over $Na_2SO_4$, filtered, and concentrated to obtain the crude compound. The crude compound was purified by preparative HPLC to obtain the title compound (30 mg, 21.81%). LC-MS: 459.2 [M+H]⁺; ¹H NMR (DMSO-D6, 400 MHz): δ 13.06 (s, 1H), 8.18 (d, 1H), 7.86-7.84 (m, 2H), 7.71 (dd, 1H), 7.61 (dd, 1H), 7.16 (d, 1H), 6.41 (dd, 1H), 5.71 (d, 1H), 5.68 (s, 2H), 3.81 (s, 3H), 3.65 (s, 3H), 1.28 (s, 9H).

Example 18: (Compound 268) 5-((1H-Pyrazol-1-yl)methyl)-N-((3-ethyl-2,4,6-trimethoxyphenyl)sulfonyl)-6-methoxypicolinamide

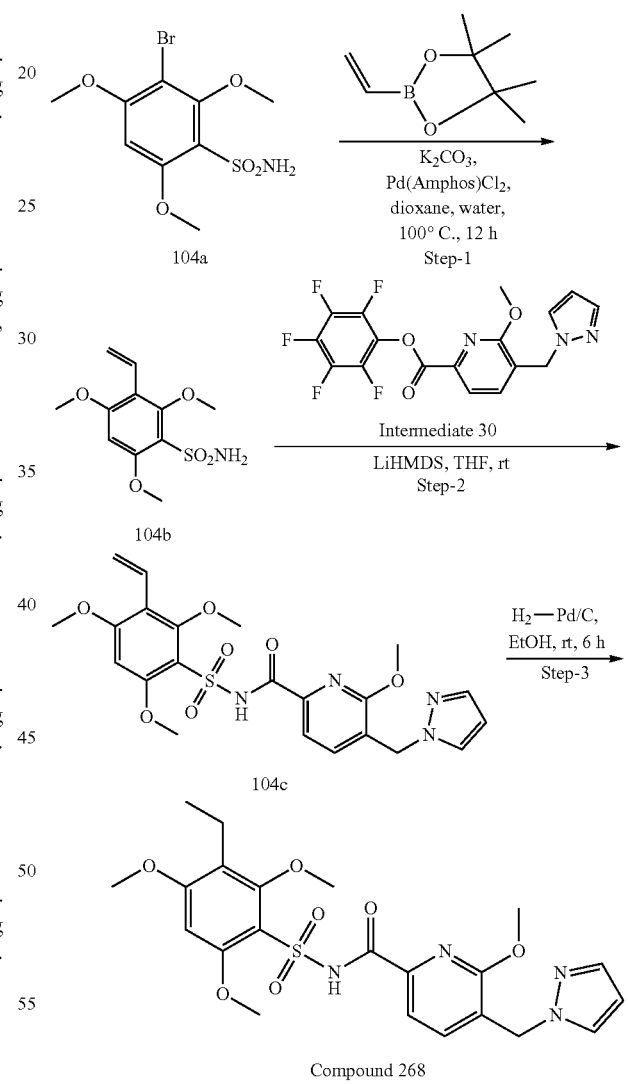

Compound 268

Step 1: 2,4,6-Trimethoxy-3-vinylbenzenesulfonamide

The title compound was prepared using a similar procedure to that described in Step 1 of Intermediate 88 using appropriate reagents with suitable modifications. ¹H NMR (DMSO-D6, 400 MHz): δ 6.68-6.61 (m, 1H), 6.54 (s, 1H), 5.91 (d, 1H), 5.27 (d, 1H), 3.95 (s, 3H), 3.88 (s, 3H), 3.71 (s, 1H).

Step 2: 5-((1H-Pyrazol-1-yl)methyl)-6-methoxy-N-((2,4,6-trimethoxy-3-vinylphenyl)sulfonyl)picolinamide The title compound was prepared using similar procedure to that described in Example 10 using appropriate reagents with suitable modifications (0.16 g). LC-MS: 489.1 [M+H]$^+$.

Step 3: 5-((1H-Pyrazol-1-yl)methyl)-N-((3-ethyl-2,4,6-trimethoxyphenyl)sulfonyl)-6-methoxypicolinamide The title compound was prepared using a similar procedure to that described in Step 2 of Intermediate 88 using appropriate reagents with suitable modifications (4 mg, 2.66%). LC-MS: 491.1 [M+H]$^+$; $^1$H NMR (DMSO-D6, 400 MHz): δ 10.24 (brs, 1H), 7.69 (d, 1H), 7.60 (d, 1H), 7.52 (d, 1H), 7.22 (d, 1H), 6.35 (dd, 1H), 6.28 (s, 1H), 5.37 (s, 2H), 4.13 (s, 3H), 4.03 (s, 3H), 3.90 (s, 3H), 3.87 (s, 3H), 2.62 (q, 2H), 1.13 (t, 3H).

Example 19: (Compound 269) 5-((1H-Pyrazol-1-yl)methyl)-N-((2,6-dimethoxy-4-(pyridin-3-ylethynyl)phenyl)sulfonyl)-6-methoxypicolinamide Step 1: 5-((1H-Pyrazol-1-yl)methyl)-N-((4-iodo-2,6-dimethoxyphenyl)sulfonyl)-6-methoxypicolinamide The title compound was prepared using a similar procedure to that described in Example 10 using appropriate reagents with suitable modifications LC-MS: 559.0 [M+H]$^+$.

Step 2: 5-((1H-Pyrazol-1-yl)methyl)-N-((2,6-dimethoxy-4-(pyridin-3-ylethynyl)phenyl)sulfonyl)-6-methoxypicolinamide To a degassed solution of 5-((1H-pyrazol-1-yl)methyl)-N-((4-iodo-2,6-dimethoxyphenyl)sulfonyl)-6-methoxypicolinamide (0.09 g, 0.16 mmol), 3-ethynylpyridine (0.019 g, 0.19 mmol) and DIPEA (0.3 mL, 1.6 mmol) in DMF (5 mL) was added copper iodide (0.003 g, 0.1 mmol) and Pd(PPh$_3$)$_2$Cl$_2$ (0.019 g, 0.1 mmol). The reaction mixture was heated at 70° C. for 12 h. The reaction mixture was cooled to RT, diluted with water, and extracted with ethyl acetate. The organic layer was dried over Na$_2$SO$_4$, filtered, and concentrated to obtain crude compound. Crude compound was purified by preparative HPLC to obtain the title compound (7 mg, 8.15%). LC-MS: 534.1 [M+H]$^+$; $^1$H NMR (DMSO-D6, 400 MHz): δ 8.82 (dd, 1H), 8.62 (d, 1H), 8.03-8.00 (m, 1H), 7.83 (d, 1H), 7.65-7.62 (m, 2H), 7.60-7.48 (m, 3H), 7.19 (d, 1H), 6.96 (brs, 1H), 6.31 (dd, 1H), 5.34 (s, 2H), 4.06 (s, 3H), 3.79 (s, 6H).

Example 20: (Compound 270) 5-((1H-pyrazol-1-yl)methyl)-6-methoxy-N-((2,4,6-tris(methoxy-d3)phenyl)sulfonyl)picolinamide

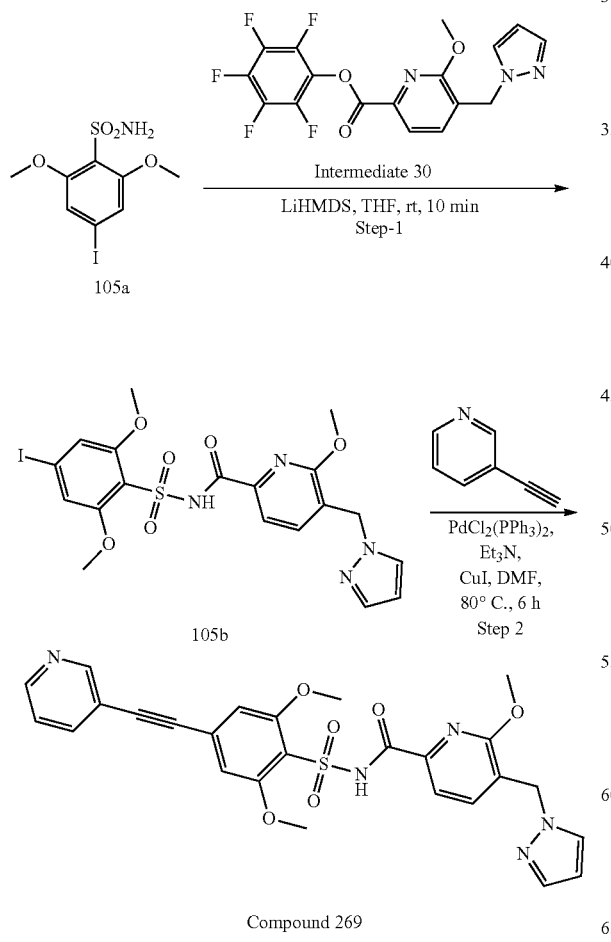

Compound 269

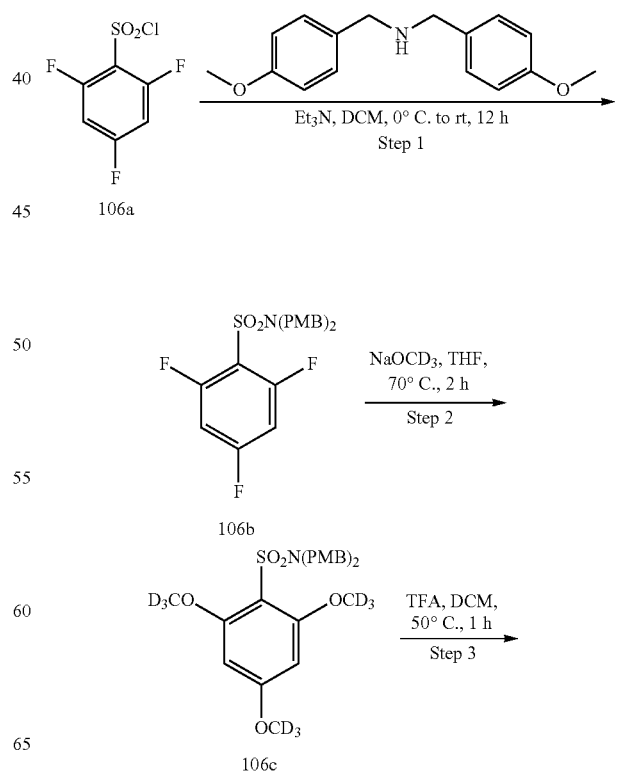

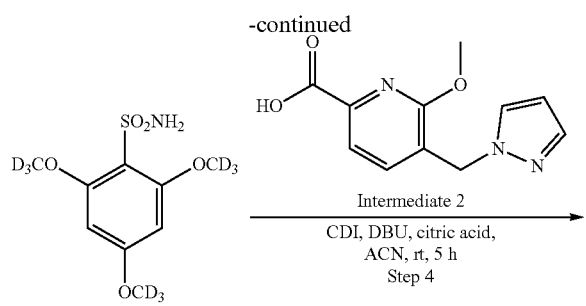

Step 1: 2,4,6-Trifluoro-N,N-bis(4-methoxybenzyl) benzenesulfonamide

To a solution of 2,4,6-trifluorobenzenesulfonyl chloride (3.0 g, 13.00 mmol), in DCM (30 mL) was added Et$_3$N (5.44 mL, 39.03 mmol) and followed by bis(4-methoxybenzyl) amine (4 g, 15.61 mmol) at 0° C. The reaction mixture was warmed to rt stirred at for 12 h. The reaction mixture was quenched with water and extracted with DCM. The organic layer was washed with brine and dried over anhydrous Na$_2$SO$_4$, filtered, and concentrated to obtain the crude compound. The crude compound was purified by silica-gel flash column chromatography using 20-30% ethyl acetate in hexane as eluent to obtain the title compound as an off-white solid. (4.9 g, 83.5%). $^1$H NMR (CDCl3, 400 MHz): δ 7.05 (d, 4H), 6.79 (d, 4H), 6.80-6.70 (m, 2H), 4.42 (s, 4H), 3.80 (s, 6H).

Step 2: 2,4,6-Tris(methoxy-d3)-N,N-bis(4-methoxybenzyl)benzenesulfonamide

To a solution of 2,4,6-trifluoro-N,N-bis(4-methoxybenzyl)benzenesulfonamide (0.1 g, 0.22 mmol), in THF (1 mL) was added freshly prepared 20% NaOCD$_3$ solution (0.25 mL, 0.88 mmol) at rt to the reaction mixture. The reaction mixture was stirred at 70° C. for 2 h. The reaction mixture was quenched with water and extracted with ethyl acetate. The organic layer was washed with brine solution and dried over anhydrous Na$_2$SO$_4$, filtered, and concentrated to obtain the crude compound. The crude compound was purified by silica-gel flash column chromatography using 30-40% ethyl acetate in hexane as eluent to obtain the title compound (0.105 g, 95.25%). LC-MS: 497.2 [M+H]$^+$.

Step 3: 2,4,6-tris(Methoxy-d3)benzene sulfonamide

To a solution of 2,4,6-tris(methoxy-d3)-N,N-bis(4-methoxybenzyl)benzenesulfonamide (2.5 g, 5.03 mmol), in DCM (10 mL) was added TFA (20 mL) at rt. The reaction mixture was heated at 60° C. for 2 h. The reaction mixture was concentrated, then neutralized with saturated NaHCO$_3$ and extracted with 10% MeOH in DCM. The organic layer was washed with brine solution and dried over anhydrous Na$_2$SO$_4$, filtered, and concentrated to get the crude. The crude compound was purified by silica-gel flash column chromatography using 80-100% ethyl acetate in hexane as eluent and was recrystallized using DCM to obtain the title compound (0.55 g, 42.6%). LC-MS: 257.1 [M+H]$^+$. $^1$H NMR (DMSO-D6, 400 MHz): δ 6.81 (brs, 2H), 6.28 (s, 2H).

Step 4: 5-((1H-Pyrazol-1-yl)methyl)-6-methoxy-N-((2,4,6-tris(methoxy-d3)phenyl)sulfonyl)picolinamide To a suspension of 5-((1H-pyrazol-1-yl)methyl)-6-methoxypicolinic acid (1.6 g, 6.86 mmol), in ACN (30 mL) was added citric acid (0.395 g, 2.05 mmol followed by CDI (1.98 g, 10.29 mmol) at rt and stirred for 2 h. 2,4,6-tris(Methoxy-d3)benzenesulfonamide (1.58 g, 6.17 mmol) and followed by DBU (2.11 g, 10.97 mmol) at rt was added to the reaction mixture and stirred at rt for 3 h. The reaction mixture was quenched with saturated citric acid solution and extracted with 10% MeOH in DCM. The organic layer was washed with brine and dried over anhydrous Na$_2$SO$_4$, filtered, and concentrated to get the crude. The crude compound was purified by silica-gel flash column chromatography using 0-1% MeOH in DCM as and recrystallized using ethyl acetate to obtain the title compound (1.6 g, 49.46%). LC-MS: 472.2 [M+H]$^+$. $^1$H NMR (DMSO-D6, 400 MHz): δ 11.16 (brs, 1H), 7.85 (dd, 1H), 7.55-7.51 (m, 2H), 7.21 (d, 1H), 6.32 (dd, 1H), 6.30 (s, 2H), 5.37 (s, 2H), 4.12 (s, 3H).

Example 21: (Compound 271) 5-((1H-Pyrazol-1-yl)methyl)-N-((5-ethyl-2-methoxyphenyl)sulfonyl)-4-methoxypyrimidine-2-carboxamide

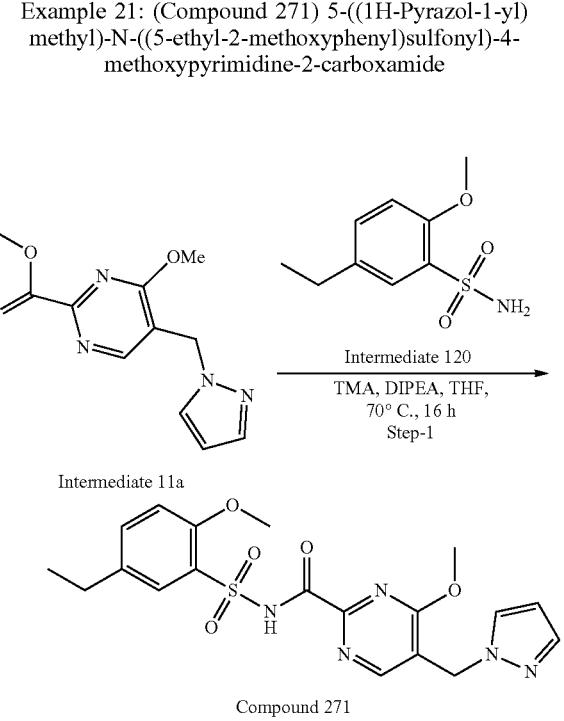

Step 1: 5-((1H-Pyrazol-1-yl)methyl)-N-((5-(tert-butyl)-2-methoxyphenyl)sulfonyl)-4-methoxypyrimidine-2-carboxamide To a solution of methyl 5-((1H-pyrazol-1-yl)methyl)-4-methoxypyrimidine-2-carboxylate (Intermediate 11a) (0.2 g, 0.806 mmol), and 5-ethyl-2-methoxybenzenesulfonamide (Intermediate 20) (0.174 g, 0.806 mmol) in THF (10 mL) was added DIPEA (0.35 mL, 2.5 mmol), trimethylaluminum (0.119 mg, 2.5 mmol) at 0° C. and then the reaction mixture stirred at 70° C. for 16 h. The reaction was cooled to RT and diluted with 10% MeOH in DCM. The reaction mixture was filtered through celite, dried over sodium sulphate, filtered, and concentrated to afford the crude compound. Crude compound was purified by preparative HPLC to obtain the title compound as an off-white solid. LC-MS: 432.1 [M+H]$^+$; $^1$H NMR (DMSO-D6, 400 MHz): δ 12.28 (brs, 1H), 8.24 (s, 1H), 7.85 (d, 1H), 7.73 (d, 1H), 7.53 (dd, 1H), 7.49 (d, 1H), 7.17 (d, 1H), 6.30 (dd, 1H), 5.36 (s, 2H), 4.05 (s, 3H), 3.83 (s, 3H), 2.65 (q, 2H), 1.19 (t, 3H).

The following compounds listed in Table 15 were prepared by following a similar procedure (Example 21) as described above using appropriate reagents with suitable modifications known to the one skilled in the art.

TABLE 15

| Com. No | Structure | Intermediates/ Coupling example | LC-MS and $^1$H NMR (400 MHz, DMSO-d$_6$) unless otherwise shown |
|---|---|---|---|
| 272 | Exact Mass: 463.12 | Commercial & Intermediate 11a/ Example 21 | LC-MS: 464.3 [M + H]$^+$; $^1$H NMR (DMSO-D6, 400 MHz): δ 11.76 (s, 1H), 8.22 (s, 1H), 7.84 (d, 1H), 7.49 (d, 1H), 6.31-6.30 (m, 3H), 5.36 (s, 2H), 4.05 (s, 3H), 3.84 (s, 3H), 3.79 (s, 6H). |
| 273 | Exact Mass: 443.13 | Intermediate 67 & Intermediate 11a/ Example 21 | LC-MS: 444.1[M + H]$^+$; $^1$H NMR (DMSO-D6, 400 MHz): δ 12.29 (brs, 1H), 8.23 (s, 1H), 7.84 (d, 1H), 7.62 (d, 1H), 7.48 (dd, 1H), 7.35 (dd, 1H), 7.13 (d, 1H) 6.30 (dd, 1H), 5.35 (s, 2H), 4.05 (s, 3H), 3.81 (s, 3H), 2.03-1.99 (m, 2H)-0.99-095 (m, 2H), 0.66-0.65 (m, 2H). |
| 274 | Exact Mass: 433.11 | Intermediate 22 & Intermediate 11a/ Example 21 | LC-MS: 434.1 [M + H]$^+$; $^1$H NMR (DMSO-D6, 400 MHz): δ 11.95 (s, 1H), 8.24 (s, 1H), 7.85 (dd, 1H), 7.54 (dd, 1H), 7.50 (dd, 1H), 6.81 (d, 2H), 6.30 (dd, 1H), 5.37 (s, 2H), 4.06 (s, 3H), 3.80 (s, 6H). |

The following compounds listed in Table 16 were prepared by following a similar procedure (Example 10) as described above using appropriate reagents with suitable modifications known to the one skilled in the art.

TABLE 16

| Com. No | Structure | Intermediates/ Coupling example | Spectral data |
|---|---|---|---|
| 275 | 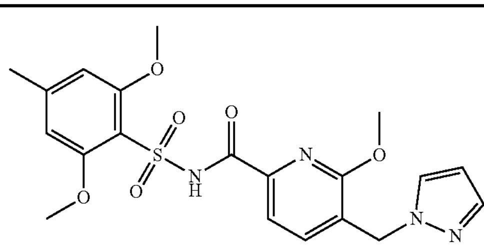 | Intermediate 98 & Intermediate 30/ Example 10 | LC-MS: 447.1 [M + H]+; 1H NMR (DMSO-D6, 400 MHz): δ 11.26 (brs, 1H), 7.85 (dd, 1H), 7.54 (d, 1H), 7.51 (dd, 1H), 7.21 (d, 1H), 6.64 (s, 2H), 6.32 (dd, 1H), 5.37 (s, 2H), 4.12 (s, 3H), 3.76 (s, 6H), 2.32 (s, 3H). |

TABLE 16-continued

| Com. No | Structure | Intermediates/ Coupling example | Spectral data |
|---|---|---|---|
| 276 | Exact Mass: 510.02 | Intermediate 26d & Intermediate 30/ Example 10 | LC-MS: 513.1 [M + 2 + H]+; 1H NMR (DMSO-D6, 400 MHz): δ 12.37 (brs, 1H), 7.94 (s, 1H), 7.81 (d, 1H), 7.50 (d, 1H), 7.49 (d, 1H), 7.15 (d, 1H), 6.76 (s, 1H), 6.29 (dd, 1H), 5.31 (s, 2H), 3.99 (s, 3H), 3.93 (s, 3H), 3.82 (s, 3H). |
| 277 | Exact Mass: 450.10 | Intermediate 26b & Intermediate 30/ Example 10 | LC-MS: 451.3 [M + H]+; 1H NMR (DMSO-D6, 400 MHz): δ 11.83 (s, 1H), 7.84 (d, 1H), 7.66 (d, 1H), 7.51-7.49 (m, 2H), 7.21 (d, 1H), 6.95 (d, 1H), 6.31 (dd, 1H), 5.36 (s, 2H), 4.13 (s, 3H), 3.96 (s, 3H), 3.89 (s, 3H). |
| 278 | Exact Mass: 458.16 | Intermediate 21 & Intermediate 99/ Example 7 | LC-MS: 457.1 [M − H]−; 1H NMR (DMSO-D6, 400 MHz): δ 13.15 (brs, 1H), 7.83 (d, 1H), 7.80 (d, 1H), 7.74 (dd, 1H), 7.48 (d, 1H), 7.21 (d, 1H), 6.92 (d, 1H), 6.35 (d, 1H), 6.28 (dd, 1H), 5.15 (s, 2H), 3.91 (s, 3H), 3.28 (s, 3H), 1.30 (s, 9H). |
| 279 | Exact Mass: 458.13 | Intermediate 107 & Intermediate 30/ Example 10 | LC-MS: 459.1 [M + H]+; 1H NMR (CDCl3, 400 MHz): δ 10.13 (brs, 1H), 7.70 (d, 1H), 7.60 (d, 1H), 7.52 (d, 1H), 7.46 (dd, 1H), 7.21 (d, 1H), 7.01 (d, 1H), 6.66 (d, 1H), 6.36 (dd, 1H), 5.38 (s, 2H), 4.13 (s, 3H), 3.93 (s, 3H), 3.84-3.83 (m, 1H), 0.83-0.81 (m, 2H), 0.80-0.77 (m, 2H). |
| 280 | Exact Mass: 470.16 | Intermediate 90 & Intermediate 30/ Example 10 | LC-MS: 471.2 [M + H]+; 1H NMR (DMSO-D6, 400 MHz): δ 11.92 (s, 1H), 7.84 (d, 1H), 7.63 (s, 1H), 7.56 (d, 1H), 7.53-7.50 (m, 2H), 7.20 (d, 1H), 6.31 (dd, 1H), 5.36 (s, 2H), 4.62 (t, 2H), 4.12 (s, 3H), 3.24 (t, 2H), 1.29 (s, 9H). |
| 281 | Exact Mass: 446.09 | Intermediate 97 & Intermediate 30/ Example 10 | LC-MS: 447.1 [M + H]+; 1H NMR (DMSO-D6, 400 MHz): δ 11.86 (brs, 1H), 7.83 (d, 1H), 7.54 (d, 1H), 7.51 (d, 1H), 7.21 (d, 1H), 7.12 (d, 1H), 6.53 (d, 1H), 6.32 (dd, 1H), 6.13 (s, 2H), 5.36 (s, 2H), 4.12 (s, 3H), 3.72 (s, 3H). |

TABLE 16-continued

| Com. No | Structure | Intermediates/ Coupling example | Spectral data |
|---|---|---|---|
| 282 | Exact Mass: 450.10 | Intermediate 91 & Intermediate 30/ Example 10 | LC-MS: 451.1 [M + H]+; 1H NMR (DMSO-D6, 400 MHz): δ 11.50 (s, 1H), 7.85 (d, 1H), 7.54 (d, 1H), 7.51 (d, 1H), 7.21 (d, 1H), 6.74 (d, 2H), 6.32 (dd, 1H), 5.37 (s, 2H), 4.12 (s, 3H), 3.80 (s, 6H). |
| 283 | Exact Mass: 466.07 | Intermediate 92 & Intermediate 30/ Example 10 | LC-MS: 467.1 [M + H]+; 1H NMR (DMSO-D6, 400 MHz): δ 11.59 (s, 1H), 7.85 (dd, 1H), 7.54 (d, 1H), 7.51 (dd, 2H), 7.21 (d, 1H), 6.93 (s, 2H), 6.32 (dd, 1H), 5.37 (s, 2H), 4.13 (s, 3H), 3.82 (s, 6H). |
| 284 | Exact Mass: 474.16 | Intermediate 1 & Intermediate 30/ Example 10 | LC-MS: 475.2 [M + H]+; 1H NMR (DMSO-D6, 400 MHz): δ 11.25 (s, 1H), 7.85 (dd, 1H), 7.59 (d, 1H), 7.52 (dd, 1H), 7.48 (d, 1H), 7.21 (d, 1H), 6.94 (d, 1H), 6.32 (dd, 1H), 5.38 (s, 2H), 4.12 (s, 3H), 4.06 (q, 2H), 3.86 (s, 3H), 2.59 (q, 2H), 1.17 (t, 6H). |
| 285 | Exact Mass: 510.02 | Intermediate 93 & Intermediate 30/ Example 10 | LC-MS: 511.0 [M + H]+; 1H NMR (DMSO-D6, 400 MHz): δ 11.62 (brs, 1H), 7.84 (d, 1H), 7.53 (d, 1H), 7.51 (dd, 1H), 7.20 (d, 1H), 7.02 (s, 2H), 6.32 (dd, 1H), 5.36 (s, 2H), 4.11 (s, 3H), 3.80 (s, 6H). |
| 286 | Exact Mass: 446.13 | Intermediate 94 & Intermediate 30/ Example 10 | LC-MS: 447.1 [M + H]+; 1H NMR (DMSO-D6, 400 MHz): δ 7.83 (d, 1H), 7.51-7.49 (m, 2H), 7.19 (d, 1H), 6.52 (s, 1H), 6.49 (s, 1H), 6.30 (dd, 1H), 5.34 (s, 2H), 4.07 (s, 3H), 3.80 (s, 3H), 3.78 (s, 3H), 2.62 (s, 3H). |
| 287 | Exact Mass: 482.09 | Intermediate 2 & Intermediate 30/ Example 10 | LC-MS: 483.0 [M + H]+; 1H NMR (DMSO-D6, 400 MHz): δ 12.39 (brs, 1H), 7.92-7.89 (m, 2H), 7.83 (d, 1H), 7.52 (d, 1H), 7.50 (dd, 1H), 7.20 (d, 1H), 6.31 (dd, 1H), 5.35 (s, 2H), 4.78 (t, 2H), 4.11 (s, 3H), 3.31 (t, 2H). |

TABLE 16-continued

| Com. No | Structure | Intermediates/ Coupling example | Spectral data |
|---|---|---|---|
| 288 | 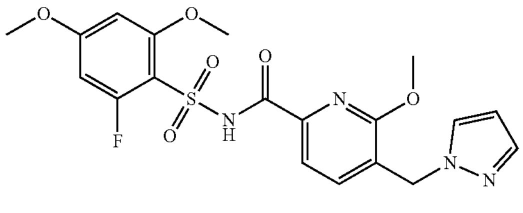 [SMILES: COc1cc(F)c(S(=O)(=O)NC(=O)c2ccc(Cn3cccn3)c(OC)n2)c(OC)c1] | & Intermediate 30/ Example 10 | LC-MS: 451.0 [M + H]+; 1H NMR (DMSO-D6, 400 MHz): δ 11.85 (s, 1H), 7.84 (d, 1H), −7.54-7.50 (m, 2H), 7.22 (d, 1H), 6.63 (dd, 1H), 6.54 (s, 1H), 6.32 (d, 1H), 5.36 (s, 2H), 4.13 (s, 3H), 3.85 (s, 3H), 3.83 (s, 3H). |
| 289 | 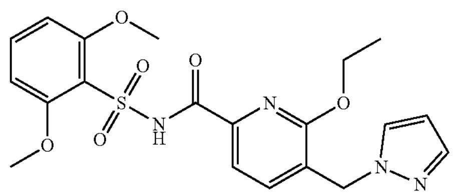 [SMILES: CCOc1nc(C(=O)NS(=O)(=O)c2c(OC)cccc2OC)ccc1Cn1cccn1] | Intermediate 22 & Intermediate 100 Example 10 | LC-MS: 447.2 [M + H]+; 1H NMR (CD3OD, 400 MHz): δ 7.88 (d, 1H), 7.63 (d, 1H), 7.56-7.54 (m, 2H), 7.34 (d, 1H), 6.81 (d, 1H), 6.38 (dd, 1H), 5.42 (s, 2H), 4.61 (q, 2H), 3.88 (s, 6H), 1.50 (t, 3H). |

Example 22: 5-((1H-Pyrazol-1-yl)methyl)-N-(5-(1-hydroxy-2-methylpropan-2-yl)-2-methoxyphenylsulfonimidoyl)-6-methoxypicolinamide (Compound 290a & 290b)

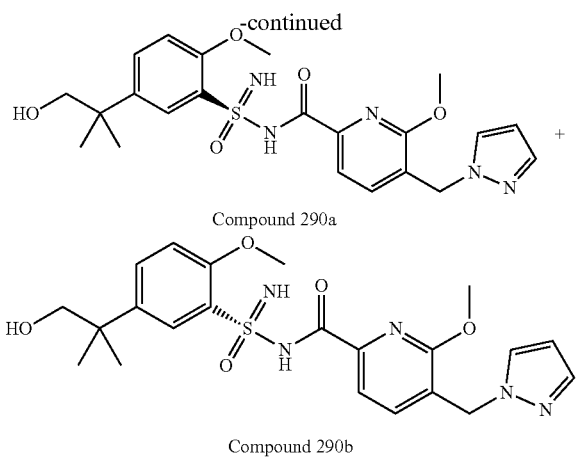

Compound 290a

Compound 290b

Step 1: 4-(1-(Benzyloxy)-2-methylpropan-2-yl)-2-bromo-1-methoxybenzene

To a stirred solution of 2-(3-bromo-4-methoxyphenyl)-2-methylpropan-1-ol (1.7 g, 6.56 mmol) in THF (30 mL) was added NaH (0.226 g, 9.84 mmol) at 0° C. After 20 min, (bromomethyl)benzene (2.2 g, 13.12 mmol) was added to the reaction mixture at 0° C. The reaction was heated 60° C. for 16 h. The reaction mixture was cooled to rt, quenched with ice water, and extracted with EtOAc. The organic layer was washed with water, brine, dried over $Na_2SO_4$ and concentrated to get crude compound. The crude compound was purified by silica-gel flash column chromatography using 20% ethyl acetate in hexane as eluent to afford the title compound (1.4 g, 61.1%). $^1$H NMR (DMSO-D6, 400 MHz): δ 7.52 (d, 1H), 7.36-7.31 (m, 3H), 7.29-7.23 (m, 3H), 7.04 (d, 1H), 4.45 (s, 2H), 3.82 (s, 3H), 3.42 (s, 2H), 1.25 (s, 6H).

Step 2: 5-(1-(benzyloxy)-2-methylpropan-2-yl)-2-methoxybenzenesulfonyl chloride The title compound was prepared using a similar procedure to that described in Step 3 of Intermediate 89 using appropriate reagents with suitable modifications. (1.4 g, 61.1%). $^1$H NMR (DMSO-D6, 400 MHz): δ 7.73 (d, 1H), 7.34-7.31 (m, 3H), 7.30-7.26 (m, 3H), 6.90 (d, 1H), 4.45 (s, 2H), 3.73 (s, 3H), 3.41 (s, 2H), 1.26 (s, 6H).

Step 3: 5-(1-(Benzyloxy)-2-methylpropan-2-yl)-2-methoxybenzenesulfinamide

The title compound was prepared using a similar procedure to that described in Step 1 of Intermediate 108 using appropriate reagents with suitable modifications. (0.29 g, 16.87%). $^1$H NMR (DMSO-D$_6$, 400 MHz): δ 7.78 (d, 1H), 7.45 (dd, 1H), 7.35-7.26 (m, 5H), 7.02 (d, 1H), 5.92 (s, 2H), 4.47 (s, 2H), 3.81 (s, 3H), 3.47-3.42 (m, 2H), 1.30 (s, 6H).

Step 4: 5-((1H-Pyrazol-1-yl)methyl)-N-((5-(1-(benzyloxy)-2-methylpropan-2-yl)-2-methoxyphenyl)sulfinyl)-6-methoxypicolinamide The title compound was prepared using a similar procedure to that described in Step 2 of Intermediate 82 using appropriate reagents with suitable modifications (0.21 g, 30.57%). LC-MS: 547.1 [M−H]$^-$.

Step 5: 5-((1H-Pyrazol-1-yl)methyl)-N-(5-(1-(benzyloxy)-2-methylpropan-2-yl)-2-methoxyphenylsulfonimidoyl)-6-methoxypicolinamide The title compound was prepared using a similar procedure to that described in Example 13 using appropriate reagents with suitable modifications (0.370 g); LC-MS: 564.2 [M+H]$^+$.

Step 6: 5-((1H-pyrazol-1-yl)methyl)-N-(5-(1-hydroxy-2-methylpropan-2-yl)-2-methoxyphenylsulfonimidoyl)-6-methoxypicolinamide To a solution of 5-((1H-pyrazol-1-yl)methyl)-N-(5-(1-(benzyloxy)-2-methylpropan-2-yl)-2-methoxyphenylsulfonimidoyl)-6-methoxypicolinamide (0.31 g, 0.0.55 mmol) in ethanol (15 mL) was carefully added 10% Pd—C (0.11 g, ~10% W/W) and stirred under positive pressure of hydrogen using a bladder for 12 h. The reaction mixture was filtered through celite and filtrate was concentrated to obtain the crude compound as a white solid. Crude compound was purified by preparative HPLC to obtain the racemic title compound (60 mg).

Step 7: Intermediate 131f was separated by chiral HPLC into its respective enantiomers. (6.2 mg (peak 1)+8.2 mg (peak 2)=(15 mg, 7.68%), with arbitrary assignment of stereochemistry.

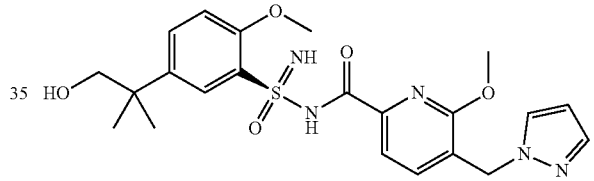

Compound 290a: peak 1; LCMS: 474.2 [M+H]$^+$; $^1$H NMR (DMSO-D$_6$, 400 MHz): δ 7.81 (d, 1H), 7.80 (dd, 1H), 7.61-7.58 (m, 2H), 7.49 (d, 1H), 7.48 (brs, 2H), 7.18 (d, 1H), 7.12 (d, 1H), 6.30 (dd, 1H), 5.32 (s, 2H), 4.77 (t, 1H), 3.93 (s, 3H), 3.80 (s, 3H), 3.40 (d, 2H), 1.23 (s, 6H).

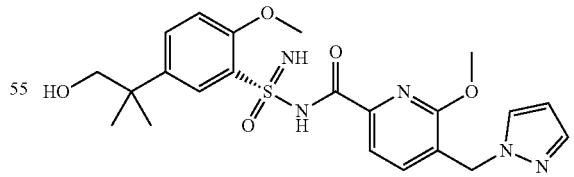

Compound 290b: peak 2; LCMS: 474.1 [M+H]$^+$; $^1$H NMR (DMSO-D$_6$, 400 MHz): δ 7.87 (d, 1H), 7.81 (dd, 1H), 7.61-7.59 (d, 2H), 7.49 (dd, 1H), 7.44 (brs, 2H), 7.18 (d, 1H), 7.11 (d, 1H), 6.30 (dd, 1H), 5.31 (s, 2H), 4.76 (t, 1H), 3.93 (s, 3H), 3.79 (s, 3H), 3.40 (d, 2H), 1.23 (s, 6H).

Example 23: 4-((1H-Pyrazol-1-yl)methyl)-N-(5-(1-hydroxy-2-methylpropan-2-yl)-2-methoxyphenylsulfonimidoyl)-3-methoxybenzamide (Compound 291a & 291b)

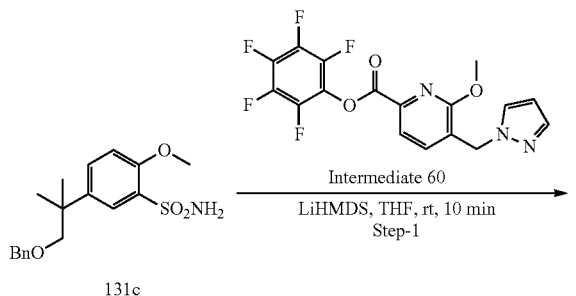

131c

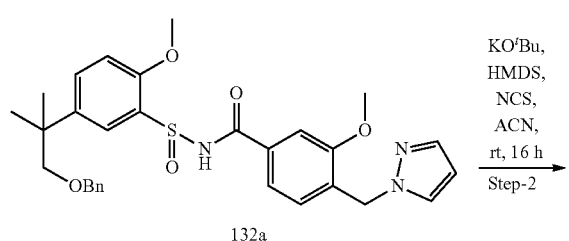

132a

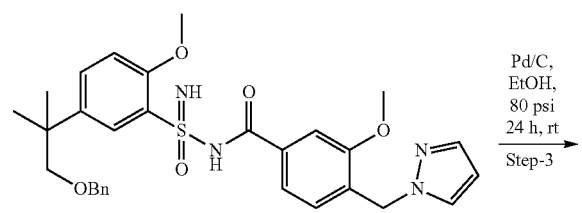

132b

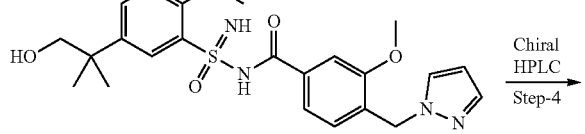

132c

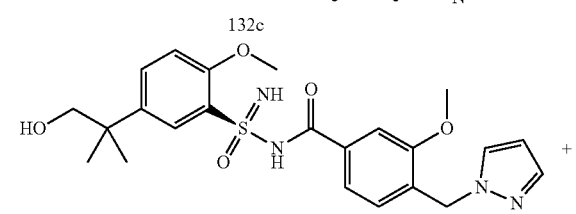

Compound 291a

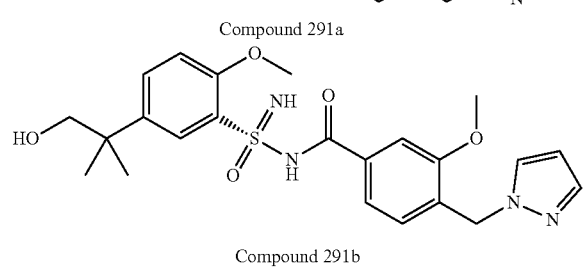

Compound 291b

Step 1: 5-((1H-pyrazol-1-yl)methyl)-N-((5-(1-(benzyloxy)-2-methylpropan-2-yl)-2-methoxyphenyl)sulfinyl)-6-methoxypicolinamide The title compound was prepared using a similar procedure to that described in Step 2 of Intermediate 82 using appropriate reagents with suitable modifications. LCMS: 548.2 [M+H]⁺

Step 2: 4-((1H-pyrazol-1-yl)methyl)-N-(5-(1-(benzyloxy)-2-methylpropan-2-yl)-2-methoxyphenylsulfonimidoyl)-3-methoxybenzamide The title compound was prepared using a similar procedure to that described in Example 13 using appropriate reagents with suitable modifications. LCMS: 563.1 [M+H]⁺

Step 3: 4-((1H-Pyrazol-1-yl)methyl)-N-(5-(1-hydroxy-2-methylpropan-2-yl)-2-methoxyphenylsulfonimidoyl)-3-methoxybenzamide The title compound was prepared using a similar procedure to that described in Step 2 of Example 88 using appropriate reagents with suitable modifications. Crude compound was purified by preparative HPLC to obtain the racemic title compound (100 mg).

Step 4: Intermediate 132c was Separated by Chiral HPLC into its Respective Enantiomers (15 Mg (Peak 1)+20 mg (Peak 2)=(35 mg, 10.7%), with Arbitrary Assignment of Stereochemistry

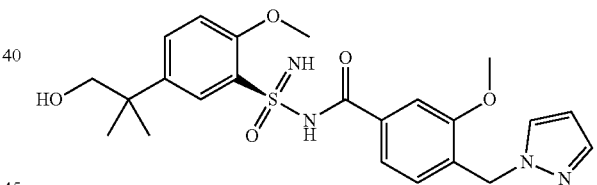

Compound-291a; LCMS: 473.2 [M+H]⁺; ¹H NMR (DMSO-D₆, 400 MHz): δ 7.87 (d, 1H), 7.75 (d, 1H), 7.59 (dd, 1H), −7.53-7.46 (m, 5H), 7.11 (d, 1H), 6.80 (d, 1H), 6.28 (dd, 1H), 5.32 (s, 2H), 4.77 (t, 1H), 3.86 (s, 3H), 3.79 (s, 3H), 3.40 (dd, 2H), 1.23 (d, 6H).

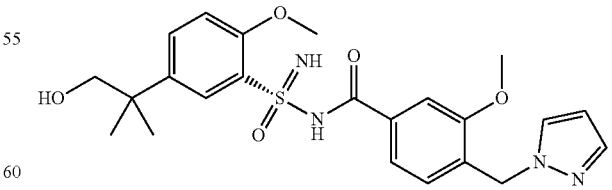

Compound-291b; LCMS: 473.2 [M+H]⁺; ¹H NMR (DMSO-D₆, 400 MHz): δ 7.85 (d, 1H), 7.76 (dd, 1H), 7.58 (dd, 1H), −7.53-7.46 (m, 5H), 7.11 (d, 1H), 6.80 (d, 1H), 6.28 (dd, 1H), 5.32 (s, 2H), 4.76 (t, 1H), 3.86 (s, 3H), 3.79 (s, 3H), 3.40 (d, 2H), 1.23 (d, 6H).

Example 24: 4-((1H-Pyrazol-1-yl)methyl)-N-((2,6-dimethoxyphenyl)(methylamino)(oxo)-16-sulfanelidene)-3-methoxybenzamide (Compound 292)

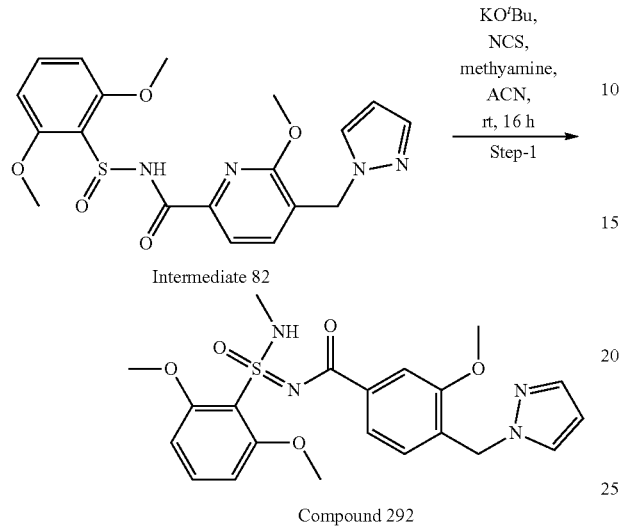

Intermediate 82

Compound 292

Step 1: 4-((1H-pyrazol-1-yl)methyl)-N-((2,6-dimethoxyphenyl)(methylamino)(oxo)-16-sulfaneylidene)-3-methoxybenzamide To a solution of 5-((1H-pyrazol-1-yl)methyl)-N-((2,6-dimethoxyphenyl)sulfinyl)-6-methoxypicolinamide (0.02 g, 0.048 mmol) in ACN (2.0 ml) was added potassium tert-butoxide (0.011 g, 0.09 mmol) followed by NCS (0.038 g, 0.28 mmol) and methylamine in THF (2.0M) (0.15 mL, 0.28 mmol) at 0° C. The reaction mixture was warmed to RT and stirred for 16 h. The reaction mixture was quenched with water and extracted with 10% methanol in DCM. The combined organic layers were washed with brine, dried over sodium sulphate, filtered, and concentrated to get the crude compound. Crude compound was purified by preparative TLC using 100% EtOAc as eluent (0.01 g, 46.87%). LC-MS: 445.1 [M+H]+; 1H NMR (CDCl3, 400 MHz): δ 7.71 (d, 1H), 7.69 (d, 1H), 7.54 (d, 1H), 7.47-7.42 (m, 2H), 7.14-7.11 (m, 1H), 6.96 (d, 1H), 6.66 (d, 2H), 6.26 (dd, 1H), 5.37 (s, 2H), 3.93 (s, 6H), 3.90 (s, 3H), 2.83 (d, 3H).

Example 25: 5-((1H-Pyrazol-1-yl)methyl)-N-(3-chloro-2,6-dimethoxyphenylsulfonimidoyl)-6-methoxypicolinamide (Compound 293a & 293b)

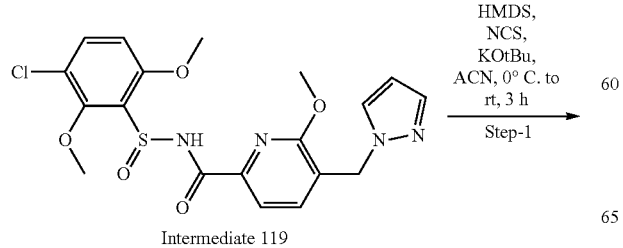

Intermediate 119

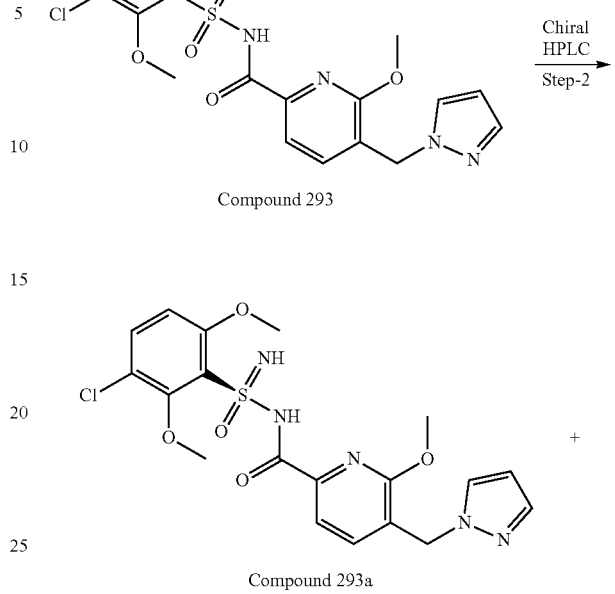

Compound 293

Compound 293a

Compound 293b

Step 1: Compound 293 was prepared using a similar procedure to that described in Example 13 using appropriate reagents with suitable modifications. Crude compound was purified by preparative HPLC to obtain the racemic title compound (70 mg).

Step 2: Compound 293 was separated by chiral HPLC into its respective enantiomers, with arbitrary assignment of stereochemistry

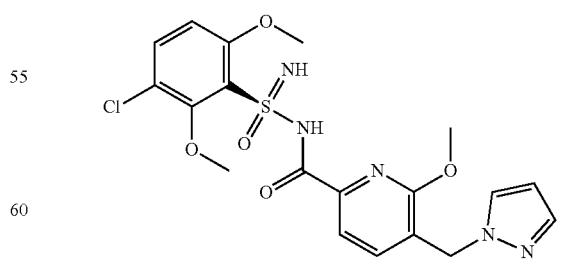

Compound 293a; LC-MS: 466.1 [M+H]+; 1H NMR (CDCl3, 400 MHz): δ 7.93 (d, 1H), 7.60 (d, 1H), 7.53-7.50 (m, 2H), 7.21 (d, 1H), 6.77 (d, 1H), 6.51 (d, 2H), 6.35 (dd, 1H), 5.38 (s, 2H), 4.12 (s, 3H), 4.05 (s, 3H), 3.80 (s, 3H).

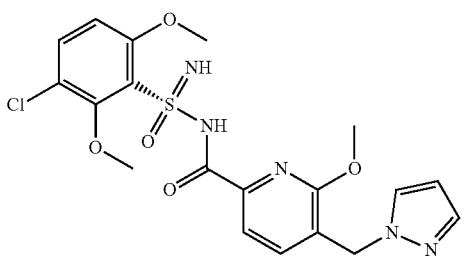 [SMILES: COc1ccc(Cl)c(OC)c1[S@@](=N)(=O)NC(=O)c1ccc(Cn2cccn2)c(OC)n1]

Compound 293b; LC-MS: 466.1 [M+H]⁺; H NMR (CDCl₃, 400 MHz): δ 7.93 (d, 1H), 7.60 (dd, 1H), 7.53-7.50 (m, 2H), 7.21 (d, 1H), 6.77 (d, 1H), 6.73 (brs, 2H), 6.35 (dd, 1H), 5.38 (s, 2H), 4.12 (s, 3H), 4.05 (s, 3H), 3.80 (s, 3H).

Example 26. Compounds 294, 294a, 294b, 295a, 295b, 296a, 296b, 297, 298a, 298b, 299, 299a, 299b, 300a, 300b, 301a, 301b, 302a, 302b, 303a, 303b, 304a, 304b, 305a. 305a, 306a, 306b, 307a, 307b, 308a, and 308b The following compounds listed in Table 17 were prepared by following a similar procedure as described above in Example 13 using appropriate reagents with suitable modifications known to the one skilled in the art.

TABLE 17

| Com. No | Structure | Intermediate/ Coupling example | Spectral data |
|---|---|---|---|
| 294 | (racemic) Exact Mass: 445.14 | Intermediate 120/ Example 13 | LC-MS: 446.2 [M + H]⁺; ¹H NMR (DMSO-D₆, 400 MHz): δ 7.80 (d, 1H), 7.59 (d, 1H), 7.49 (d, 1H), 7.32-7.28 (m, 1H), 7.14 (d, 1H), 6.68 (d, 2H), 6.29 (dd, 1H), 5.30 (s, 2H), 4.07-3.99 (m, 2H), 3.92 (s, 3H), 3.74 (s, 3H), 1.24 (t, 3H). |
| 294a | (peak 1) Exact Mass: 430.13 | Intermediate 120/ Example 13 | LC-MS: 446.05 [M + H]⁺; ¹H NMR (DMSO-D₆, 400 MHz): δ 7.82 (dd, 1H), 7.64 (d, 1H), 7.50 (dd, 1H), 7.45 (dd, 1H), 7.34 (brs, 2H), 7.17 (d, 1H), 6.77 (d, 1H), 6.76 (d, 1H), 6.31 (dd, 1H), 5.32 (s, 2H), 4.06 (q, 2H), 3.93 (s, 3H), 3.79 (s, 3H), 1.21 (t, 3H). |
| 294b | (peak 2) Exact Mass: 445.14 | Intermediate 120/ Example 13 | LC-MS: 446.1 [M + H]⁺; ¹H NMR (CDCl₃, 400 MHz): δ 7.97 (d, 1H), 7.60 (dd, 1H), 7.51 (dd, 1H), 7.40 (dd, 1H), 7.21 (d, 1H), 6.72 (brs, 2H), 6.63 (t, 2H, two H partially overlapped), 6.34 (dd, 1H), 5.38 (s, 2H), 4.15 (q, 2H), 4.12 (s, 3H), 3.79 (s, 3H), 1.38 (t, 3H). |
| 295a | (peak 1) Exact Mass: 430.13 | Intermediate 86/ Example 13 | LC-MS: 431.1 [M + H]⁺; ¹H NMR (DMSO-D₆, 400 MHz): δ 7.76 (d, 1H), 7.54 (d, 1H), 7.52-7.45 (m, 3H), 7.41 (brs, 2H), 6.80-6.76 (m, 3H), 6.28 (dd, 1H), 5.33 (s, 2H), 3.87 (s, 3H), 3.75 (s, 6H). |
| 295b | (peak 2) Exact Mass: 430.13 | Intermediate 86/ Example 13 | LC-MS: 431.1 [M + H]⁺; 1H NMR (DMSO-D₆, 400 MHz): δ 7.76 (d, 1H), 7.54 (d, 1H), 7.52-7.45 (m, 3H), 7.40 (brs, 2H), 6.80-6.75 (m, 3H), 6.28 (dd, 1H), 5.33 (s, 2H), 3.87 (s, 3H), 3.75 (s, 6H). |

TABLE 17-continued

| Com. No | Structure | Intermediate/ Coupling example | Spectral data |
|---|---|---|---|
| 296a | (peak 1) Exact Mass: 461.14 | Intermediate 85/ Example 13 | LC-MS: 462.2 [M + H]+; 1H NMR (DMSO-D6, 400 MHz): δ 7.82 (dd, 1H), 7.62 (d, 1H), 7.50 (dd, 1H), 7.31 (brs, 2H), 7.17 (d, 1H), 6.30 (dd, 1H), 6.29 (s, 2H), 5.32 (s, 2H), 3.93 (s, 3H), 3.83 (s, 3H), 3.76 (s, 6H). |
| 296b | (peak 2) Exact Mass: 461.14 | Intermediate 85/ Example 13 | LC-MS: 462.1 [M + H]+; 1H NMR (DMSO-D6, 400 MHz): δ 7.81 (dd, 1H), 7.60 (d, 1H), 7.50 (dd, 1H), 7.31 (brs, 2H), 7.17 (d, 1H), 6.30 (dd, 1H), 6.28 (s, 2H), 5.32 (s, 2H), 3.93 (s, 3H), 3.83 (s, 3H), 3.75 (s, 6H). |
| 297 | (racemic) Exact Mass: 459.16 | Intermediate 129/ Example 13 | LC-MS: 460.2 [M + H]+; 1H NMR (DMSO-D6, 400 MHz): δ 8.03 (d, 1H), 7.81 (d, 1H), 7.65 (dd, 1H), 7.61 (d, 1H), 7.50 (brs, 2H), 7.49 (d, 1H), 7.19 (d, 1H), 7.12 (d, 1H), 6.30 (dd, 1H), 5.31 (s, 2H), 5.17 (s, 1H), 3.93 (s, 3H), 3.80 (s, 3H), 1.44 (s, 6H). |
| 298a | (peak 1) Exact Mass: 471.16 | Intermediate 87/ Example 13 | LC-MS: 472.2 [M + H]+; 1H NMR (CDCl3, 400 MHz): δ 7.97 (d, 1H), 7.60 (d, 1H), 7.50 (d, 1H), 7.36 (dd, 1H), 7.24 (d, 1H), 6.60 (d, 1H), 6.48 (d, 1H), 6.34 (dd, 1H), 5.38 (s, 2H), 4.73-4.68 (m, 1H), 4.11 (s, 3H), 3.80 (s, 3H), 2.44-2.37 (m, 1H), 2.35-2.21 (m, 1H), 2.20-2.07 (m, 2H), 1.81-1.76 (m, 1H), 1.74-1.67 (m, 1H). |
| 298b | (peak 2) Exact Mass: 471.16 | Intermediate 87/ Example 13 | LC-MS: 472.2 [M + H]+; 1H NMR (CDCl3, 400 MHz): δ 7.97 (d, 1H), 7.60 (d, 1H), 7.50 (d, 1H), 7.36 (dd, 1H), 7.24 (d, 1H), 6.60 (d, 1H), 6.48 (d, 1H), 6.34 (dd, 1H), 5.38 (s, 2H), 4.73-4.69 (m, 1H), 4.12 (s, 3H), 3.81 (s, 3H), 2.44-2.39 (m, 1H), 2.31-2.25 (m, 1H), 2.19-2.06 (m, 2H), 1.79-1.75 (m, 1H), 1.67-1.59 (m, 1H). |
| 299 | (racemic) Exact Mass: 460.14 | Intermediate 127/ Example 13 | LC-MS: 461.1 [M + H]+; 1H NMR (DMSO-D6, 400 MHz): δ 7.76 (d, 1H), 7.54 (d, 1H), 7.50 (d, 1H), 7.47 (d, 1H), 7.27 (brs, 2H), 6.79 (d, 1H), 6.28 (s, 3H), 5.32 (s, 2H), 3.87 (s, 3H), 3.83 (s, 3H), 3.74 (s, 6H). |

TABLE 17-continued

| Com. No | Structure | Intermediate/ Coupling example | Spectral data |
|---|---|---|---|
| 299a | (peak 1) Exact Mass: 460.14 | Intermediate 127/ Example 13 | LC-MS: 461.2 [M + H]$^+$; $^1$H NMR (DMSO-D$_6$, 400 MHz): δ 7.76 (dd, 1H), 7.54 (d, 1H), 7.51 (dd, 1H), 7.47 (dd, 1H), 7.29 (brs, 2H), 6.79 (d, 1H), 6.28 (s, 3H), 5.33 (s, 2H), 3.87 (s, 3H), 3.83 (s, 3H), 3.74 (s, 6H). |
| 299b | (peak 2) Exact Mass: 460.14 | Intermediate 127/ Example 13 | LC-MS: 461.1 [M + H]$^+$; $^1$H NMR (DMSO-D$_6$, 400 MHz): δ 7.76 (dd, 1H), 7.53 (d, 1H), 7.51 (dd, 1H), 7.47 (dd, 1H), 7.29 (brs, 2H), 6.79 (d, 1H), 6.28 (s, 3H), 5.32 (s, 2H), 3.87 (s, 3H), 3.83 (s, 3H), 3.74 (s, 6H). |
| 300a | (peak 1) Exact Mass: 484.10 | Intermediate 130/ Example 13 | LC-MS: 485.1 [M + H]$^+$; $^1$H NMR (DMSO-D$_6$, 400 MHz): δ 7.90-7.85 (m, 3H), 7.51-7.46 (m, 4H), 7.10 (d, 1H), 6.78 (d, 2H), 6.32 (dd, 1H), 5.47 (s, 2H), 3.74 (s, 6H). |
| 300b | (peak 2) Exact Mass: 484.10 | Intermediate 130/ Example 13 | LC-MS: 485.1 [M + H]$^+$; $^1$H NMR (DMSO-D$_6$, 400 MHz): δ 7.90-7.85 (m, 3H), 7.51-7.46 (m, 4H), 7.10 (d, 1H), 6.77 (s, 2H), 6.32 (dd, 1H), 5.47 (s, 2H), 3.74 (s, 6H). |
| 301a | (peak 1) Exact Mass: 445.14 | Intermediate 126/ Example 13 | LC-MS: 446.1 [M + H]$^+$; $^1$H NMR (DMSO-D$_6$, 400 MHz): δ 7.82 (d, 1H), 7.64 (d, 1H), 7.50 (d, 1H), 7.45 (brs, 2H), 7.40 (d, 1H), 7.17 (d, 1H), 6.89 (d, 1H), 6.30 (dd, 1H), 5.32 (s, 2H), 3.92 (s, 3H), 3.76 (s, 6H), 2.18 (s, 3H). |
| 301b | (peak 2) Exact Mass: 445.14 | Intermediate 126/ Example 13 | LC-MS: 446.1 [M + H]$^+$; $^1$H NMR (DMSO-D$_6$, 400 MHz): δ 7.82 (dd, 1H), 7.62 (d, 1H), 7.50 (dd, 1H), 7.36 (d, 1H), 7.26 (brs, 2H), 7.17 (d, 1H), 6.87 (d, 1H), 6.30 (dd, 1H), 5.32 (s, 2H), 3.92 (s, 3H), 3.76 (s, 6H), 2.17 (s, 3H). |

TABLE 17-continued

| Com. No | Structure | Intermediate/ Coupling example | Spectral data |
|---|---|---|---|
| 302a | 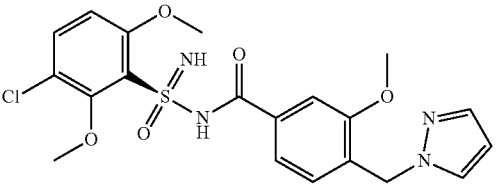 [SMILES: COc1cc(C(=O)N[S@@](=N)(=O)c2c(OC)ccc(Cl)c2OC)ccc1Cn1cccn1]<br>(peak 1)<br>Exact Mass: 464.09 | Intermediate 131/ Example 13 | LC-MS: 465.1 [M + H]$^+$; $^1$H NMR (CDCl$_3$, 400 MHz): δ 7.81 (dd, 1H), 7.76 (d, 1H), 7.58 (dd, 1H), 7.52 (d, 1H), 7.48 (dd, 1H), 6.97 (d, 1H), 6.77 (d, 1H), 6.31 (dd, 1H), 5.42 (s, 2H), 4.02 (s, 3H), 3.95 (s, 3H), 3.73 (s, 3H). |
| 302b | 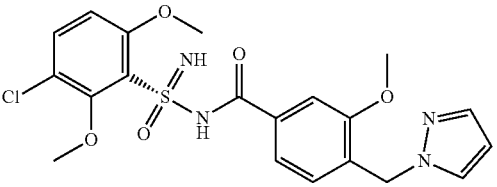 [SMILES: COc1cc(C(=O)N[S@](=N)(=O)c2c(OC)ccc(Cl)c2OC)ccc1Cn1cccn1]<br>(peak 2)<br>Exact Mass: 464.09 | Intermediate 131/ Example 13 | LC-MS: 465.1 [M + H]$^+$; $^1$H NMR (CDCl$_3$, 400 MHz): δ 7.81 (dd, 1H), 7.76 (d, 1H), 7.58 (dd, 1H), 7.52 (d, 1H), 7.48 (dd, 1H), 6.97 (d, 1H), 6.77 (d, 1H), 6.31 (dd, 1H), 5.42 (s, 2H), 4.02 (s, 3H), 3.95 (s, 3H), 3.73 (s, 3H). |
| 303a | 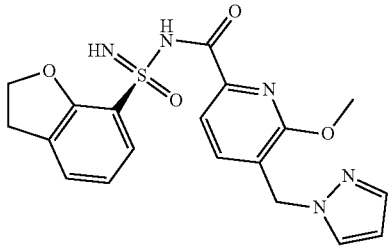 [SMILES: COc1nc(C(=O)N[S@@](=N)(=O)c2cccc3c2OCC3)ccc1Cn1cccn1]<br>(peak 1)<br>Exact Mass: 413.12 | Intermediate 121/ Example 13 | LC-MS: 414.1 [M + H]$^+$; $^1$H NMR (DMSO-D$_6$, 400 MHz): δ 7.80 (dd, 1H), 7.62-7.57 (m, 2H), 7.49 (dd, 1H), 7.43 (d, 1H), 7.19 (d, 1H), 6.95 (dd, 1H), 6.30 (dd, 1H), 5.31 (s, 2H), 4.62-4.56 (m, 2H), 3.92 (s, 3H), 3.20 (t, 2H). |
| 303b | 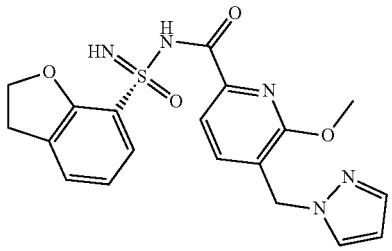 [SMILES: COc1nc(C(=O)N[S@](=N)(=O)c2cccc3c2OCC3)ccc1Cn1cccn1]<br>(peak 2)<br>Exact Mass: 413.12 | Intermediate 121/ Example 13 | LC-MS: 414.1 [M + H]$^+$; $^1$H NMR (DMSO-D$_6$, 400 MHz): δ 7.81 (dd, 1H), 7.62-7.58 (m, 2H), 7.49 (dd, 1H), 7.44 (dd, 1H), 7.19 (d, 1H), 6.96 (dd, 1H), 6.30 (dd, 1H), 5.31 (s, 2H), 4.62-4.57 (m, 2H), 3.92 (s, 3H), 3.21 (t, 2H). |
| 304a | 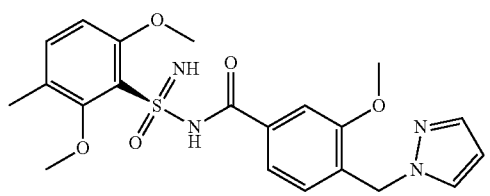<br>(peak 1)<br>Exact Mass: 444.15 | Intermediate 128/ Example 13 | LC-MS: 445.1 [M + H]$^+$; $^1$H NMR (DMSO-D$_6$, 400 MHz): δ 7.77 (dd, 1H), 7.53 (dd, 1H), 7.51 (d, 1H), 7.47 (dd, 1H), 7.42 (brs, 2H), 7.39 (d, 2H), 6.88 (d, 1H), 6.79 (d, 1H), 6.28 (dd, 1H), 5.32 (s, 2H), 3.87 (s, 3H), 3.76 (s, 3H), 3.75 (s, 3H), 2.18 (s, 3H). |
| 304b | 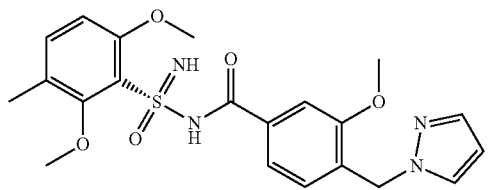 [SMILES: COc1cc(C(=O)N[S@](=N)(=O)c2c(OC)ccc(C)c2OC)ccc1Cn1cccn1]<br>(peak 2)<br>Exact Mass: 444.15 | Intermediate 128/ Example 13 | LC-MS: 445.2 [M + H]$^+$; $^1$H NMR (DMSO-D$_6$, 400 MHz): δ 7.77 (dd, 1H), 7.55 (dd, 1H), 7.51 (dd, 1H), 7.47 (dd, 1H), 7.37 (d, 1H), 6.87 (d, 1H), 6.78 (d, 1H), 6.28 (dd, 1H), 5.32 (s, 2H), 3.86 (s, 3H), 3.75 (s, 3H), 3.74 (s, 3H), 2.17 (s, 3H). |

| Com. No | Structure | Intermediate/ Coupling example | Spectral data |
|---|---|---|---|
| 305a | 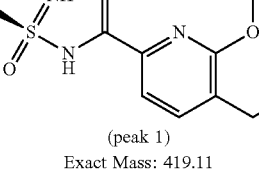<br>(peak 1)<br>Exact Mass: 419.11 | Intermediate 122/ Example 13 | LC-MS: 420.1 [M + H]$^+$; $^1$H NMR (DMSO-D$_6$, 400 MHz): δ 7.81 (dd, 1H), 7.74 (brs, 2H), 7.61(d, 1H) 7.59-7.55 (m, 1H), 7.49 (dd, 1H), 7.19 (d, 1H), 7.02 (d, 1H), 6.95-6.90 (m, 1H), 6.30 (dd, 1H), 5.32 (s, 2H), 3.92 (s, 3H), 3.84 (s, 3H). |
| 305b | 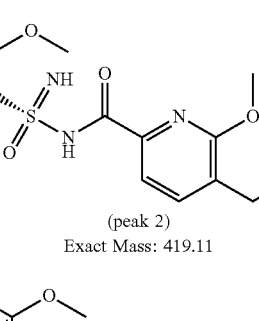<br>(peak 2)<br>Exact Mass: 419.11 | Intermediate 122/ Example 13 | LC-MS: 420.1 [M + H]$^+$; $^1$H NMR (DMSO-D6, 400 MHz): δ 7.81 (dd, 1H), 7.74 (brs, 2H), 7.61 (d, 1H), 7.59-7.54 (m, 1H), 7.49 (dd, 1H), 7.19 (d, 1H), 7.01 (d, 1H), 6.95-6.90 (m, 1H), 6.30 (dd, 1H), 5.32 (s, 2H), 3.92 (s, 3H), 3.84 (s, 3H). |
| 306a | 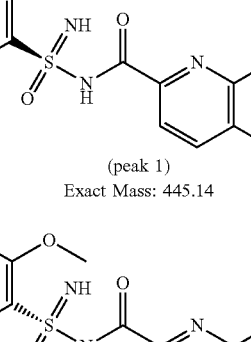<br>(peak 1)<br>Exact Mass: 445.14 | Intermediate 123/ Example 13 | LC-MS: 446.2 [M + H]$^+$; $^1$H NMR (CDCl$_3$, 400 MHz): δ 7.96 (d, 1H), 7.60 (d, 1H), 7.51 (d, 1H), 7.21 (d, 1H), 6.65 (brs, 2H), 6.44 (s, 2H), 6.34 (dd, 1H), 5.41-5.33 (m, 2H), 4.12 (s, 3H), 3.81 (s, 6H), 2.36 (s, 3H). |
| 306b | 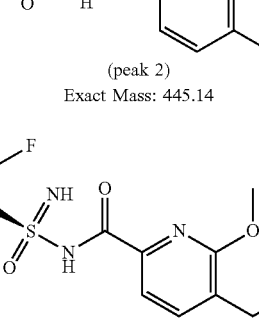<br>(peak 2)<br>Exact Mass: 445.14 | Intermediate 123/ Example 13 | LC-MS: 446.1 [M + H]$^+$; $^1$H NMR (CDCl$_3$, 400 MHz): δ 7.96 (d, 1H), 7.60 (dd, 1H), 7.51 (d, 1H), 7.20 (d, 1H), 6.63 (brs, 2H), 6.44 (s, 2H), 6.34 (dd, 1H), 5.41-5.33 (m, 2H), 4.12 (s, 3H), 3.81 (s, 6H), 2.36 (s, 3H). |
| 307a | 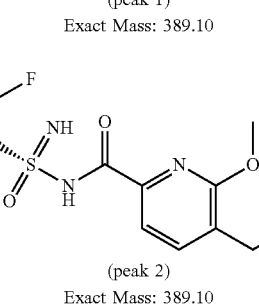<br>(peak 1)<br>Exact Mass: 389.10 | Intermediate 124/ Example 13 | LC-MS: 390.1 [M + H]$^+$; $^1$H NMR (DMSO-D$_6$, 400 MHz): δ 8.05 (brs, 2H), 7.98-7.94 (m, 1H), 7.81 (dd, 1H), −7.72-7.62 (m, 2H), 7.49 (dd, 1H), 7.44-7.37 (m, 2H), 7.20 (d, 1H), 6.30 (dd, 1H), 5.32 (s, 2H), 3.93 (s, 3H). |
| 307b | 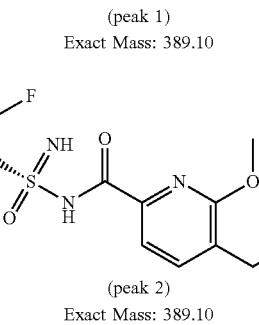<br>(peak 2)<br>Exact Mass: 389.10 | Intermediate 124/ Example 13 | LC-MS: 390.0 [M + H]$^+$; $^1$H NMR (DMSO-D$_6$, 400 MHz): δ 8.06 (brs, 2H), 7.98-7.94 (m, 1H), 7.81 (dd, 1H), −7.71-7.69 (m, 1H), 7.64 (d, 1H), 7.49 (dd, 1H), 7.43-7.38 (m, 2H), 7.21 (d, 1H), 6.30 (dd, 1H), 5.32 (s, 2H), 3.93 (s, 3H). |

TABLE 17-continued

| Com. No | Structure | Intermediate/ Coupling example | Spectral data |
|---|---|---|---|
| 308a | (peak 1) Exact Mass: 407.09 | Intermediate 125/ Example 13 | LC-MS: 408.0 [M + H]$^+$; $^1$H NMR (DMSO-D$_6$, 400 MHz): δ 8.36 (brs, 2H), 7.81 (dd, 1H), −7.72-7.63 (m, 2H), 7.50 (dd, 1H), 7.29-7.20 (m, 3H), 6.30 (dd, 1H), 5.32 (s, 2H), 3.93 (s, 3H). |
| 308b | (peak 2) Exact Mass: 407.09 | Intermediate 125/ Example 13 | LC-MS: 408.0 [M + H]$^+$; $^1$H NMR (DMSO-D$_6$, 400 MHz): δ 7.80 (dd, 1H), −7.61-7.60 (m, 2H), 7.50 (dd, 1H), 7.20-7.16 (m, 3H), 6.29 (dd, 1H), 5.31 (s, 2H), 3.92 (s, 3H) |

Example 27. Compounds 309, 310, 311, and 312

The following compounds listed in Table 18 were prepared by following a similar procedure as described above in Step 1 of Example 1 using appropriate reagents with suitable modifications known to the one skilled in the art.

TABLE 18

| Com. No | Structure | Intermediates/ Coupling example | LC-MS and $^1$H NMR (400 MHz, DMSO-d$_6$) unless otherwise shown |
|---|---|---|---|
| 309 | 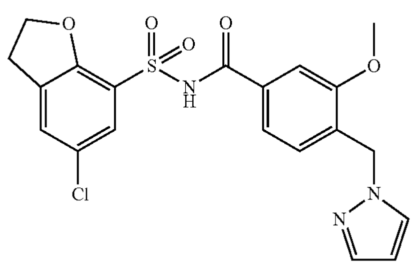 [SMILES: COc1cc(C(=O)NS(=O)(=O)c2cc(Cl)cc3c2OCC3)ccc1Cn1cccn1] | Intermediate 2/ Example 1 | LCMS: 448.0 [M + H]$^+$ $^1$H NMR (400 MHz, DMSO) δ 7.75 (d, J = 2.3 Hz, 1H), 7.54-7.50 (m, 2H), 7.47-7.41 (m, 2H), 6.77 (d, J = 7.8 Hz, 1H), 6.53 (d, J = 3.0 Hz, 1H), 6.27 (t, J = 2.1 Hz, 1H), 5.31 (s, 2H), 4.60 (s, 2H), 3.87 (s, 3H), 3.19 (t, J = 8.9 Hz, 2H). |
| 310 | 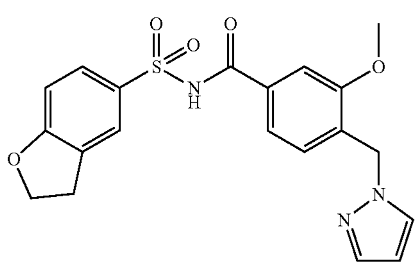 [SMILES: COc1cc(C(=O)NS(=O)(=O)c2ccc3c(c2)CCO3)ccc1Cn1cccn1] | Intermediate 2/ Example 1 | LCMS: 414.1 [M + H]$^+$ $^1$H NMR (400 MHz, DMSO) δ 7.83 (d, J = 1.9 Hz, 1H), 7.77 (dt, J = 5.6, 2.4 Hz, 2H), 7.49 (dd, J = 12.7, 1.7 Hz, 2H), 7.41 (dd, J = 7.9, 1.7 Hz, 1H), 6.96 (d, J = 8.5 Hz, 1H), 6.79 (d, J = 7.9 Hz, 1H), 6.28 (t, J = 2.1 Hz, 1H), 5.33 (s, 2H), 4.66 (t, J = 8.8 Hz, 2H), 3.90 (s, 3H), 3.27 (t, J = 8.8 Hz, 2H). |

TABLE 18-continued

| Com. No | Structure | Intermediates/ Coupling example | LC-MS and ¹H NMR (400 MHz, DMSO-$d_6$) unless otherwise shown |
|---|---|---|---|
| 311 | 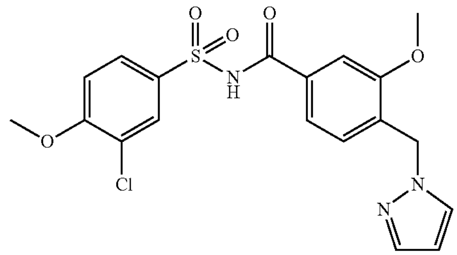 [SMILES: COc1ccc(S(=O)(=O)NC(=O)c2ccc(Cn3cccn3)c(OC)c2)cc1Cl] | Intermediate 2/ Example 1 | LCMS: 436.0 [M + H] 1H NMR (400 MHz, DMSO) δ 7.94 (d, J = 2.2 Hz, 1H), 7.90 (dd, J = 8.7, 2.3 Hz, 1H), 7.76 (dd, J = 2.2, 0.7 Hz, 1H), 7.50 (d, J = 1.6 Hz, 1H), 7.47 (dd, J = 1.9, 0.6 Hz, 1H), 7.41 (dd, J = 7.9, 1.6 Hz, 1H), 7.33 (d, J = 8.8 Hz, 1H), 6.78 (d, J = 7.9 Hz, 1H), 6.28 (t, J = 2.1 Hz, 1H), 5.32 (s, 2H), 3.95 (s, 3H), 3.88 (s, 3H). |
| 312 | 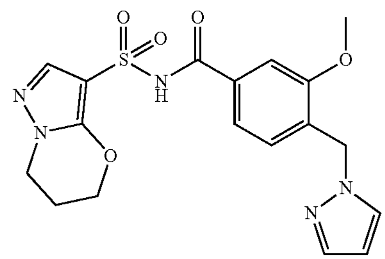 [SMILES: COc1cc(C(=O)NS(=O)(=O)c2cnn3c2OCCC3)ccc1Cn1cccn1] | Intermediate 2/ Example 1 | LCMS: m/z = 418.1 [M + H]⁺ |

Example 28: (Compound 313) 4-((1H-pyrazol-1-yl)methyl)-N-((2-cyclopropoxyphenyl)sulfonyl)-3-methoxybenzamide

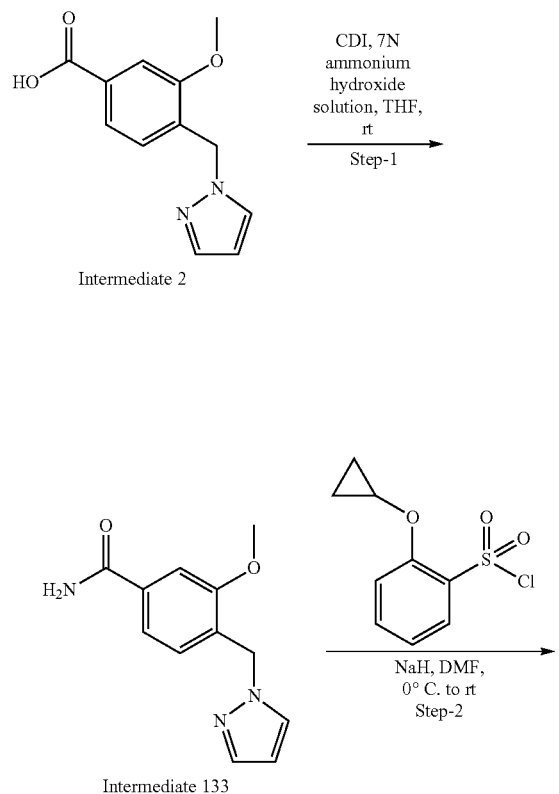

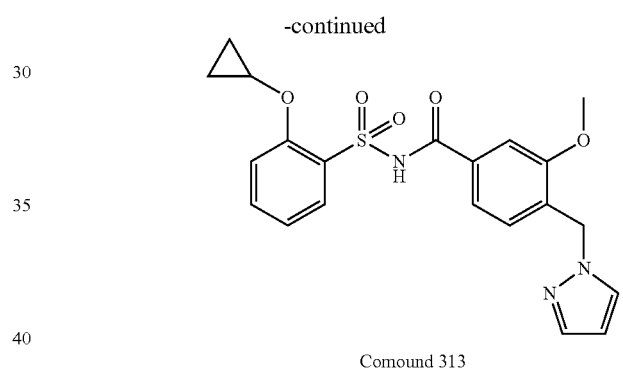

Comound 313

Step 1: 4-((1H-pyrazol-1-yl)methyl)-3-methoxybenzamide 3-Methoxy-4-(pyrazol-1-ylmethyl)benzoic acid (216 mg, 0.93 mmol) and CDI (226 mg, 1.40 mmol) were dissolved in THF (3 mL) and stirred for 1 h. 7 N ammonium hydroxide solution (0.770 mL) was added and stirred for 16 h. The solution was diluted with water, neutralized with 1 N HCl, and extracted with EtOAc. The organics were washed with 1 N HCl, water, and brine solution. They were then dried over sodium sulfate, filtered, and dried in-vacuo to give the title product (140 mg, 65% yield). LCMS: m/z=232.2 [M+H]⁺.

Step 2: 4-((1H-pyrazol-1-yl)methyl)-N-((2-cyclopropoxyphenyl)sulfonyl)-3-methoxybenzamide
3-Methoxy-4-(pyrazol-1-ylmethyl)benzamide (0.04 g, 0.17 mmol) was dissolved in DMF (0.15-0.3 M) and cooled to 0° C. and 90% sodium hydride (0.09 g, 0.34 mmol) was added and stirred for 30 min. Arylsulfonyl chloride (0.044 g, 0.19 mmol) was added and stirred for 2 h, allowing to warm to room temperature. The reaction was directly purified by HPLC on a Kintetex 5 um C18 100 Å column (size: 100×30.0 mm; gradient: 5-55% 0.1% formic acid in ACN in 0.1% formic acid in water) then lyophilized to give the title compound as a white solid. (9 mg). LCMS: m/z=428.1 [M+H]L; ¹H NMR (400 MHz, DMSO) δ 12.58 (s, 1H), 7.96-7.80 (m, 1H), 7.78 (d, J=5.9 Hz, 1H), 7.55 (s, 1H), 7.49 (dd, J=6.4, 1.5 Hz, 1H), 7.41 (dd, J=7.9, 1.6 Hz, 1H), 7.24-7.34 (m, 1H), 6.88-6.92 (m, 1H), 6.74 (d, J=7.9 Hz, 1H), 6.58-6.52 (m, 1H), 6.33-6.27 (m, 1H), 5.33 (s, 2H), 3.89 (s, 3H), 2.36-2.41 (i, 1H), 0.77-0.60 (m, 2H), 0.54-0.37 (in, 2H).

Example 29. Compounds 314 and 315

The following compounds listed in Table 19 were prepared by following a similar procedure as described above in Step 2 of Example 28 using appropriate reagents with suitable modifications known to the one skilled in the art.

TABLE 19

| Com. No | Structure | Intermediates/ Coupling example | LC-MS and $^1$H NMR (400 MHz, DMSO-$d_6$) unless otherwise shown |
|---|---|---|---|
| 314 | 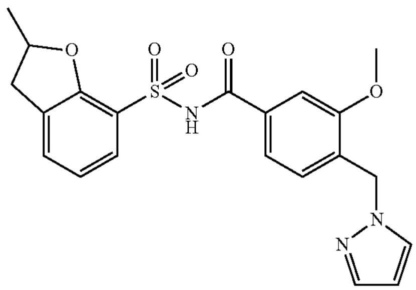 | Intermediate 133/ Example 28 | LCMS: [M + H]$^+$; $^1$H NMR (400 MHz, DMSO) δ 12.56 (s, 1H), 7.77 (d, J = 2.3 Hz, 1H), 7.58 (d, J = 7.7 Hz, 1H), 7.51 (dd, J = 29.4, 1.7 Hz, 2H), 7.42 (dd, J = 7.8, 1.6 Hz, 1H), 6.95 (s, 1H), 6.77 (d, J = 7.9 Hz, 1H), 6.53 (s, 1H), 6.28 (t, J = 2.1 Hz, 1H), 5.32 (s, 2H), 3.89 (s, 3H), 2.79 (dd, J = 15.9, 7.0 Hz, 1H), 2.38 (d, J = 6.0 Hz, 2H) 1.28 (d, J = 6.2 Hz, 3H). |
| 315 | | Intermediate 133/ Example 28 | LCMS: 414.4 [M + H]$^+$; $^1$H NMR (400 MHz, DMSO) δ 7.75 (s, 1H), 7.54 (d, J = 1.5 Hz, 2H), 7.46 (d, J = 1.8 Hz, 1H), 7.42 (dd, J = 7.8, 1.5 Hz, 1H), 6.77 (d, J = 7.8 Hz, 1H), 6.53 (d, J = 3.2 Hz, 1H), 6.33-6.28 (m, 1H), 6.27 (t, J = 2.1 Hz, 1H), 5.31 (s, 2H), 4.56 (s, 2H), 3.87 (s, 3H), 3.18 (s, 2H). | f) Biological Examples

Example 30. KAT6A Biochemical Assay

TR-FRET based methods were used for assaying compounds of the present invention for KAT6A enzyme inhibitory activity. TR-FRET is a homogeneous proximity assay where Europium-labelled anti-acetyl lysine antibody binds to the acetylated substrate labelled with biotin, which in turn binds to streptavidin-labelled APC fluorescence acceptor. Europium can transfer energy to APC in the complex and the interaction of two dye-labelled binding partners is detected by the energy transfer between a donor and an acceptor dye and the subsequent light emission by the acceptor dye. KAT6A transfer an acetyl group from acetyl CoA to lysine amino acids of histones/target proteins. Typically, 5 μL of human-KAT6A (MYST domain 507-778 aa) in assay buffer (100 mM Tris HCl (pH 7.8), 15 mM NaCl, 1 mM EDTA, 0.01% Tween-20, 0.02% BSA, 1 mM DTT) is added to 384-well plate containing 5 μL of selected test compound in final 1% DMSO, serially diluted in 1:3 in an 8-10-point titration. The selected compound of the present invention and enzyme are incubated for 30 min on plate shaker at 300 rpm at 25° C. Next, 5 μL of substrate mix containing histone H4 peptide and acetyl-CoA in assay buffer is added to the plate. The final concentrations of H4 peptide and acetyl-CoA are 200 nM and 600 nM, respectively. Following 60 min reaction at 25° C. on plate shaker at 300 rpm, 5 μL of detection mix containing Europium-labelled anti-acetyl antibody and streptavidin-APC is added to the reaction wells. The plate is further incubated at 25° C. on shaker at 300 rpm and is read in TR-FRET mode (Ex: 340 nm; Em: 615 nm and 665 nm) on a plate reader to achieve 5-7-fold activity. The percent inhibition was calculated from the ratio of the fluorescence (FL) intensities [(F665/F615)×10000] using the formula (Control FL ratio—(Sample FL ratio/Control FL ratio))×100. IC$_{50}$ values of the compounds were determined by fitting the dose-response data to sigmoidal curve fitting equation using Graph pad prism software V9. The results are summarized in Table 20 below.

TABLE 20

| KAT6A Activity | |
|---|---|
| Compound | KAT6A IC$_{50}$ (nM)* |
| 1 | 247 |
| 2 | 741 |
| 3 | 137 |
| 4 | 82 |
| 5 | 178 |
| 6 | *26% @ 10 μM |

TABLE 20-continued

KAT6A Activity

| Compound | KAT6A IC$_{50}$ (nM)* |
|---|---|
| 7 | 99 |
| 8 | 17 |
| 9 | *13% @ 10 μM |
| 10 | 1484 |
| 11 | 500 |
| 12 | 48 |
| 13 | 47 |
| 14 | 32, 7 |
| 15 | 576 |
| 16 | 26 |
| 17 | 20 |
| 18 | 70 |
| 19 | 42 |
| 20 | 39 |
| 21 | 28 |
| 22 | 49 |
| 23 | 32 |
| 24 | 12 |
| 25 | 10 |
| 26 | 25 |
| 27 | 12 |
| 28 | 19 |
| 29 | 10 |
| 30 | 11 |
| 31 | 44 |
| 32 | 16 |
| 33 | 10 |
| 34 | 36 |
| 35 | 30 |
| 36 | 198 |
| 37 | 10 |
| 38 | — |
| 39 | 24 |
| 40 | 15 |
| 41 | *35% @ 1 μM |
| 42 | 8 |
| 43 | 18 |
| 44 | 9 |
| 45 | 10 |
| 46 | 12 |
| 47 | 9 |
| 48 | 51 |
| 49 | 8 |
| 50 | 96 |
| 51 | 51 |
| 52 | 9 |
| 53 | 31 |
| 54 | 3 |
| 55 | 11 |
| 56 | 7 |
| 57 | 11 |
| 58 | 177 |
| 59 | 33 |
| 60 | 8 |
| 61 | 6 |
| 62 | 32 |
| 63 | 17 |
| 64 | 112 |
| 65 | 135 |
| 66 | 13 |
| 67 | 11 |
| 68 | 23 |
| 69 | 114 |
| 70 | — |
| 71 | 34 |
| 201 | 731 |
| 202 | 104 |
| 203 | 9 |
| 204 | 6 |
| 205 | 8 |
| 206 | 8 |
| 207 | 10 |
| 208 | 22 |
| 209 | 71 |
| 210 | 64 |
| 211 | 8 |
| 212 | 140 |
| 213 | 12 |
| 214 | 12 |
| 215 | *16% @ 1 μM |
| 216 | 12 |
| 217 | 11 |
| 218 | 8 |
| 219 | 9 |
| 220 | 7 |
| 221 | 5 |
| 222 | 18 |
| 223 | 17 |
| 224 | 11 |
| 225 | 10 |
| 226 | 27 |
| 227 | 11 |
| 228 | 21 |
| 229 | 13 |
| 230 | 11 |
| 231 | 14 |
| 232 | 95 |
| 233 | 94 |
| 234 | 42 |
| 235 | 7 |
| 236 | 4 |
| 237 | 44 |
| 238 | 37 |
| 239 | 12 |
| 240 | 11 |
| 241 | 10 |
| 242 | 10 |
| 243 | 23 |
| 243a | 17 |
| 243b | 82 |
| 244 | 14 |
| 245 | 12 |
| 253 | 9 |
| 261 | 38 |
| 262 | 115 |
| 263 | 36 |
| 264 | 12 |
| 265 | 14 |
| 266 | 10 |
| 267 | 45% @ 1 μM |
| 268 | 16 |
| 269 | 12 |
| 270 | 6 |
| 271 | 37 |
| 272 | 33 |
| 273 | 34 |
| 274 | 30 |
| 275 | 10 |
| 276 | 10 |
| 277 | 14 |
| 278 | 25% @ 1 μM |
| 279 | 14 |
| 280 | 5 |
| 281 | 10 |
| 282 | 14 |
| 283 | 10 |
| 284 | 10 |
| 285 | 6 |
| 286 | 11 |
| 287 | 11 |
| 288 | 8 |
| 289 | 19 |
| 290a | 14 |
| 290b | 33 |
| 291a | 93 |
| 291b | 9 |
| 292 | 47% @ 1 μM |
| 293a | 374 |
| 293b | 16 |
| 294 | 35 |
| 294a | 271 |
| 294b | 22 |

303

TABLE 20-continued

KAT6A Activity

| Compound | KAT6A IC$_{50}$ (nM)* |
|---|---|
| 295a | 16 |
| 295b | 271 |
| 296a | 16 |
| 296b | 677 |
| 297 | 39 |
| 298a | 23 |
| 298b | 511 |
| 299 | 25 |
| 299a | 15 |
| 299b | 226 |
| 300a | 125 |
| 300b | 18 |
| 301a | 313 |
| 301b | 17 |
| 302a | 21 |
| 302b | 304 |
| 303a | 26 |
| 303b | 108 |
| 304a | 18 |
| 304b | 130 |
| 305a | 15 |
| 305b | 318 |
| 306a | 12 |
| 306b | 280 |
| 307a | 108 |
| 307b | 46% @ 1 μM |
| 308a | 1584 |
| 308b | 49 |
| 309 | 17 |
| 310 | 112 |
| 311 | 135 |
| 312 | — |
| 313 | 32 |
| 314 | 13 |
| 315 | — |

*Percent inhibition at specific concentration reported where IC$_{50}$ could not be determined.

Example 31. Cell Proliferation for Drug Combination Analysis

Figure 2:
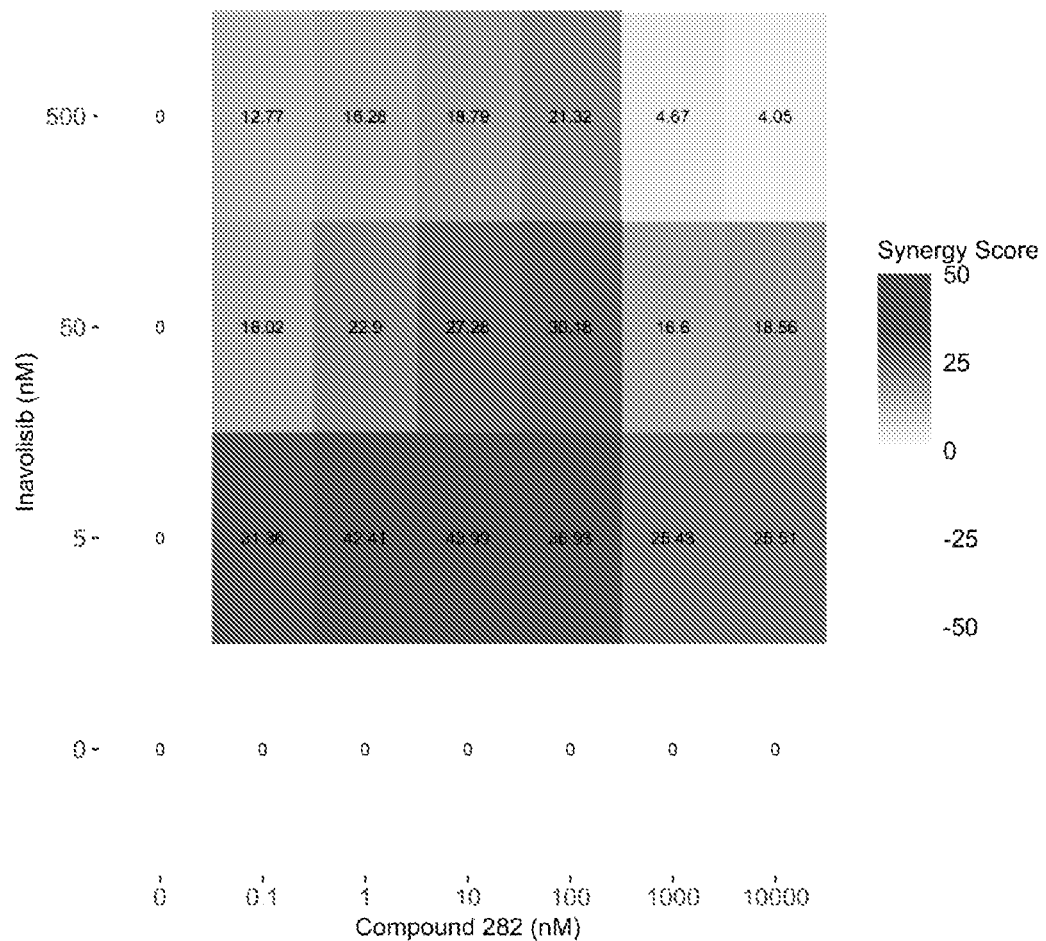
FIG. 2 provides synergy scores of Compound 282 in combination with inavolisib at various concentrations.
Figure 3:
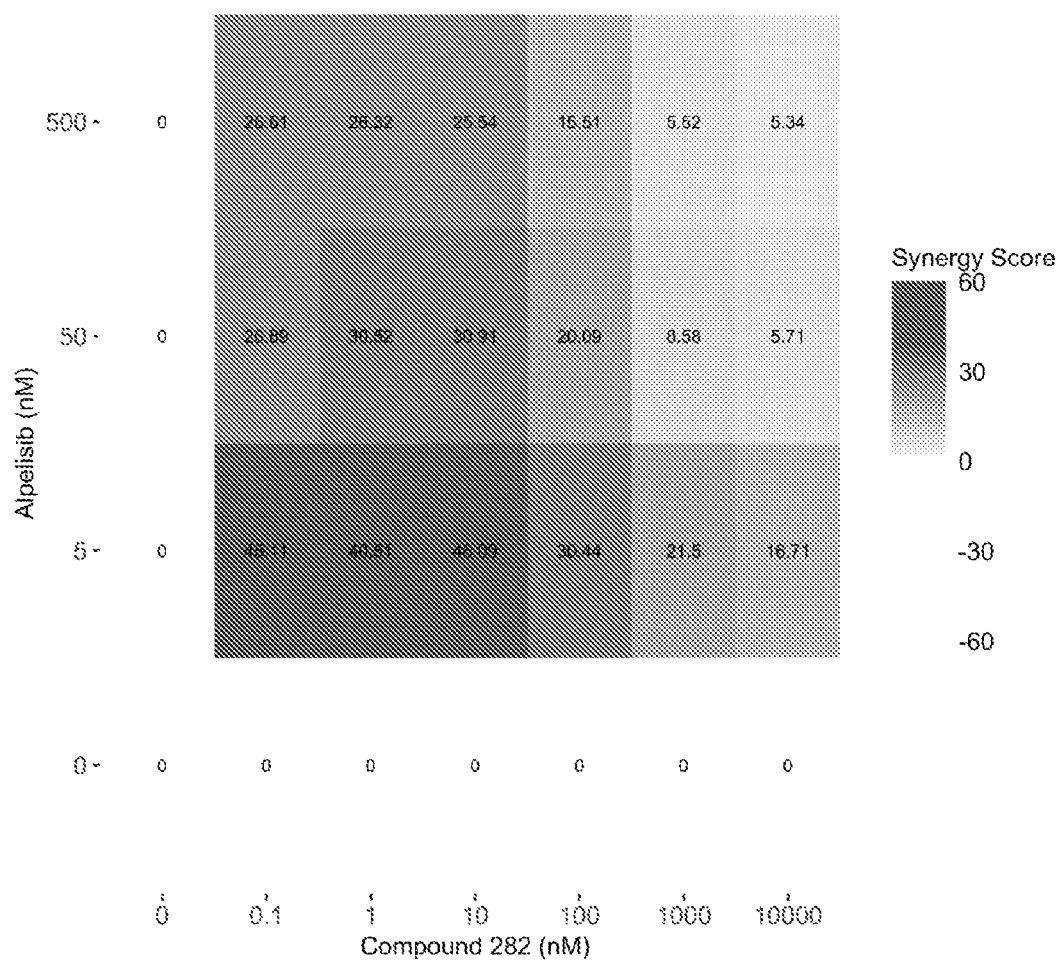
FIG. 3 provides synergy scores of Compound 282 in combination with alpelisib at various concentrations.

Cells were plated in 96-wp at optimized densities in appropriate complete medium and incubated for ~36 hours before being treated with serial dilutions of compounds for 7, 10 or 14-days. Cell number was assessed using CTG and normalized to T=0. Synergism was evaluated using the Zero Interaction Potency (ZIP) model, assuming that the combined effect of two molecules is the sum of their individual responses, without any interaction. Deviations from this predicted combined effect indicate either synergy (greater effect) or antagonism (lesser effect). FIG. 1 provides synergy scores of Compound 282 in combination with everolimus at various concentrations. FIG. 2 provides synergy scores of Compound 282 in combination with inavolisib at various concentrations. FIG. 3 provides synergy scores of Compound 282 in combination with alpelisib at various concentrations.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

304

What is claimed is:

1. A compound of Formula (IIc):

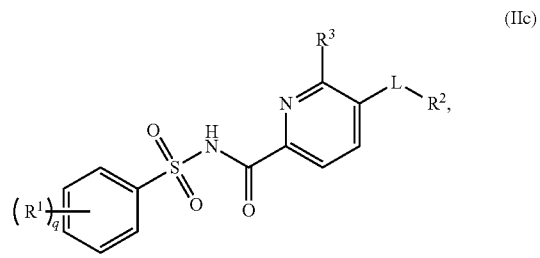

(IIc)

or a pharmaceutically acceptable salt thereof, wherein:

each $R^1$ is independently —CH$_3$, —CH$_2$CH$_3$, —C(CH$_3$)$_3$, —OCH$_3$, —OCH(CH$_3$)$_2$, —C(CH$_3$)$_2$OH, —C(CH$_3$)(CH$_2$CH$_3$)OH, —F, —Cl, —Br, —CF$_3$, —OCHF$_2$, —OCF$_3$, —OCH$_2$CF$_3$, cyclopropyl, cyclopropyloxy, cyclobutyloxy, or

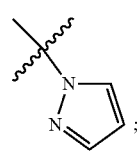

or two $R^1$ on adjacent carbons together with the atoms to which they are attached combine to form a cyclopentyl, cyclohexyl, dihydrofuran, tetrahydrofuran, methyltetrahydrofuran, 1,3-dioxole, dihydro-1,3-oxazine, or methyldihydrofuran;

L is —CH$_2$—;

$R^2$ is

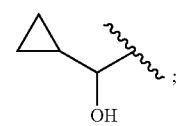 [SMILES: *C(O)C1CC1]

$R^3$ is —CH$_3$, —OCH$_3$, —CHF$_2$, —CF$_3$, —OCHF$_2$, —OCF$_3$, or cyclopropyl; and subscript q is 0, 1, 2, 3, or 4.

2. A pharmaceutical composition comprising a compound of claim 1 or a pharmaceutically acceptable salt thereof, and a pharmaceutically acceptable carrier or excipient.

3. The compound of claim 1, or a pharmaceutically acceptable salt thereof, wherein the compound is selected from:
| Compound No. | Structure |
|---|---|
| 203 | 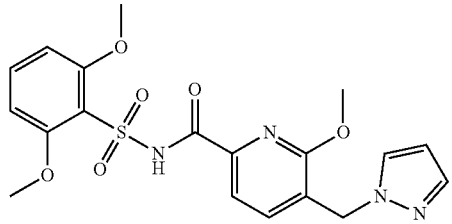 [SMILES: COc1cccc(OC)c1S(=O)(=O)NC(=O)c1ccc(Cn2cccn2)c(OC)n1] |
| 204 | 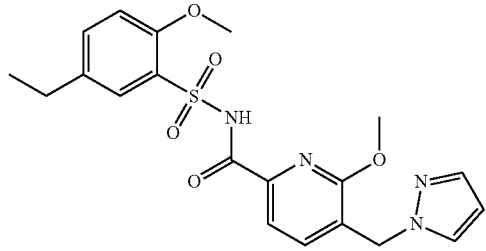 [SMILES: CCc1ccc(OC)c(S(=O)(=O)NC(=O)c2ccc(Cn3cccn3)c(OC)n2)c1] |
| 205 | 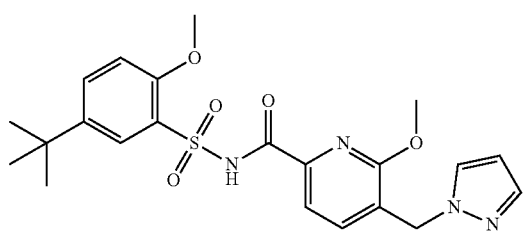 [SMILES: COc1ccc(C(C)(C)C)cc1S(=O)(=O)NC(=O)c1ccc(Cn2cccn2)c(OC)n1] |
| 206 | 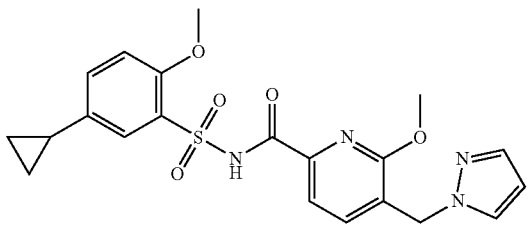 [SMILES: COc1ccc(C2CC2)cc1S(=O)(=O)NC(=O)c1ccc(Cn2cccn2)c(OC)n1] |
| 207 | 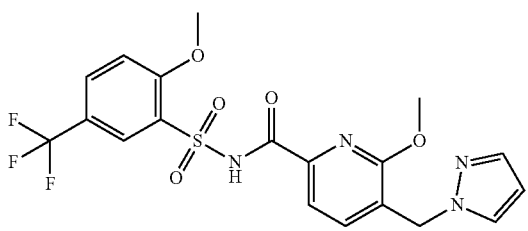 [SMILES: COc1ccc(C(F)(F)F)cc1S(=O)(=O)NC(=O)c1ccc(Cn2cccn2)c(OC)n1] |
| 208 | 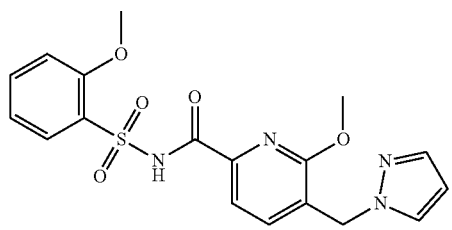 [SMILES: COc1ccccc1S(=O)(=O)NC(=O)c1ccc(Cn2cccn2)c(OC)n1] |

-continued

| Compound No. | Structure |
|---|---|
| 209 | 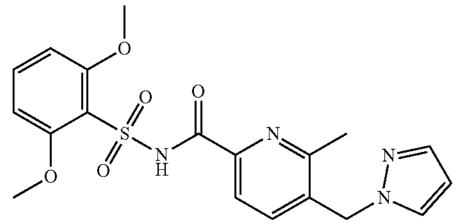 [SMILES: COc1cccc(OC)c1S(=O)(=O)NC(=O)c1ccc(Cn2cccn2)c(C)n1] |
| 211 | 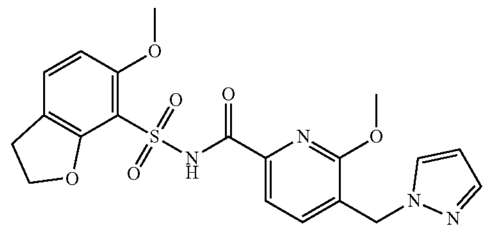 [SMILES: COc1ccc2c(c1S(=O)(=O)NC(=O)c1ccc(Cn3cccn3)c(OC)n1)OCC2] |
| 212 | 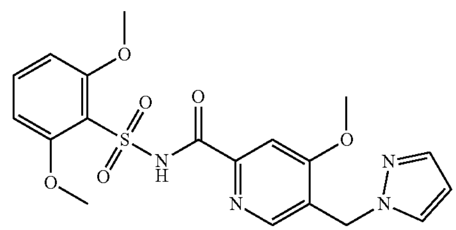 [SMILES: COc1cc(C(=O)NS(=O)(=O)c2c(OC)cccc2OC)ncc1Cn1cccn1] |
| 213 | 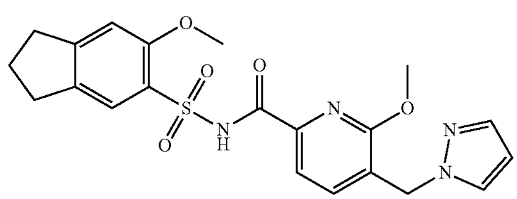 [SMILES: COc1cc2c(cc1S(=O)(=O)NC(=O)c1ccc(Cn3cccn3)c(OC)n1)CCC2] |
| 214 | 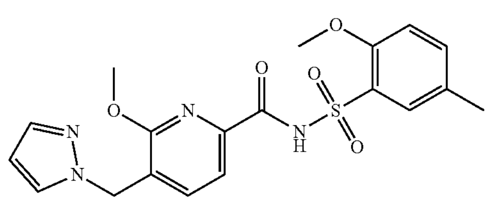 [SMILES: COc1ccc(C)cc1S(=O)(=O)NC(=O)c1ccc(Cn2cccn2)c(OC)n1] |
| 215 | 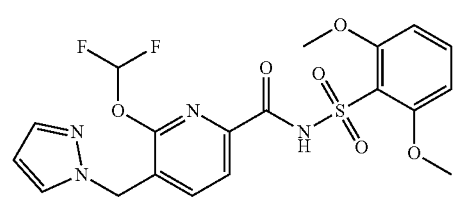 [SMILES: COc1cccc(OC)c1S(=O)(=O)NC(=O)c1ccc(Cn2cccn2)c(OC(F)F)n1] |
| 216 | 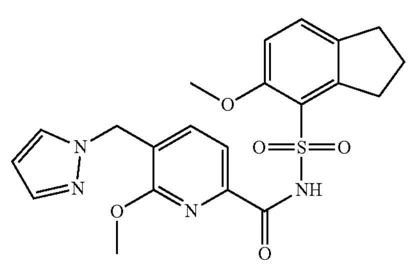 [SMILES: COc1ccc2c(c1S(=O)(=O)NC(=O)c1ccc(Cn3cccn3)c(OC)n1)CCC2] |

-continued
| Compound No. | Structure |
|---|---|
| 217 | 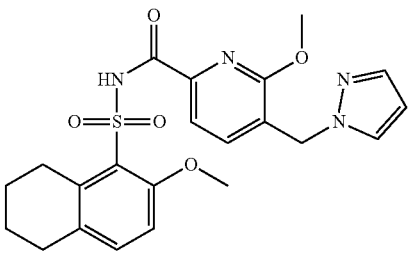 |
| 219 | 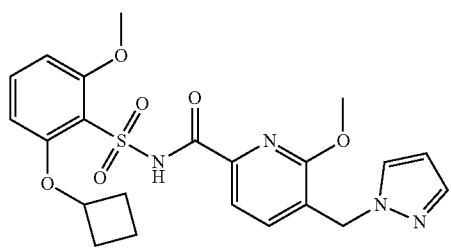 [SMILES: COc1cccc(OC2CCC2)c1S(=O)(=O)NC(=O)c1ccc(Cn2cccn2)c(OC)n1] |
| 220 | 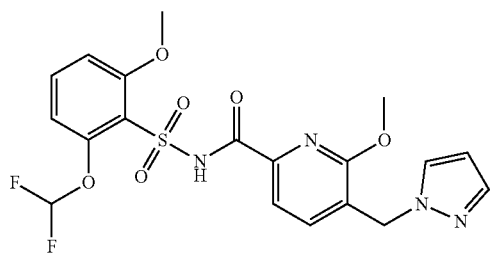 [SMILES: COc1cccc(OC(F)F)c1S(=O)(=O)NC(=O)c1ccc(Cn2cccn2)c(OC)n1] |
| 221 | 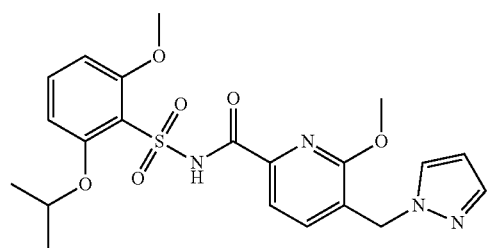 [SMILES: COc1cccc(OC(C)C)c1S(=O)(=O)NC(=O)c1ccc(Cn2cccn2)c(OC)n1] |
| 222 | 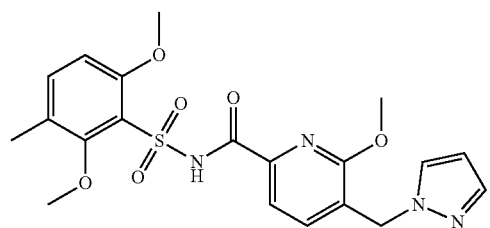 [SMILES: COc1ccc(C)c(OC)c1S(=O)(=O)NC(=O)c1ccc(Cn2cccn2)c(OC)n1] |
| 223 | 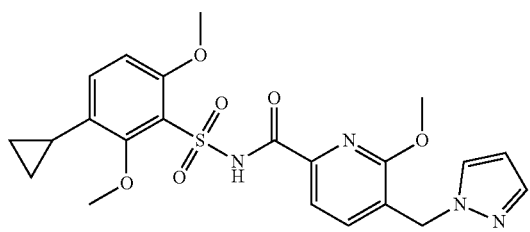 [SMILES: COc1ccc(C2CC2)c(OC)c1S(=O)(=O)NC(=O)c1ccc(Cn2cccn2)c(OC)n1] |

-continued
| Compound No. | Structure |
|---|---|
| 224 | 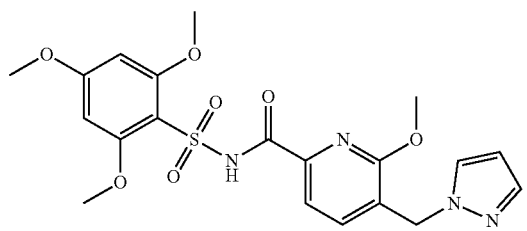 [SMILES: COc1cc(OC)c(S(=O)(=O)NC(=O)c2ccc(Cn3cccn3)c(OC)n2)c(OC)c1] |
| 225 | 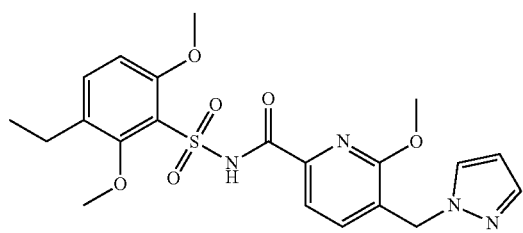 [SMILES: CCc1ccc(OC)c(S(=O)(=O)NC(=O)c2ccc(Cn3cccn3)c(OC)n2)c1OC] |
| 226 | 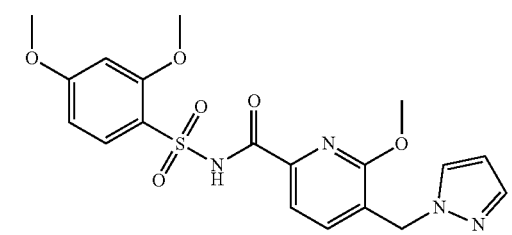 [SMILES: COc1ccc(S(=O)(=O)NC(=O)c2ccc(Cn3cccn3)c(OC)n2)c(OC)c1] |
| 227 | 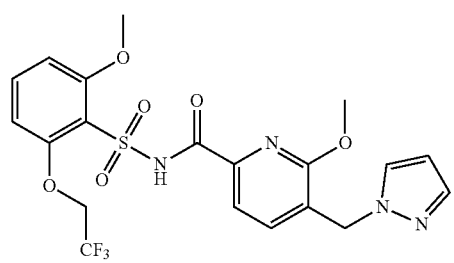 [SMILES: COc1cccc(OCC(F)(F)F)c1S(=O)(=O)NC(=O)c1ccc(Cn2cccn2)c(OC)n1] |
| 228 | 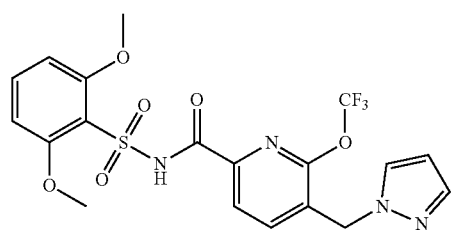 [SMILES: COc1cccc(OC)c1S(=O)(=O)NC(=O)c1ccc(Cn2cccn2)c(OC(F)(F)F)n1] |
| 229 | 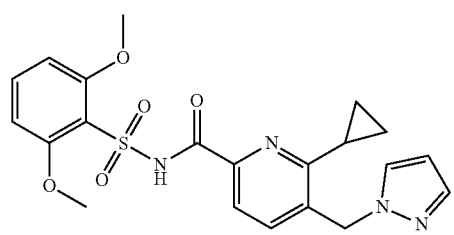 [SMILES: COc1cccc(OC)c1S(=O)(=O)NC(=O)c1ccc(Cn2cccn2)c(C2CC2)n1] |

-continued

| Compound No. | Structure |
|---|---|
| 230 | 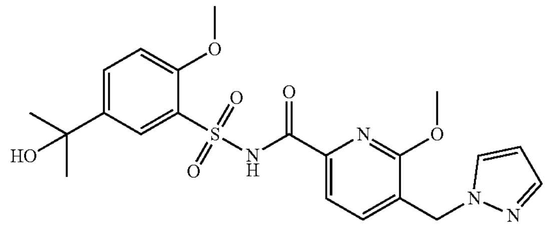 [SMILES: COc1ccc(C(C)(C)O)cc1S(=O)(=O)NC(=O)c1ccc(Cn2cccn2)c(OC)n1] |
| 231 | 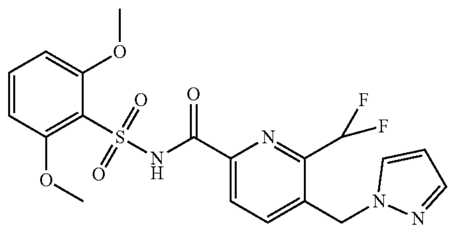 [SMILES: COc1cccc(OC)c1S(=O)(=O)NC(=O)c1ccc(Cn2cccn2)c(C(F)F)n1] |
| 233 | 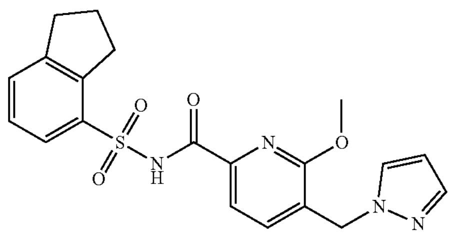 [SMILES: COc1nc(C(=O)NS(=O)(=O)c2cccc3c2CCC3)ccc1Cn1cccn1] |
| 234 | 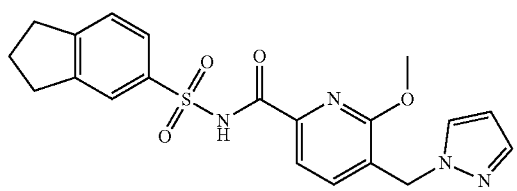 [SMILES: COc1nc(C(=O)NS(=O)(=O)c2ccc3c(c2)CCC3)ccc1Cn1cccn1] |
| 235 | 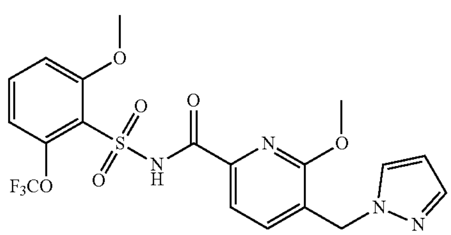 [SMILES: COc1cccc(OC(F)(F)F)c1S(=O)(=O)NC(=O)c1ccc(Cn2cccn2)c(OC)n1] |
| 236 | 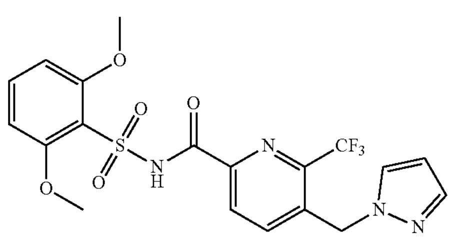 [SMILES: COc1cccc(OC)c1S(=O)(=O)NC(=O)c1ccc(Cn2cccn2)c(C(F)(F)F)n1] |
| 237 | 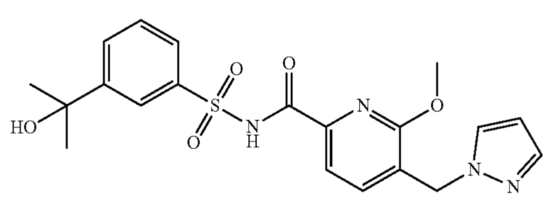 [SMILES: COc1nc(C(=O)NS(=O)(=O)c2cccc(C(C)(C)O)c2)ccc1Cn1cccn1] |

| Compound No. | Structure |
|---|---|
| 238 | 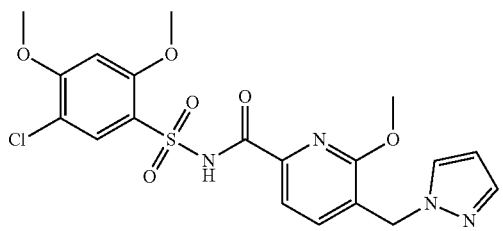 [SMILES: COc1cc(OC)c(S(=O)(=O)NC(=O)c2ccc(Cn3cccn3)c(OC)n2)cc1Cl] |
| 239 | 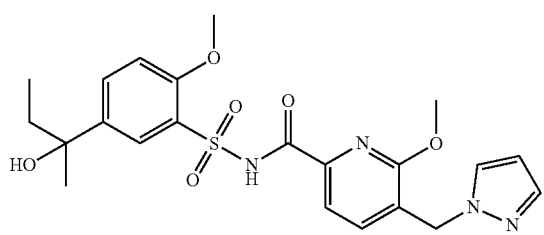 [SMILES: CCC(C)(O)c1ccc(OC)c(S(=O)(=O)NC(=O)c2ccc(Cn3cccn3)c(OC)n2)c1] |
| 241 | 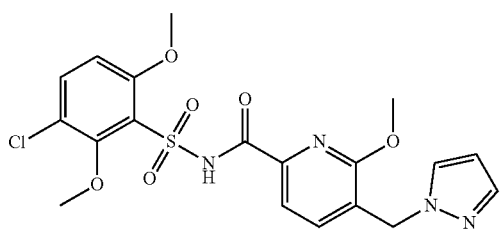 [SMILES: COc1ccc(Cl)c(OC)c1S(=O)(=O)NC(=O)c1ccc(Cn2cccn2)c(OC)n1] |
| 246 | 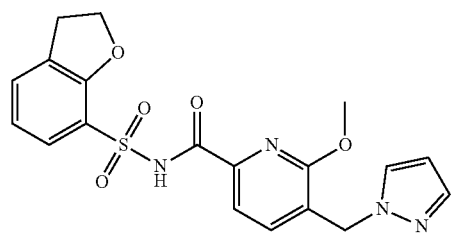 |
| 248 | 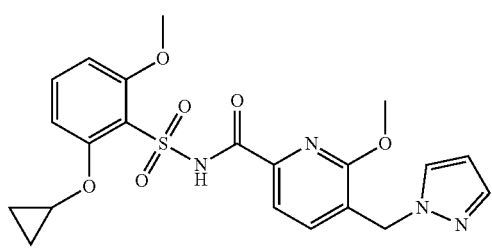 [SMILES: COc1cccc(OC2CC2)c1S(=O)(=O)NC(=O)c1ccc(Cn2cccn2)c(OC)n1] |
| 250 | 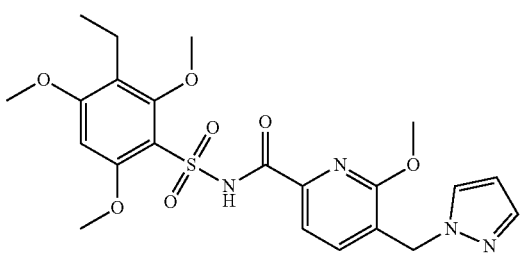 [SMILES: CCc1c(OC)cc(OC)c(S(=O)(=O)NC(=O)c2ccc(Cn3cccn3)c(OC)n2)c1OC] |

| Compound No. | Structure |
|---|---|
| 252 | 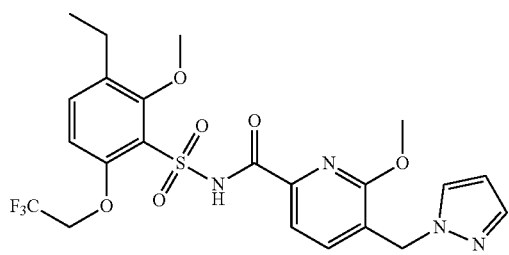 [SMILES: CCc1ccc(OCC(F)(F)F)c(S(=O)(=O)NC(=O)c2ccc(Cn3cccn3)c(OC)n2)c1OC] |
| 253 | 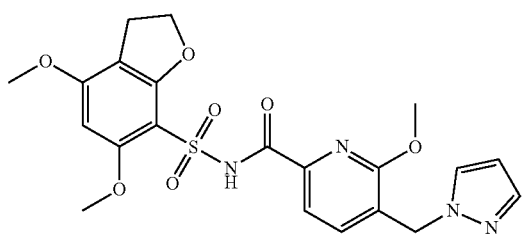 [SMILES: COc1cc(OC)c(S(=O)(=O)NC(=O)c2ccc(Cn3cccn3)c(OC)n2)c2c1CCO2] |
| 257 | 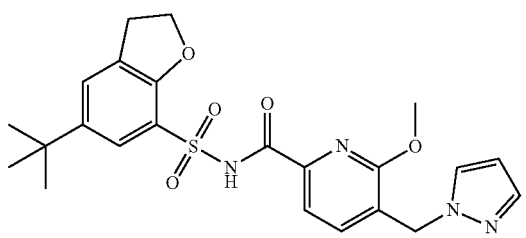 [SMILES: COc1nc(C(=O)NS(=O)(=O)c2cc(C(C)(C)C)cc3c2OCC3)ccc1Cn1cccn1] |
| 275 | 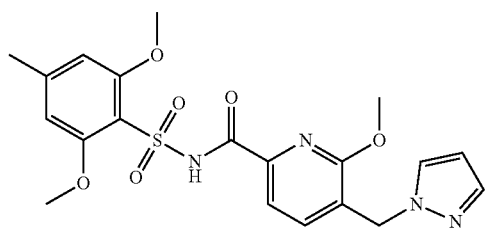 [SMILES: COc1cc(C)cc(OC)c1S(=O)(=O)NC(=O)c1ccc(Cn2cccn2)c(OC)n1] |
| 276 | 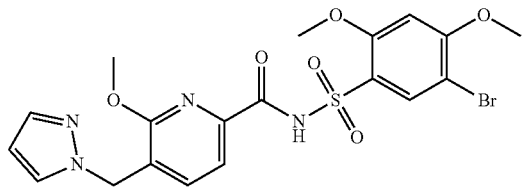 [SMILES: COc1cc(OC)c(S(=O)(=O)NC(=O)c2ccc(Cn3cccn3)c(OC)n2)cc1Br] |
| 277 | 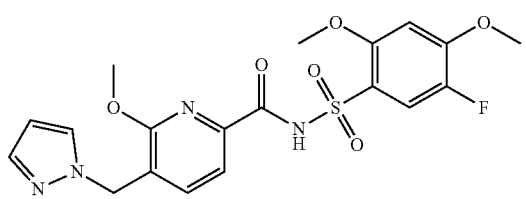 [SMILES: COc1cc(OC)c(S(=O)(=O)NC(=O)c2ccc(Cn3cccn3)c(OC)n2)cc1F] |

| Compound No. | Structure |
|---|---|
| 281 | 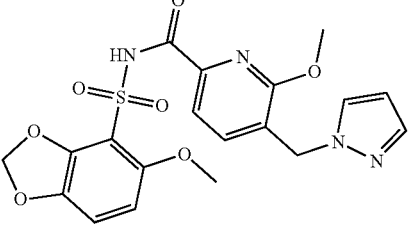 |
| 282 | 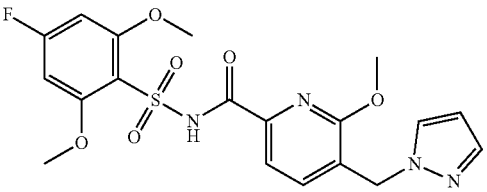 |
| 283 | 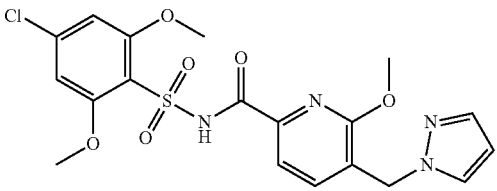 [SMILES: COc1cc(Cl)cc(OC)c1S(=O)(=O)NC(=O)c1ccc(Cn2cccn2)c(OC)n1] |
| 285 | 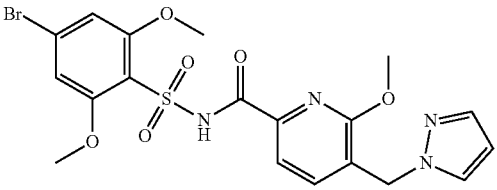 |
| 286 | 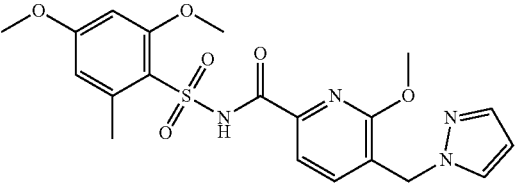 [SMILES: COc1cc(C)c(S(=O)(=O)NC(=O)c2ccc(Cn3cccn3)c(OC)n2)c(OC)c1] |
| 287 | 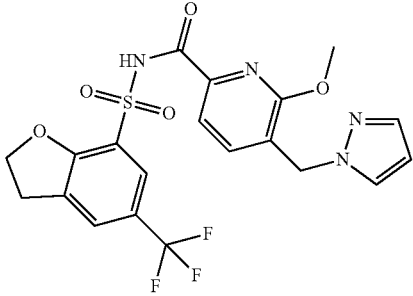 [SMILES: COc1nc(C(=O)NS(=O)(=O)c2cc(C(F)(F)F)cc3c2OCC3)ccc1Cn1cccn1] |
| 288 | 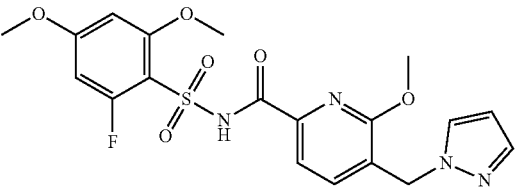 [SMILES: COc1cc(F)c(S(=O)(=O)NC(=O)c2ccc(Cn3cccn3)c(OC)n2)c(OC)c1] |

4. A pharmaceutical composition comprising a compound of claim 3 or a pharmaceutically acceptable salt thereof, and a pharmaceutically acceptable carrier or excipient.

5. The compound of claim 3, or a pharmaceutically acceptable salt thereof, having the structure:

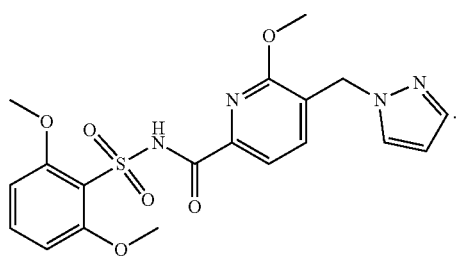 [SMILES: COc1cccc(OC)c1S(=O)(=O)NC(=O)c1ccc(Cn2cccn2)c(OC)n1]

6. A pharmaceutical composition comprising a compound of claim 5 or a pharmaceutically acceptable salt thereof, and a pharmaceutically acceptable carrier or excipient.

7. The compound of claim 3, or a pharmaceutically acceptable salt thereof, having the structure:

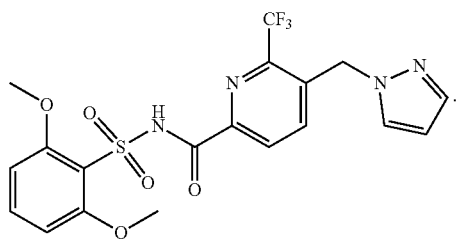 [SMILES: COc1cccc(OC)c1S(=O)(=O)NC(=O)c1ccc(Cn2cccn2)c(C(F)(F)F)n1]

8. A pharmaceutical composition comprising a compound of claim 7 or a pharmaceutically acceptable salt thereof, and a pharmaceutically acceptable carrier or excipient.

9. The compound of claim 3, or a pharmaceutically acceptable salt thereof, having the structure:

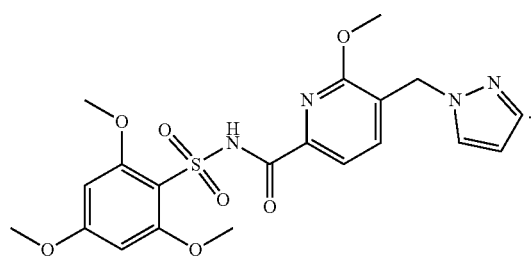 [SMILES: COc1cc(OC)c(S(=O)(=O)NC(=O)c2ccc(Cn3cccn3)c(OC)n2)c(OC)c1]

10. A pharmaceutical composition comprising a compound of claim 9 or a pharmaceutically acceptable salt thereof, and a pharmaceutically acceptable carrier or excipient.

11. The compound of claim 3, or a pharmaceutically acceptable salt thereof, having the structure:

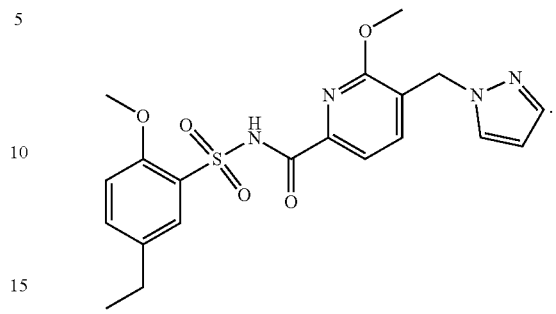

12. A pharmaceutical composition comprising a compound of claim 11 or a pharmaceutically acceptable salt thereof, and a pharmaceutically acceptable carrier or excipient.

13. The compound of claim 3, or a pharmaceutically acceptable salt thereof, having the structure:

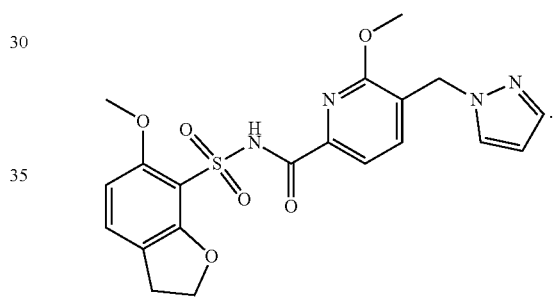

14. A pharmaceutical composition comprising a compound of claim 13 or a pharmaceutically acceptable salt thereof, and a pharmaceutically acceptable carrier or excipient.

15. The compound of claim 3, or a pharmaceutically acceptable salt thereof, having the structure:

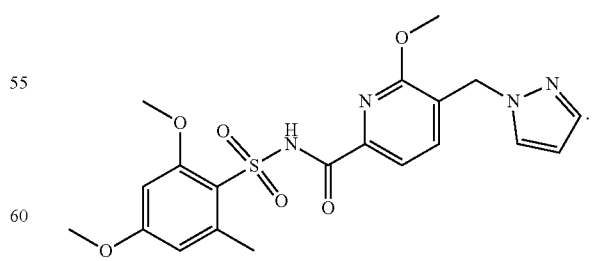

16. A pharmaceutical composition comprising a compound of claim 15 or a pharmaceutically acceptable salt thereof, and a pharmaceutically acceptable carrier or excipient.

17. The compound of claim 3, or a pharmaceutically acceptable salt thereof, having the structure:

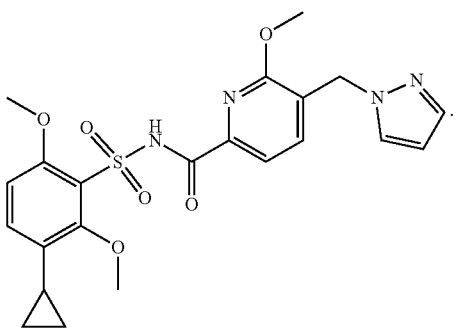 [SMILES: COc1ccc(C2CC2)c(OC)c1S(=O)(=O)NC(=O)c1ccc(Cn2cccn2)c(OC)n1]

18. A pharmaceutical composition comprising a compound of claim 17 or a pharmaceutically acceptable salt thereof, and a pharmaceutically acceptable carrier or excipient.

19. The compound of claim 3, or a pharmaceutically acceptable salt thereof, having the structure:

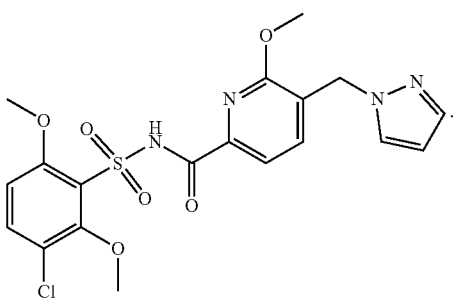 [SMILES: COc1ccc(Cl)c(OC)c1S(=O)(=O)NC(=O)c1ccc(Cn2cccn2)c(OC)n1]

20. A pharmaceutical composition comprising a compound of claim 19 or a pharmaceutically acceptable salt thereof, and a pharmaceutically acceptable carrier or excipient.

21. The compound of claim 3, or a pharmaceutically acceptable salt thereof, having the structure:

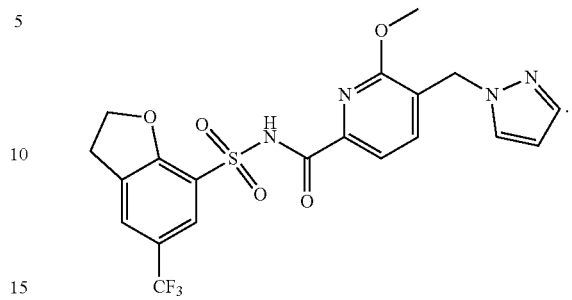

22. A pharmaceutical composition comprising a compound of claim 21 or a pharmaceutically acceptable salt thereof, and a pharmaceutically acceptable carrier or excipient.

23. A method of treating a disease or disorder mediated by KAT6A in a subject comprising administering to the subject in need thereof a therapeutically effective amount of a compound according to claim 1 or a pharmaceutically acceptable salt thereof.

24. The method of claim 23, wherein the disease or disorder is cancer.

25. The method of claim 24, wherein the cancer is selected from brain gliomas, glioblastomas, astrocytomas, multiforme, Bannayan-Zonana syndrome, Cowden disease, Lhermitte-Duclos disease, breast cancer, colon cancer, head and neck cancer, kidney, liver, lung cancer, bone cancer, colorectal cancer, germ cell cancer, melanoma, ovarian cancer, pancreatic cancer, adenocarcinoma, ductal adenocarcinoma, adenosquamous carcinoma, acinar cell carcinoma, glucagonoma, insulinoma, prostate, sarcoma and thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, uterine cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, gastrointestinal stromal tumor, neuroendocrine cancers, testicular cancer, and virus-related cancer.

26. The method of claim 25, wherein the cancer is breast cancer.

27. The method of claim 26, wherein the breast cancer is ER+ breast cancer.

* * * * *